(12) United States Patent
Johnson et al.

(10) Patent No.: US 7,160,888 B2
(45) Date of Patent: Jan. 9, 2007

(54) [1,8]NAPHTHYRIDIN-2-ONES AND RELATED COMPOUNDS FOR THE TREATMENT OF SCHIZOPHRENIA

(75) Inventors: Douglas S. Johnson, Dexter, MI (US); Joseph Thomas Repine, Ann Arbor, MI (US); Andrew David White, Pinckney, MI (US)

(73) Assignee: Warner Lambert Company LLC, Morris Plains, NJ (US)

( * ) Notice: Subject to any disclaimer, the term of this patent is extended or adjusted under 35 U.S.C. 154(b) by 141 days.

(21) Appl. No.: 10/900,210

(22) Filed: Jul. 28, 2004

(65) Prior Publication Data
US 2005/0043309 A1    Feb. 24, 2005

Related U.S. Application Data

(60) Provisional application No. 60/497,370, filed on Aug. 22, 2003.

(51) Int. Cl.
A61K 31/496 (2006.01)
C07D 471/04 (2006.01)

(52) U.S. Cl. .............. 514/253.04; 514/230.5; 514/250; 514/253.06; 514/264.1; 544/362; 544/363; 544/105; 544/279; 544/350

(58) Field of Classification Search ................ 544/362; 514/253.04
See application file for complete search history.

(56) References Cited

U.S. PATENT DOCUMENTS

| | | | |
|---|---|---|---|
| 5,006,528 | A | 4/1991 | Oshiro et al. |
| 5,206,366 | A | 4/1993 | Bowles |
| 5,350,747 | A | 9/1994 | Howard |
| 5,641,779 | A | 6/1997 | Halazy et al. |
| 5,945,422 | A | 8/1999 | Doherty et al. |
| 6,127,357 | A | 10/2000 | Cliffe et al. |
| 6,414,157 | B1 | 7/2002 | Lubisch et al. |

FOREIGN PATENT DOCUMENTS

| | | |
|---|---|---|
| EP | 0 367 141 A3 | 5/1990 |
| EP | 0 372 776 A2 | 6/1990 |
| EP | 0 431 945 A2 | 6/1991 |
| EP | 0 402 644 A1 | 8/1995 |
| EP | 0 814084 A1 | 12/1997 |
| JP | 56049361 A | 5/1981 |
| JP | 09241161 A | 9/1997 |
| WO | WO 93/04684 | 3/1993 |
| WO | WO 94/13643 | 6/1994 |
| WO | WO 94/13644 | 6/1994 |
| WO | WO 94/13661 | 6/1994 |
| WO | WO 94/13676 | 6/1994 |
| WO | WO 94/13677 | 6/1994 |
| WO | WO 96/26936 | 9/1996 |
| WO | WO 96/34867 | 11/1996 |
| WO | WO 97/03067 | 1/1997 |
| WO | WO 97/14419 | 4/1997 |
| WO | WO 98/42712 | 10/1998 |
| WO | WO 99/56672 | 11/1999 |
| WO | WO 01/46177 A1 | 6/2001 |
| WO | WO 02/16354 A1 | 2/2002 |
| WO | WO 02/48105 A2 | 6/2002 |
| WO | WO 02/56882 | 7/2002 |
| WO | WO 02/060423 A2 | 8/2002 |
| WO | WO 03/002556 A1 | 1/2003 |
| WO | WO 04/046124 A1 | 6/2004 |
| WO | WO 2004/087145 | 10/2004 |

OTHER PUBLICATIONS

Cecchetti et al, "Synthesis and B-adrenergic blocking activity of 1,4-benzothiazine oxime ethers," Eur.J.Med.Chem., (1989), pp. 479-484, vol. 24.

Chaudhary et al., "4-Dimethylaminopyridine: An Efficient and Selective Catalyst for the Silylation of Alcohols," Tetrahedron Letters, No. 2., (1979), pp. 99-102.

Freeman et al, "The Quinoxalinols. I. Correlation Between Antibacterial Activity and Chelating Ability," J. Org. Chem., (1951), pp. 438-442, vol. 16.

Hernandez et al, "Solid-Supported tert-Alkoxycarbonylation Reagents for Anchoring of Amines during Solid Phase Organic Synthesis," J. Org. Chem., (1997), pp. 3153-3157, vol. 62.

Kerrigan et al., "Synthesis of ARylpiperazines via Palladium-Catalysed Aromatic Amination Reactions of Bromoarenes with N-tert-Butoxycarbonylpiperazine," Tetrahedron Letters, (1998), pp. 2219-2222, vol. 39.

Miyaura et al., "Palladium-Catalyzed Cross-Coupling Reactions of Organoboron Compounds," Chem. Rev., (1995), pp. 2457-2483, vol. 95.

(Continued)

Primary Examiner—Emily Bernhardt
(74) Attorney, Agent, or Firm—Austin W. Zhang; Charles W. Ashbrook

(57) ABSTRACT

This invention relates to compounds of the formula 1

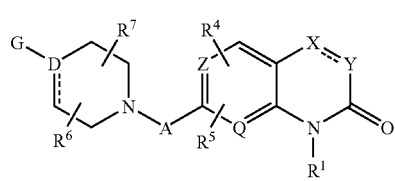

wherein G, D, A, Z, Q, X, Y, $R^1$, and $R^4$ through $R^7$ are defined as in the specification, processes for preparing the same and intermediates used in making the same, and pharmaceutical compositions containing such compounds and their use in the treatment of central nervous system disorders and other disorders.

12 Claims, No Drawings

OTHER PUBLICATIONS

Newkome et al., "Chemistry of Heterocyclic Compounds. tl. Synthesis and Conformational STudies of Macrocycles Possessing 1,8- or 1,5-Naphthyridonio Subunits Connected by Carbon-Oxygen Bridges," J. Org. Chem., (1981), pp. 833-839, vol. 46.

Pierce et al., "Practical Asymmetric Synthesis of Efavirenz (DMP 266), an HIV-1 Reverse Transcriptase Inhibitor," J. Org. Chem., (1998), pp. 8536-8543, vol. 63.

Marburg et al., "A short Efficient Synthesis of 4-Amino-2,3-dihydrobenzofuran," J. Heterocyclic Chem., (1980), pp. 1333-1335, vol. 17.

Shuto et al., "One-Pot Conversion of a,B-Unsaturated Alcohols into the Corresponding Carbon-Elongated Dienes with a Stable Phosphorus Ylide-BaMn04 system. Syntheesis fo 6'-Methylene Derivatives of Neplanocin A as Potential Antiviral Nucleosides. New Neplanocin Analogues," J. Org. Chem (1998), pp. 4489-4493, vol. 63.

Tominaga et al., "Studies on Positive Inotropic Agents.I. Synthesis of 3,4-Dihydro-6-[4-(3,4-dimethoxybenzoyl)-1-piperazinyl]-2(1H)-quinolinone and Related Compounds," Chem. Pharm. Bull., (1984), pp. 2100-2110, vol. 32.

Tuner, "A General Approach to the Synthesis of 1,6-,1,7-, and 1,8-Naphthyridines," J. Org. Chem., (1990), pp. 4744-4750, vol. 55.

Van Wijingaarden, "2-Phenylpyrroles as conformationally Restricted Benzamide Analogues. A New Class of Potential Antipsychotics. 2," J. Med. Chem., (1988), pp. 1934-1940, vol. 31.

Wolfe et al., "Simple, Efficient Gatalyst System for the Palladium-Catalyzed Amination of Aryl Chlorides, Bromides, and Triflates," J. Org. Chem., (2000), pp. 1158-1174, vol. 65.

Yoneda et al., "Facile Preparation of Aromatic Fluorides by Deaminative Fluorination of Aminoarenes Using Hydrogen Fluoride Combined with Bases," Tetrahedron, (1996), pp. 23-36, vol. 52.

PCT International Search Report, PCT/IB2004/002665.

Nobuyuki, "Carbostyril Derivative and Therapeutic Agent for Schizophrenia Containing the Same Derivative", Patent Abstracts of Japan, vol. 1996, No. 3, 1995 (JP 07 304741 abstract).

Nobuyuki, "Carbostyril Derivative", Patent Abstracts of Japan, vol. 1996, No. 3, 1995 (JP 07 304740 abstract).

Shuji, "3,4-Dihydrocarbostyril Derivative", Patent Abstracts of Japan, vol. 1996, No. 1, 1995 (JP 07 247271 abstract).

Nobuyuki, "Carbostyril Derivative and Therapeutic Agent for Schizophrenia Containing the Same Derivative", Patent Abstracts of Japan, vol. 1995, No. 9, 1995 (JP 07 165720 abstract).

Nobuyuki, "Carbostyryl Derivative and Remedy for Schizophrenia Containing the Same", Patent Abstracts of Japan, vol. 014, No. 466, 1990 (JP 02 191256 abstract).

[1,8]NAPHTHYRIDIN-2-ONES AND RELATED COMPOUNDS FOR THE TREATMENT OF SCHIZOPHRENIA

CROSS-REFERENCE TO RELATED APPLICATIONS

This application claims the benefit to U.S. Provisional Application No. 60/497,370, filed on Aug. 22, 2003.

BACKGROUND OF THE INVENTION

This invention relates to [1,8]naphthyridin-2-ones and related compounds, methods of making such compounds, pharmaceutical compositions containing them, and their use for the treatment of schizophrenia and other central nervous system (CNS).

The [1,8]naphthyridin-2-ones and related compounds of this invention bind to dopamine $D_2$ receptors. Some exhibit activity as partial agonists of $D_2$ receptors, while others exhibit activity as antagonists of such receptors.

Other heterocyclic derivatives that are useful for the treatment of schizophrenia are referred to in U.S. Pat. No. 5,350,747, which issued on Sep. 27, 1994, and in U.S. Pat. No. 6,127,357, which issued on Oct. 3, 2000. These patents are incorporated herein by reference in their entireties.

Other heterocyclic derivatives that have been stated to be useful as antipsychotic agents are those referred to in PCT patent publication WO 93/04684, which published on Mar. 18, 1993, and European patent application EP 402644A, which was published on Dec. 19, 1990. These patent applications are incorporated herein by reference in their entireties.

SUMMARY OF THE INVENTION

The present invention relates to compounds of the formula 1

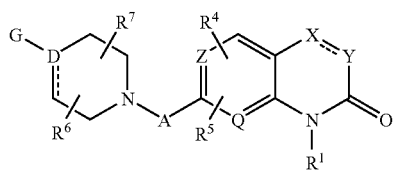

wherein G is

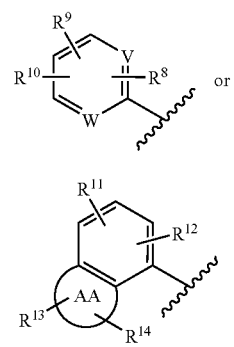

A is $-(CH_2)_mCH_2-$, $-(CH_2)_mO-$, or $-(CH_2)_mNH-$, wherein m is an integer from 2 to 5 and wherein one or two of the carbon or nitrogen atoms of $-(CH_2)_mCH_2-$, $-(CH_2)_mO-$ and $-(CH_2)_mNH-$ can be substituted, optionally and independently, with one or two substituents that are selected, independently, from fluoro and methyl, or with two substituents attached to the same carbon atom that form, together with the carbon to which they are attached, a spirocyclopropyl or spirocyclobutyl ring;

D is N, C, or CH, provided that when D is N each carbon atom covalently attached to D is attached through a single bond;

Z and Q are independently N, C, or CH, provided that at least one of Z and Q is N;

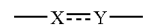

is $-CH_2-CH_2-$, $-CH=CH-$, $-CH_2-NH-$, $-NH-CH_2-$, $-N=CH-$, $CH=N-$, $-O-CH_2-$, or $-CH_2-O-$, wherein

can optionally be substituted, at any available bonding site, by one to four substituents $R^2$, $R^{2'}$, $R^3$ and $R^{3'}$;

V and W are independently N, C, or CH;

ring AA is a saturated or unsaturated 5-6- or 7-membered carbocyclic ring wherein one, two or three of the carbon atoms of ring AA that are not shared with the benzo ring of group (ii) can be replaced, optionally and independently, by a nitrogen, oxygen or sulfur atom;

$R^1$ is hydrogen, $-C(=O)CH_3$, or $(C_1-C_3)$alkyl;

$R^2$, $R^{2'}$, $R^3$ and $R^{3'}$ are independently selected from hydrogen, halo, cyano, oxo, hydroxy, $-C(=O)CH_3$, $(C_1-C_4)$alkyl, and $(C_1-C_4)$alkoxy, wherein the alkyl moieties of the $(C_1-C_4)$alkyl, $(C_1-C_4)$alkoxy, and $-C(=O)CH_3$ groups can be optionally substituted with from one to three fluoro atoms and can also be optionally substituted with an amino or hydroxy substituent;

$R^4$ and $R^5$ are independently selected from hydrogen, halo, cyano, hydroxy, $-C(=O)CH_3$, $(C_1-C_4)$alkyl, and $(C_1-C_4)$alkoxy, wherein the alkyl moieties of the $(C_1-C_4)$alkyl, $(C_1-C_4)$alkoxy, and $-C(=O)CH_3$ groups can be optionally substituted with from one to three fluoro atoms and can also be optionally substituted with an amino or hydroxy substituent;

$R^6$ and $R^7$ are selected, independently, from hydrogen and methyl;

$R^8$, $R^9$, $R^{10}$, $R^{11}$, and $R^{12}$ are independently selected from hydrogen, halo, $-C(=O)CH_3$, $(C_1-C_4)$alkyl, and $(C_1-C_4)$alkoxy, aryl, and aryloxy, wherein the alkyl moieties of the $(C_1-C_4)$alkyl, $(C_1-C_4)$alkoxy, and $-C(=O)CH_3$ groups and the aryl and aryloxy moieties can be optionally substituted with from one to three fluoro atoms and can also be optionally substituted with an amino or hydroxy substituent;

$R^{13}$ and $R^{14}$ are independently selected from hydrogen, halo, cyano, oxo, hydroxy, $-C(=O)CH_3$, $(C_1-C_4)$alkyl, and $(C_1-C_4)$alkoxy, wherein the alkyl moieties of the $(C_1-C_4)$alkyl, $(C_1-C_4)$alkoxy, and $-C(=O)CH_3$ groups can be optionally substituted with from one to three fluoro atoms and can also be optionally substituted with an amino or hydroxy substituent;

and the pharmaceutically acceptable salts of such compounds.

This invention also relates to a pharmaceutical composition comprising a therapeutically effective amount of a compound of the formula 1, or a pharmaceutically acceptable salt thereof, and a pharmaceutically acceptable carrier.

The compounds of formula 1 have useful pharmaceutical and medicinal properties.

This invention also relates to a method of treating a disorder or condition selected from the group consisting of single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; attention deficit hyperactivity disorder (ADHD); behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal, including a human, comprising administering to a mammal in need of such treatment an amount of a compound of the formula 1, or a pharmaceutically acceptable salt thereof, that is effective in treating such disorder or condition.

This invention also relates to a pharmaceutical composition for treating any disorder or condition listed immediately above, the pharmaceutical composition comprising an amount of a compound of the formula 1, or a pharmaceutically acceptable salt thereof, that is effective in treating such disorder or condition, and a pharmaceutically acceptable carrier.

This invention also relates to a process for preparing a compound of formula 2, below. The compound of formula 2 is suitable for use as an intermediate in synthesis of compounds of formula 1:

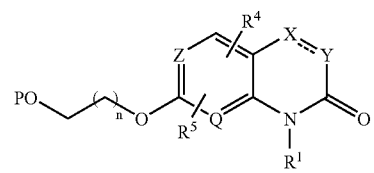

wherein

P is H, benzyl, p-methyoxybenzyl, tert-butyldimethylsilyl, tert-butyldiphenylsilyl, or tetrahydropyranyl;

n is an integer from 1 to 4;

Q, Z,

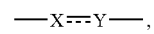

$R^1$, $R^4$, and $R^5$ are the same as defined for formula 1, above.

The process of making a compound of formula 2, comprising reacting a compound of formula 3, below:

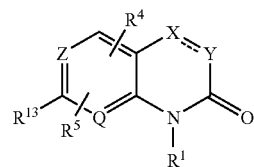

wherein

Q, Z, X, Y, $R^1$, $R^4$, and $R^5$ are defined as in formula 1 above; and $R^{13}$ is Cl, F, Br, S(O)Me, or $SO_2Me$, with a compound of formula: $PO(CH_2)_nCH_2OH$ in the presence of a base and a phase transfer catalyst.

This invention also relates to a process for preparing the compound of formula 1, wherein A is $-(CH2)_mO-$ and m is an integer from 2 to 5, the process comprising reacting a compound of formula 4a:

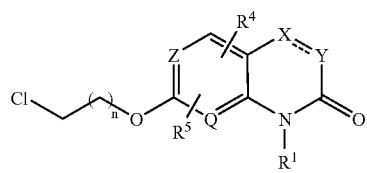

wherein Q, Z,

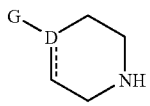

$R^1$, $R^4$, and $R^5$ are defined as in formula 1,
and n is an integer from 1 to 4, with a compound of the following formula in the presence of a base:

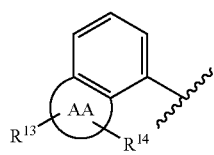

wherein G is defined as in formula 1, above. In this process, G is preferably a structure of the following formula:

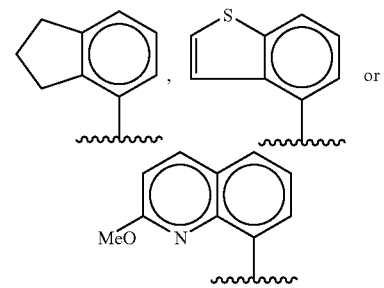

wherein

AA is a 6-membered saturated or unsaturated carbon ring; and $R^{13}$ and $R^{14}$ are independently selected from hydrogen, halo, cyano, oxo, hydroxy, —C(=O)CH$_3$, (C$_1$–C$_4$)alkyl, and (C$_1$–C$_4$)alkoxy.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "aryl", as used herein, unless otherwise indicated, refers to an aromatic 5- or 6-membered carbocyclic ring wherein one carbon of the ring is covalently attached to another subunit of a compound.

The term "aryloxy" as used herein, refers to an aryl wherein one carbon of the aromatic ring is covalently attached to another subunit of a compound through an —O—, oxy, or (C$_1$–C$_4$)alkoxy residue.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

The term "treating", as used herein, refers to reversing, alleviating, inhibiting the progress of, or preventing the disorder or condition to which such term applies, or preventing one or more symptoms of such condition or disorder.

The term "treatment", as used herein, refers to the act of treating, as "treating" is defined immediately above.

The compounds of formula 1, and the pharmaceutically acceptable salts of these compounds are referred to herein, collectively, as the "novel compounds of this invention" and the "active compounds of this invention".

DETAILED DESCRIPTION OF THE INVENTION

Preferred embodiments of this invention relate to compounds of the formula 1, and their pharmaceutically acceptable salts, wherein G is a group of the formula ii and ring AA is a benzo ring.

Other preferred embodiments of this invention relate to compounds of the formula 1, and their pharmaceutically acceptable salts, wherein

—X═Y— is —CH$_2$—NH—.

Other preferred embodiments of this invention relate to compounds of formula 1 and their pharmaceutically acceptable salts, wherein G is naphthyl, and $R^{13}$ and $R^{14}$ are independently hydrogen or flouro.

Other preferred embodiments of this invention relate to compounds of formula 1 and their pharmaceutically acceptable salts, wherein at least one of $R^{13}$ or $R^{14}$ is flouro or methoxy.

Other preferred embodiments of this invention relate to compounds of the formula 1, and their pharmaceutically acceptable salts, wherein G is a group of a formula selected from:

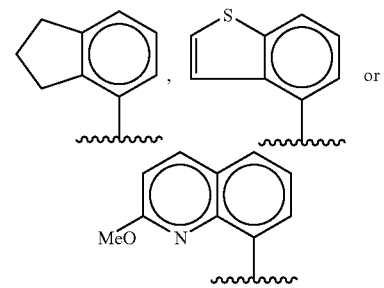

Other preferred embodiments of this invention relate to compounds of the formula 1, and their pharmaceutically acceptable salts, wherein G is 2,3-dichlorophenyl.

Other preferred embodiments of this invention relate to compounds of the formula 1, and their pharmaceutically acceptable salts, wherein W and V are C or CH.

Other preferred embodiments of this invention relate to compounds of formula 1 and their pharmaceutically acceptable salts, wherein D is N, Q is N, Z is CH,

—X═Y— is —CH$_2$—CH$_2$— or —CH═CH—, and $R^1$, $R^4$, and $R^5$ are hydrogen.

Other preferred embodiments of this invention relate to compounds of formula 1 and their pharmaceutically acceptable salts, wherein W and V are C or CH, or wherein only one of W or V is N.

Other preferred embodiments of this invention relate to compounds of formula 1 and their pharmaceutically acceptable salts, wherein Q and Z are both N.

Other preferred embodiments of this invention relate to compounds of the formula 1, and their pharmaceutically acceptable salts, wherein $R^4$ and $R^5$ are hydrogen.

Other preferred embodiments of this invention relate to compounds of the formula 1, and their pharmaceutically acceptable salts, wherein D is N.

Other preferred embodiments of this invention relate to compounds of the formula 1, and their pharmaceutically acceptable salts, wherein A is —$(CH_2)_4O$—.

Other preferred embodiments of this invention relate to compounds of the formula 1, and their pharmaceutically acceptable salts, wherein Q is N and Z is C or CH.

Other preferred embodiments of this invention relate to compounds of the formula 1, and their pharmaceutically acceptable salts, wherein Q is N and Z is N.

Other preferred embodiments of this invention relate to compounds of the formula 1, and their pharmaceutically acceptable salts, wherein

is —$CH_2$—$CH_2$— or —CH=CH—.

Other preferred embodiments of this invention relate to compounds of the formula 1, and their pharmaceutically acceptable salts, wherein $R^1$ is hydrogen.

Other embodiments of this invention relate to compounds of the formula 1, and their pharmaceutically acceptable salts, wherein Q is C or CH, and Z is N.

Other embodiments of this invention relates to compounds of the formula 1, and their pharmaceutically acceptable salts, wherein

is —O—$CH_2$—.

Other embodiments of this invention relates to compounds of the formula 1, and their pharmaceutically acceptable salts, wherein

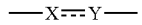

is —$CH_2$—O—.

Other embodiments of this invention relate to compounds of the formula 1, and their pharmaceutically acceptable salts, wherein A is —$(CH_2)_m$—$CH_2$— wherein m is 3 or 4.

Other embodiments of this invention relate to compounds of the formula 1 and their pharmaceutically acceptable salts, wherein G is a group of the formula (i) and W and V are both N, or W is N and V is C or CH.

One set of specific embodiments of the invention relate to compounds of formula 1 and their pharmaceutically acceptable salts, wherein all of the atoms of the carbocyclic ring M are carbon atoms. These embodiments include the following compounds and their pharmaceutically acceptable salts. Procedures for synthesis of each of these compounds are illustrated in the Examples section, below.

7-{4-[4-(2,3-Dichloro-phenyl)-piperazin-1-yl]-butoxy}-3,4-dihydro-1H-[1,8]naphthyridin-2-one;

7-{4-[4-(2-Chloro-3-methyl-phenyl)-piperazin-1-yl]-butoxy}-3,4-dihydro-1H-[1,8]naphthyridin-2-one;

7-{4-[4-(3-Chloro-2-methyl-phenyl)-piperazin-1-yl]-butoxy}-3,4-dihydro-1H-[1,8]naphthyridin-2-one;

7-{4-[4-(2,3-Dimethyl-phenyl)-piperazin-1-yl]-butoxy}-3,4-dihydro-1H-[1,8]naphthyridin-2-one;

7-{4-[4-(2-Chloro-3-fluoro-phenyl)-piperazin-1-yl]-butoxy}-3,4-dihydro-1H-[1,8]naphthyridin-2-one;

7-{4-[4-(3-Chloro-2-fluoro-phenyl)-piperazin-1-yl]-butoxy}-3,4-dihydro-1H-[1,8]naphthyridin-2-one;

7-{4-[4-(2-Chloro-3-trifluoromethyl-phenyl)-piperazin-1-yl]-butoxy}-3,4-dihydro-1H-[1,8]naphthyridin-2-one;

7-{4-[4-(2,3-Dichloro-4-fluoro-phenyl)-piperazin-1-yl]-butoxy}-3,4-dihydro-1H-[1,8]naphthyridin-2-one;

7-{4-[4-(2-Chloro-4-fluoro-phenyl)-piperazin-1-yl]-butoxy}-3,4-dihydro-1H-[1,8]naphthyridin-2-one;

7-{4-[4-(2-Chloro-phenyl)-piperazin-1-yl]-butoxy}-3,4-dihydro-1H-[1,8]naphthyridin-2-one;

7-[4-(4-Biphenyl-2-yl-piperazin-1-yl)-butoxy]-3,4-dihydro-1H-[1,8]naphthyridin-2-one;

7-{4-[4-(2,5-Dichloro-phenyl)-piperazin-1-yl]-butoxy}-3,4-dihydro-1H-[1,8]naphthyridin-2-one;

7-{4-[4-(2-Chloro-4-fluoro-5-methyl-phenyl)-piperazin-1-yl]-butoxy}-3,4-dihydro-1H-[1,8]naphthyridin-2-one;

7-{4-[4-(5-Chloro-2-methyl-phenyl)-piperazin-1-yl]-butoxy}-3,4-dihydro-1H-[1,8]naphthyridin-2-one;

7-{4-[4-(2-Chloro-4-fluoro-3-methyl-phenyl)-piperazin-1-yl]-butoxy}-3,4-dihydro-1H-[1,8]naphthyridin-2-one;

7-{4-[4-(3-Ethyl-phenyl)-piperazin-1-yl]-butoxy}-3,4-dihydro-1H-[1,8]naphthyridin-2-one;

7-{4-[4-(3-Chloro-2-methoxy-phenyl)-piperazin-1-yl]-butoxy}-3,4-dihydro-1H-[1,8]naphthyridin-2-one;

7-{4-[4-(3-Methyl-2-phenoxy-phenyl)-piperazin-1-yl]-butoxy}-3,4-dihydro-1H-[1,8]naphthyridin-2-one;

7-{4-[4-(2,3-Dimethoxy-phenyl)-piperazin-1-yl]-butoxy}-3,4-dihydro-1H-[1,8]naphthyridin-2-one;

7-{4-[4-(2-Ethoxy-phenyl)-piperazin-1-yl]-butoxy}-3,4-dihydro-1H-[1,8]naphthyridin-2-one;

7-{4-[4-(2-Chloro-3-ethoxy-phenyl)-piperazin-1-yl]-butoxy}-3,4-dihydro-1H-[1,8]naphthyridin-2-one;

7-{4-[4-(2-Chloro-3-methoxy-phenyl)-piperazin-1-yl]-butoxy}-3,4-dihydro-1H-[1,8]naphthyridin-2-one;

7-{4-[4-(2-Chloro-3-isopropoxy-phenyl)-piperazin-1-yl]-butoxy}-3,4-dihydro-1H-[1,8]naphthyridin-2-one;

7-{4-[4-(3-Methoxy-2-methyl-phenyl)-piperazin-1-yl]-butoxy}-3,4-dihydro-1H-[1,8]naphthyridin-2-one;

7-{4-[4-(5-Chloro-2-isopropoxy-phenyl)-piperazin-1-yl]-butoxy}-3,4-dihydro-1H-[1,8]naphthyridin-2-one;

7-{4-[4-(2-Isopropoxy-phenyl)-piperazin-1-yl]-butoxy}-3,4-dihydro-1H-[1,8]naphthyridin-2-one;

7-{4-[4-(2-Isobutoxy-phenyl)-piperazin-1-yl]-butoxy}-3,4-dihydro-1H-[1,8]naphthyridin-2-one;

7-{4-[4-(2-Acetyl-3-chloro-phenyl)-piperazin-1-yl]-butoxy}-3,4-dihydro-1H-[1,8]naphthyridin-2-one;

7-{4-[4-(3-Chloro-2-ethyl-phenyl)-piperazin-1-yl]-butoxy}-3,4-dihydro-1H-[1,8]naphthyridin-2-one;

7-{4-[4-(2-Acetyl-3-fluoro-phenyl)-piperazin-1-yl]-butoxy}-3,4-dihydro-1H-[1,8]naphthyridin-2-one;

7-{4-[4-(2-Ethyl-3-fluoro-phenyl)-piperazin-1-yl]-butoxy}-3,4-dihydro-1H-[1,8]naphthyridin-2-one;

7-{4-[4-(3-Acetyl-2-chloro-phenyl)-piperazin-1-yl]-butoxy}-3,4-dihydro-1H-[1,8]naphthyridin-2-one;

7-{4-[4-(3-Acetyl-phenyl)-piperazin-1-yl]-butoxy}-3,4-dihydro-1H-[1,8]naphthyridin-2-one;

7-{4-[4-(2-Acetyl-phenyl)-piperazin-1-yl]-butoxy}-3,4-dihydro-1H-[1,8]naphthyridin-2-one;

7-{4-[4-(2-Ethyl-phenyl)-piperazin-1-yl]-butoxy}-3,4-dihydro-1H-[1,8]naphthyridin-2-one;

7-[4-(4-o-Tolyl-piperazin-1-yl)-butoxy]-3,4-dihydro-1H-[1,8]naphthyridin-2-one;

7-{4-[4-(2-Trifluoromethyl-phenyl)-piperazin-1-yl]-butoxy}-3,4-dihydro-1H-[1,8]naphthyridin-2-one;

7-{4-[4-(3-Trifluoromethyl-phenyl)-piperazin-1-yl]-butoxy}-3,4-dihydro-1H-[1,8]naphthyridin-2-one;

7-[4-(4-Phenyl-piperazin-1-yl)-butoxy]-3,4-dihydro-1H-[1,8]naphthyridin-2-one;

7-{4-[4-(4-Fluoro-phenyl)-piperazin-1-yl]-butoxy}-3,4-dihydro-1H-[1,8]naphthyridin-2-one;

7-{4-[4-(2,4-Difluoro-phenyl)-piperazin-1-yl]-butoxy}-3,4-dihydro-1H-[1,8]naphthyridin-2-one;

7-(4-{4-[2-(1,1-Difluoro-ethyl)-phenyl]-piperazin-1-yl}-butoxy)-3,4-dihydro-1H-[1,8]naphthyridin-2-one;

7-[4-(4-Pyridin-2-yl-piperazin-1-yl)-butoxy]-3,4-dihydro-1H-[1,8]naphthyridin-2-one;

7-{4-[4-(6-Methyl-pyridin-2-yl)-piperazin-1-yl]-butoxy}-3,4-dihydro-1H-[1,8]naphthyridin-2-one;

7-{4-[4-(6-Ethyl-pyridin-2-yl)-piperazin-1-yl]-butoxy}-3,4-dihydro-1H-[1,8]naphthyridin-2-one;

7-{4-[4-(6-Cyclopropyl-pyridin-2-yl)-piperazin-1-yl]-butoxy}-3,4-dihydro-1H-[1,8]naphthyridin-2-one;

7-{4-[4-(4-Methyl-pyrimidin-2-yl)-piperazin-1-yl]-butoxy}-3,4-dihydro-1H-[1,8]naphthyridin-2-one;

7-[4-(4-Naphthalen-1-yl-piperazin-1-yl)-butoxy]-3,4-dihydro-1H-[1,8]naphthyridin-2-one;

7-{4-[4-(5,6,7,8-Tetrahydro-naphthalen-1-yl)-piperazin-1-yl]-butoxy}-3,4-dihydro-1H-[1,8]naphthyridin-2-one;

7-{4-[4-(3-Fluoro-5,6,7,8-tetrahydro-naphthalen-1-yl)-piperazin-1-yl]-butoxy}-3,4-dihydro-1H-[1,8]naphthyridin-2-one;

7-{4-[4-(8-Oxo-5,6,7,8-tetrahydro-naphthalen-1-yl)-piperazin-1-yl]-butoxy}-3,4-dihydro-1H-[1,8]naphthyridin-2-one;

7-{4-[4-(7,7-Dimethyl-8-oxo-5,6,7,8-tetrahydro-naphthalen-1-yl)-piperazin-1-yl]-butoxy}-3,4-dihydro-1H-[1,8]naphthyridin-2-one;

7-{4-[4-(7,7-Difluoro-8-oxo-5,6,7,8-tetrahydro-naphthalen-1-yl)-piperazin-1-yl]-butoxy}-3,4-dihydro-1H-[1,8]naphthyridin-2-one;

7-{4-[4-(7,7-Difluoro-5,6,7,8-tetrahydro-naphthalen-1-yl)-piperazin-1-yl]-butoxy}-3,4-dihydro-1H-[1,8]naphthyridin-2-one;

7-{4-[4-(7-Oxo-5,6,7,8-tetrahydro-naphthalen-1-yl)-piperazin-1-yl]-butoxy}-3,4-dihydro-1H-[1,8]naphthyridin-2-one;

7-{4-[4-(7-Hydroxy-5,6,7,8-tetrahydro-naphthalen-1-yl)-piperazin-1-yl]-butoxy}-3,4-dihydro-1H-[1,8]naphthyridin-2-one;

7-{4-[4-(5-Oxo-5,6,7,8-tetrahydro-naphthalen-1-yl)-piperazin-1-yl]-butoxy}-3,4-dihydro-1H-[1,8]naphthyridin-2-one;

7-{4-[4-(5,5-Difluoro-5,6,7,8-tetrahydro-naphthalen-1-yl)-piperazin-1-yl]-butoxy}-3,4-dihydro-1H-[1,8]naphthyridin-2-one;

7-[4-(4-Indan-4-yl-piperazin-1-yl)-butoxy]-3,4-dihydro-1H-[1,8]naphthyridin-2-one;

7-{4-[4-(2-Oxo-indan-4-yl)-piperazin-1-yl]-butoxy}-3,4-dihydro-1H-[1,8]naphthyridin-2-one;

7-{4-[4-(2,2-Difluoro-indan-4-yl)-piperazin-1-yl]-butoxy}-3,4-dihydro-1H-[1,8]naphthyridin-2-one;

7-{4-[4-(6,7,8,9-Tetrahydro-5H-benzocyclohepten-1-yl)-piperazin-1-yl]-butoxy}-3,4-dihydro-1H-[1,8]naphthyridin-2-one;

7-[4-(4-Naphthalen-1-yl-piperidin-1-yl)-butoxy]-3,4-dihydro-1H-[1,8]naphthyridin-2-one 7-{4-[4-(7-Fluoro-naphthalen-1-yl)-piperazin-1-yl]-butoxy}-3,4-dihydro-1H-[1,8]naphthyridin-2-one;

7-{4-[4-(8-Fluoro-naphthalen-1-yl)-piperazin-1-yl]-butoxy}-3,4-dihydro-1H-[1,8]naphthyridin-2-one;

7-{4-[4-(6-Fluoro-naphthalen-1-yl)-piperazin-1-yl]-butoxy}-3,4-dihydro-1H-[1,8]naphthyridin-2-one;

7-{4-[4-(5-Fluoro-naphthalen-1-yl)-piperazin-1-yl]-butoxy}-3,4-dihydro-1H-[1,8]naphthyridin-2-one;

7-{4-[4-(4-Fluoro-naphthalen-1-yl)-piperazin-1-yl]-butoxy}-3,4-dihydro-1H-[1,8]naphthyridin-2-one;

7-{4-[4-(3-Fluoro-naphthalen-1-yl)-piperazin-1-yl]-butoxy}-3,4-dihydro-1H-[1,8]naphthyridin-2-one;

7-{4-[4-(2-Fluoro-naphthalen-1-yl)-piperazin-1-yl]-butoxy}-3,4-dihydro-1H-[1,8]naphthyridin-2-one;

7-{4-[4-(6,7-Difluoro-naphthalen-1-yl)-piperazin-1-yl]-butoxy}-3,4-dihydro-1H-[1,8]naphthyridin-2-one;

7-{4-[4-(7-Methoxy-naphthalen-1-yl)-piperazin-1-yl]-butoxy}-3,4-dihydro-1H-[1,8]naphthyridin-2-one;

7-{4-[4-(7-Chloro-naphthalen-1-yl)-piperazin-1-yl]-butoxy}-3,4-dihydro-1H-[1,8]naphthyridin-2-one;

7-{4-[4-(5-Chloro-naphthalen-1-yl)-piperazin-1-yl]-butoxy}-3,4-dihydro-1H-[1,8]naphthyridin-2-one;

7-{4-[4-(6-Chloro-naphthalen-1-yl)-piperazin-1-yl]-butoxy}-3,4-dihydro-1H-[1,8]naphthyridin-2-one;

7-{4-[4-(8-Chloro-naphthalen-1-yl)-piperazin-1-yl]-butoxy}-3,4-dihydro-1H-[1,8]naphthyridin-2-one;

7-{4-[4-(7-Acetyl-naphthalen-1-yl)-piperazin-1-yl]-butoxy}-3,4-dihydro-1H-[1,8]naphthyridin-2-one;

7-{4-[4-(6-Acetyl-naphthalen-1-yl)-piperazin-1-yl]-butoxy}-3,4-dihydro-1H-[1,8]naphthyridin-2-one;

7-{4-[4-(5-Acetyl-naphthalen-1-yl)-piperazin-1-yl]-butoxy}-3,4-dihydro-1H-[1,8]naphthyridin-2-one;

7-{4-[4-(4-Acetyl-naphthalen-1-yl)-piperazin-1-yl]-butoxy}-3,4-dihydro-1H-[1,8]naphthyridin-2-one;

7-{4-[4-(2-Acetyl-naphthalen-1-yl)-piperazin-1-yl]-butoxy}-3,4-dihydro-1H-[1,8]naphthyridin-2-one;

8-{4-[4-(7-Oxo-5,6,7,8-tetrahydro-[1,8]naphthyridin-2-yloxy)-butyl]-piperazin-1-yl}-naphthalene-2-carbonitrile;

N-(8-{4-[4-(7-Oxo-5,6,7,8-tetrahydro-[1,8]naphthyridin-2-yloxy)-butyl]-piperazin-1-yl}-naphthalen-2-yl)-acetamide;

7-{4-[4-(2,3-Dichloro-phenyl)-piperazin-1-yl]-butoxy}-1H-[1,8]naphthyridin-2-one;

7-{4-[4-(2-Chloro-3-trifluoromethyl-phenyl)-piperazin-1-yl]-butoxy}-1H-[1,8]naphthyridin-2-one;

7-{4-[4-(2-Acetyl-3-chloro-phenyl)-piperazin-1-yl]-butoxy}-1H-[1,8]naphthyridin-2-one;

7-{4-[4-(3-Chloro-2-ethyl-phenyl)-piperazin-1-yl]-butoxy}-1H-[1,8]naphthyridin-2-one;

7-{4-[4-(2-Acetyl-3-fluoro-phenyl)-piperazin-1-yl]-butoxy}-1H-[1,8]naphthyridin-2-one;

7-{4-[4-(3-Acetyl-2-chloro-phenyl)-piperazin-1-yl]-butoxy}-1H-[1,8]naphthyridin-2-one;

7-{4-[4-(2-Chloro-4-fluoro-5-methyl-phenyl)-piperazin-1-yl]-butoxy}-1H-[1,8]naphthyridin-2-one;

7-{4-[4-(2-Chloro-4-fluoro-3-methyl-phenyl)-piperazin-1-yl]-butoxy}-1H-[1,8]naphthyridin-2-one;

7-{4-[4-(5-Chloro-2-isopropoxy-phenyl)-piperazin-1-yl]-butoxy}-1H-[1,8]naphthyridin-2-one;

7-{4-[4-(2-Isopropoxy-phenyl)-piperazin-1-yl]-butoxy}-1H-[1,8]naphthyridin-2-one;

7-{4-[4-(2-Isobutoxy-phenyl)-piperazin-1-yl]-butoxy}-1H-[1,8]naphthyridin-2-one;

7-[4-(4-o-Tolyl-piperazin-1-yl)-butoxy]-1H-[1,8]naphthyridin-2-one

7-{4-[4-(4-Fluoro-phenyl)-piperazin-1-yl]-butoxy}-1H-[1,8]naphthyridin-2-one;

7-{4-[4-(3-Chloro-4-fluoro-phenyl)-piperazin-1-yl]-butoxy}-1H-[1,8]naphthyridin-2-one;

7-{4-[4-(3-Trifluoromethyl-phenyl)-piperazin-1-yl]-butoxy}-1H-[1,8]naphthyridin-2-one;

7-{4-[4-(2-Trifluoromethyl-phenyl)-piperazin-1-yl]-butoxy}-1H-[1,8]naphthyridin-2-one;

7-(4-{4-[2-(1,1-Difluoro-ethyl)-phenyl]-piperazin-1-yl}-butoxy)-1H-[1,8]naphthyridin-2-one;

7-{4-[4-(2-Chloro-3-methoxy-phenyl)-piperazin-1-yl]-butoxy}-1H-[1,8]naphthyridin-2-one;

7-{4-[4-(2-Chloro-3-ethoxy-phenyl)-piperazin-1-yl]-butoxy}-1H-[1,8]naphthyridin-2-one;

7-{4-[4-(2-Chloro-3-isopropoxy-phenyl)-piperazin-1-yl]-butoxy}-1H-[1,8]naphthyridin-2-one;

7-{4-[4-(3-Methyl-2-phenoxy-phenyl)-piperazin-1-yl]-butoxy}-1H-[1,8]naphthyridin-2-one;

7-{4-[4-(3-Chloro-2-fluoro-phenyl)-piperazin-1-yl]-butoxy}-1H-[1,8]naphthyridin-2-one;

7-{4-[4-(2-Chloro-4-fluoro-phenyl)-piperazin-1-yl]-butoxy}-1H-[1,8]naphthyridin-2-one;

7-{4-[4-(2,3-Dichloro-4-fluoro-phenyl)-piperazin-1-yl]-butoxy}-1H-[1,8]naphthyridin-2-one;

7-{4-[4-(2-Chloro-phenyl)-piperazin-1-yl]-butoxy}-1H-[1,8]naphthyridin-2-one;

7-[4-(4-Biphenyl-2-yl-piperazin-1-yl)-butoxy]-1H-[1,8]naphthyridin-2-one;

7-{4-[4-(3-Methoxy-2-methyl-phenyl)-piperazin-1-yl]-butoxy}-1H-[1,8]naphthyridin-2-one;

7-{4-[4-(2-Chloro-3-fluoro-phenyl)-piperazin-1-yl]-butoxy}-1H-[1,8]naphthyridin-2-one;

7-{4-[4-(6-Cyclopropyl-pyridin-2-yl)-piperazin-1-yl]-butoxy}-1H-[1,8]naphthyridin-2-one;

7-[4-(4-Pyrimidin-2-yl-piperazin-1-yl)-butoxy]-1H-[1,8]naphthyridin-2-one;

7-{4-[4-(4-Methoxy-pyrimidin-2-yl)-piperazin-1-yl]-butoxy}-1H-[1,8]naphthyridin-2-one;

7-[4-(4-Indan-4-yl-piperazin-1-yl)-butoxy]-1H-[1,8]naphthyridin-2-one

7-{4-[4-(5,6,7,8-Tetrahydro-naphthalen-1-yl)-piperazin-1-yl]-butoxy}-1H-[1,8]naphthyridin-2-one;

7-{4-[4-(3-Fluoro-5,6,7,8-tetrahydro-naphthalen-1-yl)-piperazin-1-yl]-butoxy}-1H-[1,8]naphthyridin-2-one;

7-{4-[4-(8-Oxo-5,6,7,8-tetrahydro-naphthalen-1-yl)-piperazin-1-yl]-butoxy}-1H-[1,8]naphthyridin-2-one;

7-{4-[4-(7,7-Dimethyl-8-oxo-5,6,7,8-tetrahydro-naphthalen-1-yl)-piperazin-1-yl]-butoxy}-1H-[1,8]naphthyridin-2-one;

7-{4-[4-(7,7-Dimethyl-5,6,7,8-tetrahydro-naphthalen-1-yl)-piperazin-1-yl]-butoxy}-1H-[1,8]naphthyridin-2-one;

7-{4-[4-(7,7-Difluoro-8-oxo-5,6,7,8-tetrahydro-naphthalen-1-yl)-piperazin-1-yl]-butoxy}-1H-[1,8]naphthyridin-2-one;

7-{4-[4-(7,7-Difluoro-5,6,7,8-tetrahydro-naphthalen-1-yl)-piperazin-1-yl]-butoxy}-1H-[1,8]naphthyridin-2-one;

7-{4-[4-(7-Oxo-5,6,7,8-tetrahydro-naphthalen-1-yl)-piperazin-1-yl]-butoxy}-1H-[1,8]naphthyridin-2-one;

7-{4-[4-(7-Oxo-5,6,7,8-tetrahydro-naphthalen-1-yl)-piperazin-1-yl]-butoxy}-1H-[1,8]naphthyridin-2-one;

7-{4-[4-(7-Hydroxy-5,6,7,8-tetrahydro-naphthalen-1-yl)-piperazin-1-yl]-butoxy}-1H-[1,8]naphthyridin-2-one;

7-{4-[4-(5-Oxo-5,6,7,8-tetrahydro-naphthalen-1-yl)-piperazin-1-yl]-butoxy}-1H-[1,8]naphthyridin-2-one;

7-{4-[4-(5,5-Difluoro-5,6,7,8-tetrahydro-naphthalen-1-yl)-piperazin-1-yl]-butoxy}-1H-[1,8]naphthyridin-2-one;

7-{4-[4-(3-Oxo-indan-4-yl)-piperazin-1-yl]-butoxy}-1H-[1,8]naphthyridin-2-one;

7-{4-[4-(2-Oxo-indan-4-yl)-piperazin-1-yl]-butoxy}-1H-[1,8]naphthyridin-2-one;

7-{4-[4-(2,2-Difluoro-indan-4-yl)-piperazin-1-yl]-butoxy}-1H-[1,8]naphthyridin-2-one;

7-[4-(4-Naphthalen-1-yl-piperazin-1-yl)-butoxy]-1H-[1,8]naphthyridin-2-one;

7-{4-[4-(6-Fluoro-naphthalen-1-yl)-piperazin-1-yl]-butoxy}-1H-[1,8]naphthyridin-2-one;

7-{4-[4-(7-Fluoro-naphthalen-1-yl)-piperazin-1-yl]-butoxy}-1H-[1,8]naphthyridin-2-one;

7-{4-[4-(8-Fluoro-naphthalen-1-yl)-piperazin-1-yl]-butoxy}-1H-[1,8]naphthyridin-2-one;

7-{4-[4-(5-Fluoro-naphthalen-1-yl)-piperazin-1-yl]-butoxy}-1H-[1,8]naphthyridin-2-one;

7-{4-[4-(4-Fluoro-naphthalen-1-yl)-piperazin-1-yl]-butoxy}-1H-[1,8]naphthyridin-2-one;

7-{4-[4-(3-Fluoro-naphthalen-1-yl)-piperazin-1-yl]-butoxy}-1H-[1,8]naphthyridin-2-one;

7-{4-[4-(2-Fluoro-naphthalen-1-yl)-piperazin-1-yl]-butoxy}-1H-[1,8]naphthyridin-2-one;

7-{4-[4-(6,7-Difluoro-naphthalen-1-yl)-piperazin-1-yl]-butoxy}-1H-[1,8]naphthyridin-2-one;

7-{4-[4-(7-Chloro-naphthalen-1-yl)-piperazin-1-yl]-butoxy}-1H-[1,8]naphthyridin-2-one;

7-{4-[4-(6-Chloro-naphthalen-1-yl)-piperazin-1-yl]-butoxy}-1H-[1,8]naphthyridin-2-one;

7-{4-[4-(5-Chloro-naphthalen-1-yl)-piperazin-1-yl]-butoxy}-1H-[1,8]naphthyridin-2-one;

7-{4-[4-(8-Chloro-naphthalen-1-yl)-piperazin-1-yl]-butoxy}-1H-[1,8]naphthyridin-2-one;

7-{4-[4-(7-Methoxy-naphthalen-1-yl)-piperazin-1-yl]-butoxy}-1H-[1,8]naphthyridin-2-one;

7-{4-[4-(6-Methoxy-naphthalen-1-yl)-piperazin-1-yl]-butoxy}-1H-[1,8]naphthyridin-2-one;

7-{4-[4-(7-Acetyl-naphthalen-1-yl)-piperazin-1-yl]-butoxy}-1H-[1,8]naphthyridin-2-one;

7-{4-[4-(6-Acetyl-naphthalen-1-yl)-piperazin-1-yl]-butoxy}-1H-[1,8]naphthyridin-2-one;

7-{4-[4-(5-Acetyl-naphthalen-1-yl)-piperazin-1-yl]-butoxy}-1H-[1,8]naphthyridin-2-one;

7-{4-[4-(4-Acetyl-naphthalen-1-yl)-piperazin-1-yl]-butoxy}-1H-[1,8]naphthyridin-2-one;

7-{4-[4-(2-Acetyl-naphthalen-1-yl)-piperazin-1-yl]-butoxy}-1H-[1,8]naphthyridin-2-one;

8-{4-[4-(7-Oxo-7,8-dihydro-[1,8]naphthyridin-2-yloxy)-butyl]-piperazin-1-yl}-naphthalene-2-carbonitrile;

1-Methyl-7-[4-(4-naphthalen-1-yl-piperazin-1-yl)-butoxy]-1H-[1,8]naphthyridin-2-one;

7-{3-[4-(2,3-Dichloro-phenyl)-piperazin-1-yl]-propoxy}-1H-[1,8]naphthyridin-2-one;

7-[3-(4-Naphthalen-1-yl-piperazin-1-yl)-propoxy]-1H-[1,8]naphthyridin-2-one;

7-[3-(4-Naphthalen-1-yl-piperazin-1-yl)-propoxy]-3,4-dihydro-1H-[1,8]naphthyridin-2-one;

7-{2-[4-(2,3-Dichloro-phenyl)-piperazin-1-yl]-ethoxy}-1H-[1,8]naphthyridin-2-one;

7-{4-[4-(2,3-Dichloro-phenyl)-piperazin-1-yl]-1-methyl-butoxy}-3,4-dihydro-1H-[1,8]naphthyridin-2-one;

7-[1-Methyl-4-(4-naphthalen-1-yl-piperazin-1-yl)-butoxy]-3,4-dihydro-1H-[1,8]naphthyridin-2-one;

7-{4-[4-(2,3-Dichloro-phenyl)-piperazin-1-yl]-1,1-dimethyl-butoxy}-3,4-dihydro-1H-[1,8]naphthyridin-2-one;

7-[1,1-Dimethyl-4-(4-naphthalen-1-yl-piperazin-1-yl)-butoxy]-3,4-dihydro-1H-[1,8]naphthyridin-2-one;

7-{5-[4-(2,3-Dichloro-phenyl)-piperazin-1-yl]-pentyl}-3,4-dihydro-1H-[1,8]naphthyridin-2-one;

7-{5-[4-(2-Chloro-3-methyl-phenyl)-piperazin-1-yl]-pentyl}-3,4-dihydro-1H-[1,8]naphthyridin-2-one;

7-{5-[4-(2,3-Dichloro-4-fluoro-phenyl)-piperazin-1-yl]-pentyl}-3,4-dihydro-1H-[1,8]naphthyridin-2-one;

7-{5-[4-(5,6,7,8-Tetrahydro-naphthalen-1-yl)-piperazin-1-yl]-pentyl}-3,4-dihydro-1H-[1,8]naphthyridin-2-one;

7-[5-(4-Naphthalen-1-yl-piperazin-1-yl)-pentyl]-3,4-dihydro-1H-[1,8]naphthyridin-2-one;

7-{5-[4-(2-Chloro-4-fluoro-phenyl)-piperazin-1-yl]-pentyl}-3,4-dihydro-1H-[1,8]naphthyridin-2-one;

7-{5-[4-(2-Chloro-4-fluoro-3-methyl-phenyl)-piperazin-1-yl]-pentyl}-3,4-dihydro-1H-[1,8]naphthyridin-2-one;

7-{5-[4-(6-Methyl-pyridin-2-yl)-piperazin-1-yl]-pentyl}-3,4-dihydro-1H-[1,8]naphthyridin-2-one;

7-{5-[4-(6-Ethyl-pyridin-2-yl)-piperazin-1-yl]-pentyl}-3,4-dihydro-1H-[1,8]naphthyridin-2-one;

7-{5-[4-(6-Cyclopropyl-pyridin-2-yl)-piperazin-1-yl]-pentyl}-3,4-dihydro-1H-[1,8]naphthyridin-2-one;

7-{5-[4-(4,6-Dimethyl-pyridin-2-yl)-piperazin-1-yl]-pentyl}-3,4-dihydro-1H-[1,8]naphthyridin-2-one;

7-{5-[4-(2,3-Dichloro-phenyl)-piperazin-1-yl]-pentyl}-1H-[1,8]naphthyridin-2-one;

7-{4-[4-(2,3-Dichloro-phenyl)-piperazin-1-yl]-butoxy}-4-methyl-1H-[1,8]naphthyridin-2-one;

7-{4-[4-(2,3-Dichloro-phenyl)-piperazin-1-yl]-butoxy}-4-methyl-3,4-dihydro-1H-[1,8]naphthyridin-2-one;

7-{5-[4-(2,3-Dichloro-phenyl)-piperazin-1-yl]-pentyl}-4-methyl-1H-[1,8]naphthyridin-2-one;

7-{4-[4-(2,3-Dichloro-phenyl)-piperazin-1-yl]-butoxy}-3-methyl-1H-[1,8]naphthyridin-2-one;

7-{5-[4-(2,3-Dichloro-phenyl)-piperazin-1-yl]-pentyl}-3-methyl-1H-[1,8]naphthyridin-2-one;

7-{4-[4-(2,3-Dichloro-phenyl)-piperazin-1-yl]-butoxy}-3-methyl-3,4-dihydro-1H-[1,8]naphthyridin-2-one;

7-{4-[4-(2,3-Dichloro-phenyl)-piperazin-1-yl]-butoxy}-3,4-dimethyl-1H-[1,8]naphthyridin-2-one;

7-{5-[4-(2,3-Dichloro-phenyl)-piperazin-1-yl]-pentyl}-3,4-dimethyl-1H-[1,8]naphthyridin-2-one;

7-{4-[4-(2,3-Dichloro-phenyl)-piperazin-1-yl]-butoxy}-3-fluoro-1H-[1,8]naphthyridin-2-one;

3-Fluoro-7-[4-(4-naphthalen-1-yl-piperazin-1-yl)-butoxy]-1H-[1,8]naphthyridin-2-one;

7-[4-(4-Naphthalen-1-yl-piperazin-1-yl)-butoxy]-3-(2,2,2-trifluoro-ethyl)-1H-[1,8]naphthyridin-2-one;

7-{4-[4-(2,3-Dichloro-phenyl)-piperazin-1-yl]-butoxy}-3,3-dimethyl-3,4-dihydro-1H-[1,8]naphthyridin-2-one;

7-{4-[4-(2,3-Dichloro-phenyl)-piperazin-1-yl]-butoxy}-3,3-dimethyl-1H-[1,8]naphthyridine-2,4-dione;

7-{4-[4-(2,3-Dichloro-phenyl)-piperazin-1-yl]-butoxy}-4-hydroxy-3,3-dimethyl-3,4-dihydro-1H-[1,8]naphthyridin-2-one;

4,4-Dimethyl-7-[4-(4-naphthalen-1-yl-piperazin-1-yl)-butoxy]-3,4-dihydro-1H-[1,8]naphthyridin-2-one;

7-{4-[4-(2,3-Dichloro-phenyl)-piperazin-1-yl]-butoxy}-4,4-dimethyl-3,4-dihydro-1H-[1,8]naphthyridin-2-one;

4,4-Dimethyl-7-{4-[4-(5,6,7,8-tetrahydro-naphthalen-1-yl)-piperazin-1-yl]-butoxy}-3,4-dihydro-1H-[1,8]naphthyridin-2-one;

7-[4-(4-Indan-4-yl-piperazin-1-yl)-butoxy]-4,4-dimethyl-3,4-dihydro-1H-[1,8]naphthyridin-2-one;

7-{4-[4-(2-Chloro-3-methyl-phenyl)-piperazin-1-yl]-butoxy}-4,4-dimethyl-3,4-dihydro-1H-[1,8]naphthyridin-2-one;

7-{4-[4-(3-Chloro-2-methyl-phenyl)-piperazin-1-yl]-butoxy}-4,4-dimethyl-3,4-dihydro-1H-[1,8]naphthyridin-2-one;

7-{4-[4-(6-Cyclopropyl-pyridin-2-yl)-piperazin-1-yl]-butoxy}-4,4-dimethyl-3,4-dihydro-1H-[1,8]naphthyridin-2-one;

7-{4-[4-(2-Ethyl-phenyl)-piperazin-1-yl]-butoxy}-4,4-dimethyl-3,4-dihydro-1H-[1,8]naphthyridin-2-one;

7-{4-[4-(2-Isobutoxy-phenyl)-piperazin-1-yl]-butoxy}-4,4-dimethyl-3,4-dihydro-1H-[1,8]naphthyridin-2-one;

7-{4-[4-(2-Isopropoxy-phenyl)-piperazin-1-yl]-butoxy}-4,4-dimethyl-3,4-dihydro-1H-[1,8]naphthyridin-2-one;

7-{4-[4-(2,3-Dichloro-phenyl)-piperazin-1-yl]-butoxy}-6-methyl-3,4-dihydro-1H-[1,8]naphthyridin-2-one;

7-{4-[4-(2,3-Dichloro-phenyl)-piperazin-1-yl]-butoxy}-6-methyl-3,4-dihydro-1H-[1,8]naphthyridin-2-one;

6-Methyl-7-[4-(4-naphthalen-1-yl-piperazin-1-yl)-butoxy]-3,4-dihydro-1H-[1,8]naphthyridin-2-one;

7-{4-[4-(2,3-Dichloro-phenyl)-piperazin-1-yl]-butoxy}-6-fluoro-3,4-dihydro-1H-[1,8]naphthyridin-2-one;

6-Fluoro-7-[4-(4-naphthalen-1-yl-piperazin-1-yl)-butoxy]-3,4-dihydro-1H-[1,8]naphthyridin-2-one;

6-Fluoro-7-[4-(4-indan-4-yl-piperazin-1-yl)-butoxy]-3,4-dihydro-1H-[1,8]naphthyridin-2-one;

6-Chloro-7-[4-(4-naphthalen-1-yl-piperazin-1-yl)-butoxy]-3,4-dihydro-1H-[1,8]naphthyridin-2-one;

6-Bromo-7-{4-[4-(2,3-dichloro-phenyl)-piperazin-1-yl]-butoxy}-3,4-dihydro-1H-[1,8]naphthyridin-2-one;

6-Bromo-7-[4-(4-naphthalen-1-yl-piperazin-1-yl)-butoxy]-3,4-dihydro-1H-[1,8]naphthyridin-2-one;

7-{4-[4-(2,3-Dichloro-phenyl)-piperazin-1-yl]-butoxy}-5-methyl-3,4-dihydro-1H-[1,8]naphthyridin-2-one;

5-Methyl-7-[4-(4-naphthalen-1-yl-piperazin-1-yl)-butoxy]-3,4-dihydro-1H-[1,8]naphthyridin-2-one;

5-Methyl-7-{4-[4-(5,6,7,8-tetrahydro-naphthalen-1-yl)-piperazin-1-yl]-butoxy}-3,4-dihydro-1H-[1,8]naphthyridin-2-one;

7-[4-(4-Indan-4-yl-piperazin-1-yl)-butoxy]-5-methyl-3,4-dihydro-1H-[1,8]naphthyridin-2-one;

7-[4-(4-Indan-4-yl-piperazin-1-yl)-butoxy]-5-trifluoromethyl-3,4-dihydro-1H-[1,8]naphthyridin-2-one;

7-[4-(4-Naphthalen-1-yl-piperazin-1-yl)-butoxy]-5-trifluoromethyl-3,4-dihydro-1H-[1,8]naphthyridin-2-one;

7-{4-[4-(5,6,7,8-Tetrahydro-naphthalen-1-yl)-piperazin-1-yl]-butoxy}-5-trifluoromethyl-3,4-dihydro-1H-[1,8]naphthyridin-2-one;

7-{4-[4-(2,3-Dichloro-phenyl)-piperazin-1-yl]-butoxy}-3,4-dihydro-1H-pyrido[2,3-d]pyrimidin-2-one;

7-[4-(4-Naphthalen-1-yl-piperazin-1-yl)-butoxy]-3,4-dihydro-1H-pyrido[2,3-d]pyrimidin-2-one;

7-[4-(4-Indan-4-yl-piperazin-1-yl)-butoxy]-3,4-dihydro-1H-pyrido[2,3-d]pyrimidin-2-one;

7-{4-[4-(5,6,7,8-Tetrahydro-naphthalen-1-yl)-piperazin-1-yl]-butoxy}-3,4-dihydro-1H-pyrido[2,3-d]pyrimidin-2-one;

7-{4-[4-(7-Fluoro-naphthalen-1-yl)-piperazin-1-yl]-butoxy}-3,4-dihydro-1H-pyrido[2,3-d]pyrimidin-2-one;

8-{4-[4-(2-Oxo-1,2,3,4-tetrahydro-pyrido[2,3-d]pyrimidin-7-yloxy)-butyl]-piperazin-1-yl}-naphthalene-2-carbonitrile;

7-{4-[4-(2,3-Dichloro-phenyl)-piperazin-1-yl]-butoxy}-3-methyl-3,4-dihydro-1H-pyrido[2,3-d]pyrimidin-2-one;

3-Methyl-7-[4-(4-naphthalen-1-yl-piperazin-1-yl)-butoxy]-3,4-dihydro-1H-pyrido[2,3-d]pyrimidin-2-one;

7-{5-[4-(2,3-Dichloro-phenyl)-piperazin-1-yl]-pentyl}-4,4-dimethyl-1,4-dihydro-pyrido[2,3-d][1,3]oxazin-2-one;

6-{5-[4-(2,3-Dichloro-phenyl)-piperazin-1-yl]-pentyl}-4H-pyrido[3,2-b][1,4]oxazin-3-one;

6-{5-[4-(5,6,7,8-Tetrahydro-naphthalen-1-yl)-piperazin-1-yl]-pentyl}-4H-pyrido[3,2-b][1,4]oxazin-3-one;

6-{4-[4-(2,3-Dichloro-phenyl)-piperazin-1-yl]-butoxy}-4H-pyrido[3,2-b][1,4]oxazin-3-one;

6-[4-(4-Indan-4-yl-piperazin-1-yl)-butoxy]-4H-pyrido[3,2-b][1,4]oxazin-3-one;

6-[4-(4-Naphthalen-1-yl-piperazin-1-yl)-butoxy]-4H-pyrido[3,2-b][1,4]oxazin-3-one;

6-{4-[4-(6-Methoxy-pyridin-2-yl)-piperazin-1-yl]-butoxy}-4H-pyrido[3,2-b][1,4]oxazin-3-one;

6-{4-[4-(7-Fluoro-naphthalen-1-yl)-piperazin-1-yl]-butoxy}-4H-pyrido[3,2-b][1,4]oxazin-3-one;

6-{4-[4-(5,6,7,8-Tetrahydro-naphthalen-1-yl)-piperazin-1-yl]-butoxy}-4H-pyrido[3,2-b][1,4]oxazin-3-one;

2-{4-[4-(2,3-Dichloro-phenyl)-piperazin-1-yl]-butoxy}-8H-pyrido[2,3-d]pyrimidin-7-one;

2-{4-[4-(2-Isopropoxy-phenyl)-piperazin-1-yl]-butoxy}-8H-pyrido[2,3-d]pyrimidin-7-one;

2-[4-(4-Indan-4-yl-piperazin-1-yl)-butoxy]-8H-pyrido[2,3-d]pyrimidin-7-one;

2-[4-(4-Naphthalen-1-yl-piperazin-1-yl)-butoxy]-8H-pyrido[2,3-d]pyrimidin-7-one;

6-Fluoro-4-methyl-2-[4-(4-naphthalen-1-yl-piperazin-1-yl)-butoxy]-8H-pyrido[2,3-d]pyrimidin-7-one;

2-{4-[4-(6-Isopropyl-pyridin-2-yl)-piperazin-1-yl]-butoxy}-4-methyl-8H-pyrido[2,3-d]pyrimidin-7-one;

2-{4-[4-(6-Ethyl-pyridin-2-yl)-piperazin-1-yl]-butoxy}-4-methyl-8H-pyrido[2,3-d]pyrimidin-7-one;

2-[4-(4-Indan-4-yl-piperazin-1-yl)-butoxy]-4-methyl-8H-pyrido[2,3-d]pyrimidin-7-one;

4-Methyl-2-{4-[4-(5,6,7,8-tetrahydro-naphthalen-1-yl)-piperazin-1-yl]-butoxy}-8H-pyrido[2,3-d]pyrimidin-7-one;

2-{4-[4-(7-Fluoro-naphthalen-1-yl)-piperazin-1-yl]-butoxy}-4-methyl-8H-pyrido[2,3-d]pyrimidin-7-one;

2-{4-[4-(7-Methoxy-naphthalen-1-yl)-piperazin-1-yl]-butoxy}-4-methyl-8H-pyrido[2,3-d]pyrimidin-7-one;

4-Methyl-2-[4-(4-naphthalen-1-yl-piperazin-1-yl)-butoxy]-8H-pyrido[2,3-d]pyrimidin-7-one;

2-{4-[4-(7-Fluoro-naphthalen-1-yl)-piperazin-1-yl]-butoxy}-4,8-dimethyl-8H-pyrido[2,3-d]pyrimidin-7-one;

2-{4-[4-(7-Methoxy-naphthalen-1-yl)-piperazin-1-yl]-butoxy}-4,8-dimethyl-8H-pyrido[2,3-d]pyrimidin-7-one;

7-{5-[4-(2,3-Dichloro-phenyl)-piperazin-1-yl]-pentyl}-3,4-dihydro-1H-[1,6]naphthyridin-2-one;

7-{4-[4-(5,6,7,8-Tetrahydro-naphthalen-1-yl)-piperazin-1-yl]-butoxy}-3,4-dihydro-1H-[1,6]naphthyridin-2-one;

7-[4-(4-Naphthalen-1-yl-piperazin-1-yl)-butoxy]-3,4-dihydro-1H-[1,6]naphthyridin-2-one;

7-{4-[4-(2,3-Dichloro-phenyl)-piperazin-1-yl]-butoxy}-3,4-dihydro-1H-[1,6]naphthyridin-2-one;

7-[4-(4-Indan-4-yl-piperazin-1-yl)-butoxy]-3,4-dihydro-1H-[1,6]naphthyridin-2-one;

7-{4-[4-(7-Fluoro-naphthalen-1-yl)-piperazin-1-yl]-butoxy}-3,4-dihydro-1H-[1,6]naphthyridin-2-one;

8-Bromo-7-[4-(4-naphthalen-1-yl-piperazin-1-yl)-butoxy]-3,4-dihydro-1H-[1,6]naphthyridin-2-one;

8-Bromo-7-{4-[4-(2,3-dichloro-phenyl)-piperazin-1-yl]-butoxy}-3,4-dihydro-1H-[1,6]naphthyridin-2-one;

8-Chloro-7-{4-[4-(2,3-dichloro-phenyl)-piperazin-1-yl]-butoxy}-3,4-dihydro-1H-[1,6]naphthyridin-2-one;

8-Chloro-7-[4-(4-naphthalen-1-yl-piperazin-1-yl)-butoxy]-3,4-dihydro-1H-[1,6]naphthyridin-2-one;

7-[4-(4-Naphthalen-1-yl-piperazin-1-yl)-butoxy]-2-oxo-1,2,3,4-tetrahydro-[1,6]naphthyridine-8-carboxylic acid methyl ester;

8-Methyl-7-[4-(4-naphthalen-1-yl-piperazin-1-yl)-butoxy]-3,4-dihydro-1H-[1,6]naphthyridin-2-one;

7-{4-[4-(2,3-Dichloro-phenyl)-piperazin-1-yl]-butoxy}-1H-[1,6]naphthyridin-2-one;

7-{4-[4-(5,6,7,8-Tetrahydro-naphthalen-1-yl)-piperazin-1-yl]-butoxy}-1H-[1,6]naphthyridin-2-one;

7-[4-(4-Indan-4-yl-piperazin-1-yl)-butoxy]-1H-[1,6]naphthyridin-2-one;

7-[4-(4-Naphthalen-1-yl-piperazin-1-yl)-butoxy]-1H-[1,6]naphthyridin-2-one;

7-{4-[4-(7-Fluoro-naphthalen-1-yl)-piperazin-1-yl]-butoxy}-1H-[1,6]naphthyridin-2-one;

7-{4-[4-(2,3-Dichloro-phenyl)-piperazin-1-yl]-butylamino}-1H-[1,6]naphthyridin-2-one; and 7-{5-[4-(2,3-Dichloro-phenyl)-piperazin-1-yl]-pentyl}-4,4-dimethyl-1,4-dihydro-pyrido[4,3-d][1,3]oxazin-2-one.

This same set of specific embodiments further includes the following compounds and their pharmaceutically acceptable salts:

7-{4-[4-(7-Trifluoromethyl-naphthalen-1-yl)-piperazin-1-yl]-butoxy}-3,4-dihydro-1H-[1,8]naphthyridin-2-one;

7-{4-[4-(7-Trifluoromethyl-naphthalen-1-yl)-piperazin-1-yl]-butoxy}-1H-[1,8]naphthyridin-2-one;

7-(4-{4-[7-(2-Hydroxy-ethoxy)-naphthalen-1-yl]-piperazin-1-yl}-butoxy)-3,4-dihydro-1H-[1,8]naphthyridin-2-one;

7-(4-{4-[7-(2-Methoxy-ethoxy)-naphthalen-1-yl]-piperazin-1-yl}-butoxy)-3,4-dihydro-1H-[1,8]naphthyridin-2-one;

7-(4-{4-[7-(2-Amino-ethoxy)-naphthalen-1-yl]-piperazin-1-yl}-butoxy)-3,4-dihydro-1H-[1,8]naphthyridin-2-one;

7-(4-{4-[7-(2-Dimethylamino-ethoxy)-naphthalen-1-yl]-piperazin-1-yl}-butoxy)-3,4-dihydro-1H-[1,8]naphthyridin-2-one;

7-(4-{4-[7-(2-Hydroxy-ethoxy)-naphthalen-1-yl]-piperazin-1-yl}-butoxy)-1H-[1,8]naphthyridin-2-one;

7-(4-{4-[7-(2-Methoxy-ethoxy)-naphthalen-1-yl]-piperazin-1-yl}-butoxy)-1H-[1,8]naphthyridin-2-one;

7-(4-{4-[7-(2-Amino-ethoxy)-naphthalen-1-yl]-piperazin-1-yl}-butoxy)-1H-[1,8]naphthyridin-2-one;

7-(4-{4-[7-(2-Dimethylamino-ethoxy)-naphthalen-1-yl]-piperazin-1-yl}-butoxy)-1H-[1,8]naphthyridin-2-one;

7-{4-[4-(7-Fluoro-naphthalen-1-yl)-piperidin-1-yl]-butoxy}-3,4-dihydro-1H-[1,8]naphthyridin-2-one;

7-{4-[4-(2-Chloro-3-ethyl-phenyl)-piperazin-1-yl]-butoxy}-1H-[1,8]naphthyridin-2-one;

7-{4-[4-(7,8-Difluoro-naphthalen-1-yl)-piperazin-1-yl]-butoxy}-3,4-dihydro-1H-[1,8]naphthyridin-2-one;

7-{4-[4-(7,8-Difluoro-naphthalen-1-yl)-piperazin-1-yl]-butoxy}-1H-[1,8]naphthyridin-2-one;

7-{4-[4-(6,8-Difluoro-naphthalen-1-yl)-piperazin-1-yl]-butoxy}-3,4-dihydro-1H-[1,8]naphthyridin-2-one;

7-{4-[4-(6,8-Difluoro-naphthalen-1-yl)-piperazin-1-yl]-butoxy}-1H-[1,8]naphthyridin-2-one;

7-{4-[4-(5,7-Difluoro-naphthalen-1-yl)-piperazin-1-yl]-butoxy}-3,4-dihydro-1H-[1,8]naphthyridin-2-one;

7-{4-[4-(5,7-Difluoro-naphthalen-1-yl)-piperazin-1-yl]-butoxy}-1H-[1,8]naphthyridin-2-one;

7-{4-[4-(8-Trifluoromethyl-naphthalen-1-yl)-piperazin-1-yl]-butoxy}-3,4-dihydro-1H-[1,8]naphthyridin-2-one;

7-{4-[4-(8-Trifluoromethyl-naphthalen-1-yl)-piperazin-1-yl]-butoxy}-1H-[1,8]naphthyridin-2-one;

7-{4-[4-(2,2-Dimethyl-indan-4-yl)-piperazin-1-yl]-butoxy}-3,4-dihydro-1H-[1,8]naphthyridin-2-one;

7-{4-[4-(2,2-Dimethyl-indan-4-yl)-piperazin-1-yl]-butoxy}-1H-[1,8]naphthyridin-2-one;

7-{4-[4-(2,2-Difluoro-3-oxo-indan-4-yl)-piperazin-1-yl]-butoxy}-3,4-dihydro-1H-[1,8]naphthyridin-2-one;

7-{4-[4-(2,2-Difluoro-3-oxo-indan-4-yl)-piperazin-1-yl]-butoxy}-1H-[1,8]naphthyridin-2-one;

7-{4-[4-(2,2-Dimethyl-3-oxo-indan-4-yl)-piperazin-1-yl]-butoxy}-3,4-dihydro-1H-[1,8]naphthyridin-2-one;

7-{4-[4-(2,2-Dimethyl-3-oxo-indan-4-yl)-piperazin-1-yl]-butoxy}-1H-[1,8]naphthyridin-2-one;

7-{4-[4-(7-Fluoro-naphthalen-1-yl)-piperazin-1-yl]-butoxy}-5-methyl-3,4-dihydro-1H-[1,8]naphthyridin-2-one;

7-{4-[4-(7-Fluoro-naphthalen-1-yl)-piperazin-1-yl]-butoxy}-5-methyl-1H-[1,8]naphthyridin-2-one;

7-{4-[4-(8-Fluoro-naphthalen-1-yl)-piperazin-1-yl]-butoxy}-5-methyl-3,4-dihydro-1H-[1,8]naphthyridin-2-one;

7-{4-[4-(8-Fluoro-naphthalen-1-yl)-piperazin-1-yl]-butoxy}-5-methyl-1H-[1,8]naphthyridin-2-one;

6-Fluoro-7-{4-[4-(7-fluoro-naphthalen-1-yl)-piperazin-1-yl]-butoxy}-3,4-dihydro-1H-[1,8]naphthyridin-2-one;

6-Fluoro-7-{4-[4-(7-fluoro-naphthalen-1-yl)-piperazin-1-yl]-butoxy}-1H-[1,8]naphthyridin-2-one;

6-Fluoro-7-{4-[4-(8-fluoro-naphthalen-1-yl)-piperazin-1-yl]-butoxy}-3,4-dihydro-1H-[1,8]naphthyridin-2-one;

6-Fluoro-7-{4-[4-(8-Fluoro-naphthalen-1-yl)-piperazin-1-yl]-butoxy}-1H-[1,8]naphthyridin-2-one;

7-{4-[4-(7-Fluoro-naphthalen-1-yl)-piperazin-1-yl]-butoxy}-4,4-dimethyl-3,4-dihydro-1H-[1,8]naphthyridin-2-one;

2-{4-[4-(7-Fluoro-naphthalen-1-yl)-piperazin-1-yl]-butoxy}-8H-pyrido[2,3-d]pyrimidin-7-one;

2-{4-[4-(8-Fluoro-naphthalen-1-yl)-piperazin-1-yl]-butoxy}-8H-pyrido[2,3-d]pyrimidin-7-one;

2-{4-[4-(7-Methoxy-naphthalen-1-yl)-piperazin-1-yl]-butoxy}-8H-pyrido[2,3-d]pyrimidin-7-one;

2-{4-[4-(7-Fluoro-naphthalen-1-yl)-piperazin-1-yl]-butoxy}-5,8-dihydro-6H-pyrido[2,3-d]pyrimidin-7-one;

2-{4-[4-(8-Fluoro-naphthalen-1-yl)-piperazin-1-yl]-butoxy}-5,8-dihydro-6H-pyrido[2,3-d]pyrimidin-7-one;

2-{4-[4-(8-Fluoro-naphthalen-1-yl)-piperazin-1-yl]-butoxy}-4-methyl-8H-pyrido[2,3-d]pyrimidin-7-one;

2-{4-[4-(2,3-Dichloro-phenyl)-piperazin-1-yl]-butoxy}-4-methyl-8H-pyrido[2,3-d]pyrimidin-7-one;

2-{4-[4-(7-Fluoro-naphthalen-1-yl)-piperazin-1-yl]-butoxy}-4-methyl-5,8-dihydro-6H-pyrido[2,3-d]pyrimidin-7-one;

2-{4-[4-(2,3-Dichloro-phenyl)-piperazin-1-yl]-butoxy}-6-fluoro-4-methyl-8H-pyrido[2,3-d]pyrimidin-7-one;

6-Fluoro-2-{4-[4-(7-fluoro-naphthalen-1-yl)-piperazin-1-yl]-butoxy}-4-methyl-8H-pyrido[2,3-d]pyrimidin-7-one;

6-Fluoro-2-{4-[4-(8-fluoro-naphthalen-1-yl)-piperazin-1-yl]-butoxy}-4-methyl-8H-pyrido[2,3-d]pyrimidin-7-one;

4,4-Dimethyl-7-[4-(4-naphthalen-1-yl-piperazin-1-yl)-butoxy]-1,4-dihydro-pyrido[2,3-d][1,3]oxazin-2-one;

6-[4-(4-Naphthalen-1-yl-piperazin-1-yl)-butoxy]-4H-pyrido[2,3-b]pyrazin-3-one;

6-[4-(4-Naphthalen-1-yl-piperazin-1-yl)-butoxy]-1,4-dihydro-2H-pyrido[2,3-b]pyrazin-3-one;

7-{3-[4-(7-Fluoro-naphthalen-1-yl)-piperazin-1-yl]-propoxy}-3,4-dihydro-1H-[1,8]naphthyridin-2-one;

7-{3-[4-(7-Fluoro-naphthalen-1-yl)-piperazin-1-yl]-propoxy}-1H-[1,8]naphthyridin-2-one; and 7-[5-(4-Naphthalen-1-yl-piperazin-1-yl)-pentyloxy]-3,4-dihydro-1H-[1,8]naphthyridin-2-one.

Another set of specific embodiments of the invention relate to compounds of formula 1 and their pharmaceutically acceptable salts, wherein at least one of the carbon atoms of the carbocyclic ring AA that are not shared with the benzo ring of group (ii) has been replaced, independently, by a nitrogen, oxygen, or sulfur atom. These embodiments include the following compounds and their pharmaceutically acceptable salts. Procedures for synthesis of each of these compounds are illustrated in the Examples, below.

7-{4-[4-(2-Oxo-2,3-dihydro-benzooxazol-7-yl)-piperazin-1-yl]-butoxy}-3,4-dihydro-1H-[1,8]naphthyridin-2-one;

7-{4-[4-(2,3-Dihydro-benzofuran-7-yl)-piperazin-1-yl]-butoxy}-3,4-dihydro-1H-[1,8]naphthyridin-2-one;

7-{4-[4-(2,2-Dimethyl-2,3-dihydro-benzofuran-7-yl)-piperazin-1-yl]-butoxy}-3,4-dihydro-1H-[1,8]naphthyridin-2-one;

7-[4-(4-Chroman-8-yl-piperazin-1-yl)-butoxy]-3,4-dihydro-1H-[1,8]naphthyridin-2-one;

7-{4-[4-(2,2-Dimethyl-2H-chromen-8-yl)-piperazin-1-yl]-butoxy}-3,4-dihydro-1H-[1,8]naphthyridin-2-one;

7-{4-[4-(2,2-Dimethyl-chroman-8-yl)-piperazin-1-yl]-butoxy}-3,4-dihydro-1H-[1,8]naphthyridin-2-one;

7-{4-[4-(Spiro[chromene-2,1'-cyclopentan]-8-yl)-piperazin-1-yl]-butoxy}-3,4-dihydro-1H-[1,8]naphthyridin-2-one;

7-{4-[4-(3,4-Dihydrospiro[chromene-2,1'-cyclopentan]-8-yl)-piperazin-1-yl]-butoxy}-3,4-dihydro-1H-[1,8]naphthyridin-2-one;

7-{4-[4-(2-Methyl-2H-chromen-8-yl)-piperazin-1-yl]-butoxy}-3,4-dihydro-1H-[1,8]naphthyridin-2-one;

7-{4-[4-(2-Methyl-chroman-8-yl)-piperazin-1-yl]-butoxy}-3,4-dihydro-1H-[1,8]naphthyridin-2-one;

7-{4-[4-(2,3-Dihydro-benzofuran-4-yl)-piperazin-1-yl]-butoxy}-3,4-dihydro-1H-[1,8]naphthyridin-2-one;

7-{4-[4-(1,3-Dihydro-isobenzofuran-4-yl)-piperazin-1-yl]-butoxy}-3,4-dihydro-1H-[1,8]naphthyridin-2-one;

7-[4-(4-Chroman-5-yl-piperazin-1-yl)-butoxy]-3,4-dihydro-1H-[1,8]naphthyridin-2-one;

7-[4-(4-Isochroman-5-yl-piperazin-1-yl)-butoxy]-3,4-dihydro-1H-[1,8]naphthyridin-2-one;

7-[4-(4-Isochroman-8-yl-piperazin-1-yl)-butoxy]-3,4-dihydro-1H-[1,8]naphthyridin-2-one;

7-{4-[4-(2,3-Dihydro-benzo[1,4]dioxin-5-yl)-piperazin-1-yl]-butoxy}-3,4-dihydro-1H-[1,8]naphthyridin-2-one;

7-{4-[4-(3,4-Dihydro-2H-benzo[b][1,4]dioxepin-6-yl)-piperazin-1-yl]-butoxy}-3,4-dihydro-1H-[1,8]naphthyridin-2-one;

7-{4-[4-(2,2,3,3-Tetrafluoro-2,3-dihydro-benzo[1,4]dioxin-5-yl)-piperazin-1-yl]-butoxy}-3,4-dihydro-1H-[1,8]naphthyridin-2-one;

7-{4-[4-(2,2-Difluoro-benzo[1,3]dioxol-4-yl)-piperazin-1-yl]-butoxy}-3,4-dihydro-1H-[1,8]naphthyridin-2-one;

7-{4-[4-(4-Oxo-chroman-8-yl)-piperazin-1-yl]-butoxy}-3,4-dihydro-1H-[1,8]naphthyridin-2-one;

7-{4-[4-(3,3-Dimethyl-4-oxo-chroman-8-yl)-piperazin-1-yl]-butoxy}-3,4-dihydro-1H-[1,8]naphthyridin-2-one;

7-{4-[4-(3,3-Dimethyl-chroman-8-yl)-piperazin-1-yl]-butoxy}-3,4-dihydro-1H-[1,8]naphthyridin-2-one;

7-[4-(4-Benzofuran-7-yl-piperazin-1-yl)-butoxy]-3,4-dihydro-1H-[1,8]naphthyridin-2-one;

7-{4-[4-(1H-Indol-7-yl)-piperazin-1-yl]-butoxy}-3,4-dihydro-1H-[1,8]naphthyridin-2-one;

7-{4-[4-(1H-Indol-4-yl)-piperazin-1-yl]-butoxy}-3,4-dihydro-1H-[1,8]naphthyridin-2-one;

7-{4-[4-(1-Methyl-1H-indol-4-yl)-piperazin-1-yl]-butoxy}-3,4-dihydro-1H-[1,8]naphthyridin-2-one;
7-[4-(4-Benzo[b]thiophen-4-yl-piperazin-1-yl)-butoxy]-3,4-dihydro-1H-[1,8]naphthyridin-2-one;
7-[4-(4-Benzo[1,2,5]oxadiazol-4-yl-piperazin-1-yl)-butoxy]-3,4-dihydro-1H-[1,8]naphthyridin-2-one;
7-[4-(4-Benzo[1,2,5]thiadiazol-4-yl-piperazin-1-yl)-butoxy]-3,4-dihydro-1H-[1,8]naphthyridin-2-one;
7-{4-[4-(2-Trifluoromethyl-3H-benzoimidazol-4-yl)-piperazin-1-yl]-butoxy}-3,4-dihydro-1H-[1,8]naphthyridin-2-one;
7-{4-[4-(1-Methyl-1,2,3,4-tetrahydro-quinolin-5-yl)-piperazin-1-yl]-butoxy}-3,4-dihydro-1H-[1,8]naphthyridin-2-one;
7-{4-[4-(1-Ethyl-1,2,3,4-tetrahydro-quinolin-5-yl)-piperazin-1-yl]-butoxy}-3,4-dihydro-1H-[1,8]naphthyridin-2-one;
7-[4-(4-Quinolin-8-yl-piperazin-1-yl)-butoxy]-3,4-dihydro-1H-[1,8]naphthyridin-2-one;
7-[4-(4-Quinolin-5-yl-piperazin-1-yl)-butoxy]-3,4-dihydro-1H-[1,8]naphthyridin-2-one;
7-[4-(4-Isoquinolin-8-yl-piperazin-1-yl)-butoxy]-3,4-dihydro-1H-[1,8]naphthyridin-2-one;
7-[4-(4-Isoquinolin-5-yl-piperazin-1-yl)-butoxy]-3,4-dihydro-1H-[1,8]naphthyridin-2-one;
7-{4-[4-(3-Fluoro-quinolin-5-yl)-piperazin-1-yl]-butoxy}-3,4-dihydro-1H-[1,8]naphthyridin-2-one;
7-{4-[4-(3-Fluoro-quinolin-8-yl)-piperazin-1-yl]-butoxy}-3,4-dihydro-1H-[1,8]naphthyridin-2-one;
7-{4-[4-(2-Methyl-quinolin-8-yl)-piperazin-1-yl]-butoxy}-3,4-dihydro-1H-[1,8]naphthyridin-2-one;
7-{4-[4-(2-Methoxy-quinolin-8-yl)-piperazin-1-yl]-butoxy}-3,4-dihydro-1H-[1,8]naphthyridin-2-one;
7-{4-[4-(2-Ethoxy-quinolin-8-yl)-piperazin-1-yl]-butoxy}-3,4-dihydro-1H-[1,8]naphthyridin-2-one;
7-{4-[4-(2-Methoxy-quinolin-5-yl)-piperazin-1-yl]-butoxy}-3,4-dihydro-1H-[1,8]naphthyridin-2-one;
7-[4-(4-Quinoxalin-5-yl-piperazin-1-yl)-butoxy]-3,4-dihydro-1H-[1,8]naphthyridin-2-one;
7-{4-[4-(2-Dimethylamino-quinolin-8-yl)-piperazin-1-yl]-butoxy}-3,4-dihydro-1H-[1,8]naphthyridin-2-one;
7-{4-[4-(2-Methylamino-quinolin-8-yl)-piperazin-1-yl]-butoxy}-3,4-dihydro-1H-[1,8]naphthyridin-2-one;
7-{4-[4-(2-Oxo-1,2-dihydro-quinolin-8-yl)-piperazin-1-yl]-butoxy}-3,4-dihydro-1H-[1,8]naphthyridin-2-one;
7-{4-[4-(2-Oxo-1,2,3,4-tetrahydro-quinolin-8-yl)-piperazin-1-yl]-butoxy}-3,4-dihydro-1H-[1,8]naphthyridin-2-one;
7-{4-[4-(1-Methyl-2-oxo-1,2,3,4-tetrahydro-quinolin-8-yl)-piperazin-1-yl]-butoxy}-3,4-dihydro-1H-[1,8]naphthyridin-2-one;
7-[4-(4-Chroman-8-yl-piperazin-1-yl)-butoxy]-1H-[1,8]naphthyridin-2-one;
7-{4-[4-(2,2-Dimethyl-2H-chromen-8-yl)-piperazin-1-yl]-butoxy}-1H-[1,8]naphthyridin-2-one;
7-{4-[4-(2,2-Dimethyl-chroman-8-yl)-piperazin-1-yl]-butoxy}-1H-[1,8]naphthyridin-2-one;
7-{4-[4-(2-Methyl-2H-chromen-8-yl)-piperazin-1-yl]-butoxy}-1H-[1,8]naphthyridin-2-one;
7-{4-[4-(2-Methyl-chroman-8-yl)-piperazin-1-yl]-butoxy}-1H-[1,8]naphthyridin-2-one;
7-{4-[4-(Spiro[chromene-2,1'-cyclopentan]-8-yl)-piperazin-1-yl]-butoxy}-1H-[1,8]naphthyridin-2-one;
7-{4-[4-(3,4-Dihydrospiro[chromene-2,1'-cyclopentan]-8-yl)-piperazin-1-yl]-butoxy}-1H-[1,8]naphthyridin-2-one;
7-{4-[4-(2,3-Dihydro-benzofuran-7-yl)-piperazin-1-yl]-butoxy}-1H-[1,8]naphthyridin-2-one;
7-{4-[4-(2,2-Dimethyl-2,3-dihydro-benzofuran-7-yl)-piperazin-1-yl]-butoxy}-1H-[1,8]naphthyridin-2-one;
7-[4-(4-Chroman-5-yl-piperazin-1-yl)-butoxy]-1H-[1,8]naphthyridin-2-one;
7-{4-[4-(2,3-Dihydro-benzofuran-4-yl)-piperazin-1-yl]-butoxy}-1H-[1,8]naphthyridin-2-one;
7-{4-[4-(2,3-Dihydro-benzo[1,4]dioxin-5-yl)-piperazin-1-yl]-butoxy}-1H-[1,8]naphthyridin-2-one;
7-{4-[4-(2,2-Difluoro-benzo[1,3]dioxol-4-yl)-piperazin-1-yl]-butoxy}-1H-[1,8]naphthyridin-2-one;
7-{4-[4-(1,3-Dihydro-isobenzofuran-4-yl)-piperazin-1-yl]-butoxy}-1H-[1,8]naphthyridin-2-one;
7-{4-[4-(4-Oxo-chroman-8-yl)-piperazin-1-yl]-butoxy}-1H-[1,8]naphthyridin-2-one;
7-{4-[4-(3,3-Dimethyl-4-oxo-chroman-8-yl)-piperazin-1-yl]-butoxy}-1H-[1,8]naphthyridin-2-one;
7-{4-[4-(3,3-Dimethyl-chroman-8-yl)-piperazin-1-yl]-butoxy}-1H-[1,8]naphthyridin-2-one;
7-[4-(4-Isochroman-5-yl-piperazin-1-yl)-butoxy]-1H-[1,8]naphthyridin-2-one;
7-[4-(4-Isochroman-8-yl-piperazin-1-yl)-butoxy]-1H-[1,8]naphthyridin-2-one;
7-{4-[4-(3,4-Dihydro-2H-benzo[b][1,4]dioxepin-6-yl)-piperazin-1-yl]-butoxy}-1H-[1,8]naphthyridin-2-one;
7-[4-(4-Quinolin-8-yl-piperazin-1-yl)-butoxy]-1H-[1,8]naphthyridin-2-one;
7-[4-(4-Quinolin-5-yl-piperazin-1-yl)-butoxy]-1H-[1,8]naphthyridin-2-one;
7-[4-(4-Quinoxalin-5-yl-piperazin-1-yl)-butoxy]-1H-[1,8]naphthyridin-2-one;
7-{4-[4-(1H-Indol-4-yl)-piperazin-1-yl]-butoxy}-1H-[1,8]naphthyridin-2-one;
7-[4-(4-Benzo[b]thiophen-4-yl-piperazin-1-yl)-butoxy]-1H-[1,8]naphthyridin-2-one;
7-[4-(4-Benzofuran-7-yl-piperazin-1-yl)-butoxy]-1H-[1,8]naphthyridin-2-one;
7-{4-[4-(1-Acetyl-1,2,3,4-tetrahydro-quinolin-5-yl)-piperazin-1-yl]-butoxy}-1H-[1,8]naphthyridin-2-one;
7-{4-[4-(1-Methyl-1,2,3,4-tetrahydro-quinolin-5-yl)-piperazin-1-yl]-butoxy}-1H-[1,8]naphthyridin-2-one;
7-{4-[4-(1-Ethyl-1,2,3,4-tetrahydro-quinolin-5-yl)-piperazin-1-yl]-butoxy}-1H-[1,8]naphthyridin-2-one;
7-{4-[4-(2-Methoxy-quinolin-8-yl)-piperazin-1-yl]-butoxy}-1H-[1,8]naphthyridin-2-one;
7-{4-[4-(2-Ethoxy-quinolin-8-yl)-piperazin-1-yl]-butoxy}-1H-[1,8]naphthyridin-2-one;
7-{4-[4-(2-Dimethylamino-quinolin-8-yl)-piperazin-1-yl]-butoxy}-1H-[1,8]naphthyridin-2-one;
7-{4-[4-(2-Methylamino-quinolin-8-yl)-piperazin-1-yl]-butoxy}-1H-[1,8]naphthyridin-2-one;
7-{4-[4-(3-Fluoro-quinolin-5-yl)-piperazin-1-yl]-butoxy}-1H-[1,8]naphthyridin-2-one;
7-{4-[4-(3-Fluoro-quinolin-8-yl)-piperazin-1-yl]-butoxy}-1H-[1,8]naphthyridin-2-one;
7-{4-[4-(2-Oxo-1,2-dihydro-quinolin-8-yl)-piperazin-1-yl]-butoxy}-1H-[1,8]naphthyridin-2-one;
7-{4-[4-(2-Oxo-1,2,3,4-tetrahydro-quinolin-8-yl)-piperazin-1-yl]-butoxy}-1H-[1,8]naphthyridin-2-one;
7-{4-[4-(1-Methyl-2-oxo-1,2,3,4-tetrahydro-quinolin-8-yl)-piperazin-1-yl]-butoxy}-1H-[1,8]naphthyridin-2-one;
7-[4-(4-Benzo[1,2,5]oxadiazol-4-yl-piperazin-1-yl)-butoxy]-1H-[1,8]naphthyridin-2-one;
7-[4-(4-Benzo[1,2,5]thiadiazol-4-yl-piperazin-1-yl)-butoxy]-1H-[1,8]naphthyridin-2-one;
7-{4-[4-(2-Trifluoromethyl-3H-benzoimidazol-4-yl)-piperazin-1-yl]-butoxy}-1H-[1,8]naphthyridin-2-one;

4,4-Dimethyl-7-[4-(4-quinolin-8-yl-piperazin-1-yl)-butoxy]-3,4-dihydro-1H-[1,8]naphthyridin-2-one;

7-{4-[4-(2,3-Dihydro-benzo[1,4]dioxin-5-yl)-piperazin-1-yl]-butoxy}-4,4-dimethyl-3,4-dihydro-1H-[1,8]naphthyridin-2-one;

4,4-Dimethyl-7-{4-[4-(2-oxo-1,2,3,4-tetrahydro-quinolin-8-yl)-piperazin-1-yl]-butoxy}-3,4-dihydro-1H-[1,8]naphthyridin-2-one;

4,4-Dimethyl-7-{4-[4-(2-oxo-1,2-dihydro-quinolin-8-yl)-piperazin-1-yl]-butoxy}-3,4-dihydro-1H-[1,8]naphthyridin-2-one;

7-[4-(4-Benzofuran-7-yl-piperazin-1-yl)-butoxy]-4,4-dimethyl-3,4-dihydro-1H-[1,8]naphthyridin-2-one;

7-[4-(4-Chroman-8-yl-piperazin-1-yl)-butoxy]-4,4-dimethyl-3,4-dihydro-1H-[1,8]naphthyridin-2-one;

6-Fluoro-7-[4-(4-quinolin-8-yl-piperazin-1-yl)-butoxy]-3,4-dihydro-1H-[1,8]naphthyridin-2-one;

6-Fluoro-7-[4-(4-isoquinolin-5-yl-piperazin-1-yl)-butoxy]-3,4-dihydro-1H-[1,8]naphthyridin-2-one;

7-[4-(4-Chroman-8-yl-piperazin-1-yl)-butoxy]-1H-pyrido[2,3-d]pyrimidin-2-one;

7-[4-(4-Chroman-8-yl-piperazin-1-yl)-butoxy]-3,4-dihydro-1H-pyrido[2,3-d]pyrimidin-2-one;

7-{4-[4-(2,3-Dihydro-benzofuran-7-yl)-piperazin-1-yl]-butoxy}-3,4-dihydro-1H-pyrido[2,3-d]pyrimidin-2-one;

7-{4-[4-(3,4-Dihydro-2H-benzo[b][1,4]dioxepin-6-yl)-piperazin-1-yl]-butoxy}-3,4-dihydro-1H-pyrido[2,3-d]pyrimidin-2-one;

6-{4-[4-(2-Methyl-quinolin-8-yl)-piperazin-1-yl]-butoxy}-4H-pyrido[3,2-b][1,4]oxazin-3-one;

6-[4-(4-Quinolin-8-yl-piperazin-1-yl)-butoxy]-4H-pyrido[3,2-b][1,4]oxazin-3-one;

6-{4-[4-(2-Oxo-1,2,3,4-tetrahydro-quinolin-8-yl)-piperazin-1-yl]-butoxy}-4H-pyrido[3,2-b][1,4]oxazin-3-one;

6-[4-(4-Chroman-8-yl-piperazin-1-yl)-butoxy]-4H-pyrido[3,2-b][1,4]oxazin-3-one;

6-{4-[4-(2,3-Dihydro-benzo[1,4]dioxin-5-yl)-piperazin-1-yl]-butoxy}-4H-pyrido[3,2-b][1,4]oxazin-3-one;

2-{4-[4-(2,3-Dihydro-benzo[1,4]dioxin-5-yl)-piperazin-1-yl]-butoxy}-8H-pyrido[2,3-d]pyrimidin-7-one;

2-[4-(4-Chroman-8-yl-piperazin-1-yl)-butoxy]-8H-pyrido[2,3-d]pyrimidin-7-one;

2-[4-(4-Quinolin-8-yl-piperazin-1-yl)-butoxy]-8H-pyrido[2,3-d]pyrimidin-7-one;

2-{4-[4-(2,3-Dihydro-benzofuran-7-yl)-piperazin-1-yl]-butoxy}-8H-pyrido[2,3-d]pyrimidin-7-one;

2-{4-[4-(3,4-Dihydro-2H-benzo[b][1,4]dioxepin-6-yl)-piperazin-1-yl]-butoxy}-8H-pyrido[2,3-d]pyrimidin-7-one;

2-{4-[4-(2,2-Dimethyl-chroman-8-yl)-piperazin-1-yl]-butoxy}-8H-pyrido[2,3-d]pyrimidin-7-one;

2-{4-[4-(2,2-Difluoro-benzo[1,3]dioxol-4-yl)-piperazin-1-yl]-butoxy}-8H-pyrido[2,3-d]pyrimidin-7-one;

2-{4-[4-(2,2-Dimethyl-2,3-dihydro-benzofuran-7-yl)-piperazin-1-yl]-butoxy}-8H-pyrido[2,3-d]pyrimidin-7-one;

2-{4-[4-(2-Methyl-quinolin-8-yl)-piperazin-1-yl]-butoxy}-8H-pyrido[2,3-d]pyrimidin-7-one;

2-{4-[4-(2,3-Dihydro-benzo[1,4]dioxin-5-yl)-piperazin-1-yl]-butoxy}-4-methyl-8H-pyrido[2,3-d]pyrimidin-7-one;

2-{4-[4-(2,3-Dihydro-benzofuran-7-yl)-piperazin-1-yl]-butoxy}-4-methyl-8H-pyrido[2,3-d]pyrimidin-7-one;

2-[4-(4-Benzofuran-7-yl-piperazin-1-yl)-butoxy]-4-methyl-8H-pyrido[2,3-d]pyrimidin-7-one;

2-[4-(4-Chroman-8-yl-piperazin-1-yl)-butoxy]-4-methyl-8H-pyrido[2,3-d]pyrimidin-7-one;

4-Methyl-2-{4-[4-(2-oxo-1,2,3,4-tetrahydro-quinolin-8-yl)-piperazin-1-yl]-butoxy}-8H-pyrido[2,3-d]pyrimidin-7-one;

4-Methyl-2-[4-(4-quinolin-8-yl-piperazin-1-yl)-butoxy]-8H-pyrido[2,3-d]pyrimidin-7-one;

7-[4-(4-Chroman-8-yl-piperazin-1-yl)-butoxy]-3,4-dihydro-1H-[1,6]naphthyridin-2-one;

7-{4-[4-(2,3-Dihydro-benzofuran-7-yl)-piperazin-1-yl]-butoxy}-3,4-dihydro-1H-[1,6]naphthyridin-2-one;

7-{4-[4-(2,2,3,3-Tetrafluoro-2,3-dihydro-benzo[1,4]dioxin-5-yl)-piperazin-1-yl]-butoxy}-3,4-dihydro-1H-[1,6]naphthyridin-2-one;

7-{4-[4-(2,2-Difluoro-benzo[1,3]dioxol-4-yl)-piperazin-1-yl]-butoxy}-3,4-dihydro-1H-[1,6]naphthyridin-2-one;

7-{4-[4-(2,3-Dihydro-benzo[1,4]dioxin-5-yl)-piperazin-1-yl]-butoxy}-3,4-dihydro-1H-[1,6]naphthyridin-2-one;

7-{4-[4-(2,3-Dihydro-benzofuran-7-yl)-piperazin-1-yl]-butoxy}-1H-[1,6]naphthyridin-2-one;

7-{4-[4-(2,3-Dihydro-benzo[1,4]dioxin-5-yl)-piperazin-1-yl]-butoxy}-1H-[1,6]naphthyridin-2-one;

7-[4-(4-Chroman-8-yl-piperazin-1-yl)-butoxy]-1H-[1,6]naphthyridin-2-one; and

7-{4-[4-(2,2-Difluoro-benzo[1,3]dioxol-4-yl)-piperazin-1-yl]-butoxy}-1H-[1,6]naphthyridin-2-one.

This same set of specific embodiments further includes the following compounds and their pharmaceutically acceptable salts:

7-(4-{4-[2-(2-Hydroxy-ethoxy)-quinolin-8-yl]-piperazin-1-yl}-butoxy)-3,4-dihydro-1H-[1,8]naphthyridin-2-one;

7-(4-{4-[2-(2-Methoxy-ethoxy)-quinolin-8-yl]-piperazin-1-yl}-butoxy)-3,4-dihydro-1H-[1,8]naphthyridin-2-one;

7-(4-{4-[2-(2-Amino-ethoxy)-quinolin-8-yl]-piperazin-1-yl}-butoxy)-3,4-dihydro-1H-[1,8]naphthyridin-2-one;

7-(4-{4-[2-(2-Dimethylamino-ethoxy)-quinolin-8-yl]-piperazin-1-yl}-butoxy)-3,4-dihydro-1H-[1,8]naphthyridin-2-one;

7-(4-{4-[2-(2-Hydroxy-ethoxy)-quinolin-8-yl]-piperazin-1-yl}-butoxy)-1H-[1,8]naphthyridin-2-one;

7-(4-{4-[2-(2-Methoxy-ethoxy)-quinolin-8-yl]-piperazin-1-yl}-butoxy)-1H-[1,8]naphthyridin-2-one;

7-(4-{4-[2-(2-Amino-ethoxy)-quinolin-8-yl]-piperazin-1-yl}-butoxy)-1H-[1,8]naphthyridin-2-one;

7-(4-{4-[2-(2-Dimethylamino-ethoxy)-quinolin-8-yl]-piperazin-1-yl}-butoxy)-1H-[1,8]naphthyridin-2-one;

7-{4-[4-(2-Hydroxymethyl-chroman-8-yl)-piperazin-1-yl]-butoxy}-3,4-dihydro-1H-[1,8]naphthyridin-2-one;

7-{4-[4-(2-Aminomethyl-chroman-8-yl)-piperazin-1-yl]-butoxy}-3,4-dihydro-1H-[1,8]naphthyridin-2-one;

7-{4-[4-(3-Hydroxy-2,2-dimethyl-chroman-8-yl)-piperazin-1-yl]-butoxy}-3,4-dihydro-1H-[1,8]naphthyridin-2-one;

7-{4-[4-(2,2-Dimethyl-3-oxo-chroman-8-yl)-piperazin-1-yl]-butoxy}-3,4-dihydro-1H-[1,8]naphthyridin-2-one;

7-{4-[4-(2-Hydroxymethyl-chroman-8-yl)-piperazin-1-yl]-butoxy}-1H-[1,8]naphthyridin-2-one;

7-{4-[4-(2-Aminomethyl-chroman-8-yl)-piperazin-1-yl]-butoxy}-1H-[1,8]naphthyridin-2-one;

7-{4-[4-(3-Hydroxy-2,2-dimethyl-chroman-8-yl)-piperazin-1-yl]-butoxy}-1H-[1,8]naphthyridin-2-one;

7-{4-[4-(2,2-Dimethyl-3-oxo-chroman-8-yl)-piperazin-1-yl]-butoxy}-1H-[1,8]naphthyridin-2-one;

7-{4-[4-(3-Methyl-chroman-5-yl)-piperazin-1-yl]-butoxy}-3,4-dihydro-1H-[1,8]naphthyridin-2-one;

7-{4-[4-(3-Hydroxymethyl-chroman-5-yl)-piperazin-1-yl]-butoxy}-3,4-dihydro-1H-[1,8]naphthyridin-2-one;

7-{4-[4-(3-Aminomethyl-chroman-5-yl)-piperazin-1-yl]-butoxy}-3,4-dihydro-1H-[1,8]naphthyridin-2-one;

5-{4-[4-(7-Oxo-5,6,7,8-tetrahydro-[1,8]naphthyridin-2-yloxy)-butyl]-piperazin-1-yl}-chroman-3-carbonitrile;

7-{4-[4-(3,3-Dimethyl-4-oxo-chroman-5-yl)-piperazin-1-yl]-butoxy}-3,4-dihydro-1H-[1,8]naphthyridin-2-one;
7-{4-[4-(3,3-Dimethyl-chroman-5-yl)-piperazin-1-yl]-butoxy}-3,4-dihydro-1H-[1,8]naphthyridin-2-one;
7-{4-[4-(4-Methyl-chroman-5-yl)-piperazin-1-yl]-butoxy}-3,4-dihydro-1H-[1,8]naphthyridin-2-one;
7-{4-[4-(3-Methyl-chroman-5-yl)-piperazin-1-yl]-butoxy}-1H-[1,8]naphthyridin-2-one;
7-{4-[4-(3-Hydroxymethyl-chroman-5-yl)-piperazin-1-yl]-butoxy}-1H-[1,8]naphthyridin-2-one;
7-{4-[4-(3-Aminomethyl-chroman-5-yl)-piperazin-1-yl]-butoxy}-1H-[1,8]naphthyridin-2-one;
5-{4-[4-(7-Oxo-7,8-dihydro-[1,8]naphthyridin-2-yloxy)-butyl]-piperazin-1-yl}-chroman-3-carbonitrile;
7-{4-[4-(3,3-Dimethyl-4-oxo-chroman-5-yl)-piperazin-1-yl]-butoxy}-1H-[1,8]naphthyridin-2-one;
7-{4-[4-(3,3-Dimethyl-chroman-5-yl)-piperazin-1-yl]-butoxy}-1H-[1,8]naphthyridin-2-one;
7-{4-[4-(4-Methyl-chroman-5-yl)-piperazin-1-yl]-butoxy}-1H-[1,8]naphthyridin-2-one;
7-[3-(4-Chroman-8-yl-piperazin-1-yl)-propoxy]-3,4-dihydro-1H-[1,8]naphthyridin-2-one;
7-[3-(4-Chroman-8-yl-piperazin-1-yl)-propoxy]-1H-[1,8]naphthyridin-2-one;
7-{4-[4-(1,2,3,4-Tetrahydro-isoquinolin-8-yl)-piperazin-1-yl]-butoxy}-3,4-dihydro-1H-[1,8]naphthyridin-2-one;
7-{4-[4-(1,2,3,4-Tetrahydro-isoquinolin-8-yl)-piperazin-1-yl]-butoxy}-1H-[1,8]naphthyridin-2-one;
7-{4-[4-(1,2,3,4-Tetrahydro-isoquinolin-5-yl)-piperazin-1-yl]-butoxy}-3,4-dihydro-1H-[1,8]naphthyridin-2-one;
7-{4-[4-(1,2,3,4-Tetrahydro-isoquinolin-5-yl)-piperazin-1-yl]-butoxy}-1H-[1,8]naphthyridin-2-one;
7-{4-[4-(2-Ethyl-2,3-dihydro-1H-isoindol-4-yl)-piperazin-1-yl]-butoxy}-3,4-dihydro-1H-[1,8]naphthyridin-2-one;
8-{4-[4-(7-Oxo-5,6,7,8-tetrahydro-[1,8]naphthyridin-2-yloxy)-butyl]-piperazin-1-yl}-quinoline-2-carbonitrile;
8-{4-[4-(7-Oxo-7,8-dihydro-[1,8]naphthyridin-2-yloxy)-butyl]-piperazin-1-yl}-quinoline-2-carbonitrile;
7-{4-[4-(3-Methoxy-isoquinolin-5-yl)-piperazin-1-yl]-butoxy}-3,4-dihydro-1H-[1,8]naphthyridin-2-one;
7-{4-[4-(3-Methoxy-isoquinolin-5-yl)-piperazin-1-yl]-butoxy}-1H-[1,8]naphthyridin-2-one;
5-{4-[4-(7-Oxo-5,6,7,8-tetrahydro-[1,8]naphthyridin-2-yloxy)-butyl]-piperazin-1-yl}-quinoline-3-carbonitrile;
5-{4-[4-(7-Oxo-7,8-dihydro-[1,8]naphthyridin-2-yloxy)-butyl]-piperazin-1-yl}-quinoline-3-carbonitrile;
7-{4-[4-(3-Chloro-quinolin-5-yl)-piperazin-1-yl]-butoxy}-3,4-dihydro-1H-[1,8]naphthyridin-2-one; and
7-{4-[4-(3-Chloro-quinolin-5-yl)-piperazin-1-yl]-butoxy}-1H-[1,8]naphthyridin-2-one.

The following compounds and their pharmaceutically acceptable salts are preferred embodiments of the compound of formula 1:
7-[4-(4-Naphthalen-1-yl-piperazin-1-yl)-butoxy]-3,4-dihydro-1H-[1,8]naphthyridin-2-one;
7-[4-(4-Naphthalen-1-yl-piperazin-1-yl)-butoxy]-1H-[1,8]naphthyridin-2-one;
7-{4-[4-(7-Fluoro-naphthalen-1-yl)-piperazin-1-yl]-butoxy}-3,4-dihydro-1H-[1,8]naphthyridin-2-one;
7-{4-[4-(7-Fluoro-naphthalen-1-yl)-piperazin-1-yl]-butoxy}-1H-[1,8]naphthyridin-2-one;
7-{4-[4-(8-Fluoro-naphthalen-1-yl)-piperazin-1-yl]-butoxy}-3,4-dihydro-1H-[1,8]naphthyridin-2-one;
7-{4-[4-(8-Fluoro-naphthalen-1-yl)-piperazin-1-yl]-butoxy}-1H-[1,8]naphthyridin-2-one;
7-{4-[4-(2-Methoxy-quinolin-8-yl)-piperazin-1-yl]-butoxy}-3,4-dihydro-1H-[1,8]naphthyridin-2-one;
7-{4-[4-(2-Methoxy-quinolin-8-yl)-piperazin-1-yl]-butoxy}-1H-[1,8]naphthyridin-2-one;
2-{4-[4-(7-Fluoro-naphthalen-1-yl)-piperazin-1-yl]-butoxy}-4-methyl-8H-pyrido[2,3-d]pyrimidin-7-one;
7-{4-[4-(2,3-Dichloro-phenyl)-piperazin-1-yl]-butoxy}-3,4-dihydro-1H-[1,8]naphthyridin-2-one;
7-{4-[4-(2,3-Dichloro-phenyl)-piperazin-1-yl]-butoxy}-1H-[1,8]naphthyridin-2-one;
7-{4-[4-(5,6,7,8-Tetrahydro-naphthalen-1-yl)-piperazin-1-yl]-butoxy}-3,4-dihydro-1H-[1,8]naphthyridin-2-one;
7-[4-(4-Indan-4-yl-piperazin-1-yl)-butoxy]-3,4-dihydro-1H-[1,8]naphthyridin-2-one;
7-{4-[4-(6,7-Difluoro-naphthalen-1-yl)-piperazin-1-yl]-butoxy}-3,4-dihydro-1H-[1,8]naphthyridin-2-one;
7-{4-[4-(6,7-Difluoro-naphthalen-1-yl)-piperazin-1-yl]-butoxy}-1H-[1,8]naphthyridin-2-one;
4-Methyl-7-[4-(4-naphthalen-1-yl-piperazin-1-yl)-butoxy]-1H-[1,8]naphthyridin-2-one;
4,4-Dimethyl-7-[4-(4-naphthalen-1-yl-piperazin-1-yl)-butoxy]-3,4-dihydro-1H-[1,8]naphthyridin-2-one;
5-Methyl-7-[4-(4-naphthalen-1-yl-piperazin-1-yl)-butoxy]-3,4-dihydro-1H-[1,8]naphthyridin-2-one;
7-{4-[4-(2,3-Dichloro-phenyl)-piperazin-1-yl]-butoxy}-5-methyl-3,4-dihydro-1H-[1,8]naphthyridin-2-one;
6-Fluoro-7-[4-(4-naphthalen-1-yl-piperazin-1-yl)-butoxy]-3,4-dihydro-1H-[1,8]naphthyridin-2-one;
7-[4-(4-Benzo[b]thiophen-4-yl-piperazin-1-yl)-butoxy]-3,4-dihydro-1H-[1,8]naphthyridin-2-one;
7-[4-(4-Benzo[1,2,5]thiadiazol-4-yl-piperazin-1-yl)-butoxy]-3,4-dihydro-1H-[1,8]naphthyridin-2-one;
7-[4-(4-Benzo[1,2,5]thiadiazol-4-yl-piperazin-1-yl)-butoxy]-1H-[1,8]naphthyridin-2-one;
7-[4-(4-Naphthalen-1-yl-piperazin-1-yl)-butoxy]-3,4-dihydro-1H-pyrido[2,3-d]pyrimidin-2-one;
3-Methyl-7-[4-(4-naphthalen-1-yl-piperazin-1-yl)-butoxy]-3,4-dihydro-1H-pyrido[2,3-d]pyrimidin-2-one;
7-{4-[4-(7-Fluoro-naphthalen-1-yl)-piperazin-1-yl]-butoxy}-3,4-dihydro-1H-pyrido[2,3-d]pyrimidin-2-one;
7-{4-[4-(7-Fluoro-naphthalen-1-yl)-piperazin-1-yl]-butoxy}-3,4-dihydro-1H-[1,6]naphthyridin-2-one;
2-{4-[4-(7-Fluoro-naphthalen-1-yl)-piperazin-1-yl]-butoxy}-8H-pyrido[2,3-d]pyrimidin-7-one; and
6-{4-[4-(7-Fluoro-naphthalen-1-yl)-piperazin-1-yl]-butoxy}-4H-pyrido[3,2-b][1,4]oxazin-3-one The following compounds and their pharmaceutically acceptable salts are particularly preferred embodiments of the compound of formula 1:
7-[4-(4-Naphthalen-1-yl-piperazin-1-yl)-butoxy]-3,4-dihydro-1H-[1,8]naphthyridin-2-one;
7-[4-(4-Naphthalen-1-yl-piperazin-1-yl)-butoxy]-1H-[1,8]naphthyridin-2-one;
7-{4-[4-(7-Fluoro-naphthalen-1-yl)-piperazin-1-yl]-butoxy}-3,4-dihydro-1H-[1,8]naphthyridin-2-one;
7-{4-[4-(7-Fluoro-naphthalen-1-yl)-piperazin-1-yl]-butoxy}-1H-[1,8]naphthyridin-2-one;
7-{4-[4-(8-Fluoro-naphthalen-1-yl)-piperazin-1-yl]-butoxy}-3,4-dihydro-1H-[1,8]naphthyridin-2-one;
7-{4-[4-(8-Fluoro-naphthalen-1-yl)-piperazin-1-yl]-butoxy}-1H-[1,8]naphthyridin-2-one;
7-{4-[4-(2-Methoxy-quinolin-8-yl)-piperazin-1-yl]-butoxy}-3,4-dihydro-1H-[1,8]naphthyridin-2-one;
7-{4-[4-(2-Methoxy-quinolin-8-yl)-piperazin-1-yl]-butoxy}-1H-[1,8]naphthyridin-2-one; and
2-{4-[4-(7-Fluoro-naphthalen-1-yl)-piperazin-1-yl]-butoxy}-4-methyl-8H-pyrido[2,3-d]pyrimidin-7-one.

Compounds of the formula 1 may contain chiral centers and therefore may exist in different enantiomeric and diastereomeric forms. This invention relates to all optical isomers and all stereoisomers of compounds of the formula 1, both as racemic mixtures and as individual enantiomers and diastereoisomers of such compounds, and mixtures thereof, and to all pharmaceutical compositions and methods of treatment defined above that contain or employ them, respectively. Individual isomers can be obtained by known methods, such as optical resolution, fractional crystallization, optically selective reaction, or chromatographic separation in the preparation of the final product or its intermediate. Individual enantiomers of the compounds of formula 1 may have advantages, as compared with the racemic mixtures of these compounds, in the treatment of various disorders or conditions.

In so far as the compounds of formula 1 are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The present invention also includes isotopically labeled compounds, which are identical to those of formula 1, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula 1 and prodrugs thereof can generally be prepared by carrying out the procedures disclosed in the Schemes and/or in the Examples below, by substituting a readily available isotopically labeled reagent for a non-isotopically labeled reagent.

In one specific embodiment of the method of the present invention of treating a disorder or condition, the disorder or condition that is being treated is selected from major depression, single episode depression, recurrent depression, child abuse induced depression, postpartum depression, dysthymia, cyclothymia and bipolar disorder.

Another more specific embodiment of this invention relates to the above method wherein the disorder or condition that is being treated is selected from schizophrenia, schizoaffective disorder, delusional disorder, substance-induced psychotic disorder, brief psychotic disorder, shared psychotic disorder, psychotic disorder due to a general medical condition, and schizophreniform disorder.

Another more specific embodiment of this invention relates to the above method wherein the disorder or condition that is being treated is selected from autism, pervasive development disorder, speech impediments such as stuttering, and attention deficit hyperactivity disorder.

Another more specific embodiment of this invention relates to the above method wherein the disorder or condition that is being treated is selected from generalized anxiety disorder, panic disorder, obsessive-compulsive disorder, post-traumatic stress disorder, and phobias, including social phobia, agoraphobia, and specific phobias.

Another more specific embodiment of this invention relates to the above method wherein the disorder or condition that is being treated is selected from movement disorders such as akinesias, dyskinesias, including familial paroxysmal dyskinesias, spasticities, Tourette's syndrome, Scott syndrome, PALSYS and akinetic-rigid syndrome; and extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor.

Another more specific embodiment of this invention relates to the above method wherein the disorder or condition that is being treated is selected from delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple etiologies.

Another more specific embodiment of this invention relates to the above method wherein the compound of formula 1 is administered to a human for the treatment of any two or more comorbid disorders or conditions selected from those disorders and conditions referred to in any of the above methods.

For the treatment of depression, anxiety, schizophrenia or any of the other disorders and conditions referred to above in the descriptions of the methods and pharmaceutical compositions of this invention, the novel compounds of this invention can be used in conjunction with one or more other antidepressants or anti-anxiety agents. Examples of classes of antidepressants that can be used in combination with the active compounds of this invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Suitable tertiary amine tricyclics and secondary amine tricyclics include amitriptyline, clomipramine, doxepin, imipramine, trimipramine, dothiepin, butripyline, iprindole, lofepramine, nortriptyline, protriptyline, amoxapine, desipramine and maprotiline. Suitable selective serotonin reuptake inhibitors include fluoxetine, fluvoxamine, paroxetine and sertraline. Examples of monoamine oxidase inhibitors include isocarboxazid, pheneizine, and tranylcyclopramine. Suitable reversible inhibitors of monoamine oxidase include moclobemide. Suitable serotonin and noradrenaline reuptake inhibitors of use in the present invention include venlafaxine. Suitable CRF antagonists include those compounds described in International Patent Application Nos. WO 94/13643, WO 94/13644, WO 94/13661, WO 94/13676 and WO 94/13677. Suitable atypical anti-depressants include bupropion, lithium, nefazodone, trazodone and viloxazine. Suitable NK-1 receptor antagonists include those referred to in World Patent Publication WO 01/77100.

Suitable classes of anti-anxiety agents that can be used in combination with the active compounds of this invention include benzodiazepines and serotonin 1A (5-$HT_{1A}$) agonists or antagonists, especially 5-$HT_{1A}$ partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-$HT_{1A}$ receptor agonists or antagonists include buspirone, flesinoxan, gepirone and ipsapirone.

This invention also relates to a method of treating a disorder or condition selected from single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; attention deficit hyperactivity disorder (ADHD); behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal in need of such treatment, including a human, comprising administering to said mammal:

(a) a compound of the formula 1, or a pharmaceutically acceptable salt thereof; and (b) another pharmaceutically active compound that is an antidepressant or anti-anxiety agent, or a pharmaceutically acceptable salt thereof;

wherein the active compounds "a" and "b" are present in amounts that render the combination effective in treating such disorder or condition.

A more specific embodiment of this invention relates to the above method wherein the disorder or condition that is being treated is selected from major depression, single episode depression, recurrent depression, child abuse induced depression, postpartum depression, dysthymia, cyclothymia and bipolar disorder.

Another more specific embodiment of this invention relates to the above method wherein the disorder or condition that is being treated is selected from schizophrenia, schizoaffective disorder, delusional disorder, substance-induced psychotic disorder, brief psychotic disorder, shared psychotic disorder, psychotic disorder due to a general medical condition, and schizophreniform disorder.

Another more specific embodiment of this invention relates to the above method wherein the disorder or condition that is being treated is selected from autism, pervasive development disorder, and attention deficit hyperactivity disorder (ADHD).

Another more specific embodiment of this invention relates to the above method wherein the disorder or condition that is being treated is selected from generalized anxiety disorder, panic disorder, obsessive-compulsive disorder, post-traumatic stress disorder, and phobias, including social phobia, agoraphobia, and specific phobias.

Another more specific embodiment of this invention relates to the above method wherein the disorder or condition that is being treated is selected from movement disorders such as akinesias, dyskinesias, including familial paroxysmal dyskinesias, spasticities, Tourette's syndrome, Scott syndrome, PALSYS and akinetic-rigid syndrome; and extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor.

Another more specific embodiment of this invention relates to the above method wherein the disorder or condition that is being treated is selected from delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies.

Another more specific embodiment of this invention relates to the above method wherein the compound of formula 1 and the additional antidepressant or anti-anxiety agent are administered to a human for the treatment of any two or more comorbid disorders or conditions selected from those disorders and conditions referred to in any of the above methods.

This invention also relates to a pharmaceutical composition for treating a disorder or condition selected from single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; attention deficit hyperactivity disorder (ADHD); behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy in a mammal in need of such treatment, including a human, comprising:

(a) a compound of the formula 1, or a pharmaceutically acceptable salt thereof;

(b) another pharmaceutically active compound that is an antidepressant or anti-anxiety agent, or a pharmaceutically acceptable salt thereof; and (c) a pharmaceutically acceptable carrier;

wherein the active compounds "a" and "b" are present in amounts that render the composition effective in treating such disorder or condition.

The active compounds of this invention may be prepared as described below. Unless otherwise indicated, in the reaction schemes and discussion that follow, A, Z, D, W, Q, ring AA, G, X, Y, $R^1$ through $R^{14}$, formula 1, the dotted line connecting X and Y, and groups of the formulas (i) and (ii) are defined as above.

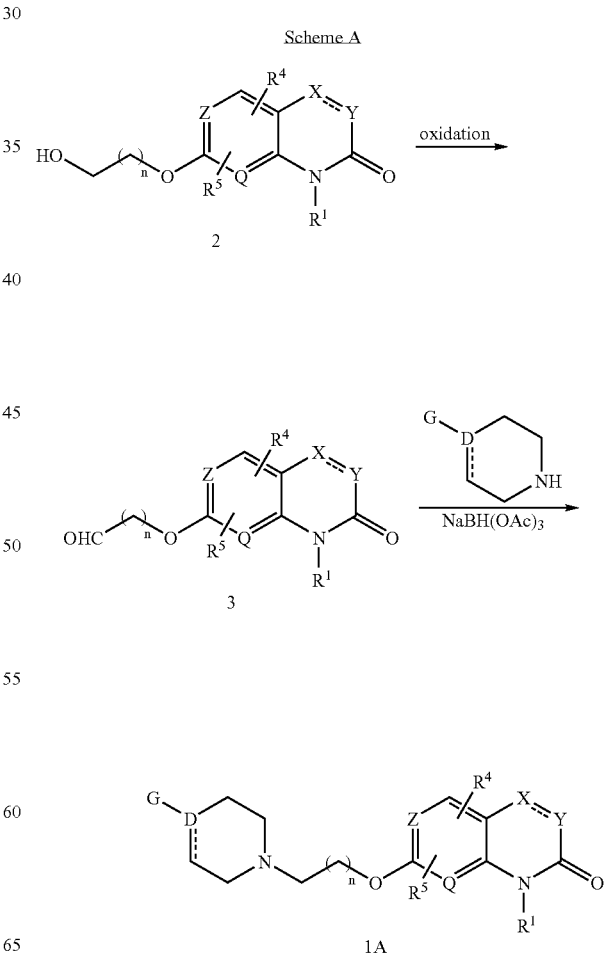

Scheme A illustrates a method for preparing compounds of the formula 1 wherein A is —(CH$_2$)$_m$O—, optionally substituted as indicated in the definition of formula 1 above (also referred to as compounds of the formula 1A). This method involves oxidation of a compound of the formula 2 with Dess-Martin Periodinane or another suitable oxidizing agent such as IBX (o-iodoxybenzoic acid), oxalyl chloride in dimethyl sulfoxide (DMSO) (Swern oxidation) or PCC (pyridinium chlorochromate) to form the corresponding aldehyde of formula 3. This reaction may be carried out in dichloromethane (CH$_2$Cl$_2$), tetrahydrofuran (THF), dimethyl sulfoxide (DMSO) or a combination of two or more of these solvents. Reductive amination of a G-substituted piperidine or piperizine, as shown in Scheme A, using methods well known to those of skill in the art, with a compound of formula 3 yields the corresponding compound of formula 1A. The reductive amination can be performed, for example, utilizing catalytic hydrogenation methods or using a hydride reducing agent such as sodium triacetoxyborohydride or sodium cyanoborohydride. The reaction solvent can be 1,2-dichloroethane, tetrahydrofuran, acetonitrile, dimethylformamide or a combination of two or more of these solvents, with the optional addition of 1–10 equivalents of acetic acid. When the piperazine or piperidine hydrochloride or hydrobromide salt is used, a base such as triethylamine is typically added.

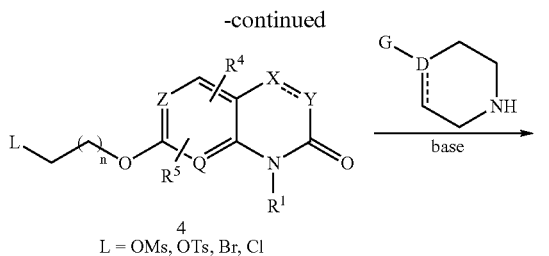

L = OMs, OTs, Br, Cl

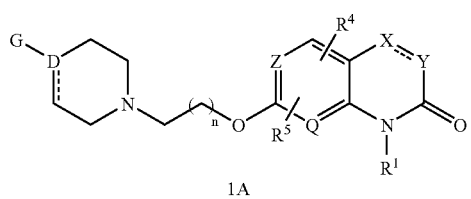

1A

Alternatively, compounds of the formula 1A can be prepared according to Scheme B. The hydroxy group of the compound of formula 2 is converted into a leaving group (L) using conventional methods to provide the corresponding compound of formula 4 wherein L is mesylate (OMs), tosylate (OTs) or a halogen such as bromide, iodide or chloride. L is preferably chlorine. The resulting compound of formula 4 is then reacted with a G-substituted piperazine or piperidine, as depicted in Scheme B, to yield the desired compound of formula 1A. This reaction is preferably run in the presence of a base such as potassium carbonate, sodium carbonate, cesium carbonate, triethylamine or diisopropylethylamine. The solvent used may be acetonitrile, water, tetrahydrofuran, dioxane, acetone, methyl isobutyl ketone, benzene or toluene, or a combination of two or more of these solvents. Inorganic salts such as sodium or potassium iodide may be employed as catalysts in the reaction. The temperature of the reaction may vary from about ambient temperature to about the reflux temperature of the solvent used. The reaction may also be conducted under microwave irradiation.

Scheme B

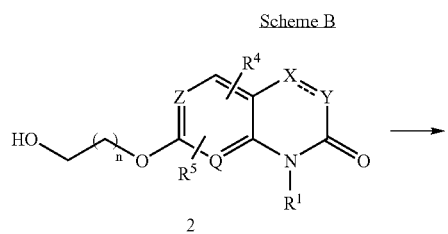

2

Scheme C

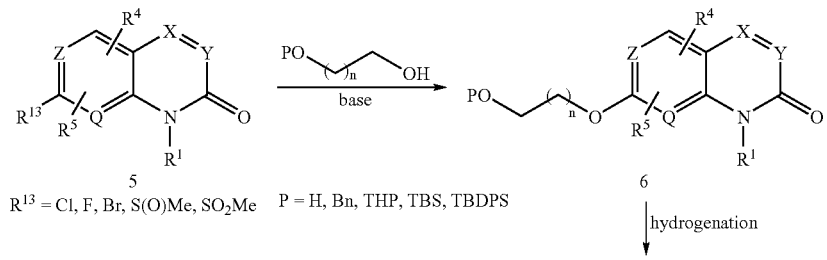

R$^{13}$ = Cl, F, Br, S(O)Me, SO$_2$Me    P = H, Bn, THP, TBS, TBDPS

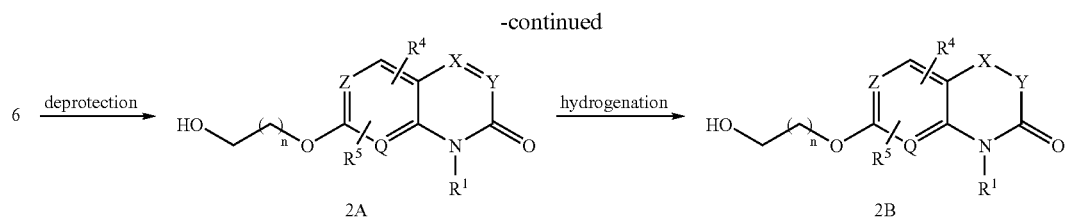

Scheme C illustrates a method for preparing compounds of the formula 2A (wherein X is double bonded to Y) and 2B (wherein X is single bonded to Y). Addition of 2 to 20 equivalents of a diol of the formula $HOCH_2(CH_2)_nOH$, wherein n is an integer from 1 to 4, or 1 to 4 equivalents of a suitably mono-protected diol of the formula $POCH_2(CH_2)_nOH$, wherein n is an integer between 1 and 4 and P is tetrahydropyranyl (THP), benzyl (Bn), p-methoxybenzyl, tert-butyldimethylsilyl (TBS), or tert-butyldiphenylsilyl (TBDPS), to a compound of the formula 5, wherein $R^{13}$ is chloro, fluoro, bromo, $S(O)CH_3$ or $SO_2CH_3$, provides the corresponding compound of formula 6 (or 2A when the unprotected diol reactant is used). $R^{13}$ is most preferably fluoro. This reaction is conducted in the presence of a base such as potassium tert-butoxide, sodium tert-butoxide, sodium hydride, potassium hydride, lithium diisopropylamide, lithium bis(trimethylsilyl)amide, potassium bis(trimethylsilyl)amide, or sodium bis(trimethylsilyl)amide. Suitable solvents for this reaction include tetrahydrofuran (THF), dioxane, ethylene glycol dimethylether, dimethylformamide (DMF), N-methylpyrrolidinone (NMP), or dimethylsulfoxide (DMSO), or a combination of two or more of these solvents. The temperature of the reaction may vary from about ambient temperature to about the reflux temperature of the solvent used.

The reaction of the compound of formula 5 with the 2 to 20 equivalents of the diol of the formula $HOCH_2(CH_2)_nOH$, wherein n is an integer from 1 to 4, or the 1 to 4 equivalents of the mono-protected diol of the formula $POCH_2(CH_2)_nOH$ to yield the compound of formula 6, as described above, is preferably conducted in the presence of a catalytic amount of a phase transfer catalyst, such as tetrabutyl ammonium chloride or bromide. The use of a phase transfer catalyst accelerates the rate of the coupling, and allows one to carry out the reaction at a lower temperature than would be possible without the catalyst. Use of the phase transfer catalyst also significantly reduces the formation of dimeric by-products.

Compounds of the formula 6 where, P is tetrahydropyranyl (THP), can be deprotected using conventional methods such as treatment with PPTS (pyridinium p-toluenesulfonate) or p-toluenesulfonic acid in ethanol to give the corresponding compounds of formula 2A. Compounds of the formula 6 wherein P is tert-butyldimethysilyl or tert-butyldiphenylsilyl can be deprotected using conventional methods such as treatment with tetrabutylammonium fluoride in tetrahydrofuran to yield compounds of the formula 2A.

Compounds of the formula 2A or compounds of the formula 6 wherein P is H or benzyl can be reduced using catalytic hydrogenation methods to provide the corresponding compounds of formula 2B. For example, the hydrogenation can be conducted using 5 to 20% palladium on activated carbon in a solvent such as methanol, ethanol, tetrahydrofuran, acetic acid, dimethylformamide, or a combination of two or more of these solvents for a period of about 5 hours to about 48 hours, preferably for about 24 hours, under a hydrogen pressure from about 1 to about 5 atmosphere, preferably about 1 atmosphere.

Alternatively, compounds of the formula 2B can be prepared by hydrogenating, using methods well known to those of skill in the art, such as those described above, compounds of the formula 8, depicted below,

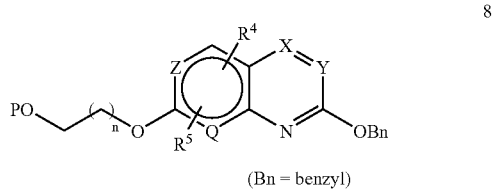

(Bn = benzyl)

which are identical to compounds of the formula 6, wherein P is benzyl, but wherein the oxo substituent is replaced by a benzyloxy substituent.

Compounds of the formula 2B can be prepared, alternatively, by first deprotecting and then hydrogenating the corresponding compounds of formula 8, using methods well known to those of skill in the art, such as those described above. Compounds of the formula 8 can be prepared by a method analogous to that used to prepare compounds of the formula 6 in Scheme C, but wherein the reactant of formula 5 is replaced by a compound having formula 7, as depicted below.

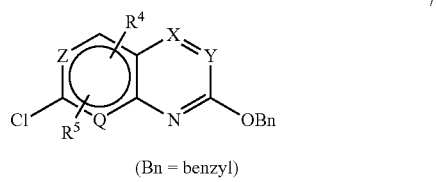

(Bn = benzyl)

Compounds of the formula 7 can be prepared by reacting the corresponding compounds of formula 5A wherein $R^{13}$ is chloro with benzyl bromide and silver carbonate in refluxing toluene. Compounds of the formula 7 wherein Z is $CR^5$ can be prepared, alternatively, by reacting the 2,7-dichloro-[1,8]naphthyridine with one equivalent of benzyl alcohol in the presence of a base such as such as potassium tert-butoxide, sodium tert-butoxide, sodium hydride, potassium hydride, lithium diisopropylamide, lithium bis(trimethylsilyl)amide, potassium bis(trimethylsilyl)amide, or sodium bis(trimethylsilyl)amide. Suitable solvents for this reaction include tetrahydrofuran (THF), dioxane, ethylene glycol dimethylether, dimethylformamide (DMF), N-methylpyrrolidinone (NMP), or dimethylsulfoxide (DMSO), or a combination of two or more of these solvents. The temperature of the reaction may vary from about −20° C. to ambient temperature.

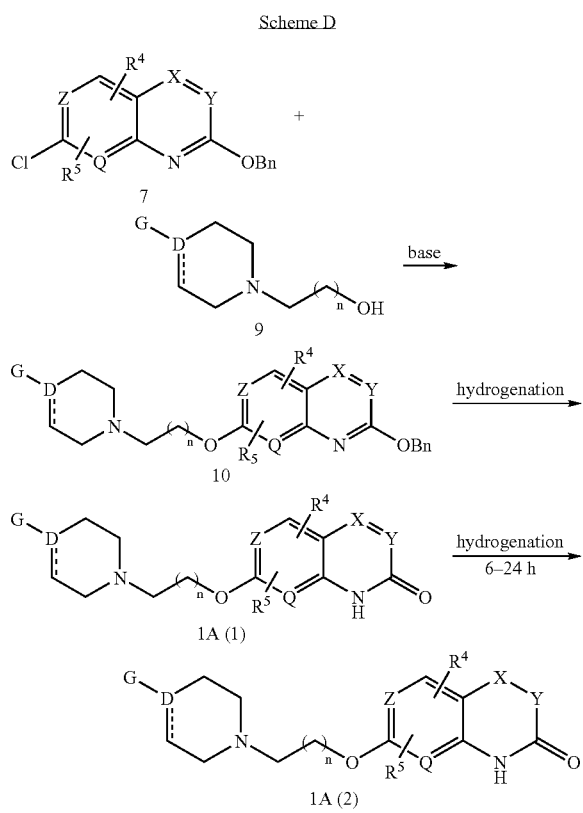

Scheme D

Scheme D illustrates another method for preparing compounds of the formula 1A. Addition of a compound of the formula 9 to a compound of the formula 7 provides the corresponding compound of formula 10. This reaction is generally conducted in the presence of a base such as potassium tert-butoxide, sodium tert-butoxide, sodium hydride, potassium hydride, lithium diisopropylamide, lithium bis(trimethylsilyl)amide, potassium bis(trimethylsilyl)amide, or sodium bis(trimethylsilyl)amide. Suitable solvents for this reaction include THF, dioxane, ethylene glycol dimethylether, DMF, NMP, and DMSO, or a combination of two or more of these solvents. The reaction temperature can range from about −78° C. to about ambient temperature, and is preferably from about −20° to about 0° C. Compounds of the formula 10 can be debenzylated using mild catalytic hydrogenation methods to provide the corresponding compounds of formula 1A(1). For example, the hydrogenation can be conducted using 5% palladium on activated carbon in a solvent such as methanol, ethanol, or THF, or a combination of two or more of these solvents, for a period of about 1 hour. More exhaustive catalytic hydrogenation of compounds of the formula 10 or 1A (when G is compatible with the hydrogenation conditions) provides compounds of formula 1A(2). For example, the hydrogenation can be conducted using 5 to 20% palladium on activated carbon in a solvent such as methanol, ethanol, THF, acetic acid, or DMF, or a combination of two or more of these solvents, for a period of about 5 hours to about 48 hours, preferably for about 12 to 24 hours.

Compounds of the formula 1A wherein D is N can also be prepared by reacting a compound of the formula 11, depicted below

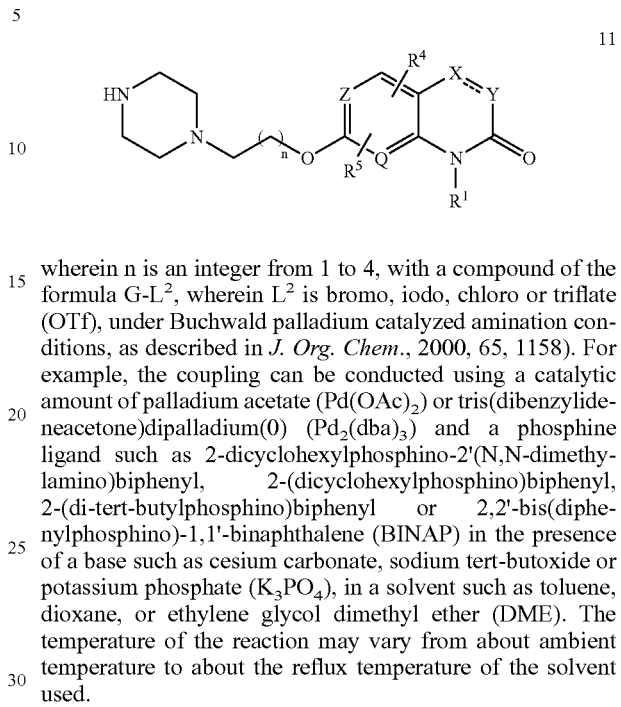

wherein n is an integer from 1 to 4, with a compound of the formula G-L$^2$, wherein L$^2$ is bromo, iodo, chloro or triflate (OTf), under Buchwald palladium catalyzed amination conditions, as described in *J. Org. Chem.*, 2000, 65, 1158). For example, the coupling can be conducted using a catalytic amount of palladium acetate (Pd(OAc)$_2$) or tris(dibenzylideneacetone)dipalladium(0) (Pd$_2$(dba)$_3$) and a phosphine ligand such as 2-dicyclohexylphosphino-2'(N,N-dimethylamino)biphenyl, 2-(dicyclohexylphosphino)biphenyl, 2-(di-tert-butylphosphino)biphenyl or 2,2'-bis(diphenylphosphino)-1,1'-binaphthalene (BINAP) in the presence of a base such as cesium carbonate, sodium tert-butoxide or potassium phosphate (K$_3$PO$_4$), in a solvent such as toluene, dioxane, or ethylene glycol dimethyl ether (DME). The temperature of the reaction may vary from about ambient temperature to about the reflux temperature of the solvent used.

Scheme E

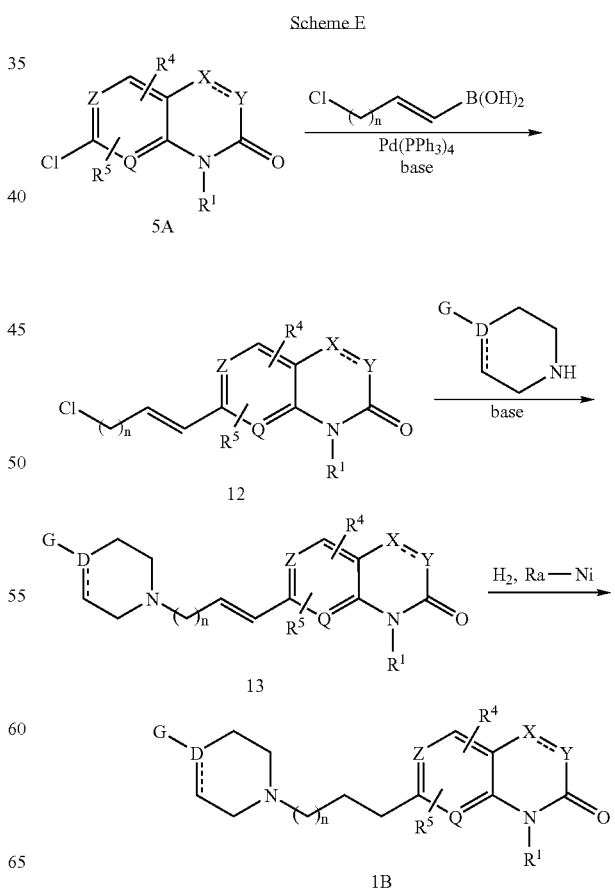

Scheme E illustrates a method for preparing compounds of the formula 1 wherein A is —(CH$_2$)$_m$CH$_2$—, optionally substituted as described in the definition of formula 1 above, (compounds of the formula 1B). Referring to Scheme E, compounds of the formula 5 can be reacted with a chloroalkenylboronic acid of the formula Cl(CH$_2$)$_n$CH=CHB(OH)$_2$, wherein n is an integer from 1 to 4, under palladium-catalyzed Suzuki cross-coupling conditions (*Chem. Rev.* 1995, 95, 2457), to give the corresponding compounds of formula 12. For example, the coupling can be conducted using a catalytic amount of tetrakis(triphenylphosphine)palladium(0) in the presence of a base such as aqueous sodium carbonate, sodium hydroxide, or sodium ethoxide, in a solvent such as THF, dioxane, ethylene glycol dimethylether, ethanol (EtOH) or benzene. The temperature of the reaction may vary from about ambient temperature to about the reflux temperature of the solvent used. The resulting compounds of the formula 12 are then reacted with a G-substituted piperazine or piperidine, as depicted in Scheme E, to yield the corresponding compounds of formula 13. This reaction is typically run in the presence of a base such as potassium carbonate, sodium carbonate, cesium carbonate, triethylamine or diisopropylethylamine. Typical solvents include acetonitrile, water, THF, dioxane, acetone, methyl isobutyl ketone, benzene or toluene, or a combination of two or more of these solvents. Inorganic salts such as sodium or potassium iodide may be employed as catalysts in the reaction. The temperature of the reaction can range from about ambient temperature to about the reflux temperature of the solvent. The reaction may also be conducted under microwave irradiation. Hydrogenation of compounds of the formula 13, using methods well known to those of skill in the art, yields the desired compounds of formula 1B. For example, the hydrogenation reaction can be conducted using catalytic Raney-nickel in a solvent such as ethanol, methanol, or THF, or a combination of two or more of these solvents, at a hydrogen pressure from about 1 atmosphere to about 5 atmospheres, preferably at about 1 atmosphere.

Compounds of the formula 5 wherein $R^{13}$ is chloro, fluoro or bromo, and X is double bonded to Y can be prepared by diazotization of the analogous compounds wherein $R^{13}$ is replaced by an amino group with sodium nitrite, followed by in situ trapping of the diazonium ion with a halogen source such as hydrogen fluoride, hydrogen bromide tetrafluoroboric acid (HBF$_4$), hydrogen chloride, copper(I) chloride, hydrogen bromide or copper(I) bromide. For example, the reaction to form a compound of the formula 5 wherein $R^{13}$ is chloro can be conducted in concentrated hydrochloric acid with the optional addition of copper(I) chloride at a temperature of about −20° C. to about ambient temperature. In the case of deaminative fluorinations, the reaction can be enhanced by employing a base such as pyridine, as described in *Tetrahedron*, 1996, 52, 23. Compounds of the formula 5 wherein $R^{13}$ is chloro, fluoro or bromo, and X is single bonded to Y can be prepared using a similar method wherein the aminated starting material described above is first subjected to hydrogenation using methods well known to those of skill in the art, for example, using 5 to 20% palladium on activated carbon in a solvent such as acetic acid, 1N to 6N hydrochloric acid, or DMF, for a period from about 12 hours to about 24 hours.

Compounds of the formula 5 wherein $R^1$ is other than hydrogen can be prepared from the analogous compounds wherein $R^1$ is hydrogen by reacting such analogous compounds with a compound of the formula $R^1$ Br in the presence of a base such as potassium t-butoxide, sodium hydride, lithium diisopropylamide or lithium bis(trimethylsilyl)amide, in a solvent such as THF, dioxane, ethylene glycol dimethylether, DMF, or DMSO, or a combination of two or more of these solvents. Suitable temperatures for this reaction range from about 0° C. to about the reflux temperature of the solvent.

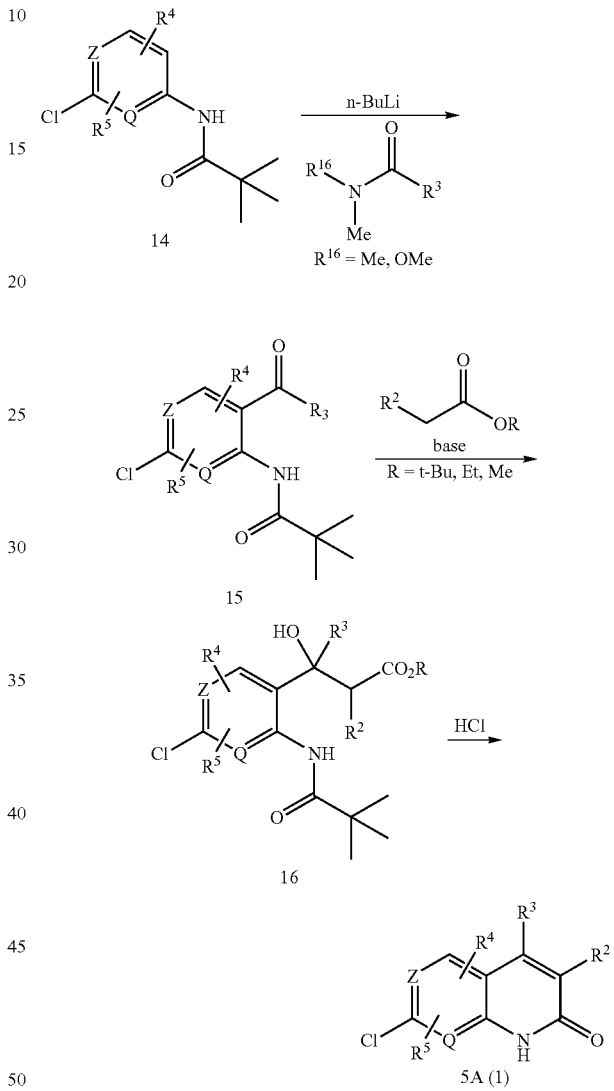

Scheme F

Scheme F illustrates an alternative method for preparing compounds of the formula 5A (1) (*J. Org. Chem.* 1990, 55, 4744). (Compounds of the formula 5A (1) are compounds of the formula 5 wherein X is CR$^3$, Y is CR$^2$ and there is a double bond between X and Y). Ortho metalation of compounds of the formula 14 and subsequent treatment with electrophiles having the formula shown in Scheme F results in compounds of the formula 15. Condensation of compounds of the formula 15 with the enolates of the alkyl esters having the formula shown in Scheme F provides the corresponding compounds of formula 16. Refluxing compounds of the formula 16 in aqueous acid such as 3N hydrochloric acid, with the optional use of a co-solvent such as dioxane, generates the corresponding compounds of formula 5A (1).

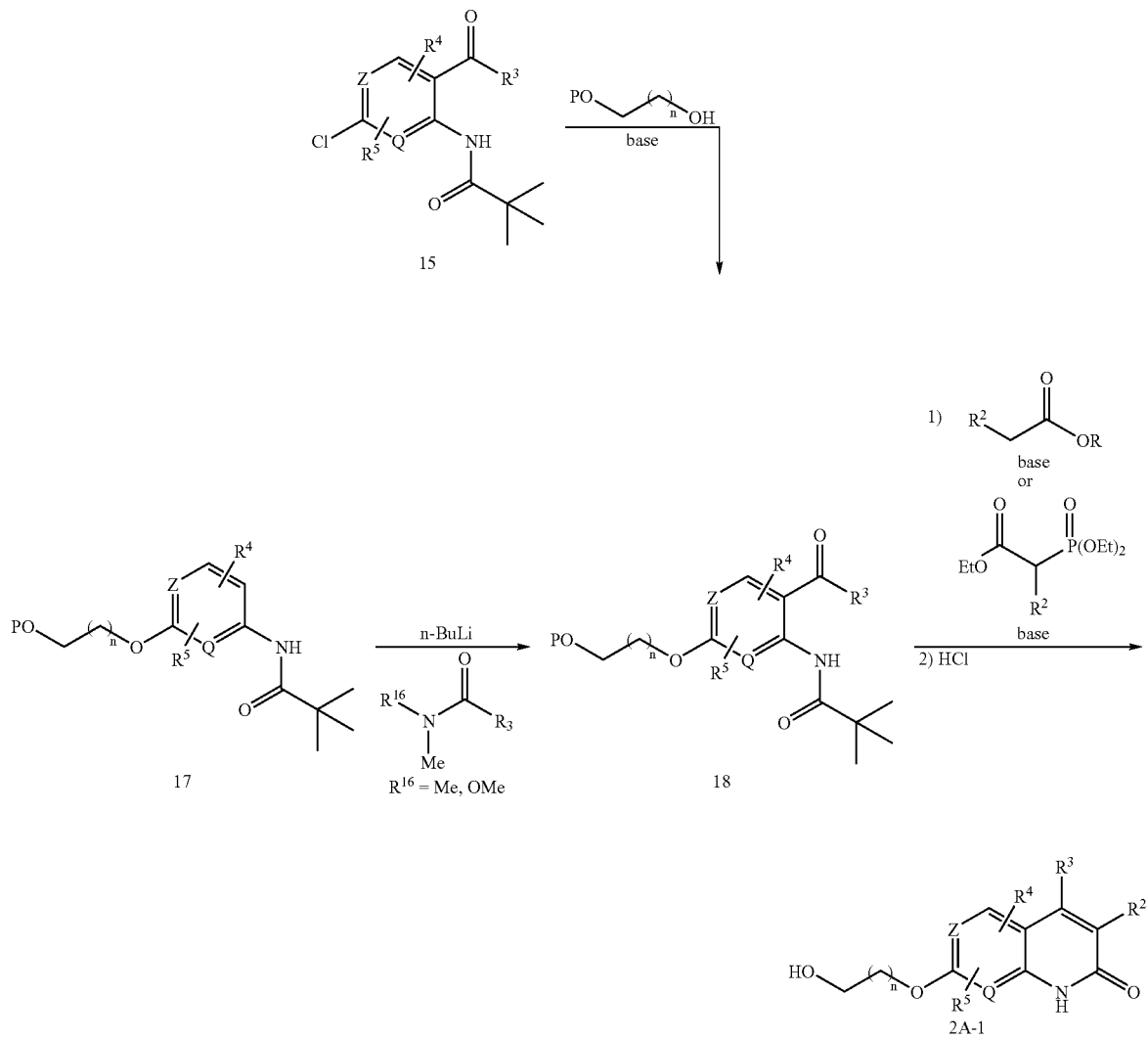

Scheme G illustrates another method for preparing compounds of the formula 2A-1. Addition of a suitably monoprotected diol, where n is an integer between 1 and 4 and P is tetrahydropyranyl (THP), benzyl, or tert-butyldimethysilyl, to compounds of the formula 17 provides compounds of the formula 18. The reaction is conducted in the presence of a base such as potassium tert-butoxide, sodium tert-butoxide, sodium hydride, potassium hydride, lithium diisopropylamide, lithium bis(trimethylsilyl)amide, potassium bis(trimethylsilyl)amide, or sodium bis(trimethylsilyl)amide. The solvents used may be THF, dioxane, ethylene glycol dimethylether, DMF, NMP, or DMSO or a combination of two or more of these solvents. The temperature of the reaction may vary from about 0° C. to about the reflux temperature of the solvent.

Alternatively, compounds of the formula 18 can be prepared from compounds of the formula 17 according to the method described in Scheme F for the preparation of compounds of the formula 15.

Condensation of compounds of the formula 18 with the enolates of the esters having the formula shown in Scheme G provides α-hydroxy ester intermediates, which are treated with an aqueous acid such as 3N hydrochloric acid, with the optional use of a co-solvent such as dioxane, at temperatures varying from about ambient temperature to about the reflux temperature of the solvent, to generate compounds of the formula 2A-1.

Alternatively, Horner-Wadsworth-Emmons reaction of compounds of the formula 18 with ketophosphonates having the formula shown in Scheme G, in the presence of a base such as sodium hydride, sodium ethoxide, or butyl lithium, in a solvent such as THF, DMSO, dioxane, ethylene glycol dimethylether, ethanol, or benzene, or a combination of two or more of these solvents, to give the corresponding intermediate α,β-unsaturated esters. This reaction can also be conducted using lithium chloride and a base, such as DBU (1,8-diazabicyclo[5.4.0]undec-7-ene) or triethylamine, in a solvent such as acetonitrile or THF. The intermediate α,β-unsaturated esters are then treated with aqueous hydrochloric acid with the optional use of a co-solvent such as dioxane to provide the desired compounds of the formula 2A-1. The temperature of this reaction may vary from about ambient temperature to about the reflux temperature of the solvent.

Scheme H

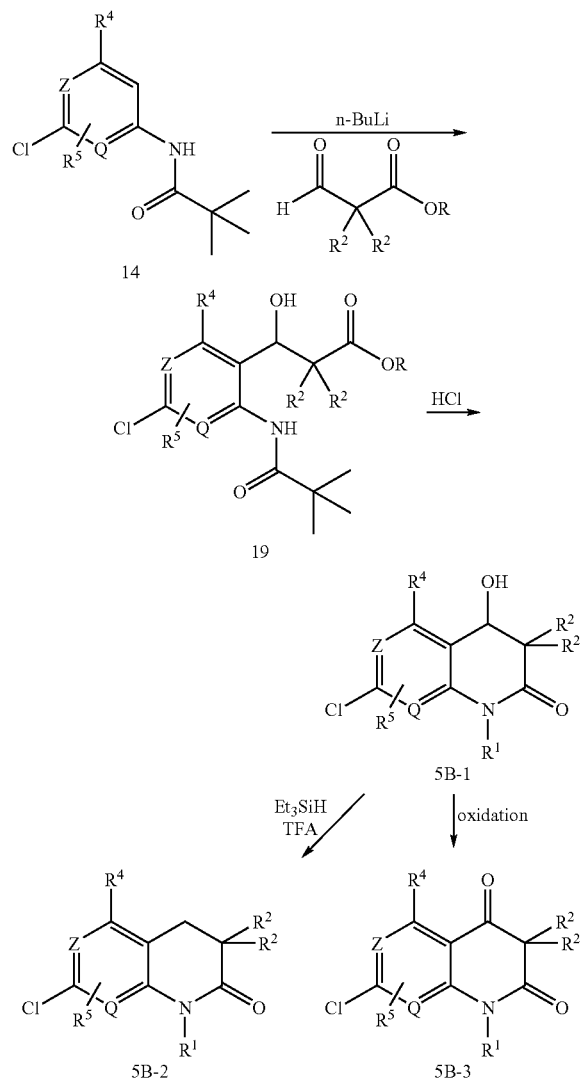

Scheme I

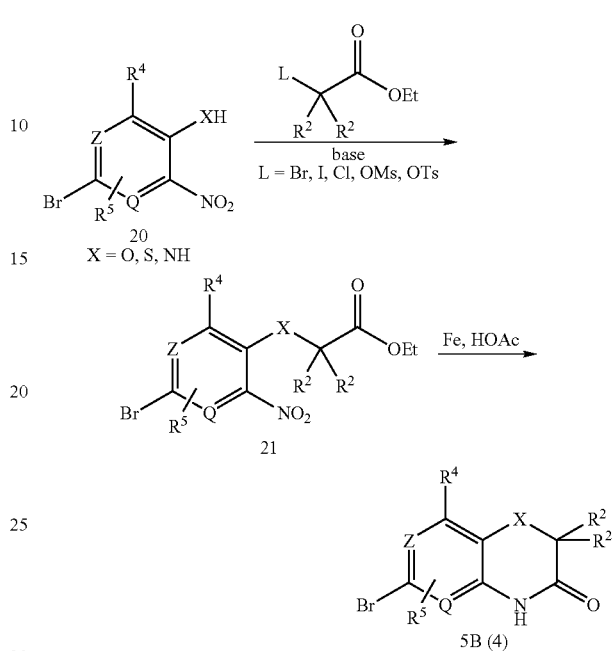

as dichloromethane, dichloroethane, THF or DMSO, or a combination of two or more of these solvents.

Scheme H illustrates a method for preparing compounds of the formula 5B-1, 5B-2 and 5B-3. Ortho metalation of compounds of the formula 14, as described in Scheme F, and subsequent treatment with 3-oxopropionic acid esters of the formula shown in Scheme H above provides the corresponding compounds of formula 19. The reaction can be conducted in a solvent such as tetrahydrofuran at temperatures ranging from about −78° C. to about ambient temperature, preferably from about −78° C. to about −20° C. Refluxing compounds of the formula 19 in an aqueous acid such as 3N hydrochloric acid, with the optional use of a co-solvent such as dioxane, generates the corresponding compounds of formula 5B-1. Compounds of the formula 5B-2 can be prepared by treating the corresponding compounds of the formula 5B-1 with triethylsilane in trifluoroacetic acid at a temperature from about room temperature to the reflux temperature of the solvent. Compounds of the formula 5B-3 can be prepared by treating the compounds of the formula 5B-1 with an oxidizing agent such as Dess Martin periodinane, IBX or PCC at about ambient temperature in a solvent such Scheme I illustrates a method for preparing compounds of the formula 5B (4) (see PCT Patent Application WO 02/056882). Alkylation of compounds of the formula 20 with an ester of the formula shown in Scheme I (L=Br, I, Cl, OMs, OTs) yields the corresponding compounds of formula 21. This reaction is typically run in the presence of a base such as potassium carbonate or sodium hydride, in a solvent such as acetonitrile, THF, dioxane, acetone, methyl isobutyl ketone, benzene, toluene or DMF, or a combination of two or more of these solvents. The temperature of the reaction may vary from about ambient temperature to about the reflux temperature of the solvent. The nitro group of compounds of the formula 21 can be reduced with iron powder and acetic acid, with or without the addition of a solvent such methanol or water, at temperatures from about room temperature to about the reflux temperature of the solvent mixture used. These conditions also result in ring closure to yield compounds of the formula 5B (4).

Scheme K

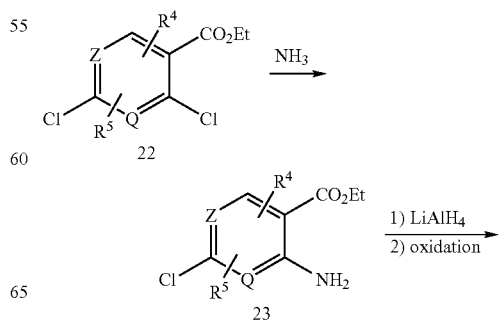

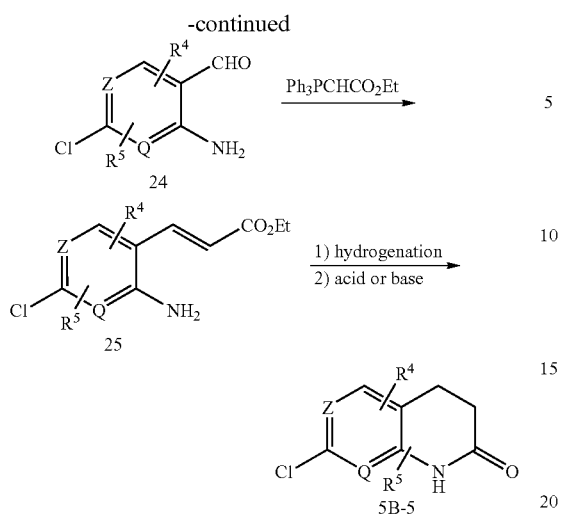
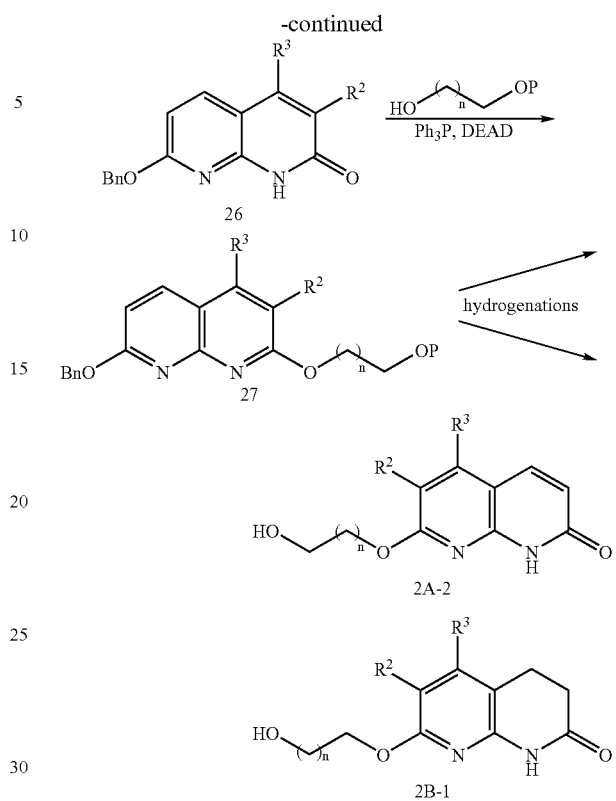

Scheme K illustrates a method for preparing compounds of the formula 5B-5. Compounds of the formula 22 can be heated with liquid ammonia in a sealed reaction vessel at temperatures of about 40° C. to about 100° C., in a solvent such as THF, to yield compounds of the formula 23. Reduction of the ester of compound 23 to the corresponding alcohol, using lithium aluminum hydride, under conventional conditions well known to those of skill in the art, followed by oxidation of the alcohol with an oxidizing agent such as barium manganate, manganese dioxide, IBX, Dess Martin periodinane, or PCC, in a solvent such as dichloromethane, THF, or DMSO, or a combination of two or more of these solvents, yields the corresponding aldehydes of formula 24. Compounds of the formula 24 can then be reacted with (carbethoxymethylene)triphenylphosphorane or a similar Wittig reagent in a solvent such as dichloromethane, chloroform, THF, benzene or toluene, at a temperature from about room temperature to about the reflux temperature of the solvent, to give the corresponding compounds of formula 25. In the case of barium manganate, the oxidation and the Wittig reaction can be carried out using a one-pot procedure (*J. Org. Chem.* 1998, 63, 4489). Hydrogenation of compounds of the formula 25, using methods known to those skilled in the art, for example, as described above, preferably using palladium on barium sulfate in a solvent such as THF, provides the corresponding amino esters. The resulting amino esters can be cyclized to give compounds of the formula 5B(5) by heating at a temperature from about 50° C. to about the reflux temperature of the solvent, in a solvent such as ethanol, methanol or isopropanol, preferably with a catalytic amount of acid (i.e., TsOH) or base (i.e., DBU).

Scheme L illustrates an alternative method for preparing compounds of the formula 2A-2 and 2B-1. Compounds of the formula 26 can be prepared by reacting compounds of the formula 5A-2 with benzyl alcohol in the presence of a base such as such as potassium tert-butoxide, sodium tert-butoxide, sodium hydride, potassium hydride, lithium diisopropylamide, lithium bis(trimethylsilyl)amide, potassium bis(trimethylsilyl)amide, or sodium bis(trimethylsilyl)amide. The solvents used may be tetrahydrofuran, dioxane, ethylene glycol dimethylether, dimethylformamide, N-methylpyrrolidinone, dimethylsulfoxide, or a combination of two of the formerly mentioned solvents. The temperature of the reaction may vary from ambient to the reflux temperature of the solvent used. Compounds of the formula 26 can be reacted with a suitably mono-protected diol, preferably P=Bn, under Mitsunobo conditions to give compounds of the formula 27. Typical reaction conditions employ diethyldiazodicarboxylate (DEAD) and triphenylphosphine in a solvent such as tetrahydrofuran. Compounds of the formula 27 can be hydrogenated to give compounds of the formula 2A-2 and 2B-1 following methods described in Scheme C for the hydrogenation of compounds of the formula 8.

Scheme L

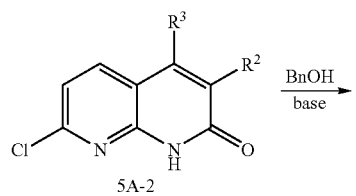

Scheme M

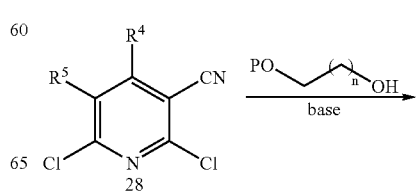

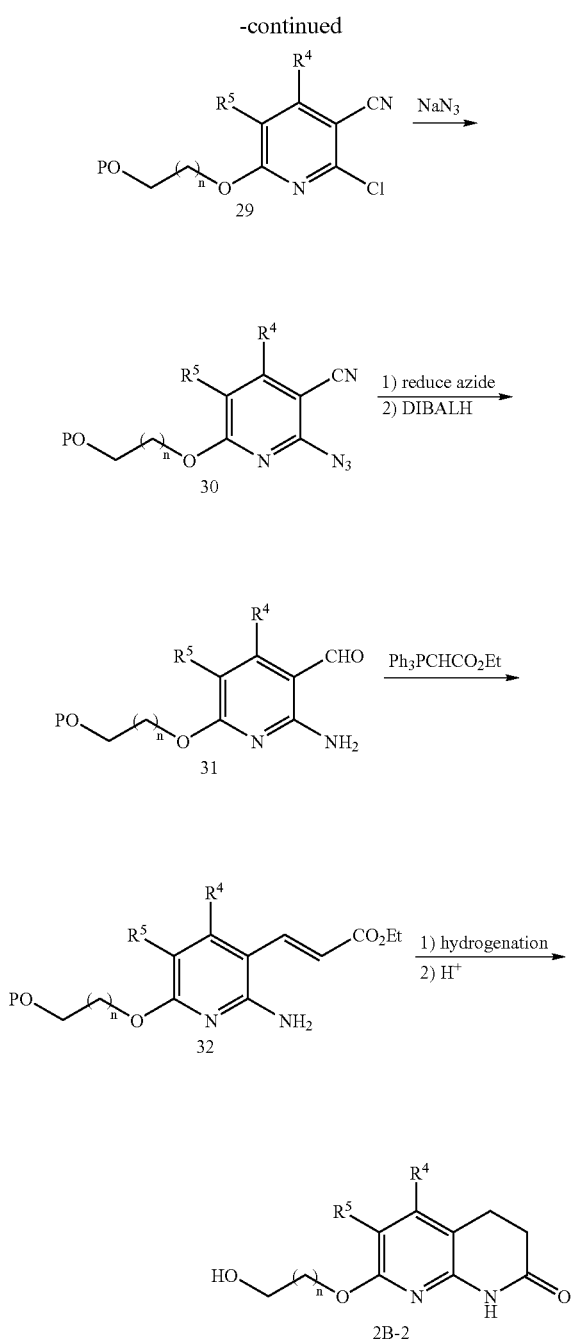

perature of the reaction may vary from about −78° C. to about room temperature. Compounds of the formula 29 can be reacted with sodium azide in solvents such as DMF, NMP or DMSO, or a combination of two or more of these solvents, to provide compounds of the formula 30. The temperature of the reaction may vary from about room temperature to about the reflux temperature of the solvent, and is preferably about 70° C. The azide of compounds of the formula 30 can be reduced to an amine using conventional reducing agents known to those skilled in the art, preferably using hexamethyldisilthiane [$(Me_3Si)_2S$] in a solvent such as methanol or ethanol. Subsequent reduction of the cyano group to an aldehyde using diisobutylaluminum hydride in a solvent such as THF at about 0° C. provides compounds of the formula 31. Compounds of the formula 31 can be reacted with (carbethoxymethylene)triphenylphosphorane or a similar Wittig reagent in a solvent such as dichloromethane, chloroform, THF, benzene or toluene, or a mixture of two or more of these solvents, at about room temperature to about the reflux temperature of the solvent, to give compounds of the formula 32. Compounds of the formula 32 can be hydrogenated using methods known to those skilled in the art, using, for example, palladium on activated carbon, palladium on barium sulfate, or Raney-nickel, in a solvent such as methanol, ethanol, THF, or a combination of two of the formerly mentioned solvents. The resulting amino esters can be cyclized to give the corresponding compounds of the formula 2B-2 by heating at a temperature from about 50° C. to about the reflux temperature of the solvent, in a solvent such as ethanol, methanol or isopropanol, or a mixture of two or more of these solvents. Preferably, a catalytic amount of acid (i.e., TsOH) or base (i.e., DBU) is used.

Scheme N

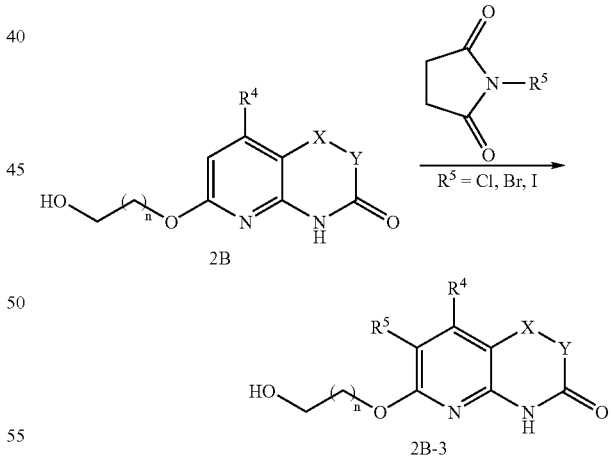

Scheme M illustrates an alternative method for preparing compounds of the formula 2B-2. Addition of a suitably mono-protected diol, where n is an integer between 1 and 4 and P is tetrahydropyranyl (THP), benzyl, or tert-butyldimethysilyl (TBS), to compounds of the formula 28 provides the corresponding compounds of formula 29. This reaction is typically conducted in the presence of a base such as potassium tert-butoxide, sodium tert-butoxide, sodium hydride, lithium diisopropylamide, lithium bis(trimethylsilyl)amide, potassium bis(trimethylsilyl)amide, or sodium bis(trimethylsilyl)amide, in a solvent such as THF, dioxane, or ethylene glycol dimethylether, preferably THF. The tem Scheme N illustrates a method for preparing compounds of the formula 2B(3). The corresponding compounds of formula 2B are halogenated regioselectively with N-bromosuccinamide, N-chlorosuccinamide, or N-iodosuccinamide in DMF at temperatures from about room temperature to about 80° C. to provide compounds of the formula 2B-3 (J. Med. Chem. 2003, 46, 702).

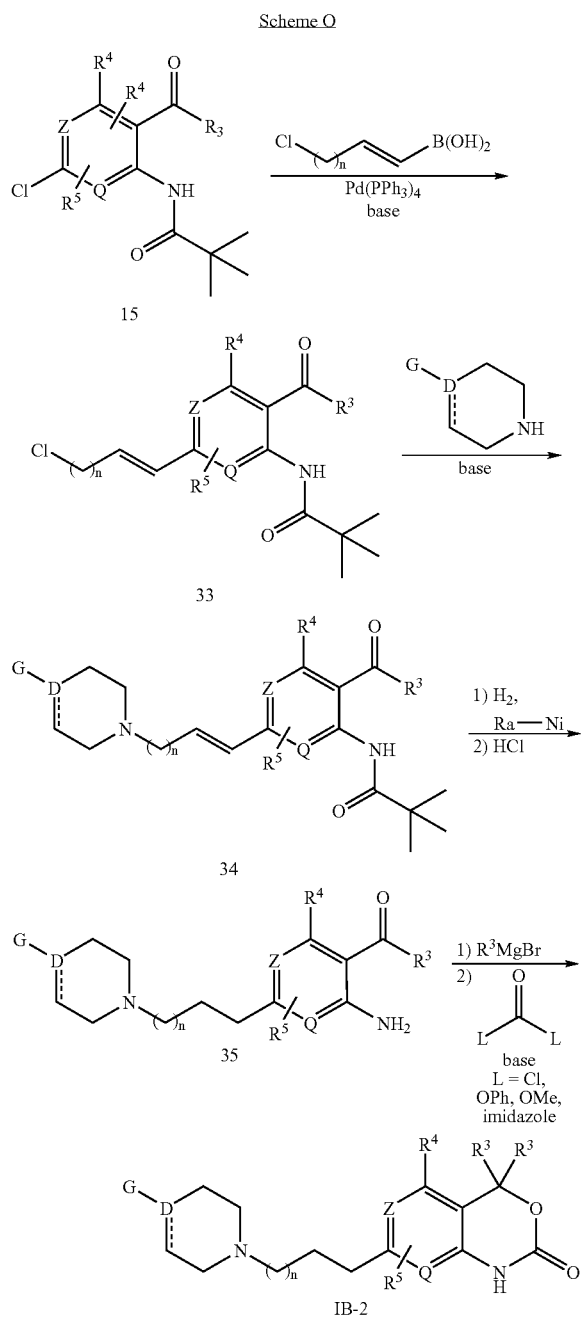

Scheme O illustrates a method for preparing compounds of the formula IB-2. Compounds of the formula 15 can be reacted with chloro-alkenylboronic acids (n=1 to 3) under palladium-catalyzed Suzuki cross-coupling conditions as described in Scheme E to give compounds of the formula 33. Subsequent reaction with the G-substituted piperazines or piperidines of the formula shown in Scheme O according to the methods described in Scheme E provide the corresponding compounds of formula 34. Compounds of the formula 34 may be hydrogenated in the presence of a catalyst such as Raney-nickel in a solvent such as ethanol, methanol, tetrahydrofuran, or a combination of two of the formerly mentioned solvents. Subsequent removal of the pivaloyl group under acidic conditions, preferably with 3N aqueous hydrochloric acid at temperatures of about room temperature to about the reflux temperature of the solvent provides compounds of the formula 35. Compounds of the formula 35 can be reacted with Grignard reagents such as alky magnesium bromides in solvents such as tetrahydrofuran, diethyl ether, toluene, or a combination of two of the formerly mentioned solvents at temperatures of about −78° C. to room temperature to give the corresponding alcohols. Subsequent treatment with reagents such as phosgene, carbonyldiimidazole (CDI), 4-nitrophenyl chloroformate, methyl chloroformate, or phenyl chloroformate, with or without a base such as triethylamine, pyridine, potassium bicarbonate, or potassium carbonate in solvents such as tetrahydrofuran, methyl tert-butyl ether (MTBE), water, toluene, hexanes, heptane or a combination of two of the formerly mentioned solvents gives compounds of the formula IB-2 (*J. Org. Chem.* 1998, 63, 8536).

The preparation of other compounds of the formula 1 not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of the formula 1 and the intermediates shown in the above reaction schemes can be isolated and purified by conventional procedures, such as recrystallization or chromatographic separation.

The compounds of the formula 1 and their pharmaceutically acceptable salts, can be administered to mammals via either the oral, parenteral (such as subcutaneous, intravenous, intramuscular, intrasternal and infusion techniques), rectal, buccal or intranasal routes. In general, these compounds are most desirably administered in doses ranging from about 3 mg to about 600 mg per day, in single or divided doses (i.e., from 1 to 4 doses per day), although variations will necessarily occur depending upon the species, weight and condition of the patient being treated and the patient's individual response to said medicament, as well as on the type of pharmaceutical formulation chosen and the time period and interval at which such administration is carried out. However, a dosage level that is in the range of about 10 mg to about 100 mg per day is most desirably employed. In some instances, dosage levels below the lower limit of the aforesaid range may be more than adequate, while in other cases still larger doses may be employed without causing any harmful side effects, provided that such higher dose levels are first divided into several small doses for administration throughout the day.

The novel compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

This invention relates to methods of treating anxiety, depression, schizophrenia and the other disorders referred to in the description of the methods of the present invention, wherein a novel compound of this invention and one or more of the other active agents referred to above (e.g., an NK1 receptor antagonist, tricyclic antidepressant, 5HT1D receptor antagonist, or serotonin reuptake inhibitor) are administered together, as part of the same pharmaceutical composition, as well as to methods in which such active agents are administered separately as part of an appropriate dose regimen designed to obtain the benefits of the combination therapy. The appropriate dose regimen, the amount of each dose of an active agent administered, and the specific intervals between doses of each active agent will depend upon the subject being treated, the specific active agent being administered and the nature and severity of the specific disorder or condition being treated. In general, the novel compounds of this invention, when used as a single active agent or in combination with another active agent, will be administered to an adult human in an amount from about 3 mg to about 300 mg per day, in single or divided doses, preferably from about 10 to about 100 mg per day. Such compounds may be administered on a regimen of up to 6 times per day, preferably 1 to 4 times per day, especially 2 times per day and most especially once daily. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

A proposed daily dose of a 5HT reuptake inhibitor, preferably sertraline, in the combination methods and compositions of this invention, for oral, parenteral or buccal administration to the average adult human for the treatment of the conditions referred to above, is from about 0.1 mg to about 2000 mg, preferably from about 1 mg to about 200 mg of the 5HT reuptake inhibitor per unit dose, which could be administered, for example, 1 to 4 times per day. A proposed daily dose of a 5HT1D receptor antagonist in the combination methods and compositions of this invention, for oral, parenteral, rectal or buccal administration to the average adult human for the treatment of the conditions referred to above, is from about 0.01 mg to about 2000 mg, preferably from about 0.1 mg to about 200 mg of the 5HT1D receptor antagonist per unit dose, which could be administered, for example, 1 to 4 times per day.

For intranasal administration or administration by inhalation, the novel compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably arranged so that each metered dose or "puff" of aerosol contains 20 μg to 1000 μg of active compound. The overall daily dose with an aerosol will be within the range 100 μg to 10 mg. Administration may be several times daily, for example 2, 3, 4 or 8 times, giving for example, 1, 2 or 3 doses each time.

The ability of the novel compounds of this invention to bind to the dopamine $D_2$ receptor can be determined using conventional radioligand receptor binding assays. All receptors can be heterologously expressed in cell lines and experiments conducted in membrane preparations from the cell lines using procedures outlined below. $IC_{50}$ concentrations can be determined by nonlinear regression of concentration-dependent reduction in specific binding. The Cheng-Prussoff equation can be used to convert the $IC_{50}$ to Ki concentrations.

Dopamine $D_2$ Receptor Binding Assay:

[$^3$H]Spiperone binding to a membrane preparation from CHO-h$D_2$L cells is carried out in 250 μl of 50 mM Tris-HCl buffer containing 100 mM NaCl, 1 mM $MgCl_2$ and 1% DMSO at pH 7.4. Duplicate samples containing (in order of addition) the test compounds, 0.4 nM [$^3$H]spiperone and approximately 12 μg protein are incubated for 120 minutes at room temperature. Bound radioligand is separated by rapid filtration under reduced pressure through Whatman GF/B glass fiber filters previously treated with 0.3% polyethyleneimine. Radioactivity retained on the filter is determined by liquid scintillation spectrophotometry.

Title compounds of the Examples, below, were tested using the above assay, in which specific binding determined in the presence of 1 mM haloperidol was 95%. All of the title compounds exhibited Ki values less than or equal to 75 nM (see Tables 1 and 2, below). Preferred embodiments of compounds of the present invention preferably exhibit Ki values of no more than 100 nM, more preferably no more than 50 nM, even more preferably no more than 25 nM, most preferably no more than 10 nM.

$D_2$ intrinsic activity of title compounds of the Examples, below, was determined using the [$^3$H]thymidine uptake assay described below.

[$^3$H]Thymidine Uptake Assay for $D_2$ Intrinsic Activity

Cells are serum deprived by washing twice with 200 μl of serum-free media. 90 μl serum-free media was added to each well. The plates ware incubated for two to three hours. 10 μl of serum-containing media, as a positive control, vehicle (serum-free media), negative control (an antagonist) or test compounds and standards (10 μl of a 10 μM solution for a final concentration of 1 μM) in serum-free media were added to wells. The plates are returned to the incubator. Eighteen hours later [$^3$H]thymidine is added (0.5 μCi/well in 10 μl of serum-free media) and the plates are returned to the incubator. Four hours later trypsin (0.25%) is added (100 μl/well). The plates are returned to the incubator, once again. One hour later the assay is terminated by rapid filtration through Whatman GF/C glass fiber filters. Filters are washed four times with 500 ml of 50 mM Tris-HCl pH 7.0 buffer, for example, using a Brandel MLR-96T cell harvester. Radioactivity remaining on the filters are estimated, for example, with a Wallac 1205 Betaplate liquid scintillation counter (50% efficiency). Intrinsic activity is defined as total uptake (1 μM Quinpirole) minus serum-free media (no uptake). Test compounds are compared to 1 μM Quinpirole (full DA agonist), which was classified as 100% intrinsic activity. All assays are preferably performed in triplicate, with each drug occupying one full column (8 wells) per plate.

Compounds of the present invention preferably exhibit at least 1% to up to 90% intrinsic activity, more preferably at least 10% to up to 90% activity, more preferably at least 10% to up to 80% activity, more preferably at least 20% to up to 60% intrinsic activity, even more preferably at least 30% to up to 50% intrinsic activity.

Each of the title compounds produced as described in the Examples, below, were also tested using the above assay. All of the title compounds tested in this assay exhibited an intrinsic activity between 2 and 83 percent. See Tables 1 and 2, below, for results obtained from each of the compounds tested.

TABLE 1

| Example | $D_2$ Ki (nM) | $D_2$ Intrinsic Activity (%) |
|---|---|---|
| A1 | 1.0 | 30 |
| A2 | 1.0 | 29 |
| A3 | 3.0 | 35 |
| A4 | 2.5 | 28 |
| A5 | 2.5 | 29 |
| A6 | 1.0 | 31 |
| A7 | 1.0 | 15 |
| A8 | 10.0 | 7 |
| A9 | 5.5 | 9 |
| A10 | 5.7 | 31 |
| A11 | 6.5 | 6 |
| A12 | 2.0 | 11 |
| A13 | 11.4 | 21 |
| A14 | 5.5 | 7 |
| A15 | 4.5 | 4 |

TABLE 1-continued

| Example | $D_2$ Ki (nM) | $D_2$ Intrinsic Activity (%) |
|---|---|---|
| A16 | 3.5 | 16 |
| A17 | 1.0 | 15 |
| A18 | 7.7 | NOT TESTED |
| A19 | 19.5 | 10 |
| A20 | 0.7 | 19 |
| A21 | 6.7 | NOT TESTED |
| A22 | 4.5 | 36 |
| A23 | 14.9 | NOT TESTED |
| A24 | 16.5 | 40 |
| A25 | 1.0 | 27 |
| A26 | 1.0 | 33 |
| A27 | 1.4 | 38 |
| A28 | 3.5 | 2 |
| A29 | 2.5 | 20 |
| A30 | 15.5 | 11 |
| A31 | 2.0 | 26 |
| A32 | 2.0 | 7 |
| A33 | 15.5 | 31 |
| A34 | 0.5 | 8 |
| A35 | 0.3 | 24 |
| A36 | 5.0 | 38 |
| A37 | 2.2 | 46 |
| A38 | 6.0 | 23 |
| A39 | 7.9 | 56 |
| A40 | 12.0 | 32 |
| A41 | 9.1 | 28 |
| A42 | 4.9 | 28 |
| A43 | 52.0 | 75 |
| A44 | 22.2 | 51 |
| A45 | 2.8 | 34 |
| A46 | 2.0 | 41 |
| A47 | 75.9 | NOT TESTED |
| A48 | 0.8 | 34 |
| A49 | 1.4 | 21 |
| A50 | 0.8 | 14 |
| A51 | 0.4 | 20 |
| A52 | 2.0 | 32 |
| A53 | 5.3 | NOT TESTED |
| A54 | 0.6 | NOT TESTED |
| A55 | 0.2 | NOT TESTED |
| A56 | 2.5 | 29 |
| A57 | 9.4 | NOT TESTED |
| A58 | 30.4 | 48 |
| A59 | 4.5 | 30 |
| A60 | 1.0 | 18 |
| A61 | 2.2 | NOT TESTED |
| A62 | 0.9 | 27 |
| A63 | 35.0 | 4 |
| A64 | 3.5 | 36 |
| A65 | 1.0 | 36 |
| A66 | 2.0 | 49 |
| A67 | 1.0 | 19 |
| A68 | 6.0 | 17 |
| A69 | 2.0 | 10 |
| A70 | 1.1 | 14 |
| A71 | 1.6 | 3 |
| A72 | 3.5 | NOT TESTED |
| A73 | 1.0 | 23 |
| A74 | 4.0 | 37 |
| A75 | 23.8 | 36 |
| A76 | 8.7 | 16 |
| A77 | 10.8 | 36 |
| A78 | 1.4 | 24 |
| A79 | 15.0 | 24 |
| A80 | 23.5 | 30 |
| A81 | 24.7 | 4 |
| A82 | 28.1 | 27 |
| A83 | 2.5 | 36 |
| A84 | 3.0 | 11 |
| B1 | 1.0 | 19 |
| B2 | 2.5 | 22 |
| B3 | 3.9 | 8 |
| B4 | 1.4 | 22 |
| B5 | 3.0 | 2 |
| B6 | 1.0 | 16 |
| B7 | 5.0 | 28 |
| B8 | 2.0 | 17 |

TABLE 1-continued

| Example | D$_2$ Ki (nM) | D$_2$ Intrinsic Activity (%) |
|---|---|---|
| B9 | 1.7 | 23 |
| B10 | 1.2 | 34 |
| B11 | 1.4 | 31 |
| B12 | 4.9 | 38 |
| B13 | 11.2 | 45 |
| B14 | 6.5 | 37 |
| B15 | 2.5 | 17 |
| B16 | 2.5 | 41 |
| B17 | 1.7 | 43 |
| B18 | 3.0 | 32 |
| B19 | 4.6 | NOT TESTED |
| B20 | 13.0 | NOT TESTED |
| B21 | 6.7 | NOT TESTED |
| B22 | 1.0 | 36 |
| B23 | 2.5 | 15 |
| B24 | 4.6 | 10 |
| B25 | 2.2 | 43 |
| B26 | 11.5 | 23 |
| B27 | 9.8 | 47 |
| B28 | 1.4 | 31 |
| B29 | 1.0 | 32 |
| B30 | 28.0 | 83 |
| B31 | 69.5 | 76 |
| B32 | <2 | 19 |
| B33 | 2.0 | 26 |
| B34 | 0.7 | 14 |
| B35 | 0.4 | 20 |
| B36 | 3.0 | 39 |
| B37 | 4.0 | NOT TESTED |
| B38 | 0.6 | NOT TESTED |
| B39 | 1.0 | NOT TESTED |
| B40 | 1.4 | 36 |
| B41 | 4.2 | NOT TESTED |
| B42 | 8.5 | 37 |
| B43 | 3.0 | 18 |
| B44 | 0.7 | 27 |
| B45 | 0.6 | NOT TESTED |
| B46 | 1.0 | 29 |
| B47 | 0.3 | 44 |
| B48 | 1.0 | 19 |
| B49 | 0.9 | 50 |
| B50 | 1.0 | 51 |
| B51 | 3.5 | 36 |
| B52 | 3.5 | 17 |
| B53 | 1.1 | 26 |
| B54 | 2.8 | 15 |
| B55 | 1.0 | NOT TESTED |
| B56 | 2.0 | 28 |
| B57 | 4.1 | 21 |
| B58 | 12.5 | 42 |
| B59 | 5.1 | 37 |
| B60 | 1.6 | 28 |
| B61 | 23.9 | 18 |
| B62 | 1.0 | 21 |
| B63 | 47.9 | 18 |
| B64 | 17.0 | 27 |
| B65 | 9.2 | 10 |
| B66 | 29.2 | 33 |
| B67 | 2.5 | 39 |
| B68 | 4.5 | 17 |
| C1 | 6.6 | 43 |
| C2 | 4.7 | 24 |
| C3 | 6.8 | 22 |
| C4 | 54.1 | 2 |
| C5 | 1.4 | 40 |
| C6 | 2.0 | 44 |
| C7 | 2.0 | 46 |
| C8 | 1.4 | 33 |
| C9 | 2.6 | 34 |
| C10 | 7.0 | 5 |
| C11 | 16.4 | 7 |
| C12 | 13.5 | 12 |
| C13 | 2.0 | 14 |
| C14 | 65.5 | 10 |
| C15 | 32.0 | 8 |
| C16 | 46.7 | 34 |
| C17 | 20.5 | 21 |
| C18 | 7.1 | 34 |
| C19 | 10.4 | 13 |
| C20 | 2.0 | 33 |
| D1 | 1.0 | 31 |
| D2a | 2.9 | 20 |
| D2b | 2.0 | 24 |
| D3 | 4.5 | 15 |
| D4 | 2.0 | 16 |
| D5 | 1.8 | 15 |
| D6a | 2.5 | 17 |
| D6b | 3.0 | 24 |
| D7 | 3.0 | 15 |
| D8 | 2.2 | 8 |
| D9 | 1.0 | 15 |
| D10 | 0.9 | 22 |
| D11 | 1.4 | 30 |
| D12 | 5.0 | 3 |
| D13 | 2.8 | 19 |
| D14 | 0.4 | 3 |
| D15 | 0.6 | 25 |
| D16 | 3.0 | 31 |
| D17 | 3.9 | 29 |
| D18 | 4.7 | 37 |
| D19 | 3.2 | 39 |
| D20 | 2.0 | 44 |
| D21 | 12.5 | 24 |
| D22 | 5.2 | 42 |
| D23 | 6.9 | 33 |
| D24 | 13.4 | 32 |
| D25 | 1.6 | 31 |
| E1 | 2.0 | 32 |
| E2 | 1.3 | 22 |
| E3 | 1.0 | 31 |
| E4 | 2.2 | 38 |
| E5 | 2.0 | 21 |
| E6 | 3.5 | 32 |
| E7 | 6.3 | 19 |
| E8 | 1.4 | 26 |
| E9 | 1.4 | 34 |
| E10 | 1.0 | 31 |
| E11 | 1.0 | 19 |
| E12 | 1.0 | 39 |
| E13 | 5.0 | 11 |
| E14 | 28.5 | 36 |
| E15 | 39.8 | 20 |
| F1 | 0.6 | 8 |
| F2 | 1.0 | 30 |
| F3 | 0.8 | 15 |
| F4 | 1.4 | 23 |
| F5 | 1.0 | 32 |
| F6 | 0.6 | 37 |
| F7 | 0.5 | 11 |
| F8 | 1.0 | 15 |
| F9 | 3.9 | 11 |
| G1 | 7.5 | 27 |
| G2 | 3.9 | 6 |
| G3 | 1.4 | 25 |
| G4 | 0.7 | NOT TESTED |
| G5 | 0.6 | NOT TESTED |
| G6 | 66.7 | NOT TESTED |
| G7 | 0.8 | NOT TESTED |
| G8 | 1.0 | NOT TESTED |
| H1 | 1.0 | 28 |
| H2 | 1.0 | 22 |
| H3 | 1.8 | 25 |
| H4 | 4.9 | 38 |
| H5 | 3.0 | 34 |
| H6 | 1.0 | 42 |
| H7 | 8.8 | 46 |
| H8 | 1.3 | NOT TESTED |
| H9 | 1.0 | NOT TESTED |
| H10 | 3.0 | 44 |
| H11 | 0.4 | 23 |
| H12 | 1.0 | 34 |
| H13 | 15.4 | 36 |
| H14 | 9.3 | 33 |
| I1 | 5.0 | 17 |

TABLE 1-continued

| Example | D₂ Ki (nM) | D₂ Intrinsic Activity (%) |
|---|---|---|
| I2 | 9.0 | 37 |
| I3 | 14.5 | 33 |
| I4 | NOT TESTED | NOT TESTED |
| I5 | 13.9 | 23 |
| I6 | 1.0 | 24 |
| I7 | 7.4 | 37 |
| I8 | 5.9 | 25 |
| I9 | 4.5 | 19 |
| I10 | 9.5 | 21 |
| I11 | 8.7 | 19 |
| I12 | NOT TESTED | NOT TESTED |
| I13 | 2.0 | 19 |
| I14 | 3.5 | 24 |
| I15 | 2.5 | 20 |
| I16 | 2.1 | 27 |
| I17 | 1.0 | 32 |
| I18 | 1.6 | 54 |
| I19 | 7.5 | 22 |

TABLE 2

| Example | D₂ Ki (nM) | D₂ Intrinsic Activity (%) |
|---|---|---|
| A1' | 0.4 | 73 |
| A2' | 1.4 | 21 |
| A3' | 1.0 | 37 |
| A4' | 1.0 | 18 |
| A5' | 2.2 | 31 |
| A6' | 2.0 | 42 |
| A7' | 4.0 | 34 |
| A8' | 1.4 | 30 |
| A9' | 1.0 | 30 |
| A10' | 0.4 | NOT TESTED |
| A11' | 3.0 | 17 |
| A12' | 2.8 | NOT TESTED |
| A13' | 0.7 | 14 |
| A14' | 3.0 | NOT TESTED |
| A15' | NOT TESTED | NOT TESTED |
| A16' | 2.5 | 15 |
| A17' | 1.0 | 15 |
| A18' | 1.4 | 13 |
| A19' | 1.4 | 40 |
| A20' | 65.1 | NOT TESTED |
| A21' | 1.0 | 24 |
| A22' | 0.7 | NOT TESTED |
| A23' | 1.1 | 39 |
| A24' | 2.0 | 6 |
| A25' | 1.4 | 36 |
| A26' | 12.5 | 12 |
| A27' | 0.5 | 21 |
| A28' | 0.3 | 21 |
| A29' | 7.4 | 33 |
| A30' | 8.9 | 41 |
| A31' | 0.6 | NOT TESTED |
| A32' | 28.0 | 27 |
| A33' | 17.3 | 18 |
| A34' | 1.0 | 38 |
| A35' | 1.4 | 20 |
| A36' | 0.6 | 62 |
| A37' | 1.6 | 45 |
| A38' | 1.0 | 20 |
| A39' | 0.4 | NOT TESTED |
| A40' | 1.0 | 30 |
| A41' | 1.0 | 32 |
| A42' | 0.7 | NOT TESTED |
| A43' | 25.2 | 32 |
| A44' | 18.6 | 29 |
| A45' | 4.2 | NOT TESTED |
| A46' | 3.2 | NOT TESTED |
| A47' | 15.9 | 32 |
| A48' | 7.4 | 34 |
| A49' | 7.5 | 38 |
| B1' | 1.0 | 22 |
| B2' | 1.0 | 33 |

TABLE 2-continued

| Example | D₂ Ki (nM) | D₂ Intrinsic Activity (%) |
|---|---|---|
| B3' | 2.0 | 50 |
| B4' | 1.0 | 28 |
| B5' | 0.3 | NOT TESTED |
| B6' | 1.0 | 33 |
| B7' | 1.0 | 48 |
| B8' | 1.0 | 21 |
| B9' | 1.0 | 40 |
| B10' | 1.0 | 22 |
| B11' | 1.0 | 21 |
| B12' | 2.0 | 24 |
| B13' | 2.0 | 33 |
| B14' | 2.0 | NOT TESTED |
| B15' | 9.4 | NOT TESTED |
| B16' | 1.1 | 4 |
| B17' | 1.4 | NOT TESTED |
| B18' | 1.4 | NOT TESTED |
| B19' | 1.0 | NOT TESTED |
| B20' | 1.0 | 16 |
| B21' | 1.0 | 18 |
| B22' | 1.0 | 12 |
| B23' | 5.5 | 21 |
| B24' | 0.8 | 42 |
| B25' | 1.0 | 21 |
| B26' | 1.2 | 26 |
| B27' | 17.9 | 34 |
| B28' | 7.5 | 44 |
| B29' | 31.9 | 26 |
| B30' | 1.0 | 42 |
| B31' | 0.6 | NOT TESTED |
| B32' | 1.4 | NOT TESTED |
| B33' | 4.2 | NOT TESTED |
| B34' | 0.7 | 35 |
| B35' | 0.4 | NOT TESTED |
| B36' | 12.9 | 36 |
| B37' | 3.2 | 39 |
| B38' | 3.0 | 46 |
| B39' | 5.7 | 29 |
| B40' | 3.9 | 49 |
| B41' | 0.8 | NOT TESTED |
| C1' | 6.2 | 38 |
| C2' | 1.9 | 22 |
| C3' | 7.0 | 19 |
| C4' | 18.4 | 21 |
| C5' | 3.0 | 23 |
| C6' | 1.4 | 24 |
| D1' | 2.0 | 24 |
| D2' | 5.0 | 40 |
| E1' | 1.0 | 12 |
| E2' | 0.5 | 9 |
| E3' | 0.7 | 8 |
| E4' | 0.4 | 26 |
| F1' | 0.7 | NOT TESTED |
| F2' | 2.4 | NOT TESTED |
| F3' | 10.1 | NOT TESTED |
| F4' | 1.0 | NOT TESTED |
| F5' | 0.8 | NOT TESTED |
| G1' | 10.0 | 20 |
| G2' | 3.5 | 21 |
| G3' | 17.6 | 28 |
| G4' | 9.0 | 13 |
| G5' | 8.5 | 7 |
| G6' | 0.7 | 17 |
| G7' | 1.4 | 38 |
| G8' | 2.5 | 32 |
| G9' | 5.5 | 21 |
| G10' | 1.0 | 18 |
| G11' | 2.0 | 39 |
| G12' | 3.0 | 36 |
| G13' | 2.5 | NOT TESTED |
| G14' | 15.0 | 44 |
| G15' | 3.4 | 41 |
| H1' | 4.9 | 22 |
| H2' | 6.9 | 15 |
| H3' | 2.0 | 22 |
| H4' | 0.6 | 21 |
| H5' | 5.5 | 14 |
| H6' | 6.5 | 21 |

TABLE 2-continued

| Example | D$_2$ Ki (nM) | D$_2$ Intrinsic Activity (%) |
|---|---|---|
| H7' | 3.9 | 17 |
| H8' | 3.5 | 32 |
| H9' | 0.6 | 31 |

The following Examples illustrate the preparation of several compounds of the present invention. Melting points are uncorrected. NMR data are reported in parts per million and are referenced to the deuterium lock signal from the sample solvent. Any reference to a "title compound" in an example, below, refers to the compound named in the title of that particular example.

EXAMPLES

Example A1

Synthesis of 7-{4-[4-(2,3-Dichloro-phenyl)-piperazin-1-yl]-butoxy}-3,4-dihydro-1H-[1,8]naphthyridin-2-one A first intermediate compound, 2-Benzyloxy-7-chloro-[1,8]naphthyridine, was produced, as follows. To a solution of benzyl alcohol (5.0 mL, 48.0 mmol) in THF (50 mL) cooled to 0° C. was added KOtBu (1M in THF, 46 mL, 46.0 mmol). The solution was stirred at 0° C. for 20 min and then added via cannula to a suspension of 2,7-dichloro-[1,8]naphthyridine (10.0 g, 50.2 mmol, J. Org. Chem. 1981, 46, 833) in DMF (50 mL) and THF (50 mL) cooled to 0° C. The orange suspension was stirred at 0° C. for 15 min and at room temperature for 30 min. The reaction was quenched with saturated NH$_4$Cl and H$_2$O. The mixture was extracted with EtOAc. The organic layer was filtered through celite to remove an orange clay-like precipitate. The organic layer was washed with H$_2$O and brine, and concentrated to give an orange solid. The solid was absorbed onto SiO$_2$ and purified by liquid chromatography (2% EtOAC/48% Hexanes/50% CH$_2$Cl$_2$) to give the first intermediate compound as a white solid (6.37 g, 23.5 mmol, 51%). MS: APCI: M+1: 271.0 (Exact Mass: 270.06).

A second intermediate compound, 2-Benzyloxy-7-(4-benzyloxy-butoxy)-[1,8]naphthyridine, was produced, as follows. To a solution of 4-benzyloxy-1-butanol (4.9 mL, 28.2 mmol, 1.2 equiv) in THF (20 mL) cooled to 0° C. was added KO$^t$Bu (1M in THF, 27 mL, 27 mmol, 1.15 equiv). The solution was stirred at 0° C. for 20 min and then added via cannula to a suspension of 2-benzyloxy-7-chloro-[1,8]naphthyridine (6.35 g, 23.5 mmol), produced as described above, in THF (70 mL), and cooled to 0° C. The reaction became homogenous. After 30 min at 0° C., saturated NH$_4$Cl and H$_2$O were added to quench the reaction. The mixture was extracted with EtOAc. The organic layer was washed with saturated NaHCO$_3$, H$_2$O and brine, dried over Na$_2$SO$_4$ and concentrated. The crude was absorbed onto SiO$_2$ and purified by liquid chromatography (10–15% EtOAc/Hexanes) to give the second intermediate compound as a yellow oil (4.64 g, 11.19 mmol, 48%). MS: APCI: M+1: 415.2 (Exact Mass: 414.19).

A third intermediate compound, 7-(4-Hydroxy-butoxy)-3,4-dihydro-1H-[1,8]naphthyridin-2-one, was produced, as follows. To a solution of 2-benzyloxy-7-(4-benzyloxy-butoxy)-[1,8]naphthyridine (4.64 g, 11.19 mmol) in MeOH (100 mL) was added 20% Pd/C (1.5 g) and the mixture was hydrogenated for 22 h. The reaction was filtered, concentrated and purified by liquid chromatography (5% MeOH/CH2Cl2) to give the title compound as a white solid (2.44 g, 10.33 mmol, 92%). MS: APCI: M+1: 237.1 (Exact Mass: 236.12).

The third intermediate compound was also prepared by hydrogenation of 7-(4-hydroxy-butoxy)-1H-[1,8]naphthyridin-2-one (an intermediate in Example B1, below).

A fourth intermediate compound, 4-(7-Oxo-5,6,7,8-tetrahydro-[1,8]naphthyridin-2-yloxy)-butyraldehyde, was produced using either a Dess-Martin oxidation reaction or a Swern oxidation reaction, as described below.

Dess-Martin oxidation: To a cloudy solution of the Dess-Martin periodinane (2.80 g, 6.60 mmol, 1.5 equiv) in CH$_2$Cl$_2$ (13 mL) was added a solution of 7-(4-hydroxy-butoxy)-3,4-dihydro-1H-[1,8]naphthyridin-2-one (1.04 g, 4.40 mmol) in CH$_2$Cl$_2$ (25 mL) via cannula. The reaction was stirred at room temperature for 5 h and stored in the freezer overnight. A 1:1 mixture of saturated Na$_2$S$_2$O$_3$ and saturated NaHCO$_3$ (50 mL) was added followed by Et$_2$O. The mixture was stirred for 10 min and then extracted with Et$_2$O/EtOAc (2:1). The organic layer was washed with saturated NaHCO$_3$ and brine, dried over Na$_2$SO$_4$ and concentrated to give the fourth intermediate compound as a pale yellow oil (1.06 g, used crude in next reaction). MS: APCI: M+1: 235.1 (Exact Mass: 234.10).

Swern oxidation: A solution of oxalyl chloride (9.97 mL, 112 mmol) in CH$_2$Cl$_2$ was cooled to −70° C. and DMSO (15.6 mL, 220 mmol) was carefully added. The solution was stirred at −60° C. for 10 min and then a solution of 7-(4-hydroxy-butoxy)-3,4-dihydro-1H-[1,8]naphthyridin-2-one (23 g, 97.5 mmol) in DMSO (70 mL) was added dropwise at ~50–~60° C. The reaction mixture was stirred at −60° C. for 20 min and then triethylamine (72 mL, 0.513 mol) was added dropwise. The reaction was warmed to room temp and stirred for 30 min. The mixture was poured into ice-water and the organic phase was separated. The aqueous phase was extracted with CH$_2$Cl$_2$, combined with the organic phase, washed with brine, dried over Na$_2$SO$_4$, and concentrated under vacuum to give the crude product. Purification by column chromatography (hexane:ethyl acetate 2:1) followed by recrystallization provided the fourth intermediate compound (12.7 g, 54.3 mmol, 56%).

In the final step of the synthesis reaction, the title compound, 7-{4-[4-(2,3-Dichloro-phenyl)-piperazin-1-yl]-butoxy}-3,4-dihydro-1H-[1,8]naphthyridin-2-one was produced as follows: To a solution of 4-(7-oxo-5,6,7,8-tetrahydro-[1,8]naphthyridin-2-yloxy)-butyraldehyde (1.06 g, crude from previous reaction) was added a solution of 2,3-dichlorophenylpiperazine (1.02 g, 4.40 mmol) in dichloroethane (5 mL). The solution was stirred for 15 min and NaBH(OAc)$_3$ (1.21 g, 5.72 mmol, 1.3 equiv) was added as a powder. The reaction was stirred at room temperature for 3 h and quenched with saturated NaHCO$_3$ and H$_2$O. The mixture was extracted with EtOAc. The organic layer was washed with saturated NaHCO$_3$, H$_2$O and brine, dried over Na$_2$SO$_4$ and concentrated to give a yellow foam/oil. Purification by liquid chromatography (4% MeOH/CH$_2$Cl$_2$) afforded the title compound as a white foam (1.20 g, 2.67 mmol, 61% over 2 steps). The HCl salt was formed by dissolving the title compound (800 mg, 1.78 mmol) in Et$_2$O (20 mL) and CH$_2$Cl$_2$ (2 mL) followed by the addition of 1N HCl in Et$_2$O (1.75 mL). The resulting white precipitate was collected by filtration, washed with Et$_2$O and dried to give a white solid (801 mg). MS: APCI: M+1: 449.1 (Exact Mass: 448.14).

A variation of this same method was used to produce other compounds as described in examples below, wherein other compounds were substituted for 2,3-dichlorophenylpiperazine in the final step of the synthesis procedure.

Example A2

Synthesis of 7-{4-[4-(2-Chloro-3-methyl-phenyl)-piperazin-1-yl]-butoxy}-3,4-dihydro-1H-[1,8]naphthyridin-2-one 7-{4-[4-(2-Chloro-3-methyl-phenyl)-piperazin-1-yl]-butoxy}-3,4-dihydro-1H-[1,8]naphthyridin-2-one was produced according to a process similar to that described in Example A1, except that in the final step of the synthesis procedure, 2-chloro-3-methylphenylpiperazine hydrochloride (506 mg, 2.05 mmol) was added to a solution of 4-(7-oxo-5,6,7,8-tetrahydro-[1,8]naphthyridin-2-yloxy)-butyraldehyde (approx. 1.9 mmol) in dichloroethane (10 mL), followed by the addition of $Et_3N$ (0.53 mL, 3.76 mmol, 2 equiv). $NaBH(OAc)_3$ (557 mg, 2.63 mmol, 1.4 equiv) was added as a powder. The reaction was stirred at room temperature (about 25° C.) for 4 hours and worked up as in Example A1.

Purification by liquid chromatography (3–4% MeOH/$CH_2Cl_2$) gave the title compound, as a white foam (430 mg, 1.00 mmol, 53% from the alcohol). The foam was dissolved in $Et_2O$ and a white solid crystallized (337 mg). MS: APCI: M+1: 429.2 (Exact Mass: 428.20).

Example A3

Synthesis of 7-{4-[4-(3-Chloro-2-methyl-phenyl)-piperazin-1-yl]-butoxy}-3,4-dihydro-1H-[1,8]naphthyridin-2-one The reductive amination procedure from Example A1 was followed, except that 2-chloro-3-methylphenylpiperazine was substituted for 2,3-dichlorophenylpiperazine in the final stage of the procedure.

Purification by liquid chromatography (3–4% MeOH/$CH_2Cl_2$) gave the title compound as a white foam (558 mg, 1.30 mmol). The foam was dissolved in $Et_2O$ and 1 N HCl in $Et_2O$ (1.3 mL) was added. The resulting white precipitate was collected by filtration, washed with $Et_2O$ and dried to give a white solid (538 mg). MS: APCI: M+1: 429.2 (Exact Mass: 428.20).

Example A4

Synthesis of 7-{4-[4-(2,3-Dimethyl-phenyl)-piperazin-1-yl]-butoxy}-3,4-dihydro-1H-[1,8]naphthyridin-2-one The reductive amination procedure from Example A1 was followed using 1-(2,3-dimethyl-phenyl)-piperazine to give the title compound. MS: APCI: M+1: 409.2 (Exact Mass: 408.25).

Example A5

Synthesis of 7-{4-[4-(2-Chloro-3-fluoro-phenyl)-piperazin-1-yl]-butoxy}-3,4-dihydro-1H-[1,8]naphthyridin-2-one The reductive amination procedure from Example A1 was followed using 1-(2-chloro-3-fluoro-phenyl)-piperazine to give the title compound (296 mg, 53%). MS: APCI: M+1: 433.2 (Exact Mass: 432.17).

Example A6

Synthesis of 7-{4-[4-(3-Chloro-2-fluoro-phenyl)-piperazin-1-yl]-butoxy}-3,4-dihydro-1H-[1,8]naphthyridin-2-one The reductive amination procedure from Example A1 was followed, using 1-(3-chloro-2-fluoro-phenyl)-piperazine to give the title compound. MS: APCI: M+1: 433.2 (Exact mass: 432.17).

Example A7

Synthesis of 7-{4-[4-(2-Chloro-3-trifluoromethyl-phenyl)-piperazin-1-yl]-butoxy}-3,4-dihydro-1H-[1,8]naphthyridin-2-one An intermediate, 1-(2-Chloro-3-trifluoromethyl-phenyl)-piperazine was produced as follows: To a stirred solution of trifluoro-methanesulfonic acid 2-chloro-3-trifluoromethyl-phenyl ester (5.0 g, 15.20 mmol) in toluene (50 mL) at room temperature, was added 1-boc-piperazine (3.39 g, 18.20 mmol), tris-(dibenzylideneacetone)di-palladium(0) ($Pd_2(dba)_3$) (3.49 g, 38.10 mmol), tert-2,2'-bis(diphenyl)phosphino-1,1'-binaphthyl (BINAP) (4.27 g, 68.60 mmol) and sodium tert-butoxide (2.04 g, 21.30 mmol). The mixture was degassed, filled with $N_2$, degassed and heated at 80° C. for 1.5 h. The mixture was diluted with ethyl acetate, celite was added and the mixture was stirred at room temperature for 15 min. It was filtered through a pad of silica gel and the pad was washed with additional amounts of ethyl acetate, The combined solvent was removed in vacuo and the residue was purified on a silica gel column using hexanes-ethyl acetate (5:1) as eluent to give 4-(2-chloro-3-trifluoromethyl-phenyl)-piperazine-1-carboxylic acid tert-butyl ester (2.30 g, 42%) as an oil. $^1$H NMR (400 MHz, $CDCl_3$): δ 7.35 (m, 2H), 7.22 (d, 1H), 3.62 (br s, 4H), 3.05 (br s, 4H), 1.55 (s, 9H).

To a stirred solution of 4-(2-chloro-3-trifluoromethyl-phenyl)-piperazine-1-carboxylic acid tert-butyl ester (2.0 g, 5.49 mmol) in dichloromethane (15 mL) cooled to 0° C., was added trifluoroacetic acid (6.26 g, 54.90 mmol). The resulting mixture was stirred at room temperature overnight and the solvent was removed in vacuo. Ether was added to the residue and the solid formed was filtered to give the intermediate compound (1.1 g, 55%) named immediately above. $^1$H NMR (400 MHz, $CDCl_3$): δ 9.85 (br s, 1H), 7.55 (d, 1H), 7.40 (d, 1H), 7.30 (m, 1H), 7.25 (s, 4H), 7.20 (s, 4H).

The reductive amination procedure from Example A1 was followed using 1-(2-chloro-3-trifluoromethyl-phenyl)-piperazine, the intermediate compound, to give the title compound (0.65 g, 71%). $^1$H NMR (400 MHz, $CDCl_3$): δ 7.65 (s, 1H), 7.40–7.20 (m, 3H), 6.40 (d, 1H), 4.25 (t, 2H), 3.15 (br s, 4H), 2.85 (t, 2H), 2.70 (br s, 4H), 2.45 (t, 2H), 1.80 (m, 2H), 1.65 (m, 2H). MS ES: m/z 483.01 $(M+H)^+$ (Exact mass: 482.17).

Example A8

Synthesis of 7-{4-[4-(2,3-Dichloro-4-fluoro-phenyl)-piperazin-1-yl]-butoxy}-3,4-dihydro-1H-[1,8]naphthyridin-2-one The reductive amination procedure from Example A1 was followed using 1-(2,3-dichloro-4-fluoro-phenyl)-piperazine to give the title compound. MS: APCI: M+1: 467.1 (Exact mass: 466.13).

Example A9

Synthesis of 7-{4-[4-(2-Chloro-4-fluoro-phenyl)-piperazin-1-yl]-butoxy}-3,4-dihydro-1H-[1,8]naphthyridin-2-one The reductive amination procedure from Example A1 was followed using 1-(2-chloro-4-fluoro-phenyl)-piperazine to give the title compound. MS: APCI: M+1: 433.2 (Exact mass: 432.17).

Example A10

Synthesis of 7-{4-[4-(2-Chloro-phenyl)-piperazin-1-yl]-butoxy}-3,4-dihydro-1H-[1,8]naphthyridin-2-one The reductive amination procedure from Example A1 was followed using 1-(2-chloro-phenyl)-piperazine to give the title compound. MS: APCI: M+1: 415.2 (Exact mass: 414.18).

Example A11

Synthesis of 7-[4-(4-Biphenyl-2-yl-piperazin-1-yl)-butoxy]-3,4-dihydro-1H-[1,8]naphthyridin-2-one The reductive amination procedure from Example A1 was followed using 1-biphenyl-2-yl-piperazine to give the title compound. MS: APCI: M+1: 457.3 (Exact mass: 456.25).

Example A12

Synthesis of 7-{4-[4-(2,5-Dichloro-phenyl)-piperazin-1-yl]-butoxy}-3,4-dihydro-1H-[1,8]naphthyridin-2-one The reductive amination procedure from Example A1 was followed using 1-(2,5-dichloro-phenyl)-piperazine to give the title compound (0.399 g, 82%). MS: APCI: M+1: 449.1 (Exact mass: 448.14).

Example A13

Synthesis of 7-{4-[4-(2-Chloro-4-fluoro-5-methyl-phenyl)-piperazin-1-yl]-butoxy}-3,4-dihydro-1H-[1,8]naphthyridin-2-one The reductive amination procedure from Example A1 was followed using 1-(2-chloro-4-fluoro-5-methyl-phenyl)-piperazine hydrochloride to give the title compound (0.277 g, 57%). MS: APCI: M+1: 447.2 (Exact mass: 446.19).

Example A14

Synthesis of 7-{4-[4-(5-Chloro-2-methyl-phenyl)-piperazin-1-yl]-butoxy}-3,4-dihydro-1H-[1,8]naphthyridin-2-one The reductive amination procedure from Example A1 was followed using 1-(5-chloro-2-methyl-phenyl)-piperazine to give the title compound (0.358 g, 77%). MS: APCI: M+1: 429.2 (Exact mass: 428.20).

Example A15

Synthesis of 7-{4-[4-(2-Chloro-4-fluoro-3-methyl-phenyl)-piperazin-1-yl]-butoxy}-3,4-dihydro-1H-[1,8]naphthyridin-2-one The reductive amination procedure from Example A1 was followed using 1-(2-chloro-4-fluoro-3-methyl-phenyl)-piperazine hydrochloride to give the title compound (0.463 g, 96%). MS: APCI: M+1: 447.2 (Exact mass: 446.19).

Example A16

Synthesis of 7-{4-[4-(3-Ethyl-phenyl)-piperazin-1-yl]-butoxy}-3,4-dihydro-1H-[1,8]naphthyridin-2-one The reductive amination procedure from Example A1 was followed using 1-(3-ethyl-phenyl)-piperazine to give the title compound. MS: APCI: M+1: 409.2 (Exact mass: 408.25).

Example A17

Synthesis of 7-{4-[4-(3-Chloro-2-methoxy-phenyl)-piperazin-1-yl]-butoxy}-3,4-dihydro-1H-[1,8]naphthyridin-2-one An intermediate compound 1-(3-Chloro-2-methoxy-phenyl)-piperazine, was produced as follows. A solution of 2,6-dichloroanisole (1.55 mL, 11.30 mmol) in dry toluene (40 mL) was degassed for 10 min by blowing nitrogen into the solution. This solution was then added via cannula to a flask containing Boc-piperazine 3.16 g, 16.90 mmol), $Cs_2CO_3$ (5.15 g, 15.80 mmol), $Pd_2(dba)_3$ (414 mg, 0.452 mmol, 4 mol %) and 2-dicyclohexylphosphino-2'-(N,N-dimethylamino)biphenyl (356 mg, 0.904 mmol, 8 mol %) under nitrogen. The reaction mixture was heated at 100° C. overnight (16 h). MS showed a small product peak and a large Boc-piperazine peak. TLC (10% EtOAc/Hex) showed a product spot. The reaction was allowed to cool to room temperature and $Et_2O$ was added. The mixture was filtered through Celite washing with $Et_2O$. The filtrate was washed 3 times with 0.5 M citric acid (to remove excess Boc-piperazine) and once with brine, dried over $MgSO_4$ and concentrated to give a brown oil. Purification by $SiO_2$ chromatography (10% EtOAC/Hexanes) gave 4-(3-chloro-2-methoxy-phenyl)-piperazine-1-carboxylic acid tert-butyl ester as a pale yellow solid (278 mg, 8%).

To a solution of 4-(3-chloro-2-methoxy-phenyl)-piperazine-1-carboxylic acid tert-butyl ester (273 mg, 0.835 mmol) in $CH_2Cl_2$ (4 mL) was added TFA (4 mL) at RT. The reaction was stirred at room temperature for 1 hour and concentrated to give a reddish brown oil. Purification by $SiO_2$ chromatography (10% MeOH/$CH_2Cl_2$ with 1% $NH_4OH$) gave 1-(3-Chloro-2-methoxy-phenyl)-piperazine as a pale yellow solid/oil (137 mg, 0.604 mmol, 72%). MS: APCI: M+1: 227.1 (Exact Mass: 226.09).

The reductive amination procedure from Example A1 was followed using 1-(3-chloro-2-methoxy-phenyl)-piperazine to give the title compound. MS: APCI: M+1: 445.2 (Exact Mass: 444.19).

Example A18

Synthesis of 7-{4-[4-(3-Methyl-2-phenoxy-phenyl)-piperazin-1-yl]-butoxy}-3,4-dihydro-1H-[1,8]naphthyridin-2-one The reductive amination procedure from Example A1 was followed using 1-(3-methyl-2-phenoxy-phenyl)-piperazine to give the title compound. MS: APCI: M+1: 487.2 (Exact Mass: 486.26).

Example A19

Synthesis of 7-{4-[4-(2,3-Dimethoxy-phenyl)-piperazin-1-yl]-butoxy}-3,4-dihydro-1H-[1,8]naphthyridin-2-one The reductive amination procedure from Example A1 was followed using 1-(2,3-dimethoxy-phenyl)-piperazine to give the title compound. MS: APCI: M+1: 441.6 (Exact Mass: 440.24).

Example A20

Synthesis of 7-{4-[4-(2-Ethoxy-phenyl)-piperazin-1-yl]-butoxy}-3,4-dihydro-1H-[1,8]naphthyridin-2-one The reductive amination procedure from Example A1 was followed using 1-(2-ethoxy-phenyl)-piperazine to give the title compound (475 mg, 87%). MS: APCI: M+1: 425.2 (Exact Mass: 424.25).

Example A21

Synthesis of 7-{4-[4-(2-Chloro-3-ethoxy-phenyl)-piperazin-1-yl]-butoxy}-3,4-dihydro-1H-[1,8]naphthyridin-2-one A first intermediate, 2-Chloro-3-ethoxy-nitro-benzene, was produced as follows: A slurry of 2-chloro-3-nitrophenol (5 g, 28.8 mmol), potassium carbonate (4.0 g, 28.8 mmol), and iodoethane (4.8 mL, 60 mmol) in acetonitrile (100 mL) was heated under reflux for 6 h. After cooling, the salts were removed by filtration and the filtrate concentrated to a solid. The solid was triturated in diethyl ether (100 mL). The triturant was concentrated to provide the first intermediate compound (6.5 g). Proton NMR indicated a spectrum consistent with that of the structure of the compound.

A second intermediate compound, 2-Chloro-3-ethoxy-aniline, was produced as follows: To a solution of 2-chloro-3-ethoxy-nitro-benzene (6.5 g, 28.8 mmol), water (50 mL), and glacial acetic acid (16.5 mL) in methanol (200 mL) was added Fe dust (16.1 g, 28.8 mmol). The slurry was heated under reflux for 90 minutes, cooled, and filtered. The filtrate was concentrated in vacuo to a solid which was triturated in water (~100 mL) to provide the acetate salt of the desired product. This salt, which was only sparingly soluble in water, was converted to the free base with $NaHCO_3$ and extracted into $CHCl_3$, dried over $Na_2SO_4$, and concentrated to provide the second intermediate compound (5 g). MS: APCI: M+1: 171.9 (Exact Mass: 171.05).

A third intermediate compound, 1-(2-Chloro-3-ethoxy-phenyl)-piperazine, was produced as follows: A mixture of 2-chloro-3-ethoxy-aniline (3.0 g, 17.5 mmol) and bis(2-chloroethyl)amine hydrochloride (3.12 g, 17.5 mmol) was heated under reflux in chlorobenzene (20 mL) for 48 h. Diethyl ether (200 mL) was added to the cooled solution to provide a crunchy solid that was collected by filtration. An aqueous solution of this material was treated with saturated NaHCO3, extracted into CHCl3, dried over Na2SO4, and concentrated to an oil which was purified by chromatography (MPLC, elution with 15% MeOH in CHCl3) to provide the third intermediate compound (3.5 g, 14.6 mmol, 83%) as an oil. MS: APCI: M+1: 241.1 (Exact Mass: 240.10).

Finally, a solution of 4-(7-oxo-5,6,7,8-tetrahydro-[1,8] naphthyridin-2-yloxy)-butyraldehyde (0.4 g, 1.17 mmol) and 1-(2-chloro-3-ethoxy-phenyl)-piperazine (0.445 g, 1.85 mmol) in 1,2-dichloroethane (30 mL) was stirred for 15 min before $NaBH(OAc)_3$ (0.46 g, 2.17 mmol) was added as a powder. The reaction was stirred at room temperature for 18 h and quenched with saturated $NaHCO_3$ and $H_2O$. The mixture was extracted with $CHCl_3$. The organic layer was washed with saturated $NaHCO_3$, $H_2O$ and brine, dried over $Na_2SO_4$ and concentrated to afford an oil. Purification by liquid chromatography (1% $MeOH/CH_2Cl_2$) gave the product as a white foam. Trituration of this foam in a minimal amount of diethyl ether provided the title compound as white crystals (300 mg, 0.655 mmol, 56%). mp 110–112° C. MS: APCI: M+1: 459.2 (Exact Mass: 458.21).

Example A22

Synthesis of 7-{4-[4-(2-Chloro-3-methoxy-phenyl)-piperazin-1-yl]-butoxy}-3,4-dihydro-1H-[1,8]naphthyridin-2-one 1-(2-Chloro-3-methoxy-phenyl)-piperazine was prepared according to the procedure for 1-(2-chloro-3-ethoxy-phenyl)-piperazine in Example A21.

The reductive amination procedure from Example A21 was followed using the 1-(2-chloro-3-methoxy-phenyl)-piperazine to give the title compound. MS: APCI: M+1: 445.6 (Exact Mass: 444.19).

Example A23

Synthesis of 7-{4-[4-(2-Chloro-3-isopropoxy-phenyl)-piperazin-1-yl]-butoxy}-3,4-dihydro-1H-[1,8] naphthyridin-2-one 1-(2-Chloro-3-isopropoxy-phenyl)-piperazine was prepared according to the procedure for 1-(2-chloro-3-ethoxy-phenyl)-piperazine in Example A21.

The reductive amination procedure from Example A21 was followed using 1-(2-chloro-3-isopropoxy-phenyl)-piperazine to give the title compound. MS: APCI: M+1: 473.2 (Exact Mass: 472.22).

Example A24

Synthesis of 7-{4-[4-(3-Methoxy-2-methyl-phenyl)-pierazin-1-yl]-butoxy}-3,4-dihydro-1H-[1,8]naphthyridin-2-one The reductive amination procedure from Example A1 was followed using 1-(3-methoxy-2-methyl-phenyl)-piperazine to give the title compound. MS: APCI: M+1: 425.2 (Exact Mass: 424.25).

Example A25

Synthesis of 7-{4-[4-(5-Chloro-2-isopropoxy-phenyl)-piperazin-1-yl]-butoxy}-3,4-dihydro-1H-[1,8]naphthyridin-2-one To a suspension of 4-(7-oxo-5,6,7,8-tetrahydro-[1,8]naphthyridin-2-yloxy)-butyraldehyde (0.241 g, 1.02 mmol, 1 eq) and 1-(5-chloro-2-isopropoxy-phenyl)-piperazine (0.382 g, 1.13 mmol, 1.1 eq) in dichloroethane (5 mL) was added $NaBH(OAc)_3$ (0.583 g, 2.75 mmol, 2.67 eq). The slurry was allowed to stir overnight at room temperature (18 h). Analysis by HPLC showed reaction mostly complete. The mixture was diluted with EtOAc and quenched with saturated $NaHCO_3$. The organic phase was then washed with brine, dried over $Na_2SO_4$, filtered and evaporated in vacuo. Purification by silica gel chromatography (100% EtOAc) followed by formation of the HCl salt using 1N HCl in ether provided the title compound (0.219 g, 25%). MS: APCI: M+1: 473.2 (Exact Mass: 472.22).

Example A26

Synthesis of 7-{4-[4-(2-Isopropoxy-phenyl)-piperazin-1-yl]-butoxy}-3,4-dihydro-1H-[1,8]naphthyridin-2-one The above reductive amination procedure in Example A25 using 1-(2-isopropoxy-phenyl)-piperazine provided the title compound (0.152 g, 32%). CHN found: C, 67.72; H, 7.81; N, 12.55. This calculates out for $C_{25}H_{34}N_4O_3$ plus 0.13 $H_2O$ (residual solvent).

Example A27

Synthesis of 7-{4-[4-(2-Isobutoxy-phenyl)-piperazin-1-yl]-butoxy}-3,4-dihydro-1H-[1,8]naphthyridin-2-one The above reductive amination procedure in Example A25 using 1-(2-isobutoxy-phenyl)-piperazine provided the title compound (0.177 g, 37%). CHN found: C, 63.22; H, 7.65; N, 11.19. This calculates out for $C_{26}H_{36}N_4O_3 \times 1.05HCl$.

Example A28

Synthesis of 7-{4-[4-(2-Acetyl-3-chloro-phenyl)-piperazin-1-yl]-butoxy}-3,4-dihydro-1H-[1,8]naphthyridin-2-one An intermediate compound, 1-(2-Chloro-6-piperazin-1-yl-phenyl)-ethanone, was produced as follows: To a 250 mL flask was added piperazine (72 g, 0.834 mol) and 1-(2-chloro-6-fluoro-phenyl)-ethanone (24 g, 0.139 mol) followed by heating to 120° C. for 2 hours. Excess piperazine was then distilled from the flask under vacuum leaving a brown oil which solidified. This oil (10 g) was purified by chromatography on silica gel (dichloromethane/methanol 98:2) to give the intermediate compound (4.89 g).

In a manner similar to that of other examples, above, 1-(2-chloro-6-piperazin-1-yl-phenyl)-ethanone was coupled by reductive amination to 4-(7-oxo-5,6,7,8-tetrahydro-[1,8]naphthyridin-2-yloxy)-butyraldehyde followed by typical workup and purification to give the title compound, mp 115° C. MS: APCI: M+1: 457.2 (Exact Mass: 456.19).

Example A29

Synthesis of 7-{4-[4-(3-Chloro-2-ethyl-phenyl)-piperazin-1-yl]-butoxy}-3,4-dihydro-1H-[1,8]naphthyridin-2-one An intermediate compound, 1-(3-Chloro-2-ethyl-phenyl)-piperazine hydrochloride, was produced as follows: To 1-(2-chloro-6-piperazin-1-yl-phenyl)-ethanone (2.45 g, 10.3 mmol) was added trifluoroacetic acid (18 g) and triethylsilane (18 g) followed by heating to reflux for 5 hours. Upon cooling, the solution was evaporated and the residue suspended in water. The pH was adjusted to 13 by addition of 4N NaOH followed by extraction with diethyl ether. The organic layer was dried over magnesium sulfate and evaporated to give a yellow oil which was distilled and crystallized as the hydrochloride salt from an ether solution by addition of ethereal HCl.

In a manner similar to that of other examples above, 1-(3-chloro-2-ethyl-phenyl)-piperazine hydrochloride was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 443.2 (Exact Mass: 442.21).

Example A30

Synthesis of 7-{4-[4-(2-Acetyl-3-fluoro-phenyl)-piperazin-1-yl]-butoxy}-3,4-dihydro-1H-[1,8]naphthyridin-2-one A first intermediate compound, 4-(2-Acetyl-3-fluoro-phenyl)-piperazine-1-carboxylic acid tert-butyl ester, was produced as follows: To acetonitrile (100 mL) was added boc-piperazine (28.63 g, 0.153 mol), 2,6-difluoroacetophenone (24 g, 0.154 mol), potassium carbonate (53 g, 0.384 mol) and potassium fluoride (8.93 g, 0.154 mol) followed by heating to 100° C. for 24 hours. Concentration of the solution in vacuo gave a mixture of solids which were isolated by filtration. The first intermediate compound was obtained by recrystallization from ethyl acetate, mp 88° C.

A second intermediate compound, 1-(2-Fluoro-6-piperazin-1-yl-phenyl)-ethanone, was produced as follows: To dichloromethane (10 mL) was added 4-(2-acetyl-3-fluoro-phenyl)-piperazine-1-carboxylic acid tert-butyl ester giving a solution. Trifluoroacetic acid (2.12 g) was added followed by stirring at 25° C. for 3 hours. The mixture was evaporated and the residue taken up into diethyl ether and water. The pH was then adjusted to 13 by addition of 4N NaOH and the ether phase was decanted. The ether phase was dried over magnesium sulfate, filtered and concentrated in vacuo to give the title compound as a white solid (1.09 g), mp 64° C.

In a manner similar to that of other examples above, 1-(2-fluoro-6-piperazin-1-yl-phenyl)-ethanone was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 441.3 (Exact Mass: 440.22).

Example A31

Synthesis of 7-{4-[4-(2-Ethyl-3-fluoro-phenyl)-piperazin-1-yl]-butoxy}-3,4-dihydro-1H-[1,8]naphthyridin-2-one An intermediate compound, 1-(2-Ethyl-3-fluoro-phenyl)-piperazine hydrochloride, was produced as follows: To 4-(2-acetyl-3-fluoro-phenyl)-piperazine-1-carboxylic acid tert-butyl ester (2.0 g, 6.2 mmol) was added trifluoroacetic acid (10.6 g) and triethylsilane (7.2 g) followed by heating to reflux for 5 hours. Upon cooling, the solution was evaporated and the residue suspended in water. The pH was adjusted to 13 by addition of 4N NaOH followed by extraction with diethyl ether. The organic layer was dried over magnesium sulfate and evaporated to give a yellow oil which was distilled and crystallized as the hydrochloride salt from an ether solution by addition of ethereal HCl giving the intermediate compound (0.907 g).

In a manner similar to that of other examples above, 1-(2-ethyl-3-fluoro-phenyl)-piperazine hydrochloride was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 427.2 (Exact Mass: 426.24).

Example A32

Synthesis of 7-{4-[4-(3-Acetyl-2-chloro-phenyl)-piperazin-1-yl]-butoxy}-3,4-dihydro-1H-[1,8]naphthyridin-2-one A first intermediate compound, 1-(3-Amino-2-chloro-phenyl)-ethanone, was produced as follows: To THF (400 mL) was added 1-(2-chloro-3-nitro-phenyl)-ethanone (13.1 g, 065.6 mmol, European Journal of Medicinal Chemistry, 1989, 24, 479–84) followed by Raney Nickel (2.0 g) and pressurization to 25 psi with hydrogen gas over 24 hours. The mixture was filtered and evaporated to an oil. The oil was resuspended in water and diethyl ether, filtered and the organic phase decanted. Addition of hexane gave a crystalline solid, which was filtered and dried in vacuo to give the first intermediate compound as a solid (9.3 g).

A second intermediate compound, 4-(3-Acetyl-2-chloro-phenyl)-piperazine-1-carboxylic acid tert-butyl ester, was produced as follows: In a manner similar to the preparation of 1-(6,7,8,9-tetrahydro-5H-benzocyclohepten-1-yl)-piperazine, 1-(3-amino-2-chloro-phenyl)-ethanone was converted to crude 1-(2-chloro-3-piperazin-1-yl-phenyl)-ethanone (8.51 g, 35.6 mmol) to which was added di-t-butyloxycarbonate (7.78 g, 35.6 mmol) as a solution in dichloromethane (40 mL). After 2 hours the mixture was concentrated and purified by chromatography on silica gel eluting with dichloromethane and ethyl acetate to give the second intermediate compound as an oil (4.96 g).

A third intermediate compound, 1-(2-Chloro-3-piperazin-1-yl-phenyl)-ethanone trifluoroacetate, was produced as follows: To dichloromethane (10 mL) was added 4-(3-acetyl-2-chloro-phenyl)-piperazine-1-carboxylic acid tert-butyl ester (1.01 g, 2.98 mmol) followed by trifluoroacetic acid (0.5 mL). The mixture was stirred at 25° C. for 2 hours, and the solvent removed by evaporation to give third intermediate compound as an oil.

In a manner similar to that of other examples above, 1-(2-chloro-3-piperazin-1-yl-phenyl)-ethanone trifluoroacetate was coupled by reductive amination to 4-(7-oxo-5,6,7,8-tetrahydro-[1,8]naphthyridin-2-yloxy)-butyraldehyde followed by typical workup and purification to give the title compound, mp 138–139° C. MS: APCI: M+1: 457.2 (Exact Mass: 456.19).

Example A33

Synthesis of 7-{4-[4-(3-Acetyl-phenyl)-piperazin-1-yl]-butoxy}-3,4-dihydro-1H-[1,8]naphthyridin-2-one The reductive amination procedure from Example A1 was followed using 1-(3-piperazin-1-yl-phenyl)-ethanone to give the title compound. MS: APCI: M+1: 423.2 (Exact Mass: 422.23).

Example A34

Synthesis of 7-{4-[4-(2-Acetyl-phenyl)-piperazin-1-yl]-butoxy}-3,4-dihydro-1H-[1,8]naphthyridin-2-one The reductive amination procedure from Example A1 was followed using 1-(2-piperazin-1-yl-phenyl)-ethanone to give the title compound. MS: APCI: M+1: 423.3 (Exact Mass: 422.23).

Example A35

Synthesis of 7-{4-[4-(2-Ethyl-phenyl)-piperazin-1-yl]-butoxy}-3,4-dihydro-1H-[1,8]naphthyridin-2-one The reductive amination procedure from Example A1 was followed using 1-(2-ethyl-phenyl)-piperazine to give the title compound. MS: APCI: M+1: 409.2 (Exact Mass: 408.25).

Example A36

Synthesis of 7-[4-(4-o-Tolyl-piperazin-1-yl)-butoxy]-3,4-dihydro-1H-[1,8]naphthyridin-2-one The reductive amination procedure from Example A1 was followed using 1-(2-methyl-phenyl)-piperazine to give the title compound. MS: APCI: M+1: 395.2 (Exact Mass: 394.24).

Example A37

Synthesis of 7-{4-[4-(2-Trifluoromethyl-phenyl)-piperazin-1-yl]-butoxy}-3,4-dihydro-1H-[1,8]naphthyridin-2-one The reductive amination procedure from Example A1 was followed using 1-(2-trifluoromethyl-phenyl)-piperazine to give the title compound. MS: APCI: M+1: 449.2 (Exact Mass: 448.21).

Example A38

Synthesis of 7-{4-[4-(3-Trifluoromethyl-phenyl)-piperazin-1-yl]-butoxy}-3,4-dihydro-1H-[1,8]naphthyridin-2-one The reductive amination procedure from Example A1 was followed using 1-(3-trifluoromethyl-phenyl)-piperazine to give the title compound. MS: APCI: M+1: 449.3 (Exact Mass: 448.21).

Example A39

Synthesis of 7-[4-(4-phenyl-piperazin-1-yl)-butoxy]-3,4-dihydro-1H-[1,8]naphthyridin-2-one The reductive amination procedure from Example A1 was followed using 1-phenyl-piperazine to give the title compound. MS: APCI: M+1: 381.1 (Exact Mass: 380.22).

Example A40

Synthesis of 7-{4-[4-(4-Fluoro-phenyl)-piperazin-1-yl]-butoxy}-3,4-dihydro-1H-[1,8]naphthyridin-2-one The reductive amination procedure from Example A1 was followed using 1-(4-Fluoro-phenyl)-piperazine to give the title compound. MS: APCI: M+1: 399.4 (Exact Mass: 398.21).

Example A41

Synthesis of 7-{4-[4-(2,4-Difluoro-phenyl)-piperazin-1-yl]-butoxy}-3,4-dihydro-1H-[1,8]naphthyridin-2-one The reductive amination procedure from Example A1 was followed using 1-(2,4-difluoro-phenyl)-piperazine to give the title compound. MS: APCI: M+1: 417.2 (Exact Mass: 416.20).

Example A42

Synthesis of 7-(4-{4-[2-(1,1-Difluoro-ethyl)-phenyl]-piperazin-1-yl}-butoxy)-3,4-dihydro-1H-[1,8]naphthyridin-2-one A first intermediate compound, 1-Bromo-2-(1,1-difluoro-ethyl)-benzene, was produced as follows: A solution of 1-(2-bromo-phenyl)-ethanone (3.98 g, 20 mmol) in DAST (5.3 mL, 40 mmol) was heated at 55° C. for 48 h, cooled to RT, diluted with CCl$_4$ (20 mL) and poured into ice (100 g). The mixture was extracted with CCl$_4$ (2×40 mL). The combined organic phases were dried, concentrated, and purified by chromatography on silica gel to give the first intermediate compound (2.2 g, 50%). $^1$H NMR (400 MHz, CDCl$_3$): δ 7.60 (m, 2H), 7.45 (t, 1H), 7.20 (m, 1H), 2.05 (t, 3H).

A second intermediate compound, 1-[2-(1,1-Difluoro-ethyl)-phenyl]-piperazine, was produced as follows: To a mixture of 1-bromo-2-(1,1-difluoro-ethyl)-benzene (1.3 g, 5.91 mmol), piperazine (0.64 g, 7.39 mmol), Pd$_2$(dba)$_3$ (1.30 g, 1.42 mmol), BINAP (0.82 g, 2.63 mmol), NaOtBu (0.80 g, 8.30 mmol) in toluene (40 mL) was bubbled N$_2$ gas for 10 min. The mixture was then heated at 110° C. for 2 h, cooled to RT, diluted with EtOAc (300 mL), filtered through a pad of celite and concentrated. The residue was treated with 1 N HCl to pH=2 and washed with ether (2×50 mL). The aqueous phase was basified with K$_2$CO$_3$ to pH=11 and extracted with CH$_2$Cl$_2$ (3×50 mL). The combined organic phases were dried and concentrated to give the second intermediate compound (0.80 g, 60%). $^1$H NMR (400 MHz, CDCl$_3$): δ 7.60 (m, 1H), 7.40 (m, 1H), 7.38 (m, 1H), 7.20 (m, 1H), 3.00 (m, 4H), 2.90 (m, 4H), 2.10 (t, 3H).

The reductive amination procedure from Example A1 was followed using 1-[2-(1,1-difluoro-ethyl)-phenyl]-piperazine to give the title compound (0.48 g, 91%). $^1$H NMR (400 MHz, DMSO-d$_6$): δ 10.40 (s, 1H), 10.20 (s, 1H), 7.50 (m, 4H), 7.35 (m, 1H), 6.40 (d, 1H), 4.20 (s, 2H), 3.60 (m, 2H), 3.30–3.00 (m, 8H), 2.80 (m, 2H), 2.50 (m, 2H), 2.10 (t, 3H), 1.90–1.70 (m, 4H).

Example A43

Synthesis of 7-[4-(4-Pyridin-2-yl-piperazin-1-yl)-butoxy]-3,4-dihydro-1H-[1,8]naphthyridin-2-one The reductive amination procedure from Example A1 was followed using 1-pyridin-2-yl-piperazine to give the title compound. MS: APCI: M+1: 382.1 (Exact Mass: 381.22).

Example A44

Synthesis of 7-{4-[4-(6-Methyl-pyridin-2-yl)-piperazin-1-yl]-butoxy}-3,4-dihydro-1H-[1,8]naphthyridin-2-one To a suspension of 1-(6-methyl-pyridin-2-yl)-piperazine bishydrochloride (0.77 g, 3.08 mmol) in dichloroethane (10 mL) was added Et$_3$N (1.0 mL, 7.17 mmol) and the mixture was stirred for 30 min. 4-(7-Oxo-5,6,7,8-tetrahydro-[1,8]naphthyridin-2-yloxy)-butyraldehyde (0.85 g, 3.63 mmol) was added as a solution in dichloroethane (3 mL) and the mixture was stirred at room temperature for 15 min. NaBH(OAc)$_3$ (1.1 g, 5.2 mmol) was added as a solid and the mixture was stirred at room temperature for 3 h. The reaction was poured into EtOAc and washed with saturated NaHCO$_3$ and brine, dried over MgSO$_4$ and concentrated. The residue was partitioned between EtOAc and pH 4.5 aqueous citric acid. The product went into the aqueous layer selectively over the impurities. The aqueous layer was neutralized with solid NaHCO$_3$ to pH 8 and extracted with EtOAc. The organic layer was washed with brine, dried over MgSO$_4$ and concentrated to give the title compound as a sticky foam (0.77 g). The foam was dissolved in Et$_2$O and treated with anhydrous HCl gas to give a white precipitate. The mixture was filtered, washed with Et$_2$O and hexanes, and dried to give a white solid (616 mg). MS: APCI: M+1: 396.1 (Exact Mass: 395.23).

Example A45

Synthesis of 7-{4-[4-(6-Ethyl-pyridin-2-yl)-piperazin-1-yl]-butoxy}-3,4-dihydro-1H-[1,8]naphthyridin-2-one To a solution of 1-(6-ethyl-pyridin-2-yl)-piperazine (0.41 g, 2.13 mmol) in dichloroethane (15 mL) was added Et$_3$N (0.22 g, 2.13 mmol) and the mixture was stirred for 5 min. 4-(7-Oxo-5,6,7,8-tetrahydro-[1,8]naphthyridin-2-yloxy)-butyraldehyde (0.50 g, 2.13 mmol) was added as a solution in dichloroethane (3 mL) and the mixture was stirred at room temperature for 15 min. NaBH(OAc)$_3$ (0.63 g, 3.00 mmol) was added as a solid and the reaction was stirred at room temperature for 2 h. The reaction was quenched with saturated NaHCO$_3$ and extracted with EtOAc. The organic layer was washed with brine, dried over MgSO$_4$ and concentrated. Purification by liquid chromatography (Biotage 40M, gradient elution 100% CH$_2$Cl$_2$ to 99% CH$_2$Cl$_2$/MeOH) afforded the title compound as a sticky white foam (413 mg, 1.01 mmol, 47%). The foam was dissolved in Et$_2$O and treated with anhydrous HCl gas to give a white precipitate. The mixture was filtered and dried to give a white powder (287 mg). MS: APCI: M+1: 410.3 (Exact Mass: 409.25).

Example A46

Synthesis of 7-{4-[4-(6-Cyclopropyl-pyridin-2-yl)-piperazin-1-yl]-butoxy}-3,4-dihydro-1H-[1,8]naphthyridin-2-one A mixture of 4-(7-oxo-5,6,7,8-tetrahydro-[1,8]naphthyridin-2-yloxy)-butyraldehyde (0.47 g, 2.0 mmol) and 1-(6-cyclopropyl-pyridin-2-yl)-piperazine (0.41 g, 2.0 mmol) in dichloroethane (12 mL) was stirred for 20 min and NaBH(OAc)$_3$ (0.55 g, 2.6 mmol) was added. The reaction was stirred at room temperature for 2.5 h. The reaction was quenched with saturated NaHCO$_3$ and extracted with Et$_2$O. The organic layer was washed with brine, dried over MgSO$_4$ and concentrated. Purification by liquid chromatography (Biotage 12M, eluted with CHCl$_3$) gave the title compound as an oil. The oil was dissolved in Et$_2$O and treated with anhydrous HCl gas to give a precipitate. The mixture was filtered, washed with Et$_2$O and hexanes and dried to give a white solid (121 mg). MS: APCI: M+1: 422.3 (Exact Mass: 421.25).

Example A47

Synthesis of 7-{4-[4-(4-Methyl-pyrimidin-2-yl)-piperazin-1-yl]-butoxy}-3,4-dihydro-1H-[1,8]naphthyridin-2-one In a manner similar to that of other examples above, 4-methyl-2-piperazin-1-yl-pyrimidine hydrochloride (U.S. Pat. No. 6,303,603) was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 397.2 (Exact Mass: 396.23).

Example A48

Synthesis of 7-[4-(4-Naphthalen-1-yl-piperazin-1-yl)-butoxy]-3,4-dihydro-1H-[1,8]naphthyridin-2-one The procedure in Example A1 was followed using 1-naphthalen-1-yl-piperazine hydrochloride. Purification by liquid chromatography (4% MeOH/CH$_2$Cl$_2$) gave the title compound as a white foam (595 mg, 1.38 mmol). The foam was dissolved in Et$_2$O and 1 N HCl in Et$_2$O (1.4 mL) was added. The resulting white precipitate was collected by filtration, washed with Et$_2$O and dried to give a white solid (600 mg). $^1$H NMR (400 MHz, d$_6$-dmso) δ 10.69 (bs, 1H), 10.26 (s, 1H), 8.10 (m, 1H), 7.88 (m, 1H), 7.63 (d, 1H), 7.52–7.41 (m, 4H), 7.14 (d, 1H), 6.34 (d, 1H), 4.20 (t, 2H), 3.59 (m, 2H), 3.39 (m, 4H), 3.22 (m, 4H), 2.75 (t, 2H), 2.44 (t, 2H), 1.87 (bm, 2H), 1.75 (m, 2H). MS: APCI: M+1: 431.2 (Exact Mass: 430.24).

Example A49

Synthesis of 7-{4-[4-(5,6,7,8-Tetrahydro-naphthalen-1-yl)-piperazin-1-yl]-butoxy}-3,4-dihydro-1H-[1,8]naphthyridin-2-one The procedure in Example A1 was followed using 1-(5,6,7,8-tetrahydro-naphthalen-1-yl)-piperazine. Purification by liquid chromatography (0–5% MeOH/CH$_2$Cl$_2$) gave the title compound as a white foam (668 mg, 1.53 mmol). The foam was dissolved in CH$_3$CN and a solid crashed out, which was collected by filtration, washed with Et$_2$O and dried to give a white solid (657 mg, 1.51 mmol, 52%). MS: APCI: M+1: 435.2 (Exact Mass: 434.27).

Example A50

Synthesis of 7-{4-[4-(3-Fluoro-5,6,7,8-tetrahydro-naphthalen-1-yl)-piperazin-1-yl]-butoxy}-3,4-dihydro-1H-[1,8]naphthyridin-2-one The reductive amination procedure from Example A1 was followed using 1-(3-fluoro-5,6,7,8-tetrahydro-naphthalen-1-yl)-piperazine to give the title compound (0.461 g; 72%). MS: APCI: M+1: 453.3 (Exact mass: 452.26).

Example A51

Synthesis of 7-{4-[4-(8-Oxo-5,6,7,8-tetrahydro-naphthalen-1-yl)-piperazin-1-yl]-butoxy}-3,4-dihydro-1H-[1,8]naphthyridin-2-one A first intermediate compound, 8-Hydroxy-3,4-dihydro-2H-naphthalen-1-one, was produced as follows: A solution of naphthalene-1,8-diol (1.00 g, 6.24 mmol, *J. Org. Chem.* 2002, 67, 5190) in ethanol (100 mL) was treated with 10% Pd/C (wet, 0.342 g), then hydrogenated at 50 psi H$_2$ for 3 hours. The mixture was filtered through a Celite pad and the pad was rinsed with ethanol. The filtrate was concentrated under vacuum to give a brown oil. The oil was purified by column chromatography (hexanes/ethyl acetate, 7:1) to afford the first intermediate compound (0.760 g, 78%) as a yellow liquid. $^1$H NMR (400 MHz, DMSO-d$_6$) δ 12.44 (s, 1H), 7.46 (t, 1H), 6.80 (d, 1H), 6.77 (d, 1H), 2.90 (t, 2H), 2.69 (t, 2H), 2.05–1.98 (m, 2H).

A second intermediate compound, trifluoro-methanesulfonic acid 8-oxo-5,6,7,8-tetrahydro-naphthalen-1-yl ester, was produced as follows: An ice-cold brown solution of 8-hydroxy-3,4-dihydro-2H-naphthalen-1-one (0.76 g, 4.68 mmol) in dichloromethane (25 mL) was treated with lithium chloride (0.20 g, 4.72 mmol), followed by triethylamine (0.65 mL, 4.66 mmol). Trifluoromethanesulfonic anhydride (0.8 mL, 4.76 mmol) was added dropwise to the mixture. After the exothermic reaction subsided, the resulting mixture was stirred at 0° C. for 1 hour, then quenched with water and extracted with dichloromethane. The extracts were dried over anhydrous Na$_2$SO$_4$, filtered and concentrated under vacuum to give a brown oil. The oil was purified by column chromatography (hexanes/ethyl acetate, 4:1) to afford the second intermediate compound (1.164 g, 84%) as a yellow liquid. $^1$H NMR (400 MHz, CDCl$_3$) δ 7.52 (t, 1H), 7.33 (d, 1H), 7.13 (d, 1H), 3.04 (t, 2H), 2.72 (t, 2H), 2.20–2.10 (m, 2H).

A third intermediate compound, 4-(8-Oxo-5,6,7,8-tetrahydro-naphthalen-1-yl)-piperazine-1-carboxylic acid tert-butyl ester, was produced as follows: Tetrahydrofuran (20 mL) was degassed with nitrogen for 15 minutes, then treated with 2-(di-tert-butylphosphino)biphenyl (0.304 g, 1.02 mmol) and degassed for another 5 minutes. To this mixture was added trifluoro-methanesulfonic acid 8-oxo-5,6,7,8-tetrahydro-naphthalen-1-yl ester (3.00 g, 10.20 mmol), Boc-piperazine (2.279 g, 12.20 mmol), and potassium phosphate (3.03 g, 14.27 mmol) followed by palladium acetate (0.228 g, 1.02 mmol) and the resulting mixture was degassed with nitrogen for 5 minutes. The brown suspension was heated at 80° C. for 3 days, then cooled to room temperature and diluted with ethyl acetate. The suspension was filtered through a Celite pad and the pad was rinsed with ethyl acetate. The filtrate was concentrated in vacuo to give a brown oil. The oil was purified by column chromatography (hexanes/ethyl acetate, 7:1 to 3:1 gradient) to afford the third intermediate compound (1.237 g, 37%) as a brown oil. $^1$H NMR (400 MHz, CDCl$_3$) δ 7.34 (t, 1H), 6.86 (t, 2H), 3.70–3.62 (m, 4H), 3.06–2.96 (m, 4H), 2.94 (t, 2H), 2.62 (t, 2H), 2.10–2.00 (m, 2H), 1.48 (s, 9H).

A fourth intermediate compound, 8-Piperazin-1-yl-3,4-dihydro-2H-naphthalen-1-one, was produced as follows: A brown solution of 4-(8-oxo-5,6,7,8-tetrahydro-naphthalen-1-yl)-piperazine-1-carboxylic acid tert-butyl ester (1.089 g, 3.30 mmol) in dichloromethane (10 mL) was treated with trifluoroacetic acid (5 mL, 64.9 mmol). The resulting mixture was stirred at room temperature for 1.5 hours. The dark brown solution was concentrated under vacuum to afford the fourth intermediate compound (1.03 g, quantitative) as a brown oil. $^1$H NMR (400 MHz, DMSO-d$_6$) δ 8.69 (br s, 2H), 7.43 (t, 1H), 6.96 (d, 2H), 3.31–3.23 (m, 4H), 3.16–3.11 (m, 4H), 2.91 (t, 2H), 2.54 (t, 2H), 1.99–1.91 (m, 2H).

The reductive amination procedure from Example A1 was followed using 8-piperazin-1-yl-3,4-dihydro-2H-naphthalen-1-one to give the title compound (0.411 g, 61%). $^1$H NMR (400 MHz, CDCl$_3$) δ 7.53 (br s, 1H), 7.36 (d, 1H), 7.32 (d, 1H), 6.88 (d, 1H), 6.81 (d, 1H), 6.35 (d, 1H), 4.22 (d, 2H), 3.14–3.05 (m, 4H), 2.92 (d, 2H), 2.85 (d, 2H), 2.75–2.67 (m, 4H), 2.67–2.59 (m, 4H), 2.49 (t, 2H), 2.08–2.00 (m, 2H), 1.84–1.75 (m, 2H), 1.75–1.66 (m, 2H). MS ES: 449.26 (M+H)$^+$ (Exact mass: 448.25).

Example A52

Synthesis of 7-{4-[4-(7,7-Dimethyl-8-oxo-5,6,7,8-tetrahydro-naphthalen-1-yl)-piperazin-1-yl]-butoxy}-3,4-dihydro-1H-[1,8]naphthyridin-2-one A first intermediate compound, 4-(7,7-Dimethyl-8-oxo-5,6,7,8-tetrahydro-naphthalen-1-yl)-piperazine-1-carboxylic acid tert-butyl ester, was produced as follows: To a stirred solution of compound 4-(8-oxo-5,6,7,8-tetrahydro-naphthalen-1-yl)-piperazine-1-carboxylic acid tert-butyl ester (1.25 g, 4.1 mmol) in anhydrous THF (20 mL) was added MeI (2.33 g, 16.4 mmol, 4.0 equiv). The reaction mixture was cooled to 0° C. and potassium tert-butoxide (1.4 g, 12.3 mmol, 3.0 equiv) was added. The reaction mixture was warmed to room temperature and stirred for 30 min. TLC indicated that the reaction was incomplete. Excess MeI (1.0 mL) was added and the stirring was continued at room temperature for an additional hour. The reaction mixture was quenched with water and extracted with ethyl acetate. The extracts were dried over Na$_2$SO$_4$ and concentrated to afford the first intermediate compound (1.20 g, 88%) as dark yellow thick oil which was carried to the next step without further purification. $^1$H NMR: δ (CDCl$_3$, 400 MHz) 7.30 (t, 1H), 6.90 (m, 2H), 3.70 (m, 4H), 3.00 (br s, 4H), 3.95 (t, 2H), 1.90 (t, 2H), 1.50 (s, 9H), 1.20 (s, 6H); ESMS: 359.23 (Exact mass: 358.23).

A second intermediate compound, 2,2-Dimethyl-8-piperazin-1-yl-3,4-dihydro-2H-naphthalen-1-one, was produced as follows: An ice cold solution of 4-(7,7-dimethyl-8-oxo-5,6,7,8-tetrahydro-naphthalen-1-yl)-piperazine-1-carboxylic acid tert-butyl ester (0.60 g, 1.8 mmol) in dichloromethane (10.0 mL) was treated with TFA (5.0 mL) and stirred for 2 h at room temperature. The solvents were removed under reduced pressure and purified by column chromatography eluting with 5% methanol in dichloromethane to afford the second intermediate compound (0.50 g, 77%) as yellow solid. $^1$H NMR: δ (CDCl$_3$, 400 MHz) 9.80 (br s, 2H), 7.30 (t, 1H), 6.90 (m, 2H), 3.50 (br s, 4H), 3.30 (br s, 4H), 3.00 (t, 2H), 1.90 (t, 3H), 1.20 (s, 6H); ESMS: 259.14 (Exact mass: 258.17).

The reductive amination procedure from Example A1 was followed using 2,2-dimethyl-8-piperazin-1-yl-3,4-dihydro-2H-naphthalen-1-one to give the title compound (0.20 g, 60%). $^1$H-NMR: δ (CDCl$_3$, 400 MHz) 7.80 (br s, 1H), 7.40–7.20 (m, 2H), 6.90 (d, 1H), 6.85 (d, 1H), 6.40 (d, 2H), 4.30 (m, 2H), 3.10 (br s, 4H), 3.00–2.80 (m, 4H), 2.80–2.60 (m, 6H), 2.50 (t, 2H), 1.90–1.60 (m, 6H), 1.15–1.05 (m, 6H); ESMS: 477.25 (Exact mass: 476.28).

Example A53

Synthesis of 7-{4-[4-(7,7-Dimethyl-5,6,7,8-tetrahydro-naphthalen-1-yl)-piperazin-1-yl]-butoxy}-3,4-dihydro-1H-[1,8]naphthyridin-2-one An intermediate compound, 1-(7,7-Dimethyl-5,6,7,8-tetrahydro-naphthalen-1-yl)-piperazine, was produced as follows: 2,2-Dimethyl-8-piperazin-1-yl-3,4-dihydro-2H-naphthalen-1-one (0.60 g, 1.8 mmol) was taken up in BF$_3$-OEt$_2$ (6.0 mL) and triethyl silane (1.8 mL, 10.8 mmol, 6.0 equiv) was added. The reaction mixture was heated in a sealed tube at 90° C. for 6 h. The sealed tube was cooled and excess ether was added to the reaction mixture. A white precipitate was formed which was collected by filtration. The intermediate compound product (0.40 g, quantitative) was used in the next step without purification. $^1$H-NMR: δ (CDCl$_3$, 400 MHz) 7.60 (d, 1H), 7.20 (m, 2H), 4.00 (m, 2H), 3.80 (m, 2H), 3.45 (m, 2H), 3.10 (m, 2H), 2.90 (t, 2H), 2.65 (s, 2H), 1.60 (t, 2H). ESMS: 245.17 (Exact mass: 244.19).

The reductive amination procedure from Example A1 was followed using 1-(7,7-dimethyl-5,6,7,8-tetrahydro-naphthalen-1-yl)-piperazine to give the title compound. $^1$H NMR: δ (CDCl$_3$, 400 MHz) 7.80 (br s, 1H), 7.40 (d, 1H), 7.10 (t, 1H), 6.90 (m, 2H), 6.40 (d, 1H), 4.15 (t, 2H), 2.95–2.45 (m, 16H), 1.80–1.70 (m, 4H), 1.50 (t, 2H), 1.25 (t, 2H), 1.00 (s, 6H). ESMS: 463.28 (Exact mass: 462.30).

Example A54

Synthesis of 7-{4-[4-(7,7-Difluoro-8-oxo-5,6,7,8-tetrahydro-naphthalen-1-yl)-piperazin-1-yl]-butoxy}-3,4-dihydro-1H-[1,8]naphthyridin-2-one A first intermediate compound, 4-(7,7-Difluoro-8-oxo-5,6,7,8-tetrahydro-naphthalen-1-yl)-piperazine-1-carboxylic acid tert-butyl ester, was produced as follows: 1M LiHMDS in THF (38.5 mL, 38.5 mmol) was cooled to −78° C. and 4-(8-oxo-5,6,7,8-tetrahydro-naphthalen-1-yl)-piperazine-1-carboxylic acid tert-butyl ester (3.64 g, 11 mmol) in THF (8 mL) was added dropwise. The reaction mixture was stirred at 0° C. for 2.5 h and re-cooled to −78° C. N-fluorobenzenesulfonimide (12.14 g, 38.5 mmol) in THF (25 mL) was added dropwise and the reaction was stirred overnight at room temperature. Saturated NH$_4$Cl solution was added and the mixture was extracted with Et$_2$O. Column chromatography of the orange oily material, eluting with EtOAc:Hex (2:8) and then changing to (2.5:7.5) gave the first intermediate compound (0.42 g) as a thick orange oil, along with a mixture of the title compound with monofluorinated compound (1.69 g). $^1$H NMR (400 MHz, CDCl$_3$) δ 7.42 (t, 1H), 6.91 (d, 1H), 6.83 (d, 1H), 3.72 (m, 4H), 3.16 (t, 2H), 3.11–2.96 (br s, 4H), 2.56–2.42 (m, 2H), 1.43 (s, 9H).

A second intermediate compound, 2,2-Difluoro-8-piperazin-1-yl-3,4-dihydro-2H-naphthalen-1-one, was produced as follows: To a solution of 4-(7,7-difluoro-8-oxo-5,6,7,8- tetrahydro-naphthalen-1-yl)-piperazine-1-carboxylic acid tert-butyl ester (0.42, 1.14 mmol) in methanol (10 mL) was added dropwise acetyl chloride (0.8 mL, 11.46 mmol). The reaction mixture was stirred overnight at room temperature. The solvent was evaporated under vacuum, and trituration with diethyl ether yielded the second intermediate compound (0.31 g, quant) as yellow solid. $^1$H NMR (400 MHz, DMSO-d$_6$) δ 7.58 (t, 1H), 7.06 (d, 1H), 7.03 (d, 1H), 3.34 (m, 6H), 3.21 (m, 4H), 3.11 (m, 2H).

The reductive amination procedure from Example A1 was followed using 2,2-difluoro-8-piperazin-1-yl-3,4-dihydro-2H-naphthalen-1-one to give the title compound. $^1$H-NMR (400 MHz, DMSO-d$_6$) δ 10.24 (s, 1H), 7.61 (t, 1H), 7.56 (d, 1H), 7.08 (d, 1H), 7.06 (d, 1H), 6.38 (d, 1H), 4.22 (t, 2H), 3.62 (m, 2H), 3.41–3.03 (m, 11), 2.78 (t, 2H), 2.62–2.42 (m, 4H) 1.98–1.74 (m, 4H).

Example A55

Synthesis of 7-{4-[4-(7,7-Difluoro-5,6,7,8-tetrahydro-naphthalen-1-yl)-piperazin-1-yl]-butoxy}-3,4-dihydro-1H-[1,8]naphthyridin-2-one A first intermediate compound, 4-(7,7-Difluoro-5,6,7,8-tetrahydro-naphthalen-1-yl)-piperazine-1-carboxylic acid tert-butyl ester, was produced as follows: An ice-cold solution of 4-(7-oxo-5,6,7,8-tetrahydro-naphthalen-1-yl)-piperazine-1-carboxylic acid tert-butyl ester (0.720 g, 2.20 mmol) in dichloromethane (10 mL) was treated with bis(2-methoxyethyl)aminosulfur trifluoride (1 mL, 5.40 mmol). The dark brown solution was warmed to room temperature and stirred overnight. The mixture was carefully diluted with water and extracted with dichloromethane. The extracts were dried over anhydrous Na$_2$SO$_4$, filtered and concentrated under vacuum to give a brown oil. The oil was purified by column chromatography (hexanes/ethyl acetate, 10:1) to afford the first intermediate compound (0.172 g, 22%) as a white solid. $^1$H NMR (400 MHz, CDCl$_3$) δ 7.19 (t, 1H), 6.98–6.92 (m, 2H), 3.66–3.40 (m, 4H), 3.24 (t 2H), 3.02 (t, 2H), 2.88–2.74 (m, 4H), 2.28–2.14 (m, 2H), 1.49 (s, 9H).

A second intermediate compound, 1-(7,7-Difluoro-5,6,7,8-tetrahydro-naphthalen-1-yl)-piperazine, was produced as follows: An ice-cold solution of methanol (3 mL) was treated with acetyl chloride (0.6 mL), then stirred at 0° C. for 15 minutes. 4-(7,7-Difluoro-5,6,7,8-tetrahydro-naphthalen-1-yl)-piperazine-1-carboxylic acid tert-butyl ester (0.172 g, 0.49 mmol) was added giving a clear yellow solution, which slowly clouded over time. After stirring at room temperature for 1.5 hours, the suspension was diluted with diethyl ether and the second intermediate compound (0.141 g, quantitative) was collected by vacuum filtration as a white solid. $^1$H NMR (400 MHz, DMSO-d$_6$) δ 9.04 (br s, 2H), 7.21 (t, 1H), 7.02–6.97 (m, 2H), 3.34–3.20 (m, 6H), 3.06–2.92 (m, 6H), 2.30–2.14 (m, 2H).

The reductive amination procedure from Example A1 was followed using 1-(7,7-difluoro-5,6,7,8-tetrahydro-naphthalen-1-yl)-piperazine to give the title compound (0.271 g, 92%). $^1$H NMR (400 MHz, CDCl$_3$) δ 7.57(br s, 1H), 7.36 (d, 1H), 7.17 (t, 1H), 7.00 (d, 1H), 6.92 (d, 1H), 6.36 (d, 1H), 4.23 (t, 2H), 3.22 (t, 2H), 3.01 (t, 2H), 2.95–2.83 (m, 6H), 2.70–2.58 (m, 6H), 2.49 (t, 2H), 2.26–2.13 (m, 2H), 1.86–1.75 (m, 2H), 1.74–1.64 (m, 2H). ES MS: 471.26 (M+1)$^+$ (Exact mass: 470.25).

Example A56

Synthesis of 7-{4-[4-(7-Oxo-5,6,7,8-tetrahydro-naphthalen-1-yl)-piperazin-1-yl]-butoxy}-3,4-dihydro-1H-[1,8]naphthyridin-2-one A first intermediate compound, 1-(7-Methoxy-5,8-dihydro-naphthalen-1-yl)-piperazine, was produced as follows: Ammonia (30 mL) was collected in a 3-neck 125 mL round bottom flask at −78° C. To this was added sequentially isopropanol (7 mL), 1-(7-methoxy-naphthalen-1-yl)-piperazine (3.0 g, 8.43 mmol), and tetrahydrofuran (7 mL). To the dark brown solution was added metallic sodium (795 mg, 35 mmol) portionwise over 10 minutes. The blue solution was stirred at −78° C. for 1 hour, then warmed to room temperature over 2 hours. Water (150 mL) was added and the mixture was stirred 10 minutes and the grey precipitate was filtered off and rinsed with water (2×20 mL) to yield the first intermediate compound (1.47 g, 71%) as a grey solid. $^1$H NMR (400 MHz, DMSO-d$_6$) δ 7.22 (t, 1H), 6.80–6.65 (m, 2H), 4.63 (t, 1H), 3.55 (s, 3H), 3.80–3.70 (m, 2H), 3.65–3.55 (m, 3H), 2.86 (t, 4H), 2.70 (t, 4H).

A second intermediate compound, 7-{4-[4-(7-Methoxy-5,8-dihydro-naphthalen-1-yl)-piperazin-1-yl]-butoxy}-3,4-dihydro-1H-[1,8]naphthyridin-2-one, was produced as follows: 1-(7-Methoxy-5,8-dihydro-naphthalen-1-yl)-piperazine (329 mg, 1.35 mmol) and 4-(7-oxo-5,6,7,8-tetrahydro-[1,8]naphthyridin-2-yloxy)-butyraldehyde (300 mg, 1.28 mmol) were dissolved in dichloroethane (10 mL). Triethylamine (329 mg, 3.85 mmol) was added and the mixture was stirred for 10 minutes. Sodium triacetoxyborohydride (285 mg, 1.35 mmol) was added and the mixture was stirred for 1 hour. The mixture was quenched with water (20 mL) and extracted with dichloromethane (20 mL). The organic layer was washed with brine (20 mL), dried over anhydrous sodium sulfate, filtered and evaporated. The crude solid was purified by column chromatography (5:95 methanol/ethyl acetate) to yield the second intermediate compound (330 mg, 56%) as a white foam. $^1$H NMR (400 MHz, CDCl$_3$) δ 7.55 (s, 1H), 7.36 (d, 1H), 7.17 (t, 1H), 7.00–6.85 (m, 2H), 6.38 (d, 1H), 4.80 (t, 1H), 4.20 (t, 2H), 3.60 (s, 3H), 3.50–3.45 (m, 2H), 3.44–3.38 (m, 2H), 3.00–2.90 (m, 4H), 2.88 (t, 2H), 2.70–2.50 (m, 6H), 2.50–2.40 (m, 2H), 1.85–1.55 (m, 4H).

7-{4-[4-(7-Methoxy-5,8-dihydro-naphthalen-1-yl)-piperazin-1-yl]-butoxy}-3,4-dihydro-1H-[1,8]naphthyridin-2-one (325 mg, 0.704 mmol) was dissolved in ethanol (5 mL) and 10% HCl (1 mL). The mixture was stirred at room temperature for 2 hours then quenched with saturated sodium bicarbonate (10 mL) and extracted with ethyl acetate (20 mL). The organic layer was washed with brine (20 mL), dried over anhydrous sodium sulfate, filtered and evaporated. The crude solid was purified by column chromatography (2:98 methanol/ethyl acetate) to yield the title compound (180 mg, 57%) as a white foam. $^1$H NMR (400 MHz, CDCl$_3$) δ 7.60 (s, 1H), 7.38 (d, 1H), 7.20 (t, 1H), 7.02–6.96 (m, 2H), 6.36 (d, 1H), 4.20 (t, 2H), 3.60 (s, 2H), 2.06 (t, 2H), 3.00–2.80 (m, 6H), 2.80–2.40 (m, 10H), 1.80–1.60 (4H); MS ES+ 449.06 (M+H)$^+$ (Exact mass: 448.25).

Example A57

Synthesis of 7-{4-[4-(7-Hydroxy-5,6,7,8-tetrahydro-naphthalen-1-yl)-piperazin-1-yl]-butoxy}-3,4-dihydro-1H-[1,8]naphthyridin-2-one To a solution of 7-{4-[4-(7-oxo-5,6,7,8-tetrahydro-naphthalen-1-yl)-piperazin-1-yl]-butoxy}-3,4-dihydro-1H-[1,8] naphthyridin-2-one (0.24 g, 0.54 mmol) in methanol (5 mL) was added portionwise $NaBH_4$ (0.081 g, 2.14 mmol). The reaction mixture was stirred at room temperature for 30 min and quenched with saturated $NH_4Cl$ solution and the compound was extracted with $CH_2Cl_2$ (2×20 mL). The organic layer was washed with brine (20 mL), dried over anhydrous $Na_2SO_4$, filtered and evaporated. The crude product was purified by column chromatography (10% methanol in ethyl acetate) to afford compound the title compound (0.16 g, 67%) as a white solid. $^1$H NMR (400 MHz, $CDCl_3$) δ 7.54 (s, 1H), 7.36 (d, 1H), 7.12 (t, 1H), 6.93–6.85 (m, 2H), 6.35 (d, 1H), 4.23 (t, 2H), 4.14–4.09 (m, 1H), 3.20–3.19 (m, 1H), 3.02–2.83 (m, 8H), 2.66–2.47 (m 10H), 1.83–1.67 (m, 6H). ES MS: 451.27 $(M+H)^+$ (Exact mass: 450.26).

Example A58

Synthesis of 7-{4-[4-(5-Oxo-5,6,7,8-tetrahydro-naphthalen-1-yl)-piperazin-1-yl]-butoxy}-3,4-dihydro-1H-[1,8]naphthyridin-2-one A first intermediate compound, 5-Amino-3,4-dihydro-2H-naphthalen-1-one, was produced as follows: 5-Nitro-3,4-dihydro-2H-naphthalen-1-one (*Chem. Pharm. Bull.* 1988, 36, 481) was dissolved in THF (400 mL) and RaNi (3 g) was added, followed by pressurization of the reaction vessel to 100 psi with hydrogen gas. Upon completion, the solution was evaporated in vacuo giving a solid, which was crystallized from dichloromethane/hexane to yield the first intermediate compound (16.54 g). mp 118–120° C.

A second intermediate compound, 3-[2-(5-Oxo-5,6,7,8-tetrahydro-naphthalen-1-ylamino)-ethyl]-oxazolidin-2-one, was produced as follows: According to a method described in the literature (Tetrahedron Lett. 1994, 35, 7331), to acetonitrile (300 mL) was added 5-amino-3,4-dihydro-2H-naphthalen-1-one (10 g), cesium carbonate (30.0 g) and toluene-4-sulfonic acid 2-(2-oxo-oxazolidin-3-yl)-ethyl ester (34 g) under nitrogen followed by heating at 100° C. for 48 hours. The solvent was removed in vacuo, and the residue was taken up in dichloromethane and diluted with brine. The dichloromethane phase was dried over sodium sulfate and charcoal. The filtrate was evaporated to an oil (17.7 g), which crystallized upon standing. Repeated trituration with diethyl ether selectively removed excess reagents and impurities. The remaining solid was dissolved in dichloromethane and chromatographed on silica gel (dichloromethane with a gradient to 4% methanol). The second intermediate compound crystallized from diethyl ether/dichloromethane (8.8 g).

A third intermediate compound, 5-Piperazin-1-yl-3,4-dihydro-2H-naphthalen-1-one, was produced as follows: 3-[2-(5-Oxo-5,6,7,8-tetrahydro-naphthalen-1-ylamino)-ethyl]-oxazolidin-2-one (8.6 g) was dissolved in 200 mL dichloromethane. The solution was sparged with anhydrous HBr gas, precipitating a yellow-green oil. The solution was evaporated to a yellow brittle foam. The foam was heated by oil bath to 175° C. for 1.5 hours. The foam melted and re-expanded as a brittle foam with off-gassing. This foam again melted and solidified. The residue was taken up into 200 mL of a 50:50 water:dichloromethane mixture. The solution was filtered, agitated and the dichloromethane phase was decanted. The pH of the aqueous phase was adjusted to 14 with 4N NaOH and the mixture was extracted with dichloromethane. The dichloromethane solution was dried over sodium sulfate and filtered thru a short plug of silica gel. The filtrate was evaporated to an oil (7.7 g). This was suspended in diethyl ether, filtered to remove minor insoluble material and sparged with anhydrous HCl gas to yield a solid precipitate. The suspension was filtered, washed with ether and dried in vacuo to give the third intermediate compound as the hydrochloride salt (5.55 g, 66%).

In a manner similar to that of other examples above, 5-piperazin-1-yl-3,4-dihydro-2H-naphthalen-1-one was coupled by reductive amination to 4-(7-oxo-5,6,7,8-tetrahydro-[1,8]naphthyridin-2-yloxy)-butyraldehyde followed by typical workup and purification to give the title compound, mp 169–170° C. MS: APCI: M+1: 449.2 (Exact Mass: 448.25).

Example A59

Synthesis of 7-{4-[4-(5,5-Difluoro-5,6,7,8-tetrahydro-naphthalen-1-yl)-piperazin-1-yl]-butoxy}-3,4-dihydro-1H-[1,8]naphthyridin-2-one A first intermediate compound, 5-Bromo-1,1-difluoro-1,2,3,4-tetrahydro-naphthalene, was produced as follows: A solution of 5-bromo-3,4-dihydro-2H-naphthalen-1-one (4.02 g, 17.86 mmol) and bis-(2-methoxyethyl)aminosulfur trifluoride (6.5 mL, 35.25 mmol) in a sealed plastic bottle was heated at 65° C. overnight. The brown solution was diluted with dichloromethane and washed with saturated sodium bicarbonate solution. The organic extract was dried over anhydrous $Na_2SO_4$, filtered and concentrated under vacuum to a brown oil. The oil was purified by column chromatography (hexane) to afford the first intermediate compound (1.749 g, 40%) as a yellow liquid. $^1$H NMR (400 MHz, $CDCl_3$) δ 7.78 (d, 1H), 7.68–7.60 (m, 1H), 7.18 (t, 1H), 2.85–2.79 (m, 2H), 2.31–2.19 (m, 2H), 2.06–1.98 (m, 2H).

A second intermediate compound, 1-(5,5-Difluoro-5,6,7,8-tetrahydro-naphthalen-1-yl)-piperazine, was produced as follows: A yellow solution of 5-bromo-1,1-difluoro-1,2,3,4-tetrahydro-naphthalene (1.024 g, 4.14 mmol) in toluene (20 mL) was degassed with nitrogen for 30 minutes. The solution was treated with 2-(dicyclohexylphosphino)biphenyl (0.145 g, 0.41 mmol) followed by piperazine (0.393 g, 4.56 mmol), sodium tert-butoxide (0.600 g, 6.22 mmol) and palladium acetate (0.093 g, 0.41 mmol). The resulting brown solution was degassed with nitrogen for 10 minutes, then heated at 110° C. for 1.5 hours. The mixture was cooled to room temperature, then filtered through a Celite pad. The pad was rinsed with dichloromethane and the filtrate was concentrated in vacuo to a brown liquid. The liquid was diluted with 3N HCl to pH 1 and then extracted with dichloromethane. The organic layer was discarded and the aqueous layer was basified with 2N KOH solution to pH 12. The aqueous layer was extracted with dichloromethane and the extracts were dried over anhydrous $Na_2SO_4$, filtered and concentrated in vacuo to afford the second intermediate compound (0.310 g, 30%) as a brown oil. $^1$H NMR (400 MHz, $CDCl_3$) δ 7.43 (d, 1H), 7.30 (t, 1H), 7.11 (d, 1H), 3.06–2.97 (m, 4H), 2.97–2.88 (m, 6H), 2.36–2.22 (m, 2H), 2.00–1.90 (m, 2H).

The reductive amination procedure from Example A1 was followed using 1-(5,5-difluoro-5,6,7,8-tetrahydro-naphthalen-1-yl)-piperazine to give the title compound (0.310 g, 60%). $^1$H NMR (400 MHz, CDCl$_3$) δ 7.58 (br s, 1H), 7.44 (d, 1H), 7.36 (d, 1H), 7.30 (t, 1H), 7.12 (d, 1H), 6.36 (d, 1H), 4.20 (t, 2H), 2.92 (t, 4H), 2.86 (t, 2H), 2.82–2.76 (m, 2H), 2.70–2.52 (m, 6H), 2.48 (t, 2H), 2.34–2.22 (m, 2H), 2.00–1.90 (m, 2H), 1.84–1.76 (m, 2H), 1.74–1.65 (m, 2H). ES MS: 471.12 (M+H)$^+$ (Exact mass: 470.25).

Example A60

Synthesis of 7-[4-(4-Indan-4-yl-piperazin-1-yl)-butoxy]-3,4-dihydro-1H-[1,8]naphthyridin-2-one The procedure in Example A1 was followed using 1-indan-4-yl-piperazine. Purification by liquid chromatography (0–5% MeOH/CH$_2$Cl$_2$) gave the title compound as a white foam (545 mg, 1.29 mmol, 48%). The foam was dissolved in Et$_2$O and 1 N HCl in Et$_2$O (1.3 mL) was added. The resulting white precipitate was collected by filtration, washed with Et$_2$O and dried to give a white solid (563 mg). MS: APCI: M+1: 421.5 (Exact Mass: 420.25).

Example A61

Synthesis of 7-{4-[4-(2-Oxo-indan-4-yl)-piperazin-1-yl]-butoxy}-3,4-dihydro-1H-[1,8]naphthyridin-2-one A first intermediate compound, 4'-Bromo-1',3'-dihydrospiro[[1,3]dioxolane-2,2'-indene], was produced as follows: To a stirred solution of 4-bromo-indan-2-one (2.20 g, 10.40 mmol) in benzene (60 mL) was added ethylene glycol and para-toluene sulfonic acid monohydrate (200 mg). The resulting mixture was heated at 110° C. for 40 h using Dean-Stark apparatus. The solvent was removed in vacuo, ethyl acetate was added and the solution was washed with saturated sodium bicarbonate solution, water and brine. It was dried (Na$_2$SO$_4$) and the solvent was removed in vacuo to give the title compound (2.40 g, 90%) as a liquid. $^1$H NMR (400 MHz, CDCl$_3$): 7.22 (d, 1H), 7.15 (d, 1H), 6.95 (m, 1H) 3.95 (s, 4H), 3.20 (s, 2H), 3.15 (s, 2H).

A second intermediate compound, 4-(1',3'-Dihydro-spiro[[1,3]dioxolane-2,2'-inden]-4'-yl)-piperazine-1-carboxylic acid tert-butyl ester, was produced as follows: To a stirred solution of 4'-bromo-1',3'-dihydro-spiro[[1,3]dioxolane-2,2'-indene] (2.12 g, 8.35 mmol) in toluene (40 mL) at room temperature, was added 1-boc-piperazine (1.86 g, 10.0 mmol), tris-(dibenzylideneacetone)di-palladium(0) (Pd$_2$(dba)$_3$, 1.91 g, 2.08 mmol), tert-2,2'-bis(diphenyl)phosphino-1,1'-binaphthyl (BINAP, 2.34 g, 3.76 mmol) and cesium carbonate (4.08 g, 12.52 mmol). The resulting mixture was degassed, filled with N$_2$, degassed and heated at 100° C. overnight. The mixture was diluted with ethyl acetate and filtered through a pad of celite. The filtrate was concentrated and the residue was purified by chromatography on silica (4:1 hexanes-ethyl acetate) to give the second intermediate compound (1.60 g, 40%) as an oil. $^1$H NMR (400 MHz, CDCl$_3$): δ: 7.18 (m, 1H), 6.90 (d, 1H), 6.75 (d, 1H), 4.05 (s, 4H), 3.58 (m, 4H), 3.20 (s, 2H), 3.10 (s, 2H), 2.95 (m, 4H), 1.50 (s, 9H).

A third intermediate compound, 4-Piperazin-1-yl-indan-2-one, was produced as follows: Trifluoroacetic acid-water (9:1, 50 mL) was added to 4-(1',3'-dihydro-spiro[[1,3]dioxolane-2,2'-inden]-4'-yl)-piperazine-1-carboxylic acid tert-butyl ester (1.65 g, 4.58 mmol) cooled to 0° C. The resulting mixture was stirred at 0° C. for 3 h and the solvent was removed in vacuo. Ether was added to the residue and the solid formed was filtered to give the third intermediate compound (1.20 g, 75%). $^1$H NMR (400 MHz, CD$_3$OD): δ: 7.30 (t, 1H), 7.15 (d, 1H), 7.05 (d, 1H), 3.58 (s, 2H), 3.55 (s, 2H), 3.30 (m, 4H), 3.20 (m, 4H).

The reductive amination procedure from Example A1 was followed using 4-piperazin-1-yl-indan-2-one to give the title compound. $^1$H NMR (400 MHz, CDCl$_3$): δ 7.55 (br s, 1H), 7.42 (d, 1H), 7.25 (t, 1H), 6.98 (d, 1H), 6.85 (d, 1H), 6.38 (d, 1H), 4.25 (t, 2H), 3.58 (s, 2H), 3.50 (s, 2H), 3.15 (br s, 4H), 2.90 (t, 2H), 2.60 (m, 6H), 2.45 (m, 2H), 1.80 (m, 2H), 1.65 (m, 2H). MS ES: m/z 435.19 (M+1)$^+$ (Exact mass: 434.23).

Example A62

Synthesis of 7-{4-[4-(2,2-Difluoro-indan-4-yl)-piperazin-1-yl]-butoxy}-3,4-dihydro-1H-[1,8]naphthyridin-2-one A first intermediate compound, 4-Bromo-2,2-difluoroindan, was produced as follows: To a stirred solution of 4-bromo-indan-2-one (5.0 g, 23.70 mmol) in dichloromethane (20 mL) cooled to 0° C. was added (diethylamino)sulfur trifluoride (DAST) (9.55 g, 59.30 mmol). The resulting mixture was stirred at room temperature overnight, diluted with additional dichloromethane (50 mL) and quenched with ice-water. The organic layer was separated, washed with saturated sodium bicarbonate solution, water, brine and dried (Na$_2$SO$_4$). The solvent was removed in vacuo and the residue was purified on a silica gel column using hexanes as eluent to give the first intermediate compound (2.54 g, 46%) as an oil. $^1$H NMR (400 MHz, CDCl$_3$): 7.40 (d, 1H), 7.15 (m, 2H), 3.49 (m, 4H).

A second intermediate compound, 4-(2,2-Difluoro-indan-4-yl)-piperazine-1-carboxylic acid tert-butyl ester, was produced as follows: To a stirred solution of 4-bromo-2,2-difluoro-indan (2.41 g, 10.34 mmol) in toluene (65 mL) at room temperature, was added 1-boc-piperazine (2.31 g, 12.42 mmol), tris-(dibenzylideneacetone)di-palladium(0) [Pd$_2$(dba)$_3$] (2.37 g, 2.58 mmol), tert-2,2'-bis(diphenyl)phosphino-1,1'-binaphthyl (BINAP) (2.90 g, 4.66 mmol) and cesium carbonate (4.77 g, 14.63 mmol). The mixture was degassed, filled with N$_2$, degassed and heated at 80° C. for 24 h. The mixture was diluted with ethyl acetate, filtered through a pad of silica gel and the pad was washed with additional amount of ethyl acetate. The combined solvent was removed in vacuo and the residue was purified on a silica gel column using hexanes:ethyl acetate (4:1) as eluent to give the title compound (1.40 g, 40%) as an oil. $^1$H NMR (400 MHz, CDCl$_3$): δ: 7.25 (m, 1H), 6.95 (d, 1H), 6.85 (d, 1H), 3.60 (m, 4H), 3.35 (m, 4H), 2.95 (m, 4H), 1.45 (s, 9H).

A third intermediate compound, 1-(2,2-Difluoro-indan-4-yl)-piperazine, was produced as follows: A solution of 4-(2,2-difluoro-indan-4-yl)-piperazine-1-carboxylic acid tert-butyl ester (0.10 g, 0.29 mmol) in methanol (30 mL) was added to a solution of acetyl chloride (0.35 g, 4.44 mmol) in methanol (50 mL), cooled to 0° C. The resulting mixture was stirred at room temperature overnight and the solvent was removed in vacuo. Diethyl ether was added to the residue and the resulting solid was filtered to give the title compound (0.07 g, 87%). 1H NMR (400 MHz, CD$_3$OD): δ: 7.50 (t, 1H), 7.15 (d, 1H), 6.90 (d, 1H), 3.45 (m, 4H), 3.35 (m, 4H), 3.15 (m, 4H).

The reductive amination procedure from Example A1 was followed using 1-(2,2-difluoro-indan-4-yl)-piperazine to give the title compound (0.360 g, 69%). ¹H NMR (400 MHz, CDCl₃): δ: 7.60 (br s, 1H), 7.39 (d, 1H), 7.25 (t, 1H), 6.96 (d, 1H), 6.85 (d, 1H), 6.39 (d, 1H), 4.26 (t, 2H), 3.35 (m, 4H), 3.15 (br s, 4H), 2.85 (m, 4H), 2.65 (m, 6H), 2.45 (m, 2H), 1.85 (m, 1H), 1.65 (m, 1H). MS ES: m/z 457.10 (M+H)⁺ (Exact mass: 456.23).

Example A63

Synthesis of 7-{4-[4-(6,7,8,9-Tetrahydro-5H-benzocyclohepten-1-yl)-piperazin-1-yl]-butoxy}-3,4-dihydro-1H-[1,8]naphthyridin-2-one A first intermediate compound, 1-Nitro-6,7,8,9-tetrahydro-benzocyclohepten-5-one, was produced as follows: To 250 g (1.56 mmol) of 1-benzosuberone in 5000-mL 4-neck round bottom flask with nitrogen inlet, mechanical stirring, and thermocouple was added 1560 mL of chloroform and 125 g (1.56 mmol) of ammonium nitrate. After the solution was cooled to −15° C., 780 mL (1160 g, 5.52 mmol) of trifluoroacetic anhydride was added dropwise keeping the temperature below −15° C. A white suspension formed. The reaction was stirred at −15° C. for 1 h and then allowed to warm to room temperature and stir for 16 h. The clear orange solution was poured over 7.8 L of water and then extracted with two 4000-mL portions of dichloromethane. The combined organic layers were washed with 4000 mL of saturated aqueous sodium bicarbonate and 4000 mL of brine, dried (Na₂SO₄), and concentrated in vacuo to give a mixture of C-8 nitration/C-6 nitration/starting material—3:1:1. This material was combined with material from 64-g and 250-g runs was taken up in approximately 2.5 L of heptane and brought to near reflux. The solid product became an oil on heating. Enough ethyl acetate was added to get the oil into solution. The solution was allowed to cool to room temperature and sit overnight. Crystals, which formed on the sides of the flasks, were determined to be mainly the C-8 isomer. The mother liquor was separated and concentrated in vacuo to give C-8 nitration/C-6 nitration/starting material—1:1:0.7. The residual solid was purified by flash column chromatography on 3000 g of silica (loaded with dichloromethane and eluted with 15% ethyl acetate-heptane) to give 82.9 g of product. This material was recrystallized with heptane-ethyl acetate (just enough ethyl acetate to keep the product from oiling out) to give 51.0 g of the title compound as pale yellow needles. The material obtained from the mother liquor was then recrystallized to give another 7.1 g of the title compound as yellow needles.

A second intermediate compound, 6,7,8,9-Tetrahydro-5H-benzocyclo-hepten-1-ylamine, was produced, as follows: TFA (10 mL) was added to a 50 mL flask and cooled in a CO₂/acetone bath. 1-Nitro-6,7,8,9-tetrahydro-benzocyclohepten-5-one (1.8 g) was added followed by triethylsilane (10 mL). The mixture was warmed to 55° C. After 5 hours, the mixture was evaporated to a residue under high vacuum at 70° C. The residue was taken up into hexane, filtered and washed with 2N HCl. The hexane layer was washed with brine, dried over sodium sulfate and evaporated to an oil (2.7 g), which contained a mixture of products. This material was dissolved in methanol and 10% Pd/C (0.6 g) was added. The mixture was pressurized to 50 psi with hydrogen gas for 2 hours, after which the mixture was filtered and evaporated to an oil (2.46 g). The oil was chromatographed on silica gel (gradient of 100% hexane to 60% ethyl acetate) to give the second intermediate compound as an oil which was crystallized from ether (0.66 g), mp 107–111° C.

A third intermediate compound, 1-(6,7,8,9-Tetrahydro-5H-benzocyclo-hepten-1-yl)-piperazine, was produced as follows: 6,7,8,9-Tetrahydro-5H-benzocyclohepten-1-ylamine (0.617 g) and bis-dichloroethyl amine HCl (1.3 g) were added to a sealable tube. Chlorobenzene (3 mL), hexanol (1 mL) and diisopropylethylamine (2 mL) were added. The solution was warmed to 45° C. for 3 hours, then warmed to 95° C. overnight. The mixture was evaporated to give a syrup, which was taken up into dichloromethane and washed twice with water. The dichloromethane layer was dried over sodium sulfate and evaporated to an oil (0.88 g). The oil was chromatographed on silica gel and recrystallized from dichloromethane and ether to give the title compound (0.183 g).

In a manner similar to that of other examples above, 6,7,8,9-tetrahydro-5H-benzocyclohepten-1-ylamine (0.178 g) was coupled by reductive amination to 4-(7-oxo-5,6,7,8-tetrahydro-[1,8]naphthyridin-2-yloxy)-butyraldehyde followed by typical workup and purification to give the title compound as the hydrochloride salt (0.109 g). MS: APCI: M+1: 449.3 (Exact Mass: 448.26).

Example A64

Synthesis of 7-[4-(4-Naphthalen-1-yl-piperidin-1-yl)-butoxy]-3,4-dihydro-1H-[1,8]naphthyridin-2-one 7-[4-(4-Naphthalen-1-yl-piperidin-1-yl)-butoxy]-3,4-dihydro-1H-[1,8]naphthyridin-2-one was produced according to a process similar to that described in Example A1, using 4-naphthalen-1-yl-piperidine hydrochloride. Purification by liquid chromatography (5% MeOH/CH₂Cl₂ with 0.8% NH₄OH) gave the title compound as a white foam (474 mg, 1.10 mmol). The foam was dissolved in Et₂O/CH₂Cl₂ and 1 N HCl in Et₂O (1.1 mL) was added. The resulting white precipitate was collected by filtration, washed with Et₂O and dried to give a white solid (466 mg). MS: APCI: M+1: 430.4 (Exact Mass: 429.24).

Example A65

Synthesis of 7-{4-[4-(7-Fluoro-naphthalen-1-yl)-piperazin-1-yl]-butoxy}-3,4-dihydro-1H-[1,8]naphthyridin-2-one A first intermediate compound, Trifluoro-methanesulfonic acid 7-fluoro-3,4-dihydro-naphthalen-1-yl ester, was produced as follows: 7-Fluoro-1-tetralone (1.0 g, 6.10 mmol, prepared according to *J. Am. Chem. Soc.* 1967, 89, 386) was dissolved in tetrahydrofuran (20 mL) then cooled to −78° C. To this solution was added lithium hexamethyldisilazane (7.32 mL, 7.32 mmol, 1.0 M in tetrahydrofuran) over 5 minutes. The mixture was stirred at −78° C. for 1 hour, and then N-phenyl triflamide (2.62 g, 7.32 mmol) was added in one portion. The mixture was allowed to warm to room temperature and stirred for 2 hours. The mixture was evaporated, dissolved in ethyl acetate (20 mL) and washed with 1N sodium hydroxide (20 mL), water (20 mL), and brine (20 mL). The organic layer was dried over anhydrous sodium sulfate, filtered and evaporated in vacuo. The crude oil was filtered through a short plug of silica gel, eluting with 9:1 hexanes/ethyl acetate to yield the first intermediate compound (2.06 g crude, quant.) as a yellow oil. ¹H NMR (400 MHz, CDCl₃) δ 7.20–7.10 (m, 1H), 7.04 (d, 1H), 6.98–6.90 (m, 1H), 6.05 (d, 1H), 2.82 (t, 2H), 2.58–2.46 (m, 2H).

A second intermediate compound, Trifluoro-methanesulfonic acid 7-fluoro-naphthalen-1-yl ester, was produced as follows: Trifluoro-methanesulfonic acid 7-fluoro-3,4-dihydro-naphthalen-1-yl ester (2.06 g, 6.96 mmol) was dissolved in dioxane (20 mL) and 2,3-dichloro-5,6-dicyano-1,4-benzoquinone (2.37 g, 10.44 mmol) was added. The mixture was refluxed for 36 hours and then cooled to room temperature. The mixture was evaporated in vacuo to a solid and purified by column chromatography (hexanes) to yield the title compound (1.48 g, 72%) as a red solid. $^1$H NMR (400 MHz, CDCl$_3$) δ 7.98–7.82 (m, 2H), 7.66 (d, 1H), 7.56–7.40 (m, 3H).

A third intermediate compound, 4-(7-Fluoro-naphthalen-1-yl)-piperazine-1-carboxylic acid tert-butyl ester, was produced as follows: Trifluoro-methanesulfonic acid 7-fluoro-naphthalen-1-yl ester (1.48 g, 5.03 mmol) and 1-Boc-piperazine (1.13 g, 6.04 mmol) were dissolved in toluene (10 mL) and the mixture was degassed for 30 minutes. To this was added 2-(dicyclohexylphosphino)-biphenyl (176 mg, 0.50 mmol), palladium acetate (113 mg, 0.50 mmol), and sodium tert-butoxide (677 mg, 7.04 mmol). The mixture was stirred at 80° C. for 16 hours and then cooled to room temperature. The mixture was washed with water (20 mL) and brine (20 mL), dried over anhydrous sodium sulfate, filtered and concentrated in vacuo. The crude oil was filtered through a short plug of silica gel, eluting with 3:1 hexanes/ethyl acetate to yield the title compound (900 mg, 54%) as a brown oil.

A fourth intermediate compound, 1-(7-Fluoro-naphthalen-1-yl)-piperazine, was produced as follows: 4-(7-Fluoro-naphthalen-1-yl)-piperazine-1-carboxylic acid tert-butyl ester (900 mg, 2.73 mmol) was dissolved in dichloromethane (10 mL) and trifluoroacetic acid (2 mL). The mixture was stirred at room temperature for 3 hours then diluted with diethyl ether. The solid was filtered off and washed with diethyl ether (2×20 mL) to yield the title compound as the TFA salt (415 mg, 1.21 mmol, 44%) as a grey powder. $^1$NMR (400 MHz, dmso-d$_6$) δ 8.80 (s, 1H), 8.04 (t, 1H), 7.82 (d, 1H), 7.58 (d, 1H), 7.44 (t, 2H), 7.24 (d, 1H), 3.40–3.30 (m, 4H), 3.20–3.00 (m, 4H).

The reductive amination procedure from Example A1 was followed using 1-(7-fluoro-naphthalen-1-yl)-piperazine to give the title compound. $^1$NMR (400 MHz, dmso-d$_6$) δ 10.25 (s, 1H), 8.00 (t, 1H), 7.80–7.60 (m, 2H), 7.46–7.40 (m, 3H), 7.20 (d, 1H), 6.38 (d, 1H), 4.20 (t, 2H), 3.06–2.90 (m, 4H), 2.80 (t, 2H), 2.80–2.60 (m, 4H), 2.50–2.40 (m, 4H), 1.80–1.70 (m, 2H), 1.64–1.55 (m, 2H), MS ES+ 449.31 (M+1)$^+$ (Exact mass: 448.23).

Example A66

Synthesis of 7-{4-[4-(8-Fluoro-naphthalen-1-yl)-piperazin-1-yl]-butoxy}-3,4-dihydro-1H-[1,8]naphthyridin-2-one A first intermediate compound, 8-Bromo-naphthalen-1-ylamine, was produced as follows: 8-Bromo-naphthalene-1-carboxylic acid (10.0 g, 39.8 mmol) was taken up in CHCl$_3$ (60 mL) and conc. H$_2$SO$_4$ (20 mL) were added. The mixture was stirred at 45° C. until all the compound was dissolved. NaN$_3$ (15.52 g, 240.0 mmol, 6.0 equiv) was then added in portions, each successive portion was added after the effervescence resulting from the previous addition had subsided. The mixture was stirred for 2 h at 45° C. and added to water (100 mL). The mixture was made alkaline with aqueous ammonia and extracted with dichloromethane (4×30 mL). The combined extracts were dried over Na$_2$SO$_4$ and evaporated to give the title compound as a dark crystalline solid (8.5 g, 96%). $^1$H NMR (400 MHz, CDCl$_3$): δ 7.70 (d, 1H), 7.65 (d, 1H), 7.30 (d, 2H), 7.05 (t, 1H), 6.65 (m, 1H), 5.20 (br s, 2H). MS (ES+): 221.99 (M$^+$), 223.99 (M$^{+2}$).

A second intermediate compound, 1-Bromo-8-fluoro-naphthalene, was produced as follows: To a cooled solution of 8-bromo-naphthalen-1-ylamine (8.0 g, 36.0 mmol) in THF (10 mL) was added 48% HBF$_4$ (50 mL) at 0° C. and the mixture was stirred for 10 min. A solution of NaNO$_2$ (7.5 g, 108.1 mmol, 3.0 equiv) in water (20 mL) was added and the stirring was continued for 1 h at 0° C., then NaBF$_4$ (20.0 g, 180.0 mmol, 5.0 equiv) was added. The mixture was allowed to warm to room temperature and stir for 1 h. The reaction was filtered and the solid was washed with ether and dried overnight under high vacuum to give a gray solid. This solid was taken up in chlorobenzene (30 mL) and refluxed for 3 h. The solvent was removed under reduced pressure and the dark residue was triturated with hexane. The yellow colored hexane layer was decanted and trituration with hexane was repeated several times until the hexane layer became colorless. The combined hexane portions were concentrated to give the second intermediate compound as a dark yellow oil (5.6 g, 69%). $^1$H NMR (400 MHz, CDCl$_3$): δ 7.78 (m, 2H), 7.60 (d, 1H), 7.35–7.15 (m, 3H).

A third intermediate compound, 1-(8-Fluoro-naphthalen-1-yl)-piperazine, was produced as follows: A solution of Pd(OAc)$_2$ (0.25 g, 1.11 mmol, 0.1 equiv)) and dicyclohexylphosphino-biphenyl (0.39 g, 1.11 mmol, 0.1 equiv) in toluene (20 mL) was degassed by bubbling N$_2$ gas for 1 h. 1-Bromo-8-fluoro-naphthalene (2.5 g, 11.1 mmol) in toluene (10 mL) and 1-Boc-piperazine (2.5 g, 13.3 mmol, 1.2 equiv) were added followed by NaO$^t$Bu (1.6 g, 16.66 mmol, 1.5 equiv). The mixture was stirred at 80° C. for 18 h. The solvent was removed under reduced pressure and the residue was taken in dichloromethane and filtered through a celite pad. The celite was rinsed with dichloromethane and the combined filtrates were concentrated. The residue was purified by silica gel chromatography (20% ethyl acetate in hexane) to give 4-(8-fluoro-naphthalen-1-yl)-piperazine-1-carboxylic acid tert-butyl ester as a dark oil (1.4 g, 38%). $^1$H NMR (400 MHz, CDCl$_3$): δ 7.60 (d, 1H), 7.50 (d, 1H), 7.40 (m, 1H), 7.10 (m, 2H), 6.95 (d, 1H), 4.50–4.00 (br s, 2H), 3.40–3.20 (m, 4H), 2.80–2.60 (m, 2H), 1.50 (s, 9H). MS (ES+): 331.08 (M+H)$^+$.

4-(8-Fluoro-naphthalen-1-yl)-piperazine-1-carboxylic acid tert-butyl ester (1.4 g, 4.2 mmol) was dissolved in dichloromethane (10 mL) and TFA (10 mL) was added at 0° C. The mixture was allowed to warm to room temperature and stir for 1 h. The solvents were removed under reduced pressure and the residue was purified by silica gel chromatography (5% methanol in dichloromethane) to give the third intermediate compound as a TFA salt (1.3 g, 89%). $^1$H NMR (400 MHz, CDCl$_3$): δ 7.65–7.58 (m, 2H), 7.40 (m, 2H), 7.10–7.00 (m, 2H), 3.60–3.40 (m, 6H), 3.40–3.20 (m, 2H). MS (ES+): 231.11 (M+H)$^+$.

The reductive amination procedure from Example A1 was followed using 1-(8-fluoro-naphthalen-1-yl)-piperazine. 1H NMR (400 MHz, CDCl$_3$): δ 7.60 (m, 2H), 7.50 (m, 1H), 7.40 (m, 3H), 7.10–7.00 (m, 2H), 6.28 (d, 1H), 4.25 (t, 2H), 3.40–3.30 (m, 2H), 3.05–2.80 (m, 6H), 2.65 (t, 2H), 2.60–2.40 (m, 4H), 1.80–1.60 (m, 4H). MS (ES+): 449.19 (M+H)+ (Exact mass: 448.23).

Example A67

Synthesis of 7-{4-[4-(6-Fluoro-naphthalen-1-yl)-piperazin-1-yl]-butoxy}-3,4-dihydro-1H-[1,8]naphthyridin-2-one A first intermediate compound, 6-Fluoro-1-tetralone, was produced as follows: 6-Amino-3,4-dihydro-2H-naphthalen-1-one (6.45 g, 40.1 mmol) was dissolved in a mixture of hydrochloric acid (9 mL) and water (6 mL) and cooled to 0° C. A solution of sodium nitrite (2.90 g, 42.0 mmol) in water (4 mL) was added dropwise to the mixture and tetrafluoroboric acid (8.0 g, 44.0 mmol, 5.71 mL, 48% in water) was added. The mixture was allowed to stand at 0° C. for 30 minutes and then cooled to −30° C. The precipitate was filtered off and rinsed with cold methanol (10 mL), and then with cold diethyl ether (10 mL) to yield the diazonium salt (6.0 g, 58%) as a brown solid. $^1$H NMR (400 MHz, dmso-$d_6$) δ 8.70 (s, 1H), 8.59 (d, 1H), 8.30 (d, 1H), 3.10 (t, 2H), 2.78 (t, 2H), 2.20–2.06 (m, 2H).

The diazonium salt (6.0 g, 23.3 mmol) was dried overnight in vacuo, then suspended in toluene (60 mL) and stirred at 110° C. for 1 hour. The mixture was cooled to room temperature and the liquid was decanted from the insoluble tar. The organic mixture was washed with water (20 mL), 1 N sodium hydroxide (20 mL), and water (20 mL). The organic layer was dried over anhydrous magnesium sulfate, filtered and concentrated in vacuo. The crude oil was purified by column chromatography (8:1, hexanes/ethyl acetate) to yield the first intermediate compound (2.87 g, 76%) as a light red oil. $^1$H NMR (400 MHz, CDCl$_3$) δ 8.04 (t, 1H), 7.00–6.84 (m, 2H), 2.95 (t, 2H), 2.62 (t, 2H), 2.20–2.02 (m, 2H).

A second intermediate compound, Trifluoro-methanesulfonic acid 6-fluoro-3,4-dihydro-naphthalen-1-yl ester, was produced as follows: 6-Fluoro-1-tetralone (1.00 g, 6.10 mmol) was dissolved in tetrahydrofuran (20 mL) and cooled to −78° C. Lithium hexamethyldisilazane (7.32 mmol, 7.32 mL, 1.0 M solution in tetrahydrofuran) was added dropwise and the mixture was stirred at −78° C. for 1 hour. N-phenyl triflamide (2.62 g, 7.32 mmol) in tetrahydrofuran (5 mL) was added and the mixture was allowed to warm to room temperature over 1.5 hours and then was poured into water (20 mL). The mixture was extracted with ethyl acetate (20 mL) and the organic layer was washed with water (2×20 mL), 1 N sodium hydroxide (20 mL), and brine (20 mL). The organic layer was dried over anhydrous sodium sulfate, filtered and concentrated in vacuo. The crude oil was filtered through a short plug of silica gel, eluting with hexanes to yield the second intermediate compound (1.69 g, 94%) as a light brown oil. $^1$H NMR (400 MHz, CDCl$_3$) δ 7.38–7.28 (m, 1H), 7.00–6.84 (m, 2H), 5.99 (t, 1H), 2.84 (t, 2H), 2.60–2.50 (m, 2H).

A third intermediate compound, Trifluoro-methanesulfonic acid 6-fluoro-naphthalen-1-yl ester, was produced as follows: Trifluoro-methanesulfonic acid 6-fluoro-3,4-dihydro-naphthalen-1-yl ester (1.69 g, 5.72 mmol) was dissolved in dioxane (20 mL) and 2,3-dichloro-5,6-dicyano-1,4-benzoquinone (1.95 g, 8.57 mmol) was added. The mixture was heated at reflux for 36 hours and then additional 2,3-dichloro-5,6-dicyano-1,4-benzoquinone (649 mg, 2.86 mmol) was added and the mixture refluxed for another 6 hours. The mixture was cooled to room temperature, evaporated to a solid and loaded onto a short plug of silica gel, eluting with hexanes to yield the first intermediate compound (1.24 g, 74%) as a yellow semi-solid. $^1$H NMR (400 MHz, CDCl$_3$) δ 8.10–8.05 (m, 1H), 7.80 (d, 1H), 7.60–7.45 (m, 2H), 7.45–7.38 (m, 2H).

A fourth intermediate compound, 1-(6-Fluoro-naphthalen-1-yl)-piperazine, was produced as follows: Trifluoromethanesulfonic acid 6-fluoro-naphthalen-1-yl ester (1.24 g, 4.23 mmol) and 1-Boc-piperazine (946 mg, 5.08 mmol) were dissolved in toluene (15 mL) and the mixture was degassed for 30 minutes. To this was added 2-(dicyclohexylphosphino)-biphenyl (148 mg, 0.42 mmol), palladium acetate (95 mg, 0.42 mmol), and sodium tert-butoxide (569 mg, 5.92 mmol). The mixture was stirred at 80° C. for 30 minutes, then cooled to room temperature, washed with water (20 mL) and brine (20 mL), dried over anhydrous sodium sulfate, filtered and concentrated in vacuo. The crude oil was filtered through a short plug of silica gel, eluting with 3:1 hexanes/ethyl acetate to yield crude 4-(6-fluoro-naphthalen-1-yl)-piperazine-1-carboxylic acid tert-butyl ester as a brown oil. The crude oil was dissolved in a mixture of dichloromethane (5 mL) and trifluoroacetic acid (5 mL) and stirred at room temperature for 4 hours. The mixture was evaporated in vacuo and diethyl ether (30 mL) was added. The grey precipitate was filtered off and rinsed with diethyl ether (20 mL) to yield the fourth intermediate compound as the TFA salt (755 mg, 52%) as a grey solid. $^1$H NMR (400 MHz, dmso-$d_6$) δ 8.80 (s, 1H), 8.24–8.18 (m, 1H), 7.72 (d, 1H), 7.68 (d, 1H), 7.50 (t, 1H), 7.40 (t, 1H), 7.18 (d, 1H), 3.40–3.10 (m, 8H).

The reductive amination procedure from Example A1 was followed using 1-(6-fluoro-naphthalen-1-yl)-piperazine to give the title compound. $^1$H NMR (400 MHz, dmso-$d_6$) δ 10.20 (s, 1H), 8.22–7.98 (m, 1H), 7.75 (d, 1H), 7.65 (d, 1H), 7.54–7.48 (m, 2H), 7.44 (t, 1H), 7.20 (d, 1H), 6.40 (d, 1H), 4.24 (t, 2H), 3.70–3.10 (m, 10H), 2.80 (t, 2H), 2.44 (t, 2H), 1.95–1.76 (m, 4H), MS ES+ 449.25 (M+H)$^+$ (Exact mass: 448.23).

Example A68

Synthesis of 7-{4-[4-(5-Fluoro-naphthalen-1-yl)-piperazin-1-yl]-butoxy}-3,4-dihydro-1H-[1,8]naphthyridin-2-one A first intermediate compound, 5-Bromo-naphthalene-1-carboxylic acid, was produced, as follows: To a suspension of naphthalene-1-carboxylic acid (20.14 g, 0.12 mmol) in HOAc (100 mL) was added Br$_2$ (6.60 mL, 0.13 mmol). The mixture was heated at 110° C. for 48 h and cooled to room temperature. It was filtered, the pad was washed with hexane and dried to give the first intermediate compound (18.0 g) as a grey solid in 62%. $^1$H NMR (400 MHz, CDCl$_3$): δ 13.40 (br s, 1H), 8.90 (d, J=6.2 Hz, 1H), 8.42 (d, J=6.0 Hz, 1H), 8.25 (d, J=5.4 Hz, 1H), 8.00 (d, J=5.3 Hz, 1H), 7.80 (m, 1H), 7.60 (m, 1H).

A second intermediate compound, 5-Bromo-naphthalen-1-ylamine, was produced as follows: To a solution of 5-bromo-naphthalene-1-carboxylic acid (10 g, 40 mmol) in t-BuOH (150 mL) was added Et$_3$N (13.6 mL, 80 mmol) and DPPA (10.5 mL, 48 mmol) successively. After the mixture was stirred at room temperature for 1 h, it was refluxed for 16 h. The solvent was then removed and the residue was purified by chromatography on silica gel to give (5-bromo-naphthalen-1-yl)-carbamic acid tert-butyl ester (8.4 g, 65%) as a white solid. $^1$H NMR (400 MHz, CDCl$_3$): δ 8.60 (d, J=6.8 Hz, 1H), 8.55 (d, J=6.6 Hz, 1H), 8.50 (d, J=6.2 Hz, 1H), 8.40 (d, J=6.4Hz, 1H), 8.20 (t, J=6.7Hz, 1H), 8.10 (t, J=6.3 Hz, 1H).

The material obtained in the last step was dissolved in dichloromethane (150 mL) and trifluoroacetic acid (15 mL) was added. The resulting mixture was stirred under reflux for 2 h. The solvent was removed. The residue was washed with hexane to give a white solid, which was suspended in dichloromethane (150 mL) and treated with aqueous KOH (50 mL containing 15 g KOH). The mixture was stirred at room temperature for 30 min. The organic layer was separated and the aqueous layer was extracted with dichloromethane (2×50 mL). The combined organic phases were dried over $Na_2SO4$ and concentrated to give the second intermediate compound (5.13 g, 85%) as a purple solid. $^1$H NMR (400 MHz, $CDCl_3$): δ 8.80 (m, 2H), 7.70 (d, J=7.4 Hz, 2H), 7.40 (t, J=6.2 Hz, 1H), 7.20 (t, J=6.0 Hz, 1H), 6.80 (d, J=6.2 Hz, 1H).

A third intermediate compound, 1-Bromo-5-fluoro-naphthalene. Was produced as follows: To a cooled (0° C.) solution of 5-bromo-naphthalen-1-ylamine (1.0 g, 4.52 mmol) in THF (1 mL) was added 48% $HBF_4$ (10 mL) followed by a solution of $NaNO_2$ (0.49 g, 13.58 mmol, 3 eq) in water (2 mL). After the addition was over, the mixture was kept stirring at 0° C. for 1 h and $NaBF_4$ (2.49 g, 22.6 mmol, 5 eq) was added. The mixture was allowed to warm up to room temperature and filtered. The solid was washed with ether and dried overnight under high vacuum to give a green solid, which was suspended in xylene (5 mL) and refluxed for 1 h. The resulting mixture was subjected to chromatography on silica gel to give the third intermediate compound (480 mg) as a yellow solid in 47% yield for two steps. $^1$H NMR (400 MHz, $CDCl_3$): δ 8.17 (d, J=7.4 Hz, 1H), 8.10 (d, J=7.4 Hz 1H), 7.90 (d, J=6.2 Hz, 1H), 7.55 (m, 1H), 7.40 (t, J=6.4 Hz, 1H), 7.20 (m, 1H).

A fourth intermediate compound, 1-(5-Fluoro-naphthalen-1-yl)-piperazine, was produced as follows: A solution of $Pd(OAc)_2$ (0.31 mg, 1.38 mmol) and dicyclohexylphosphrous-diphenyl (0.48 mg, 1.38 mmol) was degassed by bubbling $N_2$ for 20 min. 1-Bromo-5-fluoro-naphthalene (3.10 g, 13.8 mmol) and 1-Boc-piperazine (3.08 g, 16.6 mmol) were added followed by NaOt-Bu (1.86 g, 19.3 mmol). The mixture was warmed up to 80° C. and kept at this temperature for 16 h. The solvent was removed under reduced pressure and the residue was dissolved in 6 N HCl (60 mL) and washed with ether (3×50 mL). The aqueous phase was basified with solid KOH to pH=11, it was then extracted with EtOAc (3×100 mL). The combined organic phases were dried over $Na_2SO_4$ and concentrated to give the fourth intermediate compound (2.10 g, 66%) as a brown oil. $^1$H NMR (400 MHz, $CDCl_3$): δ 8.00 (d, J=6.5 Hz, 1H), 7.80 (d, J=6.3 Hz, 1H), 7.45 (m, 1H), 7.40 (m, 1H), 7.10 (m, 2H), 3.40–3.10 (m, 8H).

The reductive amination procedure from Example A1 was followed using 1-(5-fluoro-naphthalen-1-yl)-piperazine to give the first intermediate compound. $^1$H NMR (400 MHz, $CDCl_3$): δ 8.00 (d, J=6.2 Hz, 1H), 7.80 (d, J=6.0 Hz, 1H), 7.60 (br s, 1H), 7.55 (t, J=7.0 Hz, 1H), 7.42 (m, 2H), 7.10 (m, 2H), 6.40 (d, J=6.3 Hz, 1H), 4.25 (t, J=4.5 Hz, 2H), 3.20 (br s, 4H), 2.90–2.40 (m, 10H), 1.90–1.70 (m, 4H). Elemental Analysis: calculated for $C_{26}H_{29}FN_4O_2 \cdot 0.5H_2O$: C, 68.27; H, 6.35; N, 12.25. Found: C, 68.22; H, 6.50; N, 11.85.

Example A69

Synthesis of 7-{4-[4-(4-Fluoro-naphthalen-1-yl)-piperazin-1-yl]-butoxy}-3,4-dihydro-1H-[1,8]naphthyridin-2-one A first intermediate compound, 1-(4-Fluoro-naphthalen-1-yl)-piperazine, was produced as follows: A mixture of dicyclohexylphosphino biphenyl (0.155 g, 0.444 mmol, 0.1 mmol) and palladium acetate (0.099 g, 0.444 mmol, 0.1 equiv) in dry toluene (15 mL) was bubbled with $N_2$ gas for two hours. To the resultant clear solution was added 1-bromo-4-fluoro naphthalene (1.0 g, 4.44 mmol, 1.0 equiv) followed by 1-Boc-piperazine (1.0 g, 5.33 mmol, 1.2 equiv). To this mixture was added NaO$^t$Bu (0.600 g, 6.22 mmol, 1.4 equiv) and the reaction mixture was stirred at 80° C. overnight. The reaction mixture was cooled to room temperature, and the solvent was removed under reduced pressure. The residue was taken up in $CH_2Cl_2$, filtered through a celite bed, and then rinsed with $CH_2Cl_2$. The combined filtrates were concentrated and purified by column chromatography on silica (20% EtOAc in hexane). 4-(4-Fluoro-naphthalen-1-yl)-piperazine-1-carboxylic acid tert-butyl ester (1.4 g, impure) was obtained as a dark viscous liquid, which was used in the next step without further purification. $^1$H NMR: (400 MHz, $CDCl_3$) δ 8.25 (m, 1H), 8.05 (m, 1H), 7.55 (m, 2H), 7.05–6.80 (m, 2H), 4.00 (br s, 4H), 3.00 (br s, 4H), 1.45(s, 9H). MS: ES+ 331.13 (M+H)$^+$ (Exact mass: 330.17).

To a solution of 4-(4-fluoro-naphthalen-1-yl)-piperazine-1-carboxylic acid tert-butyl ester (1.1 g, 3.33 mmol) in $CH_2Cl_2$ (10 mL) was added TFA (10 mL) at 0° C. The reaction mixture was warmed to room temperature and stirred for one hour. Solvents were removed and the residue was purified by column chromatography on silica (10% MeOH in $CH_2Cl_2$) to afford the first intermediate compound (0.90 g, 78%) as a pale brown crystalline solid. $^1$H NMR: (400 MHz, DMSO-$d_6$) δ 9.0 (br s, 2H), 8.28 (m, 1H), 8.08 (m, 1H), 7.65 (m, 2H), 7.30 (m, 1H), 7.08 (m, 1H), 3.45 (br s, 4H), 3.20 (br s, 4H). MS: ES+ 231.09 (M+H)$^+$ (Exact mass: 230.12).

The reductive amination procedure from Example A1 was followed using 1-(4-fluoro-naphthalen-1-yl)-piperazine to give the title compound. $^1$H NMR: (400 MHz, $CDCl_3$) δ 8.25 (m, 1H), 8.10 (m, 1H), 7.65 (br s, 1H), 7.55 (m, 2H), 7.38 (d, 1H), 7.10–6.95 (m, 2H), 6.35 (d, 1H), 4.25 (t, 2H), 3.10–3.00 (br s, 4H), 2.90–2.40 (m, 10H), 1.85–1.55 (m, 4H). MS: ES+ 449.18 (M+H)$^+$ (Exact mass: 448.23).

Example A70

7-{4-[4-(3-Fluoro-naphthalen-1-yl)-piperazin-1-yl]-butoxy}-3,4-dihydro-1H-[1,8]naphthyridin-2-one A first intermediate, 3-Fluoro-naphthalene-1-carboxylic acid methyl ester, was produced as follows: An ice-cold mixture of 3-amino-naphthalene-1-carboxylic acid methyl ester (1.76 g, 8.75 mmol) in tetrahydrofuran (2 mL) was treated with 48% tetrafluoroboric acid (20 mL) followed by sodium nitrite (1.81 g, 26.20 mmol) in water (4 mL). The suspension was stirred for 1 hour at 0° C., then sodium tetrafluoroborate (4.80 g, 43.70 mmol) was added. The suspension was warmed to room temperature and stirred for 30 minutes. The green diazonium salt was collected by vacuum filtration, rinsed with diethyl ether and dried under high vacuum overnight. The solid was diluted with chlorobenzene (10 mL) and then refluxed for 1 hour. The brown solution was cooled to room temperature, quenched with water and extracted with dichloromethane. The extracts were dried over anhydrous $Na_2SO_4$, filtered and concentrated in vacuo to a brown oil. The oil was purified by column chromatography (5:1, hexanes/ethyl acetate) to afford the first intermediate compound (0.892 g, 50%) as a yellow liquid. $^1$H NMR (400 MHz, CDCl$_3$) δ 8.89 (d, 1H), 8.00–7.94 (m, 1H), 7.85–7.78 (m, 1H), 7.70–7.62 (m, 1H), 7.60–7.52 (m, 2H), 4.00 (s, 3H).

A second intermediate compound, (3-Fluoro-naphthalen-1-yl)-carbamic acid tert-butyl ester, was produced as follows: A mixture of 3-fluoro-naphthalene-1-carboxylic acid methyl ester (4.47 g, 21.90 mmol) in 2N KOH (15 mL, 30 mmol) and methanol (60 mL) was refluxed for 2 hours. The solution was cooled, then concentrated under reduced pressure. The residue was diluted with water and acidified to pH 1 with 3N HCl. A solid precipitated out of solution and the suspension was diluted with ethyl acetate. The organic layer was separated and the aqueous layer was extracted with ethyl acetate. The combined extracts were dried over anhydrous $Na_2SO_4$, filtered and concentrated in vacuo to afford the carboxylic acid (4.08 g, 98%) as a yellow solid.

A mixture of 3-fluoro-naphthalene-1-carboxylic acid (3.98 g, 21 mmol) in dry tert-butanol (80 mL) was treated with triethylamine (6.2 mL, 44 mmol) followed by diphenylphosphoryl azide (5.60 mL, 26 mmol). The yellow solution was refluxed overnight, then cooled and concentrated under vacuum. The residue was purified by column chromatography (7:1, hexanes/ethyl acetate) to afford the second intermediate compound (4.78 g, 87%) as a yellow solid. $^1$H NMR (400 MHz, CDCl$_3$) δ 7.96–7.87 (m, 1H), 7.84–7.75 (m, 2H), 7.56–7.43 (m, 2H), 7.21 (d, 1H), 7.03 (br s, 1H), 1.48 (s, 9H).

A third intermediate compound, 1-(3-Fluoro-naphthalen-1-yl)-piperazine, was produced as follows: A solution of (3-fluoro-naphthalen-1-yl)-carbamic acid tert-butyl ester (4.78 g, 18.30 mmol) in dichloromethane (30 mL) and trifluoroacetic acid (10 mL) was refluxed for 2 hours. The mixture was diluted with diethyl ether and the solid that precipitated out was collected by vacuum filtration as the TFA salt (2.137 g). The filtrate was neutralized with 2N KOH and extracted with dichloromethane. The extracts were dried over anhydrous $Na_2SO_4$, filtered and concentrated to a brown residue. The residue was purified by column chromatography (5:1, hexanes/ethyl acetate) to afford 3-fluoro-naphthalen-1-ylamine (0.967 g, 33%). The TFA salt (2.137 g) was stirred in a heterogeneous solution of 2N KOH (10 mL) in dichloromethane (20 mL). The organic layer was separated and the aqueous layer was extracted with dichloromethane. The combined extracts were dried over anhydrous $Na_2SO_4$, filtered and concentrated to afford an additional amount of 3-fluoro-naphthalen-1-ylamine (1.193 g, 40%). $^1$H NMR (400 MHz, CDCl$_3$) δ 7.78–7.64 (m, 2H), 7.48–7.42 (m, 1H), 7.41–7.34 (m, 1H), 6.90 (d, 1H), 6.54 (d, 1H), 4.30 (br s, 2H).

A solution of 3-fluoro-naphthalen-1-ylamine (1.00 g, 6.20 mmol), sodium iodide (0.465 g, 3.10 mmol), diisopropylethylamine (0.30 mL, 3.10 mmol) and bis(2-chloroethyl)amine hydrochloride (1.218 g, 6.82 mmol) in chlorobenzene (10 mL) and 1-hexanol (1 mL) was heated at 150° C. overnight. The solvent was removed from the brown solution by vacuum distillation and the residue was cooled to room temperature. The residue was diluted with hexanes/diethyl ether (1:1) and then the solvent was decanted. This was repeated, then the solid was collected by vacuum filtration. The brown solid was diluted with methanol/chloroform and absorbed onto $SiO_2$, then loaded onto a column for chromatography (methanol/ammonium hydroxide/chloroform, 8:1:91) to afford a brown oil. The oil was triturated with diethyl ether to afford the third intermediate compound (0.173 g, 12%), as a brown solid. $^1$H NMR (400 MHz, DMSO-d$_6$) δ 9.20 (br s, 1H), 8.10 (d, 1H), 7.88 (d, 1H), 7.60–7.41 (m, 2H), 7.02 (d, 1H), 3.20 (br s, 4H), 3.05 (br s, 4H).

The reductive amination procedure from Example A1 was followed using 1-(3-fluoro-naphthalen-1-yl)-piperazine to give the title compound. $^1$H NMR (400 MHz, CDCl$_3$) δ 8.12 (d, 1H), 7.74 (d, 1H), 7.55 (br s, 1H), 7.50–7.39 (m, 2H), 7.37 (d, 1H), 7.14 (dd, 1H), 6.86 (dd, 1H), 6.36 (d, 1H), 4.24 (t, 2H), 3.16 (br s, 4H), 2.87 (t, 2H), 2.75 (br s, 4H), 2.64 (t 2H), 2.54 (t, 2H), 1.88–1.78 (m, 2H), 1.78–1.68 (m, 2H); ES MS: 449.12 (M+H)$^+$ (Exact mass: 448.23).

Example A71

Synthesis of 7-{4-[4-(2-Fluoro-naphthalen-1-yl)-piperazin-1-yl]-butoxy}-3,4-dihydro-1H-[1,8]naphthyridin-2-one A first intermediate, 1-Bromo-naphthalen-2-ylamine, was produced as follows: To a solution of naphthalen-2-ylamine (1.03 g, 7.2 mmol) in DMF was added NBS (1.54 g, 8.6 mmol, 1.2 eq). The mixture was heated at 110° C. for 2 h, cooled to room temperature, taken up in EtOAc (150 mL) and washed with water (3×50 mL). The organic phase was dried over $Na_2SO_4$ and concentrated. The residue was purified by chromatography on silica gel to give compound the first intermediate compound (1.12 g, 70%) as a red solid. $^1$H NMR (400 MHz, CDCl$_3$): δ 8.05 (d, J=5.8 Hz, 1H), 7.70 (d, J=6.0 Hz, 1H), 7.65 (d, J=6.0 Hz, 1H), 7.58 (t, J=5.2 Hz, 1H), 7.30 (t, J=5.1 Hz, 1H), 7.00 (d, J=6.1 Hz, 1H), 4.40 (br s, 2H).

A second intermediate compound, 1-Bromo-2-fluoro-naphthalene, was produced as follows: To a cooled (0° C.) solution of 1-bromo-naphthalen-2-ylamine (1.0 g, 4.52 mmol) in THF (1 mL) was added 48% HBF$_4$ (10 mL) followed by a solution of NaNO$_2$ (0.49 g, 13.58 mmol, 3 eq) in water (2 mL). After the addition was over, the mixture was kept stirring at 0° C. for 1 h and NaBF$_4$ (2.49 g, 22.6 mmol, 5 eq) was added. The mixture was allowed to warm to room temperature and was filtered. The solid was washed with ether and dried overnight under high vacuum to give the diazonium salt as a green solid, which was used in the next step. $^1$H NMR (400 MHz, CDCl$_3$): δ 8.60 (d, J=6.8 Hz, 1H), 8.55 (d, J=6.6 Hz, 1H), 8.50 (d, J=6.2 Hz, 1H), 8.40 (d, J=6.4 Hz, 1H), 8.20 (t, J=6.7 Hz, 1H), 8.10 (t, J=6.3 Hz, 1H).

The material obtained in the last step was suspended in xylene (5 mL) and refluxed for 1 h. The resulting mixture was subjected to chromatography on silica gel to give the second intermediate compound (480 mg, 47%) as a yellow solid for two steps. $^1$H NMR (400 MHz, CDCl$_3$): δ 8.22 (d, J=7.4 Hz, 1H), 7.80 (m, 2H), 7.60 (t, J=6.2 Hz, 1H), 7.50 (t, J=6.0 Hz, 1H), 7.30 (t, J=7.6 Hz, 1H).

A third intermediate compound, 1-(2-Fluoro-naphthalen-1-yl)-piperazine, was produced as follows: A solution of Pd(OAc)$_2$ (44.8 mg, 0.2 mmol) and 2-(dicyclohexylphosphino)biphenyl (70.0 mg, 0.2 mmol) was degassed by bubbling N$_2$ for 20 min. 1-Bromo-2-fluoro-naphthalene (0.448 g, 2 mmol) and 1-Boc-piperazine (0.446 g, 2.4 mmol) were added followed by the addition of NaO$^t$Bu (0.27 g, 2.8 mmol). The mixture was warmed up to 80° C. and kept at this temperature for 16 h. The solvent was removed under reduced pressure and the residue was purified by chromatography on silica gel to give 4-(2-fluoro-naphthalen-1-yl)-piperazine-1-carboxylic acid tert-butyl ester (0.24 g, 40%).

A mixture of 4-(2-fluoro-naphthalen-1-yl)-piperazine-1-carboxylic acid tert-butyl ester (1.05 g, 2.83 mmol) and TFA (1 mL) in dichloromethane (10 ml) was refluxed for 2 h. The solvent was removed under reduced pressure to give a black solid (1.05 g), which was dissolved in dichloromethane (2 mL) and ether was added to precipitate the third intermediate compound (0.36 g) as the TFA salt. $^1$H NMR (400 MHz, CDCl$_3$): δ 8.75 (d, J=6.5 Hz, 1H), 8.00 (d, J=6.3 Hz, 1H), 7.90 (m, 1H), 7.62 (m, 1H), 7.58 (m, 1H), 7.42 (t, J=6.6 Hz, 1H), 3.60–3.10 (m, 8H).

The reductive amination procedure from Example A1 was followed using 1-(2-fluoro-naphthalen-1-yl)-piperazine to give the title compound. $^1$H NMR (400 MHz, CDCl$_3$): δ 8.40 (d, J=6.2 Hz, 1H), 7.80 (d, J=6.0 Hz, 1H), 7.60 (m, 1H), 7.55 (m, 2H), 7.42 (m, 1H), 7.37 (d, J=5.9 Hz, 1H), 7.20 (m, 1H), 6.35 (d, J=6.3 Hz, 1H), 4.25 (t, J=4.5 Hz, 2H), 3.50 (m, 2H), 3.10 (m, 1H), 2.95 (m, 2H), 2.85 (t, J=6.0 Hz, 2H), 2.65 (t, J=7.2 Hz, 2H), 2.50 (m, 2H), 2.40 (m, 2H), 1.85 (m, 2H), 1.75 (m, 2H).

Example A72

Synthesis of 7-{4-[4-(6,7-Difluoro-naphthalen-1-yl)-piperazin-1-yl]-butoxy}-3,4-dihydro-1H-[1,8]naphthyridin-2-one A first intermediate compound, Trifluoro-methanesulfonic acid 6,7-difluoro-3,4-dihydro-naphthalen-1-yl ester, was produced as follows: To a cooled (−78° C.) solution of 6,7-difluoro-3,4-dihydro-2H-naphthalen-1-one (3.64 g, 20 mmol, *Tetrahedron Lett*. 2003, 44, 4007) in THF (40 mL) was added LiHMDS (24 mL, 24 mmol) over 10 min. The resulting mixture was stirred at −78° C. for 1 h and a solution of N-phenyltrifluoromethanesulfonimide (8.59 g, 24 mmol) in THF (20 mL) was added. The mixture was stirred at −78° C. for another 3 h, quenched with H$_2$O and extracted with EtOAc (3×50 mL). The combined organic phases were dried and concentrated to give the first intermediate compound (6.28 g, 100%). $^1$H NMR (400 MHz, CDCl$_3$): δ 7.20 (m, 1H), 7.00 (m, 1H), 6.05 (t, 1H), 2.80 (m, 2H), 2.50 (m, 2H).

A second intermediate compound, Trifluoro-methanesulfonic acid 6,7-difluoro-naphthalen-1-yl ester, was produced as follows: A mixture of trifluoro-methanesulfonic acid 6,7-difluoro-3,4-dihydro-naphthalen-1-yl ester (6.28 g, 20 mmol) and DDQ (9.08 g, 40 mmol) in dioxane (60 mL) was refluxed for 24 h and then cooled to RT. The reaction mixture was partitioned between hexanes and water. The organic layer was washed with water, dried and concentrated. The residue was passed through a pad of celite eluting with hexane which gave the second intermediate compound (4.38 g, 70%) as a yellow solid. $^1$H NMR (400 MHz, CDCl$_3$): δ 7.80 (m, 2H), 7.70 (m, 1H), 7.50 (m, 2H).

A third intermediate compound, 1-(6,7-Difluoro-naphthalen-1-yl)-piperazine, was produced as follows: Nitrogen gas was bubbled through a solution of trifluoro-methanesulfonic acid 6,7-difluoro-naphthalen-1-yl ester (4.38 g, 14.04 mmol), 1-Boc-piperazine (3.18 g, 16.85 mmol), Pd(OAc)$_2$ (0.31 g, 1.4 mmol) and 2-dicyclohexylphosphino biphenyl (0.49 g, 1.4 mmol) in toluene (40 mL) for 10 min. NaOtBu (1.89 g, 19.66 mmol) was added. The resulting mixture was heated at 80° C. for 2 h, cooled to RT, diluted with EtOAC (40 mL) and filtered through a pad of celite. The filtrate was concentrated and the residue was purified by chromatography on silica gel to give 4-(6,7-difluoro-naphthalen-1-yl)-piperazine-1-carboxylic acid tert-butyl ester.

To a solution of the 4-(6,7-difluoro-naphthalen-1-yl)-piperazine-1-carboxylic acid tert-butyl ester (1.15 g) in MeOH (10 mL) was added conc. HCl (4 mL). The resulting mixture was stirred at room temperature for 16 h and concentrated under vacuum. The solid obtained was washed with a small amount of MeOH and ether and dried to give the third intermediate compound (0.43 g, 11% in two steps). $^1$H NMR (400 MHz, DMSO-d$_6$): δ 9.30 (br s, 2H), 8.10 (m, 2H), 7.70 (d, 1H), 7.50 (t, 1H), 7.30 (d, 1H), 3.40 (br s, 4H), 3.20 (br s, 4H).

The reductive amination procedure from Example A1 was followed using 1-(6,7-difluoro-naphthalen-1-yl)-piperazine to give the title compound (0.25 g, 75%). $^1$H NMR (400 MHz, DMSO-d$_6$): δ 10.30 (br s, 2H), 8.05 (m, 2H), 7.70 (d, 1H), 7.50 (m, 2H), 7.26 (d, 1H), 6.40 (d, 1H), 4.22 (t, 2H), 3.60–3.10 (m, 10H), 2.80 (m, 2H), 2.50 (m, 2H), 1.90–1.70 (m, 4H).

Example A73

Synthesis of 7-{4-[4-(7-Methoxy-naphthalen-1-yl)-piperazin-1-yl]-butoxy}-3,4-dihydro-1H-[1,8]naphthyridin-2-one A first intermediate compound, 4-(7-Methoxy-naphthalen-1-yl)-piperazine-1-carboxylic acid tert-butyl ester, was produced as follows: 4-(7-Hydroxy-naphthalen-1-yl)-piperazine-1-carboxylic acid tert-butyl ester (2.0 g, 6.10 mmol) was dissolved in dimethylsulfoxide (7 mL) and sodium hydroxide (366 mg, 9.14 mmol) was added. The mixture was stirred for 5 minutes and then methyl iodide (1.73 g, 0.76 mL, 12.20 mmol) was added. The reaction was stirred at room temperature for 3 hours, quenched with water (20 mL) and extracted with ethyl acetate (20 mL). The organic layer was washed with water (2×20 mL) and brine (20 mL), dried over anhydrous sodium sulfate, filtered and concentrated in vacuo to yield the first intermediate compound (1.91 g, 92%) as yellow oil. MS: ES+ 343.20 (M+1)$^+$.

A second intermediate compound, 1-(7-Methoxy-naphthalen-1-yl)-piperazine, was produced as follows: 4-(7-Methoxy-naphthalen-1-yl)-piperazine-1-carboxylic acid tert-butyl ester (1.70 g, 4.97 mmol) was dissolved in dichloromethane (10 mL) and trifluoroacetic acid (2 mL). The mixture was stirred at room temperature for 24 hours and then diluted with hexanes (50 mL). The solids were collected by vacuum filtration and rinsed with hexanes (2×30 mL) to yield the second intermediate compound (2.18 g, quant.) as a purple powder. $^1$H NMR (400 MHz, dmso-d$_6$) δ 8.90 (s, 2H), 7.80 (d, 1H), 7.60 (d, 1H), 7.40 (s, 1H), 7.30 (t, 1H), 7.20–7.10 (m, 2H), 3.95 (s, 3H), 3.80–3.40 (m, 8H).

The reductive amination procedure from Example A1 was followed using 1-(7-methoxy-naphthalen-1-yl)-piperazine to give the title compound. $^1$H NMR (400 MHz, dmso-d$_6$) δ 10.22 (s, 1H), 7.80 (d, 1H), 7.55–7.42 (m, 2H), 7.40 (s, 1H), 7.26 (t, 1H), 7.18 (d, 1H), 7.10 (d, 1H), 6.40 (d, 1H), 4.20 (t, 2H), 3.84 (s, 3H), 3.15–2.90 (m, 4H), 2.80–2.55 (m, 6H), 2.44–2.40 (m, 4H), 1.80–1.50 (m, 4H), MS ES+ 461.22 (M+l)$^+$.

Example A74

Synthesis of 7-{4-[4-(7-Chloro-naphthalen-1-yl)-piperazin-1-yl]-butoxy}-3,4-dihydro-1H-[1,8]naphthyridin-2-one A first intermediate compound, Trifluoro-methanesulfonic acid 7-chloro-3,4-dihydro-naphthalen-1-yl ester, was produced as follows: To a stirred solution of 7-chloro-1-tetralone (6 g, 33.33 mmol) in dry THF (140 mL) at −78° C. was added 1 M solution of lithium bis(trimethylsilyl)amide in THF (40 mL, 40 mmol) over 5 min under $N_2$. The reaction mixture was stirred for 1 h and N-phenyltrifluoromethanesulfonimide (14.44 g, 40 mmol) was added in one portion. The reaction mixture was allowed to warm to room temperature and stirred for 2 h. The solvent was removed in vaccuo and the residue was dissolved in EtOAc (200 mL), and washed successively with 2M NaOH, $H_2O$ and brine. Drying over $Na_2SO_4$ and evaporation under vaccuo yielded a brown oil. Purification by chromatography on silica gel (10% EtOAc:hexanes) gave the first intermediate compound as an oil (9.78 g, 95%). $^1$H-NMR (400 MHz, $CDCl_3$) δ 7.32 (d, 1H), 7.24 (dd, 1H), 7.12 (d, 1H), 6.06 (t, 1H), 2.84 (t, 2H), 2.53 (m, 2H).

A second intermediate compound, Trifluoro-methanesulfonic acid 7-chloro-naphthalen-1-yl ester, was produced as follows: To a stirred solution of trifluoro-methanesulfonic acid 7-chloro-3,4-dihydro-naphthalen-1-yl ester (9.0 g, 28.8 mmol) in dioxane (150 mL) was added 2,3-dichloro-5,6-dicyano-1,4-benzoquinone (13.0 g, 57.7 mmol). The reaction mixture was refluxed for 24 h, and the solvent was removed under vaccuo. EtOAc (250 mL) was added, the mixture was washed with $H_2O$ and brine, and dried over $Na_2SO_4$. Evaporation under vaccuo and column chromatography of the resulting dark brown oil on silica gel, eluting with hexanes, yielded the second intermediate compound as an oil (6.2 g, 55%). $^1$H-NMR (400 MHz, $CDCl_3$) δ 8.04 (d, 1H), 7.83 (m, 2H), 7.58–7.48 (m, 3H).

A third intermediate compound, 4-(7-Chloro-naphthalen-1-yl)-piperazine-1-carboxylic acid tert-butyl ester, was produced as follows: To an oven dried flask was added 1-boc-piperazine (3.48 g, 19.34 mmol), $K_3PO_4$ (4.78 g, 22.56 mmol), $Pd(OAc)_2$ (0.361 g, 1.61 mmol), 2-(di-tert-butylphosphino)binaphthyl (0.64 g, 1.61 mmol), THF (40 mL) and trifluoro-methanesulfonic acid 7-chloro-naphthalen-1-yl ester (5 g, 16.12 mmol). While stirring the reaction mixture at room temperature, the air in the flask was removed and refilled with $N_2$. This process was repeated three times. The reaction was heated at 80° C. for 16 h. Diethyl ether was added at room temperature and the mixture was filtered through a pad of silica gel. The brown oil was chromatographed on silica gel eluting with hexanes:chloroform (1:1) and then changing to chloroform (100%) to yield the third intermediate compound (3.65 g, 63%) as a brown oil. $^1$H-NMR (400 MHz, DMSO-$d_6$) δ 8.16 (d, 1H), 7.96 (d, 1H), 7.68 (d, 1H), 7.55 (d, 1H), 7.52 (t, 1H), 7.21 (d, 1H), 3.61 (s, 4H), 2.98 (s, 4H), 1.42 (s, 9H).

A fourth intermediate compound, 1-(7-Chloro-naphthalen-1-yl)-piperazine, was produced as follows: To a solution of 4-(7-chloro-naphthalen-1-yl)-piperazine-1-carboxylic acid tert-butyl ester (2.4 g, 6.89 mmol) in $CH_2Cl_2$ (20 mL) at 0° C. was added dropwise trifluoroacetic acid (5.24 mL, 68.96 mmol). The reaction mixture was stirred at room temperature for 2 h and the solvent was evaporated. Addition of $Et_2O$ gave the fourth intermediate compound as a white amorphous TFA salt (1.8 g, 73%). $^1$H-NMR (400 MHz, DMSO-$d_6$) δ 8.82 (s, 2H), 8.19 (d, 1H), 7.98 (d, 1H), 7.73 (d, 1H), 7.57 (m, 2H), 7.24 (d, 1H), 3.54–3.11 (m, 8H).

The reductive amination procedure from Example A1 was followed using 1-(7-chloro-naphthalen-1-yl)-piperazine to give the title compound. $^1$H-NMR (400 MHz, DMSO-$d_6$) δ 10.28 (s, 2H), 8.12 (d, 1H), 7.98 (d, 1H), 7.74 (d, 1H), 7.58–7.49 (m, 3H), 7.28 (d, 1H), 6.38 (d, 1H), 4.24 (t, 2H), 3.64 (m, 2H), 3.50–3.14 (m, 8H), 2.78 (t, 2H), 2.48 (m, 2H), 1.96–1.75 (m, 4H).

Example A75

Synthesis of 7-{4-[4-(5-Chloro-naphthalen-1-yl)-piperazin-1-yl]-butoxy}-3,4-dihydro-1H-[1,8]naphthyridin-2-one A first intermediate compound, 5-Chloro-naphthalen-1-ol, was produced as follows: To a cold solution of 5-amino-naphthalen-1-ol in conc. HCl (100 mL) and $H_2O$ (100 mL) at 0° C. was added dropwise a solution of $NaNO_2$ (12.36 g, 190 mmol) in $H_2O$ (20 mL). Freshly prepared CuCl (17.75 g, 190 mmol) was dissolved in conc. HCl (20 ml) and added to the reaction mixture. The reaction mixture became very thick and black foamy material resided on the top of the reaction mixture. $CH_3CN$ (50 ml) was added to make the reaction mixture homogenous. The reaction was brought to room temperature and stirred at 65° C. for 20 min. Ethyl acetate (500 mL) was added and the organic layer was separated and washed with $H_2O$ (3×100 mL), brine, dried over $Na_2SO_4$ and evaporated under vaccuo. The dark black material was chromatographed on a silica column, eluting with $CHCl_3$ and then changing to $CHCl_3$:MeOH (98:2), to yield compound the first intermediate compound as an oil (4.16 g, 19%). $^1$H-NMR (400 MHz, $CDCl_3$) δ 8.18 (d, 1H), 7.82 (d, 1H), 7.59 (d, 1H), 7.42–7.37 (m, 2H), 6.86 (d, 1H), 5.96 (s, 1H).

A second intermediate compound, Trifluoro-methanesulfonic acid 5-chloro-naphthalen-1-yl ester, was produced as follows: To a cold solution of 5-chloro-naphthalen-1-ol (3.7 g, 20.78 mmol) in $CH_2Cl_2$ (50 mL) at 0° C. was added dropwise $Et_3N$ (5.78 mL, 41.6 mmol), followed by trifluoromethanesulfonic anhydride (5.24 mL, 31.2 mmol). The reaction mixture was stirred at 0–5° C. for 30 min and saturated $NaHCO_3$ (50 mL) was added. The organic layer was separated and washed with saturated $NH_4Cl$ solution, brine and dried over $Na_2SO_4$. Evaporation under vaccuo and purification by chromatography on silica (3:1 $Et_2O$/hexanes) yielded the second intermediate compound as a colorless oil (5.5 g, 85%). $^1$H-NMR (400 MHz, $CDCl_3$) δ 8.38 (d, 1H), 8.02 (d, 1H), 7.71 (d, 1H), 7.60 (m, 2H), 7.58 (d, 1H).

A third intermediate compound, 4-(5-Chloro-naphthalen-1-yl)-piperazine-1-carboxylic acid tert-butyl ester, was produced as follows: To an oven dried flask, 1-boc-piperazine (2.95 g, 15.87 mmol), $K_3PO_4$ (3.92 g, 18.5 mmol), $Pd(OAc)_2$ (0.296 g, 1.32 mmol), 2-(Di-tert-butylphosphino)binaphthyl (0.525 g, 1.32 mmol), THF (40 mL) and trifluoro-methanesulfonic acid 5-chloro-naphthalen-1-yl ester (4.1 g, 13.22 mmol) were added. While stirring the reaction mixture at room temperature, the air in the flask was removed and refilled with $N_2$. This process was repeated three times. The reaction temperature was brought to 80° C. and stirred for 18 h. Diethyl ether was added at room temperature and the mixture was filtered through a pad of silica gel. The brown oily material was purified by chromatography on silica column eluting with hexanes:chloroform (1:1) and then changing to chloroform (100%) to yield the third intermediate compound (1.75 g, 41%) as a brown oil. $^1$H-NMR (400 MHz, DMSO-$d_6$) δ 8.18 (d, 1H), 7.90 (d, 1H), 7.68 (d, 1H), 7.58 (t, 1H), 7.53 (t, 1H), 7.22 (d, 1H), 3.61 (s, 4H), 2.97 (s, 4H), 1.42 (s, 9H).

A fourth intermediate compound, 1-(5-Chloro-naphthalen-1-yl)-piperazine, was produced as follows: To a solution of 4-(5-chloro-naphthalen-1-yl)-piperazine-1-carboxylic acid tert-butyl ester (1.85 g, 5.35 mmol) in $CH_2Cl_2$ (10 ml) at 0° C. was added dropwise trifluoromethanesulfonic acid (4.1 ml, 53.5 mmol). The reaction mixture was stirred at room temperature for 2 h and the solvent was evaporated under vaccuo. Addition of Et$_2$O gave the fourth intermediate compound as a white amorphous solid (1.5 g, 80%). $^1$H-NMR (400 MHz, DMSO-d$_6$) δ 8.84 (s, 2H), 8.19 (d, 1H), 7.97 (d, 1H), 7.74 (d, 1H), 7.64 (t, 1H), 7.54 (t, 1H), 7.34 (d, 1H), 3.54–3.11 (m, 8H).

The reductive amination procedure from Example A1 was followed using 1-(5-chloro-naphthalen-1-yl)-piperazine to give the title compound. $^1$H-NMR (400 MHz, DMSO-d$_6$) δ 10.76 (s, 1H), 10.29 (s, 1H), 8.21 (d, 1H), 7.98 (d, 1H), 7.74 (d, 1H), 7.68 (t, 1H), 7.54 (m, 2H), 7.36 (d, 1H), 6.37 (d, 1H), 4.24 (t, 2H), 3.63 (m, 2H), 3.52–3.13 (m, 10H), 2.78 (t, 2H), 1.98–1.68 (m, 4H).

Example A76

7-{4-[4-(6-Chloro-naphthalen-1-yl)-piperazin-1-yl]-butoxy}-3,4-dihydro-1H-[1,8]naphthyridin-2-one An intermediate compound, 1-(6-Chloro-naphthalen-1-yl)-piperazine, was produced as follows: The intermediate compound was prepared from 6-amino-naphthalen-1-ol according to the route described in Example A75 above. $^1$H-NMR (400 MHz, DMSO-d$_6$) δ 8.91 (s, 2H), 8.18 (d, 1H), 8.03 (d, 1H), 7.66 (d, 1H), 7.52 (m, 2H), 7.22 (d, 1H), 3.41 (s, 4H), 3.21 (s, 4H).

The reductive amination procedure from Example A1 was followed using 1-(6-chloro-naphthalen-1-yl)-piperazine to give the title compound (0.50 g, 60%), mp. 215–216° C. $^1$H-NMR (400 MHz, DMSO-d$_6$) δ 10.66 (s, 1H), 10.22 (s, 1H), 8.18 (d, 1H), 8.03 (d, 1H), 7.64 (d, 1H), 7.58 (m, 3H), 7.22 (d, 1H), 6.38 (d, 1H), 4.22 (t, 2H), 3.62 (m, 2H), 3.51–3.09 (m, 10H), 2.78 (t, 2H), 1.98–1.72 (m, 4H).

Example A77

7-{4-[4-(8-Chloro-naphthalen-1-yl)-piperazin-1-yl]-butoxy}-3,4-dihydro-1H-[1,8]naphthyridin-2-one A first intermediate compound, 8-Bromo-naphthalen-1-ylamine, was produced as follows: Sodium azide (7.81 g, 120 mmol) was added portionwise to a suspension of 8-bromo-naphthalene-1-carboxylic acid (5 g, 19.92 mmol) in conc. H$_2$SO$_4$ (17.5 mL) and CHCl$_3$ (17.5 mL) at 45° C. The reaction mixture was stirred for 1.5 h and water (150 mL) was added at room temperature. The mixture was made alkaline with ammonium hydroxide and extracted with CHCl$_3$. The organic layer was dried over Na$_2$SO$_4$ and evaporated to give the first intermediate compound as a brown oil (4.48 g, 99%). $^1$H-NMR (400 MHz, CDCl$_3$) δ 7.68 (dd, 1H), 7.62 (dd, 1H), 7.24 (m, 2H), 7.13 (t, 1H), 6.74 (q, 1H), 5.20 (s, 2H).

A second intermediate compound, 1-Bromo-8-chloro-naphthalene, was produced as follows: To a cold solution of 8-bromo-naphthalen-1-ylamine (4.48 g, 20 mmol) in conc. HCl (30 mL) and H$_2$O (25 mL) at 0° C. was added dropwise a solution of NaNO$_2$ (3.45 g, 50 mmol) in H$_2$O (10 mL). Freshly prepared CuCl (13.86 g, 140 mmol) was dissolved in conc. HCl (15 ml) and was added to the reaction mixture. The reaction was brought to room temperature and stirred at 65° C. for 30 min. Ethyl acetate (250 mL) was added and the organic layer was separated and washed with H$_2$O (3×100 mL), brine, dried over Na$_2$SO$_4$ and evaporated under vaccuo. The dark black material was purified by chromatography on silica, eluting with CHCl$_3$ and then changing to CHCl$_3$:MeOH (98:2), to yield the second intermediate compound as an oil (2.95 g, 72%). $^1$H NMR (400 MHz, CDCl$_3$) δ δ 7.92 (dd, 1H), 7.82–7.75 (m, 2H), 7.65 (dd, 1H), 7.36 (t, 1H), 7.26 (q, 1H).

A third intermediate compound, 1-(8-Chloro-naphthalen-1-yl)-piperazine, was produced as follows: To an oven dried flask, 1-boc-piperazine (1.2 g, 6.47 mmol), NaOtBu (0.724 g, 7.54 mmol), Pd(OAc)$_2$ (0.12 g, 0.539 mmol), 2-(dicyclohexylphosphino)biphenyl (0.12 g, 0.539 mmol), toluene (15 mL) and 1-bromo-8-chloro-naphthalene (1.3 g, 5.39 mmol) were added. While stirring the reaction mixture at room temperature, the air in the flask was removed and refilled with N$_2$. This process was repeated three times. The reaction mixture was stirred for 3 h at 80–90° C. Diethyl ether was added at room temperature and the mixture was filtered through a pad of silica gel. The brown oily material was purified by chromatography on silica, eluting with hexanes:chloroform (1:1) and then changing to 100% chloroform, to give 4-(8-chloro-naphthalen-1-yl)-piperazine-1-carboxylic acid tert-butyl ester as an oil (1.35 g, 72%). $^1$H-NMR (400 MHz, CDCl$_3$) δ 7.73 (dd, 1H), 7.56 (dd, 1H), 7.52 (dd, 1H), 7.42 (t, 1H), 7.34 (t, 1H), 7.18 (dd, 1H), 4.16 (s, 2H), 3.38 (s, 2H), 3.22 (m, 2H), 2.76 (m, 2H), 1.45 (s, 9H).

To a solution of 4-(8-chloro-naphthalen-1-yl)-piperazine-1-carboxylic acid tert-butyl ester (1.34 g, 3.87 mmol) in CH$_2$Cl$_2$ (10 mL) at 0° C. was added dropwise trifluoroacetic acid (2.94 mL, 38.7 mmol). The reaction mixture was stirred at room temperature for 1.5 h and the solvent was evaporated under vaccuo. Addition of Et$_2$O gave the third intermediate compound as a white amorphous solid (1.03 g, 74%). $^1$H-NMR (400 MHz, DMSO-d$_6$) δ 8.92 (s, 1H), 8.71 (s, 1H), 7.92 (dd, 1H), 7.76 (d, 1H), 7.62 (dd, 1H), 7.54 (t, 1H), 7.46 (m, 1H), 7.33 (dd, 1H), 3.44–3.27 (m, 4H), 3.20–2.91 (m, 4H).

The reductive amination procedure from Example A1 was followed using 1-(8-chloro-naphthalen-1-yl)-piperazine to give the title compound (0.303 g, 48%). $^1$H-NMR (400 MHz, DMSO-d$_6$) δ 10.31 (s, 1H), 10.21 (s, 1H), 7.94 (dd, 1H), 7.76 (d, 1H), 7.62 (dd, 1H), 7.54 (m, 2H), 7.46 (t, 1H), 7.32 (d, 1H), 6.38 (d, 1H), 4.22 (t, 2H), 3.62 (m, 2H), 3.44–3.22 (m, 8H), 3.08 (m, 2H), 2.79 (m, 2H), 1.92–1.72 (m, 4H).

Example A78

7-{4-[4-(7-Acetyl-naphthalen-1-yl)-piperazin-1-yl]-butoxy}-3,4-dihydro-1H-[1,8]naphthyridin-2-one A first intermediate compound, 4-(7-Trifluoromethane-sulfonyloxy-naphthalen-1-yl)-piperazine-1-carboxylic acid tert-butyl ester, was produced as follows: 4-(7-Hydroxy-naphthalen-1-yl)-piperazine-1-carboxylic acid tert-butyl ester (2.00 g, 6.09 mmol) was dissolved in dichloromethane (30 mL) and triethylamine (1.23 g, 1.70 mL, 12.2 mmol) were added. The mixture was cooled to 0° C. and trifluoromethanesulfonic anhydride (2.58 g, 1.54 mL, 9.15 mmol) was added dropwise. The mixture was stirred at 0° C. for 30 minutes and water (20 mL) was added. The organic layer was washed with saturated sodium bicarbonate (20 mL) and brine (20 mL), dried over anhydrous magnesium sulfate, filtered and concentrated in vacuo. The crude oil was purified by column chromatography (5:1, hexanes/ethyl acetate) to yield the first intermediate compound (2.50 g, 89%) as an orange oil that solidified. $^1$H NMR (400 MHz, dmso-d$_6$) δ 8.20–8.10 (m, 2H), 7.78 (d, 1H), 7.65–7.50 (m, 2H), 7.30 (d, 1H), 3.80–3.40 (m, 4H), 3.05–2.90 (m, 4H), 1.40 (s, 9H).

A second compound, 1-(8-Piperazin-1-yl-naphthalen-2-yl)-ethanone, was produced as follows: 4-(7-Trifluoromethanesulfonyloxy-naphthalen-1-yl)-piperazine-1-carboxylic acid tert-butyl ester (2.50 g, 5.44 mmol) was dissolved in dimethylformamide (15 mL) and the solution was degassed for 30 minutes. Triethylamine (1.10 g, 1.52 mL, 10.87 mmol), butyl vinyl ether (2.72 g, 3.50 mL, 27.17 mmol), palladium acetate (61 mg, 0.27 mmol), and 1,3-bis(diphenylphosphino)-propane (112 mg, 0.27 mmol) were added sequentially and the mixture was heated to 80° C. and stirred for 3 hours at this temperature, then the temperature was lowered to 40° C. and stirred for an additional 15 hours, then cooled to room temperature. The mixture was extracted with dichloromethane (30 mL), and the organic layer was washed with water (3×30 mL) and brine (30 mL), dried over anhydrous magnesium sulfate, filtered and concentrated in vacuo. The crude oil was filtered through a short plug of silica gel, eluting with 3:1 hexanes/ethyl acetate to yield a mixture of 4-[7-(1-butoxy-vinyl)-naphthalen-1-yl]-piperazine-1-carboxylic acid tert-butyl ester and 4-(7-acetyl-naphthalen-1-yl)-piperazine-1-carboxylic acid tert-butyl ester (2.14 g).

This mixture (2.14 g) was dissolved in a mixture of dichloromethane (4 mL), trifluoroacetic acid (3 mL) and water (1 mL) and stirred at room temperature for 4 hours. The mixture was evaporated in vacuo and hexanes (30 mL) were added. The precipitate was filtered off and washed with hexanes (20 mL) to yield the second intermediate compound (2.1 g, quant.) as an orange solid. $^1$H NMR (400 MHz, dmso-$d_6$) δ 8.95 (s, 1H), 8.70 (s, 1H), 8.05–7.98 (m, 2H), 7.76 (d, 1H), 7.60 (t, 1H), 7.30 (d, 1H), 3.50–3.30 (m, 4H), 3.30–3.10 (m, 4H), 2.75 (s, 3H).

The reductive amination procedure from Example A1 was followed using 1-(8-piperazin-1-yl-naphthalen-2-yl)-ethanone to give the title compound. $^1$H NMR (400 MHz, CDCl$_3$) δ 8.85 (s, 1H), 8.00 (d, 1H), 7.85 (d, 1H), 7.60–7.50 (m, 3H), 7.38 (d, 1H), 7.18 (d, 1H), 4.24 (t, 2H), 3.25–3.10 (m, 4H), 2.86 (t, 2H), 2.85–2.76 (m, 4H), 2.75 (s, 3H), 2.64 (t, 2H), 2.55 (t, 2H), 1.90–1.70 (m, 4H), MS ES+ 473.24 (M+H)$^+$.

Example A79

Synthesis of 7-{4-[4-(6-Acetyl-napthalen-1-yl)-piperazin-1-yl]-butoxy}-3,4-dihydro-1H-[1,8]naphthyridin-2-one An intermediate compound, 1-(5-Piperazin-1-yl-naphthalen-2-yl)-ethanone, was produced as follows: The intermediate compound was prepared from 4-(6-hydroxy-naphthalen-1-yl)-piperazine-1-carboxylic acid tert-butyl ester according to the route described in Example A78. $^1$H NMR (400 MHz, dmso-$d_6$) δ 8.90 (s, 1H), 8.65 (s, 1H), 8.20 (d, 1H), 7.98 (d, 1H), 7.86 (d, 1H), 7.60 (t, 1H), 7.36 (d, 1H), 3.60–3.18 (m, 8H), 2.70 (s, 3H).

The reductive amination procedure from Example A1 was followed using 1-(5-piperazin-1-yl-naphthalen-2-yl)-ethanone to give the title compound (366 mg, 83%). $^1$H NMR (400 MHz, dmso-$d_6$) δ 10.30 (s, 1H), 8.70 (s, 1H), 8.20 (d, 1H), 7.99 (d, 1H), 7.88 (d, 1H), 7.60 (t, 1H), 7.54 (d, 1H), 7.36 (d, 1H), 6.40 (d, 1H), 4.20 (t, 2H), 3.80–3.60 (m, 6H), 3.40 (t, 2H), 3.30–3.10 (m, 4H), 2.80 (t, 2H), 2.70 (s, 3H), 1.96–1.70 (m, 4H), MS ES+ 473.19 (M+H)$^+$ (Exact mass: 472.25).

Example A80

Synthesis of 7-{4-[4-(5-Acetyl-naphthalen-1-yl)-piperazin-1-yl]-butoxy}-3,4-dihydro-1H-[1,8]naphthyridin-2-one An intermediate compound, 1-(5-Piperazin-1-yl-naphthalen-1-yl)-ethanone, was produced as follows: The intermediate compound was prepared from 4-(5-hydroxy-naphthalen-1-yl)-piperazine-1-carboxylic acid tert-butyl ester according to the route described in Example A78. 1H-NMR (400 MHz, CDCl$_3$): 8.80 (br s, 2H), 8.42 (d, J=7.7Hz, 1H), 8.35 (d, J=7.8Hz, 1H), 8.12 (d, J=7.0 Hz, 1H), 7.65 (m, 1H), 7.57 (m, 1H), 7.25 (d, J=6.8 Hz, 1H), 3.60–3.10 (m, 8H).

The reductive amination procedure from Example A1 was followed using 1-(5-piperazin-1-yl-naphthalen-1-yl)-ethanone to give the title compound (0.41 g, 76%). $^1$H-NMR (400 MHz, CDCl$_3$): 10.05 (s, 1H), 8.40 (d, J=7.8 Hz, 1H), 8.30 (d, J=7.5 Hz, 1H), 8.13 (d, J=6.6 Hz, 1H), 7.70–7.50 (m, 3H), 7.30 (d, J=6.5 Hz, 1H), 6.40 (d, J=7.9 Hz, 1H), 4.30 (t, J=3.2 Hz, 2H), 3.70 (m, 2H), 3.60–3.20 (m, 8H), 2.80 (t, J=8 Hz, 2H), 2.70 (s, 3H), 2.50 (m, 2H), 2.00–1.80 (m, 4H).

Example A81

Synthesis of 7-{4-[4-(4-Acetyl-naphthalen-1-yl)-piperazin-1-yl]-butoxy}-3,4-dihydro-1H-[1,8]naphthyridin-2-one An intermediate compound, 1-(4-Piperazin-1-yl-naphthalen-1-yl)-ethanone, was produced as follows: The intermediate compound was prepared from 4-(4-bromo-naphthalen-1-yl)-piperazine-1-carboxylic acid tert-butyl ester according to the route described in Example A78. $^1$H-NMR (400 MHz, DMSO-$d_6$): δ 8.90 (s, 2H), 8.80 (d, 1H), 8.20 (d, 1H), 8.10 (d, 1H), 7.60 (m, 2H), 7.20 (d, 1H), 3.45 (s, 4H), 3.25 (s, 4H), 2.65 (s, 3H).

The reductive amination procedure from Example A1 was followed using 1-(4-piperazin-1-yl-naphthalen-1-yl)-ethanone to give the title compound (0.40 g, 80%). $^1$H-NMR (400 MHz, DMSO-$d_6$): δ: 10.40 (s, 1H), 10.25 (s, 1H), 8.80 (d, 1H), 8.20 (m, 2H), 7.60 (m, 2H), 7.50 (d, 1H), 7.20 (d, 1H), 6.40 (d, 1H), 4.23 (m, 2H), 3.80–3.20, 10H), 2.80 (m, 2H), 2.70 (s, 3H), 2.50 (m, 2H), 2.00–1.75 (m, 4H).

Example A82

Synthesis of 7-{4-[4-(2-Acetyl-naphthalen-1-yl)-piperazin-1-yl]-butoxy}-3,4-dihydro-1H-[1,8]naphthyridin-2-one An intermediate compound, 1-(1-Piperazin-1-yl-naphthalen-2-yl)-ethanone, was produced as follows: The intermediate compound was prepared from 4-(2-hydroxy-naphthalen-1-yl)-piperazine-1-carboxylic acid tert-butyl ester according to the route described in Example A78. $^1$H-NMR (400 MHz, DMSO-$d_6$): δ: 8.35 (m, 1H), 8.00 (m, 1H), 7.80 (m, 1H), 7.60 (m, 3H), 3.40–3.20 (m, 8H), 2.70 (s, 3H).

The reductive amination procedure from Example A1 was followed using 1-(1-piperazin-1-yl-naphthalen-2-yl)-ethanone to give the title compound. $^1$H-NMR (400 MHz, DMSO-$d_6$): δ: 12.90 (s, 1H), 8.30 (s, 1H), 7.90 (m, 2H), 7.80 (m, 1H), 7.70–7.50 (m, 3H), 7.45 (m, 2H), 6.40 (d, J=6.5 Hz, 1H), 4.40–4.10 (m, 4H), 3.70 (m, 2H), 3.40–3.00 (m, 6H), 2.90 (m, 2H), 2.67 (m, 5H), 2.40–1.90 (m, 4H).

Example A83

Synthesis of 8-{4-[4-(7-Oxo-5,6,7,8-tetrahydro-[1,8]naphthyridin-2-yloxy)-butyl]-piperazin-1-yl}-naphthalene-2-carbonitrile A first intermediate compound, (7-Cyano-naphthalen-1-yl)-carbamic acid benzyl ester, was produced as follows: Tris(dibenzylideneacetone)dipalladium(0)-chloroform adduct (0.24 g, 0.23 mmol), 1,1'-bis(diphenylphosphino)-ferrocene (1.04 g, 1.87 mmol), KCN (3.05 g, 47.0 mmol), trifluoro-methanesulfonic acid 8-benzyloxycarbonylamino-naphthalen-2-yl ester (10 g, 23.52 mmol), and NMP (20 mL) were combined sequentially and stirred at room temperature for 20 minutes until a yellow reaction complex was formed. The reaction mixture was stirred for 1 h at 80° C. and then cooled to room temperature. The dark brown reaction mixture was purified by chromatography on silica, eluting with hexanes:EtOAc (8.5:1.5) and then changing to hexanes:EtOAc (8:2), to give the first intermediate compound (5.81 g, 82%) as a brown oil which solidified upon standing at room temperature. $^1$H-NMR (400 MHz, CDCl$_3$) δ 8.34 (s, 1H), 7.93 (d, 2H), 7.70 (d, 1H), 7.62 (m, 2H), 7.46–7.32 (m, 5H), 5.24 (s, 2H).

A second intermediate compound, 8-Amino-naphthalene-2-carbonitrile, was produced as follows: To (7-cyano-naphthalen-1-yl)-carbamic acid benzyl ester (5.81 g, 19.23 mmol) was added 33% HBr in HOAC (35 mL) and the mixture was stirred at room temperature for 6 h. Et$_2$O was added and the product was crystallized as a yellow solid. The solid was washed three times with Et$_2$O to give the second intermediate compound (4.22 g, 88%) as yellow solid. $^1$H-NMR (400 MHz, DMSO-d$_6$) δ 8.68 (s, 1H), 8.16 (d, 1H), 7.86 (m, 2H), 7.69 (t, 1H), 7.49 (d, 1H).

A third intermediate compound, 8-Piperazin-1-yl-naphthalene-2-carbonitrile, was produced as follows: A mixture of 8-amino-naphthalene-2-carbonitrile (1 g, 4.03 mmol), bis-(2-chloroethyl)amine hydrochloride (0.778 g, 4.4 mmol), NaI (0.299 g, 2.01 mmol), and 1-hexanol (1 mL) in chlorobenzene was heated at 140° C. for 20 h. The reaction mixture was concentrated and the residue was stirred with Et$_2$O:hexanes (1:1) and the solvent was decanted. The brown material was purified by chromatography on silica, eluting with MeOH:CHCl$_3$ (3:97) and then changed to MeOH:CHCl$_3$:NH$_3$ (10:89:1), to yield the third intermediate compound (0.75 g, 79%) as a light yellow oil. $^1$H-NMR (400 MHz, CDCl$_3$) δ 8.79 (s, 1H), 8.64 (s, 1H), 8.13 (d, 1H), 7.80 (m, 2H), 7.64 (t, 1H), 7.37 (d, 1H), 3.62 (m, 2H), 3.42 (m, 2H), 3.12–3.05 (m, 4H).

The reductive amination procedure from Example A1 was followed using 8-piperazin-1-yl-naphthalene-2-carbonitrile to give the title compound (0.245 g, 37%). $^1$H-NMR (400 MHz, DMSO-d$_6$) δ 10.21 (s, 1H), 8.64 (s, 1H), 8.14 (d, 1H), 7.82 (m, 2H), 7.69 (t, 1H), 7.52 (d, 1H), 7.36 (d, 1H), 6.38 (d, 1H), 4.22 (t, 2H), 3.82–3.15 (m, 12H), 2.79 (m, 2H), 1.96–1.76 (m, 4H).

Example A84

Synthesis of N-(8-{4-[4-(7-Oxo-5,6,7,8-tetrahydro-[1,8]naphthyridin-2-yloxy)-butyl]-piperazin-1-yl}-naphthalen-2-yl)-acetamide The reductive amination procedure from Example A1 was followed using N-(8-piperazin-1-yl-naphthalen-2-yl)-acetamide to give the title compound. MS: APCI: M+1: 488.2 (Exact Mass: 487.26).

Example A85

Synthesis of 7-[4-(4-Naphthalen-1-yl-piperazin-1-yl)butoxy]-3,4-dihydro-1H-[1,8]naphthyridin-2-one A first intermediate compound, 7-(4-benzyloxybutoxy)-[1,8]naphthyridin-2-one, was produced according to the reaction summarized below, as follows. 7-Fluoro-1H-[1,8]naphthyridin-2-one (210 g, 1.28 moles), tetrabutylammonium bromide (20 g, 0.064 mole), 4-benzyloxybutanol (235.8 mL, 1.34 mole), and THF (2.5 L) were charged to a 12 L three-neck round bottom flask equipped with a mechanical stirrer, an addition funnel, and inerted with nitrogen (g). The suspension was stirred at 25° C. for 30 minutes. An ice bath was used to cool the reaction mixture and 1 M potassium tert-butoxide in THF (2.87 L, 2.87 mole) was added via addition funnel at a rate to keep the internal temperature below 30° C. Upon complete addition, the thick slurry became a solution and was stirred at 25° C. for 4 hours or until the reaction was complete by LC/MS analysis. 1 N HCl (1.6 L, 1.6 mole) was added slowly to keep the reaction temperature below 30° C. and stirred for 30 minutes. THF was removed using a rotoevaporator and 7 L of ethyl acetate was added to form a biphasic mixture. The mixture was transferred to a separatory funnel, where the aqueous layer was collected and reextracted with 1 L of ethyl acetate. The ethyl acetate layers were combined, filtered through Celite, washed with water, then with brine, and collected. MgSO$_4$ was added, then filtered, and product was concentrated under vacuum to a yellow solid (405 g, 1.25 mole, 97.8%). MS: APCI: M+1: 325.1 (Exact Mass: 324.15). $^1$H NMR (CDCl$_3$).

A second intermediate compound, 7-(4-Hydroxybutoxy)-3,4-dihydro-1H-[1,8]naphthyridin-2-one, was produced according to the reaction summarized below, as follows. The first intermediate compound, 7-(4-Benzyloxybutoxy)-1H-[1,8]naphthyridin-2-one (132.4 g, 0.408 mole), and MeOH (1.3 L) were charged to a pressure reactor with 20% Palladium on Carbon (20.0 g, 50% water-wet) and hydrogenated for 48 hours at 45° C. and 50 psi. The reaction was monitored by mass spectroscopy or HPLC. Upon completion, the palladium catalyst was filtered and the filtrate was concentrated to an off-white solid. Yield=96.3 g, Quantitative. MS: APCI: M+1: 237.1. $^1$H NMR (CDCl$_3$).

A third intermediate compound, 7-(4-chlorobutoxy)-3,4-dihydro-1H-[1,8]naphthyridin-2-one, was produced according to the reaction summarized below, as follows. The second intermediate compound, 7-(4-Hydroxybutoxy)-3,4-dihydro-1H-[1,8]naphthyridin-2-one (121 g, 0.515 mole), was stirred with THF (1.2 L) in a 3 L round-bottom flask equipped with an addition funnel, thermocouple, and inerted with nitrogen. Methane sulfonyl chloride (48 mL, 0.618 mole) was added and the reaction was cooled to −11° C. with an acetone/ice bath. Triethylamine (100 mL, 0.721 mole) was added via addition funnel at a rate to keep the internal temperature below 0° C. Following complete addition, the reaction was warmed to ambient temperature. TLC (50% CH$_2$Cl$_2$—Ethyl Acetate) showed the reaction was complete. LiCl (43.6 g, 1.03 mole) was added to the reaction suspension and refluxed for 12 hours. TLC showed the reaction was complete. THF was removed via vacuum distillation and Ethyl Acetate (1.2 L) was added. The organic layer was washed with water (500 mL), sat. NaHCO$_3$ (500 mL), and brine. MgSO$_4$ was used to dry the organic solution, which was filtered, concentrated, and dried to a solid that stuck tightly to the walls of the flask. Yield=120 g, 92%. MS: APCI: M+1: 255.0. $^1$H NMR (CDCl$_3$).

Finally, 7-[4-(4-Naphthalen-1-yl-piperazin-1-yl)butoxy]-3,4-dihydro-1H-[1,8]naphthyridin-2-one was produced according to the following reaction, as described below. The third intermediate compound, 7-(4-Chlorobutoxy)-3,4-dihydro-1H-[1,8]naphthyridin-2-one (119 g, 0.469 mole), 1-naphthalen-1-yl-piperazine hydrochloride (110.7 g, 0.446 mole), and potassium carbonate (185 g, 1.339 mole) were charged to a 2 L round bottomed flask equipped with mechanical stirring and a condenser. Water (1.2 L) was added and the reaction was refluxed for 12 hours under nitrogen gas. The reaction was cooled to ambient temperature and the water was decanted, leaving a clump of tan solids. Ethyl acetate (1.2 L) was added, along with water (500 mL), and the solids were stirred for 30 minutes to form a bi-layer. Water (500 mL) was added to the ethyl acetate layer for another wash, followed by a wash with brine (500 mL). $MgSO_4$ was added to the ethyl acetate, which was then filtered and concentrated to a brown solid. Yield=164 g, 85%. MS: APCI: M+1: 431.2. $^1$H NMR ($CDCl_3$).

The resulting product was recrystallized from acetitrile (7 mL/g) by heating the acetonitrile slurry to 60° C., where a solution developed. The solution was then cooled at a rate of −3° C./hr to get to ambient temperature. The recrystallized slurry was then cooled to 0° C. with an ice-bath, filtered cold, and dried to give the purified material in greater than 97% HPLC purity (294 nm). Recrystallization yield=80–85%.

Example B1

Synthesis of 7-{4-[4-(2,3-Dichloro-phenyl)-piperazin-1-yl]-butoxy}-1H-[1,8]naphthyridin-2-one A first intermediate compound, 2-Benzyloxy-7-[4-(tetrahydro-pyran-2-yloxy)-butoxy]-[1,8]naphthyridine, was produced as follows: To a solution of 4-(tetrahydro-pyran-2-yloxy)-1-butanol (3.27 g, 18.8 mmol, 1.2 equiv) in THF (20 mL) cooled to 0° C. was added KO$^t$Bu (1M in THF, 18 mL, 18 mmol, 1.15 equiv). The solution was stirred at 0° C. for 20 min and then added via cannula to a suspension of 2-benzyloxy-7-chloro-[1,8]naphthyridine (4.24 g, 15.66 mmol) in THF (50 mL) cooled to 0° C. The reaction turned orange and became homogenous. After 30 min at 0° C., saturated $NH_4Cl$ and $H_2O$ were added to quench the reaction. The mixture was extracted with EtOAc. The organic layer was washed with saturated $NaHCO_3$, $H_2O$ and brine, dried over $Na_2SO_4$ and concentrated. The crude was absorbed onto $SiO_2$ and purified by liquid chromatography (20–30% EtOAc/Hexanes) to give the first intermediate compound as a pale yellow oil (3.71 g, 9.08 mmol, 58%). MS: APCI: M+1: 409.2 (Exact Mass: 408.20).

A third intermediate compound, 7-(4-Hydroxy-butoxy)-1H-[1,8]naphthyridin-2-one, was produced as follows: 2-Benzyloxy-7-[4-(tetrahydro-pyran-2-yloxy)-butoxy]-[1,8]naphthyridine (620 mg, 1.52 mmol) was hydrogenated using 5% Pd/C in MeOH for 40 min. The reaction was filtered and concentrated. The residue was dissolved in EtOH (5 mL) and PPTS (25 mg, 0.10 mmol) was added. The mixture was heated at 60° C. overnight. The reaction was concentrated and purified by liquid chromatography (6% MeOH/$CH_2Cl_2$) to give the third intermediate compound as a white solid (282 mg, 1.20 mmol, 79%). MS: APCI: M+1: 235.1 (Exact Mass: 234.10).

This intermediate was also prepared using the following procedure:

To a suspension of 60% NaH (83.6 g, 2.09 mol) in NMP (1 L) was added dry 1,4-butanediol (300 mL, 3.39 mol, concentrated from toluene) dropwise to control foaming. The reaction temperature increased to 50° C. and the mixture was stirred at 60° C. for 15 min. 7-Chloro-1H-[1,8]naphthyridin-2-one (146 g, 0.813 mol) was added with stirring and the reaction was heated at 68° C. for 20 h. $CH_3CN$ (5 L) was added and the mixture was filtered and the filter cake was washed with $CH_3CN$ (500 mL) and THF (500 mL). The filter cake was reslurried with THF (3 L) and 3N HCl in MeOH (290 mL, 0.870 mol) was added. The mixture was heated at 60° C. for 1 h and then filtered through celite washing with THF (1 L). The filtrate was concentrated to a volume of 500 mL and THF (1.5 L), Darco (10 g) and magnesol (100 mL) was added. The mixture was stirred at 40° C. for 30 min and then filtered washing with THF (500 mL). The filtrate was concentrated to 500 mL, $CH_3CN$ was added and the mixture was concentrated to 1 L. The resulting solid was filtered, washed with $CH_3CN$ (200 mL) and $Et_2O$ (300 mL) and dried at 50° C. to yield the title compound (101 g, 53%). The filtrate upon standing gave additional crystals, which were collected by filtration, washed and dried as before to give additional title compound (17 g, total yield of 62%).

A fourth intermediate compound, 4-(7-Oxo-7,8-dihydro-[1,8]naphthyridin-2-yloxy)-butyraldehyde, was produced as follows: Using Swern oxidation: To a solution of oxalyl chloride (0.12 mL, 1.32 mmol, 1.1 equiv) in $CH_2Cl_2$ (2.5 mL) cooled to −78° C. was added DMSO (0.18 mL, 2.6 mmol). The reaction was stirred for 5 min and then 7-(4-hydroxy-butoxy)-1H-[1,8]naphthyridin-2-one (282 mg, 1.20 mmol) was added as a solution in $CH_2Cl_2$ (4.5 mL) and DMSO (1.2 mL) via cannula over 5 min. The DMSO was necessary to dissolve the alcohol. The reaction was stirred for 15 min and $Et_3N$ (0.83 mL, 6.0 mmol, 5 equiv) was added. The reaction turned cloudy. The reaction was allowed to stir at −78° C. for 10 min and then warmed to RT. After 30 min at RT, $H_2O$ was added and the mixture was extracted with $CH_2Cl_2$. The organic layer was washed with brine, dried over $MgSO_4$ and concentrated to give the fourth intermediate compound as a light brown oil (340 mg), which was used in the next reaction. MS: APCI: M+1: 233.1 (Exact Mass: 232.08).

Using IBX oxidation: To a solution of 7-(4-hydroxy-butoxy)-1H-[1,8]naphthyridin-2-one (223 mg, 0.952 mmol) in DMSO (3 mL) was added a solution of IBX (400 mg, 1.43 mmol) in DMSO (4.8 mL, 0.3 M). The reaction was stirred at room temperature for 6 h, cooled to 0° C. and quenched with 5% NaHCO3. The mixture was extracted with CH2Cl2 (4×). The organic layer was washed with 5% NaHCO3, dried over MgSO4 and concentrated to give the title compound as a pale yellow solid (175 mg, 0.754 mmol, 79%). MS: APCI: M+1: 233.1 (Exact Mass: 232.08).

To a solution of 4-(7-oxo-7,8-dihydro-[1,8]naphthyridin-2-yloxy)-butyraldehyde (crude from previous reaction) in dichloroethane (6 mL) was added 2,3-dichlorophenylpiperazine hydrochloride (321 mg, 1.20 mmol) followed by $Et_3N$ (0.34 mL, 2.40 mmol, 2 equiv). The resulting suspension was stirred for 5 min and NaBH(OAc)$_3$ (356 mg, 1.68 mmol, 1.4 equiv) was added as a powder. The reaction was stirred at room temperature for 2 h. The reaction was quenched with saturated $NaHCO_3$ and $H_2O$ and the mixture was extracted with EtOAc. The organic layer was washed with saturated $NaHCO_3$ and brine, dried over $Na_2SO_4$ and concentrated. Purification by liquid chromatography (4–5% MeOH/$CH_2Cl_2$) gave the title compound as a white foam (378 mg, 0.845 mmol, 70% over 2 steps). The foam was dissolved in $Et_2O$/$CH_2Cl_2$ and 1 N HCl in $Et_2O$ (0.82 mL) was added.

The resulting white precipitate was collected by filtration, washed with Et$_2$O and dried to give a white solid (355 mg). MS: APCI: M+1: 447.1 (Exact Mass: 446.13).

Example B2

Synthesis of 7-{4-[4-(2-Chloro-3-trifluoromethyl-phenyl)-piperazin-1-yl]-butoxy}-1H-[1,8]naphthyridin-2-one The reductive amination procedure from Example B1 was followed using 1-(2-chloro-3-trifluoromethyl-phenyl)-piperazine to give the title compound (0.55 g, 60%). $^1$H NMR (400 MHz, CDCl$_3$): δ 9.45 (s, 1H), 7.75 (d, 1H), 7.65 (d, 1H), 7.35 (m, 3H), 6.60 (d, 1H), 6.55 (d, 1H), 4.40 (t, 2H), 3.15 (br s, 4H), 2.65 (br s, 4H), 2.50 (m, 2H), 1.85 (m, 2H), 1.75 (m, 2H). MS ES: m/z 480.93 (M+H)$^+$ (Exact mass: 480.15).

Example B3

Synthesis of 7-{4-[4-(2-Acetyl-3-chloro-phenyl)-piperazin-1-yl]-butoxy}-1H-[1,8]naphthyridin-2-one In a manner similar to that of other examples above, 1-(2-chloro-6-piperazin-1-yl-phenyl)-ethanone was coupled by reductive amination to 4-(7-oxo-7,8-dihydro-[1,8]naphthyridin-2-yloxy)-butyraldehyde followed by typical workup and purification to give the title compound. MS: APCI: M+1: 455.2 (Exact Mass: 454.18).

Example B4

Synthesis of 7-{4-[4-(3-Chloro-2-ethyl-phenyl)-piperazin-1-yl]-butoxy}-1H-[1,8]naphthyridin-2-one In a manner similar to that of other examples above, 1-(3-chloro-2-ethyl-phenyl)-piperazine hydrochloride was coupled by reductive amination to 4-(7-oxo-7,8-dihydro-[1,8]naphthyridin-2-yloxy)-butyraldehyde followed by typical workup and purification to give the title compound. MS: APCI: M+1: 441.2 (Exact Mass: 440.20).

Example B5

Synthesis of 7-{4-[4-(2-Acetyl-3-fluoro-phenyl)-piperazin-1-yl]-butoxy}-1H-[1,8]naphthyridin-2-one In a manner similar to that of other examples above, 1-(2-fluoro-6-piperazin-1-yl-phenyl)-ethanone was coupled by reductive amination to 4-(7-oxo-7,8-dihydro-[1,8]naphthyridin-2-yloxy)-butyraldehyde followed by typical workup and purification to give the title compound. MS: APCI: M+1: 439.2 (Exact Mass: 438.21).

Example B6

Synthesis of 7-{4-[4-(3-Acetyl-2-chloro-phenyl)-piperazin-1-yl]-butoxy}-1H-[1,8]naphthyridin-2-one In a manner similar to that of other examples above, 1-(2-chloro-3-piperazin-1-yl-phenyl)-ethanone trifluoroacetate was coupled by reductive amination to 4-(7-oxo-7,8-dihydro-[1,8]naphthyridin-2-yloxy)-butyraldehyde followed by typical workup and purification to give the title compound, mp 108–110° C. MS: APCI: M+1: 455.2 (Exact Mass: 454.18).

Example B7

Synthesis of 7-{4-[4-(2-Chloro-4-fluoro-5-methyl-phenyl)-piperazin-1-yl]-butoxy}-1H-[1,8]naphthyridin-2-one The reductive amination procedure from Example B1 was followed using 1-(2-chloro-4-fluoro-5-methyl-phenyl)-piperazine hydrochloride to give the title compound (0.246 g, 51%). MS: APCI: M+1: 445.2 (Exact mass: 444.17).

Example B8

Synthesis of 7-{4-[4-(2-Chloro-4-fluoro-3-methyl-phenyl)-piperazin-1-yl]-butoxy}-1H-[1,8]naphthyridin-2-one The reductive amination procedure from Example B1 was followed using 1-(2-chloro-4-fluoro-3-methyl-phenyl)-piperazine hydrochloride to give the title compound (0.223 g, 46%). MS: APCI: M+1: 445.2 (Exact mass: 444.17).

Example B9

Synthesis of 7-{4-[4-(5-Chloro-2-isopropoxy-phenyl)-piperazin-1-yl]-butoxy}-1H-[1,8]naphthyridin-2-one To a suspension of 4-(7-oxo-7,8-dihydro-[1,8]naphthyridin-2-yloxy)-butyraldehyde (0.206 g, 0.887 mmol, 1 eq) and 1-(5-chloro-2-isopropoxy-phenyl)-piperazine (0.328 g, 0.977 mmol, 1.1 eq) in dichloroethane (5 mL) was added NaBH(OAc)$_3$ (0.535 g, 2.524 mmol, 2.84 eq). The slurry was allowed to stir overnight at room temperature (18 h). Analysis by HPLC showed reaction mostly complete. The mixture was diluted with Ethyl Acetate and quenched with saturated NaHCO$_3$. The organic phase was washed with brine, dried over Na$_2$SO$_4$, filtered and evaporated in vacuo. Purification by silica gel chromatography (2% MeOH/CH$_2$Cl$_2$) followed by formation of the HCl salt using 1N HCl in ether provided the title compound (0.164 g, 39%). MS: APCI: M+1: 471.2 (Exact Mass: 470.21).

Example B10

Synthesis of 7-{4-[4-(2-Isopropoxy-phenyl)-piperazin-1-yl]-butoxy}-1H-[1,8]naphthyridin-2-one The above reductive amination procedure using 1-(2-isopropoxy-phenyl)-piperazine afforded the title compound. MS: APCI: M+1: 437.3 (Exact Mass: 436.25).

Example B11

Synthesis of 7-{4-[4-(2-Isobutoxy-phenyl)-piperazin-1-yl]-butoxy}-1H-[1,8]naphthyridin-2-one The above reductive amination procedure using 1-(2-isobutoxy-phenyl)-piperazine afforded the title compound. MS: APCI: M+1: 451.2 (Exact Mass: 450.26).

Example B12

Synthesis of 7-[4-(4-o-Tolyl-piperazin-1-yl)-butoxy]-1H-[1,8]naphthyridin-2-one

The reductive amination procedure from Example B1 was followed using 1-o-tolyl-piperazine to give the title compound. MS: APCI: M+1: 393.2 (Exact mass: 392.22).

Example B13

Synthesis of 7-{4-[4-(4-Fluoro-phenyl)-piperazin-1-yl]-butoxy}-1H-[1,8]naphthyridin-2-one The reductive amination procedure from Example B1 was followed using 1-(4-fluoro-phenyl)-piperazine to give the title compound. MS: APCI: M+1: 397.1 (Exact mass: 396.20).

Example B14

Synthesis of 7-{4-[4-(3-Chloro-4-fluoro-phenyl)-piperazin-1-yl]-butoxy}-1H-[1,8]naphthyridin-2-one The reductive amination procedure from Example B1 was followed using 1-(3-chloro-4-fluoro-phenyl)-piperazine to give the title compound. MS: APCI: M+1: 431.2 (Exact mass: 430.16).

Example B15

Synthesis of 7-{4-[4-(3-Trifluoromethyl-phenyl)-piperazin-1-yl]-butoxy}-1H-[1,8]naphthyridin-2-one The reductive amination procedure from Example B1 was followed using 1-(3-trifluoromethyl-phenyl)-piperazine to give the title compound. MS: APCI: M+1: 447.2 (Exact mass: 446.19).

Example B16

Synthesis of 7-{4-[4-(2-Trifluoromethyl-phenyl)-piperazin-1-yl]-butoxy}-1H-[1,8]naphthyridin-2-one The reductive amination procedure from Example B1 was followed using 1-(2-trifluoromethyl-phenyl)-piperazine to give the title compound. MS: APCI: M+1: 447.2 (Exact mass: 446.19).

Example B17

Synthesis of 7-(4-{4-[2-(1,1-Difluoro-ethyl)-phenyl]-piperazin-1-yl}-butoxy)-1H-[1,8]naphthyridin-2-one The reductive amination procedure from Example B1 was followed using 1-[2-(1,1-difluoro-ethyl)-phenyl]-piperazine to give the title compound (0.45 g, 79%). $^1$H-NMR (400 MHz, DMSO-$d_6$): δ 12.00 (s, 1H), 10.65 (s, 1H), 8.00 (d, 1H), 7.81 (d, 1H), 7.58 (m, 2H), 7.50 (m 1H), 7.30 (m 1H), 6.70 (d, 1H), 6.40 (d, 1H), 4.40 (t, 2H), 3.60 (m, 2H), 3.30–3.00 (m, 8H), 2.10 (t, 3H), 2.00–1.70 (m, 4H).

Example B18

Synthesis of 7-{4-[4-(2-Chloro-3-methoxy-phenyl)-piperazin-1-yl]-butoxy}-1H-[1,8]naphthyridin-2-one The reductive amination procedure from Example B1 was followed using 1-(2-chloro-3-methoxy-phenyl)-piperazine to give the title compound. MS: APCI: M+1: 443.3 (Exact mass: 442.18).

Example B19

Synthesis of 7-{4-[4-(2-Chloro-3-ethoxy-phenyl)-piperazin-1-yl]-butoxy}-1H-[1,8]naphthyridin-2-one The reductive amination procedure from Example B1 was followed using 1-(2-chloro-3-ethoxy-phenyl)-piperazine to give the title compound. MS: APCI: M+1: 457.2 (Exact mass: 456.19).

Example B20

Synthesis of 7-{4-[4-(2-Chloro-3-isopropoxy-phenyl)-piperazin-1-yl]-butoxy}-1H-[1,8]naphthyridin-2-one The reductive amination procedure from Example B1 was followed using 1-(2-chloro-3-isopropoxy-phenyl)-piperazine to give the title compound. MS: APCI: M+1: 471.2 (Exact mass: 470.21).

Example B21

Synthesis of 7-{4-[4-(3-Methyl-2-phenoxy-phenyl)-piperazin-1-yl]-butoxy}-1H-[1,8]naphthyridin-2-one The reductive amination procedure from Example B1 was followed using 1-(3-methyl-2-phenoxy-phenyl)-piperazine to give the title compound. MS: APCI: M+1: 485.2 (Exact mass: 484.25).

Example B22

Synthesis of 7-{4-[4-(3-Chloro-2-fluoro-phenyl)-piperazin-1-yl]-butoxy}-1H-[1,8]naphthyridin-2-one The reductive amination procedure from Example B1 was followed using 1-(3-chloro-2-fluoro-phenyl)-piperazine to give the title compound. MS: APCI: M+1: 431.2 (Exact mass: 430.16).

Example B23

Synthesis of 7-{4-[4-(2-Chloro-4-fluoro-phenyl)-piperazin-1-yl]-butoxy}-1H-[1,8]naphthyridin-2-one The reductive amination procedure from Example B1 was followed using 1-(2-chloro-4-fluoro-phenyl)-piperazine to give the title compound. MS: APCI: M+1: 431.2 (Exact mass: 430.16).

Example B24

Synthesis of 7-{4-[4-(2,3-Dichloro-4-fluoro-phenyl)-piperazin-1-yl]-butoxy}-1H-[1,8]naphthyridin-2-one The reductive amination procedure from Example B1 was followed using 1-(2,3-dichloro-4-fluoro-phenyl)-piperazine to give the title compound. MS: APCI: M+1: 465.1 (Exact mass: 464.12).

Example B25

Synthesis of 7-{4-[4-(2-Chloro-phenyl)-piperazin-1-yl]-butoxy}-1H-[1,8]naphthyridin-2-one The reductive amination procedure from Example B1 was followed using 1-(2-chloro-phenyl)-piperazine to give the title compound. MS: APCI: M+1: 413.1 (Exact mass: 412.17).

Example B26

Synthesis of 7-[4-(4-Biphenyl-2-yl-piperazin-1-yl)-butoxy]-1H-[1,8]naphthyridin-2-one The reductive amination procedure from Example B1 was followed using 1-biphenyl-2-yl-piperazine to give the title compound. MS: APCI: M+1: 455.0 (Exact mass: 454.24).

Example B27

Synthesis of 7-{4-[4-(3-Methoxy-2-methyl-phenyl)-piperazin-1-yl]-butoxy}-1H-[1,8]naphthyridin-2-one The reductive amination procedure from Example B1 was followed using 1-(3-methoxy-2-methyl-phenyl)-piperazine to give the title compound. MS: APCI: M+1: 423.2 (Exact mass: 422.23).

Example B28

Synthesis of 7-{4-[4-(2-Chloro-3-fluoro-phenyl)-piperazin-1-yl]-butoxy}-1H-[1,8]naphthyridin-2-one The reductive amination procedure from Example B1 was followed using 1-(2-chloro-3-fluoro-phenyl)-piperazine to give the title compound. MS: APCI: M+1: 431.2 (Exact mass: 430.16).

Example B29

Synthesis of 7-{4-[4-(6-Cyclopropyl-pyridin-2-yl)-piperazin-1-yl]-butoxy}-1H-[1,8]naphthyridin-2-one The reductive amination procedure from Example B1 was followed using 1-(6-cyclopropyl-pyridin-2-yl)-piperazine to give the title compound. MS: APCI: M+1: 420.2 (Exact mass: 419.23).

Example B30

Synthesis of 7-[4-(4-Pyrimidin-2-yl-piperazin-1-yl)-butoxy]-1H-[1,8]naphthyridin-2-one In a manner similar to that of other examples above, 2-piperazin-1-yl-pyrimidine hydrobromide was coupled by reductive amination to 4-(7-Oxo-7,8-dihydro-[1,8]naphthyridin-2-yloxy)-butyraldehyde followed by typical workup and purification to give the title compound, MS: APCI: M+1: 381.1 (Exact Mass: 380.20).

Example B31

Synthesis of 7-{4-[4-(4-Methoxy-pyrimidin-2-yl)-piperazin-1-yl]-butoxy}-1H-[1,8]naphthyridin-2-one In a manner similar to that of other examples above, 4-methoxy-2-piperazin-1-yl-pyrimidine hydrochloride (U.S. Pat. No. 6,303,603) was coupled by reductive amination to 4-(7-oxo-7,8-dihydro-[1,8]naphthyridin-2-yloxy)-butyraldehyde followed by typical workup and purification to give the title compound. MS: APCI: M+1: 411.2 (Exact Mass: 410.21).

Example B32

Synthesis of 7-[4-(4-Indan-4-yl-piperazin-1-yl)-butoxy]-1H-[1,8]naphthyridin-2-one The reductive amination procedure from Example B1 was followed using 1-indan-4-yl-piperazine to give the title compound. MS: APCI: M+1: 419.2 (Exact mass: 418.24).

Example B33

Synthesis of 7-{4-[4-(5,6,7,8-Tetrahydro-naphthalen-1-yl)-piperazin-1-yl]-butoxy}-1H-[1,8]naphthyridin-2-one The reductive amination procedure from Example B1 was followed using 1-(5,6,7,8-tetrahydro-naphthalen-1-yl)-piperazine to give the title compound. MS: APCI: M+1: 433.3 (Exact mass: 432.25).

Example B34

Synthesis of 7-{4-[4-(3-Fluoro-5,6,7,8-tetrahydro-naphthalen-1-yl)-piperazin-1-yl]-butoxy}-1H-[1,8]naphthyridin-2-one The reductive amination procedure from Example B1 was followed using 1-(3-fluoro-5,6,7,8-tetrahydro-naphthalen-1-yl)-piperazine to give the title compound (0.364 g; 54%). MS: APCI: M+1: 451.3 (Exact mass: 450.24).

Example B35

Synthesis of 7-{4-[4-(8-Oxo-5,6,7,8-tetrahydro-naphthalen-1-yl)-piperazin-1-yl]-butoxy}-1H-[1,8]naphthyridin-2-one The reductive amination procedure from Example B1 was followed using 8-piperazin-1-yl-3,4-dihydro-2H-naphthalen-1-one to give the title compound (0.391 g, 59%). $^1$H NMR (400 MHz, CDCl$_3$): δ 8.89 (br s, 1H), 7.71 (d, 1H), 7.63 (d, 1H), 7.33 (t, 1H), 6.90 (d, 1H), 6.82 (d, 1H), 6.60 (d, 1H), 6.51 (d, 1H), 4.38 (t, 2H), 3.16–3.04 (m, 4H), 2.93 (t, 2H), 2.78–2.68 (m, 4H), 2.63 (t, 2H), 2.56–2.48 (m, 2H), 2.10–2.00 (m, 2H), 1.88–1.79 (m, 2H), 1.79–1.67 (m, 2H). MS ES: 447.26 (M+H)$^+$ (Exact mass: 446.23).

Example B36

Synthesis of 7-{4-[4-(7,7-Dimethyl-8-oxo-5,6,7,8-tetrahydro-naphthalen-1-yl)-piperazin-1-yl]-butoxy}-1H-[1,8]naphthyridin-2-one The reductive amination procedure from Example B1 was followed using 2,2-dimethyl-8-piperazin-1-yl-3,4-dihydro-2H-naphthalen-1-one to give the title compound. $^1$H NMR (CDCl$_3$, 400 MHz): δ 9.15 (br s, 1H), 7.75 (d, 1H), 7.70 (d, 1H), 7.30 (m, 2H), 6.65 (d, 1H), 6.55 (d, 1H), 6.60 (d, 1H), 6.50 (d, 1H), 4.40 (t, 2H), 3.10 (br s, 4H), 2.90 (t, 2H), 2.60 (br s, 4H), 2.50 (br s, 2H), 1.90 (t, 2H), 1.90–1.60 (m, 4H), 1.20 (s, 6H). ESMS: 475.26 (Exact mass: 474.26).

Example B37

Synthesis of 7-{4-[4-(7,7-Dimethyl-5,6,7,8-tetrahydro-naphthalen-1-yl)-piperazin-1-yl]-butoxy}-1H-[1,8]naphthyridin-2-one The reductive amination procedure from Example B1 was followed using 1-(7,7-dimethyl-5,6,7,8-tetrahydro-naphthalen-1-yl)-piperazine to give the title compound. $^1$H NMR (CDCl$_3$, 400 MHz): δ 9.30 (br s, 1H), 7.75 (d, 1H), 7.65 (d, 1H), 7.10 (t, 1H), 6.90 (m, 2H), 6.60 (d, 1H), 6.50 (d, 1H), 4.40 (t, 2H), 2.95–2.40 (m, 14H), 1.90(m, 2H), 1.70 (m, 2H), 1.50 (m, 2H), 1.00 (s, 6H). ESMS: 461.29 (Exact mass: 460.28).

Example B38

Synthesis of 7-{4-[4-(7,7-Difluoro-8-oxo-5,6,7,8-tetrahydro-naphthalen-1-yl)-piperazin-1-yl]-butoxy}-1H-[1,8]naphthyridin-2-one The reductive amination procedure from Example B1 was followed using 2,2-difluoro-8-piperazin-1-yl-3,4-dihydro-2H-naphthalen-1-one to give the title compound. $^1$H NMR (400 MHz, DMSO-d$_6$): δ 12.03 (s, 1H), 8.02 (s, 1H), 7.84 (d, 1H), 7.60 (t, 1H), 7.09 (d, 1H), 7.06 (d, 1H), 6.64 (d, 1H), 6.38 (d, 1H), 4.20 (t, 2H), 3.61 (m, 2H), 3.98–3.03 (m, 13), 1.98–1.78 (m, 4H).

Example B39

Synthesis of 7-{4-[4-(7,7-Difluoro-5,6,7,8-tetrahydro-naphthalen-1-yl)-piperazin-1-yl]-butoxy}-1H-[1,8]naphthyridin-2-one The reductive amination procedure from Example B1 was followed using 1-(7,7-difluoro-5,6,7,8-tetrahydro-naphthalen-1-yl)-piperazine to give the title compound (0.329 g, 78%). $^1$H NMR (400 MHz, CDCl$_3$) δ 9.02 (br s, 1H), 7.72 (d, 1H), 7.62 (d, 1H), 7.18 (t, 1H), 6.99 (d, 1H), 6.92 (d, 1H), 6.60 (d, 1H), 6.52 (d, 1H), 4.39 (t, 2H), 3.23 (t, 2H), 3.01 (t, 2H), 2.95–2.84 (m, 4H), 2.74–2.56 (m, 4H), 2.54–2.46 (m, 2H), 2.28–2.13 (m, 2H), 1.90–1.81 (m, 2H), 1.79–1.68 (m, 2H). ES MS: 469.27 (M+1)$^+$ (Exact mass: 468.23).

Example B40

Synthesis of 7-{4-[4-(7-Oxo-5,6,7,8-tetrahydro-naphthalen-1-yl)-piperazin-1-yl]-butoxy}-1H-[1,8] naphthyridin-2-one An intermediate compound, 7-{4-[4-(7-Methoxy-5,8-dihydro-naphthalen-1-yl)-piperazin-1-yl]-butoxy}-1H-[1,8] naphthyridin-2-one, was produced as follows:

1-(7-Methoxy-5,8-dihydro-naphthalen-1-yl)-piperazine (578 mg, 2.37 mmol) and 4-(7-oxo-7,8-dihydro-[1,8]naphthyridin-2-yloxy)-butyraldehyde (500 mg, 2.16 mmol) were dissolved in dichloroethane (10 mL). Triethylamine (655 mg, 6.47 mmol) was added and the mixture was stirred for 10 minutes. Sodium triacetoxyborohydride (548 mg, 2.59 mmol) was added and the mixture was stirred for 1.5 hours. The mixture was quenched with water (20 mL) and extracted with dichloromethane (20 mL). The organic layer was washed with brine (20 mL), dried over anhydrous sodium sulfate, filtered and evaporated. The crude solid was purified by column chromatography (5:95 triethylamine/ ethyl acetate) to yield the intermediate compound (589 mg, 59%) as a white foam. $^1$H NMR (400 MHz, CDCl$_3$) δ 9.40 (s, 1H), 7.75 (d, 1H), 7.60 (d, 1H), 7.18 (t, 1H), 7.00–6.90 (m, 2H), 6.60 (d, 1H), 6.54 (d, 1H), 4.80 (t, 1H), 4.40 (t, 2H), 3.60 (s, 3H), 3.50–3.48 (m, 2H), 3.44–3.38 (m, 2H), 2.95 (t, 4H), 2.80–2.50 (m, 4H), 2.44 (t, 2H), 1.90–1.65 (m, 4H).

7-{4-[4-(7-Methoxy-5,8-dihydro-naphthalen-1-yl)-piperazin-1-yl]-butoxy}-1H-[1,8]naphthyridin-2-one (360 mg, 0.78 mmol) was dissolved in a mixture of ethanol (6 mL) and tetrahydrofuran (2 mL). To this was added 10% hydrochloric acid (1.5 mL) and the mixture was stirred at room temperature for 15 minutes, then quenched with saturated sodium bicarbonate (10 mL). The mixture was extracted with ethyl acetate (20 mL) and the organic layer was washed with brine (20 mL), dried over anhydrous sodium sulfate, filtered and evaporated. The crude solid was purified by column chromatography (6:94 triethylamine/ethyl acetate) to yield the title compound (263 mg, 75%) as a white foam. $^1$H NMR (400 MHz, CDCl$_3$) δ 9.15 (s, 1H), 7.76 (d, 1H), 7.60 (d, 1H), 7.20 (t, 1H), 7.00–6.95 (m, 2H), 6.60 (d, 1H), 6.50 (d, 1H), 4.40 (t, 2H), 3.60 (s, 2H), 3.04 (t, 2H), 2.90–2.80 (m, 4H), 2.80–2.40 (m, 8H), 1.90–1.60 (m, 4H), MS ES+ 447.05 (M+H)$^+$ (Exact mass: 446.23).

Example B41

Synthesis of 7-{4-[4-(7-Hydroxy-5,6,7,8-tetrahydro-naphthalen-1-yl)-piperazin-1-yl]-butoxy}-1H-[1,8] naphthyridin-2-one To a solution of 7-{4-[4-(7-oxo-5,6,7,8-tetrahydro-naphthalen-1-yl)-piperazin-1-yl]-butoxy}-1H-[1,8]naphthyridin-2-one (1.20 g, 2.69 mmol) in methanol (10 mL) was added portionwise NaBH$_4$ (0.41 g, 10.76 mmol). The reaction mixture was stirred at room temperature for 30 min and quenched with saturated NH$_4$Cl solution and the compound was extracted with CH$_2$Cl$_2$ (2×20 mL). The organic layer was washed with brine (20 mL), dried over anhydrous Na$_2$SO$_4$, filtered and evaporated. The crude product was purified by column chromatography (10% methanol in ethyl acetate) to afford the title compound (0.60 g, 50%), as a white solid. $^1$H NMR (400 MHz, CDCl$_3$) δ 9.25 (s, 1H), 7.72 (d, 1H), 7.63 (d, 1H), 7.12 (t, 1H), 6.91 (d, 1H), 6.85 (d, 1H), 6.59 (d, 1H), 6.52 (d, 1H), 4.23 (t, 2H), 4.13–4.08 (m, 1H), 3.25–3.20 (m, 1H), 3.02–2.83 (m, 6H), 2.61–2.47 (m 6H), 1.88–1.71 (m, 6H). ES MS: 449.26 (M+1)$^+$ (Exact mass: 448.25).

Example B42

Synthesis of 7-{4-[4-(5-Oxo-5,6,7,8-tetrahydro-naphthalen-1-yl)-piperazin-1-yl]-butoxy}-1H-[1,8]naphthyridin-2-one In a manner similar to that of other examples above, 5-piperazin-1-yl-3,4-dihydro-2H-naphthalen-1-one was coupled by reductive amination to 4-(7-oxo-7,8-dihydro-[1,8]naphthyridin-2-yloxy)-butyraldehyde followed by typical workup and purification to give the title compound, mp 158–160° C. MS: APCI: M+1: 447.3 (Exact Mass: 446.23).

Example B43

Synthesis of 7-{4-[4-(5,5-Difluoro-5 6,7,8-tetrahydro-naphthalen-1-yl)-piperazin-1-yl]-butoxy}-1H-[1,8]naphthyridin-2-one The reductive amination procedure from Example B1 was followed using 1-(5,5-difluoro-5,6,7,8-tetrahydro-naphthalen-1-yl)-piperazine to give the title compound (0.227 g, 37%). $^1$H NMR (400 MHz, CDCl$_3$) δ 9.00 (br s, 1H), 7.72 (d, 1H), 7.64 (d, 1H), 7.44 (d, 1H), 7.30 (t, 1H), 7.12 (d, 1H), 6.60 (d, 1H), 6.52 (d, 1H), 4.40 (t, 2H), 2.98–2.88 (m, 4H), 2.82–2.76 (m, 2H), 2.70–2.54 (m, 4H), 2.48 (t, 2H), 2.36–2.22 (m, 2H), 2.00–1.91 (m, 2H), 1.89–1.80 (m, 2H), 1.77–1.66 (m, 2H). ES MS: 469.03 (M+H)$^+$ (Exact mass: 468.23).

Example B44

Synthesis of 7-{4-[4-(3-Oxo-indan-4-yl)-piperazin-1-yl]-butoxy}-1H-[1,8]naphthyridin-2-one The reductive amination procedure from Example B1 was followed using 7-piperazin-1-yl-indan-1-one to give the title compound. $^1$H NMR (400 MHz, CDCl$_3$) δ 8.92 (br s, 1H), 7.72 (d, 1H), 7.64 (d, 1H), 7.45 (t, 1H), 6.97 (d, 1H), 6.77 (d, 1H), 6.60 (d, 1H), 6.52 (d, 1H), 4.38 (t, 2H), 3.32–3.16 (m, 4H), 3.10–3.02 (m, 2H), 2.80–2.66 (m, 4H), 2.66–2.62 (m, 2H), 2.58–2.46 (m, 2H), 1.92–1.80 (m, 2H), 1.80–1.66 (m, 2H). ES MS: 432.94 (M+1)$^+$ (Exact mass: 432.22).

Example B45

Synthesis of 7-{4-[4-(2-Oxo-indan-4-yl)-piperazin-1-yl]-butoxy}-1H-[1,8]naphthyridin-2-one The reductive amination procedure from Example B1 was followed using 4-piperazin-1-yl-indan-2-one to give the title compound. $^1$H NMR (400 MHz, CDCl$_3$): δ: 9.20 (br s, 1H), 7.75 (d, 1H), 7.65 (d, 1H), 7.25 (t, 1H), 7.05 (d, 1H), 6.90 (d, 1H), 4.40 (t, 2H), 3.55 (s, 2H), 3.45 (s, 2H), 3.05 (br s, 4H), 2.70 (br s, 4H), 2.45 (t, 2H), 1.85 (m, 2H), 1.65 (m, 2H). MS ES: m/z 433.21 (M+H)$^+$ (Exact mass: 432.22).

Example B46

Synthesis of 7-{4-[4-(2,2-Difluoro-indan-4-yl)-piperazin-1-yl]-butoxy}-1H-[1,8]naphthyridin-2-one The reductive amination procedure from Example B1 was followed using 1-(2,2-difluoro-indan-4-yl)-piperazine to give the title compound (0.208 g, 40%). $^1$H NMR (400 MHz, CDCl$_3$): δ: 9.15 (br s, 1H), 7.75 (d, 1H), 7.65 (d, 1H), 7.25 (t, 1H), 6.90 (d, 1H), 6.85 (d, 1H), 6.65 (d, 1H), 6.50 (d, 1H), 4.40 (t, 2H), 3.35 (m, 4H), 3.05 (br s, 4H), 2.75 (br s, 4H), 2.50 (m, 2H), 1.90 (m, 2H), 1.75 (m, 2H). MS ES: m/z 455.11 (M+H)$^+$ (Exact mass: 454.22).

Example B47

Synthesis of 7-[4-(4-Naphthalen-1-yl-piperazin-1-yl)-butoxy]-1H-[1,8]naphthyridin-2-one To a mixture of 4-(7-oxo-7,8-dihydro-[1,8]naphthyridin-2-yloxy)-butyraldehyde (175 mg, 0.754 mmol) and 1-naphthalen-1-yl-piperazine hydrochloride (206 mg, 0.829 mmol) in DCE (4 mL) was added Et$_3$N (0.23 mL, 1.66 mmol). The mixture was stirred for 10 min and NaBH(OAc)$_3$ (224 mg, 1.06 mmol) was added as a powder. The reaction was stirred at room temperature for 2 h and then quenched with saturated NaHCO$_3$. The mixture was extracted with EtOAc. The organic layer was washed with saturated NaHCO$_3$ and brine, dried over Na$_2$SO$_4$ and concentrated to give a white foam. Purification by liquid chromatography (5% MeOH/CH$_2$Cl$_2$) gave the title compound as a white foam (260 mg, 0.607 mmol, 80%). The foam was dissolved in a minimal amount of CH$_2$Cl$_2$ and Et$_2$O was added. 1M HCl in Et$_2$O (0.6 mL) was added and a white precipitate formed. The solid was collected by filtration, washed with Et$_2$O and dried to give a white fluffy solid (257 mg). MS: APCI: M+1: 429.2 (Exact Mass: 428.22).

Example B48

Synthesis of 7-{4-[4-(6-Fluoro-naphthalen-1-yl)-piperazin-1-yl]-butoxy}-1H-[1,8]naphthyridin-2-one The reductive amination procedure from Example B1 was followed using 1-(6-fluoro-naphthalen-1-yl)-piperazine to give the title compound (195 mg, 72%). $^1$H NMR (400 MHz, dmso-d$_6$) δ 12.00 (s, 1H), 8.20–8.15 (m, 1H), 8.10 (d, 1H), 7.80 (d, 1H), 7.76–7.60 (m, 2H), 7.60–7.40 (m, 2H), 7.20 (d, 1H), 6.65 (d, 1H), 6.40 (d, 1H), 4.40 (t, 2H), 3.70–3.20 (m, 10H), 2.00–1.80 (m, 4H), MS ES+ 447.18 (M+H)$^+$ (Exact mass: 446.21).

Example B49

Synthesis of 7-{4-[4-(7-Fluoro-naphthalen-1-yl)-piperazin-1-yl]-butoxy}-1H-[1,8]naphthyridin-2-one The reductive amination procedure from Example B1 was followed using 1-(7-fluoro-naphthalen-1-yl)-piperazine to give the title compound (250 mg, 85%). $^1$H NMR (CDCl$_3$, 400 MHz) δ 9.02 (s, 1H), 7.82–7.79 (m, 2H), 7.75 (d, 1H), 7.62 (d, 1H), 7.58 (d, 1H), 7.36 (t, 1H), 7.30–7.20 (m, 1H), 7.18 (d, 1H), 6.60 (d, 1H), 6.56 (d, 1H), 4.40 (t, 2H), 3.20–3.00 (m, 4H), 2.90–2.60 (m, 4H), 2.60 (t, 2H), 1.96–1.70 (m, 4H). MS ES+ 447.17 (M+1)$^+$ (Exact mass: 446.21).

Example B50

Synthesis of 7-{4-[4-(8-Fluoro-naphthalen-1-yl)-piperazin-1-yl]-butoxy}-1H-[1,8]naphthyridin-2-one The reductive amination procedure from Example B1 was followed using 1-(8-fluoro-naphthalen-1-yl)-piperazine to give the title compound (0.32 g, 42%). $^1$H NMR (400 MHz, CDCl$_3$): δ 9.20 (br s, 1H), 7.75 (d, 1H), 7.60 (m, 2H), 7.45 (d, 1H), 7.40–7.30 (m, 2H), 7.15–7.05 (m, 2H), 6.60 (d, 1H), 6.48 (d, 1H), 4.40 (t, 2H), 3.40–3.25 (m, 2H), 3.05–2.80 (m, 4H), 2.60–2.40 (m, 4H), 1.90–1.65 (m, 4H). MS (ES+): 447.17 (M+H)$^+$ (Exact mass: 446.21).

Example B51

Synthesis of 7-{4-[4-(5-Fluoro-naphthalen-1-yl)-piperazin-1-yl]-butoxy}-1H-[1,8]naphthyridin-2-one The reductive amination procedure from Example B1 was followed using 1-(5-fluoro-naphthalen-1-yl)-piperazine to give the title compound. $^1$H NMR (400 MHz, DMSO-d$_6$): δ 12.00 (s, 1H), 8.03 (d, J=6.3 Hz, 1H), 7.97 (d, J=6.2 Hz, 1H), 7.85 (d, J=6.1 Hz, 1H), 7.75 (d, J=5.8 Hz, 1H), 7.50 (m, 2H), 7.35 (m, 1H), 7.22 (d, J=5.5 Hz, 1H), 6.68 (d, J=6.6 Hz, 1H), 6.40 (d, J=6.70 Hz, 1H), 4.40 (t, J=3.5 Hz, 2H), 3.00 (s, 4H), 2.70 (s, 4H), 2.50 (br s, 2H), 1.80 (m, 2H), 1.60 (m, 2H).

Example B52

Synthesis of 7-{4-[4-(4-Fluoro-naphthalen-1-yl)-piperazin-1-yl]-butoxy}-1H-[1,8]naphthyridin-2-one The reductive amination procedure from Example B1 was followed using 1-(4-fluoro-naphthalen-1-yl)-piperazine to give the title compound. $^1$H NMR (400 MHz, CDCl$_3$): δ 9.20 (br s, 1H), 8.25 (m, 1H), 8.10 (m, 1H), 7.75 (d, 1H), 7.62 (d, 1H), 7.58 (dd, 2H), 7.10–6.95 (m, 2H), 6.60 (d, 1H), 6.45 (d, 1H), 4.40 (t, 2H), 3.22–3.00 (br s, 4H), 2.85–2.60 (br s, 4H), 2.55 (m, 2H), 1.95–1.65 (m, 4H). MS: ES+ 447.23 (M+H)$^+$ (Exact mass: 446.21).

Example B53

Synthesis of 7-{4-[4-(3-Fluoro-naphthalen-1-yl)-piperazin-1-yl]-butoxy}-1H-[1,8]naphthyridin-2-one The reductive amination procedure from Example B1 was followed using 1-(3-fluoro-naphthalen-1-yl)-piperazine to give the title compound. $^1$H NMR (400 MHz, CDCl$_3$) δ 9.00 (br s, 1H), 8.12 (d, 1H), 7.78–7.70 (m, 2H), 7.64 (d, 1H), 7.50–7.38 (m, 2H), 7.14 (dd, 1H), 6.86 (dd, 1H), 6.62 (d, 1H), 6.52 (d, 1H), 4.40 (t, 2H), 3.15 (br s, 4H), 2.76 (br s, 4H), 2.56 (t, 2H), 1.94–1.84 (m, 2H), 1.81–1.70 (m, 2H). MS (ES+): 447.05 (M+H)$^+$ (Exact mass: 446.21).

Example B54

Synthesis of 7-{4-[4-(2-Fluoro-naphthalen-1-yl)-piperazin-1-yl]-butoxy}-1H-[1,8]naphthyridin-2-one The reductive amination procedure from Example B1 was followed using 1-(2-fluoro-naphthalen-1-yl)-piperazine to give the title compound (175 mg, 43%). $^1$H-NMR (400 MHz, DMSO-d$_6$): δ: 12.00 (s, 1H), 8.30 (d, J=6.5 Hz, 1H), 7.97 (m, 2H), 7.83 (m, 2H), 7.60–7.30 (m, 3H), 6.65 (d, J=8.2 Hz, 1H), 6.40 (d, J=8.0 Hz, 1H), 4.40 (m, 2H), 4.00 (br s, 4H), 3.40–3.10 (m, 6H), 2.00–1.77 (m, 4H).

Example B55

Synthesis of 7-{4-[4-(6,7-Difluoro-naphthalen-1-yl)-piperazin-1-yl]-butoxy}-1H-[1,8]naphthyridin-2-one The reductive amination procedure from Example B1 was followed using 1-(6,7-difluoro-naphthalen-1-yl)-piperazine to give the title compound (0.25 g, 70%). $^1$H NMR (400 MHz, DMSO-d$_6$): δ 12.30 (s, 1H), 10.55 (br s, 1H), 8.03 (m, 3H), 7.80 (d, 1H), 7.70 (d, 1H), 7.55 (t, 1H), 7.22 (d, 1H), 6.65 (d, 1H), 6.40 (d, 1H), 4.40 (t, 2H), 3.70–3.10 (m, 10H), 1.90–1.70 (m, 4H).

Example B56

Synthesis of 7-{4-[4-(7-Chloro-naphthalen-1-yl)-piperazin-1-yl]-butoxy}-1H-[1,8]naphthyridin-2-one The reductive amination procedure from Example B1 was followed using 1-(7-chloro-naphthalen-1-yl)-piperazine to give the title compound (0.373 g, 45%). $^1$H NMR (400 MHz, DMSO-d$_6$) δ 12.01 (s, 1H), 10.78 (s, 1H), 8.12 (d, 1H), 8.01 (t, 2H), 7.85 (d, 1H), 7.74 (d, 1H), 7.58–7.48 (m, 2H), 7.28 (d, 1H), 6.68 (d, 1H), 6.37 (d, 1H), 4.40 (t, 2H), 3.64 (m, 2H), 3.48–3.19 (m, 8H), 1.98–1.81 (m, 4H).

Example B57

Synthesis of 7-{4-[4-(6-Chloro-naphthalen-1-yl)-piperazin-1-yl]-butoxy}-1H-[1,8]naphthyridin-2-one The reductive amination procedure from Example B1 was followed using 1-(6-chloro-naphthalen-1-yl)-piperazine to give the title compound (0.403 g, 48%). mp. 208–209° C. $^1$H NMR (400 MHz, DMSO-d$_6$) δ 12.01 (s, 1H), 8.16 (d, 1H), 8.06 (d, 1H), 8.02 (d, 1H), 7.83 (d, 1H), 7.64 (d, 1H), 7.55 (m, 2H), 7.22 (d, 1H), 6.64 (d, 1H), 6.39 (d, 1H), 4.40 (t, 2H), 3.62 (m, 2H), 3.53–3.09 (m, 8H), 1.98–1.73 (m, 4H).

Example B58

Synthesis of 7-{4-[4-(5-Chloro-naphthalen-1-yl)-piperazin-1-yl]-butoxy}-1H-[1,8]naphthyridin-2-one The reductive amination procedure from Example B1 was followed using 1-(5-chloro-naphthalen-1-yl)-piperazine to give the title compound. $^1$H NMR (400 MHz, DMSO-d$_6$) δ 12.01 (s, 1H), 8.18 (d, 1H), 8.01 (d, 1H), 7.98 (d, 1H), 7.83 (d, 1H), 7.77 (d, 1H), 7.63 (t, 1H), 7.54 (t, 1H), 7.32 (d, 1H), 6.68 (d, 1H), 6.38 (dd, 1H), 4.40 (t, 2H), 3.64 (m, 2H), 3.48–3.15 (m, 8H), 1.98–1.81 (m, 4H).

Example B59

Synthesis of 7-{4-[4-(8-Chloro-naphthalen-1-yl)-piperazin-1-yl]-butoxy}-1H-[1,8]naphthyridin-2-one The reductive amination procedure from Example B1 was followed using 1-(8-chloro-naphthalen-1-yl)-piperazine to give the title compound (0.257 g, 41%). $^1$H NMR (400 MHz, DMSO-d$_6$) δ 12.04 (s, 1H), 8.02 (d, 1H), 7.92 (dd, 1H), 7.84 (d, 1H), 7.76 (d, 1H), 7.62 (dd, 1H), 7.54 (t, 1H), 7.46 (t, 1H), 7.32 (dd, 1H), 6.66 (d, 1H), 6.38 (d, 1H), 4.38 (t, 2H), 3.62 (m, 2H), 3.55–3.24 (m, 6H), 3.12 (m, 2H), 1.96–1.78 (m, 4H).

Example B60

Synthesis 7-{4-[4-(7-Methoxy-naphthalen-1-yl)-piperazin-1-yl]-butoxy}-1H-[1,8]naphthyridin-2-one The reductive amination procedure from Example B1 was followed using 1-(7-methoxy-naphthalen-1-yl)-piperazine to give the title compound. $^1$H NMR (400 MHz, CDCl$_3$) δ 8.90 (s, 1H), 7.78–7.74 (m, 2H), 7.62 (d, 1H), 7.60–7.40 (m, 2H), 7.26–7.24 (m, 1H), 7.18–7.06 (m, 2H), 6.60 (d, 1H), 6.50 (d, 1H), 4.40 (t, 2H), 3.90 (s, 3H), 3.30–2.80 (m, 8H), 2.60 (t, 2H), 1.90–1.65 (m, 4H). MS ES+ 459.21 (M+1)$^+$ (Exact mass: 458.23).

Example B61

Synthesis of 7-{4-[4-(6-Methoxy-naphthalen-1-yl)-piperazin-1-yl]-butoxy}-1H-[1,8]naphthyridin-2-one The reductive amination procedure from Example B1 was followed using 1-(6-methoxy-naphthalen-1-yl)-piperazine to give the title compound. $^1$H NMR (400 MHz, CDCl$_3$) δ 8.90 (s, 1H), 8.10 (d, 1H), 7.74 (d, 1H), 7.60 (d, 1H), 7.40 (d, 1H), 7.38 (t, 1H), 7.18–7.10 (m, 2H), 6.98 (d, 1H), 6.60 (d, 1H), 6.50 (d, 1H), 4.40 (t, 2H), 3.90 (s, 3H), 3.20–2.80 (m, 8H), 2.58 (t, 2H), 1.90–1.65 (m, 4H). MS ES+ 459.20 (M+H)$^+$ (Exact mass: 458.23).

Example B62

Synthesis of 7-{4-[4-(7-Acetyl-naphthalen-1-yl)-piperazin-1-yl]-butoxy}-1H-[1,8]naphthyridin-2-one The reductive amination procedure from Example B1 was followed using 1-(8-piperazin-1-yl-naphthalen-2-yl)-ethanone to give the title compound (400 mg, 83%). $^1$H NMR (400 MHz, dmso-d$_6$) δ 12.00 (s, 1H), 8.70 (s, 1H), 8.10–8.00 (m, 3H), 7.85 (d, 1H), 7.80 (d, 1H), 7.60 (t, 1H), 7.30 (d, 1H), 6.65 (d, 1H), 6.40 (d, 1H), 4.40 (t, 2H) 3.70–3.60 (m, 2H), 3.60–3.20 (m, 8H), 2.80 (s, 3H), 2.00–1.80 (m, 4H), MS ES+ 471.23 (M+H)$^+$ (Exact mass: 470.23).

Example B63

Synthesis of 7-{4-[4-(6-Acetyl-naphthalen-1-yl)-piperazin-1-yl]-butoxy}-1H-[1,8]naphthyridin-2-one The reductive amination procedure from Example B1 was followed using 1-(5-piperazin-1-yl-naphthalen-2-yl)-ethanone to give the title compound (300 mg, 85%). $^1$H NMR (400 MHz, dmso-d$_6$) δ 12.00 (s, 1H), 8.64 (s, 1H), 8.20 (d, 1H), 8.05–7.95 (m, 2H), 7.90–7.80 (m, 2H), 7.60 (t, 1H), 7.36 (d, 1H), 6.64 (d, 1H), 6.40 (d, 1H), 4.40 (t, 2H), 3.70–3.60 (m, 2H), 3.50–3.32 (m, 4H), 3.30–3.10 (m, 4H), 2.70 (s, 3H), 2.00–1.80 (m, 4H), MS ES+ 471.17 (M+H)$^+$ (Exact mass: 470.23).

Example B64

Synthesis of 7-{4-[4-(5-Acetyl-naphthalen-1-yl)-piperazin-1-yl]-butoxy}-1H-[1,8]naphthyridin-2-one The reductive amination procedure from Example B1 was followed using 1-(5-piperazin-1-yl-naphthalen-1-yl)-ethanone to give the title compound (0.39 g, 77%). $^1$H NMR (400 MHz, CDCl$_3$): δ 8.45 (d, J=7.7 Hz, 1H), 8.30 (d, J=7.6 Hz, 1H), 7.90 (d, J=5.8 Hz, 1H), 7.75 (m, 2H), 7.55 (m, 2H), 7.30 (d, J=6.2 Hz, 1H), 6.70 (m, 2H), 4.50 (t, J=3.6 Hz, 2H), 4.00–3.60 (m, 4H), 3.40–3.10 (m, 4H), 2.80 (s, 3H), 2.30 (m, 2H), 2.00 (m, 4H).

Example B65

Synthesis of 7-{4-[4-(4-Acetyl-naphthalen-1-yl)-piperazin-1-yl]-butoxy}-1H-[1,8]naphthyridin-2-one The reductive amination procedure from Example B1 was followed using 1-(4-piperazin-1-yl-naphthalen-1-yl)-ethanone to give the title compound (0.42 g, 69%). $^1$H NMR (400 MHz, DMSO-d$_6$): δ 12.00 (s, 1H), 10.60 (s, 1H), 8.80 (d, 1H), 8.15 (m, 2H), 8.00 (d, 1H), 7.80 (d, 1H), 7.60 (m, 2H), 7.20 (d, 1H), 6.63 (d, 1H), 6.40 (d, 1H), 4.40 (m, 2H), 3.80–3.20 (m, 10H), 2.70 (s, 3H), 2.00–1.80 (m, 4H).

Example B66

Synthesis of 7-{4-[4-(2-Acetyl-naphthalen-1-yl)-piperazin-1-yl]-butoxy}-1H-[1,8]naphthyridin-2-one The reductive amination procedure from Example B1 was followed using 1-(1-piperazin-1-yl-naphthalen-2-yl)-ethanone to give the title compound. $^1$H NMR (400 MHz, CDCl$_3$): δ 12.00 (s, 1H), 8.37 (m, 1H), 7.80 (m, 2H), 7.60 (m, 3H), 6.70 (d, J=8.8 Hz, 1H), 6.40 (d, J=8.6 Hz, 1H), 4.40 (m, 2H), 3.60–3.40 (m, 10H), 2.66 (s, 3H), 1.90 (m, 4H).

Example B67

Synthesis of 8-{4-[4-(7-Oxo-7,8-dihydro-[1,8]naphthyridin-2-yloxy)-butyl]-piperazin-1-yl}-naphthalene-2-carbonitrile The reductive amination procedure from Example B1 was followed using 8-piperazin-1-yl-naphthalene-2-carbonitrile to give the title compound (0.341 g, 24%). $^1$H NMR (400 MHz, DMSO-d$_6$) δ 12.03 (s, 1H), 11.24 (s, 1H), 8.63 (s, 1H), 8.13 (d, 1H), 8.20 (d, 1H), 7.83 (m, 2H), 7.70 (t, 1H), 7.37 (d, 1H), 6.68 (d, 1H), 6.38 (d, 1H), 4.40 (t, 2H), 3.68–3.21 (m, 16H), 2.40–1.90 (m, 4H).

Example B68

Synthesis of 1-Methyl-7-[4-(4-naphthalen-1-yl-piperazin-1-yl)-butoxy]-1H-[1,8]naphthyridin-2-one An intermediate compound, 7-Chloro-1-methyl-1H-[1,8] naphthyridin-2-one, was produced as follows: To a suspension of 7-chloro-1H-[1,8]naphthyridin-2-one (1.17 g, 6.49 mmol) in THF (32 mL) cooled to 0° C. was added potassium tert-butoxide (1 M in THF, 9.7 mL, 9.7 mmol). After stirring for 15 min, MeI (0.81 mL, 13.0 mmol) was added. The reaction was stirred at 0° C. for 1 h and at room temperature for 5 h. The reaction was quenched with saturated NH$_4$Cl and H$_2$O. The mixture was extracted with EtOAc. The organic layer was washed with saturated NaHCO$_3$ and brine, dried over Na$_2$SO$_4$ and concentrated. Purification by liquid chromatography (Analogix, RS-120, 10–50% EtOAc/Hexanes) gave the intermediate compound as a white solid (0.88 g, 4.52 mmol, 70%). MS: APCI: M+1: 195.0 (Exact Mass: 194.02).

To a solution of 4-(4-naphthalen-1-yl-piperazin-1-yl)-butan-1-ol (422 mg, 1.48 mmol) in THF (5 mL) cooled to 0° C. was added 7-chloro-1-methyl-1H-[1,8]naphthyridin-2-one (303 mg, 1.56 mmol) as a solution in THF (9 mL) via cannula. The reaction was stirred for about 2 h at 0° C. The reaction was quenched with saturated NH₄Cl and the mixture was extracted with EtOAc. The organic layer was washed with saturated NaHCO₃ and brine, dried over Na₂SO₄ and concentrated. Purification by LC (4% MeOH/ CH₂Cl₂) gave the title compound as a white foam (507 mg, 1.15 mmol, 77%). A portion of the title compound (243 mg, 0.549 mmol) was dissolved in Et₂O and 1 N HCl in Et₂O (0.55 mL) was added. The resulting white precipitate was collected by filtration, washed with Et₂O and dried to give a white solid (248 mg). MS: APCI: M+1: 443.3 (Exact Mass: 442.24).

Example C1

Synthesis of 7-{3-[4-(2,3-Dichloro-phenyl)-piperazin-1-yl]-propoxy}-1H-[1,8]naphthyridin-2-one An intermediate compound, 2-Benzyloxy-7-{3-[4-(2,3-dichloro-phenyl)-piperazin-1-yl]-propoxy}-[1,8]naphthyridine, was produced as follows: To a suspension of 3-[4-(2, 3-dichloro-phenyl)-piperazin-1-yl]-propan-1-ol hydrochloride (400 mg, 1.23 mmol) in THF (5 mL) cooled to −40° C. was added KO'BU (1 M in THF, 2.3 mL, 2.3 mmol, 1.9 equiv). The mixture became a cloudy solution. After stirring for 20 min at −40° C., 2-benzyloxy-7-chloro-[1,8]naphthyridine (333 mg, 1.23 mmol) was added as a solution in THF (8 mL) via cannula. The reaction was allowed to warm to 0° C. slowly over 1 h. The reaction was quenched with saturated NH₄Cl and H₂O and extracted with EtOAc. The organic layer was washed with saturated NaHCO₃ and brine, dried over Na₂SO₄ and concentrated. Purification by liquid chromatography (CH₂Cl₂ to 2% MeOH/CH₂Cl₂) gave the title compound as a clear oil/foam (367 mg, 0.701 mmol, 57%). MS: APCI: M+1: 523.0 (Exact Mass: 522.16).

2-Benzyloxy-7-{3-[4-(2,3-dichloro-phenyl)-piperazin-1-yl]-propoxy}-[1,8]naphthyridine (367 mg, 0.701 mmol) was hydrogenated using 5% Pd/C (0.1 g) in MeOH (50 mL) for 1 h. The reaction was filtered and concentrated. Purification by liquid chromatography (4–5% MeOH/CH₂Cl₂) gave the title compound as a white foam (181 mg, 0.418 mmol, 60%). MS: APCI: M+1: 433.1 (Exact Mass: 432.11).

Example C2

Synthesis of 7-[3-(4-Naphthalen-1-yl-piperazin-1-yl)-propoxy]-1H-[1,8]naphthyridin-2-one A first intermediate compound, 4-(3-Hydroxy-propyl)-piperazine-1-carboxylic acid tert-butyl ester, was produced as follows: A 12 L, 4-necked RB flask, equipped with a mechanical stirrer, thermometer, nitrogen inlet and an addition funnel is charged with a solution of N-boc-piperazine, (600 g, 3.225 mol) in DMF (3.9 L) followed by anhydrous potassium carbonate (666 g, 4.82 mol) then sodium iodide (72.5 g, 1.25 mol). The reaction mixture is stirred at ~80° C. for 16 h, cooled to room temperature, filtered, washed with DMF (2×200 mL) and evaporated to a thick mass, which is set aside for a day at ~5° C. The solids are filtered, washed with hexanes (3×300 mL) and dried in vacuum at ~50° C. to get 438 g crude as a white powder. The crude compound is dissolved in 10% methanol in ether (2.5 L) and passed through a small silica gel column (previously washed with ether containing 2% triethylamine). The filtrates are evaporated to thick liquid and added to a mixture of hexanes-ether (2:1, 2.5 L) while stirring and continued the stirring for 12 h at ~5° C., filtered, washed with hexanes and dried the product to give the title compound, as a white crystalline solid (308 g, 39%).

A second intermediate compound, 4-[3-(7-Benzyloxy-[1, 8]naphthyridin-2-yloxy)-propyl]-piperazine-1-carboxylic acid tert-butyl ester, was produced as follows: A 5 L 4-necked flask, equipped with a mechanical stirrer, thermometer, nitrogen inlet and an addition funnel is charged with a solution of 4-(3-hydroxy-propyl)-piperazine-1-carboxylic acid tert-butyl ester, (129 g, 0.528 mol) in anhydrous THF (1.6 L) and cooled to −40° C. To this potassium tert-butoxide solution (580 mL, 1M in THF, 0.58 mol) is added drop-wise during 1 h, and stirred further for 30 min. 2-Benzyloxy-7-chloro-[1,8]naphthyridine (130 g, 0.48 mol) is added to the reaction mixture in portions at −40° C. during 1 h. The reaction is stirred for 4 h to bring to 0° C., then quenched with saturated ammonium chloride solution (1.5 L) and extracted with ethyl acetate (2 L and 1 L). The combined organic extracts are washed with brine (1 L), dried over anhydrous sodium sulfate and concentrated to afford the crude as a dark brown thick paste. The crude is purified by silica gel chromatography using 20–25% ethyl acetate in hexanes for elution to give the second intermediate compound as a thick almost colorless thick paste (126 g, 49.8%).

A third intermediate compound, 4-[3-(7-Oxo-7,8-dihydro-[1,8]naphthyridin-2-yloxy)-propyl]-piperazine-1-carboxylic acid tert-butyl ester, was produced as follows: To a solution of 4-[3-(7-benzyloxy-[1,8]naphthyridin-2-yloxy)-propyl]-piperazine-1-carboxylic acid tert-butyl ester (62 g, 0.129 mol) in methanol (600 mL) and THF (150 mL) is added 10% Pd/C (6 g) and the mixture is hydrogenated at atmospheric pressure at room temperature for 20 h. The reaction mixture is filtered, washed with methanol, concentrated and vacuum dried at ~50° C. to afford the third intermediate compound as a pale yellow thick gummy solid (48.8 g, 94%).

A fourth intermediate compound, 7-(3-Piperazin-1-yl-propoxy)-1H-[1,8]naphthyridin-2-one, was produced as follows: A 2 L, 3-necked RB flask, equipped with mechanical stirrer and a nitrogen inlet is charged with a solution of 4-[3-(7-oxo-5,6,7,8-tetrahydro-[1,8]naphthyridin-2-yloxy)-propyl]-piperazine-1-carboxylic acid tert-butyl ester (43.4 g, 0.111 mol) in dichloromethane (500 mL) followed by trifluoroacetic acid (187 mL) at room temperature. The reaction mixture is stirred at room temperature by occasionally evacuating the reaction flask with vacuum. After ensuring the absence of starting material by TLC (10% methanol in CH₂Cl₂), the solvents are removed by co-distilling with toluene (3×). The residue is triturated in ether to obtain 62 g of the crude as a TFA salt. The crude TFA salt is suspended in water (50 mL), basified with 4N NaOH (100 mL), stirred, washed with CH₂Cl₂ and passed through a column of HP-20 (300 mL) previously washed with methanol followed by water. The column is thoroughly washed with water to eliminate any basic impurities and eluted with methanol. The methanol solution thus obtained is evaporated and the residue is triturated in ether to afford the fourth intermediate compound as an off-white powder (33 g, 100%), m.p. 192–195° C.

7-(3-Piperazin-1-yl-propoxy)-1H-[1,8]naphthyridin-2-one (1.5 g, 4.2 mmol) was placed in a 25 mL flask with 15 mL toluene and azeotroped to dryness. The mixture was cooled to 25° C. and 1-bromo-naphthalene (4.45 g, 21 5 mmol) was added. In a separate flask, Pd(OAc)₂ (0.073 g, 0.325 mmol) and 2-dicyclohexylphosphino biphenyl (0.180 g, 0.514 mmol) were dissolved in degassed anhydrous toluene (3 mL). This solution was then added to the suspension of the two reactants via syringe. Sodium tert-butoxide, (0.8 g, 8.32 mmol) was added which gave a suspension upon stirring. After the mixture had been heated to reflux overnight, the mixture was evaporated and the residue was taken up into dichloromethane and water. The pH was adjusted to 4.5 with 1N citric acid followed by separation of the aqueous phase. The organic phase was washed with water and the pH adjusted to 12 by addition of 1N sodium hydroxide and brine. The organic phase was separated, dried over sodium sulfate, filtered and evaporated to an oil with suspended solids. The residue was purified by chromatography on silica gel eluting with dichloromethane and then a gradient to 20% methanol in ethyl acetate. The title compound was recovered as a crystalline solid (0.262 g). MS: APCI: M+1: 415.5 (Exact Mass: 414.21).

Example C3

Synthesis of 7-[3-(4-Naphthalen-1-yl-piperazin-1-yl)-propoxy]-3,4-dihydro-1H-[1,8]naphthyridin-2-one A first intermediate compound, 4-[3-(7-Oxo-5,6,7,8-tetrahydro-[1,8]naphthyridin-2-yloxy)-propyl]-piperazine-1-carboxylic acid tert-butyl ester, was produced as follows: To a solution of 4-[3-(7-oxo-7,8-dihydro-[1,8]naphthyridin-2-yloxy)-propyl]-piperazine-1-carboxylic acid tert-butyl ester (62 g, 0.129 mol) in methanol (600 mL) and THF (150 mL) is added 10% Pd/C (6 g) and the mixture is hydrogenated at atmospheric pressure at room temperature for 20 h. The reaction mixture is filtered, washed with methanol, concentrated and vacuum dried at ~50° C. to afford 43 g of a pale yellow thick gummy solid. It is again subjected to hydrogenation by dissolving in DMF-dioxane-ethanol (0.3 L:1 L:0.2 L) and adding fresh Pd/C (8 g). After a similar workup, the first intermediate compound was obtained as a thick gum (37 g, 73.5%).

A second intermediate, 7-(3-Piperazin-1-yl-propoxy)-3,4-dihydro-1H-[1,8]naphthyridin-2-one, was produced as follows: A 2 L, 3-necked RB flask, equipped with a mechanical stirrer, and a nitrogen inlet is charged with a solution of 4-[3-(7-oxo-5,6,7,8-tetrahydro-[1,8]naphthyridin-2-yloxy)-propyl]-piperazine-1-carboxylic acid tert-butyl ester (35 g, 0.089 mol) in dichloromethane (500 mL) followed by trifluoroacetic acid (150 mL) at room temperature. The reaction mixture is stirred at room temperature by occasionally evacuating the reaction flask with vacuum. After ensuring the absence of starting material by TLC (10% methanol in $CH_2Cl_2$), the solvents are removed by co-distilling with toluene (3×) to get the crude TFA salt as a light brown thick paste. The crude material is suspended in water (50 mL), basified with 4N NaOH (100 mL), stirred, filtered, washed thoroughly with water followed by ether and dried under vacuum over $P_2O_5$ at ~50° C. to afford the second intermediate compound as an off-white powder (24.4 g, 93%), m.p. 142–46° C.

In a similar manner to the example shown above, 7-(3-piperazin-1-yl-propoxy)-3,4-dihydro-1H-[1,8]naphthyridin-2-one was coupled to 1-bromo-naphthalene to give the title compound (0.189 g). MS: APCI: M+1: 417.2 (Exact Mass: 416.22).

Example C4

Synthesis of 7-{2-[4-(2,3-Dichloro-phenyl)-piperazin-1-yl]-ethoxy}-1H-[1,8]naphthyridin-2-one An intermediate compound, 2-Benzyloxy-7-{2-[4-(2,3-dichloro-phenyl)-piperazin-1-yl]-ethoxy}-[1,8]naphthyridine, was produced as follows: To a solution of 2-[4-(2,3-dichloro-phenyl)-piperazin-1-yl]-ethanol (1.0 g, 3.63 mmol) in THF (6 mL) cooled to −20° C. was added 1M KO$^t$Bu in THF (3.6 mL, 3.6 mmol). After 15 min, a solution of 2-benzyloxy-7-chloro-[1,8]naphthyridine (1.18 g, 4.35 mmol, 1.2 equiv) in THF (25 mL) was added quickly via cannula. The reaction became a brown solution. The reaction was slowly allowed to warm to 0° C. over 90 min and then quenched with saturated $NH_4Cl$ and $H_2O$. The mixture was extracted with EtOAc. The organic layer was washed with saturated $NaHCO_3$ and brine, dried over $Na_2SO_4$ and concentrated. Purification by liquid chromatography ($CH_2Cl_2$ to 2% MeOH/$CH_2Cl_2$) gave the product with some lower Rf impurities. Further purification by liquid chromatography (75% EtOAc/Hexanes) afforded the intermediate compound as a clear oil/white foam (1.36 g, 2.67 mmol, 74%). MS: APCI: M+1: 509.0 (Exact Mass: 508.14).

2-Benzyloxy-7-{2-[4-(2,3-dichloro-phenyl)-piperazin-1-yl]-ethoxy}-[1,8]naphthyridine (1.30 g, 2.55 mmol) was hydrogenated using 5% Pd/C (0.4 g) in MeOH (100 mL) for 40 min. The reaction was filtered and concentrated. Purification by liquid chromatography (2–3% MeOH/EtOAc with 1% $NH_4OH$) gave the title compound as a white foam (600 mg, 1.43 mmol, 56%). The HCl salt was prepared using 1 N HCl in $Et_2O$ to give a white solid. MS: APCI: M+1: 419.1 (Exact Mass: 418.10).

Example C5

Synthesis of 7-{4-[4-(2,3-Dichloro-phenyl)-piperazin-1-yl]-1-methyl-butoxy}-3,4-dihydro-1H-[1,8]naphthyridin-2-one A first intermediate compound, 2-Benzyloxy-7-[4-(tert-butyl-dimethyl-silanyloxy)-1-methyl-butoxy]-[1,8]naphthyridine, was produced as follows: To a solution of the 5-(tert-butyl-dimethyl-silanyloxy)-pentan-2-ol (1.61 g, 7.39 mmol, *Tetrahedron Lett.* 1979, 99) in THF (7 mL) cooled to −30° C. was added 1M KOtBu in THF (7.4 mL, 7.4 mmol). The solution was stirred for 15 min and 2-benzyloxy-7-chloro-[1,8]naphthyridine (2.0 g, 7.39 mmol) was added as a solution in THF (40 mL). The reaction was allowed to warm to room temperature over 6 h. The reaction was quenched with saturated NH4Cl and H2O and extracted with EtOAc. The organic layer was washed with saturated NaHCO3 and brine, dried over Na2SO4 and concentrated. Purification by liquid chromatography (5% EtOAc/Hexanes) gave the first intermediate compound as a clear oil (1.77 g, 3.91 mmol, 53%). MS: APCI: M+1: 453.2 (Exact Mass: 452.25).

A second intermediate compound, 4-(7-Benzyloxy-[1,8]naphthyridin-2-yloxy)-pentan-1-ol, was produced as follows: To a solution of 2-benzyloxy-7-[4-(tert-butyl-dimethyl-silanyloxy)-1-methyl-butoxy]-[1,8]naphthyridine (1.77 g, 3.91 mmol) in THF (8 mL) was added 1 M TBAF in THF (7.8 mL, 7.8 mmol). The reaction turned purple instantly. The reaction was stirred at room temperature for 1 h. Saturated $NaHCO_3$ was added and the mixture was extracted with EtOAc. The organic layer was washed with $H_2O$ and brine, dried over $Na_2SO_4$ and concentrated to give a pale brown oil. Purification by liquid chromatography (35–40% EtOAc/Hexanes) gave the second intermediate compound as a clear oil (1.29 g, 3.81 mmol, 97%).

A third intermediate compound, 7-(4-Hydroxy-1-methylbutoxy)-3,4-dihydro-1H-[1,8]naphthyridin-2-one, was produced as follows: 4-(7-Benzyloxy-[1,8]naphthyridin-2-yloxy)-pentan-1-ol (1.29 g, 3.81 mmol) was hydrogenated using 20% Pd/C (0.35 g) in MeOH (50 mL) for 18 h. The reaction was filtered and concentrated. Purification by liquid chromatography (5% MeOH/$CH_2Cl_2$) gave the third intermediate compound as a clear oil (0.898 g, 3.59 mmol, 94%).

A fourth intermediate compound, 4-(7-Oxo-5,6,7,8-tetrahydro-[1,8]naphthyridin-2-yloxy)-pentanal, was produced as follows: To a cloudy solution of the Dess-Martin reagent (2.28 g, 5.38 mmol) in $CH_2Cl_2$ (10 mL) was added 7-(4-hydroxy-1-methyl-butoxy)-3,4-dihydro-1H-[1,8]naphthyridin-2-one (0.895 g, 3.59 mmol) as a solution in $CH_2Cl_2$ (10 mL). The reaction turned clear and then became pale yellow. The reaction was stirred at room temperature for 6 h. Saturated $NaHCO_3$ and saturated $Na_2S_2O_3$ (1:1) was added and the mixture was stirred for 10 min. The mixture was extracted with EtOAc/$Et_2O$ (2×). The organic layer was washed with saturated $NaHCO_3$, $H_2O$ and brine, dried over $MgSO_4$ and concentrated to give a brown oil (901 mg, used crude in subsequent reductive aminations). MS: APCI: M+1: 249.1 (Exact Mass: 248.12).

To a solution of 4-(7-oxo-5,6,7,8-tetrahydro-[1,8]naphthyridin-2-yloxy)-pentanal (450 mg, crude) in DCE (10 mL) was added 2,3-dichlorophenyl-piperazine hydrochloride (495 mg, 1.85 mmol) followed by $Et_3N$ (0.55 mL, 3.96 mmol). The mixture was stirred for 10 min and then powdered $NaBH(OAc)_3$ (534 mg, 2.52 mmol) was added. The reaction was stirred at room temperature for 2 h and then quenched with saturated $NaHCO_3$. The mixture was extracted with EtOAc (2×). The organic layer was washed with saturated $NaHCO_3$ and brine, dried over $Na_2SO_4$ and concentrated to give a foam. Purification by liquid chromatography (4% MeOH/$CH_2Cl_2$) gave the title compound as a white foam (507 mg, 1.09 mmol, 61%). MS: APCI: M+1: 463.1 (Exact Mass: 462.16). The enantiomers were separated by chiral HPLC (Chiralcel OD).

Example C6

Synthesis of 7-[1-Methyl-4-(4-naphthalen-1-yl-piperazin-1-yl)-butoxy]-3,4-dihydro-1H-[1,8]naphthyridin-2-one The procedure above was followed using 1-naphthalen-1-yl-piperazine hydrochloride (460 mg, 1.85 mmol). Purification by liquid chromatography (4% MeOH/$CH_2Cl_2$) gave the title compound as a white foam (539 mg, 1.21 mmol, 67%). MS: APCI: M+1: 445.2 (Exact Mass: 444.25). The enantiomers were separated by chiral HPLC (Chiralcel OD).

Example C7

Synthesis of 7-{4-[4-(2,3-Dichloro-phenyl)-piperazin-1-yl]-1,1-dimethyl-butoxy}-3,4-dihydro-1H-[1,8]naphthyridin-2-one A first intermediate compound, 2-Benzyloxy-7-[4-(tert-butyl-dimethyl-silanyloxy)-1,1-dimethyl-butoxy]-[1,8]naphthyridine, was produced as follows: To a mixture of the 5-(tert-butyl-dimethyl-silanyloxy)-2-methyl-pentan-2-ol (3.0 g, 12.91 mmol, J. Org. Chem. 1997, 62, 3153 and Tetrahedron Lett. 1979, 99) and 2-benzyloxy-7-chloro-[1,8]naphthyridine (3.49 g, 12.91 mmol) in THF (100 mL) cooled to 0° C. was added KHMDS (0.5 M in toluene, 25.8 mL, 12.91 mmol). The reaction turned dark green. After 30 min at 0° C., the ice bath was removed and the reaction was stirred for 2 h at RT. Saturated $NH_4Cl$ was added and the mixture was extracted with $CH_2Cl_2$ (2×). The organic layer was washed with saturated $NH_4Cl$ and concentrated to give a dark orange oil. Purification by liquid chromatography (5% EtOAc/Hexanes) gave the first intermediate compound as a clear oil (1.64 g, 3.51 mmol, 27%). MS: APCI: M+1: 467.1, fragment: 253.1 (Exact Mass: 466.27).

A second intermediate compound, 7-(4-Hydroxy-1,1-dimethyl-butoxy)-3,4-dihydro-1H-[1,8]naphthyridin-2-one, was produced as follows: 2-Benzyloxy-7-[4-(tert-butyl-dimethyl-silanyloxy)-1,1-dimethyl-butoxy]-[1,8]naphthyridine (1.64 g, 3.51 mmol) was hydrogenated using 20% Pd/C (0.5 g) in MeOH (50 mL) for 22 h. The TBS group was removed under the reaction conditions. The reaction was filtered and concentrated. The residue was dissolved in EtOAc and washed with saturated $NaHCO_3$ and brine. The organics were concentrated and purified by liquid chromatography (5% MeOH/$CH_2Cl_2$) to give the second intermediate compound as a clear oil which solidified under vacuum to give a white solid (648 mg, 2.45 mmol, 70%). MS: APCI: M+1: 265.1 (Exact Mass: 264.15).

A third intermediate compound, 4-Methyl-4-(7-oxo-5,6,7,8-tetrahydro-[1,8]naphthyridin-2-yloxy)-pentanal, was produced as follows: To a cloudy solution of the Dess-Martin reagent (1.66 g, 3.92 mmol) in $CH_2Cl_2$ (10 mL) was added 7-(4-hydroxy-1,1-dimethyl-butoxy)-3,4-dihydro-1H-[1,8]naphthyridin-2-one (648 mg, 2.45 mmol) as a solution in $CH_2Cl_2$ (5 mL). The reaction was stirred at room temperature for 5 h. Saturated $NaHCO_3$ and saturated $Na_2S_2O_3$ (1:1) was added and the mixture was stirred for 10 min. The mixture was extracted with EtOAc/$Et_2O$ (2×). The organic layer was washed with saturated $NaHCO_3$, $H_2O$ and brine, dried over $MgSO_4$ and concentrated to give a yellow solid/oil (679 mg, used crude in subsequent reductive aminations). MS: APCI: M+1: 263.1 (Exact Mass: 262.13).

To a solution of 4-methyl-4-(7-oxo-5,6,7,8-tetrahydro-[1,8]naphthyridin-2-yloxy)-pentanal (335 mg, crude) in DCE (6 mL) was added 2,3-dichlorophenyl-piperazine hydrochloride (335 mg, 1.25 mmol) followed by $Et_3N$ (0.35 mL, 2.50 mmol). The mixture was stirred for 10 min and then powdered $NaBH(OAc)_3$ (365 mg, 1.72 mmol) was added. The reaction was stirred at room temperature for 2 h and then quenched with saturated $NaHCO_3$. The mixture was extracted with EtOAc (2×). The organic layer was washed with saturated $NaHCO_3$, $H_2O$ and brine, dried over $Na_2SO_4$ and concentrated. Purification by liquid chromatography (4% MeOH/$CH_2Cl_2$) gave the title compound as a white foam (395 mg, 0.827 mmol, 67% over 2 steps). The foam was dissolved in $Et_2O$ and 1 N HCl in $Et_2O$ (0.85 mL) was added. The resulting white precipitate was collected by filtration, washed with $Et_2O$ and dried to give a white solid (386 mg). MS: APCI: M+1: 477.1 (Exact Mass: 476.17).

Example C8

Synthesis of 7-[1,1-Dimethyl-4-(4-naphthalen-1-yl-piperazin-1-yl)-butoxy]-3,4-dihydro-1H-[1,8]naphthyridin-2-one The procedure above was followed using 1-naphthalen-1-yl-piperazine hydrochloride (311 mg, 1.25 mmol). Purification by liquid chromatography (4% MeOH/$CH_2Cl_2$)

gave the title compound as a white foam (384 mg, 0.837 mmol, 68% over 2 steps). The HCl salt was prepared as above to give a white solid (385 mg). MS: APCI: M+1: 459.2 (Exact Mass: 458.27).

Example C9

7-{5-[4-(2,3-Dichloro-phenyl)-piperazin-1-yl]-pentyl}-3,4-dihydro-1H-[1,8]naphthyridin-2-one A first intermediate compound, 7-Amino-3,4-dihydro-1H-[1,8]naphthyridin-2-one, was produced as follows: A solution of 7-amino-[1,8]naphthyridin-2-ol.$H_2SO_4$ (36.0 g, 139 mmol, *J. Org. Chem.* 1981, 46, 833) in 6 N HCl (600 mL) was hydrogenated using 20% Pd/C for 2 d. The reaction was filtered and then cooled to −50° C. A thick white precipitate formed which was filtered and washed with $Et_2O$. The resulting solid was slurried with $Et_2O$, filtered and dried to give the first intermediate compound as the hydrochloride salt (21.5 g, 108 mmol, 78%). MS: APCI: M+1: 164.0 (Exact Mass: 163.07).

A second intermediate compound, 7-Chloro-3,4-dihydro-1H-[1,8]naphthyridin-2-one, was produced as follows: To concentrated HCl (80 mL) cooled to −5° C. and saturated with HCl gas was added 7-amino-3,4-dihydro-1H-[1,8] naphthyridin-2-one (9.0 g, 55.0 mmol) to give a solution. A solution of $NaNO_2$ (9.6 g, 137.0 mmol) in $H_2O$ (15 mL) was added subsurface via a syringe pump over 20 min. The temperature was between −5 to −7° C. The mixture was a yellow-orange suspension during the addition and turned dark green after the addition. The reaction was poured into saturated $NaHCO_3$ (500 mL) at 10° C. and additional solid $NaHCO_3$ was added to bring pH to 7. The mixture was extracted with EtOAc. The organic layer was dried over $MgSO_4$ and concentrated. The residue was dissolved in warm EtOAc (125 mL) and the insoluble material was filtered off. The filtrate was washed with saturated $Na_2CO_3$, dried over $MgSO_4$ and concentrated to a smaller volume. The resulting solid was filtered and dried to give the second intermediate compound (4.4 g, 24.2 mmol, 44%). MS: APCI: M+1: 183.0 (Exact Mass: 182.02).

A third intermediate compound, 7-(5-Chloro-pent-1-enyl)-3,4-dihydro-1H-[1,8]naphthyridin-2-one, was produced as follows: To a solution of 7-chloro-3,4-dihydro-1H-[1,8]naphthyridin-2-one (9.0 g, 49.0 mmol) in dimethoxyethane (160 mL) was added Pd(PPh3)4 (1.60 g, 1.48 mmol) followed by a slurry of 5-chloro-1-pentenyl boronic acid (10.97 g, 74.0 mmol) in dimethoxyethane (20 mL). A solution of Na2CO3 (10.7 g) in H2O (50 mL) was added and the mixture was heated overnight at 85° C. More Pd(PPh3)4 (0.44 g) was added and the reaction was heated at 104° C. overnight. The reaction was complete. The reaction was cooled to room temperature and the organic layer was separated. The organic layer was cooled to −10° C. and a precipitate formed. The solid was filtered off and the filtrate was concentrated to give a brown oil. The oil was dissolved in $Et_2O$, washed with 2N NaOH and brine, dried over MgSO4 and concentrated to give a solid. $Et_2O$ (450 mL) was added and a yellow solid remained insoluble which was filtered off. The filtrate was treated with charcoal and concentrated to give a solid. The solid was washed with cold $Et_2O$ and dried to give the third intermediate compound as a white solid (7.97 g, 49.0 mmol, 71%). mp 70–73° C. MS: APCI: M+1: 251.1 (Exact Mass: 250.09).

A fourth intermediate compound, 7-{5-[4-(2,3-Dichloro-phenyl)-piperazin-1-yl]-pent-1-enyl}-3,4-dihydro-1H-[1,8] naphthyridin-2-one, was produced as follows: To a mixture of 2,3-dichlorophenylpiperazine (2.2 g, 9.52 mmol) and 7-(5-chloro-pent-1-enyl)-3,4-dihydro-1H-[1,8]naphthyridin-2-one (2.15 g, 8.58 mmol) in $CH_3CN$ (20 mL) was added a solution of $K_2CO_3$ (2.5 g, 18.1 mmol) in $H_2O$ (10 mL) followed by KI (0.1 g). The reaction was heated at 78° C. for 3 d. The reaction was about 50% complete so it was heated by microwave at 120° C. for 90 min. The reaction was allowed to cool to room temperature and solids precipitated. The mixture was cooled in the refrigerator. The solids were collected by filtration and washed with $H_2O$ and brine. The solids were dissolved in EtOAc, washed with saturated $NaHCO_3$ and brine, and dried over $MgSO_4$. The solution was concentrated to a reduced volume and the resulting white precipitate was filtered and washed with $Et_2O$ to give a white solid. Recrystallization from $CH_3CN$ gave the fourth intermediate compound as a white solid (2.08 g, 4.57 mmol, 54%). MS: APCI: M+1: 445.1 (Exact Mass: 444.15).

7-{5-[4-(2,3-Dichloro-phenyl)-piperazin-1-yl]-pent-1-enyl}-3,4-dihydro-1H-[1,8]naphthyridin-2-one (1.85 g, 4.16 mmol) was hydrogenated using Ra—Ni (1 g) in EtOH/THF (50 mL) for 1.4 h. The reaction was filtered and concentrated to give a solid. Recrystallization from hot $CH_3CN$ gave the title compound as a white solid (1.58 g, 3.54 mmol, 85%). MS: APCI: M+1: 447.1 (Exact Mass: 446.16).

Example C10

Synthesis of 7-{5-[4-(2-Chloro-3-methyl-phenyl)-piperazin-1-yl]-pentyl}-3,4-dihydro-1H-[1,8]naphthyridin-2-one An intermediate compound, 7-{5-[4-(2-Chloro-3-methyl-phenyl)-piperazin-1-yl]-pent-1-enyl}-3,4-dihydro-1H-[1,8] naphthyridin-2-one, was produced as follows: To a solution of $Na_2CO_3$ (0.28 g, 2.6 mmol) in $H_2O$ (2 mL) was added 2-chloro-3-methylphenylpiperazine hydrochloride (0.311 g, 1.26 mmol) and 7-(5-chloro-pent-1-enyl)-3,4-dihydro-1H-[1,8]naphthyridin-2-one (0.30 g, 1.20 mmol) followed by a catalytic amount of NaI. The mixture was heated at 95° C. overnight. After cooling to RT, the solid was washed several times with $H_2O$ and dried over a stream of $N_2$. Purification by liquid chromatography ($SiO_2$, 5% EtOH/$CH_2Cl_2$ to 5% MeOH/$CH_2Cl_2$) gave the intermediate compound (471 mg, 1.11 mmol, 92%). MS: APCI: M+1: 425.2 (Exact Mass: 424.20).

7-{5-[4-(2-Chloro-3-methyl-phenyl)-piperazin-1-yl]-pent-1-enyl}-3,4-dihydro-1H-[1,8]naphthyridin-2-one (0.322 g, 0.758 mmol) was hydrogenated using Ra—Ni (0.5 g) in 1:1 EtOH/THF (50 mL) for 21 h. The reaction was filtered and concentrated. Purification by liquid chromatography (SiO2, 5% MeOH/CH2Cl2 to 7% MeOH/CH2Cl2) gave the title compound as a light yellow foam (282 mg, 0.660 mmol, 87%). MS: APCI: M+1: 427.3 (Exact Mass: 426.22).

Example C11

Synthesis of 7-{5-[4-(2,3-Dichloro-4-fluoro-phenyl)-piperazin-1-yl]-pentyl}-3,4-dihydro-1H-[1,8] naphthyridin-2-one An intermediate compound, 7-{5-[4-(2,3-Dichloro-4-fluoro-phenyl)-piperazin-1-yl]-pent-1-enyl}-3,4-dihydro-1H-[1,8]naphthyridin-2-one, was produced as follows: To a mixture of 7-(5-chloro-pent-1-enyl)-3,4-dihydro-1H-[1,8] naphthyridin-2-one (500 mg, 1.99 mmol) and 4-fluoro-2,3- dichlorophenylpiperazine bishydrochloride (805 mg, 2.50 mmol, 1.25 equiv) in $CH_3CN$ (10 mL) was added $K_2CO_3$ (1.10 g, 7.98 mmol, 4 equiv) followed by KI (66 mg, 0.40 mmol, 0.2 equiv). The reaction was refluxed for 2 d. $H_2O$ was added to dissolve the salts and the mixture was extracted with EtOAc. The organic layer was washed with saturated $NaHCO_3$ and brine, dried over $Na_2SO_4$ and concentrated. Purification by liquid chromatography (4% $MeOH/CH_2Cl_2$) gave the intermediate compound as a white foam (768 mg, 1.66 mmol, 83%). MS: APCI: M+1: 463.1 (Exact Mass: 462.14).

7-{5-[4-(2,3-Dichloro-4-fluoro-phenyl)-piperazin-1-yl]-pent-1-enyl}-3,4-dihydro-1H-[1,8]naphthyridin-2-one (633 mg, 1.37 mmol) was hydrogenated using Ra—Ni (0.65 g) in 1:1 EtOH/THF (50 mL) for 21 h. The reaction was filtered and concentrated. Purification by liquid chromatography (4% $MeOH/CH_2Cl_2$) gave a white foam (425 mg). The foam was dissolved in $CH_3CN$ and the compound crystallized. The solid was collected by filtration, washed with $Et_2O$ and dried to give the title compound as a white solid (366 mg, 0.786 mmol, 57%). MS: APCI: M+1: 465.1 (Exact Mass: 464.15).

Example C12

Synthesis of 7-{5-[4-(5,6,7,8-Tetrahydro-naphthalen-1-yl)-piperazin-1-yl]-pentyl}-3,4-dihydro-1H-[1,8]naphthyridin-2-one A first intermediate compound, 1-(5,6,7,8-Tetrahydro-naphthalen-1-yl)-piperazine, was produced as follows: To a reaction flask containing a solution of 5,6,7,8-tetrahydro-naphthalen-1-ylamine (10.0 g, 67.9 mmol) in chlorobenzene (10 mL), was added bis-(2-chloro-ethyl)-amine hydrochloride (12.12 g, 67.92 mmol). The reaction was refluxed for 14 hours. The reaction was cooled and the precipitate was filtered. The filtrate was partitioned between ethyl acetate and water. The organic layer was washed with brine, dried over $Na_2SO_4$, and concentrated. Purification by chromatography on silica gel (0–40% $MeOH/CH_2Cl_2$) afforded the first intermediate compound as a grayish white solid (8.25 g, 56%). MS: APCI: M+1: 217.2 (Exact Mass: 216.16).

A second intermediate compound, 7-{5-[4-(5,6,7,8-Tetrahydro-naphthalen-1-yl)-piperazin-1-yl]-pent-1-enyl}-3,4-dihydro-1H-[1,8]naphthyridin-2-one, was produced as follows: To a flask containing a solution of 7-(5-chloro-pent-1-enyl)-3,4-dihydro-1H-[1,8]naphthyridin-2-one (0.330 g, 1.19 mmol) in $CH_3CN$ (8 ml) was added 1-(5,6,7,8-tetrahydro-naphthalen-1-yl)-piperazine (0.388 g, 1.79 mmol), followed by $K_2CO_3$ (0.328 g, 2.38 mmol) and KI (0.039 g, 0.238 mmol). The reaction was refluxed for 18 hours. The reaction was cooled to room temperature and partitioned between EtOAc and aqueous $NaHCO_3$. The organic layer was washed with brine, dried over $Na_2SO_4$ and concentrated to give an oil. Purification by chromatography on silica gel (0–10% MeOH/EtOAc) afforded the second intermediate compound as a white foam (0.308 g, 60%). A small portion (81 mg) was then dissolved in $Et_2O$ and 1M HCl in $Et_2O$ (1 equiv) was added. A precipitate formed and was filtered. The product was a white solid (90 mg). MS: APCI: M+1: 431.3 (Exact Mass: 430.27).

7-{5-[4-(5,6,7,8-Tetrahydro-naphthalen-1-yl)-piperazin-1-yl]-pent-1-enyl}-3,4-dihydro-1H-[1,8]naphthyridin-2-one (0.225 g, 0.523 mmol) was hydrogenated using Ra—Ni (0.25 g) in THF for 16 hours. The reaction was filtered and concentrated to give a foam. This was dissolved in $Et_2O$ and 1M HCl in $Et_2O$ (1 equiv) was added. The precipitate was filtered and dried to give the title compound as a white solid (0.157 g, 70%). MS: APCI: M+1: 433.4 (Exact Mass: 432.29).

Example C13

Synthesis of 7-[5-(4-Naphthalen-1-yl-piperazin-1-yl)-pentyl]-3,4-dihydro-1H-[1,8]naphthyridin-2-one An intermediate compound, 7-[5-(4-Naphthalen-1-yl-piperazin-1-yl)-pent-1-enyl]-3,4-dihydro-1H-[1,8]naphthyridin-2-one, was produced as follows: Reaction of 7-(5-chloro-pent-1-enyl)-3,4-dihydro-1H-[1,8]naphthyridin-2-one with 1-naphthalen-1-yl-piperazine according to the procedure in Example C9 gave the intermediate compound (0.340 g, 0.80 mmol, 50%). MS: APCI: M+1: 427.2 (Exact Mass: 426.24).

Hydrogenation of 7-[5-(4-naphthalen-1-yl-piperazin-1-yl)-pent-1-enyl]-3,4-dihydro-1H-[1,8]naphthyridin-2-one according to the procedure in Example C9 gave the title compound (0.250 g, 0.48 mmol, 75%). MS: APCI: M+1: 429.3 (Exact Mass: 428.26).

Example C14

Synthesis of 7-{5-[4-(2-Chloro-4-fluoro-phenyl)-piperazin-1-yl]-pentyl}-3,4-dihydro-1H-[1,8]naphthyridin-2-one An intermediate compound, 7-{5-[4-(2-Chloro-4-fluoro-phenyl)-piperazin-1-yl]-pent-1-enyl}-3,4-dihydro-1H-[1,8]naphthyridin-2-one, was produced as follows: To a flask containing a solution of 7-(5-chloro-pent-1-enyl)-3,4-dihydro-1H-[1,8]naphthyridin-2-one (0.300 g, 1.19 mmol) in $CH_3CN$ (8 mL) and $H_2O$ (3 mL), was added 1-(2-chloro-4-fluoro-phenyl)-piperazine (0.516 g, 1.79 mmol), followed by $K_2CO_3$ (0.493 g, 3.57 mmol) and KI (0.027 g, 0.238 mmol). The reaction was refluxed for 12 hours. The reaction was cooled to room temperature, diluted with EtOAc and washed with $NaHCO_3$ and brine. The organic layer was dried over $Na_2SO_4$ and concentrated to give an oil. Purification by chromatography on silica gel (0–10% MeOH/EtOAc) afforded the intermediate compound as a white foam (0.363 g, 71%). A small portion (93 mg) was then dissolved in $Et_2O$ and 1M HCl in $Et_2O$ (1 equiv) was added. A precipitate formed which was filtered and dried to give a white solid (97 mg). MS: APCI: M+1: 429.2 (Exact Mass: 428.18).

7-{5-[4-(2-Chloro-4-fluoro-phenyl)-piperazin-1-yl]-pent-1-enyl}-3,4-dihydro-1H-[1,8]naphthyridin-2-one (0.268 g, 0.623 mmol) was hydrogenated using Ra—Ni (0.2 g) in THF for 13 hours. The reaction was filtered and concentrated to give an oil. $Et_2O$ was added and the product crashed out. The mixture was filtered and dried to give the title compound as a white solid (0.214 g, 80%). MS: APCI: M+1: 431.3 (Exact Mass: 430.19).

Example C15

Synthesis 7-{5-[4-(2-Chloro-4-fluoro-3-methyl-phenyl)-piperazin-1-yl]-pentyl}-3,4-dihydro-1H-[1,8]naphthyridin-2-one of An intermediate compound, 7-{5-[4-(2-Chloro-4-fluoro-3-methyl-phenyl)-piperazin-1-yl]-pent-1-enyl}-3,4-dihydro-1H-[1,8]naphthyridin-2-one, was produced as follows:

To a solution of Na$_2$CO$_3$ (93 mg, 0.88 mmol) in H$_2$O (2 mL) was added 2-chloro-4-fluoro-3-methylphenylpiperazine hydrochloride (106 mg, 0.40 mmol) and 7-(5-chloro-pent-1-enyl)-3,4-dihydro-1H-[1,8]naphthyridin-2-one (100 mg, 0.40 mmol) followed by a catalytic amount of NaI. The mixture was heated at 95° C. overnight. After cooling to RT, the solid was washed several times with H$_2$O and dried over a stream of N$_2$. Purification by liquid chromatography (SiO$_2$, 5% EtOH/CH$_2$Cl$_2$ to 5% MeOH/CH$_2$Cl$_2$) gave the intermediate compound (134 mg, 0.303 mmol, 76%). MS: APCI: M+1: 443.2 (Exact Mass: 442.19).

7-{5-[4-(2-Chloro-4-fluoro-3-methyl-phenyl)-piperazin-1-yl]-pent-1-enyl}-3,4-dihydro-1H-[1,8]naphthyridin-2-one (0.382 g, 0.862 mmol) was hydrogenated using Ra—Ni (0.5 g) in 1:1 EtOH/THF (50 mL) for 12 h. The reaction was filtered and concentrated. Purification by liquid chromatography (SiO2, 5% MeOH/CH2Cl2 to 7% MeOH/CH2Cl2) gave the title compound as a light yellow foam (342 mg, 0.769 mmol, 89%). MS: APCI: M+1: 445.2 (Exact Mass: 444.21).

Example C16

Synthesis of 7-{5-[4-(6-Methyl-pyridin-2-yl)-piperazin-1-yl]-pentyl}-3,4-dihydro-1H-[1,8]naphthyridin-2-one An intermediate compound, 7-{5-[4-(6-Methyl-pyridin-2-yl)-piperazin-1-yl]-pent-1-enyl}-3,4-dihydro-1H-[1,8]naphthyridin-2-one, was produced as follows: To a solution of K$_2$CO$_3$ (1.16 g, 8.38 mmol) in H$_2$O (3 mL) was added CH$_3$CN (9 mL), 1-(6-methyl-pyridin-2-yl)-piperazine (0.84 g, 3.35 mmol) and 7-(5-chloro-pent-1-enyl)-3,4-dihydro-1H-[1,8]naphthyridin-2-one (0.70 g, 2.80 mmol) followed by a catalytic amount of KI (8 mg). The mixture was stirred for 15 min and then heated in a microwave (300 W) at 120° C. for 150 min. After cooling to RT, saturated NaHCO$_3$ was added and the mixture was extracted with EtOAC. The organic layer was washed with brine, dried over MgSO$_4$ and concentrated to give a yellow oil. Purification by liquid chromatography (40M Biotage SiO$_2$ column, CH$_2$Cl$_2$ to 2% MeOH/CH$_2$Cl$_2$) gave the intermediate compound as a foam (426 mg, 1.09 mmol, 39%). MS: APCI: M+1: 392.1 (Exact Mass: 391.24).

7-{5-[4-(6-Methyl-pyridin-2-yl)-piperazin-1-yl]-pent-1-enyl}-3,4-dihydro-1H-[1,8]naphthyridin-2-one (0.343 g, 0.876 mmol) was hydrogenated using 20% Pd/C in EtOH for 103 h. The reaction was filtered and concentrated. Purification by liquid chromatography (Biotage 12 SiO$_2$ column, CH$_2$Cl$_2$ to 1% MeOH/CH$_2$Cl$_2$) followed by recrystallization from Et$_2$O gave the title compound as a white powder (42 mg, 0.01 mmol, 12%). MS: APCI: M+1: 394.2 (Exact Mass: 393.25).

Example C17

Synthesis of 7-{5-[4-(6-Ethyl-pyridin-2-yl)-piperazin-1-yl]-pentyl}-3,4-dihydro-1H-[1,8]naphthyridin-2-one An intermediate compound, 7-{5-[4-(6-Ethyl-pyridin-2-yl)-piperazin-1-yl]-pent-1-enyl}-3,4-dihydro-1H-[1,8]naphthyridin-2-one, was produced as follows: To a solution of K$_2$CO$_3$ (1.16 g, 8.38 mmol) in H$_2$O (3 mL) was added CH$_3$CN (9 mL), 1-(6-ethyl-pyridin-2-yl)-piperazine (0.64 g, 3.36 mmol) and 7-(5-chloro-pent-1-enyl)-3,4-dihydro-1H-[1,8]naphthyridin-2-one (0.70 g, 2.80 mmol) followed by a catalytic amount of KI (8 mg). The mixture was stirred for 15 min and then heated in a microwave (300 W) at 120° C. for 150 min. After cooling to RT, saturated NaHCO$_3$ was added and the mixture was extracted with EtOAC. The organic layer was washed with brine, dried over MgSO$_4$ and concentrated to give a yellow oil. Purification by liquid chromatography (40M Biotage SiO$_2$ column, CH$_2$Cl$_2$ to 1% MeOH/CH$_2$Cl$_2$) gave the intermediate compound (845 mg, 2.08 mmol, 74%). MS: APCI: M+1: 406.3 (Exact Mass: 405.25).

7-{5-[4-(6-Ethyl-pyridin-2-yl)-piperazin-1-yl]-pent-1-enyl}-3,4-dihydro-1H-[1,8]naphthyridin-2-one (0.515 g, 1.27 mmol) was hydrogenated using 20% Pd/C in EtOH for 103 h. The reaction was filtered and concentrated. Purification by liquid chromatography (Biotage 12 SiO$_2$ column, CH$_2$Cl$_2$ to 1% MeOH/CH$_2$Cl$_2$) followed by recrystallization from Et$_2$O gave the title compound as a solid (50 mg, 0.012 mmol, 10%). MS: APCI: M+1: 408.2 (Exact Mass: 407.27).

Example C18

Synthesis of 7-{5-[4-(6-Cyclopropyl-pyridin-2-yl)-piperazin-1-yl]-pentyl}-3,4-dihydro-1H-[1,8]naphthyridin-2-one An intermediate compound, 7-{5-[4-(6-Cyclopropyl-pyridin-2-yl)-piperazin-1-yl]-pent-1-enyl}-3,4-dihydro-1H-[1,8]naphthyridin-2-one, was produced as follows: To a solution of K$_2$CO$_3$ (1.16 g, 8.38 mmol) in H$_2$O (6 mL) was added CH$_3$CN (9 mL), 1-(6-cyclopropyl-pyridin-2-yl)-piperazine (0.68 g, 3.35 mmol) and 7-(5-chloro-pent-1-enyl)-3,4-dihydro-1H-[1,8]naphthyridin-2-one (0.70 g, 2.80 mmol). The mixture was stirred for 15 min and then heated in a microwave (300 W) at 120° C. for 150 min. After cooling to RT, saturated NaHCO$_3$ was added and the mixture was extracted with EtOAC. The organic layer was washed with brine, dried over MgSO$_4$ and concentrated to give a yellow oil/foam. Purification by liquid chromatography (40M Biotage SiO$_2$ column, CH$_2$Cl$_2$ to 2% MeOH/CH$_2$Cl$_2$) gave the intermediate compound as a yellow oil/foam (443 mg, 1.06 mmol, 38%). MS: APCI: M+1: 418.3 (Exact Mass: 417.25).

7-{5-[4-(6-Cyclopropyl-pyridin-2-yl)-piperazin-1-yl]-pent-1-enyl}-3,4-dihydro-1H-[1,8]naphthyridin-2-one (0.347 g, 0.831 mmol) was hydrogenated using 20% Pd/C in THF for 15 h. The reaction was filtered and concentrated. Recrystallization from hot CH$_3$CN gave the title compound as a white powder (288 mg, 0.686 mmol, 83%). MS: APCI: M+1: 420.3 (Exact Mass: 419.27).

Example C19

Synthesis of 7-{5-[4-(4,6-Dimethyl-pyridin-2-yl)-piperazin-1-yl]-pentyl}-3,4-dihydro-1H-[1,8]naphthyridin-2-one An intermediate compound, 7-{5-[4-(4,6-Dimethyl-pyridin-2-yl)-piperazin-1-yl]-pent-1-enyl}-3,4-dihydro-1H-[1,8]naphthyridin-2-one, was produced as follows: To a solution of K$_2$CO$_3$ (1.16 g, 8.38 mmol) in H$_2$O (3 mL) was added CH$_3$CN (9 mL), 1-(4,6-dimethyl-pyridin-2-yl)-piperazine (0.909 g, 3.34 mmol) and 7-(5-chloro-pent-1-enyl)-3,4-dihydro-1H-[1,8]naphthyridin-2-one (0.70 g, 2.80 mmol) followed by a catalytic amount of KI (8 mg). The mixture was stirred for 15 min and then heated in a microwave (300 W) at 120° C. for 150 min. After cooling to RT, saturated NaHCO$_3$ was added and the mixture was extracted with EtOAC. The organic layer was washed with brine, dried over MgSO$_4$ and concentrated to give a yellow oil/foam. Purification by liquid chromatography (40M Biotage SiO$_2$ column, CHCl$_3$ to 1% MeOH/CHCl$_3$) gave the intermediate compound as a foam (540 mg, 1.33 mmol, 48%). MS: APCI: M+1: 406.2 (Exact Mass: 405.25).

7-{5-[4-(4,6-Dimethyl-pyridin-2-yl)-piperazin-1-yl]-pent-1-enyl}-3,4-dihydro-1H-[1,8]naphthyridin-2-one (0.54 g, 1.33 mmol) was hydrogenated using 20% Pd/C in EtOH for 58 h. The reaction was filtered and concentrated. Purification by liquid chromatography (Biotage 12 SiO$_2$ column, CHCl$_3$ to 1% MeOH/CHCl$_3$) followed by recrystallization from Et$_2$O/hexanes gave the title compound as an off-white solid (313 mg, 0.761 mmol, 57%). MS: APCI: M+1: 408.2 (Exact Mass: 407.27).

Example C20

Synthesis of 7-{5-[4-(2,3-Dichloro-phenyl)-piperazin-1-yl]-pentyl}-1H-[1,8]naphthyridin-2-one A first intermediate compound, 7-Chloro-1H-[1,8]naphthyridin-2-one, was produced as follows: To a stirred solution of lithium hexamethyldisilazane (26.3 mmol, 1.0 M in THF) in THF (10 mL) at −78° C. is added t-butyl acetate (3.53 mL, 26.3 mmol) dropwise. The mixture is stirred at −78° C. for 30 min and N-(6-chloro-3-formyl-pyridin-2-yl)-2,2-dimethyl-propionamide (3.00 g, 12.5 mmol) in THF (20 mL) is added dropwise. A yellow precipitate forms and the mixture is stirred at −78° C. for 30 minutes and warmed to room temperature over 3 hours. H$_2$O (10 mL) is added, the mixture stirred for 5 minutes and then diluted with ethyl acetate (20 mL) and brine (10 mL). The organic layer is separated, washed with brine (20 mL), dried over Na$_2$SO$_4$, filtered and concentrated under vacuum. The compound is recrystallized from ethyl acetate and hexanes to yield 3-[6-chloro-2-(2,2-dimethyl-propionylamino)-pyridin-3-yl]-3-hydroxy-propionic acid tert-butyl ester (3.52 g, 79%); mp 130–132° C., $^1$H NMR (400 MHz, CDCl$_3$) δ 8.25 (br s, 1H), 7.76 (d, 1H), 7.16 (d, 1H), 5.05–4.98 (m, 1H), 4.08 (d, 1H), 2.80 (dd, 1H), 2.70 (dd, 1H), 1.41 (s, 9H), 1.36 (s, 9H); MS ES+ 357.03 (M+H)$^+$.

3-[6-Chloro-2-(2,2-dimethyl-propionylamino)-pyridin-3-yl]-3-hydroxy-propionic acid tert-butyl ester (15.43 g, 43.3 mmol) is dissolved in dioxane (60 mL) and 3 N HCl (60 mL) is added. The mixture is refluxed for 4 hours, cooled to room temperature, and poured over ice. The resulting precipitate is filtered, washed with H$_2$O (2×20 mL) and dried to afford the first intermediate compound (7.80 g, >99%); mp 258–259° C., $^1$H NMR (400 MHz, DMSO-d$_6$) δ 12.38 (br s, 1H), 8.14 (d, 1H), 7.94 (d, 1H), 7.30 (d, 1H), 6.54 (d, 1H); MS ES+ 180.76 (M$^+$) (Exact Mass: 180.01).

A second intermediate compound, 7-(5-Chloro-pent-1-enyl)-1H-[1,8]naphthyridin-2-one, was produced as follows: 7-Chloro-1H-[1,8]naphthyridin-2-one (0.10 g, 0.56 mmol) is dissolved in dioxane (4 mL) and Pd(Ph$_3$P)$_4$ (19 mg, 0.02 mmol) is added. The solution is stirred for 5 minutes at room temperature and 5-chloro-1-pentenylboronic acid (0.13 g, 0.84 mmol) is added followed immediately by aqueous Na$_2$CO$_3$ (2 mL, 2 M). The mixture is heated at 100° C. for 18 hours. The mixture is cooled to RT, filtered through Celite and diluted with ethyl acetate (10 mL). The organic layer is washed with brine (10 mL), dried over Na$_2$SO$_4$, filtered and concentrated under vacuum. The residue was purified by column chromatography (ethyl acetate) to yield the second intermediate compound (45 mg, 33%); mp 125–127° C., $^1$H NMR (200 MHz, CDCl$_3$) δ 9.35 (br s, 1H), 7.80 (d, 1H), 7.65 (d, 1H), 7.05 (d, 1H), 6.70 (dt, 1H), 6.60 (d, 1H), 6.55 (d, 1H), 3.60 (t, 2H), 2.60–2.40 (m, 2H), 2.10–1.90 (m, 2H), MS ES+ 248.79 (M$^+$) (Exact Mass: 248.07).

A third intermediate compound, 7-{5-[4-(2,3-Dichloro-phenyl)-piperazin-1-yl]-pent-1-enyl}-1H-[1,8]naphthyridin-2-one, was produced as follows: Sodium iodide (2.18 g, 14.52 mmol) is added to a stirred solution of 7-(5-chloro-pent-1-enyl)-1H-[1,8]naphthyridin-2-one (1.8 g, 7.26 mmol) in CH$_3$CN (40 mL). The mixture is refluxed for 1 hour and cooled to room temperature. Triethylamine (2.20 g, 21.78 mmol) and 1-(2,3-Dichlorophenyl)piperazine monohydrochloride (2.91 g, 10.9 mmol) are added and the mixture is refluxed for 5 hours and cooled to RT. The mixture is filtered and the solids are washed with ethyl acetate (10 mL). The filtrate is diluted with ethyl acetate (20 mL), washed with saturated NH$_4$Cl (20 mL), saturated NaHCO$_3$ (20 mL), water (20 mL), and brine (20 mL). The organic layer is dried over Na$_2$SO$_4$, filtered and concentrated under vacuum. The crude solid is purified by column chromatography (triethylamine/CH$_2$Cl$_2$, 5:95) to yield the third intermediate compound as an orange solid (700 mg, 22%). mp 176–178° C. $^1$H NMR (400 MHz, CDCl$_3$) δ 8.98 (s, 1H), 7.80 (d, 1H), 7.66 (d, 1H), 7.20–7.10 (m, 3H), 7.00–6.85 (m, 2H), 6.62 (d, 1H), 6.53 (d, 1H), 3.20–3.00 (m, 4H), 2.76–2.60 (m, 4H), 2.50 (t, 2H), 2.40–2.36 (m, 2H), 1.82–1.75 (m, 2H). MS ES+ 443.06 (M$^+$) (Exact mass: 442.13).

7-{5-[4-(2,3-Dichloro-phenyl)-piperazin-1-yl]-pent-1-enyl}-1H-[1,8]naphthyridin-2-one (160 mg, 0.361 mmol) was hydrogenated using Raney Nickel (0.2 g) in MeOH for 42 h. The reaction was filtered and concentrated. Purification by liquid chromatography (5% MeOH/CH$_2$Cl$_2$ with 1% NH$_4$OH) gave the title compound as a white foam (109 mg, 0.245 mmol, 68%), which was further purified by HPLC to remove a small amount of over-reduced side-product. MS: APCI: M−1: 443.1 (Exact Mass: 444.15).

Example D1

Synthesis of 7-{4-[4-(2,3-Dichloro-phenyl)-piperazin-1-yl]-butoxy}-4-methyl-1H-[1,8]naphthyridin-2-one A first intermediate compound, 7-Chloro-4-methyl-1H-[1,8]naphthyridin-2-one, was produced as follows: A solution of tert-butyl acetate (0.6 mL, 4.45 mmol) is added dropwise to a solution of lithium bis(trimethylsilyl)amide (1.0 M in THF, 4.2 mL, 4.2 mmol) in THF (5 mL) at −78° C. The yellow solution is stirred for 1 hour and N-(3-acetyl-6-chloro-pyridin-2-yl)-2,2-dimethyl-propionamide (0.503 g, 1.97 mmol) in THF (5 mL) is added dropwise to the mixture. The yellow suspension is stirred at −78° C. for 30 minutes and warmed to RT. The suspension clears to a yellow solution and the mixture is stirred at room temperature for 1.5 hours. The mixture is quenched with water and extracted with CH$_2$Cl$_2$. The organic extracts are washed with brine, dried over Na$_2$SO$_4$, filtered and concentrated in vacuo to a brown liquid. The liquid is purified by column chromatography (2:1 hexanes/ethyl acetate) to afford 3-[6-chloro-2-(2,2-dimethyl-propionylamino)-pyridin-3-yl]-3-hydroxy-butyric acid tert-butyl ester (0.548 g, 75%) as a yellow oil. $^1$H NMR (CDCl$_3$, 400 MHz): δ 10.40 (br s, 1H), 7.37 (d, 1H), 6.98 (d, 1H), 5.61 (s, 1H), 3.03 (d, 1H), 2.67 (d, 1H), 1.56 (s, 3H), 1.45 (s, 9H), 1.32 (s, 9H). MS ES: m/z=370.86, 372.56.

A light yellow solution of 3-[6-chloro-2-(2,2-dimethyl-propionylamino)-pyridin-3-yl]-3-hydroxy-butyric acid tert-butyl ester (0.473 g, 1.28 mmol) in 3N HCl (10 mL) and dioxane (10 mL) is refluxed for 1 hour. The yellow mixture is cooled to room temperature and extracted with $Et_2O$. The aqueous layer is separated and neutralized with $Na_2CO_3$. A white solid separates out of solution and the solid is collected by filtration to afford the first intermediate compound (0.232 g, 94%) as a white solid. mp 238–239° C. $^1$H NMR (DMSO-$d_6$, 400 MHz): δ 12.20 (br s, 1H), 8.14 (d, 1H), 7.31 (d, 1H), 6.45 (d, 1H), 2.39 (d, 3H). MS ES: m/z=194.74, 196.62.

A second intermediate compound, 2-Benzyloxy-7-chloro-4-methyl-[1,8]naphthyridine, was produced as follows: A mixture of 7-chloro-4-methyl-1H-[1,8]naphthyridin-2-one (0.208 g, 1.07 mmol), silver carbonate (0.176 g, 0.64 mmol), and benzyl bromide (0.15 mL, 1.26 mmol) in toluene (5 mL) is heated at 70° C. overnight. The grey suspension is filtered through Celite and the yellow filtrate is concentrated under vacuum to a yellow solid. The solid is purified by column chromatography (3:1 hexanes/ethyl acetate) to afford the second intermediate compound (0.196 g, 64%) as an off-white solid. mp 150–151° C. $^1$H NMR (CDCl$_3$, 400 MHz): δ 8.19 (d, 1H), 7.53–7.48 (m, 2H), 7.43–7.34 (m, 4H), 6.92–6.90 (s, 1H), 5.61 (s, 2H), 2.67 (s, 3H). MS ES: m/z=285.02, 287.03.

A third intermediate compound, 2-Benzyloxy-7-(4-benzyloxy-butoxy)-4-methyl-[1,8]naphthyridine, was produced as follows: A mixture of 4-benzyloxy-1-butanol (1.40 mL, 7.96 mmol) in THF (20 mL) is treated with potassium tert-butoxide (0.892 g, 7.95 mmol). The yellow solution is stirred for 15 minutes at RT. 2-Benzyloxy-7-chloro-4-methyl-[1,8]naphthyridine (1.84 g, 6.46 mmol) in THF (20 mL) is added to the mixture at −40° C. The dark red/brown mixture is warmed to room temperature and stirred for 10 minutes. The mixture is quenched with saturated $NaHCO_3$ solution (20 mL) and extracted with ethyl acetate (3×30 mL). The organic extracts are washed with brine (30 mL), dried over $Na_2SO_4$, filtered and concentrated in vacuo to a brown residue. The residue is purified by column chromatography (5:1 hexanes/ethyl acetate) to afford the third intermediate compound (1.146 g, 41%) as a yellow liquid. $^1$H NMR (CDCl$_3$, 400 MHz): δ 8.08 (d, 1H), 7.54–7.48 (m, 2H), 7.42–7.26 (m, 8H), 6.84 (d, 1H), 6.75 (s, 1H), 5.60 (s, 2H), 4.59 (t, 2H), 4.54 (s, 2H), 3.58 (t, 2H), 2.58 (s, 3H), 2.00–1.90 (m, 2H), 1.90–1.80 (m, 2H). MS ES: m/z=428.92 (MH$^+$).

A fourth intermediate compound, 7-(4-Hydroxy-butoxy)-4-methyl-1H-[1,8]naphthyridin-2-one, was produced as follows: Hydrogen gas (35 psi) is applied to a mixture of 2-benzyloxy-7-(4-benzyloxy-butoxy)-4-methyl-[1,8]naphthyridine (1.188 g, 2.77 mmol), 10% Pd/C (wet, 0.364 g) and methanol (160 mL) in a Parr bottle under agitation for 4.5 hours. The catalyst is filtered through a pad of Celite and the pad is rinsed with methanol. The filtrate is concentrated under vacuum to afford the fourth intermediate compound (0.580 g, 84%) as a white solid. mp 172–173° C. $^1$H NMR (DMSO-$d_6$, 400 MHz): δ 11.79 (br s, 1H), 8.02 (d, 1H), 6.65 (d, 1H), 6.25 (s, 1H), 4.47 (t, 1H), 4.33 (t, 2H), 3.45 (q, 2H), 2.36 (s, 3H), 1.82–1.72 (m, 2H), 1.60–1.50 (m, 2H).

Alternatively, a mixture of 1,4-butanediol (0.177 g, 1.96 mmol) in THF (2 mL) is placed in a sealed glass pressure tube. The mixture is treated with potassium tert-butoxide (0.252 g, 2.25 mmol) and the cloudy white suspension is stirred at room temperature for 15 minutes. The suspension is treated with 7-chloro-4-methyl-1H-[1,8]naphthyridin-2-one (0.100 g, 0.51 mmol) in THF (2 mL). The pressure tube is sealed and heated at 100° C. for 16 hours. The mixture is cooled to room temperature and diluted with saturated $NaHCO_3$ solution (10 mL) and extracted with $CH_2Cl_2$ (2×30 mL). The organic extracts are washed with brine (20 mL), dried over $Na_2SO_4$, filtered and concentrated under vacuum to a white residue. The residue is purified by column chromatography (5:95 methanol/chloroform) to afford the fourth intermediate compound (0.081 g, 63%) as a white solid. mp 172–173° C. $^1$H NMR (DMSO-$d_6$, 400 MHz): δ 11.79 (br s, 1H), 8.02 (d, 1H), 6.65 (d, 1H), 6.25 (s, 1H), 4.47 (t, 1H), 4.33 (t, 2H), 3.45 (q, 2H), 2.36 (s, 3H), 1.82–1.72 (m, 2H), 1.60–1.50 (m, 2H). MS ES: m/z=248.90 (MH$^+$).

A fifth intermediate compound, 4-(5-Methyl-7-oxo-7,8-dihydro-[1,8]naphthyridin-2-yloxy)-butyraldehyde, was produced as follows: A mixture of Dess-Martin periodinane (1.764 g, 4.16 mmol) in $CH_2Cl_2$ (30 mL) is treated with 7-(4-hydroxy-butoxy)-4-methyl-1H-[1,8]naphthyridin-2-one (0.798 g, 3.21 mmol) in THF (10 mL) at RT. The slightly cloudy yellow solution is stirred for 2 hours, diluted with $Et_2O$ and poured into a solution of aqueous saturated $NaHCO_3$ solution (20 mL) containing sodium thiosulfate (3.8 g, 24.0 mmol). The immiscible solution is stirred for 5 minutes and the organic layer is separated out. The aqueous layer is extracted with $Et_2O$. The combined organic extracts are washed with brine, dried over $Na_2SO_4$, filtered and concentrated under vacuum to a white solid. The crude aldehyde is used directly in the next step without purification.

The crude 4-(5-methyl-7-oxo-7,8-dihydro-[1,8]naphthyridin-2-yloxy)-butyraldehyde from the previous reaction in 1,2-dichloroethane (30 mL) is treated with 1-(2,3-dichlorophenyl)piperazine monohydrochloride (1.144 g, 4.20 mmol), followed by triethylamine (0.90 mL, 6.46 mmol) and sodium triacetoxyborohydride (0.955 g, 4.50 mmol). The cloudy yellow solution is stirred at room temperature for 1 hour. The mixture is quenched with $H_2O$ and saturated $NaHCO_3$ solution and extracted with $CH_2Cl_2$. The organic extracts are washed with brine, dried over $Na_2SO_4$, filtered and concentrated under vacuum to a yellow oil. The oil is purified by column chromatography (5:95 methano/vethyl acetate) to afford the title compound (0.97 g, 63% over 2 steps) as a white solid. mp 181–182° C. $^1$H NMR (CDCl$_3$, 400 MHz): δ 7.57 (br s, 1H), 7.40 (d, 1H), 7.18–7.12 (m, 2H), 7.00–6.94 (m, 1H), 6.38 (d, 1H), 4.23 (t, 2H), 3.16–3.00 (m, 5H), 2.77–2.68 (m, 4H), 2.75–2.56 (m, 1H), 2.52–2.36 (m, 3H), 1.86–1.75 (m, 2H), 1.75–1.64 (m, 2H), 1.28 (d, 3H). MS ES: m/z=460.70, 462.58.

Example D2a and D2b

Synthesis of 7-{4-[4-(2,3-Dichloro-phenyl)-piperazin-1-yl]-butoxy}-4-methyl-3,4-dihydro-1H-[1,8] naphthyridin-2-one A First intermediate compound, 7-(4-Hydroxy-butoxy)-4-methyl-3,4-dihydro-1H-[1,8]naphthyridin-2-one, was produced as follows: Hydrogen gas (40 psi) is applied to a mixture of 7-(4-hydroxy-butoxy)-4-methyl-1H-[1,8]naphthyridin-2-one (0.640 g, 2.58 mmol), 10% Pd/C (wet, 0.310 g) and methanol (160 mL) in a Parr bottle under agitation overnight. The catalyst is filtered through a pad of Celite and the pad is rinsed with methanol. The filtrate is concentrated under vacuum to a colorless semi-solid. The semi-solid is purified by column chromatography (5:95 methanol/chloroform) to afford the first intermediate compound (0.510 g, 79%) as a white solid. Mp 99–100° C. $^1$H NMR (CDCl$_3$, 400 MHz): δ 7.60 (br s, 1H), 7.40 (d, 1H), 6.39 (d, 1H), 4.24 (t, 2H), 3.77–3.68 (m, 2H), 3.11–3.00 (m, 2H), 2.77–2.68 (m, 2H), 2.46–2.37 (m, 2H), 1.50 (br s, 1H), 1.24 (d, 3H). MS ES: m/z=250.89 (MH$^+$).

A second intermediate compound, 4-(5-Methyl-7-oxo-5,6,7,8-tetrahydro-[1,8]naphthyridin-2-yloxy)-butyraldehyde, was produced as follows: A mixture of Dess-Martin periodinane (1.511 g, 3.56 mmol) in $CH_2Cl_2$ (30 mL) is treated with 7-(4-hydroxy-butoxy)-4-methyl-3,4-dihydro-1H-[1,8]naphthyridin-2-one (0.742 g, 2.96 mmol) in THF (10 mL) at RT. The slightly cloudy yellow solution is stirred for 2 hours, diluted with $Et_2O$ and poured into a solution of aqueous saturated $NaHCO_3$ (20 mL) containing sodium thiosulfate (3.5 g, 21.1 mmol). The immiscible solution is stirred for 5 minutes and the organic layer is separated out. The aqueous layer is extracted with $Et_2O$. The combined organic extracts are washed with brine, dried over $Na_2SO_4$, filtered and concentrated under vacuum to a yellow solid. The crude aldehyde is used directly in the next step without purification.

The crude 4-(5-methyl-7-oxo-5,6,7,8-tetrahydro-[1,8]naphthyridin-2-yloxy)-butyraldehyde in 1,2-dichloroethane (50 mL) is treated with 1-(2,3-dichlorophenyl)piperazine monohydrochloride (1.104 g, 4.13 mmol), followed by triethylamine (0.80 mL, 5.69 mmol) and sodium triacetoxyborohydride (0.911 g, 4.30 mmol). The cloudy yellow solution is stirred at room temperature for 1 hour. The mixture is quenched with water and saturated $NaHCO_3$ solution and extracted with $CH_2Cl_2$. The organic extracts are washed with brine, dried over $Na_2SO_4$, filtered and concentrated under vacuum to a yellow oil. The oil is purified by column chromatography (5:95 methanol/ethyl acetate) to afford the title compound (1.08 g, 79% over 2 steps) as a white solid. Mp 53–54° C. $^1$H NMR ($CDCl_3$, 400 MHz): δ 8.94 (br s, 1H), 7.83 (d, 1H), 7.18–7.13 (m, 2H), 6.98–6.94 (m, 1H), 6.62 (d, 1H), 6.38 (d, 1H), 4.38 (t, 2H), 3.16–3.02 (m, 4H), 2.76–2.60 (m, 4H), 2.55–2.46 (m, 2H), 1.90–1.82 (m, 2H), 1.77–1.64 (m, 2H). MS ES: m/z=462.72, 464.58.

The enantiomers were separated by chiral HPLC (Chiralcel OD) to give the enantiomers D2a and D2 b.

Example D3

Synthesis of 7-{5-[4-(2,3-Dichloro-phenyl)-piperazin-1-yl]-pentyl}-4-methyl-1H-[1,8]naphthyridin-2-one A first intermediate compound, 7-(5-Chloro-pent-1-enyl)-4-methyl-1H-[1,8]naphthyridin-2-one, was produced as follows: To a solution of 7-chloro-4-methyl-1H-[1,8]naphthyridin-2-one (1.01 g, 5.20 mmol) in dioxane was added $Pd(PPh_3)_4$ (234 mg, 0.20 mmol) followed by 5-chloro-1-pentenyl boronic acid (1.21 g, 8.10 mmol). $Na_2CO_3$ (1.21 g, 11.40 mmol) and water (2 mL) were added and the resulting mixture was refluxed overnight. The orange heterogeneous mixture was cooled to room temperature and some crystals precipitated out of solution. The mixture was filtered and the filtrate was partitioned between EtOAc and water. The organic layer was dried over $Na_2SO_4$ and concentrated to give a yellow solid. Recrystallization from EtOAc/Hexanes afforded the first intermediate compound as a golden solid (815 mg, 60%). mp 137–138° C.; $^1$H NMR ($CDCl_3$, 400 MHz): δ 9.00 (br s, 1H), 7.88 (d, 1H), 7.13 (d, 1H), 6.94–6.82 (m, 1H), 6.58–6.46 (m, 2H), 3.61 (t, 2H), 2.52–2.42 (m, 2H), 2.45 (d, 3H), 2.06–1.98 (m, 2H); MS ES: m/z=263.02, 265.00.

A second intermediate compound, 7-{5-[4-(2,3-Dichloro-phenyl)-piperazin-1-yl]-pent-1-enyl}-4-methyl-1H-[1,8]naphthyridin-2-one, was produced as follows: A mixture of 7-(5-chloro-pent-1-enyl)-4-methyl-1H-[1,8]naphthyridin-2-one (500 mg, 1.90 mmol) and KI (316 mg, 1.90 mmol) was refluxed for 30 min. The mixture was cooled to room temperature and then treated with 1-(2,3-dichlorophenyl)piperazine monohydrochloride (630 mg, 2.40 mmol) followed by $K_2CO_3$ (611 mg, 4.40 mmol). The yellow suspension was refluxed for 2 d and then quenched with water. The mixture was extracted with EtOAc. The organic layer was washed with brine, dried over $Na_2SO_4$ and concentrated to give a yellow oil. Purification by column chromatography (5% MeOH/EtOAc) afforded the second intermediate compound as a yellow solid (371 mg, 42%). mp 198–199° C.; $^1$H NMR ($CDCl_3$, 400 MHz): δ 9.03 (br s, 1H), 7.84 (d, 1H), 7.18–7.12 (m, 3H), 7.00–6.92 (m, 2H), 6.59–6.46 (m, 2H), 3.16–3.02 (m, 4H), 2.74–2.60 (m, 4H), 2.54–2.47 (m, 2H), 2,45 (d, 3H), 2.40–2.32 (m, 2H), 1.83–1.72 (m, 2H); MS ES: m/z=457.40, 459.35.

7-{5-[4-(2,3-Dichloro-phenyl)-piperazin-1-yl]-pent-1-enyl}-4-methyl-1H-[1,8]naphthyridin-2-one (880 mg, 1.92 mmol) was dissolved in THF (50 mL) and added to a Parr bottle containing a suspension of Raney-Nickel (1.5 mL of a settled suspension in water) in EtOH (50 mL). The mixture was hydrogenated at 45 psi for 5.5 h. The reaction was not complete so additional Raney-Nickel (1 mL of a suspension in water) was added and the mixture was hydrogenated at 45 psi for 2.5 h. The reaction mixture was filtered through a bed of Celite and washed with EtOH. The filtrate was concentrated to give a white solid. Purification by column chromatography (10% MeOH/EtOAc) afforded the title compound as a white solid (780 mg, 88%). mp 195–196° C.; $^1$H NMR ($CDCl_3$, 400 MHz): δ 9.16 (br s, 1H), 7.88 (d, 1H), 7.18–7.12 (m, 2H), 7.06 (d, 1H), 7.00–6.92 (m, 1H), 6.50 (s, 1H), 3.14–3.00 (m, 4H), 2.85 (t, 2H), 2.72–2.54 (m, 4H), 2.46 (d, 3H), 2.42 (t, 2H), 1.85–1.72 (m, 2H), 1.64–1.52 (m, 2H), 1.48–1.36 (m, 2H); MS ES: m/z=459.08, 461.03.

Example D4

Synthesis of 7-{4-[4-(2,3-Dichloro-phenyl)-piperazin-1-yl]-butoxy}-3-methyl-1H-[1,8]naphthyridin-2-one A first intermediate compound, 7-Chloro-3-methyl-1H-[1,8]naphthyridin-2-one, was produced as follows: Diisopropyl amine (freshly distilled over sodium, 12.8 mL, 91.4 mmol, 2.2 equiv.) was dissolved in $Et_2O$ (40 mL) and cooled to −78° C. Butyl lithium (2.5 M solution in hexane, 37.0 mL, 91.4 mmol, 2.2 equiv.) was added slowly under nitrogen atmosphere. The mixture was stirred for 15 min and t-butyl propionate (13.8 mL, 91.4 mmol, 2.2 equiv.) was added as a solution in dry THF (20 mL). The reaction mixture was stirred for 30 min and N-(6-chloro-3-formyl-pyridin-2-yl)-2,2-dimethyl-propionamide (10.0 g, 42.0 mmol, 1.0 equiv.) was added as a solution in a minimum amount of dry THF (35 mL). A bright yellow precipitate was formed within 10 min and stirring became difficult. The reaction was allowed to warm up to RT. The reaction mixture turned dark red and was poured into saturated $NH_4Cl$ (100 mL). The organic layer was separated and the aqueous layer was extracted with $CH_2Cl_2$. The combined organic layers were dried over $Na_2SO_4$ and concentrated. 3-[6-Chloro-2-(2,2-dimethyl-propionylamino)-pyridin-3-yl]-3-hydroxy-2-methyl-propionic acid tert-butyl ester was obtained as a yellow thick syrup which upon drying under high vacuum became a foamy solid (20.0 g, crude). The product was used in the next step without further purification.

3-[6-Chloro-2-(2,2-dimethyl-propionylamino)-pyridin-3-yl]-3-hydroxy-2-methyl-propionic acid tert-butyl ester (20.0 g) was dissolved in dioxane (100 mL) and 3N HCl (100 mL) was added. The mixture was stirred under reflux conditions. After 30 min, more dioxane (15 mL) was added as there was some precipitation in the reaction mixture and the resultant clear solution was refluxed overnight. The reaction mixture was cooled in a cold water bath, diluted with 20 mL water and neutralized with saturated $K_2CO_3$ (80 mL). A pale yellow precipitate was formed which was separated by filtration. The precipitate was washed thoroughly with water and dried under vacuum to give the first intermediate compound as a pale yellow shiny solid (7.43 g, 38.18 mmol, 93% over 2 steps). mp 259–261° C.; MS: ES$^+$ 194.78, 196.64 (Exact Mass: 194.02).

A second intermediate compound, 2-Benzyloxy-7-chloro-3-methyl-[1,8]naphthyridine, was produced as follows: To a mixture of 7-chloro-3-methyl-1H-[1,8]naphthyridin-2-one (0.30 g, 1.54 mmol, 1.0 equiv) and silver carbonate (0.30 g, 1.08 mmol, 0.7 equiv) in toluene (10 mL) was added benzyl bromide (257 µL, 2.156 mmol, 1.4 equiv). The reaction was stirred at 60° C. overnight. TLC (50% EtOAc in hexanes) indicated the completion of the reaction. The reaction mixture was filtered through Celite and rinsed thoroughly with toluene and $CH_2Cl_2$. The combined filtrates were concentrated under reduced pressure and hexane (20–30 mL) was added to the residue. A white precipitate formed which was collected by filtration and washed with hexane until all the yellow color was washed out. The second intermediate compound was obtained as a white solid (0.24 g, 56%). m.p. 133° C.; MS: ES$^+$ 284.90, 286.56 (Exact Mass: 284.07).

A third intermediate compound, 2-Benzyloxy-7-(4-benzyloxy-butoxy)-3-methyl-[1,8]naphthyridine, was produced ad follows: To a solution of 4-benzyloxy-1-butanol (0.254 g, 1.4 mmol, 2.0 equiv) in anhydrous THF (5.0 mL) cooled to −40° C. was added potassium tert-butoxide (0.158 g, 1.4 mmol, 2.0 equiv) and the mixture was stirred for 10 min. A solution of 2-benzyloxy-7-chloro-3-methyl-[1,8]naphthyridine (0.20 g, 0.70 mmol, 1.0 equiv) in anhydrous THF (5.0 mL) was added and the reaction mixture was allowed to warm to RT.

The reaction mixture was stirred for 10 min at room temperature and quenched with water (5.0 mL). The organic phase was separated and the aqueous phase was extracted with ethyl acetate (2×10 mL). The combined organic extracts were dried over $Na_2SO_4$ and concentrated in vacuo to give a yellow oily residue which was purified by column chromatography (silica gel, hexane:EtOAc, 8:1) to afford the third intermediate compound as a pale yellow oil (0.160 g, 55%). MS: ES$^+$ 428.98 (Exact Mass: 428.21).

A fourth intermediate compound, 7-(4-Hydroxy-butoxy)-3-methyl-1H-[1,8]naphthyridin-2-one, was produced as follows: To a solution of 2-benzyloxy-7-(4-benzyloxy-butoxy)-3-methyl-[1,8]naphthyridine (1.0 g, 4.2 mmol) in methanol (200 mL) and THF (20 mL) was added 5% Pd/C (0.3 g) and the mixture was hydrogenated at 35 psi for 4 hours. The slurry was filtered through a pad of Celite, rinsed with methanol and the filtrate was concentrated in vacuo to provide the fourth intermediate compound as a white solid (0.58 g, 98%). $^1$H NMR was very clean so the product was used in the next step without further purification. MS: ES$^+$ 249.03 (Exact Mass: 248.12).

A fifth intermediate compound, 4-(6-Methyl-7-oxo-7,8-dihydro-[1,8]naphthyridin-2-yloxy)-butyraldehyd, was produced as follows: A mixture of pyridinium chlorochromate (PCC) (1.195 g, 5.5 mmol, 2.5 equiv) and neutral alumina (4.2 g, 3.5 g/1.0 g of PCC) in anhydrous $CH_2Cl_2$ (20 mL) was stirred for 30 min at RT. A solution of 7-(4-hydroxy-butoxy)-3-methyl-1H-[1,8]naphthyridin-2-one (0.55 g, 2.22 mmol, 1.0 equiv) in $CH_2Cl_2$ (20 mL) and THF (5 mL) was added to the reaction mixture and stirred for 2 h. The reaction mixture was filtered through a pad of silica and rinsed with $CH_2Cl_2$ and then 5% MeOH/$CH_2Cl_2$. The combined filtrates were concentrated in vacuo to give the fifth intermediate compound as a dark brown oil (0.65 g) which was used without purification in the next reaction.

To a solution of crude 4-(6-methyl-7-oxo-7,8-dihydro-[1,8]naphthyridin-2-yloxy)-butyraldehyde (0.65 g, 2.24 mmol, 1.0 equiv) in anhydrous methanol (40 mL) cooled to 0° C. was added 2,3-dichlorophenylpiperazine (1.2 g, 4.0 mmol, 2.0 equiv). The mixture was stirred for 5 min and NaBH(OAc)$_3$ (2.3 g, 11.2 mmol, 5.0 equiv) was added. The reaction mixture was brought to room temperature and stirred overnight. The reaction was quenched with water and was concentrated to remove methanol completely. The resultant pale green residue was dissolved in ethyl acetate and washed with 0.5 N HCl (1×10 mL), saturated NaHCO$_3$ solution (1×10 mL) and brine. The organic layer was dried over Na$_2$SO$_4$ and concentrated. The residue was purified by column chromatography (silica gel, 2% MeOH/CH$_2$Cl$_2$) to afford the title compound as a white foamy solid (0.2 g, 30%). MS: ES$^+$ 461.03, 463.03 (Exact Mass: 460.14).

Example D5

Synthesis of 7-{5-[4-(2,3-Dichloro-phenyl)-piperazin-1-yl]-pentyl}-3-methyl-1H-[1,8]naphthyridin-2-one A first intermediate compound, 7-(5-Chloro-pent-1-enyl)-3-methyl-1H-[1,8]naphthyridin-2-one, was produced as follows: To a solution of compound 7-chloro-3-methyl-1H-[1,8]naphthyridin-2-one (0.75 g, 4.11 mmol, 1.0 equiv) in anhydrous dioxane (60 mL) were added 5-chloro-1-pentenylboronic acid (0.92 g, 6.17 mmol, 1.5 equiv), K$_2$CO$_3$ (5.70 g, 41.1 mmol, 10.0 equiv) followed by Pd(PPh$_3$)$_4$ (0.19 g, 0.16 mmol, 0.04 equiv). The mixture was refluxed for 48 h, cooled and filtered through a small celite bed. The filtrate was concentrated to give a pale yellow residue. Purification by column chromatography on silica gel (EtOAc:Hexanes: MeOH, 1:1:0.2) gave the first intermediate compound as a pale yellow solid (0.70 g, 79%). mp: 128–129° C.; $^1$H NMR (CDCl$_3$, 400 MHz): δ 9.22 (br s, 1H), 7.75 (d, 1H), 7.50 (s, 1H), 7.10 (d, 1H), 6.90–6.80 (m, 1H), 6.55 (dd, 1H), 3.60 (t, 2H), 2.55–2.45 (m, 2H), 2.25 (s, 3H), 2.10–1.90 (m, 2H); MS: ES$^+$: 263.05 (M+H)$^+$, 265.06, (Exact mass: 262.09)

A second intermediate compound, 7-{5-[4-(2,3-Dichloro-phenyl)-piperazin-1-yl]-pent-1-enyl}-3-methyl-1H-[1,8]naphthyridin-2-one, was produced as follows: KI (0.30 g, 1.79 mmol, 1.0 equiv) was added to a stirred solution of 7-(5-chloro-pent-1-enyl)-3-methyl-1H-[1,8]naphthyridin-2-one (0.47 g, 1.79 mmol, 1.0 equiv) in CH$_3$CN (25 mL) and stirred for 1 h. Triethylamine (1 mL), 1-(2,3-dichlorophenyl)piperazine monohydrochloride (0.47 g, 1.79 mmol, 1.0 equiv) and K$_2$CO$_3$ (1.0 g, 7.16 mmol, 4.0 equiv) were added and the mixture was refluxed for 48 h. The reaction mixture was cooled to room temperature and filtered. The solids were washed with EtOAc (5 mL). The filtrate was diluted with EtOAc (20 mL) and washed with water (20 mL), saturated NaHCO$_3$ (10 mL) and brine. The organic layer was dried over Na$_2$SO$_4$ and concentrated. Purification of the residue by column chromatography on silica (EtOAc:Hexanes:MeOH, 4:4:0.5 to 1:1:0.5) gave the second intermediate compound as a pale yellow solid (0.28 g, 34%). mp:

82–84° C.; ¹H NMR (400 MHz, CDCl₃) δ 9.40 (br s, 1H), 7.75 (d, 1H), 7.55 (s, 1H), 7.20–7.10 (m, 3H), 6.90–6.88 (m, 2H), 6.50 (dd, 1H), 3.10 (br s, 4H), 2.75 (br s, 4H), 2.52–2.50 (m, 2H), 2.32–2.28 (m, 2H), 2.20 (s, 3H), 1.72–1.68 (m, 2H); MS: ES+: 457.01 (M+H)⁺, 459.00. (Exact mass: 456.15).

A solution of 7-{5-[4-(2,3-dichloro-phenyl)-piperazin-1-yl]-pent-1-enyl}-3-methyl-1H-[1,8]naphthyridin-2-one (0.43 g, 0.94 mmol) in THF was added to a slurry of Raney Ni in EtOH. The mixture was hydrogenated for 4 h at 40 psi. The reaction mixture was filtered through a small celite bed and rinsed with CH₂Cl₂ and mMeOH. The filtrate was concentrated and purified by column chromatography on silica (10% MeOH/EtOAc) to afford the title compound as a pale yellow solid (0.22 g, 51.4%). mp: 157–158° C.; ¹H NMR (400 MHz, CDCl₃) δ 9.00 (br s, 1H), 7.75 (d, 1H), 7.50 (s, 1H), 7.15 (m, 2H), 7.00–6.90 (m, 2H), 3.10 (br s, 4H), 2.80 (t, 2H), 2.60 (br s, 4H), 2.42–2.38 (m, 2H), 2.20 (s, 3H), 1.82–1.80 (m, 2H), 1.70–1.60 (m, 4H); MS: ES+: 459.01 (M+H)⁺, 460.97 (Exact mass: 458.16).

Example D6a and D6b

Synthesis of 7-{4-[4-(2,3-Dichloro-phenyl)-piperazin-1-yl]-butoxy}-3-methyl-3,4-dihydro-1H-[1,8]naphthyridin-2-one A first intermediate compound, 7-(4-Hydroxy-butoxy)-3-methyl-3,4-dihydro-1H-[1,8]naphthyridin-2-one, was produced as follows: A mixture of 2-benzyloxy-7-(4-benzyloxy-butoxy)-3-methyl-[1,8]naphthyridine (1.8 g, 4.2 mmol) and 5% Pd/C (0.5 g) in methanol (250 mL) was hydrogenated overnight at 35 psi. The slurry was filtered through a pad of Celite washing with methanol and the filtrate was concentrated in vacuo to provide a mixture of 7-(4-hydroxy-butoxy)-3-methyl-3,4-dihydro-1H-[1,8]naphthyridin-2-one and 7-(4-hydroxy-butoxy)-3-methyl-1H-[1,8]naphthyridin-2-one as a colorless viscous material (0.9 g). The products were separated by column chromatography (silica gel, 5% methanol/CH₂Cl₂) to afford the first intermediate compound (0.45 g, 1.80 mmol, 43%) as a viscous material and 7-(4-hydroxy-butoxy)-3-methyl-1H-[1,8]naphthyridin-2-one (0.28 g) as a white powder. The combined yield was 73%. MS: ES⁺ 251.15 (Exact Mass: 250.13).

A second intermediate compound, 4-(6-Methyl-7-oxo-5,6,7,8-tetrahydro-[1,8]naphthyridin-2-yloxy)-butyraldehyde, was produced as follows: A mixture of pyridinium chlorochromate (PCC) (0.13 g, 0.6 mmol, 2.5 equiv) and neutral alumina (0.45 g, 3.5 g/1.0 g of PCC) in anhydrous CH₂Cl₂ (5.0 mL) was stirred for 30 min at RT. A solution of 7-(4-hydroxy-butoxy)-3-methyl-3,4-dihydro-1H-[1,8]naphthyridin-2-one (0.06 g, 0.24 mmol, 1.0 equiv) in CH₂Cl₂ (5.0 mL) and THF (2.0 mL) was added to the reaction mixture and stirred for 2.0 h. The reaction mixture was filtered through a pad of silica and rinsed with CH₂Cl₂. The combined filtrates were concentrated in vacuo to give the second intermediate compound as a pale yellow oil. The crude (0.05 g) was used in the next step without purification.

To a solution of crude 4-(6-methyl-7-oxo-5,6,7,8-tetrahydro-[1,8]naphthyridin-2-yloxy)-butyraldehyde (0.5 g, 2.0 mmol, 1.0 equiv) in anhydrous methanol (40 mL) cooled to 0° C. was added 2,3-dichlorophenylpiperazine (1.1 g, 4.0 mmol, 2.0 equiv). The mixture was stirred for 5 min and NaBH(OAc)₃ (2.14 g, 10.0 mmol, 5.0 equiv) was added. The reaction mixture was brought to room temperature and stirred overnight. TLC indicated a trace amount of aldehyde was still left. More NaBH(OAc)₃ was added and stirring continued for one more hour. TLC indicated the reaction was complete. The reaction mixture was concentrated to dryness. The resultant pale green residue was dissolved in ethyl acetate and washed with 0.5 N HCl (1×10 mL), saturated NaHCO₃ solution (1×10 mL) and brine. The organic layer was dried over Na₂SO₄ and concentrated. The residue was purified by column chromatography (silica gel, 2% MeOH/CH₂Cl₂) to afford the title compound as a colorless viscous material (0.63 g, 75% over 2 steps). The enantiomers were separated by chiral HPLC (Chiralpak AD, 40:60 Hexane/EtOH) to give the enantiomers D6a and D6b. MS: APCI: M+1: 463.1 (Exact Mass: 462.16).

Example D7

Synthesis of 7-{4-[4-(2,3-Dichloro-phenyl)-piperazin-1-yl]-butoxy}-3,4-dimethyl-1H-[1,8]naphthyridin-2-one A first intermediate compound, 7-Chloro-3,4-dimethyl-1H-[1,8]naphthyridin-2-one, was produced as follows: To a stirred solution of diisopropylamine (0.60 g, 0.83 mL, 5.9 mmol) in Et₂O (15 mL) at −78° C. is added n-butyl lithium (2.4 mL, 2.5 M in hexanes, 5.9 mmol). The mixture is stirred at −78° C. for 30 minutes and t-butyl propionate (0.77 g, 0.89 mL, 5.9 mmol) is added dropwise. The mixture is stirred at −78° C. for 30 minutes and N-(3-acetyl-6-chloropyridin-2-yl)-2,2-dimethyl-propionamide (0.50 g, 1.9 mmol) in Et₂O (3 mL) is added dropwise. A yellow precipitate forms and the mixture is stirred at −78° C. for 30 minutes and warmed to room temperature over 3 hours. Water (10 mL) is added, the mixture stirred for 5 minutes and then diluted with ethyl acetate (20 mL) and brine (10 mL). The organic layer is separated, washed with brine (2×20 mL), dried over Na₂SO₄, filtered and concentrated under vacuum. The crude oil is recrystallized from hexanes to yield 3-[6-chloro-2-(2,2-dimethyl-propionylamino)-pyridin-3-yl]-3-hydroxy-2-methyl-butyric acid tert-butyl ester (0.48 g, 64%). mp 146–148° C., ¹H NMR (200 MHz, CDCl₃) δ 10.50 (br s, 1H), 7.50 (d, 1H), 6.95 (d, 1H), 5.30 (s, 1H), 3.10 (q, 1H), 1.48 (s, 3H), 1.45 (s, 9H), 1.30 (s, 9H), 1.22 (d, 3H), MS ES+ 384.82 (M⁺).

Aqueous 3 N HCl (20 mL) is added to 3-[6-chloro-2-(2,2-dimethyl-propionylamino)-pyridin-3-yl]-3-hydroxy-2-methyl-butyric acid tert-butyl ester (4.5 g, 15.8 mmol) in dioxane (20 mL). The mixture is refluxed for 4 hours, cooled to RT, and poured over ice. The resulting precipitate is filtered, washed with water (2×20 mL) and dried to afford the first intermediate compound (2.4 g, 96%). mp 239–241° C., ¹H NMR (200 MHz, CDCl₃) δ 10.0 (br s, 1H), 7.95 (d, 1H), 7.20 (d, 1H), 2.45 (s, 3H), 2.30 (s, 3H), MS ES+ 208.99 (M+H)⁺ (Exact Mass: 208.04).

A second intermediate compound, 2-Benzyloxy-7-chloro-3,4-dimethyl-[1,8]naphthyridine, was produced as follows: 7-Chloro-3,4-dimethyl-1H-[1,8]naphthyridin-2-one (0.20 g, 0.96 mmol) in toluene (10 mL) is treated with silver carbonate (0.20 g, 0.73 mmol) followed by benzyl bromide (0.25 g, 0.17 mL, 1.4 mmol). The mixture is stirred at 60° C. for 16 hours. The mixture is cooled to RT, filtered and concentrated under vacuum. The crude oil is recrystallized from hexanes to give the second intermediate compound (87 mg, 30%). mp 140–141° C., ¹H NMR (400 MHz, CDCl₃) δ 8.20 (d, 1H), 7.55 (d, 1H), 7.42–7.30 (m, 5H), 5.62 (s, 2H), 2.58 (s, 3H), 2.40 (s, 3H), MS ES+ 299.04 (M+H)⁺ (Exact Mass: 298.09).

A third intermediate compound, 2-Benzyloxy-7-(4-benzyloxy-butoxy)-3,4-dimethyl-[1,8]naphthyridine, was produced as follows: To a stirred solution of 4-benzyloxy-1-butanol (500 mg, 0.49 mL, 2.77 mmol) in THF (6 mL) at −45° C. is added potassium tert-butoxide (311 mg, 2.77 mmol). The mixture is stirred at −45° C. for 10 minutes and then 2-benzyloxy-7-chloro-3,4-dimethyl-[1,8]naphthyridine (661 mg, 2.31 mmol) in THF (5 mL) is added. The solution turns a reddish color and is allowed to warm to room temperature over 2 hours. Saturated NH$_4$Cl (3 mL) is added and the solution is diluted with ethyl acetate (20 mL) and washed with water (20 mL), brine (20 mL), dried over Na$_2$SO$_4$, filtered and concentrated under vacuum. The crude oil is purified by column chromatography (2:1 hexane/Et$_2$O) to afford the third intermediate compound (580 mg, 57%) as a clear oil. $^1$H NMR (400 MHz, CDCl$_3$) δ 8.10 (d, 1H), 7.55–7.50 (m, 2H), 7.40–7.20 (m, 8H), 6.80 (d, 1H), 5.60 (s, 2H), 4.56 (t, 2H), 4.54 (s, 2H), 3.58 (t, 2H), 2.55 (s, 3H), 2.30 (s, 3H), 2.00–1.80 (m, 4H), MS ES+ 442.93 M$^+$) (Exact Mass: 442.23).

A fourth intermediate compound, 7-(4-Hydroxy-butoxy)-3,4-dimethyl-1H-[1,8]naphthyridin-2-one, was produced as follows: To a solution of 2-benzyloxy-7-(4-benzyloxy-butoxy)-3,4-dimethyl-[1,8]naphthyridine (500 mg, 1.1 mmol) in MeOH (20 mL) is added 10% Pd/C (200 mg) and the mixture is shaken under 45 psi H$_2$ for 3 hours. The mixture is then filtered through Celite and concentrated under vacuum to yield the fourth intermediate compound (272 mg, 92%) as a white solid. mp 172–174° C., $^1$H NMR (400 MHz, DMSO-d$_6$) δ 11.80 (s, 1H), 8.02 (d, 1H), 6.61 (d, 1H), 4.42 (t, 1H), 4.34 (t, 2H), 3.45 (t, 2H), 2.34 (s, 3H), 2.04 (s, 3H), 1.80–1.70 (m, 2H), 1.60–1.55 (m, 2H), MS ES+ 263.06 (M+H)$^+$ (Exact Mass: 262.13).

A fifth intermediate compound, 4-(5,6-Dimethyl-7-oxo-7,8-dihydro-[1,8]naphthyridin-2-yloxy)-butyraldehyde, was produced as follows: To a stirred solution of Dess-Martin periodinane (178 mg, 0.42 mmol) in CH$_2$Cl$_2$ (10 mL) at room temperature is added 7-(4-hydroxy-butoxy)-3,4-dimethyl-1H-[1,8]naphthyridin-2-one (100 mg, 0.38 mmol) in THF (6 mL). The resulting mixture is stirred for 1 hour and then Et$_2$O (10 mL) is added. The resulting suspension is poured into a mixture of saturated NaHCO$_3$ (10 mL) and Na$_2$S$_2$O$_3$ (464 mg, 2.94 mmol) and stirred for 10 minutes. The organic layer is separated, washed with saturated NaHCO$_3$ (10 mL) and brine (10 mL), dried over Na$_2$SO$_4$, filtered and concentrated under vacuum. The crude aldehyde is used without purification in the next step.

The crude 4-(5,6-dimethyl-7-oxo-7,8-dihydro-[1,8]naphthyridin-2-yloxy)-butyraldehyde (100 mg, 0.38 mmol) is dissolved in dichloroethane (7 mL) and 1-(2,3-dichlorophenyl)piperazine monohydrochloride (112 mg, 0.42 mmol) is added, followed by triethylamine (39 mg, 0.05 mL, 1.14 mmol). The mixture is stirred for 5 minutes and NaBH(OAc)$_3$ (81 mg, 0.38 mmol) is added. The mixture is stirred at room temperature for 1 hour and water (5 mL) is added. The organic layer is separated, washed with brine (10 mL), dried over Na$_2$SO$_4$, filtered and concentrated under vacuum. The crude solid is purified by column chromatography (1:9 methanol/ethyl acetate) to yield the title compound (123 mg, 68%) as a white solid. mp 161–163° C., $^1$H NMR (400 MHz, CDCl$_3$) δ 8.98 (br s, 1H), 7.80 (d, 1H), 7.20–7.10 (m, 2H), 7.00–6.90 (m, 1H), 6.60 (d, 1H), 4.20 (t, 2H), 3.15–3.00 (m, 4H), 2.75–2.60 (m, 4H), 2.50 (t, 2H), 2.40 (s, 3H), 2.20 (s, 3H), 1.85–1.60 (m, 4H), MS ES+ 474.76 (M)$^+$ (Exact Mass: 474.16).

Example D8

Synthesis of 7-{5-[4-(2,3-Dichloro-phenyl)-piperazin-1-yl]-pentyl}-3,4-dimethyl-1H-[1,8]naphthyridin-2-one A first intermediate compound, 7-(5-Chloro-pent-1-enyl)-3,4-dimethyl-1H-[1,8]naphthyridin-2-one, was produced as follows: To a stirred solution of 7-chloro-3,4-dimethyl-1H-[1,8]naphthyridin-2-one (2.0 g, 9.6 mmol) in dioxane (20 mL) was added Pd(PPh$_3$)$_4$ (334 mg, 0.29 mmol) and the mixture was stirred for 5 min. 5-Chloro-1-pentenyl boronic acid (2.140 g, 14.42 mmol) was added followed by aqueous Na$_2$CO$_3$ (2 M, 20 mL) and the mixture was heated at 100° C. for 18 h. The mixture was cooled to room temperature and diluted with water (20 mL) and ethyl acetate (30 mL). The organic layer was separated and washed with brine (20 mL), dried over anhydrous Na$_2$SO$_4$, filtered and evaporated. The crude solid was recrystallized from CH$_2$Cl$_2$/hexanes to yield the first intermediate compound as a light yellow solid (1.12 g, 42%). mp 152–153° C., $^1$H NMR (400 MHz, CDCl$_3$) δ 8.95 (s, 1H), 7.88 (d, 1H), 7.05 (d, 1H), 6.82 (dt, 1H), 6.50 (d, 1H), 3.60 (t, 2H), 2.46–2.40 (m, 2H), 2.39 (s, 3H), 2.22 (s, 3H), 2.04–1.98 (m, 2H), MS ES+ 277.06 (M+H)$^+$.

A second intermediate compound, 7-{5-[4-(2,3-Dichloro-phenyl)-piperazin-1-yl]-pent-1-enyl}-3,4-dimethyl-1H-[1,8]naphthyridin-2-one, was produced as follows: To a stirred solution of 7-(5-chloro-pent-1-enyl)-3,4-dimethyl-1H-[1,8]naphthyridin-2-one (500 mg, 1.81 mmol) in CH$_3$CN (20 mL) were added 1-(2,3-dichlorophenyl)piperazine monohydrochloride (581 mg, 2.17 mmol), KI (361 mg, 2.17 mmol) and K$_2$CO$_3$ (1.25 g, 9.05 mmol). The mixture was refluxed for 48 h, cooled to room temperature, and diluted with water (10 mL) and CH$_2$Cl$_2$ (10 mL). The organic layer was separated, washed with water (10 mL) and brine (10 mL), dried over anhydrous Na$_2$SO$_4$, filtered and evaporated in vacuo. The crude solid was purified by column chromatography (5% MeOH/CH$_2$Cl$_2$) to yield the second intermediate compound as a yellow solid (416 mg, 49%). mp 92–97° C., $^1$H NMR (400 MHz, CDCl$_3$) δ 10.00 (br s, 1H), 7.85 (d, 1H), 7.10–7.03 (m, 3H), 6.98–6.80 (m, 2H), 6.56 (d, 1H), 3.10–3.00 (m, 4H), 2.80–2.60 (m, 4H), 2.50 (t, 2H), 2.40 (s, 3H), 2.38–2.24 (m, 2H), 2.22 (s, 3H), 1.82–1.70 (m, 2H), MS ES+ 471.02 (M+H)$^+$ (Exact Mass: 470.16).

7-{5-[4-(2,3-Dichloro-phenyl)-piperazin-1-yl]-pent-1-enyl}-3,4-dimethyl-1H-[1,8]naphthyridin-2-one (80 mg, 0.17 mmol) was dissolved in a minimal amount of THF (2 mL) and the solution was diluted with ethanol (10 mL). The solution was treated with Raney Nickel (0.5 mL slurry in water) and shaken under 45 psi H$_2$ for 3 h. The mixture was filtered through celite. The celite pad was washed with THF (2×10 mL), and the filtrate was evaporated in vacuo. The crude solid was purified by column chromatography (5% MeOH/CH$_2$Cl$_2$) to yield the title compound as a white solid (64 mg, 80%). mp 202–203° C., $^1$H NMR (400 MHz, CDCl$_3$) δ 8.98 (br s, 1H) 7.84 (d, 1H), 7.20–7.15 (m, 2H), 7.04 (d, 1H), 6.98–6.95 (m, 1H), 3.15–3.00 (m, 4H), 2.81 (t, 2H), 2.70–2.55 (m, 4H), 2.46–2.36 (m, 5H), 2.22 (s, 3H), 1.82–1.75 (m, 2H), 1.60–1.50 (m, 2H), 1.45–1.36 (m, 2H), MS ES+ 473.00 (M+H)$^+$ (Exact Mass: 472.18).

Example D9

Synthesis of 7-{4-[4-(2,3-Dichloro-phenyl)-piperazin-1-yl]-butoxy}-3-fluoro-1H-[1,8]naphthyridin-2-one A first intermediate compound, N-{3-Formyl-6-[4-(tetrahydro-pyran-2-yloxy)-butoxy]-pyridin-2-yl}-2,2-dimethyl-propionamide, was produced as follows: To a cooled (−78° C.) solution of 2,2-dimethyl-N-{6-[4-(tetrahydro-pyran-2-yloxy)-butoxy]-pyridin-2-yl}-propionamide (7.0 g, 20 mmol) in THF was added n-BuLi (20 mL, 2.5 M in Hexane, 50 mmol). The mixture was stirred at 0° C. for 3.5 h and then cooled back to −78° C. DMF (4.6 mL, 60 mmol) was added dropwise with vigorous stirring. The cooling bath was removed and the reaction was allowed to warm to 0° C. The reaction was quenched with saturated aqueous NH$_4$Cl (20 mL) and extracted with EtOAc (300 mL). The organic layer was washed with water (2×20 mL) and brine (20 mL), dried over Na$_2$SO$_4$ and concentrated to give an oil which was purified by column chromatography (20% EtOAc/Hexanes) to give the first intermediate compound as a pale yellow oil (5.8 g, 77%). $^1$H NMR (400 MHz, δ ppm): 11.50 (br s, 1H), 9.85 (s, 1H), 7.80 (d, 1H), 6.50 (d, 1H), 4.55 (m, 3H), 3.85 (m, 2H), 3.45 (m, 2H), 2.00–1.50 (m, 10H), 1.40 (s, 9H).

A second intermediate compound, 3-Fluoro-7-(4-hydroxy-butoxy)-1H-[1,8]naphthyridin-2-one, was produced as follows: To a mixture of N-{3-formyl-6-[4-(tetrahydropyran-2-yloxy)-butoxy]-pyridin-2-yl}-2,2-dimethyl-propionamide (4.10 g, 10.85 mmol), triethyl-2-fluoro-2-phosphonoacetate (5.30 g, 21.70 mmol, 2 eq) and LiCl (0.91 g, 21.70 mmol, 2 eq) in CH$_3$CN was added DBU (3.30 g, 21.70 mmol, 2 eq) dropwise at such a rate that the temperature of the mixture did not exceed 30° C. The mixture was stirred at room temperature overnight and quenched with saturated NH$_4$Cl (30 mL). The mixture was extracted with EtOAc (200 mL). The organic layer was washed with water (20 mL) and brine (20 mL), dried over Na$_2$SO$_4$ and concentrated to give a mixture of cis- and trans-α,β-unsaturated esters. This mixture was dissolved in dioxane (40 mL) and 3 N HCl (20 mL) and refluxed for 2 h. The reaction was cooled in an ice-bath and neutralized with K$_2$CO$_3$ (pH 8). The mixture was extracted with THF (250 mL). The organic layer was washed with brine (30 mL), dried over Na$_2$SO$_4$ and concentrated. The residue was purified by column chromatography (5% MeO/CH$_2$Cl$_2$) to give the second intermediate compound as a pale yellow solid (700 mg, 26%). $^1$H NMR (400 MHz, δ ppm): 7.90 (d, J=8.5 Hz, 1H), 7.70 (d, J=8.6 Hz, 1H), 6.75 (d, J=8.5 Hz, 1H), 4.42 (t, J=6.7 Hz, 2H), 3.61 (t, J=6.0 Hz, 2H), 1.90 (m, 2H), 1.70 (m, 2H).

To a suspension of Dess-Martin periodinane (1.09 g, 2.56 mmol, 1.2 eq) in CH$_2$Cl$_2$ (30 mL) was added a solution of 3-fluoro-7-(4-hydroxy-butoxy)-1H-[1,8]naphthyridin-2-one (0.538 g, 2.13 mmol) in THF (10 mL)/DMSO (2 mL). The mixture was stirred at room temperature for 1.5 h. The reaction mixture was diluted with Et$_2$O (100 mL) and quenched with aqueous NaHCO$_3$ (30 mL) containing Na$_2$S$_2$O$_3$ (2.36 g, 14.91 mmol, 7 eq). After extraction with Et$_2$O (3×50 mL), the combined organic layer was washed with brine (20 mL), dried over Na$_2$SO$_4$ and concentrated to give the crude aldehyde as a pale yellow solid. To a solution of the aldehyde in 1,2-dichloroethane (40 mL) was added 1-(2,3-dichlorophenyl)piperazine monohydrochloride (0.803 g, 3.0 mmol, 1.4 eq), Et$_3$N (0.54 mL, 4.0 mmol, 1.9 eq), and NaBH(OAc)$_3$ (0.631 g, 3.0 mmol, 1.4 eq). The mixture was stirred at room temperature for 1 h and then quenched with water and saturated NaHCO$_3$. After extraction with CH$_2$Cl$_2$ (3×50 mL), the combined organic layer was dried over Na$_2$SO$_4$ and concentrated. The residue was purified by column chromatography (3% MeOH/CH$_2$Cl$_2$) to give the title compound (900 mg, 91% in two steps). $^1$H NMR (400 MHz, δ ppm): 12.60 (brs, 1H), 8.00 (d, J=8.5 Hz, 1H), 7.80 (d, J=8.3 Hz, 1H), 7.30 (m, 2H), 7.10 (m, 1H), 6.75 (d, J=8.5 Hz, 1H), 4.40 (t, J=7.0 Hz, 2H), 3.00 (brs, 4H), 2.50 (brs, 4H), 2.40 (t, J=6.5 Hz, 2H), 1.80 (m, 2H), 1.60 (m, 2H); $^{19}$F NMR: −140 ppm; MS: 465 (M+H)$^+$ (Exact Mass: 464.12).

Example D10

Synthesis of 3-Fluoro-7-[4-(4-naphthalen-1-yl-piperazin-1-yl)-butoxy]-1H-[1,8]naphthyridin-2-one To a suspension of Dess-Martin periodinane (0.79 g, 1.86 mmol, 1.2 eq) in CH$_2$Cl$_2$ (20 mL) was added a solution of 3-fluoro-7-(4-hydroxy-butoxy)-1H-[1,8]naphthyridin-2-one (0.39 g, 1.5 mmol) in THF (6 mL)/DMSO (2 mL). The mixture was stirred at room temperature for 1.5 h. The reaction mixture was diluted with Et$_2$O (100 mL) and quenched with aqueous NaHCO$_3$ (20 mL) containing Na$_2$S$_2$O$_3$ (1.66 g, 10.5 mmol, 7 eq). After extraction with Et$_2$O (3×40 mL), the combined organic layer was washed with brine (20 mL), dried over Na$_2$SO$_4$ and concentrated to give the crude aldehyde as a pale yellow solid. To a solution of the aldehyde in 1,2-dichloroethane (20 mL) was added 1-naphthalen-1-yl-piperazine monohydrochloride (0.522 g, 2.1 mmol, 1.4 eq), Et$_3$N (0.38 mL, 2.85 mmol, 1.9 eq) and NaBH(OAc)$_3$ (0.445 g, 2.1 mmol, 1.4 eq). The mixture was stirred at room temperature for 1 h and quenched with water and saturated NaHCO$_3$. After extraction with CH$_2$Cl$_2$ (3×50 mL), the combined organic layer was dried over Na$_2$SO$_4$ and concentrated. The residue was purified by column chromatography (3% MeOH/CH$_2$Cl$_2$) to give the title compound (430 mg, 62% in two steps). $^1$H NMR (400 MHz, δ ppm): 12.60 (br s, 1H), 8.10 (d, J=6.0 Hz, 1H), 8.00 (d, J=7.2 Hz, 1H), 7.85 (m, 2H), 7.60 (d, J=6.0 Hz, 1H), 7.50 (m, 2H), 7.40 (d, J=6.0 Hz, 1H), 7.10 (d, J=6.0 Hz, 1H), 6.75 (d, J=7.0 Hz, 1H), 4.35 (t, J=4.0 Hz, 2H), 3.00 (br s, 4H), 2.60 (br s, 4H), 2.40 (t, J=3.8 Hz, 2H), 1.80 (m, 2H), 1.60 (m, 2H); $^{19}$F NMR: −140 ppm; MS: 447 (M+H)$^+$ (Exact Mass: 446.21).

Example D11

Synthesis of 7-[4-(4-Naphthalen-1-yl-piperazin-1-yl)-butoxy]-3-(2,2,2-trifluoro-ethyl)-1H-[1,8]naphthyridin-2-one An intermediate compound, 7-(4-Hydroxy-butoxy)-3-(2,2,2-trifluoro-ethyl)-1H-[1,8]naphthyridin-2-one, was produced as follows: To a cooled (−78° C.) solution of LiHMDS (47.6 mL, 1 M in THF) was added ethyl 4,4,4-trifluorobutyrate (8.10 g, 47.6 mmol) dropwise and the mixture was stirred for 1 hour. A solution of N-{3-formyl-6-[4-(tetrahydro-pyran-2-yloxy)-butoxy]-pyridin-2-yl}-2,2-dimethyl-propionamide (3.0 g, 7.93 mmol) in THF (15 mL) was added. The cooling bath was then removed and the reaction was allowed to gradually warm to 0° C. The reaction was quenched with aqueous NH$_4$Cl (30 mL) and the mixture was extracted with EtOAc. The organic layer was washed with water and brine, dried over Na$_2$SO$_4$ and concentrated to give the condensation product which was used in the next step without further purification.

The crude material obtained in the last step was dissolved in dioxane (30 mL) and 3 N HCl (15 mL). The resulting solution was refluxed overnight and neutralized with $K_2CO_3$ (pH 8) while cooling with an ice-bath. The mixture was extracted with EtOAc (3×50 mL). The combined organic layers were dried over $Na_2SO_4$ and concentrated to give a mixture of the desired product, 7-(4-hydroxy-butoxy)-3-(2,2,2-trifluoro-ethyl)-1H-[1,8]naphthyridin-2-one, and a side-product, 2-[2-amino-6-(4-hydroxy-butoxy)-pyridin-3-ylmethylene]-4,4,4-trifluoro-butyric acid ethyl ester. The crude mixture was dissolved in MeOH (20 mL) and water (10 mL) and KOH (1.07 g) was added. The resulting mixture was stirred overnight at RT. The mixture was concentrated and the residue was extracted with EtOAc (3×50 mL). The combined organic layers were dried over $Na_2SO_4$ and concentrated to give an oil which was purified by chromatography on silica gel (3% MeOH/$CH_2Cl_2$) to give the intermediate compound as a yellow solid (260 mg, 10% in three steps). $^1$H NMR (400 MHz, δ ppm): 9.78 (br s, 1H), 7.75 (d, J=5.6 Hz, 2H), 6.60 (d, J=5.6 Hz), 4.70 (t, J=3.4 Hz), 4.50 (t, J=3.6 Hz), 3.80 (m, 2H), 3.50 (q, J=7 Hz, 2H), 1.60–2.00 (m, 4H). $^{19}$F NMR: −65 ppm, MS: 317 ($M^+$).

To a suspension of Dess-Martin periodinane (0.419 g, 0.99 mmol, 1.2 eq) in $CH_2Cl_2$ (20 mL) was added a solution of 7-(4-hydroxy-butoxy)-3-(2,2,2-trifluoro-ethyl)-1H-[1,8]naphthyridin-2-one (0.26 g, 0.82 mmol) in THF (8 mL). The mixture was stirred at room temperature for 1 h. $Et_2O$ (100 mL) was added to dilute the reaction mixture. The reaction was quenched with aqueous $NaHCO_3$ (20 mL) containing $Na_2S_2O_3$ (0.91 g, 5.74 mmol, 7 eq). After extraction with $Et_2O$ (3×50 mL), the combined organic layer was washed with brine (20 mL), dried over $Na_2SO_4$, and concentrated to give the crude aldehyde as a pale yellow solid. To a solution of the crude aldehyde in 1,2-dichloroethane (20 mL) was added 1-naphthalen-1-yl-piperazine monohydrochloride (0.286 g, 1.15 mmol, 1.4 eq), $Et_3N$ (0.21 mL, 1.56 mmol, 1.9 eq) and $NaBH(OAc)_3$ (0.241 g, 1.15 mmol, 1.4 eq). The mixture was stirred at room temperature for 1 h. The reaction was quenched with water and saturated $NaHCO_3$. After extraction with $CH_2Cl_2$ (3×50 mL), the combined organic layer was dried over $Na_2SO_4$ and concentrated. The residue was purified by column chromatography (2% MeOH/$CH_2Cl_2$) to give the title compound (200 mg, 50% in two steps). $^1$H NMR (400 MHz, δ ppm): 9.05 (br s, 1H), 8.20 (d, J=6.2 Hz, 1H), 7.80 (d, J=6.0 Hz, 1H), 7.75 (m, 2H), 7.58 (d, J=6.3 Hz, 1H), 7.50 (m, 2H), 7.40 (t, J=6.3 Hz, 1H), 7.10 (d, J=5.3 Hz, 1H), 6.40 (d, J=6.5 Hz, 1H), 4.40 (t, J=4.2 Hz, 2H), 3.50 (q, J=7.5 Hz, 2H), 3.20 (br s, 4H), 2.80 (br s, 4H), 2.60 (m, 2H), 1.90 (m, 2H), 1.72 (m, 2H). $^{19}$F NMR: −65.6 ppm. MS: 511 ($M^+$). Elemental Analysis calculated for $C_{28}H_{29}F_3N_4O_2$: C, 65.88; H, 5.69; N, 10.98. Found: C, 66.08; H, 5.89; N, 10.67.

Example D12

Synthesis of 7-{5-[4-(2,3-Dichloro-phenyl)-piperazin-1-yl]-pentyl}-3,3-dimethyl-3,4-dihydro-1H-[1,8]naphthyridin-2-one A first intermediate compound, 3-[6-Chloro-2-(2,2-dimethyl-propionylamino)-pyridin-3-yl]-3-hydroxy-2,2-dimethyl-propionic acid methyl ester, was produced as follows: To a stirred solution of oxalyl chloride (11.0 g, 87.0 mmol) in $CH_2Cl_2$ (180 mL) at −60° C. was added a solution of DMSO (12.9 mL, 182 mmol) in $CH_2Cl_2$ (40 mL), dropwise at a rapid rate. The resulting solution was stirred for 5 min, then a solution of methyl-2,2-dimethyl-3-hydroxypropionate (10.0 g, 75.6 mmol) in $CH_2Cl_2$ (10 mL) was added dropwise over 10 min. The cloudy mixture was then stirred for 15 min, at which time triethylamine (52 mL, 380 mmol) was added dropwise, maintaining the temperature at or below −50° C. After stirring for 5 min, the mixture was allowed to warm to room temperature and water (200 mL) was then added. The layers were separated and the aqueous layer extracted with $CH_2Cl_2$ (2×100 mL). The combined organic layers were washed successively with 1 M HCl (100 mL), water (100 mL), saturated $NaHCO_3$ solution (100 mL), water (100 mL) and brine (100 mL), dried over $Na_2SO_4$, filtered and concentrated in vacuo until only a small volume of $CH_2Cl_2$ remained, to minimize the loss of the volatile product. The crude product was purified by vacuum distillation affording the desired product 2,2-dimethyl-3-oxopropionic acid methyl ester (8.1 g, 83%, 89° C., ca 80 mmHg). $^1$H NMR (CDCl$_3$) δ 9.67 (s, 1H), 3.76 (s, 3H), 1.36 (s, 6H).

To a stirred solution of N-(6-chloro-pyridin-2-yl)-2,2-dimethyl-propionamide (12.0 g, 56.6 mmol) in THF (180 mL) at −78° C., was added dropwise, n-butyllithium (95.0 mL, 153 mmol, 1.6 M in hexanes). After the addition was complete, the mixture was warmed to −20° C. and stirred at this temperature for 3 h. The reaction mixture was then cooled to −78° C. and added, via cannula, to a stirred solution of 2,2-dimethyl-3-oxopropionic acid methyl ester (14.7 g, 130 mmol) in THF (50 mL) at −78° C. After stirring for 2 h, the reaction was quenched by the addition of a saturated $NH_4Cl$ solution, diluted with ethyl acetate (50 mL) and warmed to RT. The organic layer was removed and washed with water (50 mL), saturated $NaHCO_3$ (50 mL), water (50 mL) and brine (50 mL), dried over $Na_2SO_4$, filtered and concentrated in vacuo. The crude product was purified by silica gel chromatography (90:10 to 50:50 hexanes/ethyl acetate) to afford the first intermediate compound (10.7 g, 55%) as a pale yellow solid. $^1$H NMR (CDCl$_3$) δ 8.77 (br s, 1H), 7.65 (d, J=8.1 Hz, 1H), 7.13 (d, J=8.1 Hz, 1H), 5.06 (d, J=3.8 Hz, 1H), 3.70 (s, 3H), 3.61 (d, J=3.9 Hz, 1H), 1.33 (s, 9H), 1.24 (s, 3H), 1.21 (s, 3H); MS (ESI) m/z 343 [$C_{16}H_{23}ClN_2O_4$+H]$^+$.

A second intermediate compound, 7-Chloro-4-hydroxy-3,3-dimethyl-3,4-dihydro-1H-[1,8]naphthyridin-2-one, was produced as follows: 3-[6-Chloro-2-(2,2-dimethyl-propionylamino)-pyridin-3-yl]-3-hydroxy-2,2-dimethyl-propionic acid methyl ester (2.0 g, 5.8 mmol) was partially dissolved in a mixture of 3M HCl and dioxane (1:1, 120 mL). The mixture was refluxed for 90 min, cooled to room temperature and concentrated in vacuo. The residue was partitioned between ethyl acetate (100 mL) and a saturated $NaHCO_3$ solution (100 mL). The aqueous layer was removed and extracted with ethyl acetate (2×30 mL). The combined organic layers were washed with brine (50 mL), dried over $Na_2SO_4$, filtered and concentrated. The crude residue was purified by silica gel chromatography (80:20 to 40:60 hexanes/ethyl acetate) to afford the second intermediate compound (0.85 g, 65%) as a pale yellow foamy solid. $^1$H NMR (CDCl$_3$) δ 7.78 (br s, 1H), 7.69 (d, J=7.7 Hz, 1H), 7.04 (d, J=7.7 Hz, 1H), 4.53 (d, J=4.7 Hz, 1H), 2.12 (d, J=5.0 Hz, 1H), 1.26 (s, 3H), 1.23 (s, 3H); MS (ESI) m/z 227 [$C_{10}H_{11}ClN_2O_2$+H]$^+$; Anal. Calcd for $C_{10}H_{11}ClN_2O_2$: C, 52.99; H, 4.89; N, 12.36; Cl, 15.64. Found: C, 53.17; H, 4.88; N, 12.27; Cl, 15.63.

A third intermediate compound, 7-Chloro-3,3-dimethyl-3,4-dihydro-1H-[1,8]naphthyridin-2-one, was produced as follows: To a solution of 7-chloro-4-hydroxy-3,3-dimethyl-3,4-dihydro-1H-[1,8]naphthyridin-2-one (0.71 g, 3.14 mmol) in TFA (10 mL) was added triethylsilane (1.5 mL, 9.7 mmol, 3.1 equiv). The mixture was heated at reflux for 2 h. The reaction was cooled to room temperature and concentrated. The residue was dissolved in $CH_2Cl_2$, washed with saturated NaHCO₃ and brine, and concentrated to give a solid. The solid was triturated with hexanes and filtered to give the third intermediate compound (520 mg, 80%). MS: ESI: m/z: 210.98 (Exact Mass: 210.06).

A fourth intermediate compound, 7-(5-Chloro-pent-1-enyl)-3,3-dimethyl-3,4-dihydro-1H-[1,8]naphthyridin-2-one, was produced as follows: A 100 mL round bottom flask was charged with 7-chloro-3,3-dimethyl-3,4-dihydro-1H-[1,8]naphthyridin-2-one (520 mg, 2.47 mmol), 5-chloro-pent-1-enyl-boronic acid (769 mg, 5.2 mmol), Pd(PPh₃)₄ (0.14 g, 0.12 mmol, 5 mol %) and Na₂CO₃ (262 mg, 2.47 mmol). DME (20 mL) and H₂O (5 mL) were added and the reaction was heated at reflux for 11 h. The reaction was cooled to room temperature and stirred overnight. The solvents were evaporated and the residue was partitioned between EtOAc (50 mL) and H₂O (50 mL). The organic layer was washed with H₂O, saturated NaHCO₃ and brine, dried over Na₂SO₄ and concentrated. Purification by liquid chromatography (SiO₂, 5 to 35% EtOAc/Hexanes) afforded the fourth intermediate compound (560 mg, 82%). MS: ESI: m/z 279.12 (Exact Mass: 278.12).

A fifth intermediate compound, 7-{5-[4-(2,3-Dichloro-phenyl)-piperazin-1-yl]-pent-1-enyl}-3,3-dimethyl-3,4-dihydro-1H-[1,8]naphthyridin-2-one, was produced as follows: To a solution of 7-(5-chloro-pent-1-enyl)-3,3-dimethyl-3,4-dihydro-1H-[1,8]naphthyridin-2-one (0.55 g, 1.98 mmol) in CH₃CN (50 mL) was added 1-(2,3-dichloro-phenyl)-piperazine (0.63 g, 2.37 mmol), K₂CO₃ (0.87 g, 6.34 mmol) and NaI (0.35 g, 2.37 mmol). The mixture was heated at reflux for 3 days. The reaction mixture was poured into H₂O and extracted with CH₂Cl₂. The organic layer was washed with brine, dried over Na₂SO₄ and concentrated. Purification by liquid chromatography (Biotage 25M, CH₂Cl₂ to 5% MeOH/CH₂Cl₂) gave the product contaminated with a small amount of starting chloro compound. Repurification by liquid chromatography (Biotage 25M, EtOAc to 5% MeOH/EtOAc) afforded the pure fifth intermediate compound (640 mg, 68%). MS: ESI: m/z: 473.34 (Exact Mass: 472.18).

A Parr shaker was charged with PtO₂ (0.12 g) and EtOAc (25 mL) was added under N₂. The catalyst was shaken under a H₂ atmosphere (50 psi) for 10 min and a suspension of 7-{5-[4-(2,3-dichloro-phenyl)-piperazin-1-yl]-pent-1-enyl}-3,3-dimethyl-3,4-dihydro-1H-[1,8]naphthyridin-2-one (0.54 g, 1.15 mmol) in EtOAc (125 mL) was added. The mixture was shaken under H₂ (50 psi) for 1.5 h. The reaction was filtered through Celite washing with MeOH and the filtrate was concentrated to give an oily residue. Hexanes was added and the mixture was concentrated to give the title compound as a white solid (0.54 g, 99%). MS: ESI: m/z: 475.32 (Exact Mass: 474.20).

Example D13

Synthesis of 7-{4-[4-(2,3-Dichloro-phenyl)-piperazin-1-yl]-butoxy}-3,3-dimethyl-3,4-dihydro-1H-[1,8]naphthyridin-2-one A first intermediate compound, 7-Chloro-3, 3-dimethyl-1H-[1,8]naphthyridine-2,4-dione, was produced as follows: To a suspension of Dess Martin periodinane (5.61 g, 13.23 mmol) in CH₂Cl₂ (25 mL) was added a solution of 7-chloro-4-hydroxy-3, 3-dimethyl-3,4-dihydro-1H-[1,8]naphthyridin-2-one (2.0 g, 8.82 mmol) in CH₂Cl₂/THF (40 mL/10 mL) via cannula. The reaction was stirred at room temperature for 2 hours. Upon completion, a 1:1 mixture of saturated Na₂S₂O₃ and saturated NaHCO₃ (75ml) were added, followed by Et₂O. The mixture was stirred for 20 minutes, and then extracted with a mixture of EtOAc/Et₂O (1:2). The organic layer was washed with saturated NaHCO₃ and brine, dried over Na₂SO₄ and concentrated to give the first intermediate compound as a pale yellow solid (1.96 g, 98%). MS: APCI: M+1: 225.1 (Exact Mass: 224.04).

A second intermediate compound, 7-(4-Benzyloxy-butoxy)-3,3-dimethyl-1H-[1,8]naphthyridine-2,4-dione, was produced as follows: To a solution of 4-benzyloxy-butan-1-ol (4.7 mL, 26.70 mmol) in dry THF was added KO$^t$Bu (1M in THF, 25.3 mL, 25.34 mmol). The mixture was stirred for 20 minutes and then added to a solution of 7-chloro-3,3-dimethyl-1H-[1,8]naphthyridine-2,4-dione (1.5 g, 6.67 mmol) in dry THF. The reaction was stirred at room temperature for 1 hour. The reaction was quenched with saturated NH₄Cl and partitioned between water and EtOAc. The organic layer was washed with saturated NaHCO₃ and brine, dried over Na₂SO₄ and concentrated. Purification by liquid chromatography on silica gel (10–40% EtOAc/Hexanes) gave the second intermediate compound as a colorless oil (2.25 g, 91%). MS: APCI: M+1: 369.5 (Exact Mass: 368.17).

A third intermediate compound, 7-(4-Hydroxy-butoxy)-3,3-dimethyl-3,4-dihydro-1H-[1,8]naphthyridin-2-one, was produced as follows: 7-(4-Benzyloxy-butoxy)-3,3-dimethyl-1H-[1,8]naphthyridine-2,4-dione (2.26 g, 6.13 mmol) was hydrogenated using 20% Pd/C (0.25 g) in THF for 1 h. A mixture of the title compound and 4-hydroxy-7-(4-hydroxy-butoxy)-3,3-dimethyl-3,4-dihydro-1H-[1,8]naphthyridin-2-one was obtained. The mixture was filtered and concentrated to give an oil. Purification by liquid chromatography on silica gel (50–100% EtOAc/Hexanes) gave the third intermediate compound (0.321 g, 19%). MS: APCI: M+1: 265.1 (Exact Mass: 264.15).

A fourth intermediate compound, 4-(6,6-Dimethyl-7-oxo-5,6,7,8-tetrahydro-[1,8]naphthyridin-2-yloxy)-butyraldehyde, was produced as follows: To a suspension of Dess Martin periodinane (0.693 g, 1.63 mmol) in dry CH₂Cl₂ (5 mL) was added a solution of 7-(4-hydroxy-butoxy)-3,3-dimethyl-3,4-dihydro-1H-[1,8]naphthyridin-2-one (0.287 g, 1.08 mmol) in dry CH₂Cl₂ (5 mL) via cannula. The reaction was stirred at room temperature for 7 hours. A 1:1 mixture of saturated NaHCO₃ and saturated Na₂S₂O₃ was added (30 mL), followed by Et₂O. The mixture was stirred for 15 minutes and then extracted with Et₂O/EtOAc. The organic layer was washed with saturated NaHCO₃ and brine, dried over Na₂SO₄ and concentrated to afford the fourth intermediate compound as a white solid (0.268 g, 1.02 mmol, 94%). MS: APCI: M–1: 261.0 (Exact Mass: 262.13).

To a solution of 4-(6,6-dimethyl-7-oxo-5,6,7,8-tetrahydro-[1,8]naphthyridin-2-yloxy)-butyraldehyde (0.250 g, 0.953 mmol) in DCE (6 mL) was added 1-(2,3-dichloro-phenyl)-piperazine hydrochloride (0.255 g, 0.953 mmol) followed by Et₃N (0.27 mL, 1.90 mmol). The mixture was stirred for 20 minutes at room temperature and NaBH(OAc)₃ (0.282 g, 1.33 mmol) was added. The reaction was stirred for 2.5 h and quenched with saturated NaHCO₃ and water. The mixture was extracted with EtOAc and the organic layer was washed with saturated NaHCO₃, water and brine, dried over Na₂SO₄ and concentrated.

Purification by liquid chromatography on silica gel (0–5% MeOH/CH₂Cl₂) gave a foam (0.214 g, 0.443 mmol, 46%). The foam was dissolved in Et₂O and treated with maleic acid to give a white solid. MS: APCI: M+1: 477.1 (Exact Mass: 476.17).

Example D14

Synthesis of 7-{4-[4-(2,3-Dichloro-phenyl)-piperazin-1-yl]-butoxy}-3,3-dimethyl-1H-[1,8]naphthyridine-2,4-dione A first intermediate compound, 3,3-Dimethyl-7-[4-(tetrahydro-pyran-2-yloxy)-butoxy]-1H-[1,8]naphthyridine-2, 4-dione, was produced as follows: To a solution of 4-(tetrahydro-pyran-2-yloxy)-butan-1-ol (1.93 g, 11.07 mmol) in dry THF (4 mL) was added KO$^t$Bu (1M in THF, 10.5 mL, 10.5 mmol). The mixture was stirred for 20 minutes and then added to a solution of 7-chloro-3,3-dimethyl-1H-[1,8]naphthyridine-2,4-dione (0.621 g, 2.76 mmol) in dry THF (5 mL). The reaction was stirred at room temperature for 1 hour. The reaction was quenched with saturated NH$_4$Cl and partitioned between water and EtOAc. The organic layer was washed with saturated NaHCO$_3$ and brine, dried over Na$_2$SO$_4$ and concentrated. Purification by liquid chromatography on silica gel (10–40% EtOAc/Hexanes) gave the first intermediate compound as an orange oil (0.89 g, 2.40 mmol, 88%). MS: APCI: M+1: 363.1 (Exact Mass: 362.18).

A second intermediate compound, 7-(4-Hydroxy-butoxy)-3,3-dimethyl-1H-[1,8]naphthyridine-2,4-dione, was produced as follows: To a solution of 3,3-dimethyl-7-[4-(tetrahydro-pyran-2-yloxy)-butoxy]-1H-[1,8]naphthyridine-2,4-dione (1.22 g, 3.37 mmol) in EtOH (15 mL) was added PPTS. The reaction was heated to 60° C. for 3 hours. The reaction was cooled and concentrated to give an oil. Purification by liquid chromatography on silica gel (30–70% EtOAc/Hexanes) gave the second intermediate compound as a white solid (0.373 g, 40%). MS: APCI: M+1: 279.1 (Exact Mass: 278.13).

A third intermediate compound, 4-(6,6-Dimethyl-5,7-dioxo-5,6,7,8-tetrahydro-[1,8]naphthyridin-2-yloxy)-butyraldehyde, was produced as follows: To a suspension of Dess Martin periodinane (2.256 g, 5.31 mmol) in dry CH$_2$Cl$_2$ (5 mL) was added a solution of 7-(4-hydroxy-butoxy)-3,3-dimethyl-1H-[1,8]naphthyridine-2,4-dione (0.37 g, 1.30 mmol) in dry CH$_2$Cl$_2$ (5 mL) via cannula. The reaction was stirred at room temperature for 4 hours. A 1:1 mixture of saturated NaHCO$_3$ and saturated Na$_2$S$_2$O$_3$ was added (40 mL), followed by Et$_2$O. The mixture was stirred for 15 minutes and then extracted with Et$_2$O/EtOAc. The organic layer was washed with saturated NaHCO$_3$ and brine, dried over Na$_2$SO$_4$ and concentrated to afford the third intermediate compound as a yellow film (0.52 g, 1.22 mmol, 65%). MS: APCI: M+1: 277.1 (Exact Mass: 276.11).

To a solution of 4-(6,6-dimethyl-5,7-dioxo-5, 6,7,8-tetrahydro-[1,8]naphthyridin-2-yloxy)-butyraldehyde (0.520 g, 1.88 mmol) in DCE (6 mL) was added 1-(2,3-dichlorophenyl)-piperazine hydrochloride (0.503 g, 1.88 mmol) followed by Et$_3$N (0.53 mL, 3.76 mmol). The mixture was stirred for 20 minutes at room temperature and NaBH (OAc)$_3$ (0.56 g, 2.60 mmol) was added. The reaction was stirred for 2.5 h and quenched with saturated NaHCO$_3$ and water. The mixture was extracted with EtOAc and the organic layer was washed with saturated NaHCO$_3$, water and brine, dried over Na$_2$SO$_4$ and concentrated. Purification by liquid chromatography on silica gel (0–5% MeOH/ CH$_2$Cl$_2$) gave a white solid (0.277 g, 0.564 mmol, 30%). MS: APCI: M+1: 491.1 (Exact Mass: 490.15).

Example D15

Synthesis of 7-{4-[4-(2,3-Dichloro-phenyl)-piperazin-1-yl]-butoxy}-4-hydroxy-3,3-dimethyl-3,4-dihydro-1H-[1,8]naphthyridin-2-one To a solution of 7-{4-[4-(2,3-dichloro-phenyl)-piperazin-1-yl]-butoxy}-3,3-dimethyl-1H-[1,8]naphthyridine-2,4-dione (0.132 g, 0.268 mmol) in THF (2 mL), cooled to 0° C. was added NaBH$_4$ (0.013 g, 0.335 mmol). The reaction was warmed to room temperature and stirred for 3 hours. The reaction was quenched with saturated NaHCO$_3$ and partitioned between EtOAc and water. The organic layer was washed with brine, dried over Na$_2$SO$_4$ and concentrated to give the title compound as a white solid (0.095 g, 0.192 mmol, 57%). MS: APCI: M+1: 493.1 (Exact Mass: 492.17).

Example D16

Synthesis of 4,4-Dimethyl-7-[4-(4-naphthalen-1-yl-piperazin-1-yl)-butoxy]-3,4-dihydro-1H-[1,8]naphthyridin-2-one A first intermediate compound, 3-Methyl-but-3-enoic acid (6-amino-pyridin-2-yl)-amide, was produced as follows: 2,5-Diaminopyridine (70 g, 0.641 mol) was dissolved in 2100 mL THF in a 5 L 4-neck flask equipped with mechanical stirring, N$_2$ line and a 500 mL addition funnel. Et$_3$N (447 mL, 5 eq.) was added to the reaction flask. 3,3-Dimethylacryloyl chloride (76 g, 0.641 mol) was diluted with 700 mL THF and this solution was added dropwise to the reaction flask. The moderate exotherm observed was controlled with an ice/water bath to maintain a temperature <15° C. After the addition was complete, the reaction was allowed to warm to room temperature and stirred under N$_2$ for 1.5 h. The reaction mixture was concentrated and CH$_2$Cl$_2$ was added. The CH$_2$Cl$_2$ solution was washed with H$_2$O and the aqueous layer was back extracted with CH$_2$Cl$_2$. The organic layers were combined and dried over Na$_2$SO$_4$, filtered and concentrated to an oil. The crude product was purified by column chromatography using a gradient mobile phase of 10%–30% EtOAc in hexanes. All fractions containing the desired product were pooled and concentrated to an oil. NMR analysis of the product indicated the product was a 1:1 mixture of 2 isomers, the alpha beta unsaturated and the beta gamma unsaturated isomer resulting in first intermediate compound (90.0 g, 0.47 mol, 73%). MS: APCI: M+1: 192.0 (Exact Mass: 191.11).

A second intermediate compound, 7-Amino-4,4-dimethyl-3,4-dihydro-1H-[1,8]naphthyridin-2-one, was produced as follows: 3-Methyl-but-3-enoic acid (6-amino-pyridin-2-yl)-amide (49.2 g, 0.26 mol) was dissolved in 500 mL CH$_2$Cl$_2$ in a 1000 mL 3-neck flask equipped with mechanical stirring, a 125 mL addition funnel and a thermal couple. While stirring, MeSO$_3$H (50 mL, 0.78 mol) was added to the flask dropwise. The exotherm upon addition was controlled to maintain a temperature <20° C. by an ice/water bath. The mixture was allowed to stir for 15 minutes. AlCl$_3$ (274 g, 2.08 mol) was suspended in 1500 mL CH$_2$Cl$_2$ in a 5 L 4-neck flask equipped with mechanical stirring, 1000 mL addition funnel, N$_2$ line and a thermal couple. To this suspension, the amide solution was added dropwise. The exotherm from the addition was again controlled to maintain a temperature <20° C. with an ice/water bath. The reaction was allowed to warm to room temperature and stir overnight. The reaction had consumed all the beta gamma unsaturated isomer and was deemed complete. The reaction mixture was slowly added to ice as an inverse quench. The quenched mixture was brought to pH 8–10 with 2 N KOH. The salts precipitated out of solution and saturated the aqueous phase. The suspension was transferred to a separatory funnel and extracted twice with 100:8:1 $CH_2Cl_2$:EtOH:$NH_4OH$. The organic layers were combined, dried over $Na_2SO_4$, filtered and concentrated to a crude solid. The solid was triturated with EtOAc and filtered. The resulting solids were pure second intermediate compound (22.4 g, 0.117 mol, 46%). MS: APCI: M+1: 192.2 (Exact Mass: 191.11).

A third intermediate compound, 7-Fluoro-4,4-dimethyl-3,4-dihydro-1H-[1,8]naphthyridin-2-one, was produced as follows: HF-pyridine (100 mL) was cooled to −42° C. in a 1000 mL HDPE bottle using an $CH_3CN$ dry ice bath. While stirring vigorously, 7-amino-4,4-dimethyl-3,4-dihydro-1H-[1,8]naphthyridin-2-one (24.6 g, 0.129 mol) was added portionwise to control the exotherm. After the addition, $NaNO_2$ (8.9 g, 0.1291 mol) was added portionwise. Significant exotherms were observed for both additions. The reaction mixture was then allowed to warm to 0° C. and stir for 2 h. The reaction mixture was quenched into a 4 L HDPE bottle full of ice. The aqueous slurry was then neutralized using 2 N KOH. The resulting aqueous solution was extracted 3 times with $CH_2Cl_2$. The organic layers were dried over $Na_2SO_4$, filtered and concentrated to dryness. Excess pyridine was azeotroped with heptane. The product was dried under vacuum (2 mm Hg) for 3 h. The third intermediate compound was isolated as a white powder (23.06 g, 0.119 mol, 92%). MS: APCI: M+1: 195.1 (Exact Mass: 194.09).

7-Fluoro-4,4-dimethyl-3,4-dihydro-1H-[1,8]naphthyridin-2-one (247 mg, 1.272 mmol), 4-(4-naphthalen-1-yl-piperazin-1-yl)-butan-1-ol (365 mg, 1.285 mmol) and sodium t-butoxide (367 mg, 3.82 mmol) were combined in a dried flask 3 necked flask under $N_2$. NMP was added and the solution was heated in an oil bath to 70° C. for 4 hours. The reaction was cooled to room temperature and poured into ice water. The solid that was collected was slurried in $CH_2Cl_2$ and ethyl acetate and purified by liquid chromatography (MPLC, gradient of 100% $CH_2Cl_2$ to 100% ethyl acetate) to give the title compound as a foam (280 mg, 0.610 mmol, 48%). MS: APCI: M+1: 459.2 (Exact Mass: 458.27).

Example D17

Synthesis of 7-{4-[4-(2,3-Dichloro-phenyl)-piperazin-1-yl]-butoxy}-4,4-dimethyl-3,4-dihydro-1H-[1,8]naphthyridin-2-one A first intermediate compound, 7-(4-Hydroxy-butoxy)-4,4-dimethyl-3,4-dihydro-1H-[1,8]naphthyridin-2-one, was produced as follows: The 7-fluoro-4,4-dimethyl-3,4-dihydro-1H-[1,8]naphthyridin-2-one (5.09 g, 26.2 mmol) and butane-1,4-diol (11.81 g, 131.0 mmol) were combined in a dried 2-necked flask under $N_2$. NMP (50 mL) was added and the solution was heated in an oil bath to 70° C. overnight. The reaction was cooled to room temperature and poured into ice water. The solid that formed was collected and triturated in acetonitrile to give the title compound as a tan powder (1.72 g). The mother liquor was extracted with $CH_2Cl_2$, dried over $Na_2SO_4$, filtered and purified by MPLC (gradient of 100% $CH_2Cl_2$ to 100% ethyl acetate). The compound was isolated as a mixture with diol byproducts. The title compound was formed as clear crystals (1.09 g) after recrystallization in acetonitrile and another 340 mg was obtained from a second recrystallization. The products were combined to give a total of 3.15 g of the first intermediate compound (11.9 mmol, 45.5%). MS: APCI: M+1: 265.1 (Exact Mass: 264.15).

A second intermediate compound, 4-(5,5-Dimethyl-7-oxo-5,6,7,8-tetrahydro-[1,8]naphthyridin-2-yloxy)-butyraldehyde, was produced as follows: 7-(4-Hydroxy-butoxy)-4,4-dimethyl-3,4-dihydro-1H-[1,8]naphthyridin-2-one (1.72 g, 6.51 mmol) was dissolved in ethyl acetate (50 mL, 0.14 M solution) and IBX (13 g, 46.4 mmol) was added. The suspension was immersed in an oil bath set at 80° C. and stirred vigorously with a condenser. After 1.5 h, the reaction mixture was cooled to room temperature and filtered. The filtrate was concentrated to give the second intermediate compound as a tan solid (1.62 g, 6.18 mmol, 95%). MS: APCI: M+1: 263.1 (Exact Mass: 262.13).

The naphthyridinones of Examples D17-D25 were synthesized in a combinatorial library format by reductive amination of the appropriate piperazine starting materials with 4-(5,5-dimethyl-7-oxo-5,6,7,8-tetrahydro-[1,8]naphthyridin-2-yloxy)-butyraldehyde following the procedure outlined in Example H7. The final products were made into hydrochloride salts by treatment with a solution of saturated HCl in MeOH.

The title compound was isolated (182 mg, 0.381 mmol, 63.5%). MS: APCI: M+1: 477.1 (Exact Mass: 476.17).

Example D18

Synthesis of 4,4-Dimethyl-7-{4-[4-(5,6,7,8-tetrahydro-naphthalen-1-yl)-piperazin-1-yl]-butoxy}-3,4-dihydro-1H-[1,8]naphthyridin-2-one The title compound was isolated as a hygroscopic foam (149 mg, 0.322 mmol, 53.6%). MS: APCI: M+1: 463.2 (Exact Mass: 462.30).

Example D19

Synthesis of 7-[4-(4-Indan-4-yl-piperazin-1-yl)-butoxy]-4,4-dimethyl-3,4-dihydro-1H-[1,8]naphthyridin-2-one The title compound was isolated as a foam (158 mg, 0.352 mmol, 58.7%). MS: APCI: M+1: 449.2 (Exact Mass: 448.28).

Example D20

Synthesis of 7-{4-[4-(2-Chloro-3-methyl-phenyl)-piperazin-1-yl]-butoxy}-4,4-dimethyl-3,4-dihydro-1H-[1,8]naphthyridin-2-one The title compound was isolated as a hygroscopic foam (159 mg, 0.349 mmol, 58.1%). MS: APCI: M+1: 457.2 (Exact Mass: 456.23).

Example D21

Synthesis of 7-{4-[4-(3-Chloro-2-methyl-phenyl)-piperazin-1-yl]-butoxy}-4,4-dimethyl-3,4-dihydro-1H-[1,8]naphthyridin-2-one The title compound was isolated as a hygroscopic foam (144 mg, 0.315 mmol, 52.5%). MS: APCI: M+1: 457.2 (Exact Mass: 456.23).

Example D22

Synthesis of 7-{4-[4-(6-Cyclopropyl-pyridin-2-yl)-piperazin-1-yl]-butoxy}-4,4-dimethyl-3,4-dihydro-1H-[1,8]naphthyridin-2-one The title compound was isolated as a foam (143 mg, 0.318 mmol, 53.0%). MS: APCI: M+1: 450.2 (Exact Mass: 449.28).

Example D23

Synthesis of 7-{4-[4-(2-Ethyl-phenyl)-piperazin-1-yl]-butoxy}-4,4-dimethyl-3,4-dihydro-1H-[1,8]naphthyridin-2-one The title compound was isolated as a solid (144 mg, 0.330 mmol, 55%). MS: APCI: M+1: 437.2 (Exact Mass: 436.28).

Example D24

Synthesis of 7-{4-[4-(2-Isobutoxy-phenyl)-piperazin-1-yl]-butoxy}-4,4-dimethyl-3,4-dihydro-1H-[1,8]naphthyridin-2-one The title compound was isolated as the hydrochloride salt (237 mg, 0.458 mmol, 60.1%). MS: APCI: M+1: 481.2 (Exact Mass: 480.31).

Example D25

Synthesis of 7-{4-[4-(2-Isopropoxy-phenyl)-piperazin-1-yl]-butoxy}-4,4-dimethyl-3,4-dihydro-1H-[1,8]naphthyridin-2-one The title compound was isolated as the hydrochloride salt (213 mg, 0.423 mmol, 55.5%). MS: APCI: M+1: 467.3 (Exact Mass: 466.29).

Example E1

Synthesis of 7-{4-[4-(2,3-Dichloro-phenyl)-piperazin-1-yl]-butoxy}-6-methyl-3,4-dihydro-1H-[1,8]naphthyridin-2-one A first intermediate compound, 7-Benzyloxy-3-methyl-1H-[1,8]naphthyridin-2-one, was produced, ad follows: To a solution of benzyl alcohol (4.3 mL, 41.4 mmol, 2.3 equiv) in DMF (15 mL) was added NaH (1.5 g, 54.0 mmol, 3.0 equiv) in portions. $H_2$ gas was liberated and the resultant slurry was stirred for 30 minutes at RT. A solution of 7-chloro-3-methyl-1H-[1,8]naphthyridin-2-one (3.5 g, 18.0 mmol, 1.0 equiv) in DMF (40 mL) was added to the reaction mixture slowly via a syringe. The reaction mixture was stirred overnight at 100° C., cooled and water was added until all the solids had precipitated. The precipitate was collected by filtration and dried to give the first intermediate compound as a pale yellow solid (3.75 g, 78%). mp: 220–221° C.; $^1$H NMR: (400 MHz, $CDCl_3$) δ 9.55 (br s, 1H), 7.70 (d, 1H), 7.45–7.35 (m, 6H), 6.65 (d, 1H), 5.40 (s, 2H), 2.15 (s, 3H). MS: ES+ 267.02 (M+H)$^+$, exact mass: 266.11.

A second intermediate compound, 7-Benzyloxy-2-(4-benzyloxy-butoxy)-3-methyl-[1,8]naphthyridine, was produced as follows: To a stirred mixture of 7-benzyloxy-3-methyl-1H-[1,8]naphthyridin-2-one (2.5 g, 9.4 mmol, 1.0 equiv), triphenylphosphine (7.4 g, 28.2 mmol, 3.0 equiv) and 4-benzyloxy butanol (4.9 mL, 28.2 mmol, 3.0 equiv) in THF (250 mL) was added DEAD (4.5 mL, 28.2 mmol, 3.0 equiv) dropwise under nitrogen atmosphere. The reaction mixture was stirred for 2 hours and quenched with MeOH (10 mL). The solvents were evaporated and the residue was purified by column chromatography (25% EtOAc/hexanes) to afford the second intermediate compound as a pale yellow viscous oil (1.27 g, 32%). $^1$H NMR: (400 MHz, $CDCl_3$) δ 7.85 (d, 1H), 7.70 (s, 1H), 7.50–7.25 (m, 10H), 6.85 (d, 1H), 5.60 (s, 2H), 4.62 (t, 2H), 4.55 (s, 2H), 3.58 (t, 2H), 2.30 (s, 3H). MS: ES+ 429.07 (M+H)$^+$, exact mass: 428.21.

A third intermediate compound, 7-(4-Hydroxy-butoxy)-6-methyl-3,4-dihydro-1H-[1,8]naphthyridin-2-one, was produced as follows: To a solution of 7-benzyloxy-2-(4-benzyloxy-butoxy)-3-methyl-[1,8]naphthyridine (1.25 g, 2.92 mmol) in THF (20 mL) and MeOH (100 mL) was added 10% Pd—C (1.0 g) and the mixture was hydrogenated at 40 psi for 48 hours. The reaction mixture was filtered through a celite bed rinsing with MeOH and $CH_2Cl_2$. The filtrate was concentrated and the residue was purified by column chromatography (10% MeOH/EtOAc) to afford the third intermediate compound as a white shiny solid (0.55 g, 76%). mp: 118–119° C.; $^1$H NMR: (400 MHz, $CDCl_3$) δ 7.65 (br s, 1H), 7.20 (s, 1H), 4.30 (t, 2H), 3.75 (t, 2H), 2.85 (t, 2H), 2.60 (t, 2H), 2.10 (s, 3H), 1.90–1.85 (m, 2H), 1.78–1.62 (m, 2H). MS: ES+ 251.02 (M+H)$^+$, exact mass: 250.13.

To a clear solution of the Dess-Martin reagent (0.90 g, 2.12 mmol, 1.3 equiv) in $CH_2Cl_2$ (40 mL) was added 7-(4-hydroxy-butoxy)-6-methyl-3,4-dihydro-1H-[1,8]naphthyridin-2-one (0.40 g, 1.6 mmol, 1.0 equiv) and the mixture was stirred at room temperature for 3 hours. TLC indicated the presence of a trace amount of starting material and hence more Dess-Martin reagent (0.1 g) was added and the mixture was stirred for an additional 1 hour. The reaction mixture was diluted with $CH_2Cl_2$ and poured into a saturated solution of $NaHCO_3$ containing $Na_2S_2O_3$ (2.0 g). The layers were separated and the aqueous layer was extracted with $CH_2Cl_2$ (2×20 mL). The combined organic layer was dried over $Na_2SO_4$ and concentrated. The crude aldehyde was dissolved in DCE and 1-(2,3-dichlorophenyl)piperazine monohydrochloride, $Et_3N$ and $NaBH(OAc)_3$ were added. The reaction mixture was stirred for 1 hour, diluted with $CH_2Cl_2$ and washed with saturated $NaHCO_3$ and brine. The organic layer was dried over Na2SO4 and concentrated. Purification of the residue by column chromatography (10% MeOH/EtOAc) gave the title compound as a white solid (0.51 g, 54%). mp: 138–139° C.; $^1$H NMR: (400 MHz, $CDCl_3$) δ 7.50 (br s, 1H), 7.25–7.15 (m, 3H), 6.95 (m, 1H), 4.25 (t, 2H), 3.10 (br s, 4H), 2.82 (t, 2H), 2.65 (br s, 4H), 2.60 (t, 2H), 2.50 (t, 2H), 2.10 (s, 3H), 1.80–1.60 (m, 4H). MS: ES+ 463.11 (M+H)$^+$, 465.12, exact mass: 462.16.

Example E2

Synthesis of 6-Methyl-7-[4-(4-naphthalen-1-yl-piperazin-1-yl)-butoxy]-3,4-dihydro-1H-[1,8]naphthyridin-2-one To a clear solution of Dess-Martin reagent (1.40 g, 3.3 mmol, 1.3 equiv) in $CH_2Cl_2$ (200 mL) was added 7-(4-hydroxy-butoxy)-6-methyl-3,4-dihydro-1H-[1,8]naphthyridin-2-one (0.55 g, 2.2 mmol, 1.0 equiv) and the mixture was stirred at room temperature for 4 hours. TLC confirmed the completion of the reaction. The reaction mixture was diluted with $CH_2Cl_2$ and poured into a saturated solution of $NaHCO_3$ containing $Na_2S_2O_3$ (3.0 g). The mixture was stirred and the organic layer was separated. The aqueous layer was extracted with $CH_2Cl_2$ (2×30 mL) and the combined organic layer was dried over $Na_2SO_4$ and concentrated. The crude aldehyde was dissolved in DCE and 1-naphthalen-1-yl-piperazine monohydrochloride (0.76 g, 3.08 mmol, 1.4 equiv), $Et_3N$ (0.5 mL, 1.7 equiv) and $NaBH(OAc)_3$ (0.65 g, 3.08 mmol, 1.4 equiv) were added. The reaction mixture was stirred for 1 hour, diluted with $CH_2Cl_2$ and washed with saturated $NaHCO_3$ and brine. The organic layer was dried over $Na_2SO_4$ and concentrated. Purification of the residue by column chromatography (5% MeOH/EtOAc) gave the title compound as a white solid (0.40 g, 41%). mp: 76–78° C.; $^1H$ NMR: (400 MHz, $CDCl_3$) δ 8.22 (d, 1H), 7.85 (d, 1H), 7.58–7.38 (m, 5H), 7.25 (s, 1H), 7.05 (d, 1H), 4.25 (t, 2H), 3.30–3.10 (br s, 4H), 2.82–2.65 (m, 4H), 2.65–2.45 (m, 4H), 2.15 (s, 3H), 1.88–1.35 (m, 6H). MS: ES+ 445.41 $(M+H)^+$, exact mass: 444.25.

Example E3

Synthesis of 7-{4-[4-(2,3-Dichloro-phenyl)-piperazin-1-yl]-butoxy}-6-fluoro-3,4-dihydro-1H-[1,8]naphthyridin-2-one A first intermediate compound, 6-(4-Benzyloxy-butoxy)-2-chloro-5-fluoro-nicotinonitrile, was produced as follows: To a solution of 4-benzyloxy-1-butanol (19.44 g, 108 mmol) in THF (200 mL) cooled to –40° C. was added 1M $KO^tBu$ in THF (108 mL, 108 mmol). The mixture was stirred for 5 min at –10° C. and then added to a solution of 2,6-dichloro-5-fluoro-nicotinonitrile (20.0 g, 105 mmol) in THF (300 mL) cooled to –70° C. over 25 min. The mixture turned brownish yellow with some cloudiness. The reaction was allowed to warm to room temperature over 2 h. The THF was evaporated and the residue was diluted with $Et_2O$. The mixture was washed with water, brine, 1N citric acid, water and brine, dried over $Na_2SO_4$ and concentrated to an oil. The oil was dissolved in $Et_2O$/hexanes and cooled in the refrigerator overnight. A crystalline solid formed which was collected by filtration, washed with hexanes and dried to give the first intermediate compound as a white solid (17.0 g). The filtrate was concentrated and purified by silica gel chromatography (Biotage 40L, 0–6% EtOAc/Hexanes) to give additional first intermediate compound as a white solid (total of 26.9 g, 80.4 mmol, 77%). MS: APCI: M+1: 335.1 (Exact Mass: 334.09).

A second intermediate compound, 2-Azido-6-(4-benzyloxy-butoxy)-5-fluoro-nicotinonitrile, was produced as follows: To a solution of 6-(4-benzyloxy-butoxy)-2-chloro-5-fluoro-nicotinonitrile (20.0 g, 60.0 mmol) in DMF (40 mL) was added sodium azide (4.27 g, 65.7 mmol) and the mixture was heated at 70° C. overnight. The mixture was poured into $Et_2O$ and washed with water and brine. The $Et_2O$ solution was passed through a silica gel Biotage 12M column, dried over $MgSO_4$ and charcoal, and concentrated to give an oil (19.67 g). Recrystallization from $Et_2O$/MeOH gave the second intermediate compound as a solid (17.24 g, 50.5 mmol, 84%). MS: APCI: M+1: (Exact Mass: 341.13).

A third intermediate compound, 2-Amino-6-(4-benzyloxy-butoxy)-5-fluoro-nicotinonitrile, was produced as follows: To a solution of 2-azido-6-(4-benzyloxy-butoxy)-5-fluoro-nicotinonitrile (17.2 g, 50.4 mmol) in MeOH (450 mL) was added hexamethyldisilthiane (19.0 g, 106.5 mmol). The reaction gives off a gas and a precipitate forms after 15 min. The reaction was stirred overnight at room temperature and then filtered to remove the precipitated sulfur. The mixture was concentrated and then redissolved in $Et_2O$. The mixture was filtered again to remove additional precipitated sulfur. The filtrate was concentrated and recrystallized from MeOH/hexanes. The solid was collected by filtration, washed with hexane/MeOH and dried to give the third intermediate compound (13.74 g, 43.57 mmol, 86%). MS: APCI: M+1: 316.4 (Exact Mass: 315.14).

A fourth intermediate compound, 2-Amino-6-(4-benzyloxy-butoxy)-5-fluoro-pyridine-3-carbaldehyde, was produced as follows: To a solution of 2-amino-6-(4-benzyloxy-butoxy)-5-fluoro-nicotinonitrile (7.25 g, 23.0 mmol) in THF (40 mL) cooled to 0° C. is added DIBALH (1M in THF, 69 mL, 69 mmol). The reaction was complete after 5 min. Chilled 2N HCl was added very slowly (strong exotherm) to quench the reaction. The mixture forms a red gelatinous material. $Et_2O$ was added and the layers were separated. The organic layer was washed with brine and saturated $NaHCO_3$ and then filtered through Celite. There may still have been some aluminum complexed product so the organic solution was washed again with 2N HCl, brine, saturated $NaHCO_3$ and brine, dried over $MgSO_4$ and concentrated to give the crude fourth intermediate compound as an orange oil (5.23 g, 16.4 mmol, 71%). MS: APCI: M+1: 319.2 (Exact Mass: 318.14).

A fifth intermediate compound, 3-[2-Amino-6-(4-benzyloxy-butoxy)-5-fluoro-pyridin-3-yl]-acrylic acid ethyl ester, was produced as follows: To a solution of 2-amino-6-(4-benzyloxy-butoxy)-5-fluoro-pyridine-3-carbaldehyde (5.23 g, 16.4 mmol, crude from previous reaction) in THF (50 mL) was added (carbethoxymethylene)triphenylphosphorane (5.72 g, 16.43 mmol) and the solution was heated at 67° C. overnight. The reaction was concentrated and the residue was purified by liquid chromatography (Biotage 65M, 0–10% EtOAc/$CH_2Cl_2$) to give the fifth compound as a yellow solid (73%). MS: APCI: M+1: 389.4 (Exact Mass: 388.18).

A sixth intermediate compound, 7-(4-Benzyloxy-butoxy)-6-fluoro-3,4-dihydro-1H-[1,8]naphthyridin-2-one, was produced as follows: 3-[2-Amino-6-(4-benzyloxy-butoxy)-5-fluoro-pyridin-3-yl]-acrylic acid ethyl ester (7.18 g, 18.5 mmol) was hydrogenated under an atmosphere of $H_2$ (4300 psi) using Ra—Ni (2 g) in MeOH (100 mL). The reaction was filtered and concentrated. MS indicated the double bond had been reduced and some of the material cyclized. The material was suspended in $^iPROH$ and p-toluenesulfonic acid hydrate (0.41 g) was added. The mixture was heated at 80° C. for 30 min. Saturated $NaHCO_3$ was added and the mixture was concentrated. The residue was partitioned between $Et_2O$ and water. The organic layer was washed with saturated $NaHCO_3$ and brine, dried over $MgSO_4$ and concentrated to give a yellow oil which solidified. Recrystallization from $Et_2O$/hexane afforded the sixth intermediate compound as a pale yellow solid. MS: APCI: M+1: 345.1 (Exact Mass: 344.15).

A seventh intermediate compound, 6-Fluoro-7-(4-hydroxy-butoxy)-3,4-dihydro-1H-[1,8]naphthyridin-2-one, was produced as follows: 7-(4-Benzyloxy-butoxy)-6-fluoro-3,4-dihydro-1H-[1,8]naphthyridin-2-one (4.79 g, 13.9 mmol) was hydrogenated under an atmosphere of $H_2$ using 20% Pd/C (1.0 g) in EtOH (100 mL). The reaction was filtered and concentrated to give a slurry. $Et_2O$ was added and the solids were filtered. The filtrate was concentrated and the process was repeated to give the seventh intermediate compound as a solid (3.2 g, 13.0 mmol, 91%). MS: APCI: M+1: 255.1 (Exact Mass: 254.11).

An eighth intermediate compound, 4-(3-Fluoro-7-oxo-5,6,7,8-tetrahydro-[1,8]naphthyridin-2-yloxy)-butyraldehyde, was produced as follows: To a solution of oxalyl chloride (1.78 g, 14.0 mmol) in CH$_2$Cl$_2$ (25 mL) cooled to −70° C. was added a solution of DMSO (2.15 g, 27.6 mmol) in CH$_2$Cl$_2$ (1.5 mL) over 4 min. The mixture was stirred for 5 min and a solution of 6-fluoro-7-(4-hydroxy-butoxy)-3,4-dihydro-1H-[1,8]naphthyridin-2-one (3.1 g, 12.0 mmol) in DMSO (4.5 mL) and CH$_2$Cl$_2$ (44 mL) cooled to −50° C. was added over 5 min. The mixture was stirred for 10 min at −70° C. and it solidified. The reaction was warmed to −30° C. and triethylamine (8.9 mL, 63.8 mmol) was added resulting in a stirable suspension. The reaction was warmed to room temperature over 30 min. The mixture was added to water and the layers were separated. The organic layer was washed with water and dilute brine, dried over MgSO$_4$ and concentrated to give an oil. The residue was partitioned between Et$_2$O and aqueous citric acid (pH 4.5). The organic layer was washed with dilute aqueous NaHCO$_3$ and brine, dried over MgSO$_4$ and concentrated to give the eighth intermediate compound as a yellow oil (1.89 g) which was used directly in the next reaction. MS: APCI: M+1: 253.2 (Exact Mass: 252.09).

To a suspension of 1-(2,3-dichloro-phenyl)-piperazine hydrochloride (0.80 g, 3.0 mmol) in 1,2-dichloroethane (10 mL) was added triethylamine (0.61 mL, 6.0 mmol). The mixture was stirred for 30 min at room temperature and 4-(3-fluoro-7-oxo-5,6,7,8-tetrahydro-[1,8]naphthyridin-2-yloxy)-butyraldehyde (0.76 g, 3.0 mmol) was added as a suspension in 1,2-dichloroethane (5 mL). The mixture was stirred for 30 min and NaBH(OAc)$_3$ (0.89 g, 4.2 mmol) was added as a solid. The reaction was stirred at room temperature for 4 h. The mixture was poured into EtOAc/dichloroethane and washed with saturated NaHCO$_3$ and brine. The organic layer was washed with aqueous citric acid (pH 4.5) and brine, dried over Na$_2$SO$_4$ and concentrated to a slurry. Et$_2$O was added and the solid was collected by filtration. Purification by liquid chromatography (Biotage 40S, gradient of CH$_2$Cl$_2$ to 10% MeOH/CHCl$_3$) gave the title compound as a white solid (738 mg, 1.58 mmol, 53%). MS: APCI: M+1: 467.3 (Exact Mass: 466.13).

Example E4

Synthesis of 6-Fluoro-7-[4-(4-naphthalen-1-yl-piperazin-1-yl)-butoxy]-3,4-dihydro-1H-[1,8]naphthyridin-2-one The title compound was prepared by reductive amination of 4-(3-fluoro-7-oxo-5,6,7,8-tetrahydro-[1,8]naphthyridin-2-yloxy)-butyraldehyde with 1-naphthalen-1-yl-piperazine hydrochloride according to the above procedure. MS: APCI: M+1: 449.1 (Exact Mass: 448.23).

Example E5

Synthesis of 6-Fluoro-7-[4-(4-indan-4-yl-piperazin-1-yl)-butoxy]-3,4-dihydro-1H-[1,8]naphthyridin-2-one The title compound was prepared by reductive amination of 4-(3-fluoro-7-oxo-5,6,7,8-tetrahydro-[1,8]naphthyridin-2-yloxy)-butyraldehyde with 1-indan-4-yl-piperazine according to the above procedure. MS: APCI: M+1: 439.2 (Exact Mass: 438.24).

Example E6

Synthesis of 6-Chloro-7-[4-(4-naphthalen-1-yl-piperazin-1-yl)-butoxy]-3,4-dihydro-1H-[1,8]naphthyridin-2-one A first intermediate compound, 6-Chloro-7-(4-hydroxy-butoxy)-3,4-dihydro-1H-[1,8]naphthyridin-2-one, was produced as follows: To a solution of 7-(4-hydroxy-butoxy)-3,4-dihydro-1H-[1,8]naphthyridin-2-one (2.0 g, 8.46 mmol) in DMF (17 mL) was added NCS (1.24 g, 9.31 mmol). The solution was stirred at room temperature for 1 hour. There was no reaction so the mixture was heated at 80° C. for 5 hours. Water was added and the mixture was extracted with EtOAc. The organic layer was washed with water and brine, dried over Na$_2$SO$_4$ and concentrated. Purification by liquid chromatography (0–5% MeOH/CH$_2$Cl$_2$) gave the first intermediate compound as an off-white solid (0.71 g, 2.62 mmol, low yield was due to chromatography mishap). MS: APCI: M+1: 271.0 (Exact Mass: 270.08).

A second intermediate compound, 4-(3-Chloro-7-oxo-5,6,7,8-tetrahydro-[1,8]naphthyridin-2-yloxy)-butyraldehyde, was produced as follows: A suspension of the Dess-Martin reagent (1.67 g, 3.93 mmol) in CH$_2$Cl$_2$ (6 mL) was stirred for 30 min and a solution of 6-chloro-7-(4-hydroxy-butoxy)-3,4-dihydro-1H-[1,8]naphthyridin-2-one (0.71 g, 2.62 mmol) in CH$_2$Cl$_2$ (5 mL)/THF (15 mL) was added via cannula. The reaction mixture became homogenous and turned yellow. The reaction was stirred at room temperature for 6 h. A 1:1 mixture of saturated NaHCO$_3$ and saturated Na$_2$S$_2$O$_3$ was added and the mixture was stirred for 15 min. The mixture was extracted with EtOAc (2×). The organic layer was washed with saturated NaHCO$_3$ and brine, dried over MgSO$_4$ and concentrated to give a yellow solid (0.74 g, approx. 80% pure, used crude in the next reaction). MS: APCI: M+1: 269.0 (Exact Mass: 268.06).

To a solution of 4-(3-chloro-7-oxo-5,6,7,8-tetrahydro-[1,8]naphthyridin-2-yloxy)-butyraldehyde (400 mg, approx. 1.49 mmol, crude from previous reaction) in DCE (7 mL) was added 1-naphthalen-1-yl-piperazine hydrochloride (370 mg, 1.49 mmol) followed by Et$_3$N (0.42 mL, 2.98 mmol). The solution was stirred for 15 min and NaBH(OAc)$_3$ (410 mg, 1.94 mmol) was added as a powder. The reaction was stirred at room temperature for 2 h and quenched with saturated NaHCO$_3$ and H$_2$O. The mixture was extracted with EtOAc. The organic layer was washed with saturated NaHCO$_3$, H$_2$O and brine, dried over Na$_2$SO$_4$ and concentrated. Purification by liquid chromatography (0–3% MeOH/CH$_2$Cl$_2$) afforded the title compound as an off-white foam (324 mg, 0.697 mmol, 47%). Et$_2$O was added and the foam turned into a white solid after 5 minutes of stirring. The solid was collected by filtration, washed with Et$_2$O and dried to give a white solid. MS: APCI: M+1: 465.2 (Exact Mass: 464.20).

Example E7

Synthesis of 6-Bromo-7-{4-[4-(2,3-dichloro-phenyl)-piperazin-1-yl]-butoxy}-3,4-dihydro-1H-[1,8]naphthyridin-2-one A first intermediate compound, 6-Bromo-7-(4-hydroxy-butoxy)-3,4-dihydro-1H-[1,8]naphthyridin-2-one, was produced as follows: To a solution of 7-(4-hydroxy-butoxy)-3,4-dihydro-1H-[1,8]naphthyridin-2-one (2.0 g, 8.46 mmol) in DMF (18 mL) was added NBS (1.70 g, 9.30 mmol). The solution was stirred at room temperature overnight. Within 2 hours, the reaction had turned purple. Water was added and the mixture was extracted with EtOAc. The organic layer was washed with water and brine, dried over $Na_2SO_4$ and concentrated to give a brown oil. Purification by liquid chromatography (0–5% $MeOH/CH_2Cl_2$) gave the first intermediate compound as an off-white solid (2.13, 6.76 mmol, 80%). MS: APCI: M+1: 315.0, 317.0 (Exact Mass: 314.03).

A second intermediate compound, 4-(3-Bromo-7-oxo-5,6,7,8-tetrahydro-[1,8]naphthyridin-2-yloxy)-butyraldehyde, was produced as follows: A suspension of the Dess-Martin reagent (3.28 g, 7.74 mmol) in $CH_2Cl_2$ (15 mL) was stirred for 30 min and a solution of 6-bromo-7-(4-hydroxy-butoxy)-3,4-dihydro-1H-[1,8]naphthyridin-2-one (1.524 g, 4.84 mmol) in $CH_2Cl_2$ (5 mL)/THF (20 mL) was added via cannula. The reaction mixture became homogenous and turned yellow. The reaction was stirred at room temperature for 6 h and then stored in the refrigerator overnight. A 1:1 mixture of saturated $NaHCO_3$ and saturated $Na_2S_2O_3$ was added and the mixture was stirred for 15 min. The mixture was extracted with EtOAc (2×). The organic layer was washed with saturated $NaHCO_3$ and brine, dried over $Na_2SO_4$ and concentrated to give a yellow solid/oil (1.51 g, used crude in the next reaction). MS: APCI: M+1: 313.0, 315.0 (Exact Mass: 312.01).

To a solution of 4-(3-bromo-7-oxo-5,6,7,8-tetrahydro-[1,8]naphthyridin-2-yloxy)-butyraldehyde (0.43 g, approx. 1.37 mmol, crude from previous reaction) in DCE (6 mL) was added 1-(2,3-dichloro-phenyl)-piperazine hydrochloride (367 mg, 1.37 mmol) followed by $Et_3N$ (0.38 mL, 2.75 mmol). The solution was stirred for 15 min and NaBH(OAc)$_3$ (407 mg, 1.92 mmol) was added as a powder. The reaction was stirred at room temperature for 2 h and quenched with saturated $NaHCO_3$ and $H_2O$. The mixture was extracted with EtOAc. The organic layer was washed with saturated $NaHCO_3$, $H_2O$ and brine, dried over $Na_2SO_4$ and concentrated. Purification by liquid chromatography (4% $MeOH/CH_2Cl_2$) afforded the title compound as a white foam (497 mg, 0.941 mmol, 69%). MS: APCI: M+1: 527.0, 529.0, 531.0 (Exact Mass: 526.05).

Example E8

Synthesis of 6-Bromo-7-[4-(4-naphthalen-1-yl-piperazin-1-yl)-butoxy]-3,4-dihydro-1H-[1,8]naphthyridin-2-one To a solution of 4-(3-bromo-7-oxo-5,6,7,8-tetrahydro-[1,8]naphthyridin-2-yloxy)-butyraldehyde (1.11 g, approx. 3.54 mmol, crude) in DCE (17 mL) was added 1-naphthalen-1-yl-piperazine hydrochloride (0.882 g, 3.54 mmol) followed by $Et_3N$ (1.0 mL, 7.1 mmol). The solution was stirred for 15 min and NaBH(OAc)$_3$ (1.05 g, 4.96 mmol) was added as a powder. The reaction was stirred at room temperature for 2 h and quenched with saturated $NaHCO_3$ and $H_2O$. The mixture was extracted with EtOAc. The organic layer was washed with saturated $NaHCO_3$, $H_2O$ and brine, dried over $Na_2SO_4$ and concentrated. Purification by liquid chromatography (4% $MeOH/CH_2Cl_2$) afforded the title compound as an off-white foam (1.37 g, 2.69 mmol, 76%). The HCl salt was formed by dissolving the title compound (138 mg, 0.27 mmol) in $Et_2O/CH_2Cl_2$ followed by the addition of 1N HCl in $Et_2O$ (0.3 mL). The resulting white precipitate was collected by filtration, washed with $Et_2O$ and dried to give a white solid (125 mg). MS: APCI: M+1: 509.1, 511.1 (Exact Mass: 508.15).

Example E9

Synthesis of 7-{4-[4-(2,3-Dichloro-phenyl)-piperazin-1-yl]-butoxy}-5-methyl-3,4-dihydro-1H-[1,8]naphthyridin-2-one A first intermediate compound, N-(7-Hydroxy-5-methyl-[1,8]naphthyridin-2-yl)-acetamide, was produced as follows: A suspension of 7-amino-4-methyl-[1,8]naphthyridin-2-ol (25.6 g, 146 mmol) in acetic anhydride (375 mL) was heated at reflux for 4.5 hours. The mixture was filtered hot and washed with acetic anhydride and $Et_2O$. The resulting solid was dried to give the first intermediate product (28.8 g, 132.6 mmol, 91%, >95% purity). Calcd for $C_{11}H_{11}N_3O_2$: C, 60.82, H, 5.10, N, 19.34; Found C, 60.88, H, 5.03, N, 19.39.

A second intermediate compound, N-(7-Chloro-5-methyl-[1,8]naphthyridin-2-yl)-acetamide, was produced as follows: N-(7-Hydroxy-5-methyl-[1,8]naphthyridin-2-yl)-acetamide (28.5 g, 131.2 mmol) was suspended in $POCl_3$ (280 mL) and heated to reflux for 90 min giving a dark solution. The reaction was quenched by slowly adding it to a 3 L flask containing ice with mechanical stirring (total volume of 1 L). The mixture was cooled and neutralized to pH 6.5 using 15% to 50% aqueous NaOH to give a precipitate. The mixture was filtered overnight, washed with $H_2O$ and dried to give a light brown solid (36 g, contains product and deacetylated compound). The solid was suspended in refluxing toluene and the mixture was filtered while hot. The insoluble solids were mostly more polar side products. The filtrate was cooled to give a precipitate which was collected by filtration and washed with toluene to give material that was enriched in the desired product. This solid was suspended in $CH_2Cl_2$ and the insoluble material was collected by filtration to give pure second intermediate compound. Several additional crops were collected (total of 18.5 g, 78.5 mmol, 60%). MS: APCI: M+1: 236.1, 238.1 (Exact Mass: 235.05).

A third intermediate compound, 7-Chloro-5-methyl-[1,8]naphthyridin-2-ylamine, was produced as follows: N-(7-Chloro-5-methyl-[1,8]naphthyridin-2-yl)-acetamide (11.5 g, 48.8 mmol) was suspended in 10% $H_2SO_4$ (180 mL). The mixture was heated at 110° C. for 2 h and filtered hot to remove the minor insoluble solids. $H_2O$ (180 mL) was added to the filtrate and a precipitate formed. The mixture was heated again to give a solution. The heating was removed and concentrated $NH_4OH$ was added with rapid stirring until the mixture was at pH 10. The mixture was cooled and the precipitate was collected by filtration, washed with $H_2O$ and dried to give the third intermediate compound as a pale yellow solid (9.24 g, 47.7 mmol, 98%). mp 264–266° C. MS: APCI: M+1: 194.0, 196.0 (Exact Mass: 193.04).

A fourth intermediate compound, 7-Chloro-5-methyl-1H-[1,8]naphthyridin-2-one, was produced as follows: To a mixture of 7-chloro-5-methyl-[1,8]naphthyridin-2-ylamine (13.7 g, 70.7 mmol) in concentrated $H_2SO_4$ (55 mL) cooled to 0° C. was added a solution of $NaNO_2$ (6.3 g, 92.0 mmol) in $H_2O$ (25 mL) dropwise. Additional $H_2O$ was added and the mixture was stirred at 20° C. for 1 h. The mixture was poured into ice. The resulting precipitate was filtered, washed with $H_2O$, EtOH and $Et_2O$ and dried to give the fourth intermediate compound as a powder (13.45 g, 69.1 mmol, 98%).

A fifth intermediate compound, 7-(4-Benzyloxy-butoxy)-5-methyl-1H-[1,8]naphthyridin-2-one, was produced as follows: To a suspension of 60% NaH (5.7 g, 144 mmol, washed with THF to remove the oil) in DMF (80 mL) was added 4-benzyloxy-1-butanol (25.0 g, 137 mmol) slowly.

The mixture was warmed to 70° C. and then cooled to RT. This mixture was added to a suspension of 7-chloro-5-methyl-1H-[1,8]naphthyridin-2-one (12.7 g, 65.3 mmol) in DMF (40 mL) to give a brown solution. The mixture was heated at 90° C. for 30 min and at 120° C. for 2 h. The reaction was allowed to cool to room temperature and stir overnight. The reaction was poured into a separatory funnel and $Et_2O$ was added followed by a minimal amount of $H_2O$. The ether phase contained excess 4-benzyloxy-1-butanol. The pH of the DMF/aqueous layer was adjusted to 11.5 by adding 1 N citric acid and a precipitate formed. The precipitate was filtered and washed with $Et_2O$. The solid was resuspended in $H_2O$ (100 mL) and EtOH (200 mL) was added to dissolve the solid. The mixture was filtered through celite to remove the insoluble solids. The filtrate was diluted with $H_2O$ (700 mL) and a pale yellow solid precipitated. The solid was collected by filtration, washed with $H_2O$ and dried to give the fifth intermediate compound as a solid (7.38 g, 21.8 mmol, 33%). MS: APCI: M+1: 339.2 (Exact Mass: 338.16).

A sixth intermediate compound, 7-(4-Hydroxy-butoxy)-5-methyl-3,4-dihydro-1H-[1,8]naphthyridin-2-one, was produced as follows: 7-(4-Benzyloxy-butoxy)-5-methyl-1H-[1,8]naphthyridin-2-one (7.31 g, 21.6 mmol) was hydrogenated using 20% Pd/C (1.0 g) in EtOH (100 mL). The product precipitated out of solution before the double bond was reduced. DMF (75 mL) was added and the mixture was heated to dissolve the solids. More 20% Pd/C (1.0 g) was added and the hydrogenation was continued, however the double bond was resistant to further hydrogenation under these conditions. The reaction mixture was filtered and the solvent was concentrated to give a slurry. $Et_2O$ was added and the solid was collected by filtration and dried to give 7-(4-hydroxy-butoxy)-5-methyl-1H-[1,8]naphthyridin-2-one (4.37 g, 17.6 mmol, 81%). 7-(4-Hydroxy-butoxy)-5-methyl-1H-[1,8]naphthyridin-2-one (3.0 g, 12.08 mmol) was hydrogenated using 20% Pd/C in acetic acid (mL) for x h. The reaction mixture was filtered and concentrated to give a mixture of the sixth intermediate compound and the corresponding acetylated compound. The mixture was suspended in MeOH (30 mL) and $H_2O$ (10 mL) and the pH was adjusted to 14 by addition of 50% aqueous NaOH. The mixture was warmed to 45° C. Glacial acetic acid was added to bring the pH to 7.5 and the MeOH was removed under reduced pressure. The resulting solid was filtered, washed with $H_2O$ and dried to give the sixth intermediate compound as a solid (2.78 g, 11.1 mmol, 92%). MS: APCI: M+1: 251.1 (Exact Mass: 250.13).

A seventh intermediate compound, 4-(4-Methyl-7-oxo-5,6,7,8-tetrahydro-[1,8]naphthyridin-2-yloxy)-butyraldehyde, was produced as follows: To a solution of oxalyl chloride (1.57 g, 12.4 mmol) in $CH_2Cl_2$ (20 mL) cooled to −70° C. was added a solution of DMSO (1.90 g, 24.38 mmol) in $CH_2Cl_2$ (4 mL) over 4 min. The mixture was stirred for 5 min and a solution of 7-(4-hydroxy-butoxy)-5-methyl-3,4-dihydro-1H-[1,8]naphthyridin-2-one (2.70 g, 11.0 mmol) in DMSO (8 mL) and $CH_2Cl_2$ (40 mL) was added over 5 min. The reaction was stirred at −70° C. for 10 min and a solid precipitated. The mixture was warmed to −50° C. for 5 min and recooled to −70° C. $Et_3N$ (7.9 mL, 56.4 mmol) was added and the mixture was warmed to room temperature over 30 min. The reaction mixture was added to $H_2O$ and the layers were separated. The organic layer was washed with $H_2O$, 1N citric acid (2×) and saturated $NaHCO_3$, dried over $Na_2SO_4$ and concentrated to a slurry. $Et_2O$ was added and the solid was collected by filtration to give the seventh intermediate compound (2.38 g, 9.59 mmol, 89%). MS: APCI: M+1: 249.2 (Exact Mass: 248.12).

To a suspension of 1-(2,3-dichloro-phenyl)-piperazine hydrochloride (0.93 g, 3.48 mmol) in dichloroethane (10 mL) was added $Et_3N$ (0.96 mL, 6.92 mmol). The mixture was stirred for 15 min and a suspension of 4-(4-methyl-7-oxo-5,6,7,8-tetrahydro-[1,8]naphthyridin-2-yloxy)-butyraldehyde (0.86 g, 3.46 mmol) in dichloroethane (5 mL) was added. After 20 min at RT, $NaBH(OAc)_3$ (1.03 g, 4.85 mmol) was added and the reaction was stirred at room temperature for 4 h. The reaction mixture was poured into $CH_2Cl_2$ and washed with $H_2O$, 1N citric acid, saturated $NaHCO_3$ and brine, dried over $Na_2SO_4$ and concentrated to an oil. $Et_2O$ was added and the organics were decanted from an insoluble gum. The filtrate yielded a crystalline solid, which was collected by filtration and dried. Purification by liquid chromatography (gradient elution, 100% $CHCl_3$ to 2% $MeOH/CHCl_3$, Biotage 40m column) provided the title compound as a white solid (1.12 g, 2.44 mmol, 70%). MS: APCI: M+1: 463.1 (Exact Mass: 462.16).

Example E10

Synthesis of 5-Methyl-7-[4-(4-naphthalen-1-yl-piperazin-1-yl)-butoxy]-3,4-dihydro-1H-[1,8]naphthyridin-2-one The title compound was prepared by reductive amination of 4-(4-methyl-7-oxo-5,6,7,8-tetrahydro-[1,8]naphthyridin-2-yloxy)-butyraldehyde with 1-naphthalen-1-yl-piperazine hydrochloride according to the above procedure. MS: APCI: M+1: 445.2 (Exact Mass: 444.25).

Example E11

Synthesis of 5-Methyl-7-{4-[4-(5,6,7,8-tetrahydro-naphthalen-1-yl)-piperazin-1-yl]-butoxy}-3,4-dihydro-1H-[1,8]naphthyridin-2-one The title compound was prepared by reductive amination of 4-(4-methyl-7-oxo-5,6,7,8-tetrahydro-[1,8]naphthyridin-2-yloxy)-butyraldehyde with 1-(5,6,7,8-tetrahydro-naphthalen-1-yl)-piperazine according to the above procedure. MS: APCI: M+1: 450.0 (Exact Mass: 448.28).

Example E12

Synthesis of 7-[4-(4-Indan-4-yl-piperazin-1-yl)-butoxy]-5-methyl-3,4-dihydro-1H-[1,8]naphthyridin-2-one The title compound was prepared by reductive amination of 4-(4-methyl-7-oxo-5,6,7,8-tetrahydro-[1,8]naphthyridin-2-yloxy)-butyraldehyde with 1-indan-4-yl-piperazine according to the above procedure. MS: APCI: M+1: 435.6 (Exact Mass: 434.27).

Example E13

Synthesis of 7-[4-(4-Indan-4-yl-piperazin-1-yl)-butoxy]-5-trifluoromethyl-3,4-dihydro-1H-[1,8] naphthyridin-2-one A first intermediate compound, 6-(4-Benzyloxy-butoxy)-2-chloro-4-trifluoromethyl-nicotinonitrile, was produced as follows: A solution of 2,6-dichloro-4-(trifluoromethyl)nicotinonitrile (20 g, 83 mmol) in THF (200 mL) was cooled to −70° C. Separately, a solution of 4-benzyloxy-1-butanol (15.41 g, 85.5 mmol) in THF (150 mL) was cooled to −40° C. and 1M potassium t-butoxide in THF (85.5 mL) was added dropwise and the temperature was allowed to reach 10° C. over 15 minutes. The solution thus prepared was added to the solution of 2,6-dichloro-4-(trifluoromethyl) niconitrile at −70° C. over 2 hours, followed by warming to 25° C. for 16 hours. The THF was removed in vacuo and the residue was partitioned between ether and water. The ether phase was washed with 1N citric acid, brine, dried over magnesium sulfate and filtered. The filtrate was evaporated to an oil, which was sufficiently pure to be used in the next step.

A second intermediate compound, 2-Azido-6-(4-benzyloxy-butoxy)-4-trifluoromethyl-nicotinonitrile, was produced as follows: To DMF (60 mL) was added 6-(4-benzyloxy-butoxy)-2-chloro-4-trifluoromethyl-nicotinonitrile (32 g, 83.1 mmol) and sodium azide (5.9 g, 91 mmol) followed by heating at 70° C. for 16 hours. The mixture was partitioned between water and ether. The ether phase was washed with brine, dried over magnesium sulfate, filtered and evaporated to give the second intermediate compound as an oil (30.7 g) of sufficient purity to be used in the next step.

A third intermediate compound, 2-Amino-6-(4-benzyloxy-butoxy)-4-trifluoromethyl-nicotinonitrile, was produced as follows: To a solution of 2-azido-6-(4-benzyloxy-butoxy)-4-trifluoromethyl-nicotinonitrile (30.7 g, 78.5 mmol) in methanol (150 mL) cooled to 0° C. was added 1,1,1,3,3,3-hexamethyl-disilathiane (28.02 g, 157 mmol). The reaction was exothermic and off-gassing occurred over 3 hours. A minor amount of precipitate was filtered off and the filtrate was refrigerated giving a solid precipitate. The solid was filtered, washed with hexane and dried to a weight of 19.7 g. The solid was purified by chromatography on silica gel eluting with dichloromethane to give the third intermediate compound as a solid (6.08 g), mp 94–96° C.

A fourth intermediate compound, 2-Amino-6-(4-benzyloxy-butoxy)-4-trifluoromethyl-pyridine-3-carbaldehyde, was produced as follows: To solution of 2-amino-6-(4-benzyloxy-butoxy)-4-trifluoromethyl-nicotinonitrile (8.76 g, 24 mmol) in THF (40 mL) cooled to 0° C. was added 1M DIBAL in THF (96 mL). After warming to 25° C. for 1 hour, the mixture was quenched by addition of a solution of cold 2N HCl (200 mL). After stirring and warming to 25° C., the mixture was neutralized to pH 7 by addition of potassium carbonate and the mixture extracted with diethyl ether. The ether washings were dried over magnesium sulfate, filtered and evaporated to give the fourth intermediate compound as an oil (7.5 g).

A fifth intermediate compound, 3-[2-Amino-6-(4-benzyloxy-butoxy)-4-trifluoromethyl-pyridin-3-yl]-acrylic acid ethyl ester, was produced as follows: To a solution of 2-amino-6-(4-benzyloxy-butoxy)-4-trifluoromethyl-pyridine-3-carbaldehyde (4.66 g, 10.6 mmol) in methanol (100 mL) was added (triphenylphosphanylidene)acetic acid ethyl ester (7.09 g, 20.4 mmol). The mixture was heated to 67° C. for 16 hours and evaporated to an oil. Purification by chromatography on silica gel eluting with hexane/ethyl acetate provided the fifth intermediate compound as an oil (4.66 g).

A sixth intermediate compound, 7-(4-Benzyloxy-butoxy)-5-trifluoromethyl-3,4-dihydro-1H-[1,8]naphthyridin-2-one, was produced as follows: To a solution of 3-[2-amino-6-(4-benzyloxy-butoxy)-4-trifluoromethyl-pyridin-3-yl]-acrylic acid ethyl ester (7.5 g, 20 mmol) in THF (70 mL) was added Raney Nickel (1.5 g). The reaction was pressurized to 50 psi with hydrogen gas for 16 hours. The mixture was filtered, evaporated to an oil, redissolved in isopropanol (20 mL) and p-toluene sulfonic acid (0.24 g) was added. The mixture was heated at reflux for 45 minutes. The mixture was poured into a mixture of saturated sodium carbonate and diethyl ether and the ether phase was separated. The ether layer was washed with brine, dried over anhydrous magnesium sulfate, filtered and evaporated to give the sixth intermediate compound as an oil (3.29 g).

A seventh intermediate compound, 7-(4-Hydroxy-butoxy)-5-trifluoromethyl-3,4-dihydro-1H-[1,8]naphthyridin-2-one, was produced as follows: To a 50:50 mixture of THF/methanol (50 mL) was added 7-(4-benzyloxy-butoxy)-5-trifluoromethyl-3,4-dihydro-1H-[1,8]naphthyridin-2-one (3.29 g, 8.3 mmol) followed by 20% Pd on charcoal (2.0 g). The reaction was pressurized to 50 psi with hydrogen gas for 48 hours. The mixture was filtered and evaporated to give the seventh intermediate compound as a solid (3.29 g).

An eighth intermediate compound, 4-(7-Oxo-4-trifluoromethyl-5,6,7,8-tetrahydro-[1,8]naphthyridin-2-yloxy)-butyraldehyde, was produced as follows: To a solution of oxallyl chloride (1.1 g, 8.77 mmol) and DMSO (1.35 g, 17.2 mmol) in dichloromethane (20 mL) at −70° C. was added a solution of 7-(4-hydroxy-butoxy)-5-trifluoromethyl-3,4-dihydro-1H-[1,8]naphthyridin-2-one (2.32 g, 7.62 mmol) in DMSO over 10 minutes. To the mixture was added triethylamine (4.0 g, 40 mmol) and the reaction was warmed to 25° C. over 45 minutes. The mixture was washed consecutively with 1N citric acid, saturated sodium bicarbonate and brine, followed by drying of the organic phase over magnesium sulfate and filtration. The filtrate was evaporated to give the eighth intermediate compound as a solid (2.28 g).

In a manner similar to that of other examples above, 1-indan-4-yl-piperazine hydrochloride was coupled by reductive amination to 4-(7-oxo-4-trifluoromethyl-5,6,7,8-tetrahydro-[1,8]naphthyridin-2-yloxy)-butyraldehyde followed by typical workup and purification to give the title compound. MS: APCI: M+1: 489.4 (Exact Mass: 488.24).

Example E14

Synthesis of 7-[4-(4-Naphthalen-1-yl-piperazin-1-yl)-butoxy]-5-trifluoromethyl-3,4-dihydro-1H-[1,8] naphthyridin-2-one In a manner similar to that of other examples above, 1-naphthalen-1-yl-piperazine hydrochloride was coupled by reductive amination to 4-(7-oxo-4-trifluoromethyl-5,6,7,8-tetrahydro-[1,8]naphthyridin-2-yloxy)-butyraldehyde followed by typical workup and purification to give the title compound. MS: APCI: M+1: 499.1 (Exact Mass: 489.22).

Example E15

Synthesis of 7-{4-[4-(5,6,7,8-Tetrahydro-naphthalen-1-yl)-piperazin-1-yl]-butoxy}-5-trifluoromethyl-3,4-dihydro-1H-[1,8]naphthyridin-2-one In a manner similar to that of other examples above, 1-(5,6,7,8-tetrahydro-naphthalen-1-yl)-piperazine was coupled by reductive amination to 4-(7-oxo-4-trifluoromethyl-5,6,7,8-tetrahydro-[1,8]naphthyridin-2-yloxy)-butyraldehyde followed by typical workup and purification to give the title compound. MS: APCI: M+1: 503.1 (Exact Mass: 502.26).

Example F1

Synthesis of 7-{4-[4-(2,3-Dichloro-phenyl)-piperazin-1-yl]-butoxy}-3,4-dihydro-1H-pyrido[2,3-d]pyrimidin-2-one A first intermediate compound, N-{3-Hydroxymethyl-6-[4-(tetrahydro-pyran-2-yloxy)-butoxy]-pyridin-2-yl}-2,2-dimethyl-propionamide, was produced as follows: An ice-cold mixture of N-{3-formyl-6-[4-(tetrahydro-pyran-2-yloxy)-butoxy]-pyridin-2-yl}-2,2-dimethyl-propionamide (2.20 g, 5.80 mmol) in methanol (20 mL) was treated with NaBH$_4$ (0.394 g, 10.40 mmol) in portions. Bubbles evolved from the mixture. The mixture was warmed to room temperature and stirred for 1 hour. The colorless solution was quenched with water and concentrated under vacuum. The residue was diluted with water and EtOAc. The organic layer was separated and the aqueous layer was extracted with EtOAc. The combined organic extracts were washed with brine, dried over Na$_2$SO$_4$, filtered, and concentrated under vacuum to afford the first intermediate compound as a yellow oil (2.21 g, quantitative). $^1$H NMR (400 MHz, CDCl$_3$): δ 7.69 (d, 1H), 7.68 (br s, 1H), 6.62 (d, 1H), 4.62–4.58 (m, 1H), 4.38 (d, 2H), 4.26 (t, 2H), 4.04–3.96 (m, 1H), 3.92–3.77 (m, 2H), 3.55–3.42 (m, 2H), 1.92–1.67 (m, 6H), 1.63–1.48 (m, 4H), 1.36 (s, 9H). MS ES: m/z=381.10.

A second intermediate compound, N-{3-Azidomethyl-6-[4-(tetrahydro-pyran-2-yloxy)-butoxy]-pyridin-2-yl}-2,2-dimethyl-propionamide, was produced as follows: An ice-cold mixture of N-{3-hydroxymethyl-6-[4-(tetrahydro-pyran-2-yloxy)-butoxy]-pyridin-2-yl}-2,2-dimethyl-propionamide (1.00 g, 2.60 mmol) and diphenylphosphoryl azide (1.44 g, 4.20 mmol) in toluene was treated with DBU (7.27 g, 4.78 mmol). The reaction mixture was warmed to room temperature and stirred for 1 hour. The brown mixture was concentrated under vacuum and diluted with EtOAc and water. The organic layer was separated and the aqueous layer was extracted with EtOAc. The combined organic extracts were dried over Na$_2$SO$_4$, filtered and concentrated under vacuum. The residue was purified by column chromatography (3:1, hexanes/EtOAc) to afford the second intermediate compound as a light yellow oil (0.800 g, 75%). $^1$H NMR (400 MHz, CDCl$_3$): δ 7.63 (d, 1H), 7.58 (s, 1H), 6.62 (d, 1H), 4.62–4.59 (m, 1H), 4.30 (s, 2H), 4.26 (s, 2H), 3.92–3.77 (m, 2H), 3.54–3.42 (m, 2H), 1.92–1.67 (m, 6H), 1.63–1.46 (m, 4H), 1.35 (s, 9H). MS ES: m/z=406.10.

A third intermediate compound, N-[3-Azidomethyl-6-(4-hydroxy-butoxy)-pyridin-2-yl]-2,2-dimethyl-propionamide, was produced as follows: A mixture of N-{3-azidomethyl-6-[4-(tetrahydro-pyran-2-yloxy)-butoxy]-pyridin-2-yl}-2,2-dimethyl-propionamide (0.730 g, 1.80 mmol), pyridinium p-toluenesulphonic acid (0.100 g, 0.40 mmol) in EtOH (50 mL) was refluxed for 1 hour. The solution was concentrated under vacuum, then diluted with water and EtOAc. The organic layer was separated and the aqueous layer was extracted with EtOAc. The combined organic extracts were dried over Na$_2$SO$_4$, filtered and concentrated under vacuum to afford the third intermediate compound as a yellow oil (0.570 g, 99%). $^1$H NMR (400 MHz, CDCl$_3$): δ 7.70–7.62 (br s, 1H), 7.63 (d, 1H), 6.63 (d, 1H), 4.31 (s, 2H), 4.29 (t, 2H), 3.73 (t, 2H), 1.92–1.82 (m, 2H), 1.78–1.68 (m, 3H), 1.35 (s, 9H). MS ES: m/z=322.20.

A fourth intermediate compound, N-[3-Azidomethyl-6-(4-oxo-butoxy)-pyridin-2-yl]-2,2-dimethyl-propionamide, was produced as follows: A solution of Dess-Martin periodinane (0.982 g, 2.20 mmol) in CH$_2$Cl$_2$ (20 mL) was treated with N-[3-azidomethyl-6-(4-hydroxy-butoxy)-pyridin-2-yl]-2,2-dimethyl-propionamide (0.470 g, 1.46 mmol) in CH$_2$Cl$_2$ (5 mL) at RT. The yellow mixture was stirred for 1.5 hours, then diluted with Et$_2$O and poured into saturated NaHCO$_3$ containing Na$_2$S$_2$O$_3$ (2.50 g, 15.80 mmol). The mixture was stirred for 10 minutes and the organic layer was separated. The aqueous layer was extracted with Et$_2$O and the combined organic extracts were washed with brine, dried over Na$_2$SO$_4$, filtered and concentrated under vacuum to afford the crude aldehyde, which was used in the next step without further purification.

A fifth intermediate compound, N-(3-Azidomethyl-6-{4-[4-(2,3-dichloro-phenyl)-piperazin-1-yl]-butoxy}-pyridin-2-yl)-2,2-dimethyl-propionamide, was produced as follows: To a solution of N-[3-azidomethyl-6-(4-oxo-butoxy)-pyridin-2-yl]-2,2-dimethyl-propionamide in DCE (50 mL) was added 1-(2,3-dichlorophenyl)piperazine (0.553 g, 2.10 mmol), Et$_3$N (0.295 g, 2.90 mmol) and NaBH(OAc)$_3$ (0.433 g, 2.00 mmol). The mixture was stirred at room temperature for 1 hour, then quenched with water and saturated NaHCO$_3$. The mixture was extracted with CH$_2$Cl$_2$ and the combined extracts were washed with brine, dried over Na$_2$SO$_4$, filtered and concentrated in vacuo. The residue was purified by column chromatography (10% MeOH/EtOAc) to afford the fifth intermediate compound as a yellow oil (0.455 g, 58%). $^1$H NMR (400 MHz, CDCl$_3$): δ 7.62 (d, 1H), 7.61–7.55 (br s, 1H), 7.20–7.14 (m, 2H), 7.00–6.92 (m, 1H), 6.61 (d, 1H), 4.33 (s, 2H), 4.27 (t, 2H), 3.18–3.00 (m, 4H), 2.78–2.58 (m, 4H), 2.47–2.41 (m, 2H), 1.89–1.62 (m, 4H), 1.36 (s, 9H). MS ES: m/z=534.09, 536.04.

A sixth intermediate compound, [6-{4-[4-(2,3-Dichloro-phenyl)-piperazin-1-yl]-butoxy}-2-(2,2-dimethyl-propionylamino)-pyridin-3-ylmethyl]-carbamic acid tert-butyl ester, was produced as follows: A mixture of N-(3-azidomethyl-6-{4-[4-(2,3-dichloro-phenyl)-piperazin-1-yl]-butoxy}-pyridin-2-yl)-2,2-dimethyl-propionamide (0.808 g, 1.51 mmol) and di-tert-butyl dicarbonate (0.326 g, 1.54 mmol) in EtOH (40 mL) was treated with Raney-Nickel (2 mL suspension in water). The mixture was shaken under 45 psi of H$_2$ for 3 hours. The suspension was filtered through Celite and the Celite pad was washed with EtOH. The filtrate was concentrated in vacuo. The residue was purified by column chromatography (10% MeOH/EtOAc) to afford the sixth intermediate compound as a white solid (0.619 g, 67%). mp 143–144° C.; $^1$H NMR (400 MHz, CDCl$_3$): δ 8.12–8.04 (br s, 1H), 7.67 (d, 1H), 7.18–7.12 (m, 2H), 7.00–6.92 (m, 1H), 6.58 (d, 1H), 5.64–5.50 (br s, 1H), 4.24 (t, 2H), 4.08 (d, 2H), 3.15–3.01 (m, 4H), 2.70–2.59 (m, 4H), 2.48 (t, 2H), 1.85–1.64 (m, 4H), 1.43 (s, 9H), 1.35 (s, 9H). MS ES: m/z=608.22, 610.17.

A seventh intermediate compound, 3-Aminomethyl-6-{4-[4-(2,3-dichloro-phenyl)-piperazin-1-yl]-butoxy}-pyridin-2-ylamine, was produced as follows: A mixture of [6-{4-[4-(2,3-dichloro-phenyl)-piperazin-1-yl]-butoxy}-2-(2,2-dimethyl-propionylamino)-pyridin-3-ylmethyl]-carbamic acid tert-butyl ester (0.557 g, 0.91 mmol) in 2 N aqueous KOH (5 mL) and EtOH (20 mL) was refluxed for 5 hours. The reaction was not complete (judged by $^1$H NMR), so an additional amount of 2 N KOH (5 mL) was added and the resulting mixture was refluxed overnight. The mixture was cooled to RT, then diluted with water and extracted with EtOAc. The organic extracts were dried over Na$_2$SO$_4$, filtered and concentrated in vacuo to afford a brown oil, which was used in the next step without further purification. $^1$H NMR (400 MHz, CDCl$_3$) δ: 7.20–7.10 (m, 3H), 7.00–6.92 (m, 1H), 5.98 (s, 1H), 5.17–5.00 (br s, 2H), 4.82–4.71 (br s, 2H), 4.18 (t, 2H), 4.14 (d, 2H), 3.19–2.97 (m, 4H), 2.78–2.50 (m, 4H), 2.45 (t, 2H), 1.85–1.62 (m, 4H), 1.44 (s, 9H).

To a solution of crude (2-amino-6-{4-[4-(2,3-dichlorophenyl)-piperazin-1-yl]-butoxy}-pyridin-3-ylmethyl)-carbamic acid tert-butyl ester in dioxane (15 mL) was added 3 N HCl (15 mL). The resulting mixture was refluxed for 2 hours, cooled to RT, then neutralized with saturated $Na_2CO_3$. The neutralized solution was extracted with EtOAc and the organic extracts were washed with brine, dried over $Na_2SO_4$, filtered and concentrated in vacuo to afford the title compound as a brown oil (0.367 g, 94% over two steps). $^1$H NMR (400 MHz, $CDCl_3$): δ 7.21–7.10 (m, 3H), 7.00–6.91 (m, 1H), 6.00 (d, 1H), 5.40–5.21 (br s, 2H), 4.12 (t, 2H), 3.82 (s, 2H), 3.71 (s, 2H), 3.19–2.98 (m, 4H), 2.81–2.55 (m, 4H), 2.50 (t, 2H), 1.91–1.43 (m, 4H). MS ES: m/z=424.00, 425.99.

A mixture of 3-aminomethyl-6-{4-[4-(2,3-dichloro-phenyl)-piperazin-1-yl]-butoxy}-pyridin-2-ylamine (0.260 g, 0.61 mmol) in THF (10 mL) was treated with 4-nitrophenyl chloroformate (0.160 g, 0.79 mmol). The mixture was stirred at room temperature for 30 minutes, then cooled to 0° C. and treated with LDA (0.9 mL, 3.8 mmol, 2.0 M in heptane/THF/ethylbenzene). The brown mixture was stirred at room temperature for 1 hour, then quenched with water and extracted with EtOAc. The organic extracts were washed with water and brine, dried over $Na_2SO_4$, filtered, and concentrated in vacuo. The residue was purified by preparative thin layer chromatography (10% MeOH/EtOAc) to afford the title compound as a light yellow solid (0.071 g, 25%). mp 166–167° C.; 1 H NMR (400 MHz, $CDCl_3$): δ 7.25 (s, 1H), 7.19–7.14 (m, 2H), 7.14–7.09 (br s, 1H), 6.99–6.94 (m, 1H), 6.32 (d, 1H), 5.57–5.51 (br s, 1H), 4.45 (s, 2H), 4.24 (t, 2H), 3.16–3.02 (m, 4H), 2.75–2.58 (m, 4H), 2.49 (t, 2H), 1.84–1.64 (m, 4H). MS ES: m/z=450.03, 452.02.

Example F2

Synthesis of 7-[4-(4-Naphthalen-1-yl-piperazin-1-yl)-butoxy]-3,4-dihydro-1H-pyrido[2,3-d]pyrimidin-2-one A first intermediate compound, N-{3-Azidomethyl-6-[4-(4-naphthalen-1-yl-piperazin-1-yl)-butoxy]-pyridin-2-yl}-2,2-dimethyl-propionamide, was produced as follows: To a solution of N-[3-azidomethyl-6-(4-oxo-butoxy)-pyridin-2-yl]-2,2-dimethyl-propionamide in DCE (250 mL) was added 1-naphthalen-1-yl-piperazine monohydrochloride (2.81 g, 11.30 mmol), $Et_3N$ (2.00 g, 19.80 mmol) and $NaBH(OAc)_3$ (2.38 g, 11.20 mmol). The mixture was stirred at room temperature for 1 hour, then quenched with water and saturated $NaHCO_3$. The mixture was extracted with $CH_2Cl_2$ and the combined extracts were washed with brine, dried over $Na_2SO_4$, filtered and concentrated in vacuo. The residue was purified by column chromatography (1:19, $Et_3N$/EtOAc) to afford the first intermediate compound as a brown oil (2.36 g, 59%). $^1$H NMR (400 MHz, $CDCl_3$): δ 8.26–8.17 (m, 1H), 7.85–7.80 (m, 1H), 7.64 (d, 1H), 7.60 (s, 1H), 7.55 (d, 1H), 7.50–7.44 (m, 2H), 7.41 (t, 1H), 7.10 (d, 1H), 6.64 (d, 1H), 4.31 (s, 2H), 4.28 (t, 2H), 3.25–3.05 (m, 4H), 2.90–2.62 (m, 4H), 2.55 (t, 2H), 1.90–1.68 (m, 4H), 1.35 (s, 9H). MS ES: m/z=516.20.

A second intermediate compound, {2-(2,2-Dimethyl-propionylamino)-6-[4-(4-naphthalen-1-yl-piperazin-1-yl)-butoxy]-pyridin-3-ylmethyl}-carbamic acid tert-butyl ester, was produced as follows: A mixture of N-{3-azidomethyl-6-[4-(4-naphthalen-1-yl-piperazin-1-yl)-butoxy]-pyridin-2-yl}-2,2-dimethyl-propionamide (2.36 g, 4.60 mmol) and di-tert-butyl dicarbonate (1.035 g, 4.74 mmol) in EtOH (80 mL) was treated with Palladium on charcoal (10% wet, 1.254 g). The mixture was shaken under 45 psi of $H_2$ for 3.5 hours. The suspension was filtered through Celite and the Celite pad was washed with EtOH. The filtrate was concentrated in vacuo to afford the second intermediate compound as a white solid (2.64 g, 97%). mp 80–82° C. $^1$H NMR (400 MHz, $CDCl_3$): δ 8.24–8.16 (m, 1H), 8.00 (br s, 1H), 7.86–7.80 (m, 1H), 7.66 (d, 1H), 7.55 (d, 1H), 7.50–7.42 (m, 2H), 7.40 (t, 1H), 7.10 (d, 1H), 6.59 (d, 1H), 5.45 (br s, 1H), 4.28 (t, 2H), 4.09 (d, 2H), 3.25–3.05 (m, 4H), 2.85–2.60 (m, 4H), 2.60–2.50 (m, 2H), 1.89–1.60 (m, 4H), 1.42 (s, 9H), 1.35 (s, 9H). MS ES: m/z=590.33.

A third intermediate compound, {2-Amino-6-[4-(4-naphthalen-1-yl-piperazin-1-yl)-butoxy]-pyridin-3-ylmethyl}-carbamic acid tert-butyl ester, was produced as follows: A mixture of {2-(2,2-dimethyl-propionylamino)-6-[4-(4-naphthalen-1-yl-piperazin-1-yl)-butoxy]-pyridin-3-ylmethyl}-carbamic acid tert-butyl ester (2.64 g, 4.48 mmol) in 2 N aqueous. KOH (40 mL) and EtOH (40 mL) was refluxed overnight. The mixture was cooled to RT, then diluted with water and extracted with EtOAc. The organic extracts were dried over $Na_2SO_4$, filtered and concentrated in vacuo. The residue was purified by column chromatography (2.5% $Et_3N$/EtOAc) to afford the third intermediate compound as a white solid (1.30 g, 58%). mp 67–68° C. $^1$H NMR (400 MHz, $CDCl_3$): δ 8.42–8.30 (m, 1H), 7.85–7.60 (m, 1H), 7.55 (d, 1H), 7.51–7.40 (m, 2H), 7.39 (t, 1H), 7.16 (d, 1H), 7.08 (d, 1H), 6.00 (d, 1H), 5.13–5.00 (br s, 2H), 4.85–4.70 (br s, 1H), 4.20 (t, 2H), 4.14 (d, 2H), 3.28–3.04 (m, 4H), 2.90–2.62 (m, 4H), 2.54 (t, 2H), 1.88–1.66 (m, 4H), 1.54 (s, 9H). MS ES: m/z=506.19.

A fourth intermediate compound, 3-Aminomethyl-6-[4-(4-naphthalen-1-yl-piperazin-1-yl)-butoxy]-pyridin-2-ylamine, was produced as follows: To a solution of {2-amino-6-[4-(4-naphthalen-1-yl-piperazin-1-yl)-butoxy]-pyridin-3-ylmethyl}-carbamic acid tert-butyl ester (1.17 g, 2.31 mmol) in dioxane (10 mL) was added 3 N HCl (10 mL). The resulting mixture was refluxed for 1 hour, cooled to RT, then neutralized with saturated $Na_2CO_3$. The neutralized solution was extracted with EtOAc and the organic extracts were washed with brine, dried over $Na_2SO_4$, filtered and concentrated in vacuo to afford the fourth intermediate compound as a brown oil (0.92 g, 98%). $^1$H NMR (400 MHz, $CDCl_3$): δ 8.22–8.15 (m, 1H), 7.85–7.78 (m, 1H), 7.55 (d, 1H), 7.50–7.40 (m, 2H), 7.40 (t, 1H), 7.18 (d, 1H), 7.09 (d, 1H), 6.00 (d, 1H), 5.30 (br s, 2H), 4.20 (t, 2H), 3.79 (s, 2H), 3.71 (s, 2H), 3.28–3.06 (m, 4H), 2.96–2.64 (m, 4H), 2.56 (t, 2H), 1.88–1.68 (m, 4H). MS ES: m/z=406.10.

A mixture of 3-aminomethyl-6-[4-(4-naphthalen-1-yl-piperazin-1-yl)-butoxy]-pyridin-2-ylamine (0.92 g, 2.27 mmol) in THF (25 mL) was treated with phenyl chloroformate (0.40 mL, 3.18 mmol) followed by $Et_3N$ (0.46 g, 4.54 mmol). The mixture was stirred at room temperature for 1 hour, then cooled to 0° C. and treated with LDA (5.6 mL, 11.20 mmol, 2.0 M in heptane/THF/ethylbenzene). The brown mixture was stirred at room temperature for 1 hour, then quenched with water and extracted with EtOAc. The organic extracts were washed with water, and brine, dried over $Na_2SO_4$, filtered, and concentrated in vacuo. The residue was purified by column chromatography (2.5% $Et_3N$/EtOAc) to afford the title compound as a light yellow solid (0.204 g, 21%). mp 136–138; $^1$H NMR (400 MHz, $CDCl_3$): δ 8.24–8.16 (m, 1H), 7.85–7.78 (m, 1H), 7.55 (d, 1H), 7.50–7.42 (m, 2H), 7.40 (t, 1H), 7.25 (d, 1H), 7.09 (d, 1H), 6.84 (br s, 1H), 6.34 (d, 1H), 5.05 (br s, 1H), 4.48 (s, 2H), 4.45 (t, 2H), 3.30–2.05 (m, 4H), 2.93–2.60 (m, 4H), 2.55 (t, 2H), 1.90–1.70 (m, 4H). MS ES: m/z=432.11.

Example F3

Synthesis of 7-[4-(4-Indan-4-yl-piperazin-1-yl)-butoxy]-3,4-dihydro-1H-pyrido[2,3-d]pyrimidin-2-one A first intermediate compound, 2-Amino-6-[4-(tetrahydro-pyran-2-yloxy)-butoxy]-pyridine-3-carbaldehyde, was produced as follows: A mixture of N-{3-formyl-6-[4-(tetrahydro-pyran-2-yloxy)-butoxy]-pyridin-2-yl}-2,2-dimethyl-propionamide (9.8 g, 25.9 mmol), 2 N KOH (35 mL) and EtOH (40 mL) was heated at 80° C. for 2 h. Ethanol was removed under reduced pressure and the residue was extracted with EtOAc (3×100 mL). The combined organic phases were washed with $H_2O$ (40 mL) and brine (40 mL), dried over $Na_2SO_4$, and concentrated to give the first intermediate compound as an oil which was used in the next step without further purification. $^1$H NMR (400 MHz, $CDCl_3$): δ 9.70 (s, 1H), 7.62 (d, 1H), 6.17 (d, 1H), 4.60 (m, 1H), 4.40 (m, 2H), 3.90 (m, 2H), 3.50 (m, 2H), 2.00–1.50 (m, 10H).

A second intermediate compound, 7-[4-(Tetrahydro-pyran-2-yloxy)-butoxy]-1H-pyrido[2,3-d]pyrimidin-2-one, was produced as follows: To a solution of 2-amino-6-[4-(tetrahydro-pyran-2-yloxy)-butoxy]-pyridine-3-carbaldehyde obtained in the last step in $CH_2Cl_2$ (50 mL) was added trichloroacetyl isocyanate (5.85 g, 31.08 mmol) dropwise. After the addition was over, the mixture was stirred at room temperature for 1 h. To this mixture, MeOH (50 mL) and 1 N NaOH (40 mL) were added successively. The mixture thus obtained was kept stirring at room temperature for another 1 h. The solvent was then removed under reduced pressure and the residue was extracted with $CH_2Cl_2$ (3×100 mL). The combined organic phases were washed with brine, dried and concentrated. The residue was crystallized from ether to give the second intermediate compound (6.6 g, 79% in two steps) as a pale yellow solid. $^1$H NMR (400 MHz, DMSO-$d_6$): δ 9.00 (S, 1H), 8.00 (d, 1H), 6.60 (d, 1H), 4.60 (m, 1H), 4.40 (m, 2H), 3.70 (m, 2H), 3.40 (m, 2H), 1.90–1.30 (m, 10H).

A third intermediate, 7-(4-Hydroxy-butoxy)-1H-pyrido[2,3-d]pyrimidin-2-one, was produced as follows: A mixture of 7-[4-(tetrahydro-pyran-2-yloxy)-butoxy]-1H-pyrido[2,3-d]pyrimidin-2-one (4.9 g, 15 mmol), MeOH (30 mL), THF (15 mL) and 3 N HCl (7.5 mL) was stirred at room temperature for 1 h. The mixture was concentrated under reduced pressure. The residue was dissolved in $H_2O$ (30 mL) and neutralized carefully with saturated $NaHCO_3$. The mixture was extracted with THF (5×100 mL). The combined organic phases were washed with brine, dried and concentrated to give the third intermediate compound (3.3 g, 90%) which was used in the next step without further purification. $^1$H NMR (400 MHz, DMSO-$d_6$): δ 9.03 (s, 1H), 8.17 (d, 1H), 6.67 (d, 1H), 4.50 (m, 1H), 4.40 (m, 2H), 3.50 (m, 3H), 1.80 (m, 2H), 1.55 (m, 2H).

A fourth intermediate compound, 4-(2-Oxo-1,2-dihydro-pyrido[2,3-d]pyrimidin-7-yloxy)-butyraldehyde, was produced as follows: A mixture of 7-(4-hydroxy-butoxy)-1H-pyrido[2,3-d]pyrimidin-2-one (0.512 g, 2.18 mmol) and IBX (1.9 g, 6.6 mmol) in $CH_3CN$ (40 mL) was heated at 87° C. for 7 h. It was cooled to RT, diluted with EtOAc (80 mL) and filtered. The pad was washed thoroughly with EtOAc. The combined filtrate was concentrated to give the fourth intermediate compound as a solid which was contaminated with some byproduct from the reaction. This solid was used in the next step without further purification. $^1$H NMR (400 MHz, DMSO-$d_6$): δ 12.18 (s, 1H), 9.77 (s, 1H), 8.20 (d, 1H), 6.70 (d, 1H), 4.40 (m, 2H), 2.70 (m, 2H), 2.00 (m, 2H).

To a mixture of 4-(2-oxo-1,2-dihydro-pyrido[2,3-d]pyrimidin-7-yloxy)-butyraldehyde, 1-indan-4-yl-piperazine (0.581 g, 2.44 mmol), $Et_3N$ (1.70 mL, 12.2 mmol) in 1-methyl-2-pyrrolidinone (20 mL) was added $NaBH(OAc)_3$ (0.65 g, 3.05 mmol) in portions over 20 min. After the addition was over, the mixture was left stirring overnight. After quenching with $H_2O$ (50 mL), the reaction mixture was extracted with $CH_2Cl_2$ (3×100 mL). The combined organic phases were washed with brine (100 mL), dried and concentrated. The residue was purified by chromatography on silica gel to give a gum (350 mg). To a solution of this gum in THF (6 mL) and MeOH (2 mL) was added $NaBH_4$ (63 mg) in portions. After the addition was over, the mixture was kept stirring overnight. The reaction was quenched with $H_2O$. The mixture was extracted with $CH_2Cl_2$ (3×50 mL). The combined organic phases were dried over $Na_2SO_4$ and concentrated. The residue was purified by chromatography on silica gel to give a semi-solid which was converted to its HCl salt by treating with 1 equivalent of 1 N HCl in a mixed solvent of THF and $Et_2O$ to give the title compound (176 mg) as a white solid. $^1$H NMR (400 MHz, DMSO-$d_6$): δ 10.2 (s, 1H), 9.30 (s, 1H), 7.40 (d, 1H), 7.10 (t, 1H), 6.95 (m, 2H), 6.77 (d, 1H), 6.30 (d, 1H), 4.25 (m, 4H), 4.00 (m, 2H), 3.60 (m, 2H), 3.30–3.00 (m, 6H), 2.80 (m, 4H), 2.00–1.70 (m, 6H).

Example F4

Synthesis of 7-{4-[4-(5,6,7,8-Tetrahydro-naphthalen-1-yl)-piperazin-1-yl]-butoxy}-3,4-dihydro-1H-pyrido[2,3-d]pyrimidin-2-one The procedure from Example F3 was followed using 1-(5,6,7,8-tetrahydro-naphthalen-1-yl)-piperazine to give the title compound. $^1$H-NMR (400 MHz, DMSO-$d_6$): δ 10.20 (s, 1H), 9.22 (s, 1H), 7.40 (d, 1H), 7.10 (m, 1H), 6.95 (s, 1H), 6.85 (m 2H), 6.30 (d, 1H), 4.30 (m, 4H), 3.70–3.00 (m, 10H), 2.80–2.60 (m, 4H), 1.90–1.60 (m, 8H).

Example F5

Synthesis of 7-{4-[4-(7-Fluoro-naphthalen-1-yl)-piperazin-1-yl]-butoxy}-3,4-dihydro-1H-pyrido[2,3-d]pyrimidin-2-one The procedure from Example F3 was followed using 1-(7-fluoro-naphthalen-1-yl)-piperazine to give the title compound. $^1$H NMR (400 MHz, DMSO-$d_6$): δ 9.25 (s, 1H), 8.00 (m, 1H), 7.80 (m, 1H), 7.75 (m, 1H), 7.40 (m, 3H), 7.20 (d, 1H), 6.95 (s, 1H), 6.30 (d, 1H), 4.23 (m, 4H), 3.70–3.10 (m, 10H), 1.90–1.70 (m, 4H).

Example F6

Synthesis of 8-{4-[4-(2-Oxo-1,2,3,4-tetrahydro-pyrido[2,3-d]pyrimidin-7-yloxy)-butyl]-piperazin-1-yl}-naphthalene-2-carbonitrile The procedure from Example F3 was followed using 8-piperazin-1-yl-naphthalene-2-carbonitrile to give the title compound. $^1$H NMR (400 MHz, DMSO-$d_6$): 9.25 (s, 1H), 8.60 (s, 1H), 8.10 (d, 1H), 7.80 (m, 1H), 7.70 (m, 1H), 7.45–7.30 (m, 2H), 6.90 (s, 1H), 6.30 (d, 1H), 4.25 (m, 4H), 3.80–3.10 (m, 10H), 1.90–1.70 (m, 4H).

Example F7

Synthesis of 7-{4-[4-(2,3-Dichloro-phenyl)-piperazin-1-yl]-butoxy}-3-methyl-3,4-dihydro-1H-pyrido[2,3-d]pyrimidin-2-one A first intermediate compound, N-[6-(4-Benzyloxy-butoxy)-3-formyl-pyridin-2-yl]-2,2-dimethyl-propionamide, was produced as follows: To a stirred solution of 4-benzyloxy-1-butanol (300 mg, 1.66 mmol) in DMF (5 mL) at 0° C. was added NaH (50 mg, 2.08 mmol). The resulting grey slurry was stirred at 0° C. for 15 minutes and N-(6-chloro-3-formyl-pyridin-2-yl)-2,2-dimethyl-propionamide (200 mg, 0.83 mmol) was added portionwise. The mixture became a light orange color and bubbles were evolved. The orange mixture was allowed to warm to room temperature over 1 hour. Water (10 mL) was added and the mixture was diluted with EtOAc (20 mL). The organic layer was separated, washed with water (2×10 mL) and brine (20 mL), dried over $Na_2SO_4$, filtered, and concentrated in vacuo. The residual oil was purified by column chromatography (3:1, hexane/EtOAc) to yield the first intermediate compound as a clear oil (266 mg, 83%). $^1$H NMR (400 MHz, $CDCl_3$) δ 11.55 (s, 1H), 9.75 (s, 1H), 7.80 (d, 1H), 7.40–7.20 (m, 5H), 6.44 (d, 1H), 4.60–4.44 (m, 4H), 3.50 (t, 2H), 1.95–1.70 (m, 4H), 1.36 (s, 9H).

A second intermediate compound, N-[6-(4-Benzyloxy-butoxy)-3-methylaminomethyl-pyridin-2-yl]-2,2-dimethyl-propionamide, was produced as follows: To a stirred solution of N-[6-(4-benzyloxy-butoxy)-3-formyl-pyridin-2-yl]-2,2-dimethyl-propionamide (1.40 g, 3.65 mmol) in EtOH (20 mL) at room temperature was added methylamine monohydrochloride (295 mg, 4.37 mmol) and $Et_3N$ (443 mg, 0.61 mL, 4.37 mmol). The mixture was stirred for 24 hours and then cooled to 0° C. $NaBH_4$ (138 mg, 3.65 mmol) was added and the mixture was warmed to room temperature over 1 hour, then heated at 50° C. for 3 hours. The mixture was cooled to RT, water (20 mL) was added, and the mixture was extracted with EtOAc (30 mL). The organic layer was separated, washed with water (20 mL) and brine (20 mL), dried over $Na_2SO_4$, filtered, and concentrated in vacuo. The impure oil was purified by column chromatography (5% MeOH/$CH_2Cl_2$) to yield the second intermediate compound as a clear oil (1.22 g, 84%). $^1$H NMR (400 MHz, $CDCl_3$) δ 10.55 (s, 1H), 7.38–7.22 (m, 6H), 6.39 (d, 1H), 4.46 (s, 2H), 4.38 (t, 2H), 3.64 (s, 2H), 3.53 (t, 2H), 2.42 (s, 3H), 1.90–1.75 (m, 4H), 1.58 (br s, 1H), 1.36 (s, 9H).

A third intermediate compound, [6-(4-Benzyloxy-butoxy)-2-(2,2-dimethyl-propionylamino)-pyridin-3-ylmethyl]-methyl-carbamic acid tert-butyl ester, was produced as follows: N-[6-(4-Benzyloxy-butoxy)-3-methylaminomethyl-pyridin-2-yl]-2,2-dimethyl-propionamide (1.22 g, 3.06 mmol) was dissolved in MeOH (20 mL) and di-tert-butyl dicarbonate (701 mg, 3.21 mmol) was added. The mixture was stirred at room temperature overnight and water (10 mL) was added. The mixture was extracted with EtOAc (20 mL). The organic layer was washed with water (20 mL) and brine (20 mL), dried over $Na_2SO_4$, filtered and concentrated in vacuo to yield the third intermediate compound as a clear oil (1.48 g, 97%). $^1$H NMR (200 MHz, DMSO-$d_6$) δ 9.55 (s, 1H), 7.44 (d, 1H), 7.40–7.20 (m, 5H), 6.72 (d, 1H), 4.48 (s, 2H), 4.25 (t, 2H), 4.15 (s, 2H), 3.50 (t, 2H), 2.70 (s, 3H), 1.90–1.60 (m, 4H), 1.45 (s, 9H), 1.25 (s, 9H).

A fourth intermediate compound, [2-(2,2-Dimethyl-propionylamino)-6-(4-hydroxy-butoxy)-pyridin-3-ylmethyl]-methyl-carbamic acid tert-butyl ester, was produced as follows: [6-(4-Benzyloxy-butoxy)-2-(2,2-dimethyl-propionylamino)-pyridin-3-ylmethyl]-methyl-carbamic acid tert-butyl ester (1.48 g, 2.96 mmol) was dissolved in MeOH (20 mL) and treated with 10% palladium on charcoal (400 mg). The mixture was shaken under an atmosphere of $H_2$ (45 psi) for 3 hours, filtered through celite and the celite was washed with EtOAc (2×20 mL). The filtrate was concentrated in vacuo to yield the fourth intermediate compound as a clear oil (1.21 g, 99%). $^1$H NMR (400 MHz, DMSO-$d_6$) δ 9.60 (s, 1H), 7.42 (d, 1H), 6.68 (d, 1H), 4.42 (t, 1H), 4.21 (t, 2H), 4.15 (s, 2H), 3.44–3.41 (m, 2H), 2.70 (s, 3H), 1.80–1.70 (m, 2H), 1.60–1.54 (m, 2H), 1.40 (s, 9H), 1.20 (s, 9H).

A fifth intermediate compound, [6-{4-[4-(2,3-Dichloro-phenyl)-piperazin-1-yl]-butoxy}-2-(2,2-dimethyl-propionylamino)-pyridin-3-ylmethyl]-methyl-carbamic acid tert-butyl ester, was produced as follows: To a stirred solution of Dess-Martin periodinane (926 mg, 2.18 mmol) in $CH_2Cl_2$ (20 mL) was added [2-(2,2-dimethyl-propionylamino)-6-(4-hydroxy-butoxy)-pyridin-3-ylmethyl]-methyl-carbamic acid tert-butyl ester (746 mg, 1.82 mmol) in $CH_2Cl_2$ (3 mL). The mixture was stirred at room temperature for 3.5 hours, then poured into a solution of saturated $NaHCO_3$ (20 mL) containing $Na_2S_2O_3$ (2.01 g, 12.7 mmol). The biphasic mixture was stirred vigorously for 15 minutes and the organic layer was separated. The organic layer was washed with saturated $NaHCO_3$ (20 mL) and brine (20 mL), dried over $Na_2SO_4$, filtered and concentrated in vacuo to yield the crude aldehyde (920 mg, 99%). The aldehyde (920 mg, 1.82 mmol) was dissolved in 1,2-dichloroethane (20 mL) and 1-(2,3-dichlorophenyl)piperazine monohydrochloride (536 mg, 2.00 mmol), $Et_3N$ (553 mg, 0.76 mL, 5.46 mmol), and $NaBH(OAc)_3$ (540 mg, 2.55 mmol) were added. The mixture was stirred at room temperature for 3 hours and water (10 mL) was added. The organic layer was washed with water (20 mL) and brine (20 mL), dried over $Na_2SO_4$, filtered, and concentrated in vacuo. The crude oil was purified by column chromatography (5% MeOH/$CH_2Cl_2$) to yield the fifth intermediate compound as a foam (686 mg, 61%). mp 57–59° C.; $^1$H NMR (400 MHz, DMSO-$d_6$) δ 9.56 (s, 1H), 7.44 (d, 1H), 7.38–7.25 (m, 2H), 7.18–7.14 (m, 1H), 6.78 (d, 1H), 4.24 (t, 2H), 4.15 (s, 2H), 3.00–2.95 (m, 4H), 2.64 (s, 3H), 2.60–2.56 (m, 4H), 2.39 (t, 2H), 1.80–1.75 (m, 2H), 1.63–1.55 (m, 2H), 1.40 (s, 9H), 1.20 (s, 9H).

A sixth intermediate compound, 6-{4-[4-(2,3-Dichloro-phenyl)-piperazin-1-yl]-butoxy}-3-methylaminomethyl-pyridin-2-ylamine, was produced as follows:

[6-{4-[4-(2,3-Dichloro-phenyl)-piperazin-1-yl]-butoxy}-2-(2,2-dimethyl-propionylamino)-pyridin-3-ylmethyl]-methyl-carbamic acid tert-butyl ester (686 mg, 1.11 mmol) was dissolved in dioxane (4 mL) and 3 N HCl (4 mL) was added. The solution was heated at 60° C. for 15 hours. The solution was cooled to room temperature and neutralized with saturated $Na_2CO_3$. The mixture was diluted with water (20 mL) and EtOAc (20 mL). The organic layer was washed with water (2×20 mL) and brine (20 mL), dried over $Na_2SO_4$, filtered and concentrated in vacuo to yield the sixth intermediate compound as a brown powder (458 mg, 95%). mp 119–121° C.; $^1$H NMR (400 MHz, $CDCl_3$) δ 7.20–7.03 (m, 3H), 7.00–6.95 (m, 1H), 5.97 (d, 1H), 5.20 (br s, 2H), 4.18 (t, 2H), 3.65 (s, 2H), 3.25 (br s, 1H), 3.15–3.00 (m, 4H), 2.80–2.58 (m, 4H), 2.45 (t, 2H), 2.40 (s, 3H), 1.83–1.63 (m, 4H).

To a stirred solution of 6-{4-[4-(2,3-dichloro-phenyl)-piperazin-1-yl]-butoxy}-3-methylaminomethyl-pyridin-2-ylamine (203 mg, 0.47 mmol) in THF (10 mL) at 0° C. was added 4-nitrobenzyl chloroformate (105 mg, 0.49 mmol). The mixture was stirred at 0° C. for 45 minutes and LDA (1.16 mL, 2.32 mmol, 2.0 M solution in heptane/THF/ethylbenzene) was added dropwise. The mixture was stirred for 1.5 hours at 0° C. and then poured over ice. EtOAc (30 mL) was added to the quenched mixture and the organic layer was separated. The organic layer was washed with water (20 mL) and brine (20 mL), dried over $Na_2SO_4$, filtered, and concentrated in vacuo. The crude oil was purified by preparative TLC (6% MeOH/EtOAc) to yield the title compound as a light orange foam (66 mg, 31%). $^1$H NMR (400 MHz, $CDCl_3$) δ 7.22 (d, 1H), 7.19–7.10 (m, 2H), 7.00–6.92 (m, 1H), 6.76 (s, 1H), 6.34 (d, 1H), 4.38 (s, 2H), 4.22 (t, 2H), 3.14–3.00 (m, 4H), 3.00 (s, 3H), 2.77–2.58 (m, 4H), 2.44 (t, 2H), 1.83–1.60 (m, 4H).

Example F8

Synthesis of 3-Methyl-7-[4-(4-naphthalen-1-yl-piperazin-1-yl)-butoxy]-3,4-dihydro-1H-pyrido[2,3-d]pyrimidin-2-one A first intermediate compound, {2-(2,2-Dimethyl-propionylamino)-6-[4-(4-naphthalen-1-yl-piperazin-1-yl)-butoxy]-pyridin-3-ylmethyl}-methyl-carbamic acid tert-butyl ester, was produced as follows: To a stirred solution of Dess-Martin periodinane (3.10 g, 7.32 mmol) in $CH_2Cl_2$ (40 mL) was added [2-(2,2-dimethyl-propionylamino)-6-(4-hydroxy-butoxy)-pyridin-3-ylmethyl]-methyl-carbamic acid tert-butyl ester (2.00 g, 4.88 mmol) in $CH_2Cl_2$ (5 mL). The mixture was stirred at room temperature for 3.5 hours and then poured into a solution of saturated $NaHCO_3$ (40 mL) containing $Na_2S_2O_3$ (5.40 g, 34.2 mmol). The biphasic mixture was stirred vigorously for 20 minutes and the organic layer was separated, washed with saturated $NaHCO_3$ (30 mL) and brine (30 mL), dried over $Na_2SO_4$, filtered and concentrated in vacuo to yield the crude aldehyde (1.95 g, 99%). The aldehyde (1.95 g, 4.88 mmol) was dissolved in 1,2-dichloroethane (40 mL) and 1-naphthalen-1-yl-piperazine monohydrochloride (1.34 g, 5.39 mmol), $Et_3N$ (1.49 g, 2.05 mL, 5.46 mmol), and $NaBH(OAc)_3$ (1.45 g, 6.86 mmol) were added. The mixture was stirred at room temperature for 3 hours and water (20 mL) was added. The organic layer was washed with water (30 mL) and brine (30 mL), dried over $Na_2SO_4$, filtered and concentrated in vacuo. The crude oil was purified by column chromatography (5% MeOH/$CH_2Cl_2$) to yield the first intermediate compound as a foam (1.39 g, 47%). mp 69–71° C.; $^1$H NMR (400 MHz, DMSO-$d_6$) δ 9.58 (s, 1H), 8.15 (d, 1H), 7.85 (d, 1H), 7.60 (d, 1H), 7.56–7.40 (m, 4H), 7.10 (d, 1H), 6.77 (d, 1H), 4.22 (t, 2H), 4.10 (s, 2H), 3.08–2.98 (m, 4H), 2.70 (s, 3H), 2.70–2.58 (m, 4H), 2.45 (t, 2H), 1.85–1.70 (m, 2H), 1.70–1.58 (m, 2H), 1.40 (s, 9H), 1.20 (s, 9H).

A second intermediate compound, 3-Methylaminomethyl-6-[4-(4-naphthalen-1-yl-piperazin-1-yl)-butoxy]-pyridin-2-ylamine, was produced as follows: {2-(2,2-Dimethyl-propionylamino)-6-[4-(4-naphthalen-1-yl-piperazin-1-yl)-butoxy]-pyridin-3-ylmethyl}-methyl-carbamic acid tert-butyl ester (1.39 g, 3.31 mmol) was dissolved in dioxane (6 mL) and 3 N HCl (6 mL) was added. The solution was heated at 60° C. for 8 hours. The solution was cooled to room temperature and neutralized with saturated $Na_2CO_3$. The mixture was diluted with water (30 mL) and EtOAc (30 mL). The organic layer was washed with water (2×30 mL) and brine (30 mL), dried over $Na_2SO_4$, filtered and concentrated in vacuo to yield the second intermediate compound as a brown oil (709 mg, 73%). $^1$H NMR (400 MHz, $CDCl_3$) δ 8.20 (d, 1H), 7.80 (d, 1H), 7.60–7.40 (m, 4H), 7.20 (d, 1H), 7.10 (d, 1H), 6.00 (d, 1H), 5.40 (s, 2H), 4.20 (t, 2H), 3.60 (s, 2H), 3.24–3.00 (m, 4H), 2.90–2.60 (m, 4H), 2.57 (t, 2H), 2.40 (s, 3H), 1.85–1.65 (m, 4H), 1.44 (s, 1H).

3-Methylaminomethyl-6-[4-(4-naphthalen-1-yl-piperazin-1-yl)-butoxy]-pyridin-2-ylamine (709 mg, 1.69 mmol) was dissolved in THF (10 mL) and cooled to 0° C. Phenyl chloroformate (291 mg, 0.23 mL, 1.86 mmol) was added dropwise followed by $Et_3N$ (342 mg, 0.47 mL, 3.38 mmol). The mixture was allowed to warm to room temperature for 45 minutes. Water (20 mL) and EtOAc (20 mL) were added. The organic layer was separated, washed with water (2×20 mL) and brine (20 mL), dried over Na2SO4, filtered and concentrated in vacuo to give a yellow foam (850 mg, 93%). $^1$H NMR (400 MHz, $CDCl_3$) δ 8.23–8.18 (m, 1H), 7.81 (d, 1H), 7.60–7.04 (m, 11H), 6.02 (d, 1H), 5.24 (s, 2H), 4.38 (s, 2H), 4.20 (t, 2H), 3.24–3.00 (m, 4H), 2.99 (s, 3H), 2.95–2.64 (m, 4H), 2.60–2.50 (m, 2H), 1.90–1.70 (m, 4H).

The foam (850 mg, 1.57 mmol) was dissolved in THF (20 mL) and the solution was cooled to 0° C. LDA (3.94 mL, 7.89 mmol, 2.0 M solution in heptane/THF/ethylbenzene) was added dropwise and the mixture became a dark orange color. The mixture was allowed to warm to room temperature over 1 hour and water (10 mL) and EtOAc (20 mL) were added. The organic layer was separated, washed with water (2×20 mL) and brine (20 mL), dried over $Na_2SO_4$, filtered and concentrated in vacuo. The residual oil was purified by column chromatography (6% MeOH/EtOAc) to yield the title compound as a light yellow powder (308 mg, 41%). mp 180–182° C.; $^1$H NMR (400 MHz, $CDCl_3$) δ 8.20 (d, 1H), 7.82 (d, 1H), 7.60–7.40 (m, 4H), 7.23–7.20 (m, 1H), 7.10 (d, 1H), 6.75 (s, 1H), 6.30 (d, 1H), 4.39 (s, 2H), 4.23 (t, 2H), 3.24 (m, 4H), 3.02 (s, 3H), 2.84–2.60 (m, 4H), 2.80–2.70 (m, 2H), 1.85–1.64 (m, 4H).

Example F9

Synthesis of 7-{5-[4-(2,3-Dichloro-phenyl)-piperazin-1-yl]-pentyl}-4,4-dimethyl-1,4-dihydro-pyrido[2,3-d][1,3]oxazin-2-one A first intermediate compound, N-[3-Acetyl-6-(5-chloro-pent-1-enyl)-pyridin-2-yl]-2,2-dimethyl-propionamide, was produced as follows: To a solution of N-(3-acetyl-6-chloro-pyridin-2-yl)-2,2-dimethyl-propionamide (7.0 g, 27.5 mmol) in DME (110 mL) purged and degassed with $N_2$ was added $Pd(Ph_3P)_4$ (953 mg, 0.83 mmol, 3 mol %, Strem). 5-Chloro-1-pentenyl boronic acid (6.12 g, 41.2 mmol, 1.5 equiv) was added followed by 2M $Na_2CO_3$ (6.12 g, 57.8 mmol in 28 mL of $H_2O$). The mixture was refluxed overnight. The reaction was concentrated and then diluted with THF (100 mL) and sonicated for 3 min. A white sticky precipitate formed. The mixture was filtered and washed with THF. The filtrate was concentrated and absorbed onto $SiO_2$. Purification by liquid chromatography (20–25% EtOAc/Hexanes) gave the product as a yellow solid. Recrystallization from $Et_2O$/Hexanes gave the first intermediate compound as a pale yellow crystalline solid (6.49 g, 20.1 mmol, 73%). MS: APCI: M+1: 323.2 (Exact Mass: 322.14).

A second intermediate compound, N-(3-Acetyl-6-{5-[4-(2,3-dichloro-phenyl)-piperazin-1-yl]-pent-1-enyl}-pyridin-2-yl)-2,2-dimethyl-propionamide, was produced as follows: To a mixture of N-[3-acetyl-6-(5-chloro-pent-1-enyl)-pyridin-2-yl]-2,2-dimethyl-propionamide (6.34 g, 19.7 mmol)

and 2,3-dichlorophenylpiperazine hydrochloride (6.35 g, 23.75 mmol, 1.2 equiv) in CH$_3$CN (100 mL) was added K$_2$CO$_3$ (8.2 g, 59.4 mmol, 3 equiv) followed by KI (332 mg, 2 mmol, 0.1 equiv). The mixture was refluxed for 2 days. H$_2$O was added to dissolve the salts and the mixture was extracted with EtOAc. The organic layer was washed with saturated NaHCO$_3$ and brine, dried over Na$_2$SO$_4$ and concentrated to give a dark brown oil. Purification by liquid chromatography (5% EtOAc/CH$_2$Cl$_2$ to 4% MeOH/CH$_2$Cl$_2$) gave a light brown foam (5.0 g). Recrystallization from CH$_3$CN gave the second intermediate compound as a light tan solid (2.45 g, 4.73 mmol, 24%). The filtrate was concentrated and purified by liquid chromatography (3–4% MeOH/CH$_2$Cl$_2$) to give additional product as a yellow foam (1.27 g, 2.45 mmol, 12%). MS: APCI: M+1: 517.1 (Exact Mass: 516.21).

A third intermediate compound, N-(3-Acetyl-6-{5-[4-(2,3-dichloro-phenyl)-piperazin-1-yl]-pentyl}-pyridin-2-yl)-2,2-dimethyl-propionamide, was produced as follows: N-(3-Acetyl-6-{5-[4-(2,3-dichloro-phenyl)-piperazin-1-yl]-pent-1-enyl}-pyridin-2-yl)-2,2-dimethyl-propionamide (2.40 g, 4.62 mmol) was hydrogenated using Ra—Ni (0.3 g) in 1:1 EtOH/THF (50 mL) for 2 h. The reaction was filtered and concentrated. Purification by liquid chromatography (4% MeOH/CH$_2$Cl$_2$) gave the third intermediate compound as a yellow oil (2.09 g, 4.02 mmol, 87%). MS: APCI: M+1: 519.2 (Exact Mass: 518.22).

A fourth intermediate compound, 1-(2-Amino-6-{5-[4-(2,3-dichloro-phenyl)-piperazin-1-yl]-pentyl}-pyridin-3-yl)-ethanone, was produced as follows: A solution of N-(3-acetyl-6-{5-[4-(2,3-dichloro-phenyl)-piperazin-1-yl]-pentyl}-pyridin-2-yl)-2,2-dimethyl-propionamide (2.08 g, 4.00 mmol) in 3N HCl (50 mL) was refluxed overnight. The reaction was cooled to room temperature and a precipitate formed. The solid was collected by filtration, washed with H$_2$O and dried to give the title compound as a yellow solid (HCl salt, 1.15 g, 2.44 mmol, 61%). The filtrate was made basic with 6N NaOH and extracted with CH$_2$Cl$_2$ (4×). The organic layer was washed with brine, dried over Na$_2$SO$_4$ and concentrated to give additional fourth intermediate compound (582 mg, 1.34 mmol, 33%) which looked clean by NMR and was used in the next step without purification. MS: APCI: M+1: 435.2 (Exact Mass: 434.16).

A fifth intermediate compound, 2-(2-Amino-6-{5-[4-(2,3-dichloro-phenyl)-piperazin-1-yl]-pentyl}-pyridin-3-yl)-propan-2-ol, was produced as follows: To a solution of 1-(2-amino-6-{5-[4-(2,3-dichloro-phenyl)-piperazin-1-yl]-pentyl}-pyridin-3-yl)-ethanone (575 mg, 1.32 mmol) in THF (8 mL) cooled to 0° C. was added MeMgBr (3M in Et$_2$O, 2.2 mL, 6.60 mmol, 5 equiv) slowly. The reaction was exothermic and turned orange and then a precipitate formed. The reaction was stirred at 0° C. for 15 min and at room temperature for 2 h. The reaction was quenched with careful addition of saturated NH$_4$Cl and H$_2$O. The mixture was extracted with EtOAc. The organic layer was washed with H$_2$O and brine, dried over Na$_2$SO$_4$ and concentrated. Purification by liquid chromatography (6% MeOH/CH$_2$Cl$_2$ with 1% NH$_4$OH) gave a white crystalline solid (490 mg, 1.09 mmol, 82%). MS: APCI: M+1: 451.2 (Exact Mass: 450.20).

To a solution of 2-(2-amino-6-{5-[4-(2,3-dichloro-phenyl)-piperazin-1-yl]-pentyl}-pyridin-3-yl)-propan-2-ol (442 mg, 0.98 mmol) in THF (4 mL) and toluene (1 mL) was added Et$_3$N (0.30 mL, 2.15 mmol, 2.2 equiv). The mixture was cooled to 0° C. and phosgene (20% in toluene, 0.65 mL, 1.3 mmol) was added. A precipitate formed. The reaction was stirred at 0° C. for 15 min and at room temperature for 2 h. MeOH was added to quench the excess phosgene. Saturated NaHCO$_3$ and H$_2$O were added and the mixture was extracted with EtOAc. The organic layer was washed with H$_2$O and brine, dried over Na$_2$SO$_4$ and concentrated. Purification by liquid chromatography (3.5% MeOH/CH$_2$Cl$_2$) gave the title compound as a white foam (411 mg, 0.861 mmol, 88%). The foam was dissolved in Et$_2$O/CH$_2$Cl$_2$ and 1 M HCl in Et$_2$O (0.86 mL) was added. The resulting white precipitate was collected by filtration, washed with Et$_2$O and dried to give a fluffy white solid (400 mg). MS: APCI: M+1: 477.1 (Exact Mass: 476.17).

Example G1

Synthesis of 6-{5-[4-(2,3-Dichloro-phenyl)-piperazin-1-yl]-pentyl}-4H-pyrido[3,2-b][1,4]oxazin-3-one A first intermediate compound, 6-(5-Chloro-pent-1-enyl)-4H-pyrido[3,2-b][1,4]oxazin-3-one, was produced as follows: To a solution of 6-bromo-4H-pyrido[3,2-b][1,4]oxazin-3-one (2.0 g, 8.73 mmol, WO 02/056882) in DME (45 mL) was added 5-chloro-pent-1-enyl-boronic acid (1.94 g, 13.09 mmol), followed by Pd(PPh$_3$)$_4$ (0.252 g, 0.218 mmol) and 2M Na$_2$CO$_3$ (1.855 g in 8.7 mL H$_2$O). The reaction was refluxed for 14 hours. The reaction was cooled, and partitioned between ethyl acetate and water. The organic layer was washed with brine, dried over Na$_2$SO$_4$ and concentrated. Purification by chromatography on silica gel (0–40% EtOAc/Hexanes) gave the first intermediate compound as a white solid (1.935 g, 88%). MS: APCI: M+1: 253.1 (Exact Mass: 252.07).

A second intermediate compound, 6-{5-[4-(2,3-Dichloro-phenyl)-piperazin-1-yl]-pent-1-enyl}-4H-pyrido[3,2-b][1,4]oxazin-3-one, was produced as follows: To a solution of 6-(5-chloro-pent-1-enyl)-4H-pyrido[3,2-b][1,4]oxazin-3-one (0.710 g, 2.80 mmol) in CH$_3$CN (10 mL) was added 1-(2,3-dichloro-phenyl)-piperazine (0.974 g, 4.21 mmol), followed by potassium carbonate (0.77 g, 5.6 mmol) and potassium iodide (0.092 g, 0.56 mmol). The reaction was refluxed for 14 hours. The reaction was cooled to room temperature and partitioned between EtOAc and H$_2$O. The organic layer was washed with saturated NaHCO$_3$ and brine, dried over Na$_2$SO$_4$ and concentrated to give an oil. Purification by chromatography on silica gel (0–7% MeOH/EtOAc) afforded the second intermediate compound as a white solid (0.903 g, 72%). MS: APCI: M+1: 447.1 (Exact Mass: 446.13).

6-{5-[4-(2,3-Dichloro-phenyl)-piperazin-1-yl]-pent-1-enyl}-4H-pyrido[3,2-b][1,4]oxazin-3-one (0.774 g, 1.73 mmol) was hydrogenated using Ra—Ni (0.25 g) in THF for 16 hours. The reaction was filtered and concentrated to give an oil. Ethyl acetate was added and the product crashed out. The precipitate was filtered and dried to give the title compound as a white solid (0.645 g, 83%). MS: APCI: M+1: 449.1 (Exact Mass: 448.14).

Example G2

Synthesis of 6-{5-[4-(5,6,7,8-Tetrahydro-naphthalen-1-yl)-piperazin-1-yl]-pentyl}-4H-pyrido[3,2-b][1,4]oxazin-3-one An intermediate compound, 6-{5-[4-(5,6,7,8-Tetrahydro-naphthalen-1-yl)-piperazin-1-yl]-pent-1-enyl}-4H-pyrido[3, 2-b][1,4]oxazin-3-one, was produced as follows: To a solution of 6-(5-chloro-pent-1-enyl)-4H-pyrido[3,2-b][1,4]oxazin-3-one (0.408 g, 1.61 mmol) in $CH_3CN$ (7 mL) was added 1-(5,6,7,8-tetrahydro-naphthalen-1-yl)-piperazine (0.523 g, 2.41 mmol), followed by potassium carbonate (0.445 g) and potassium iodide (0.053 g, 0.322 mmol). The reaction was refluxed for 14 hours. The reaction was cooled to room temperature and partitioned between EtOAc and $H_2O$. The organic layer was washed with saturated $NaHCO_3$ and brine, dried over $Na_2SO_4$ and concentrated to give an oil. Purification by chromatography on silica gel (0–5% MeOH/EtOAc) afforded the first intermediate compound as a yellow solid (0.172 g, 72%). MS: APCI: M+1: 433.2 (Exact Mass: 432.25).

6-{5-[4-(5,6,7,8-Tetrahydro-naphthalen-1-yl)-piperazin-1-yl]-pent-1-enyl}-4H-pyrido[3,2-b][1,4]oxazin-3-one (0.098 g, 0.226 mmol) was hydrogenated using Ra—Ni in THF for 16 hours. The reaction was filtered and concentrated to give an oil. Purification by chromatography on silica gel (0–5% MeOH/EtOAc) afforded the title compound as a film (0.059 g, 61%). This was dissolved in $Et_2O$ and 1M HCl in $Et_2O$ (1 equivalent) was added. The resulting precipitate was filtered and dried to give a white solid. MS: APCI: M+1: 435.5 (Exact Mass: 434.27).

Example G3

Synthesis of 6-{4-[4-(2,3-Dichloro-phenyl)-piperazin-1-yl]-butoxy}-4H-pyrido[3,2-b][1,4]oxazin-3-one A first intermediate compound, 6-Amino-4H-pyrido[3,2-b][1,4]oxazin-3-one, was produced as follows: A mixture of 6-nitro-4H-pyrido[3,2-b][1,4]oxazin-3-one (34.23 g, 0.1755 mol), 20% Pd—C (3.0 g, 50% $H_2O$) and DMF (1 L) was hydrogentated at 20 psi $H_2$ pressure. After 2 h, uptake of $H_2$ ceased with 141 psi of $H_2$ being absorbed. The reaction mixture was filtered through a pad of Celite®, washing with DMF (500 mL). The filtrate was diluted with cold $H_2O$ (2 L) to give a solid. The solid was collected, washed with $H_2O$, slurried in EtOH (150 mL), collected, washed with heptane and dried to give the first intermediate compound (23.60 g, 81%) as a gray-tan solid.

A second intermediate compound, 6-Fluoro-4H-pyrido[3,2-b][1,4]oxazin-3-one, was produced as follows: A 1 gallon Nalgene jar (with openings in the top for a $N_2$ inlet and addition of solids) was cooled in an ice/salt bath and hydrogen fluoride-pyridine (500 g) was added. With magnetic stirring and under a stream of $N_2$, 6-amino-4H-pyrido[3,2-b][1,4]oxazin-3-one (88.48 g, 0.5362 mol, 1.0 equiv) was added slowly portion-wise. When addition was complete, the red-brown mixture was stirred for 0.25 h to ensure complete solution. Sodium nitrite (44.40 g, 0.6435 mol, 1.2 equiv) was added cautiously portion-wise over 0.5 hr. Each addition was exothermic and accompanied by the evolution of HF and $N_2$. When addition was complete the reaction mixture was stirred in the ice/salt bath for 1 h. The reaction was quenched by the slow, careful addition of ice-cold $H_2O$ (2 L). The resulting solid was collected, washed with $H_2O$, resuspended in $H_2O$ (3×1 L), collected, washed with $H_2O$ and dried on the filter for 1 h. The solid was washed with heptane and dried under a $N_2$ stream for 2 h. Final drying in a vacuum oven for 24 h at ~40° C. gave the second intermediate compound (69.03 g, 76%) as an orange-brown solid. Mp 179.9–181.2°.

A third intermediate compound, 6-(4-Benzyloxy-butoxy)-4H-pyrido[3,2-b][1,4]oxazin-3-one, was produced as follows: A solution of 4-benzyloxy-butan-1-ol I (34.31 g, 33.37 mL, 190.3 mmol) and potassium t-butoxide (1 M solution; 181 mL) in THF (60 mL) was prepared and stirred at room temperature for 20 min. A suspension of 6-fluoro-4H-pyrido [3,2-b][1,4]oxazin-3-one (8 g, 48 mmol) in THF (100 mL) was prepared, and the alcohol/base solution was added to this solution via canula. The reaction was heated at reflux for 25 hours. The reaction was quenched with saturated $NH_4Cl$ and water. The solution was brought to a pH of 8 and extracted with ethyl acetate. The organic layer was washed with brine and concentrated to give a solid. Purification by $SiO_2$ chromatography (0–70% EtOAc/hexanes) gave the third intermediate compound as a white solid (6.6 g, 42%). MS: APCI: M+1: 329.2 (Exact Mass: 328.14).

A fourth intermediate compound, 6-(4-Hydroxy-butoxy)-4H-pyrido[3,2-b][1,4]oxazin-3-one, was produced as follows: To a solution of 6-(4-benzyloxy-butoxy)-4H-pyrido [3,2-b][1,4]oxazin-3-one (6.4 g, 19 mmol) in MeOH/THF (100 mL) was added 20% Pd/C (1.5 g) and the mixture was hydrogenated for 12 h. The reaction was filtered, concentrated and purified by liquid chromatography (0–10% MeOH/$CH_2Cl_2$) to give the fourth intermediate compound as a white solid (4.3 g, 18 mmol, 93%). MS: APCI: M+1: 239.1 (Exact Mass: 238.10).

A fifth intermediate compound, 4-(3-Oxo-3,4-dihydro-2H-pyrido[3,2-b][1,4]oxazin-6-yloxy)-butyraldehyde, was produced as follows: To a suspension of 6-(4-hydroxy-butoxy)-4H-pyrido[3,2-b][1,4]oxazin-3-one (4.3 g, 18.02 mmol) in dichloroethane (30 mL) was added IBX (15 g, 54 mmol). This mixture was heated at 80° C. for 5 hours. The reaction was cooled and stirred, and then filtered. The filter cake was washed with $CH_2Cl_2$ until the product was removed. The filtrate was concentrated to give a red oil, which was purified by $SiO_2$ chromatography (0–7% MeOH/$CH_2Cl_2$) to give the fifth intermediate compound as a red oil (3.90 g, 16.5 mmol, 92%). MS: APCI: M+1: 237.1 (Exact Mass: 236.08).

To a solution of 4-(3-oxo-3,4-dihydro-2H-pyrido[3,2-b] [1,4]oxazin-6-yloxy)-butyraldehyde (0.325 g, 1.37 mmol) in dichloroethane (6 mL) was added a solution of 1-(2,3-dichloro-phenyl)-piperazine (0.318 g, 1.37 mmol) in dichloroethane (3 mL) via cannula. The mixture was stirred for 20 minutes at room temperature and $NaBH(OAc)_3$ (0.377 g, 1.78 mmol) was added. The reaction was stirred for 2.5 h and quenched with saturated $NaHCO_3$ and water. The mixture was extracted with EtOAc and the organic layer was washed with saturated $NaHCO_3$, water and brine, dried over $Na_2SO_4$ and concentrated. Purification by chromatography on silica gel (0–5% MeOH/$CH_2Cl_2$) gave a foam. $Et_2O$ was added and product crashed out. The precipitate was filtered and dried to give the title compound as a white solid (0.386 g, 0.854 mmol, 63%). MS: APCI: M+1: 451.1 (Exact Mass: 450.12).

Example G4

Synthesis of 6-[4-(4-Indan-4-yl-piperazin-1-yl)-butoxy]-4H-pyrido[3,2-b][1,4]oxazin-3-one The reductive amination procedure from Example G3 was followed using 1-indan-4-yl-piperazine to give the title compound (0.24 g; 69%). MS: APCI: M+1: 423.3 (Exact Mass: 422.23).

Example G5

Synthesis of 6-[4-(4-Naphthalen-1-yl-piperazin-1-yl)-butoxy]-4H-pyrido[3,2-b][1,4]oxazin-3-one The reductive amination procedure from Example G3 was followed using 1-naphthalen-1-yl-piperazine to give the title compound (0.24 g, 56%). MS: APCI: M+1: 433.1 (Exact Mass: 432.22).

Example G6

Synthesis of 6-{4-[4-(6-Methoxy-pyridin-2-yl)-piperazin-1-yl]-butoxy}-4H-pyrido[3,2-b][1,4]oxazin-3-one The reductive amination procedure from Example G3 was followed using 1-(6-methoxy-pyridin-2-yl)-piperazine to give the title compound (0.21 g, 62%). MS: APCI: M+1: 414.2 (Exact Mass: 413.21).

Example G7

Synthesis of 6-{4-[4-(7-Fluoro-naphthalen-1-yl)-piperazin-1-yl]-butoxy}-4H-pyrido[3,2-b][1,4]oxazin-3-one The reductive amination procedure from Example G3 was followed using 1-(7-fluoro-naphthalen-1-yl)-piperazine to give the title compound (0.31 g, 64%). MS: APCI: M+1: 451.3 (Exact Mass: 450.21).

Example G8

Synthesis of 6-{4-[4-(5,6,7,8-Tetrahydro-naphthalen-1-yl)-piperazin-1-yl]-butoxy}-4H-pyrido[3,2-b][1,4]oxazin-3-one The reductive amination procedure from Example G3 was followed using 1-(5,6,7,8-tetrahydro-naphthalen-1-yl)-piperazine to give the title compound (0.23 g, 65%). MS: APCI: M+1: 437.3 (Exact Mass: 436.25).

Example H1

Synthesis of 2-{4-[4-(2,3-Dichloro-phenyl)-piperazin-1-yl]-butoxy}-8H-pyrido[2,3-d]pyrimidin-7-one A first intermediate compound, 2-Methanesulfinyl-8H-pyrido[2,3-d]pyrimidin-7-one, was produced as follows: To a suspension of 2-methylsulfanyl-8H-pyrido[2,3-d]pyrimidin-7-one (5.0 g, 25.9 mmol) in $CH_2Cl_2$ (100 mL), $CHCl_3$ (50 mL) and MeOH (10 mL, the starting material still did not dissolve) was added the oxaziridine (8.11 g, 31.05 mmol, 1.2 equiv) as a solid. The reaction became homogenous after 3 h and was stirred overnight at RT. The reaction was concentrated and $CH_2Cl_2$/MeOH was added to dissolve the residue. Much of the solid did not dissolve so the mixture was filtered to give an off-white solid which was the first intermediate compound (2.31 g, 11.04 mmol, 43%). MS: APCI: M+1: 210.1 (Exact Mass: 209.03).

A second intermediate compound, 2-[4-(Tetrahydro-pyran-2-yloxy)-butoxy]-8H-pyrido[2,3-d]pyrimidin-7-one, was produced as follows: To a solution of 4-(tetrahydro-pyran-2-yloxy)-1-butanol (4.45 g, 25.3 mmol, 2.5 equiv) in THF (20 mL) cooled to 0° C. was added 1M KOtBu in THF (25 mL, 25 mmol). The solution was stirred at 0° C. for 20 min and then added to a suspension of 2-methanesulfinyl-8H-pyrido[2,3-d]pyrimidin-7-one (2.12 g, 10.13 mmol) in DMF (30 mL) at RT. The reaction became homogenous and was stirred at room temperature for 1 h. Saturated NH4Cl and H2O were added to quench the reaction. The mixture was extracted with EtOAc. The organic layer was washed with H2O and brine, dried over Na2SO4 and concentrated. Purification by liquid chromatography (70% EtOAc/Hexanes to 100% EtOAc) gave the second intermediate compound as a white solid (1.95 g, 6.11 mmol, 60%). MS: APCI: M+1: 320.2 (Exact Mass: 319.15).

A third intermediate compound, 2-(4-Hydroxy-butoxy)-8H-pyrido[2,3-d]pyrimidin-7-one, was produced as follows: To a suspension of 2-[4-(tetrahydro-pyran-2-yloxy)-butoxy]-8H-pyrido[2,3-d]pyrimidin-7-one (1.95 g, 6.11 mmol) in EtOH (30 mL) and $CH_2Cl_2$ (2 mL, added to help dissolve the starting material) was added PPTS (151 mg, 0.6 mmol). The solution was stirred overnight at room temperature and then heated at 60° C. for 5 h. The reaction was concentrated to give a white solid. Purification by liquid chromatography (6% MeOH/CH2Cl2) gave the third intermediate compound as a white solid (1.22 g, 5.19 mmol, 85%). MS: APCI: M+1: 236.1 (Exact Mass: 235.10).

A fourth intermediate compound, 4-(7-Oxo-7,8-dihydro-pyrido[2,3-d]pyrimidin-2-yloxy)-butyraldehyde, was produced as follows: To a solution of 2-(4-hydroxy-butoxy)-8H-pyrido[2,3-d]pyrimidin-7-one (251 mg, 1.07 mmol) in DMSO (3 mL) was added a solution of IBX (597 mg, 2.13 mmol) in DMSO (7 mL, 0.3 M). The reaction was stirred at room temperature for 90 min, cooled to 0° C. and quenched with 5% NaHCO3. The mixture was extracted with $CH_2Cl_2$ (4×). The organic layer was washed with 5% NaHCO3 and brine, dried over $Na_2SO_4$ and concentrated to give the fourth intermediate compound as a white solid (171 mg, 0.733 mmol, 69%). MS: APCI: M+1: 234.1 (Exact Mass: 233.08).

To a suspension of 4-(7-oxo-7,8-dihydro-pyrido[2,3-d]pyrimidin-2-yloxy)-butyraldehyde (235 mg, 1.01 mmol) in dichloroethane (5 mL) was added 1-(2,3-dichloro-phenyl)-piperazine hydrochloride (270 mg, 1.01 mmol) followed by Et3N (0.28 mL, 2.0 mmol, 2 equiv). After 10 min at RT, NaBH(OAc)3 (297 mg, 1.4 mmol) was added as a powder. The reaction was stirred for 2 h at room temperature and quenched with saturated NaHCO3 and H2O. The mixture was extracted with EtOAc (with a little MeOH to help dissolve the solids). The organic layer was washed with brine and concentrated. Purification by liquid chromatography (5% MeOH/CH2Cl2 with 1% NH4OH) gave the title compound as a white solid (375 mg, 0.836 mmol, 83%). MS: APCI: M+1: 448.1 (Exact Mass: 447.12).

The pyrimidines of Examples H2 and H3 were synthesized in a combinatorial library format by reductive amination of the appropriate piperazine starting materials with 4-(7-oxo-7,8-dihydro-pyrido[2,3-d]pyrimidin-2-yloxy)-butyraldehyde using the procedure outlined in Example H1.

Example H2

Synthesis of 2-{4-[4-(2-Isopropoxy-phenyl)-piperazin-1-yl]-butoxy}-8H-pyrido[2,3-d]pyrimidin-7-one The title compound was isolated as a white solid (223 mg, 0.510 mmol, 59.4%). MS: APCI: M+1: 438.1 (Exact Mass: 437.24).

Example H3

Synthesis of 2-[4-(4-Indan-4-yl-piperazin-1-yl)-butoxy]-8H-pyrido[2,3-d]pyrimidin-7-one The title compound was isolated as a white solid (270 mg, 0.643 mmol, 75.1%). MS: APCI: M+1: 420.3 (Exact Mass: 419.23).

Example H4

Synthesis of 2-[4-(4-Naphthalen-1-yl-piperazin-1-yl)-butoxy]-8H-pyrido[2,3-d]pyrimidin-7-one Following the same procedure as in Example H12 and starting from 2-methanesulfonyl-8H-pyrido[2,3-d]pyrimidin-7-one (300 mg, 1.332 mmol, U.S. Pat. No. 6,498,163) and 4-(4-naphthalen-1-yl-piperazin-1-yl)-butan-1-ol (416 mg, 1.465 mmol), the title compound was made as a solid (300 mg, 0.683 mmol, 51.3%). MS: APCI: M+1: 430.2 (Exact Mass: 429.22).

Example H5

Synthesis of 6-Fluoro-4-methyl-2-[4-(4-naphthalen-1-yl-piperazin-1-yl)-butoxy]-8H-pyrido[2,3-d]pyrimidin-7-one Following the same procedure as in Example H12 and starting from 6-fluoro-2-methanesulfonyl-4-methyl-8H-pyrido[2,3-d]pyrimidin-7-one (300 mg, 1.166 mmol, U.S. Pat. No. 6,498,163) and 4-(4-naphthalen-1-yl-piperazin-1-yl)-butan-1-ol (331 mg, 1.166 mmol), the title compound was made as a solid (323 mg, 0.684 mmol, 58.7%). MS: APCI: M+1: 462.1 (Exact Mass: 461.22).

Example H6

Synthesis of 2-{4-[4-(6-Isopropyl-pyridin-2-yl)-piperazin-1-yl]-butoxy}-4-methyl-8H-pyrido[2,3-d]pyrimidin-7-one A first intermediate compound, 2-Methanesulfonyl-4-methyl-8H-pyrido[2,3-d]pyrimidin-7-one, was produced as follows: A solution of 4-methyl-2-methylsulfanyl-8H-pyrido[2,3-d]pyrimidin-7-one (24 g, 0.1158 mol, U.S. Pat. No. 6,498,163) in a mixture of $CH_2Cl_2$ (1.9 L) and methanol (300 mL) is treated with m-chloroperbenzoic acid (103 g, 60%, 0.345 mol) in portions at room temperature. The mixture is stirred for 24 h, cooled to ~5° C. and quenched with saturated sodium bicarbonate solution. The solids are filtered, washed thoroughly with water followed by ether and dried in vacuum to give the first compound as a solid (10 g, 0.042 mol, 36%). MS: APCI: M+1: 240.0 (Exact Mass: 239.04).

A second intermediate compound, 4-Methyl-2-[4-(tetrahydro-pyran-2-yloxy)-butoxy]-8H-pyrido[2,3-d]pyrimidin-7-one, was produced as follows: To a ice bath cooled solution of 4-(tetrahydro-pyran-2-yloxy)-butan-1-ol (27.3 g, 0.1567 mol) in dry THF (125 mL) is added drop wise a solution of KOtBu (1M, 155 mL, 0.155 mol) in THF within 15 min. The mixture is then stirred at 0° C. for 2 h. To this mixture is added a suspension of 2-methanesulfonyl-4-methyl-8H-pyrido[2,3-d]pyrimidin-7-one (15 g, 0.0627 mol) in DMF (225 mL) at room temperature within 15 min. The orange red colored reaction mixture is stirred at room temperature for 1.5 h, cooled and quenched with saturated $NH_4Cl$ solution (150 mL) and water (2 L). The mixture is extracted with ethyl acetate (2×0.75 L) and the organic layer is washed with brine (300 mL), dried over anhydrous sodium sulfate, filtered through a small bed of silica gel eluting with 5% methanol in ethyl acetate (750 mL) and concentrated. The residue is then triturated with hexane, filtered and dried to give the second intermediate compound as a white solid (16.5 g, 0.0495 mol 78%). MS: APCI: M+1: 334.0 (Exact Mass: 333.17).

A third intermediate compound, 2-(4-Hydroxy-butoxy)-4-methyl-8H-pyrido[2,3-d]pyrimidin-7-one, was produced as follows: A mixture of 4-methyl-2-[4-(tetrahydro-pyran-2-yloxy)-butoxy]-8H-pyrido[2,3-d]pyrimidin-7-one (16.5 g, 0.049 mol) and PPTS (1.24 g, 0.0049 mol) in ethanol (250 mL) and $CH_2Cl_2$ (20 mL) is stirred at room temperature for 16 h, followed by heating at reflux (~90° C.) for 3 h. The cloudy reaction mixture is evaporated under vacuum and the residue is triturated in hexane-ethyl acetate (150 mL, 1:1) and dried to give the third intermediate compound as a yellow powder (12.5 g, 0.049 mol, 100%). MS: APCI: M+1: 250.0 (Exact Mass: 249.11).

A fourth intermediate compound, 4-(4-Methyl-7-oxo-7,8-dihydro-pyrido[2,3-d]pyrimidin-2-yloxy)-butyraldehyde, was produced as follows: A stirred solution of IBX (26 g, 0.092 mol) in DMSO (220 ml) is treated with 2-(4-hydroxy-butoxy)-4-methyl-8H-pyrido[2,3-d]pyrimidin-7-one (11 g, 0.0467 mol) portion wise while stirring at room temperature during 30 min and the reaction is stirred at room temperature for an additional 2 h. The mixture is cooled and treated with saturated $NaHCO_3$ (150 mL) and extracted with chloroform (4×0.5 L). The combined organic layer is washed with brine/ice (2×), dried over $Na_2SO_4$, filtered and concentrated. The residue is stirred with ether, filtered, washed with ether and dried to give 6 g of the crude, which shows it to be a mixture. The ether filtrate residue also shows some product, but mostly starting material. The residue from the filtrate and the crude (11 g) are subjected to re-oxidation as above using fresh IBX (15.5 g, 0.055 mol) in DMSO (150 mL), but stirred at 30° C. for 3 h. Workup as above yielded the fourth intermediate compound as an off-white powder (8.3 g, 0.057 mol, 66.8%). MS: APCI: M+1: 248.0 (Exact Mass: 247.10).

4-(4-Methyl-7-oxo-7,8-dihydro-pyrido[2,3-d]pyrimidin-2-yloxy)-butyraldehyde (74.2 mg, 0.3 mmol) and 1-(6-isopropyl-pyridin-2-yl)-piperazine (62.8 mg, 0.306 mmol) were combined in methylene chloride and stirred in a vial over sieves for 10 min. Sodium triacetoxyborohydride (89 mg, 0.42 mmol) was added and the reaction was stirred overnight. The reaction was quenched by slowly adding water and then the mixture was filtered. The residue was partitioned between $CH_2Cl_2$ and water and the organic layer was concentrated. Purification by liquid chromatography (MPLC, gradient of 100% $CH_2Cl_2$ to 100% of a 10% MeOH in $CH_2Cl_2$ solution) gave the title compound as a low melting solid (55 mg, 0.126 mmol, 42%). MS: APCI: M+1: 437.3 (Exact Mass: 436.26).

The pyrimidines of Examples H6–H11 were synthesized in combinatorial library format by reductive amination of the appropriate piperazine starting materials with 4-(4-methyl-7-oxo-7,8-dihydro-pyrido[2,3-d]pyrimidin-2-yloxy)-butyraldehyde following the procedure outlined in Example H7.

Example H7

Synthesis of 2-{4-[4-(6-Ethyl-pyridin-2-yl)-piperazin-1-yl]-butoxy}-4-methyl-8H-pyrido[2,3-d]pyrimidin-7-one The title compound was isolated as a low melting solid (87 mg, 0.206 mmol, 68.6%). MS: APCI: M+1: 423.3 (Exact Mass: 422.24).

Example H8

Synthesis of 2-[4-(4-Indan-4-yl-piperazin-1-yl)-butoxy]-4-methyl-8H-pyrido[2,3-d]pyrimidin-7-one The title compound was isolated as a white powder (66 mg, 0.152 mmol, 50.74%). MS: APCI: M+1: 434.2 (Exact Mass: 433.25).

Example H9

Synthesis of 4-Methyl-2-{4-[4-(5,6,7,8-tetrahydro-naphthalen-1-yl)-piperazin-1-yl]-butoxy}-8H-pyrido[2,3-d]pyrimidin-7-one The title compound was isolated as a white powder (75 mg, 0.167 mmol, 55.86%). MS: APCI: M+1: 448.3 (Exact Mass: 447.26).

Example H10

Synthesis of 2-{4-[4-(7-Fluoro-naphthalen-1-yl)-piperazin-1-yl]-butoxy}-4-methyl-8H-pyrido[2,3-d]pyrimidin-7-one The title compound was isolated as a solid (61 mg, 0.132 mmol, 44.06%). MS: APCI: M+1: 462.2 (Exact Mass: 461.22).

Example H11

Synthesis of 2-{4-[4-(7-Methoxy-naphthalen-1-yl)-piperazin-1-yl]-butoxy}-4-methyl-8H-pyrido[2,3-d]pyrimidin-7-one The title compound was isolated as a solid (43 mg, 0.09 mmol, 30.3%). MS: APCI: M+1: 474.3 (Exact Mass: 473.24).

Example H12

Synthesis of 4-Methyl-2-[4-(4-naphthalen-1-yl-piperazin-1-yl)-butoxy]-8H-pyrido[2,3-d]pyrimidin-7-one 2-Methanesulfonyl-4-methyl-8H-pyrido[2,3-d]pyrimidin-7-one (300 mg, 1.245 mmol, U.S. Pat. No. 6,498,163), 4-(4-naphthalen-1-yl-piperazin-1-yl)-butan-1-ol (392 mg, 1.379 mmol) and sodium t-butoxide (362 mg, 3.76 mmol) were combined in a vial. Dioxane (10 mL) was added and the solution was stirred for 1 h. The reaction mixture was concentrated and then partitioned between ethyl acetate and water. The organic layer was washed with water, dried over Na$_2$SO$_4$, filtered and concentrated. Purification by liquid chromatography (MPLC, gradient of 100% CH$_2$Cl$_2$ to 100% of 100:8:1 CH$_2$Cl$_2$:EtOH:NH$_4$OH solution) gave the title compound as a solid (220 mg, 0.485 mmol, 38%). MS: APCI: M+1: 444.2 (Exact Mass: 443.23).

Example H13

Synthesis of 2-{4-[4-(7-Fluoro-naphthalen-1-yl)-piperazin-1-yl]-butoxy}-4,8-dimethyl-8H-pyrido[2,3-d]pyrimidin-7-one A first intermediate compound, 2-Methanesulfonyl-4,8-dimethyl-8H-pyrido[2,3-d]pyrimidin-7-one, was produced as follows: A solution of 4,8-dimethyl-2-methylthio-8-hydropyridino[2,3-d]pyrimidin-7-one (48.0 g, 0.216 mol) in a mixture of CH$_2$Cl$_2$ (2.8 L) and methanol (410 mL) is treated with m-chloroperbenzoic acid (100 g, 57–86%) in portions at room temperature. The mixture is stirred for 24 h, filtered and the filtrate is concentrated. The residue is dissolved in chloroform, washed with saturated NaHCO$_3$ (2×300 mL), dried over Na$_2$SO$_4$, filtered and concentrated to give the crude which upon purification by column chromatography (EtOAc/Hexanes) gave the first intermediate compound as white solid (38 g, mmol, 0.150 mol, 69%). MS: APCI: M+1: 254.0 (Exact Mass: 253.05).

A second intermediate compound 4,8-Dimethyl-2-[4-(tetrahydro-pyran-2-yloxy)-butoxy]-8H-pyrido[2,3-d]pyrimidin-7-one, was produced as follows: To a solution of 4-(tetrahydro-pyran-2-yloxy)-butan-1-ol (82.3 g, 0.472 mol) in dry THF (450 mL) cooled to 0° C. is added drop-wise a solution of KOtBu (1M in THF, 473 mL, 0.472 mol) within 1 h. The mixture is stirred at 0° C. for 1 h and then a solution of 2-methanesulfonyl-4,8-dimethyl-8H-pyrido[2,3-d]pyrimidin-7-one (38 g, 0.15 mol) in DMF (475 mL) is added at room temperature within 15 min. The mixture is stirred at room temperature for 1 h, cooled and quenched with saturated NH$_4$Cl (300 mL) followed by water (2 L) and extracted with EtOAc (3×1 L). The organic layer is washed with brine (3×500 mL), dried over MgSO$_4$, filtered and concentrated. The residue is purified by column chromatography (EtOAc/Hexane, 70%–100%) to afford the second intermediate compound as an oil (24.6 g, 0.071 mol, 47.2%). MS: APCI: M+1: 348.0 (Exact Mass: 347.18).

A third intermediate compound, 2-(4-Hydroxy-butoxy)-4,8-dimethyl-8H-pyrido[2,3-d]pyrimidin-7-one, was produced as follows: A mixture of 4,8-dimethyl-2-[4-(tetrahydro-pyran-2-yloxy)-butoxy]-8H-pyrido[2,3-d]pyrimidin-7-one (24 g, 0.069 mol) and PPTS (1.9 g, 0.0075 mol) in ethanol (200 mL) is heated to ~65° C. overnight. The mixture is evaporated under vacuum. The residue is dissolved in CH$_2$Cl$_2$ (500 mL), washed with water (3×100 mL), NaHCO$_3$ solution (2×100 mL), dried over MgSO$_4$, filtered and evaporated under vacuum. The residue obtained is stirred in ether, filtered, washed with ether and dried to give the third intermediate compound as an off-white solid (9.5 g, 0.361 mol, 52.5%). MS: APCI: M+1: 264.0 (Exact Mass: 263.13).

A fourth intermediate compound, 4-(4,8-Dimethyl-7-oxo-7,8-dihydro-pyrido[2,3-d]pyrimidin-2-yloxy)-butyraldehyde, was produced as follows: A stirred solution of 2-(4-hydroxy-butoxy)-4,8-dimethyl-8H-pyrido[2,3-d]pyrimidin-7-one (9.26 g, 0.0351 mol) in DMSO (180 mL) is treated with IBX (19.7 g, 0.070 mol) and the mixture is stirred at room temperature for 1.5 h. The mixture is cooled to 0° C., treated with saturated NaHCO$_3$ (400 mL) and extracted with CH$_2$Cl$_2$ (4×200 mL). The combined organic layer is washed with 15% NaHCO$_3$ brine/ice (2×100 mL), dried over Na$_2$SO$_4$, filtered and concentrated. The residue obtained is stirred with ether, filtered, washed with ether and dried to give the fourth intermediate compound as a cream white solid (6.9 g, 0.026 mol, 75.2%). MS: APCI: M+1: 262.0 (Exact Mass: 261.11).

4-(4,8-dimethyl-7-oxo-7,8-dihydro-pyrido[2,3-d]pyrimidin-2-yloxy)-butyraldehyde (78.4 mg, 0.30 mmol) and 1-(7-fluoro-naphthalen-1-yl)-piperazine trifluoroacetic acid (105 mg, 0.306 mmol) were combined in methylene chloride and triethylamine (63 mg, 0.63 mmol) was added. The mixture was stirred in a vial over sieves for 10 min. Sodium triacetoxyborohydride (89 mg, 0.420 mmol) was added and the reaction was stirred overnight. The reaction was quenched slowly with water and the mixture was filtered. The residue was partitioned between $CH_2Cl_2$ and water. The organic layer was washed with water and concentrated. Purification by liquid chromatography (MPLC, gradient of 100% $CH_2Cl_2$ to 100% of a 10% MeOH in $CH_2Cl_2$ solution) gave the title compound as a white foam (89 mg, 0.187 mmol, 62.4%). MS: APCI: M+1: 476.2 (Exact Mass: 475.24).

Example H14

Synthesis of 2-{4-[4-(7-Methoxy-naphthalen-1-yl)-piperazin-1-yl]-butoxy}-4,8-dimethyl-8H-pyrido[2,3-d]pyrimidin-7-one The title compound was prepared as described above using 1-(7-methoxy-naphthalen-1-yl)-piperazine to give a pale yellow foam (91 mg, 0.186 mmol, 62.2%). MS: APCI: M+1: 488.2 (Exact Mass: 487.26).

Example I1

Synthesis of 7-{5-[4-(2,3-Dichloro-phenyl)-piperazin-1-yl]-pentyl}-3,4-dihydro-1H-[1,6]naphthyridin-2-one A first intermediate compound, (4-Amino-6-chloro-pyridin-3-yl)-methanol, was produced as follows: To a suspension of $LiAlH_4$ (2.20 g, 58 mmol) in THF (100 mL) was added a solution of 4-amino-6-chloro-nicotinic acid ethyl ester (8.0 g, 36.2 mmol) via cannula. After 90 minutes, $H_2O$ (2.2 mL) was added slowly and the mixture was stirred for 20 minutes. 3M NaOH (2.2 mL) was added, followed by $H_2O$ (6.6 mL) and the mixture was stirred for 1 hour. The precipitate was filtered. The organic layer was washed with saturated $NaHCO_3$ and brine, dried over $Na_2SO_4$ and concentrated to give the first intermediate compound as a yellow solid (6.39 g, 69%). MS: APCI: M+1: 159.1 (Exact Mass: 158.03).

A second intermediate compound, 3-(4-Amino-6-chloro-pyridin-3-yl)-acrylic acid ethyl ester, was produced as follows: To a suspension of (4-amino-6-chloro-pyridin-3-yl)-methanol (6.39 g, 40.29 mmol) in $CH_2Cl_2$, was added barium manganate (17.55 g, 68.49 mmol), followed by (carbethoxymethylene)triphenylphosphorane (19.71 g, 52.37 mmol). The reaction was refluxed for 5 hours and then stirred at room temperature for 14 hours. The reaction was filtered through Celite, washed with $CH_2Cl_2$ and the filtrate was concentrated. $Et_2O$ was added and the mixture was stirred for 14 hours. The precipitate ($Ph_3PO$) was filtered off and the filtrate was concentrated. Purification by liquid chromatography (30–50% EtOAc/Hexanes) gave the second intermediate compound as a white solid (5.85 g, 64%). MS: APCI: M+1: 227.2 (Exact Mass: 226.05).

A third intermediate compound, 3-(4-Amino-6-chloro-pyridin-3-yl)-propionic acid ethyl ester, was produced as follows: 3-(4-Amino-6-chloro-pyridin-3-yl)-acrylic acid ethyl ester (2.51 g, 11.0 mmol) was hydrogenated using 5% Pd/$BaSO_4$ in THF (100 mL) for 28 hours. The reaction was filtered and concentrated to give a yellow oil. Purification by liquid chromatography (20–40% EtOAc/Hexanes) afforded the third intermediate compound as a colorless oil (1.191 g, 48%). MS: APCI: M+1: 229.0 (Exact Mass: 228.05).

A fourth intermediate compound, 7-Chloro-3,4-dihydro-1H-[1,6]naphthyridin-2-one, was produced as follows: To a solution of 3-(4-amino-6-chloro-pyridin-3-yl)-propionic acid ethyl ester (1.034 g, 4.53 mmol) in ethanol, was added DBU. The reaction was heated to 70° C. and stirred for 20 hours. The reaction was cooled and concentrated. Purification by liquid chromatography (20–50% EtOAc/Hexanes) gave the fourth intermediate compound as a white solid (0.794 g, 96%). MS: APCI: M+1: 183.0 (Exact Mass: 182.02).

A fifth intermediate compound, 7-(5-Chloro-pent-1-enyl)-3,4-dihydro-1H-[1,6]naphthyridin-2-one, was produced as follows: To a solution of 7-chloro-3,4-dihydro-1H-[1,6]naphthyridin-2-one (0.908 g, 4.97 mmol) in DME (20 mL) was added 5-chloro-pent-1-enyl-boronic acid (1.475 g, 9.94 mmol), followed by $Pd(PPh_3)_4$ (0.144 g, 0.124 mmol) and 2M $Na_2CO_3$ (1.053 g in 5.0 mL $H_2O$). The reaction was refluxed for 14 hours. The reaction was cooled, and partitioned between EtOAc and water. The organic layer was washed with brine, dried over $Na_2SO_4$ and concentrated. Purification by chromatography on silica gel (0–40% EtOAc/Hexanes) gave the fifth intermediate compound as a white solid (0.763 g, 61%). MS: APCI: M+1: 253.1 (Exact Mass: 252.10).

A sixth intermediate compound, 7-{5-[4-(2,3-Dichloro-phenyl)-piperazin-1-yl]-pent-1-enyl}-3,4-dihydro-1H-[1,6]naphthyridin-2-one, was produced as follows: To a solution of 7-(5-chloro-pent-1-enyl)-3,4-dihydro-1H-[1,6]naphthyridin-2-one (0.72 g, 2.87 mmol) in $CH_3CN$ (10 mL) was added 1-(2,3-dichloro-phenyl)-piperazine (0.994 g, 4.30 mmol), followed by $K_2CO_3$ (0.793 g, 5.74 mmol) and KI (0.095 g, 0.574 mmol). The reaction was refluxed for 14 hours. The reaction was cooled to room temperature and partitioned between EtOAc and H2O. The organic layer was washed with saturated $NaHCO_3$ and brine, dried over $Na_2SO_4$ and concentrated to give an oil. Purification by chromatography on silica gel (10–40% MeOH/EtOAc) afforded the sixth intermediate compound as a white solid (0.903 g, 72%). MS: APCI: M+1: 445.1 (Exact Mass: 444.15).

7-{5-[4-(2,3-Dichloro-phenyl)-piperazin-1-yl]-pent-1-enyl}-3,4-dihydro-1H-[1,6]naphthyridin-2-one (0.417 g, 0.937 mmol) was hydrogenated using Ra—Ni (0.25 g) in THF for 2 hours. The reaction was filtered and concentrated to give a white solid. EtOAc was added and the product crashed out. The precipitate was filtered and dried to give the title compound as a white solid (0.391 g, 93%). MS: APCI: M+1: 447.2 (Exact Mass: 446.16).

Example I2

Synthesis of 7-{4-[4-(5,6,7,8-Tetrahydro-naphthalen-1-yl)-piperazin-1-yl]-butoxy}-3,4-dihydro-1H-[1,6]naphthyridin-2-one The first intermediate compound, 3-(4,6-Diamino-pyridin-3-yl)-acrylic acid ethyl ester, was produced as follows: A mixture of (carbethoxymethylene)triphenylphosphorane (436 g, 1.25 mol) and 4,6-diaminopyridine-3-carbaldehyde (131.8 g, 0.96 mol) in 1,4-dioxane (2.0 L) was refluxed for 2.0 h. The mixture was cooled and filtered through silica gel (800 g) eluting with 0–10% MeOH/EtOAc. The filtrate was concentrated and the residue (~580 g) was used in the next step without further purification.

A second intermediate compound, 7-Amino-1H-[1,6] naphthyridin-2-one, was produced as follows: The residue obtained from the above procedure was refluxed in conc. HCl (1.5 L) for 1.5 h. The mixture was cooled and diluted with water (2.5 L). At 35–40° C., the mixture was washed with EtOAc (3×). The aqueous layer was made basic with 50% NaOH to pH>10 while cooling with a cold water bath. The resulting solid was collected via filtration, rinsed with water, methanol, and oven dried to afford the second intermediate compound (106 g, 68% for two steps) as off-white crystals.

A third intermediate compound, 7-Fluoro-1H-[1,6]naphthyridin-2-one, was produced as follows: To a stirred mixture of HF-pyridine (660 g) and 7-amino-1H-[1,6]naphthyridin-2-one (58 g, 0.36 mol) in a plastic bottle was added $NaNO_2$ (39.7 g, 0.57 mol) in small portions over 30–40 min while cooled with a cold (~10° C.) water bath in order to keep the internal temperature at around RT. After the addition, the mixture was further stirred at room temperature for 20 min before it was poured into water (2.6 L) and stirred for 3.0 h. The resulting solid was collected via filtration, rinsed with water (2×), EtOAc-heptane (1:1, 2×), and oven dried to afford the third intermediate compound (48.6 g, 82%) as pale solid.

A fourth intermediate compound, 7-(4-Benzyloxy-butoxy)-1H-[1,6]naphthyridin-2-one, was produced as follows: A solution of 4-benzyloxy-butan-1-ol (35.98 g, 199.6 mmol) and potassium t-butoxide (21 g, 188 mmol) in THF (60 mL) was prepared and stirred at room temperature for 20 min. A suspension of 7-fluoro-1H-[1,6]naphthyridin-2-one (8.1 g, 49 mmol) in THF (100 mL) was prepared, and the alcohol solution was added to this solution via canula. The reaction was stirred at 80° C. overnight. MS showed mostly product. So reaction quenched with saturated $NH_4Cl$ and water. The solution was brought to a pH of 8 and extracted with ethyl acetate. The organic layer was washed with brine and concentrated to give a silky solid. EtOAc was added and the mixture was filtered to give a beige solid. The NMR indicated that it was the product and it was recrystallized from acetonitrile to give clean product. (9.70 g). The filtrate was concentrated and filtered to give more precipitate (0.788 g). The filtrate was concentrated and purified by chromatography (0–70% EtOAc/hexanes) to give additional product as a beige solid (2.716 g). (Total Product: 13.21 g, 82%). MS: APCI: M+1: 325.2 (Exact Mass: 324.15).

A fifth intermediate compound, 7-(4-Hydroxy-butoxy)-3,4-dihydro-1H-[1,6]naphthyridin-2-one, was produced as follows: To a solution of 7-(4-benzyloxy-butoxy)-1H-[1,6]naphthyridin-2-one (7.92 g, 24.4 mmol) in MeOH/THF (100 mL) was added 20% Pd/C (1.5 g) and the mixture was hydrogenated for 59 h. The reaction was filtered, concentrated and purified by liquid chromatography (0–10% MeOH/CH2Cl2) to give the fifth intermediate compound as a white solid (4.11 g, 17.4 mmol, 71%). MS: APCI: M+1: 237.1 (Exact Mass: 236.12).

A sixth intermediate compound, 4-(2-Oxo-1,2,3,4-tetrahydro-[1,6]naphthyridin-7-yloxy)-butyraldehyde, was produced as follows: To a suspension of 7-(4-hydroxy-butoxy)-3,4-dihydro-1H-[1,6]naphthyridin-2-one (2.0 g, 8.5 mmol) in dichloroethane (20 mL) was added IBX (7 g, 25 mmol). This was heated at 80° C. for 5 hours. The reaction was cooled and then filtered. The filter cake was washed with $CH_2CH_2$ until the product was removed. The filtrate was concentrated to give a yellow solid (1.88 g, used crude in next reaction). MS: APCI: M+1: 235.1 (Exact Mass: 234.10).

A reductive amination procedure similar to Example A1 was followed using 1-(5,6,7,8-tetrahydro-naphthalen-1-yl)-piperazine to give the title compound (0.33 g; 56%). MS: APCI: M+1: 435.2 (Exact Mass: 434.27).

Example I3

Synthesis of 7-[4-(4-Naphthalen-1-yl-piperazin-1-yl)-butoxy]-3,4-dihydro-1H-[1,6]naphthyridin-2-one A reductive amination procedure similar to Example A1 was followed using 1-naphthalen-1-yl-piperazine to give the title compound (0.480 g, 87%). MS: APCI: M+1: 431.2 (Exact Mass: 430.24).

Example I4

Synthesis of 7-{4-[4-(2,3-Dichloro-phenyl)-piperazin-1-yl]-butoxy}-3,4-dihydro-1H-[1,6]naphthyridin-2-one A reductive amination procedure similar to Example A1 was followed using 1-(2,3-dichloro-phenyl)-piperazine to give the title compound (0.48 g; 81%). MS: APCI: M+1: 449.1 (Exact Mass: 448.14).

Example I5

Synthesis of 7-[4-(4-Indan-4-yl-piperazin-1-yl)-butoxy]-3,4-dihydro-1H-[1,6]naphthyridin-2-one A reductive amination procedure similar to Example A1 was followed using 1-indan-4-yl-piperazine to give the title compound (0.36 g; 66%). MS: APCI: M+1: 421.2 (Exact Mass: 420.25).

Example I6

Synthesis of 7-{4-[4-(7-Fluoro-naphthalen-1-yl)-piperazin-1-yl]-butoxy}-3,4-dihydro-1H-[1,6]naphthyridin-2-one A reductive amination procedure similar to Example A1 was followed using 1-(7-fluoro-naphthalen-1-yl)-piperazine to give the title compound (0.31 g; 68%). MS: APCI: M+1: 449.3 (Exact Mass: 448.23).

Example I7

Synthesis of 8-Bromo-7-[4-(4-naphthalen-1-yl-piperazin-1-yl)-butoxy]-3,4-dihydro-1H-[1,6]naphthyridin-2-one The first intermediate compound, 8-Bromo-7-(4-hydroxy-butoxy)-3,4-dihydro-1H-[1,6]naphthyridin-2-one, was produced as follows: To a solution of 7-(4-hydroxy-butoxy)-3,4-dihydro-1H-[1,6]naphthyridin-2-one (1.1 g, 4.7 mmol) in DMF (10 mL) was added NBS (0.91 g, 5.1 mmol). The solution was stirred at room temperature for 2.5 h. The reaction turned a deeper yellow color. $H_2O$ was added and the mixture was extracted with EtOAc. The organic layer was washed with $H_2O$, and brine, dried over $MgSO_4$ and concentrated. Purification by $SiO_2$ chromatography (0–7%

MeOH/CH$_2$Cl$_2$) gave the first intermediate compound as an off-white solid (1.16 g, 3.69 mmol, 79%). MS: APCI: M+1: 315.0 (Exact Mass: 314.03).

A second intermediate compound, 4-(8-Bromo-2-oxo-1,2,3,4-tetrahydro-[1,6]naphthyridin-7-yloxy)-butyraldehyde, was produced as follows: To a suspension of 8-bromo-7-(4-hydroxy-butoxy)-3,4-dihydro-1H-[1,6]naphthyridin-2-one (1.1 g, 3.5 mmol) in dichloroethane (20 mL) was added IBX (3 g, 10 mmol). This was heated at 80° C. for 5 hours. The reaction was cooled and then filtered. The filter cake was washed with CH$_2$CH$_2$ until the product was removed. The filtrate was concentrated to give a yellow oil. Purification by SiO$_2$ chromatography (0–7% MeOH/CH$_2$Cl$_2$) gave the second intermediate compound as a yellow solid (1.01 g). MS: APCI: M+1: 313.1 (Exact Mass: 312.01).

A reductive amination procedure similar to Example A1 was followed using 1-naphthalen-1-yl-piperazine to give the title compound (0.62 g; 76%). MS: APCI: M+1: 509.4 (Exact Mass: 508.15).

Example I8

Synthesis of 8-Bromo-7-{4-[4-(2,3-dichloro-phenyl)-piperazin-1-yl]-butoxy}-3,4-dihydro-1H-[1,6]naphthyridin-2-one A reductive amination procedure similar to Example A1 was followed using 1-(2,3-dichloro-phenyl)-piperazine to give the title compound (0.43 g; 51%). MS: APCI: M+1: 527.0 (Exact Mass: 526.05).

Example I9

Synthesis of 8-Chloro-7-{4-[4-(2,3-dichloro-phenyl)-piperazin-1-yl]-butoxy}-3,4-dihydro-1H-[1,6]naphthyridin-2-one A first intermediate compound, 8-Chloro-7-(4-hydroxy-butoxy)-3,4-dihydro-1H-[1,6]naphthyridin-2-one, was produced as follows: To a solution of 7-(4-hydroxy-butoxy)-3,4-dihydro-1H-[1,6]naphthyridin-2-one (2.0 g, 8.46 mmol) in DMF (23 mL) was added NCS (1.2 g, 9.3 mmol). The solution was stirred at room temperature for 2 hours and there was no reaction. The reaction was heated to 80° C. overnight and it went from a colorless solution to a dark brown solution. The reaction was cooled and then water was added. The mixture was extracted with EtOAc (3×). The organic layer was washed with H$_2$O and brine, dried over Na$_2$SO$_4$ and concentrated to give a brown oil. Purification by SiO$_2$ chromatography (0–10% MeOH/CH$_2$Cl$_2$) gave the first intermediate compound as a yellow solid (1.10 g, 48%). MS: APCI: M+1: 271.0 (Exact Mass: 270.08).

A second intermediate compound, 4-(8-Chloro-2-oxo-1,2,3,4-tetrahydro-[1,6]naphthyridin-7-yloxy)-butyraldehyd, was produced as follows: To a solution of 8-chloro-7-(4-hydroxy-butoxy)-3,4-dihydro-1H-[1,6]naphthyridin-2-one (1.05 g, 3.88 mmol) in DCE (25 mL) was added IBX (3.0 g, 12 mmol). The reaction was heated at 80° C. for 4.5 h. The reaction was cooled and filtered. The filter cake was washed with CH$_2$Cl$_2$ until all product washed off. The filtrate was concentrated to give a yellow oil, which solidified on the pump. Purification by SiO$_2$ chromatography (0–10% MeOH/CH$_2$Cl$_2$) gave a mixture of spots. The second intermediate compound was obtained in low yield (0.128 g, 12%). MS: APCI: M+1: 269.0 (Exact Mass: 268.06).

A reductive amination procedure similar to Example A1 was followed using 1-(2,3-dichloro-phenyl)-piperazine to give the title compound. MS: APCI: M+1: 483.1 (Exact Mass: 482.10).

Example I10

Synthesis of 8-Chloro-7-[4-(4-naphthalen-1-yl-piperazin-1-yl)-butoxy]-3,4-dihydro-1H-[1,6]naphthyridin-2-one A reductive amination procedure similar to Example A1 was followed using 1-naphthalen-1-yl-piperazine to give the title compound (0.041 g; 38%). MS: APCI: M+1: 465.2 (Exact Mass: 464.20).

Example I11

Synthesis of 7-[4-(4-Naphthalen-1-yl-piperazin-1-yl)-butoxy]-2-oxo-1,2,3,4-tetrahydro-[1,6]naphthyridine-8-carboxylic acid methyl ester A first intermediate compound, 8-Bromo-7-[4-(tetrahydro-pyran-2-yloxy)-butoxy]-3,4-dihydro-1H-[1,6]naphthyridin-2-one, was produced as follows: To a solution of 8-bromo-7-(4-hydroxy-butoxy)-3,4-dihydro-1H-[1,6]naphthyridin-2-one (1.24 g, 3.93 mmol) in dry CH$_2$Cl$_2$ was added dihydropyran (0.49 g, 5.9 mmol), followed by pyridinium p-toluenesulfonate (0.099 g, 0.39 mmol). The reaction was stirred at room temperature for 2 days. The reaction mixture was partitioned between ether and brine. The organic layer was dried over MgSO$_4$ and concentrated. The residue solidified in the refrigerator to give the first intermediate compound as a white solid (1.57 g). MS: APCI: M+1: 399.1 (Exact Mass: 398.08).

A second intermediate compound, 7-(4-Hydroxy-butoxy)-2-oxo-1,2,3,4-tetrahydro-[1,6]naphthyridine-8-carboxylic acid methyl ester, was produced as follows: A 300 mL high pressure reaction vessel was charged with 8-bromo-7-[4-(tetrahydro-pyran-2-yloxy)-butoxy]-3,4-dihydro-1H-[1,6]naphthyridin-2-one (0.70 g 1.75 mmol), DPPF (0.149 g, 0.175 mmol, 0.1 eq), Et$_3$N (0.29 mL, 2.10 mmol, 1.2 eq), and MeOH (100 mL). The vessel was purged and charged to 400 psi with CO. The reaction was heated and stirred at 100° C. for 60 hours. The mixture was filtered and concentrated to give a pink solid. Purification by SiO$_2$ chromatography (0–20% MeOH/CH$_2$Cl$_2$) gave the second intermediate compound as a solid (0.381 g, 74%). MS: APCI: M+1: 295.1 (Exact Mass: 294.12).

A third intermediate compound, 2-Oxo-7-(4-oxo-butoxy)-1,2,3,4-tetrahydro-[1,6]naphthyridine-8-carboxylic acid methyl ester, was produced as follows: To a suspension of 7-(4-hydroxy-butoxy)-2-oxo-1,2,3,4-tetrahydro-[1,6]naphthyridine-8-carboxylic acid methyl ester (0.340 g, 1.15 mmol) in dichloroethane (6 mL) was added IBX (1.0 g, 3 mmol). This was heated at 80° C. for 5 hours. The reaction was cooled and stirred, and then filtered. The filter cake was washed with CH$_2$Cl$_2$ until the product was removed. The filtrate was concentrated to give the third intermediate compound as a yellow solid (0.327 g, 97%). MS: APCI: M+1: 293.0 (Exact Mass: 292.11).

A reductive amination procedure similar to Example A1 was followed using 1-naphthalen-1-yl-piperazine to give the title compound (0.219 g; 40%). MS: APCI: M+1: 489.1 (Exact Mass: 488.24).

Example I12

Synthesis of 8-Methyl-7-[4-(4-naphthalen-1-yl-piperazin-1-yl)-butoxy]-3,4-dihydro-1H-[1,6]naphthyridin-2-one A first intermediate compound, 7-(4-Hydroxy-butoxy)-8-methyl-3,4-dihydro-1H-[1,6]naphthyridin-2-one, was produced as follows: To a solution of 8-bromo-7-(4-hydroxy-butoxy)-3,4-dihydro-1H-[1,6]naphthyridin-2-one (0.1 g, 0.3 mmol) in DME (5 mL) was added methylboronic acid (28 mg, 0.48 mmol), followed by Pd(PPh$_3$)$_4$ (9 mg, 2.5 mol %), and 2M Na$_2$CO$_3$. The reaction was heated at 90° C. for 2 days. The reaction was cooled and extracted with EtOAc (3×), dried over MgSO$_4$ and concentrated. Purification by SiO$_2$ chromatography (0–20% MeOH/CH$_2$Cl$_2$) gave the first intermediate compound (0.036 g, 23%). MS: APCI: M+1: 251.1 (Exact Mass: 250.13)

A second intermediate compound, 4-(8-Methyl-2-oxo-1,2,3,4-tetrahydro-[1,6]naphthyridin-7-yloxy)-butyraldehyde, was produced as follows: To a suspension of 7-(4-hydroxy-butoxy)-8-methyl-3,4-dihydro-1H-[1,6]naphthyridin-2-one (60 mg, 18.02 mmol) in dichloroethane (6 mL) was added IBX (15 g, 54 mmol). The mixture was heated at 80° C. for 5 hours. The reaction was cooled and stirred, and then filtered. The filter cake was washed with CH$_2$Cl$_2$ until the product was removed. The filtrate was concentrated to give a red oil. Purification by SiO$_2$ chromatography (0–7% MeOH/CH$_2$Cl$_2$) gave the second intermediate compound as a yellow solid (50 mg, 84%). MS: APCI: M+1: 249.1 (Exact Mass: 248.12).

A reductive amination procedure similar to Example A1 was followed using 1-naphthalen-1-yl-piperazine to give the title compound. MS: APCI: M+1: 445.3 (Exact Mass: 444.25).

Example I13

Synthesis of 7-{4-[4-(2,3-Dichloro-phenyl)-piperazin-1-yl]-butoxy}-1H-[1,6]naphthyridin-2-one A first intermediate compound, 7-(4-Hydroxy-butoxy)-1H-[1,6]naphthyridin-2-one, was produced as follows: Butane-1,4-diol (8.24 g, 8.12 mL, 91.3 mmol) was added to solid KO$^t$Bu (6 g, 55 mmol). The very viscous mixture was stirred for 15 min before adding 7-fluoro-1H-[1,6]naphthyridin-2-one (3 g, 18 mmol). NMP (60 mL) was then added and the reaction was heated at 70° C. overnight. The reaction was cooled and poured into ice water. No precipitate formed, so the mixture was extracted with EtOAc. The organic layer was washed with brine, dried over Na$_2$SO$_4$ and concentrated. Purification by SiO$_2$ chromatography (0–50% EtOAc/Hex) gave the first intermediate compound (2.36 g, 55%). MS: APCI: M+1: 235.0 (Exact Mass: 234.10).

A second intermediate compound, 4-(2-Oxo-1,2-dihydro-[1,6]naphthyridin-7-yloxy)-butyraldehyde, was produced as follows: To a suspension of 7-(4-hydroxy-butoxy)-1H-[1,6]naphthyridin-2-one (2.33 g, 9.95 mmol) in dichloroethane (30 mL) was added IBX (8 g, 30 mmol). The mixture was heated at 80° C. for 5 hours. The reaction was cooled and stirred, and then filtered. The filter cake was washed with CH$_2$Cl$_2$ until the product was removed. The filtrate was concentrated to give the second intermediate compound as a yellow solid (2.45 g). MS: APCI: M+1: 233.1 (Exact Mass: 232.08).

A reductive amination procedure similar to Example A1 was followed using 1-(2,3-dichloro-phenyl)-piperazine to give the title compound. MS: APCI: M+1: 447.1 (Exact Mass: 446.13).

Example I14

Synthesis of 7-{4-[4-(5,6,7,8-Tetrahydro-naphthalen-1-yl)-piperazin-1-yl]-butoxy}-1H-[1,6]naphthyridin-2-one A reductive amination procedure similar to Example A1 was followed using 1-(5,6,7,8-tetrahydro-naphthalen-1-yl)-piperazine to give the title compound (0.37 g, 66%). MS: APCI: M+1: 433.3 (Exact Mass: 432.25).

Example I15

Synthesis of 7-[4-(4-Indan-4-yl-piperazin-1-yl)-butoxy]-1H-[1,6]naphthyridin-2-one A reductive amination procedure similar to Example A1 was followed using 1-indan-4-yl-piperazine to give the title compound (0.206 g, 57%). MS: APCI: M+1: 419.2 (Exact Mass: 418.24).

Example I16

Synthesis of 7-[4-(4-Naphthalen-1-yl-piperazin-1-yl)-butoxy]-1H-[1,6]naphthyridin-2-one A reductive amination procedure similar to Example A1 was followed using 1-naphthalen-1-yl-piperazine to give the title compound (0.18 g, 56%). MS: APCI: M+1: 429.2 (Exact Mass: 428.22).

Example I17

Synthesis of 7-{4-[4-(7-Fluoro-naphthalen-1-yl)-piperazin-1-yl]-butoxy}-1H-[1,6]naphthyridin-2-one A reductive amination procedure similar to Example A1 was followed using 1-(7-fluoro-naphthalen-1-yl)-piperazine to give the title compound (0.31 g, 65%). MS: APCI: M+1: 447.3 (Exact Mass: 446.21).

Example I18

Synthesis of 7-{4-[4-(2,3-Dichloro-phenyl)-piperazin-1-yl]-butylamino}-1H-[1,6]naphthyridin-2-one To a mixture of 4-(4-naphthalen-1-yl-piperazin-1-yl)-butylamine (1.00 g, 3.31 mmol) and 7-fluoro-1H-[1,6]naphthyridin-2-one (517 mg, 3.15 mmol) in xylenes (6 mL) was added Et$_3$N (0.7 mL, 4.8 mmol). The mixture was heated at 140° C. for 2 days. The reaction was partitioned between CH$_2$Cl$_2$ and water. The solubility of the compound in CH$_2$Cl$_2$ is poor so some MeOH was added. The organic layer was washed with saturated NaHCO$_3$ and brine, dried over Na$_2$SO$_4$ and concentrated. Purification by liquid chromatography (6–8% MeOH/CH$_2$Cl$_2$ with 1% NH$_4$OH) gave the title compound as a pale yellow solid (252 mg, 0.565 mmol, 18%). MS: APCI: M+1: 446.1 (Exact Mass: 445.14).

Example I19

Synthesis of 7-{5-[4-(2,3-Dichloro-phenyl)-piperazin-1-yl]-pentyl}-4,4-dimethyl-1,4-dihydro-pyrido[4,3-d][1,3]oxazin-2-one A first intermediate compound, 4-Amino-6-chloro-nicotinic acid ethyl ester, was produced as follows: To a solution of 4,6-dichloro-nicotinic acid ethyl ester (15.0 g, 68.2 mmol) in THF was added liquid $NH_3$. The bomb was sealed and heated at 65° C. overnight. The reaction was concentrated and partitioned between EtOAc and water. The aqueous layer was extracted with EtOAc. The combined organic layer was washed with saturated $NaHCO_3$ and brine, dried over $Na_2SO_4$ and concentrated to give a solid. Recrystallization from EtOAc/Hexanes gave an off-white solid (1 g) which was not product. The filtrate was concentrated, absorbed onto $SiO_2$ and purified by liquid chromatography (20–25% EtOAc/Hexanes) to give the first intermediate compound as a white crystalline solid (10.20 g, 50.8 mmol, 75%). The structure was confirmed by NMR and mass spectrometry. MS: APCI: M+1: 201.0 (Exact Mass: 200.04).

A second intermediate compound, 2-(4-Amino-6-chloro-pyridin-3-yl)-propan-2-ol, was produced as follows: A solution of 4-amino-6-chloro-nicotinic acid ethyl ester (2.50 g, 12.5 mmol) in $Et_2O$ (20 mL) and THF (10 mL) was added via cannula to a solution of MeMgBr (3M in $Et_2O$, 20 mL, 60 mmol) in $Et_2O$ (10 mL) cooled to 0° C. The reaction was allowed to warm to room temperature and stir overnight. A thick green precipitate formed on the bottom of the flask. The reaction was quenched by slow addition of water and 1N HCl. The precipitate dissolved and the green color disappeared. The mixture was extracted with $Et_2O$. The organic layer was washed with brine, dried over $Na_2SO_4$ and concentrated to give the second intermediate compound as a white solid (2.13 g, 11.41 mmol, 91%). The structure was confirmed by NMR and mass spectrometry. MS: APCI: M+1: 187.0 (Exact Mass: 186.06).

A third intermediate compound, 7-Chloro-4,4-dimethyl-1,4-dihydro-pyrido[4,3-d][1,3]oxazin-2-one, was produced as follows: To a solution of 2-(4-amino-6-chloro-pyridin-3-yl)-propan-2-ol (500 mg, 2.68 mmol) in toluene (2 mL) and THF (4 mL) was added triethylamine (0.82 mL, 5.90 mmol). The reaction was cooled to 0° C. and a 20% solution of phosgene in toluene (1.5 mL, 3.21 mmol) was added. The reaction was allowed to warm to room temperature and stir for 4 h. MeOH was added to quench excess phosgene. Dilute aqueous $NaHCO_3$ was added and the mixture was extracted with EtOAc. The organic layer was washed with saturated $NaHCO_3$ and brine, dried over $Na_2SO_4$ and concentrated. Purification by liquid chromatography (30–35% EtOAc/Hexanes) afforded the third intermediate compound as a white solid (0.43 g, 2.02 mmol, 75%). The structure was confirmed by NMR and mass spectrometry. MS: APCI: M+1: 213.0 (Exact Mass: 212.04).

A fourth intermediate compound, 7-(5-Chloro-pent-1-enyl)-4,4-dimethyl-1,4-dihydro-pyrido[4,3-d][1,3]oxazin-2-one, was produced as follows: To a solution of 7-chloro-4,4-dimethyl-1,4-dihydro-pyrido[4,3-d][1,3]oxazin-2-one (444 mg, 2.09 mmol) in dimethoxyethane (10 mL) was added $Pd(Ph_3P)_4$ (72 mg, 0.063 mmol, 3 mol %). 5-Chloro-1-pentenyl boronic acid (700 mg, 4.72 mmol) was added as a slurry in DME (2 mL) via a pipet, followed by 2M $Na_2CO_3$ (465 mg in 2.2 mL $H_2O$, 4.39 mmol). The reaction was refluxed overnight. The reaction was concentrated and THF was added. The mixture was sonicated for 2 min and the resulting suspension was filtered through Celite. The filtrate was concentrated and purified by liquid chromatography (50–60% EtOAC/Hexanes) to give the fourth intermediate compound as a white solid (440 mg, 1.57 mmol, 75%). The structure was confirmed by NMR and mass spectrometry. MS: APCI: M+1: 281.0 (Exact Mass: 280.10).

A fifth intermediate compound, 7-{5-[4-(2,3-Dichloro-phenyl)-piperazin-1-yl]-pent-1-enyl}-4,4-dimethyl-1,4-dihydro-pyrido[4,3-d][1,3]oxazin-2-one, was produced as follows: To a mixture of 7-(5-chloro-pent-1-enyl)-4,4-dimethyl-1,4-dihydro-pyrido[4,3-d][1,3]oxazin-2-one (435 mg, 1.55 mmol) in $CH_3CN$ was added a solution of 1-(2,3-dichloro-phenyl)-piperazine (620 mg, 2.68 mmol) in $CH_3CN$ (5 mL) via cannula. $K_2CO_3$ (428 mg, 3.1 mmol) and KI (52 mg, 0.31 mmol) were added and the reaction was refluxed for 40 h. The mixture was filtered and washed with $CH_3CN$. The filtrate was concentrated and partitioned between EtOAc and water. The organic layer was washed with saturated $NaHCO_3$ and brine, dried over $Na_2SO_4$ and concentrated. Purification by liquid chromatography (5% MeOH/$CH_2Cl_2$ with 0.5% $NH_4OH$) afforded the fourth intermediate compound as a pinkish-white foam (558 mg, 1.17 mmol, 76%). MS: APCI: M+1: 475.1 (Exact Mass: 474.16).

7-{5-[4-(2,3-Dichloro-phenyl)-piperazin-1-yl]-pent-1-enyl}-4,4-dimethyl-1,4-dihydro-pyrido[4,3-d][1,3]oxazin-2-one (452 mg, 0.95 mmol) was hydrogentated using Ra—Ni in EtOH/THF. The reaction was filtered and concentrated. Purification by liquid chromatography (5% MeOH/$CH_2Cl_2$ with 0.5% $NH_4OH$) gave a white foam (385 mg, 85% pure). The foam was dissolved in a minimal amount of EtOAc and, upon standing, a white precipitate formed. The precipitate was filtered and washed with $Et_2O$ to give the title compound as a white solid (200 mg, 0.42 mmol, 44%). MS: APCI: M+1: 477.1 (Exact Mass: 476.17).

EXAMPLES SET 3

Example A1'

Synthesis of 7-{4-[4-(2-Oxo-2,3-dihydro-benzooxazol-7-yl)-piperazin-1-yl]-butoxy}-3,4-dihydro-1H-[1,8]naphthyridin-2-one A first intermediate compound, 2-Benzyloxy-7-chloro-[1,8]naphthyridine, was produced as follows: To a solution of benzyl alcohol (5.0 mL, 48.0 mmol) in THF (50 mL) cooled to 0° C. was added KO$^t$Bu (1 M in THF, 46 mL, 46.0 mmol). The solution was stirred at 0° C. for 20 min and then added via cannula to a suspension of 2,7-dichloro-[1,8]naphthyridine (10.0 g, 50.2 mmol, J. Org. Chem. 1981, 46, 833) in DMF (50 mL) and THF (50 mL) cooled to 0° C. The orange suspension was stirred at 0° C. for 15 min and at room temperature for 30 min. The reaction was quenched with saturated $NH_4Cl$ and $H_2O$. The mixture was extracted with EtOAc. The organic layer was filtered through celite to remove an orange clay-like precipitate. The organic layer was washed with $H_2O$ and brine, and concentrated to give an orange solid. The solid was absorbed onto $SiO_2$ and purified by liquid chromatography (2% EtOAc/48% Hexanes/50% $CH_2Cl_2$) to give the first intermediate compound as a white solid (6.37 g, 23.5 mmol, 51%). MS: APCI: M+1: 271.0 (Exact Mass: 270.06).

A second intermediate compound, 2-Benzyloxy-7-(4-benzyloxy-butoxy)-[1,8]naphthyridine, was produced as follows: To a solution of 4-benzyloxy-1-butanol (4.9 mL, 28.2 mmol, 1.2 equiv) in THF (20 mL) cooled to 0° C. was added KO$^t$Bu (1M in THF, 27 mL, 27 mmol, 1.15 equiv). The solution was stirred at 0° C. for 20 min and then added via cannula to a suspension of 2-benzyloxy-7-chloro-[1,8]naphthyridine (6.35 g, 23.5 mmol) in THF (70 mL) cooled to 0° C. The reaction became homogenous. After 30 min at 0° C., saturated NH$_4$Cl and H$_2$O were added to quench the reaction. The mixture was extracted with EtOAc. The organic layer was washed with saturated NaHCO$_3$, H$_2$O and brine, dried over Na$_2$SO$_4$ and concentrated. The crude was absorbed onto SiO$_2$ and purified by liquid chromatography (10–15% EtOAc/Hexanes) to give the second intermediate compound as a yellow oil (4.64 g, 11.19 mmol, 48%). MS: APCI: M+1: 415.2 (Exact Mass: 414.19).

A third intermediate compound, 7-(4-Hydroxy-butoxy)-3,4-dihydro-1H-[1,8]naphthyridin-2-one, was produced as follows: To a solution of 2-benzyloxy-7-(4-benzyloxy-butoxy)-[1,8]naphthyridine (4.64 g, 11.19 mmol) in MeOH (100 mL) was added 20% Pd/C (1.5 g) and the mixture was hydrogenated for 22 h. The reaction was filtered, concentrated and purified by liquid chromatography (5% MeOH/CH2Cl2) to give the third intermediate compound as a white solid (2.44 g, 10.33 mmol, 92%). MS: APCI: M+1: 237.1 (Exact Mass: 236.12).

7-(4-Hydroxy-butoxy)-3,4-dihydro-1H-[1,8]naphthyridin-2-one was also prepared by hydrogenation of 7-(4-hydroxy-butoxy)-1H-[1,8]naphthyridin-2-one (intermediate in Example B1).

A fourth intermediate compound, 4-(7-Oxo-5,6,7,8-tetrahydro-[1,8]naphthyridin-2-yloxy)-butyraldehyde was produced by oxidizing the third intermediate compound using either a Dess-Martin oxidation reaction or a Swern oxidation reaction, as follows:

Dess-Martin oxidation: To a cloudy solution of Dess-Martin periodinane (2.80 g, 6.60 mmol, 1.5 equiv) in CH$_2$Cl$_2$ (13 mL) was added a solution of 7-(4-hydroxy-butoxy)-3,4-dihydro-1H-[1,8]naphthyridin-2-one (1.04 g, 4.40 mmol) in CH$_2$Cl$_2$ (25 mL) via cannula. The reaction was stirred at room temperature for 5 h and stored in the freezer overnight. A 1:1 mixture of saturated Na$_2$S$_2$O$_3$ and saturated NaHCO$_3$ (50 mL) was added followed by Et$_2$O. The mixture was stirred for 10 min and then extracted with Et$_2$O/EtOAc (2:1). The organic layer was washed with saturated NaHCO$_3$ and brine, dried over Na$_2$SO$_4$ and concentrated to give the fourth intermediate compound as a pale yellow oil (1.06 g, used crude in next reaction). MS: APCI: M+1: 235.1 (Exact Mass: 234.10).

Swern oxidation: A solution of oxalyl chloride (9.97 mL, 112 mmol) in CH$_2$Cl$_2$ was cooled to −70° C. and DMSO (15.6 mL, 220 mmol) was carefully added. The solution was stirred at −60° C. for 10 min and then a solution of 7-(4-hydroxy-butoxy)-3,4-dihydro-1H-[1,8]naphthyridin-2-one (23 g, 97.5 mmol) in DMSO (70 mL) was added dropwise at −50~−60° C. The reaction mixture was stirred at −60° C. for 20 min and then triethylamine (72 mL, 0.513 mol) was added dropwise. The reaction was warmed to room temp and stirred for 30 min. The mixture was poured into ice-water and the organic phase was separated. The aqueous phase was extracted with CH$_2$Cl$_2$, combined with the organic phase, washed with brine, dried over Na$_2$SO$_4$, and concentrated under vacuum to give the crude product. Purification by column chromatography (hexane:ethyl acetate 2:1) followed by recrystallization provided the fourth intermediate compound (12.7 g, 54.3 mmol, 56%).

To a solution of 4-(7-oxo-5,6,7,8-tetrahydro-[1,8]naphthyridin-2-yloxy)-butyraldehyde (300 mg, 1.28 mmol) in DCE (6 mL) was added 7-piperazin-1-yl-3H-benzooxazol-2-one (309 mg, 1.41 mmol, prepared according to EP 0189612 and/or EP 0138280; Drugs of the Future, 2001, 26,128). The piperazine did not dissolve so DMF (1 mL) was added. The reaction was stirred for 10 min and NaBH(OAc)3 (380 mg, 1.79 mmol) was added. The reaction was stirred for 2 h at RT. Saturated NaHCO3 was added and the mixture was extracted with EtOAc (along with a little MeOH). The organic layer was washed with H2O and brine, and concentrated to give a light brown solid. The solid was dissolved in CH2Cl2/MeOH, absorbed onto SiO$_2$ and purified by liquid chromatography (AnaLogix, RS-40, 0–5% MeOH/CH2Cl2) to give a white solid. Et$_2$O was added and the solid was collected by filtration and dried to give the product as a white solid (360 mg, 0.823 mmol, 64%). MS: APCI: M+1: 438.2 (Exact Mass: 437.21).

A variation of this same method was used to produce other compounds as described in examples below, wherein other compounds were substituted for 7-piperazin-1-yl-3H-benzooxazol-2-one in the final step of the synthesis procedure.

Example A2'

Synthesis of 7-{4-[4-(2,3-Dihydro-benzofuran-7-yl)-piperazin-1-yl]-butoxy}-3,4-dihydro-1H-[1,8]naphthyridin-2-one A first intermediate compound 4-(2,3-Dihydro-benzofuran-7-yl)-piperazine-1-carboxylic acid tert-butyl ester, was produced as follows: A solution of bis-(dibenzylideneacetone)palladium(0) (4.92 g, 0.16 mol) and toluene (2500 ml) was degassed with nitrogen for 15 minutes. (Note: Degassing was continued during each addition. Time between additions was 15 minutes.) Then added was tri-o-tolylphosphine (4.92 g, 0.16 mol) then sodium t-butoxide (53.8 g, 0.56 mol) then Boc-piperazine (86.8 g, 0.47 mol) then a solution of 7-bromo-2,3-dihydro-benzofuran (79.6 g, 0.40 mol, prepared according to *Tetrahedron Lett.* 1998, 39, 2219) in toluene (100 ml). The reaction mixture was stirred at reflux for 16 h. By TLC, all starting material had been consumed. The cooled reaction mixture was filtered over a pad of Celite. The filtrate was concentrated under reduced pressure and the residue was triturated with ethyl acetate in heptane (50%). The insoluble material was filtered off and that filtrate was concentrated under reduced pressure. The crude residue was purified by flash column chromatography using ethyl acetate in heptane (50%) to give 46.4 g (38% yield) of the first intermediate compound as a tan solid.

A second intermediate compound, 1-(2,3-Dihydro-benzofuran-7-yl)-piperazine dihydrochloride, was produced as follows: A solution of 4-(2,3-dihydro-benzofuran-7-yl)-piperazine-1-carboxylic acid tert-butyl ester (42.3 g, 0.139 mol) in ethyl acetate (420 ml) was cooled in an ice bath to 0° C. HCl in ethyl acetate (3 M, 1.05 mol, 350 ml) was added dropwise. The reaction mixture was stirred at 0° C. for 1 h, at ambient temperature for 6 h, at 50° C. for 2 h, at ambient temperature for 16 h, and at 50° C. for 2 h. The resulting suspension was cooled and the resulting solid was collected and washed with ethyl acetate then dried in a vacuum oven at 70° C. to give 32.76 g (79% yield as the di-HCl salt) of the second intermediate compound as a tan solid. Mp: decomposition at 200° C.

A reductive amination procedure similar to Example A1' was followed using 1-(2,3-dihydro-benzofuran-7-yl)-piperazine dihydrochloride to give the title compound. MS: APCI: M+1: 423.2 (Exact Mass: 422.23).

Example A3'

Synthesis of 7-{4-[4-(2,2-Dimethyl-2,3-dihydro-benzofuran-7-yl)-piperazin-1-yl]-butoxy}-3,4-dihydro-1H-[1,8]naphthyridin-2-one A first intermediate compound 2,2-Dimethyl-2,3-dihydro-benzofuran-7-ylamine, was produced as follows: To a mixture of 2,2-dimethyl-2,3-dihydro-benzofuran-7-carboxylic acid (Maybridge, 6.15 g, 32.0 mmol) in dry tert-butanol (100 mL) was added $Et_3N$ (8.9 mL, 64.0 mmol) and the mixture became homogenous. DPPA (8.3 mL, 38.4 mmol) was added and the reaction was refluxed overnight. The reaction was concentrated and diluted with EtOAc. The organics were washed with water (2x) and brine, dried over $Na_2SO_4$ and concentrated. Purification by $SiO_2$ chromatography (AnaLogix RS-120, 2–25% EtOAc/Hex) gave (2,2-dimethyl-2,3-dihydro-benzofuran-7-yl)-carbamic acid tert-butyl ester as a clear oil (6.33 g, 24.0 mmol, 75%).

To a solution of (2,2-dimethyl-2,3-dihydro-benzofuran-7-yl)-carbamic acid tert-butyl ester (6.33 g, 24.0 mmol) in $CH_2Cl_2$ (30 mL) was added TFA (25 mL). The reaction bubbled for about 5 minutes and was stirred at room temperature for 1 h. The reaction was concentrated. The crude material was partitioned between EtOAc and aqueous $NaHCO_3$. The organic layer was washed with brine, dried over $Na_2SO_4$ and concentrated to give the first intermediate compound as a light brown liquid (3.83 g, 23.5 mmol, 97%). MS: APCI: M+1: 164.1 (Exact Mass: 163.10).

A second intermediate compound, 1-(2,2-Dimethyl-2,3-dihydro-benzofuran-7-yl)-piperazine, was produced as follows: A mixture of 2,2-dimethyl-2,3-dihydro-benzofuran-7-ylamine (3.83 g, 23.5 mmol), bis-(2-chloroethyl)amine hydrochloride (4.61 g, 25.8 mmol), NaI (1.76 g, 11.7 mmol) and hexyl alcohol (3 mL) in chlorobenzene (60 mL) was heated at 140° C. overnight. The mixture was concentrated and the residue was stirred 2x with 50% $Et_2O$/Hexanes. The solvent was decanted and a light brown solid remained in the flask. The residue was dissolved in MeOH/$CH_2Cl_2$ and absorbed onto $SiO_2$. Purification by $SiO_2$ chromatography (8% MeOH/$CH_2Cl_2$ with 1% $NH_4OH$) gave the second intermediate compound as a light brown oil which partially solidified on the pump (5.05 g, 21.7 mmol, 93%). The gooey solid was triturated with ether to give an off-white solid which was filtered, washed with ether and dried. MS: APCI: M+1: 233.2 (Exact Mass: 232.16).

A reductive amination procedure similar to Example A1' was followed using 1-(2,2-dimethyl-2,3-dihydro-benzofuran-7-yl)-piperazine to give the title compound. MS: APCI: M+1: 451.2 (Exact Mass: 450.26).

Example A4'

Synthesis of 7-[4-(4-Chroman-8-yl-piperazin-1-yl)-butoxy]-3,4-dihydro-1H-[1,8]naphthyridin-2-one A first intermediate compound 4-Chroman-8-yl-piperazine-1-carboxylic acid tert-butyl ester, was produced as follows: The reaction was done in two batches on the following scale: A suspension of $Pd_2(dba)_3$ (0.48 g, 0.53 mmol) in toluene (500 mL) was purged/degassed with $N_2$ (directly into the solution). To this was charged rac-BINAP (0.99 g, 1.6 mmol), sodium t-butoxide (28.4 g, 0.30 mol), Boc-piperazine (46 g, 0.247 mol) and lastly 8-bromo-chroman (45 g, 0.21 mol, prepared according to *Tetrahedron Lett*. 1998, 39, 2219) after which time the purge line was removed and the reaction continued under an atmosphere of $N_2$. The reaction was heated to 80–85° C. over ~16 h (monitor by TLC, 9:1 heptane:EtOAc, UV, $I_2$). After cooling the two batches were filtered through Celite, combined and the solvent evaporated. Chromatography (3:1 heptane:EtOAc) and trituration of the resulting solid gave 98.6 g (74%) of the first intermediate compound in two crops.

A second intermediate compound, 1-Chroman-8-yl-piperazine dihydrochloride, was produced as follows: A solution of 4-chroman-8-yl-piperazine-1-carboxylic acid tert-butyl ester (75.0 g, 0.236 mol) and ethyl acetate (590 ml) was cooled in an ice bath to 0° C. HCl in ethyl acetate (3 M; 1.77 mol; 590 ml) was added dropwise. The reaction mixture was stirred at 0° C. for 1 h, at ambient temperature for 20 h and at 50° C. for 6 h (monitor by LCMS). The resulting suspension was cooled and the solid was collected, washed with ethyl acetate then dried in a vacuum oven at 70° C. to give 67.41 g (94% yield as the di-HCl salt) of the second intermediate compound as a white solid.

A reductive amination procedure similar to Example A1' was followed using 1-chroman-8-yl-piperazine dihydrochloride to give the title compound. MS: APCI: M+1: 437.2 (Exact Mass: 436.25).

Example A5'

Synthesis of 7-{4-[4-(2,2-Dimethyl-2H-chromen-8-yl)-piperazin-1-yl]-butoxy}-3,4-dihydro-1H-[1,8]naphthyridin-2-one A first intermediate compound 1-Bromo-2-(1,1-dimethyl-prop-2-ynyloxy)-benzene, was produced as follows: To a solution of 2-methyl-3-butyn-2-ol (4.47 g, 53.2 mmol) in $CH_3CN$ (30 mL) cooled to 0° C. was added DBU (10.4 mL, 1.5 eq), followed by dropwise addition of trifluoroacetic acid anhydride (7.5 mL, 53.2 mmol) over 20 min. The resultant yellow solution was stirred at 0° C. for 40 min. In a separate flask, a solution of 2-bromophenol (8.00 g, 46.2 mmol) in $CH_3CN$ (30 mL) cooled to 0° C. was treated with DBU (9.0 mL, 1.3 eq), followed by $CuCl_2$ (17 mg). To this green solution was added the above 2-methyl-3-butyn-2-ol trifluoroacetate solution via cannula over 20 min at 0° C. The reaction was stirred to 2 h at 0° C. and then stored in the refrigerator overnight. The reaction was concentrated and then partitioned between hexanes and water. The aqueous layer was extracted with hexanes. The combined organic layer was washed with 1N HCl, 1N NaOH (2x) and brine, dried over $MgSO_4$ and concentrated to give the first intermediate compound as a clear oil (8.25 g, 34.5 mmol, 75%). Crude NMR looked clean.

A second intermediate compound, 8-Bromo-2,2-dimethyl-2H-chromene, was produced as follows: To 20 mL of N,N-diethylaniline at 180° C. was added 1-bromo-2-(1,1-dimethyl-prop-2-ynyloxy)-benzene (8.0 g, 33.5 mmol) via syringe under nitrogen. The solution was heated at 190° C. overnight (22 h). The reaction is difficult to follow by TLC. The reaction was allowed to cool and then poured into a mixture of hexanes and 1N HCl. The organic layer was washed with 1N HCl (2x) and brine, dried over $MgSO_4$ and concentrated to give the second intermediate compound as a yellow liquid (7.40 g, 30.9 mmol, 92%). Crude NMR looks good.

A third intermediate compound, 4-(2,2-Dimethyl-2H-chromen-8-yl)-piperazine-1-carboxylic acid tert-butyl ester, was produced as follows: A solution of 8-bromo-2,2-dimethyl-2H-chromene (7.22 g, 30.2 mmol) in dry toluene (60 mL) was degassed for 10 min by blowing nitrogen into the solution. This solution was then added via cannula to a flask containing Pd$_2$(dba)$_3$ (360 mg, 0.393 mmol, 2.5 mol % in Pd), di-tert-butylphosphino biphenyl (451 mg, 1.51 mmol, 5 mol %), NaOtBu (4.06 g, 42.3 mmol) and Boc-piperazine (6.75 g, 36.2 mmol) under nitrogen. The reaction mixture was heated at 80° C. overnight (17 h). MS showed a large product peak. The reaction was allowed to cool to room temperature and Et$_2$O was added. The mixture was filtered through Celite washing with Et$_2$O. The filtrate was washed with 0.5 M citric acid (3×, to remove excess Boc-piperazine) and once with brine, dried over Na$_2$SO$_4$ and concentrated to give a dark red oil (approx. 10 g). Purification by SiO$_2$ chromatography (10% EtOAc/Hexanes) gave the third intermediate compound as a yellow oil which partially solidified under vacuum (4.94 g, 14.3 mmol, 48%). MS: APCI: M+1: 345.2 (Exact Mass: 344.21).

A fourth intermediate compound, 1-(2,2-Dimethyl-2H-chromen-8-yl)-piperazine, was produced as follows: To a solution of 4-(2,2-dimethyl-2H-chromen-8-yl)-piperazine-1-carboxylic acid tert-butyl ester (2.43 g, 7.05 mmol) in CH2Cl2 (15 mL) was added TFA (12 mL). The reaction turned brown and was stirred at room temperature for 2 h. The reaction was concentrated 2× from CH2Cl2. The residue was taken up in 5% MeOH/CH2Cl2 with 1% NH4OH and the mixture smoked. The solution was concentrated to give a brown oil. Purification by SiO$_2$ chromatography (8% MeOH/CH2Cl2 with 1% NH4OH) gave the fourth intermediate compound as pale brown oil which solidified to give a tan solid (1.19 g, 4.87 mmol, 69%).

A reductive amination procedure similar to Example A1' was followed using 1-(2,2-dimethyl-2H-chromen-8-yl)-piperazine to give the title compound. MS: APCI: M+1: 463.2 (Exact Mass: 462.26).

Example A6'

Synthesis of 7-{4-[4-(2,2-Dimethyl-chroman-8-yl)-piperazin-1-yl]-butoxy}-3,4-dihydro-1H-[1,8]naphthyridin-2-one A first intermediate compound 4-(2,2-Dimethyl-chroman-8-yl)-piperazine-1-carboxylic acid tert-butyl ester, was produced as follows: 4-(2,2-Dimethyl-2H-chromen-8-yl)-piperazine-1-carboxylic acid tert-butyl ester (2.50 g, 7.26 mmol) was hydrogenated in the HPL using 10% Pd/C (1.0 g) in MeOH (50 mL) for 1.5 h. The reaction was filtered and concentrated to give a yellow oil. The crude oil was absorbed onto SiO$_2$ and purified by chromatography (10% EtOAc/Hexanes) to give the first intermediate compound as a clear oil which solidified to give a white solid (1.92 g, 5.54 mmol, 76%). MS: APCI: M+1: 347.1 (Exact Mass: 346.23).

A second intermediate compound, 1-(2,2-Dimethyl-chroman-8-yl)-piperazine, was produced as follows: To a solution of 4-(2,2-dimethyl-chroman-8-yl)-piperazine-1-carboxylic acid tert-butyl ester (1.90 g, 5.48 mmol) in CH$_2$Cl$_2$ (10 mL) cooled to 0° C. was added TFA (10 mL). The ice bath was removed and the solution was stirred at room temperature for 1 h. The reaction was concentrated 2× from CH$_2$Cl$_2$ to give a light brown oil which solidified on the pump to give the second intermediate compound as a white solid as the tris-TFA salt (3.12 g, 5.30 mmol, 97%). MS: APCI: M+1: 247.2 (Exact Mass: 246.17).

A reductive amination procedure similar to Example A1' was followed using 1-(2,2-dimethyl-chroman-8-yl)-piperazine to give the title compound. MS: APCI: M+1: 465.2 (Exact Mass: 464.28).

Example A7'

Synthesis of 7-{4-[4-(Spiro[chromene-2,1'-cyclopentan]-8-yl)-piperazin-1-yl]-butoxy}-3,4-dihydro-1H-[1,8]naphthyridin-2-one An intermediate compound, 1-Spiro[chromene-2,1'-cyclopentan]-8-ylpiperazine was produced as follows: The procedures in Example A5' were followed starting from 1-ethynyl-cyclopentanol to give the intermediate compound. MS: APCI: M+1: 271.0 (Exact Mass: 270.17).

A reductive amination procedure similar to Example A1' was followed using 1-spiro[chromene-2,1'-cyclopentan]-8-ylpiperazine to give the title compound. MS: APCI: M+1: 489.3 (Exact Mass: 488.28).

Example A8'

Synthesis of 7-{4-[4-(3,4-Dihydrospiro[chromene-2,1'-cyclopentan]-8-yl)-piperazin-1-yl]-butoxy}-3,4-dihydro-1H-[1,8]naphthyridin-2-one An intermediate compound 1-(3,4-Dihydrospiro[chromene-2,1'-cyclopentan]-8-yl)piperazine, was produced as follows: The procedure in Example A6' was followed to give the intermediate compound. MS: APCI: M+1: 273.1 (Exact Mass: 272.19).

A reductive amination procedure similar to Example A1' was followed using 1-(3,4-dihydrospiro[chromene-2,1'-cyclopentan]-8-yl)piperazine to give the title compound. MS: APCI: M+1: 491.3 (Exact Mass: 490.29).

Example A9'

Synthesis of 7-{4-[4-(2-Methyl-2H-chromen-8-yl)-piperazin-1-yl]-butoxy}-3,4-dihydro-1H-[1,8]naphthyridin-2-one An intermediate compound 1-(2-Methyl-2H-chromen-8-yl)-piperazine, was produced as follows: The procedures in Example A5' were followed starting from but-3-yn-2-ol to give the intermediate compound. MS: APCI: M+1: 231.1 (Exact Mass: 230.14).

A reductive amination procedure similar to Example A1' was followed using 1-(2-methyl-2H-chromen-8-yl)-piperazine to give the title compound. MS: APCI: M+1: 449.3 (Exact Mass: 448.25).

Example A10'

Synthesis of 7-{4-[4-(2-Methyl-chroman-8-yl)-piperazin-1-yl]-butoxy}-3,4-dihydro-1H-[1,8]naphthyridin-2-one An intermediate compound, 1-(2-Methyl-chroman-8-yl)-piperazine, was produced as follows: The procedure in Example A6' was followed to give the intermediate compound. MS: APCI: M+1: 233.1 (Exact Mass: 232.16).

A reductive amination procedure similar to Example A1' was followed using 1-(2-methyl-chroman-8-yl)-piperazine to give the title compound. MS: APCI: M+1: 451.3 (Exact Mass: 450.26).

Example A11'

Synthesis of 7-{4-[4-(2,3-Dihydro-benzofuran-4-yl)-piperazin-1-yl]-butoxy}-3,4-dihydro-1H-[1,8]naphthyridin-2-one An intermediate compound, 1-(2,3-Dihydro-benzofuran-4-yl)-piperazine, was produced as follows: A 1 L, 3-necked flask equipped with a mechanical stirrer, thermometer and a nitrogen inlet was charged with a solution of 2,3-dihydro-benzofuran-4-ylamine (12.5 g, 0.092 mol, *J. Heterocyclic Chem*. 1980, 17, 1333) in chlorobenzene (220 mL) and 1-hexanol (10 mL). The mixture was treated with diisopropylethylamine (8.2 g, 0.063 mol), stirred for 10min, and then NaI was added (4.4 g, 0.029 mol), followed by bis-(2-chloroethyl)amine hydrochloride (16.9 g, 0.094 mol). The mixture was refluxed for 16 h at an external temperature of 140° C. The reaction mixture was cooled to room temperature, evaporated under vacuum and the dark thick liquid was dissolved in chloroform-methanol (9:1) containing a few drops of ammonia, absorbed onto silica gel and purified by silica gel chromatography, using 5% methanol in chloroform for elution. The product was obtained as a thick paste after evaporation of the main fractions, which upon trituration with $CH_2Cl_2$ gave the intermediate compound as white powder (8.0 g, 38%).

A reductive amination procedure similar to Example A1' was followed using 1-(2,3-dihydro-benzofuran-4-yl)-piperazine to give the title compound. MS: APCI: M+1: (Exact Mass: 422.23).

Example A12'

Synthesis of 7-{4-[4-(1,3-Dihydro-isobenzofuran-4-yl)-piperazin-1-yl]-butoxy}-3,4-dihydro-1H-[1,8]naphthyridin-2-one A first intermediate compound 1,2-Bis-bromomethyl-3-nitro-benzene, was produced as follows: To a dry flask under an inert atmosphere containing 1,2-dimethyl-3-nitro-benzene (17.00 g, 112.4 mmol, 1 eq) in 70 mL of $CCl_4$ was added NBS (43.06 g, 241.9 mmol, 2.1 eq) and benzoyl peroxide (0.274 g, 1.131 mmol, 0.01 eq). The orange colored suspension was refluxed for two hours before an additional 1.074 g benzoyl peroxide was added. The reaction was refluxed for two hours and then cooled to room temperature. The reaction mixture was filtered and washed with $CCl_4$ to remove a white solid. The yellow filtrate was concentrated to give the first intermediate compound as a crude oil (30.954 g, 89%).

A second intermediate compound, 4-Nitro-1,3-dihydro-isobenzofuran, was produced as follows: To a flask containing 1,2-bis-bromomethyl-3-nitro-benzene (1.129 g, 3.655 mmol, 1 eq) was added alumina (15 g, 147 mmol, 40 eq) and toluene (10 mL) and the mixture was heated at 120° C. for two hours. The reaction mixture was filtered to remove the alumina and washed with ethyl acetate. The filtrate was concentrated to give a yellow solid which was purified by chromatography on silica gel (0–10% EtOAc:hexane) to afford the second intermediate compound (0.546 g, 90%). MS: APCI: M–1: 164.9 (Exact Mass: 165.04).

A third intermediate compound, 1,3-Dihydro-isobenzofuran-4-ylamine, was produced as follows: A solution of 4-nitro-1,3-dihydro-isobenzofuran (5.976 g, 36.19 mmol) in 100 mL of THF was hydrogenated using Ra/Ni. The reaction was filtered and then concentrated to obtain the third intermediate compound (4.996 g, 100%). MS: APCI: M+1: 136.2 (Exact Mass: 135.07).

A fourth intermediate compound, 1-(1,3-Dihydro-isobenzofuran-4-yl)-piperazine, was produced as follows: To a reaction flask containing a solution of 1,3-dihydro-isobenzofuran-4-ylamine (0.488 g, 3.610 mmol, 1 eq) in chlorobenzene (6 mL), was added bis-(2-chloro-ethyl)-amine hydrochloride (0.907 g, 4.260 mmol, 1.18 eq) and diisopropylethyl amine (0.297 g, 2.30 mmol, 0.64 eq). The reaction was refluxed for 14 hours. The reaction was cooled and concentrated. Purification by chromatography on silica gel (0–40% MeOH/NH4OH:CH2Cl2) afforded the fourth intermediate compound (0.400 g, 54%). MS: APCI: M+1: 205.1 (Exact Mass: 204.13).

To a suspension of 4-(7-oxo-5,6,7,8-tetrahydro-[1,8]naphthyridin-2-yloxy)-butyraldehyde (0.278 g, 1.186 mmol, 1.1 eq) and 1-(1,3-dihydro-isobenzofuran-4-yl)-piperazine (0.217 g, 1.064 mmol, 1 eq) in dichloroethane (5 mL) was added $NaBH(OAc)_3$ (0.469 g, 4.425 mmol, 3.73 eq). The slurry was allowed to stir overnight at room temperature (18 h). The mixture was diluted with EtOAc and quenched with saturated $NaHCO_3$. The organic phase was then washed with brine, dried over $Na_2SO_4$, filtered and evaporated in vacuo. Purification by silica gel chromatography (2% MeOH/$CH_2Cl_2$) followed by formation of the HCl salt using 1 N HCl in ether provided the title compound (0.143 g, 26%). CHN Found: C, 64.37; H, 6.54; N, 12.13. This calculates out for C24H30N4O3×1.00 HCl.

Example A13'

Synthesis of 7-[4-(4-Chroman-5-yl-piperazin-1-yl)-butoxy]-3,4-dihydro-1H-[1,8]naphthyridin-2-one A first intermediate compound 3-Nitro-2-vinyl-phenol, was produced as follows: To a degassed solution of 2-bromo-3-nitro-phenol (3.00 g, 13.8 mmol) and tributylvinyltin (4.4 mL, 15.1 mmol) in toluene (70 mL) was added tetrakis(triphenylphosphine)palladium(0) (1.59 g, 1.38 mmol, 10 mol %). The reaction was refluxed overnight. The mixture was filtered through celite washing with EtOAc. The solvent was removed and the residue was purified by $SiO_2$ chromatography (AnaLogix RS-120, 10–30% EtOAc/Hexanes) to give the first intermediate compound as a yellowish orange solid (1.00 g, 6.06 mmol, 44%). MS: APCI: M–1: 163.9 (Exact Mass: 165.04).

A second intermediate compound, 1-Allyloxy-3-nitro-2-vinyl-benzene, was produced as follows: To a solution of 3-nitro-2-vinyl-phenol (1.0 g, 6.1 mmol) in acetone (20 mL). was added allyl bromide (1.05 mL, 12.1 mmol, 2 eq) followed by $K_2CO_3$ (1.67 g, 12.1 mmol, 2 eq). The mixture was refluxed for 30 min and stirred at room temperature overnight. The reaction mixture was filtered washing with acetone and then concentrated. Purification by $SiO_2$ chromatography (AnaLogix RS-40, 2–5% EtOAc/Hexanes) gave the second intermediate compound as an orange oil (1.00 g, 4.87 mmol, 80%).

A third intermediate compound, 5-Nitro-2H-chromene, was produced as follows: To a solution of 1-allyloxy-3-nitro-2-vinyl-benzene (1.0 g, 4.9 mmol) in $CH_2Cl_2$ (25 mL) was added the 2nd generation Grubbs catalyst (207 mg, 5 mol %). The reaction was stirred at room temperature for 3 h. The mixture was concentrated and purified by $SiO_2$ chromatography (AnaLogix RS-40, 2–5% EtOAc/Hexanes) to give the third intermediate compound as a yellow solid (852 mg, 4.81 mmol, 98%). MS: APCI: M−1: 175.9 (Exact Mass: 177.04).

A fourth intermediate compound, Chroman-5-ylamine, was produced as follows: 5-Nitro-2H-chromene (800 mg, 4.52 mmol) was hydrogenated using 10% Pd/C in MeOH (50 mL) for 4.6 h. The yellow solution turned clear. The reaction mixture was concentrated to give the fourth intermediate compound as a light brown oil which looked pure by NMR and TLC (679 mg, quant). MS: APCI: M+1: 150.3 (Exact Mass: 149.08).

A fifth intermediate compound, 1-Chroman-5-yl-piperazine, was produced as follows: To a solution of chroman-5-ylamine (679 mg, 4.55 mmol) in chlorobenzene (12 mL) and hexanol (0.6 mL) was added bis(2-chloroethyl)amine hydrochloride (894 mg, 5.01 mmol), NaI (341 mg, 2.28 mmol) and diisopropylethylamine (0.44 mL, 2.50 mmol). The reaction was refluxed at 140° C. for 20 h. A tan ppt formed. The reaction was allowed to cool to room temperature and hexanes was added. The mixture was filtered and washed with hexanes. The solid was dissolved in MeOH/CH$_2$Cl$_2$ and absorbed ontio SiO$_2$. Purification by SiO$_2$ chromatography (8–10% MeOH/CH$_2$Cl$_2$ with 1% NH$_4$OH) gave the fifth intermediate compound as a light tan solid (548 mg, 2.51 mmol, 55%). MS: APCI: M+1: 219.1 (Exact Mass: 218.14).

A reductive amination procedure similar to Example A1' was followed using 1-chroman-5-yl-piperazine to give the title compound. MS: APCI: M+1: 437.3 (Exact Mass: 436.25).

Example A14'

Synthesis of 7-[4-(4-Isochroman-5-yl-piperazin-1-yl)-butoxy]-3,4-dihydro-1H-[1,8]naphthyridin-2-one A first intermediate compound 1-Bromo-2-[2-(2-methoxy-ethoxymethoxy)-ethyl]-benzene, was produced as follows: To a solution of 2-(2-bromo-phenyl)-ethanol (7.8 g, 38.8 mmol) and diisopropylethylamine (8.02 g, 62 mmol) in 50 mL of dry CH$_2$Cl$_2$ was added MEM chloride (6.26 g, 50.4 mmol) dropwise at 0° C. The resulting mixture was stirred at the same temperature for 2 h and treated with 1 N HCl and CH$_2$Cl$_2$. The organic layer was washed with H$_2$O, dried over Na$_2$SO$_4$, concentrated under vacuum. The residue was purified by chromatography (25% EtOAc/hexanes) to give the first intermediate compound (9.0 g, 80%). $^1$H NMR (400 MHz, CDCl$_3$) δ 7.53 (dd, J=1.5 Hz, J=7.8 Hz, 1H), 7.29–7.23 (m, 2H), 7.09–7.05 (m, 1H), 4.71 (s, 2H), 3.80 (t, J=7.8 Hz, 2H), 3.62–3.60 (m, 2H), 3.51–3.49 (m, 2H), 3.37 (s, 3H), 3.04 (t, J=7.8 Hz, 4H).

A second intermediate compound, 5-Bromo-isochroman, was produced as follows: To a solution of 1-bromo-2-[2-(2-methoxy-ethoxymethoxy)-ethyl]-benzene (4.5 g, 15.56 mmol) in 100 mL of CH$_2$Cl$_2$ was added a solution of TiCl$_4$ in CH$_2$Cl$_2$ dropwise at 0° C. The resulting mixture was stirred at the same temperature for 1 h and treated with H$_2$O and CH$_2$Cl$_2$. The organic layer was washed with H$_2$O, dried over Na$_2$SO$_4$, and concentrated under vacuum. The residue was purified by chromatography (25% EtOAc/hexanes) to give the second intermediate compound (2.7 g, 82%). $^1$H NMR (400 MHz, CDCl$_3$) δ 7.43 (d, J=7.8 Hz, 1H), 7.05 (t, J=7.8 Hz, 1H), 6.95 (d, J=7.3 Hz, 1H), 4.73 (s, 2H), 4.00 (t, J=5.9 Hz, 2H), 3.82 (t, J=5.9 Hz, 2H).

A third intermediate compound, 1-Isochroman-5-yl-piperazine, was produced as follows: To a mixture of 5-bromo-isochroman (1 g, 4.69 mmol), 1-boc-piperazine (1.05 g, 5.6 mmol), 2-dicyclohexylphosphino biphenyl (0.066 g, 0.19 mmol), and Pd(OAc)$_2$ (0.42 g, 0.19 mmol) in 10 mL of dry degassed C$_6$H$_5$CH$_3$ was added NaOtBu (0.63 g, 6.6 mmol) at room temperature. The resulting mixture was stirred at 80–90° C. for 1 h, cooled and passed through a pad of celite and the filtrate was concentrated under vacuum. The residue was purified by chromatography (25–50% EtOAc/hexanes) to give 4-isochroman-5-yl-piperazine-1-carboxylic acid tert-butyl ester (0.89 g, 60%). MS (ES) m/z: 319.19 [M+1]. $^1$H NMR (400 MHz, CDCl$_3$) δ 7.16 (t, J=7.8 Hz, 1H), 6.88 (d, J=7.8 Hz, 1H), 6.75 (d, J=7.8 Hz, 1H), 4.79 (s, 2H), 3.94 (t, J=5.9 Hz, 2H), 3.55 (br s, 4H), 2.86–2.80 (m, 4H), 1.49 (s, 9H).

To a solution of 4-isochroman-5-yl-piperazine-1-carboxylic acid tert-butyl ester (0.5 g, 1.57 mmol) in dry CH$_2$Cl$_2$ was added 3 mL of TFA at 0° C. dropwise. The resulting mixture was stirred at room temperature for 2 h. The evaporation of the solvent gave the third intermediate compound (0.52 g, quantitative). MS (ES) m/z: 219.12 [M+1]. $^1$H NMR (400 MHz, CDCl$_3$) δ 8.12 (br s, 1H), 7.19 (t, J=7.3 Hz, 1H), 6.95 (d, J=7.8 Hz, 1H), 6.82 (d, J=7.8 Hz, 1H), 4.82 (s, 2H), 3.98 (t, J=5.8 Hz, 2H), 3.54 (br s, 4H), 3.21–3.19 (m, 4H), 2.80 (t, J=5.4 Hz, 2H).

A reductive amination procedure similar to Example A1' was followed using 1-isochroman-5-yl-piperazine to give the title compound (0.40 g, 58%). MS (ES) m/z: 437.26 [M+1] (Exact mass: 436.25). $^1$H NMR (400 MHz, CDCl$_3$) δ 7.69 (br s, 1H), 7.36 (d, J=8.3 Hz, 1H), 7.63 (d, J=7.3 Hz, 1H), 7.18 (t, J=7.8 Hz, 1H), 6.92 (d, J=7.8 Hz, 1H), 6.72 (d, J=7.3 Hz, 1H), 6.36 (d, J=7.3 Hz, 1H), 4.80 (s, 2H), 4.22 (t, J=6.3 Hz, 2H), 3.93 (t, J=5.4 Hz, 2H), 2.95 (t, J=4.9 Hz, 4H), 2.88–2.80 (m, 4H), 2.67–2.63 (m, 4H), 2.47 (t, J=7.2 Hz, 4H), 1.82–1.78 (m, 2H), 1.72–1.69 (m, 2H).

Example A15'

Synthesis of 7-[4-(4-Isochroman-8-yl-piperazin-1-yl)-butoxy]-3,4-dihydro-1H-[1,8]naphthyridin-2-one A first intermediate compound 8-Bromo-isochroman and 6-Bromo-isochroman, was produced as follows: To a solution of 1-bromo-3-[2-(2-methoxy-ethoxymethoxy)-ethyl]-benzene (2.8 g, 9.7 mmol) in 50 mL of CH$_2$Cl$_2$ was added a solution of TiCl$_4$ (14.5 mmol) in CH$_2$Cl$_2$ dropwise at 0° C. The resulting mixture was stirred at the same temperature for 1 h and treated with H$_2$O and CH$_2$Cl$_2$. The organic layer was washed with H$_2$O, dried over Na$_2$SO$_4$ and concentrated under vacuum. The residue was purified by chromatography (25% EtOAc/hexanes) to give 1.8 g of a mixture of the first intermediate compounds, 8-bromo-isochroman and 6-bromo-isochroman (~1:4 by HPLC) in 90% yield.

A second intermediate compound, 4-Isochroman-8-yl-piperazine-1-carboxylic acid tert-butyl ester, was produced as follows: To a mixture of 8-bromo-isochroman and 6-bromo-isochroman (1.8 g, 8.4 mmol), 1-boc-piperazine (1.9 g, 10.15 mmol), 2-dicyclohexylphosphino biphenyl (0.12 g, 0.34 mmol), and Pd(OAc)$_2$ (0.076 g, 0.34 mmol) in 15 mL of dry degassed toluene was added NaOtBu (1.13 g, 11.8 mmol) at room temperature. The resulting mixture was stirred at 80–90° C. for 1 h, cooled and passed through a pad of celite and the filtrate was concentrated under vacuum. The residue was subjected to chromatography (10% EtOAc/hexanes) to give 0.2 g of the second intermediate compound, 4-isochroman-8-yl-piperazine-1-carboxylic acid tert-butyl ester, and 0.8 g of the regioisomer, 4-isochroman-6-yl-piperazine-1-carboxylic acid tert-butyl ester, in 37% yield.

Second intermediate compound: $^1$H NMR (400 MHz, CDCl$_3$) δ 7.17 (t, J=7.8 Hz, 1H), 6.90 (d, J=7.8 Hz, 2H), 4.80 (s, 2H), 3.96 (t, J=5.9 Hz, 2H), 3.53 (br s, 4H), 2.87 (t, J=5.8 Hz, 4H), 2.80 (t, J=4.4 Hz, 4H), 1.48 (s, 9H). MS (ES) m/z: 319.19 [M+1] (Exact mass: 318.19).

A third intermediate compound, 1-Isochroman-8-yl-piperazine, was produced as follows: To a solution of 4-isochroman-8-yl-piperazine-1-carboxylic acid tert-butyl ester (0.9 g, 2.8 mmol) in 30 mL of dry CH2Cl2 was added 5 mL of TFA at 0° C. dropwise. The resulting mixture was stirred at room temperature for 2 h. The evaporation of the solvent gave 0.92 g of the third intermediate compound in 98% yield. 1H NMR (400 MHz, CDCl$_3$) δ 8.18 (br s, 1H), 7.25 (t, J=8.0 Hz, 1H), 7.02 (d, J=8.0 Hz, 2H), 4.89 (s, 2H), 4.07 (t, J=6.0 Hz, 2H), 3.46 (br s, 4H), 3.18–3.15 (m, 4H), 2.94 (t, J=6.0 Hz, 2H). MS (ES) m/z: 219.13 [M+1] (Exact mass: 218.14).

A reductive amination procedure similar to Example A1' was followed using 1-isochroman-8-yl-piperazine to give the title compound (0.6 g, 65%). MS (ES) m/z: 437.26 [M+1] (Exact mass: 436.25). $^1$H NMR (400 MHz, CDCl$_3$) δ 7.69 (br s, 1H), 7.35 (d, J=7.8 Hz, 1H), 7.16 (t, J=7.8 Hz, 1H), 6.95 (d, J=7.8 Hz, 1H), 6.88 (d, J=7.3 Hz, 1H), 6.35 (d, J=8.3 Hz, 1H), 4.78 (s, 2H), 4.22 (t, J=6.3 Hz, 2H), 3.94 (t, J=5.8 Hz, 2H), 2.93 (t, J=4.9 Hz, 4H), 2.88–2.84 (m, 4H), 2.70–2.62 (m, 6H), 2.55 (t, J=7.8 Hz, 2H), 1.82–1.77 (m, 2H), 1.75–1.72 (m, 2H).

Example A16'

Synthesis of 7-{4-[4-(2,3-Dihydro-benzo[1,4]dioxin-5-yl)-piperazin-1-yl]-butoxy}-3,4-dihydro-1H-[1,8]naphthyridin-2-one A reductive amination procedure similar to Example A1' was followed using 1-(2,3-dihydro-benzo[1,4]dioxin-5-yl)-piperazine (WO 97/03067) to give the title compound. MS: APCI: M+1: 439.3 (Exact Mass: 438.23).

Example A17'

Synthesis of 7-{4-[4-(3,4-Dihydro-2H-benzo[b][1,4]dioxepin-6-yl)-piperazin-1-yl]-butoxy}-3,4-dihydro-1H-[1,8]naphthyridin-2-one In a manner similar to that of other examples above, 1-(3,4-dihydro-2H-benzo[b][1,4]dioxepin-6-yl)-piperazine hydrochloride (*J. Med. Chem.* 1988, 31, 1934–1940) was coupled by reductive amination to 4-(7-oxo-5,6,7,8-tetrahydro-[1,8]naphthyridin-2-yloxy)-butyraldehyde followed by typical workup and purification to give the intermediate compound. MS: APCI: M+1: 453.6 (Exact Mass: 452.55).

Example A18'

Synthesis of 7-{4-[4-(2,2,3,3-Tetrafluoro-2,3-dihydro-benzo[1,4]dioxin-5-yl)-piperazin-1-yl]-butoxy}-3,4-dihydro-1H-[1,8]naphthyridin-2-one An intermediate compound, 1-(2,2,3,3-Tetrafluoro-2,3-dihydro-benzo[1,4]dioxin-5-yl)-piperazine, was produced as follows: To the mixture of 2,2,3,3-tetrafluoro-2,3-dihydro-benzo[1,4]dioxin-5-ylamine (8.9 g, 40 mmol) and bis-(2-chloro-ethyl)-carbamic acid tert-butyl ester (14.5 g, 60 mmol) in DMF (200 mL) was added NaH (3.2 g, 60% oil dispersion, 80 mmol) at 0° C. and the resulting mixture was stirred at the same temperature for 1.0 h. No reaction was observed by TLC. The mixture was further stirred at room temperature for 4.0 h until LCMS indicated the starting material disappeared. The reaction was quenched with aq. NH$_4$Cl, extracted with EtOAc, washed with brine, dried and concentrated. The residue was purified by flash chromatography (Et$_3$N:EtOAc:heptane/1:10:100) to afford 4-(2,2,3,3-tetrafluoro-2,3-dihydro-benzo[1,4]dioxin-5-yl)-piperazine-1-carboxylic acid tert-butyl ester (5.2 g, 33%) as colorless crystals.

A solution of 4-(2,2,3,3-tetrafluoro-2,3-dihydro-benzo[1,4]dioxin-5-yl)-piperazine-1-carboxylic acid tert-butyl ester (12.5 g, 0.0319 mol) in 1,4-dioxane (150 mL) was treated with 4 N HCl in 1,4-dioxane (100 mL) and the mixture was stirred at room temperature for 16 h, and then 35° C. for 2.0 h until LCMS indicated completion. The resulting solid was collected via filtration, rinsed with 1,4-dioxane, ether, and oven-dried to afford the title compound as the hydrochloride salt (8.9 g, 85%) as an off-white powder.

A reductive amination procedure similar to Example A1' was followed using 1-(2,2,3,3-tetrafluoro-2,3-dihydro-benzo[1,4]dioxin-5-yl)-piperazine hydrochloride to give the title compound. MS: APCI: M+1: 511.1 (Exact Mass: 510.19).

Example A19'

Synthesis of 7-{4-[4-(2,2-Difluoro-benzo[1,3]dioxol-4-yl)-piperazin-1-yl]-butoxy}-3,4-dihydro-1H-[1,8]naphthyridin-2-one An intermediate compound, 1-(2,2-Difluoro-benzo[1,3]dioxol-4-yl)-piperazine, was produced as follows: To the mixture of 2,2-difluoro-benzo[1,3]dioxol-4-ylamine (27 g, 0.156 mol) and bis-(2-chloro-ethyl)-carbamic acid tert-butyl ester (75.5 g, 0.31 mol) in DMF (500 mL) was added NaH (15.6 g, 60% oil dispersion, 0.39 mol) at 0° C. and the resulting mixture was stirred at room temperature for 24 h until LCMS indicated the starting material disappeared. The reaction was quenched with aq. NH4Cl, extracted with EtOAc, washed with brine, dried and concentrated. The residue was purified by flash chromatography (Et$_3$N:EtOAc:heptane/1:10:100) to afford 4-(2,2-difluoro-benzo[1,3]dioxol-4-yl)-piperazine-1-carboxylic acid tert-butyl ester (12.0 g, 22%) as colorless crystals.

A solution of 4-(2,2-difluoro-benzo[1,3]dioxol-4-yl)-piperazine-1-carboxylic acid tert-butyl ester (9.9 g, 0.029 mol) in 1,4-dioxane (100 ml) was treated with 4 N HCl in 1,4-dioxane (75 mL) and the mixture was stirred at room temperature for 20 h, and then 35–40° C. for 2.0 h until LCMS indicated completion. The resulting solid was collected via filtration, rinsed with ether, and oven-dried to afford the intermediate compound as the hydrochloride salt (7.8 g, 97%) as white powder.

A reductive amination procedure similar to Example A1' was followed using 1-(2,2-difluoro-benzo[1,3]dioxol-4-yl)-piperazine hydrochloride to give the title compound. MS: APCI: M+1: 461.2 (Exact Mass: 460.19).

Example A20'

Synthesis of 7-{4-[4-(4-Oxo-chroman-8-yl)-piperazin-1-yl]-butoxy}-3,4-dihydro-1H-[1,8]naphthyridin-2-one A first intermediate compound 8-Bromo-2,3-dihydrospiro[chromene-4,2'-[1,3]dioxolane], was produced as follows: A mixture of 8-bromo-chroman-4-one (0.87 g, 3.8 mmol), ethylene glycol (0.23 g, 3.8 mmol) and TsOH in benzene (50 mL) was refluxed using a Dean-Stark apparatus for 16 h. It was cooled to RT, diluted with EtOAc (50 mL), washed with aqueous NaHCO$_3$, dried and concentrated to give the first intermediate compound (1.05 g). $^1$H NMR (400 MHz, CDCl$_3$): δ 7.50 (d, 1H), 7.40 (d, 1H), 6.90 (t, 1H), 4.30 (m, 2H), 4.10 (m, 2H), 4.10 (m, 2H), 2.20 (m, 2H).

A second intermediate compound, 4-(2,3-Dihydrospiro[chromene-4,2'-[1,3]dioxolan-8-yl])-piperazine-1-carboxylic acid tert-butyl ester, was produced as follows: Nitrogen gas was bubbled through a solution of 8-bromo-2,3-dihydrospiro[chromene-4,2'-[1,3]dioxolane] (1.05 g, 3.89 mmol), 1-Boc-piperazine (0.86 g, 4.67 mmol), Pd(OAc)$_2$ (88 mg) and 2-dicyclohexylphosphino biphenyl (0.14 g) in toluene (40 mL) for 10 min. NaOtBu (0.52 g, 5.45 mmol) was added and the resulting mixture was heated at 110° C. for 3 h. The mixture was cooled to RT, diluted with EtOAC (40 mL) and filtered through a pad of celite. The filtrate was concentrated and the residue was purified by chromatography on silica gel to give the second intermediate compound (0.55 g, 38%). $^1$H NMR (400 MHz, CDCl$_3$): δ 7.15 (m, 1H), 6.90 (m, 2H), 4.47 (m, 2H), 4.22 (m, 2H), 4.10 (m, 2H), 3.60 (m, 4H), 3.00 (m, 4H), 2.20 (m, 2H), 1.44 (s, 9H).

A third intermediate compound, 8-Piperazin-1-yl-chroman-4-one, was produced as follows: To a solution of 4-(2,3-dihydrospiro[chromene-4,2'-[1,3]dioxolan-8-yl])-piperazine-1-carboxylic acid tert-butyl ester (0.55 g, 1.46 mmol) in MeOH (10 mL) was added conc. HCl (4 mL). The resulting mixture was stirred at room temperature for 16 h and concentrated under vacuum. The solid obtained was washed with a small amount of MeOH and ether and dried to give the third intermediate compound (0.31 g, 69%).

A reductive amination procedure similar to Example A1' was followed using 8-piperazin-1-yl-chroman-4-one to give the title compound (0.32 g, 83%). $^1$H NMR (400 MHz, CDCl$_3$): δ 7.60 (d, 1H), 7.56 (d, 1H), 7.10 (d, 1H), 6.96 (t, 1H), 6.39 (d, 1H) 4.60 (t, 2H), 4.22 (t, 2H), 3.10 (br s, 4H), 2.85 (m, 4H), 2.70 (m, 6H), 2.46 (m, 2H), 1.85–1.60 (m, 4H).

Example A21'

Synthesis of 7-{4-[4-(3,3-Dimethyl-4-oxo-chroman-8-yl)-piperazin-1-yl]-butoxy}-3,4-dihydro-1H-[1,8]naphthyridin-2-one A first intermediate compound 3-(2-Bromo-phenoxy)-2,2-dimethyl-propionic acid, was produced as follows: To a mixture of 3-methanesulfonyloxy-2,2-dimethyl-propionic acid methyl ester (20.00 g, 95.23 mmol) and 2-bromophenol (16.48 g, 95.23 mmol) in acetonitrile (200 mL) was added Cs$_2$CO$_3$ (46.50 g, 142.80 mmol) and the mixture was heated at 100° C. in a sealed flask overnight. The resulting suspension was filtered. The solvent was evaporated and the crude material was partitioned between dichloromethane (100 mL) and water (100 mL). The organic layer was separated and the aqueous layer was extracted with dichloromethane (50 mL), dried over Na$_2$SO$_4$ and evaporation of the solvent gave 3-(2-bromo-phenoxy)-2,2-dimethyl-propionic acid methyl ester (19.00 g, 70%) as a colorless oil. $^1$H NMR (400 MHz, CDCl$_3$): δ 7.55 (d, 1H), 7.26–7.22 (m, 1H), 6.87–6.80 (m, 2H), 4.02 (s, 2H), 3.72 (s, 3H), 1.40 (s, 6H).

To a solution of the methyl ester (19.00 g, 66.20 mmol) in THF:H$_2$O (4:1, 50 mL) was added LiOH·H$_2$O (8.34 g, 198.60 mmol) and the mixture was stirred at room temperature overnight. The organic solvent was evaporated, and the aqueous layer was diluted with water (10 mL). The pH of the reaction mixture was adjusted to 3 using 1N HCl. The compound was extracted with dichloromethane (2×100 mL). The organic layer was dried over Na$_2$SO$_4$ and evaporation of the solvent gave the first intermediate compound (18.00 g, quantitative) as a colorless solid. $^1$H NMR (400 MHz, CDCl$_3$): δ 7.52–7.50 (m, 1H), 7.26–7.22 (m, 1H), 6.89–6.80 (m, 2H), 4.03 (s, 2H), 1.41 (s, 6H).

A second intermediate compound, 8-Bromo-3,3-dimethyl-chroman-4-one, was produced as follows: To a solution of 3-(2-bromo-phenoxy)-2,2-dimethyl-propionic acid (6.00 g, 21.98 mmol) in chlorobenzene (150 mL) was added Yb(OTf)$_3$ (1.36 g, 2.20 mmol) and the mixture was heated at 190° C. in a sealed flask overnight. The resulting suspension was filtered. The solvent was evaporated and the crude material was partitioned between diethyl ether (100 mL) and water (50 mL). The organic layer was separated and the aqueous layer was extracted with diethyl ether (50 mL), dried over Na$_2$SO$_4$ and evaporation of the solvent gave the second intermediate compound (4.00 g, 71%) as a pale yellow oil. $^1$H NMR (400 MHz, CDCl$_3$): δ 7.89 (d, 1H), 6.75 (d, 1H), 6.90–6.81 (m, 1H), 4.25 (s, 2H), 1.20 (s, 6H).

A third intermediate compound, 4-(3,3-Dimethyl-4-oxo-chroman-8-yl)-piperazine-1-carboxylic acid tert-butyl ester, was produced as follows: To a mixture of 8-bromo-3,3-dimethyl-chroman-4-one (1.60 g, 6.27 mmol) and Boc-piperazine (1.40 g, 7.53 mmol) in degassed toluene (30 mL) was added palladium acetate (0.14 g, 0.63 mmol), 2-(di-tert-butylphosphino)biphenyl (0.37 g, 1.25 mmol) and sodium t-butoxide (0.84 g, 8.78 mmol). The reaction mixture was heated overnight at 100° C. The solvent was removed, and the compound was purified by flash column chromatography using 10% ethyl acetate in hexanes to give the third intermediate compound (1.30 g, 58%). $^1$H NMR (400 MHz, CDCl$_3$): δ 7.60 (d, 1H), 7.10 (br d, 1H), 6.95–6.90 (m, 1H), 4.20 (s, 2H), 3.63–3.60 (m, 4H), 3.04–3.00 (m, 4H), 1.50 (s, 9H), 1.21 (s, 6H).

A fourth intermediate compound, 3,3-Dimethyl-8-piperazin-1-yl-chroman-4-one, was produced as follows: A solution of 4-(3,3-dimethyl-4-oxo-chroman-8-yl)-piperazine-1-carboxylic acid tert-butyl ester (1.30 g, 3.61 mmol) in dichloromethane (10 mL) was treated with trifluoroacetic acid (10 mL). The resulting mixture was stirred at room temperature for 2 h. The brown solution was concentrated under vacuum and diluted with water (20 mL) and pH was adjusted to 7 using saturated NaHCO$_3$ solution. The compound was extracted with dichloromethane (2×40 mL). The organic layer was dried over Na$_2$SO$_4$ and evaporation of the solvent gave the fourth intermediate compound (0.77 g, 83%) as a colorless oil. $^1$H NMR (400 MHz, CDCl$_3$): δ 7.62 (d, 1H), 7.11 (br d, 1H), 7.00–6.95 (m, 1H), 4.20 (s, 2H), 3.25–3.19 (m, 8H), 1.22 (s, 6H).

A reductive amination procedure similar to Example A1' was followed using 3,3-dimethyl-8-piperazin-1-yl-chroman-4-one to give the title compound (0.41 g, 51%). $^1$H NMR (400 MHz, CDCl$_3$) δ7.73 (br s, 1H), 7.60–7.58 (d, 1H), 7.37–7.35 (m, 1H), 7.11–7.09 (m, 1H), 6.99–6.95 (m, 1H), 6.35 (d, 1H), 4.24–4.21 (m, 4H), 3.11 (br, 4H), 2.87 (t, 2H), 2.69–2.63 (m, 6H), 2.49 (t, 2H), 1.82–1.67 (m, 8H).

Example A22'

Synthesis of 7-{4-[4-(3,3-Dimethyl-chroman-8-yl)-piperazin-1-yl]-butoxy}-3,4-dihydro-1H-[1,8]naphthyridin-2-one A first intermediate compound 8-Bromo-3,3-dimethyl-chroman, was produced as follows: To a solution of 8-bromo-3,3-dimethyl-chroman-4-one (1.90 g, 7.45 mmol) in BF$_3$-Et$_2$O (6 mL) was added Et$_3$SiH (5.19 g, 44.71 mmol) and the mixture was heated at 90° C. in a sealed tube overnight. The solvent was evaporated and the crude material was partitioned between CH$_2$Cl$_2$ (20 mL) and water (20 mL). The organic layer was separated and the aqueous layer was extracted with CH$_2$Cl$_2$ (20 mL), dried over Na$_2$SO$_4$ and evaporation of the solvent gave the first intermediate compound (1.10 g, 61%) as an oil. $^1$H NMR (400 MHz, CDCl$_3$): δ 7.34 (d, 1H), 6.96 (d, 1H), 6.74–6.70 (m, 1H), 3.86 (s, 2H), 2.57 (s, 2H), 1.03 (s, 6H).

A second intermediate compound, 4-(3,3-Dimethyl-chroman-8-yl)-piperazine-1-carboxylic acid tert-butyl ester, was produced as follows: To a mixture of 8-bromo-3,3-dimethyl-chroman (0.90 g, 3.73 mmol) and Boc-piperazine (0.83 g, 4.48 mmol) in degassed toluene (20 mL) was added palladium acetate (0.08 g, 0.37 mmol), 2-(di-tert-butylphosphino)biphenyl (0.22 g, 0.75 mmol) and sodium t-butoxide (0.50 g, 5.23 mmol). The reaction mixture was heated overnight at 100° C. The solvent was removed, and the compound was purified by flash column chromatography using 10% ethyl acetate in hexanes to give the second intermediate compound (0.65 g, 50%). $^1$H NMR (400 MHz, CDCl$_3$): δ 6.83–6.71 (m, 3H), 3.83 (s, 2H), 3.62–2.96 (br m, 4H), 2.99–2.96 (br m, 4H), 2.55 (s, 2H), 1.48 (s, 9H), 1.03 (s, 6H).

A third intermediate compound, 1-(3,3-Dimethyl-chroman-8-yl)-piperazine, was produced as follows: A solution of 4-(3,3-dimethyl-chroman-8-yl)-piperazine-1-carboxylic acid tert-butyl ester (0.65 g, 1.88 mmol) in dichloromethane (5 mL) was treated with trifluoroacetic acid (5 mL). The resulting mixture was stirred at room temperature for 1 h. The brown solution was concentrated under vacuum and diluted with water (20 mL) and the pH was adjusted to 7 using saturated NaHCO$_3$ solution. The compound was extracted with dichloromethane (2×40 mL). The organic layer was dried over Na$_2$SO$_4$ and evaporation of the solvent gave the third intermediate compound (0.55 g, quant.) as a colorless oil. $^1$H NMR (400 MHz, CDCl$_3$): δ 6.84–6.74 (m, 3H), 3.81 (s, 2H), 3.30–3.22 (m, 8H), 2.55 (s, 2H), 1.03 (s, 6H).

A reductive amination procedure similar to Example A1' was followed using 1-(3,3-dimethyl-chroman-8-yl)-piperazine to give the title compound (0.25 g, 53%). $^1$H NMR (400 MHz, CDCl$_3$): δ 7.56 (br s, 1H), 7.39 (d, 1H), 6.82–6.78 (m, 2H), 6.70 (br s, 1H), 6.36 (d, 1H), 4.21 (m, 2H), 3.81 (s, 2H), 3.20–3.00 (br s, 3H), 2.82 (t, 2H), 2.70–2.60 (m, 6H), 2.55 (s, 2H), 2.30–2.20 (br t, 2H), 1.82–1.63 (m, 4H), 1.03 (s, 6H).

Example A23'

Synthesis of 7-[4-(4-Benzofuran-7-yl-piperazin-1-yl)-butoxy]-3,4-dihydro-1H-[1,8]naphthyridin-2-one A reductive amination procedure similar to Example A1' was followed using 1-benzofuran-7-yl-piperazine to give the title compound. MS: APCI: M+1: 421.2 (Exact Mass: 420.22).

Example A24'

Synthesis of 7-{4-[4-(1H-Indol-7-yl)-piperazin-1-yl]-butoxy}-3,4-dihydro-1H-[1,8]naphthyridin-2-one A reductive amination procedure similar to Example A1' was followed using 7-piperazin-1-yl-1H-indole to give the title compound. MS: APCI: M+1: 420.2 (Exact Mass: 419.23).

Example A25'

Synthesis of 7-{4-[4-(1H-Indol-4-yl)-piperazin-1-yl]-butoxy}-3,4-dihydro-1H-[1,8]naphthyridin-2-one A reductive amination procedure similar to Example A1' was followed using 4-piperazin-1-yl-1H-indole. Purification by liquid chromatography (0–7% MeOH/CH$_2$Cl$_2$) gave the title compound as a foam. The foam was dissolved in Et$_2$O and a solid crashed out (305 mg, 0.727 mmol, 43%). MS: APCI: M+1: 420.2 (Exact Mass: 419.23).

Example A26'

Synthesis of 7-{4-[4-(1-Methyl-1H-indol-4-yl)-piperazin-1-yl]-butoxy}-3,4-dihydro-1H-[1,8]naphthyridin-2-one A reductive amination procedure similar to Example A1' was followed using 1-methyl-4-piperazin-1-yl-1H-indole. MS: APCI: M+1: (Exact Mass: 433.25).

Example A27'

Synthesis of 7-{4-[4-(2-Methyl-1H-indol-4-yl)-piperazin-1-yl]-butoxy}-3,4-dihydro-1H-[1,8]naphthyridin-2-one A reductive amination procedure similar to Example A1' was followed using 2-methyl-4-piperazin-1-yl-1H-indole. Purification by liquid chromatography (6% MeOH/CH$_2$Cl$_2$) gave the title compound as a tan foam (618 mg, 1.43 mmol, 83%). MS: APCI: M+1: 434.2 (Exact Mass: 433.25).

Example A28'

Synthesis of 7-[4-(4-Benzo[b]thiophen-4-yl-piperazin-1-yl)-butoxy]-3,4-dihydro-1H-[1,8]naphthyridin-2-one A reductive amination procedure similar to Example A1' was followed using 1-benzo[b]thiophen-4-yl-piperazine. Purification by liquid chromatography (0–10% MeOH/CH$_2$Cl$_2$) gave the title compound as an oil. Et$_2$O was added and a solid crashed out to give a yellow solid (241 mg, 0.552 mmol, 89%). MS: APCI: M+1: 437.2 (Exact Mass: 436.19).

Example A29'

Synthesis of 7-[4-(4-Benzo[1,2,5]oxadiazol-4-yl-piperazin-1-yl)-butoxy]-3,4-dihydro-1H-[1,8]naphthyridin-2-one A reductive amination procedure similar to Example A1' was followed using 4-piperazin-1-yl-benzo[1,2,5]oxadiazole hydrochloride (Vogel, Martin; Karst, Uwe. (2001), DE 19936731) to give the title compound (0.395 g; 74%). MS: APCI: M+1: 423.2 (Exact mass: 422.21).

Example A30'

Synthesis of 7-[4-(4-Benzo[1,2,5]thiadiazol-4-yl)-piperazin-1-yl)-butoxy]-3,4-dihydro-1H-[1,8]naphthyridin-2-one A reductive amination procedure similar to Example A1' was followed using 4-piperazin-1-yl-benzo[1,2,5]thiadiazole (Lowe, John A., III.; Nagel, Arthur A. (1989), U.S. Pat. No. 4,831,031) to give the title compound (0.336 g; 60%). MS: APCI: M+1: 439.2 (Exact mass: 438.18).

Example A31'

Synthesis of 7-{4-[4-(2-Trifluoromethyl-3H-benzoimidazol-4-yl)-piperazin-1-yl]-butoxy}-3,4-dihydro-1H-[1,8]naphthyridin-2-one A first intermediate compound, 4-Nitro-2-trifluoromethyl-1H-benzoimidazole, was produced as follows: To a chilled flask containing 3-nitro-benzene-1,2-diamine (3.454 g, 22.557 mmol, 1 eq) was added trifluoroacetic anhydride (19.33 g, 92.04 mmol, 4 eq) drop wise. The suspension was stirred for two hours and then the light brown solid was filtered off. To the solid was added toluene (55 mL) and p-toluenesulfonic acid (10.13 g, 53.25 mmol, 2.361 eq) and the mixture was heated at 120° C. for two hours. The reaction was cooled to room temperature and diluted with ethyl acetate. The solution was washed with 1 N NaOH and then brine. The organic solution was concentrated to provide the first intermediate compound as a brown solid (4.622 g, 88%). MS: APCI: M+1: 232.0 (Exact Mass: 231.03).

A second intermediate compound, 2-Trifluoromethyl-1H-benzoimidazol-4-ylamine, was produced as follows: A solution of 4-nitro-2-trifluoromethyl-1H-benzoimidazole (3.73 g, 16.1 mmol) in 100 mL (1:1 THF:methanol) was hydrogenated using Ra/Ni. The reaction was filtered and then concentrated to obtain second intermediate compound (3.527 g, 100%). MS: APCI: M+1: 202.0 (Exact Mass: 201.05).

A third intermediate compound, 4-Piperazin-1-yl-2-trifluoromethyl-1H-benzoimidazole, was produced as follows: To a reaction flask containing a mixture of 2-trifluoromethyl-1H-benzoimidazol-4-ylamine (0.325 g, 1.618 mmol, 1 eq) and alumina (3.27 g, 32.1 mmol, 19.8 eq) was added bis-(2-chloro-ethyl)-amine hydrochloride (0.600 g, 3.363 mmol, 2.1 eq). The reaction was heated to 140° C. for 6 hours. The reaction was cooled and treated with 10 mL of 1 N NaOH (1 mL) in methanol. The mixture was filtered and concentrated. Purification by chromatography on silica gel (0–40% MeOH/NH$_4$OH:CH$_2$Cl$_2$) afforded the third intermediate compound (0.181 g, 41%). MS: APCI: M+1: 271.0 (Exact Mass: 270.11).

To a suspension of 4-(7-oxo-5,6,7,8-tetrahydro-[1,8]-naphthyridin-2-yloxy)-butyraldehyde (0.297 g, 1.266 mmol, 1.32 eq) and 4-piperazin-1-yl-2-trifluoromethyl-1H-benzoimidazole (0.258 g, 0.953 mmol, 1 eq) in dichloroethane (5 mL) was added NaBH(OAc)$_3$ (0.723 g, 3.413 mmol, 3.58 eq). The slurry was allowed to stir overnight at room temperature (18 h). Analysis by HPLC showed reaction mostly complete. The mixture was diluted with Ethyl Acetate and quenched with saturated NaHCO$_3$. The organic phase was then washed with brine, dried over Na$_2$SO$_4$, filtered and evaporated in vacuo. Purification by silica gel chromatography (2% MeOH/CH$_2$Cl$_2$) followed by formation of the HCl salt using 1N HCl in ether provided the title compound (0.166 g, 35%). MS: APCI: M+1: 489.2 (Exact Mass: 488.21).

Example A32'

Synthesis of 7-{4-[4-(1-Methyl-1,2,3,4-tetrahydro-quinolin-5-yl)-piperazin-1-yl]-butoxy}-3,4-dihydro-1H-[1,8]naphthyridin-2-one An intermediate compound, 1-Methyl-5-piperazin-1-yl-1,2,3,4-tetrahydro-quinoline, was produced as follows: To a stirred solution of 4-(1,2,3,4-tetrahydro-quinolin-5-yl)-piperazine-1-carboxylic acid tert-butyl ester (1.30 g, 4.10 mmol) in THF-DMF (1:1, 40 mL) was added NaH (60% dispersion in oil, 0.58 g, 24.16 mmol) at room temperature. The resulting mixture was stirred at room temperature for 1 h, cooled to 0° C. and iodomethane (1.75 g, 12.30 mmol) was added. The mixture was stirred at room temperature overnight and diluted with ethyl acetate. Water was added and the organic layer was separated. The aqueous layer was extracted with ethyl acetate. The combined organic extracts were washed with water, brine, dried (Na$_2$SO$_4$) and the solvent was removed in vacuo. The residue was purified on a silica gel column using hexanes-ethyl acetate (3:1) as eluent to give 4-(1-methyl-1,2,3,4-tetrahydro-quinolin-5-yl)-piperazine-1-carboxylic acid tert-butyl ester (0.90 g, 66%) as a liquid. $^1$H NMR (400 MHz, CDCl$_3$): δ 7.10 (t, 1H), 6.40 (m, 2H), 3.50 (br s , 4H), 3.25 (t, 2H), 2.90 (s, 3H), 2.80 (br s, 4H), 2.75 (t, 2H), 1.90 (t, 3H), 1.45 (s, 9H).

To a stirred solution of 4-(1-methyl-1,2,3,4-tetrahydro-quinolin-5-yl)-piperazine-1-carboxylic acid tert-butyl ester (0.90 g, 2.72 mmol) in dichloromethane (15 mL) cooled to 0° C., was added trifluoroacetic acid (3.10 g, 27.20 mmol). The resulting mixture was stirred at room temperature overnight and the solvent was removed in vacuo to give the intermediate compound (0.90 g, 97%) as a foam. $^1$H NMR (400 MHz, CDCl$_3$): δ 9.60 (br s, 1H), 7.25 (d, 1H), 6.90 (d, 1H), 6.79 (d, 1H), 3.39 (t, 2H), 3.30 (br s, 4H), 3.19 (br s, 4H), 3.10 (s, 3H), 2.78 (t, 2H), 2.15 (t, 2H), 1.65 (t, 2H). MS ES: m/z 232.12 (M+H)$^+$ (Exact mass: 231.17).

A reductive amination procedure similar to Example A1' was followed using 1-methyl-5-piperazin-1-yl-1,2,3,4-tetrahydro-quinoline to give the title compound. $^1$H NMR (400 MHz, CDCl$_3$): δ 12.95 (br s, 1H), 7.80 (br s, 1H), 7.42 (d, 1H), 7.30 (d, 1H), 7.15 (d, 1H), 6.39 (d, 1H), 4.28 (t, 2H), 3.80–3.60 (br, 4H), 3.45 (br s, 2H), 3.18(s, 3H), 3.15 (br, 6H), 2.85 (br s, t, 4H), 2.65(t, 2H), 2.18 (br, 4H), 1.85 (t, 2H). MS ES: m/z 450.13 (M+H)$^+$ (Exact mass: 449.28).

Example A33'

Synthesis of 7-{4-[4-(1-Ethyl-1,2,3,4-tetrahydro-quinolin-5-yl)-piperazin-1-yl]-butoxy}-3,4-dihydro-1H-[1,8]naphthyridin-2-one A reductive amination procedure similar to Example A1' was followed using 1-ethyl-5-piperazin-1-yl-1,2,3,4-tetrahydro-quinoline to give the title compound. $^1$H NMR (400 MHz, CDCl$_3$): δ 8.50 (s, 1H), 7.35 (d, 1H), 7.00 (t, 1H), 6.28 (m, 2H), 4.30 (t, 2H), 3.60–2.20 (m, 8H), 2.95–2.40 (m, 12H), 1.95–1.75 (m, 4H), 1.05 (t, 3H). MS ES: m/z 464.18 (M+H)$^+$ (Exact mass: 463.29).

Example A34'

Synthesis of 7-[4-(4-Quinolin-8-yl-piperazin-1-yl)-butoxy]-3,4-dihydro-1H-[1,8]naphthyridin-2-one A reductive amination procedure similar to Example A1' was followed using 8-piperazin-1-yl-quinoline. Purification by liquid chromatography (0–10% MeOH/CH$_2$Cl$_2$) gave the title compound as a foam (460 mg, 1.06 mmol, 62%). MS: APCI: M+1: 432.2 (Exact Mass: 431.23).

Example A35'

Synthesis of 7-[4-(4-Quinolin-5-yl-piperazin-1-yl)-butoxy]-3,4-dihydro-1H-[1,8]naphthyridin-2-one A reductive amination procedure similar to Example A1' was followed using 5-piperazin-1-yl-quinoline. Purification by liquid chromatography (0–10% MeOH/CH$_2$Cl$_2$) gave the title compound as a white solid (517 mg, 1.20 mmol, 70%). MS: APCI: M+1: 432.2 (Exact Mass: 431.23).

Example A36'

Synthesis of 7-[4-(4-Isoquinolin-8-yl-piperazin-1-yl)-butoxy]-3,4-dihydro-1H-[1,8]naphthyridin-2-one A reductive amination procedure similar to Example A1' was followed using 8-piperazin-1-yl-isoquinoline to give the title compound as a yellow foam. MS: APCI: M+1: 432.5 (Exact Mass: 431.23).

Example A37'

Synthesis of 7-[4-(4-Isoquinolin-5-yl-piperazin-1-yl)-butoxy]-3,4-dihydro-1H-[1,8]naphthyridin-2-one A reductive amination procedure similar to Example A1' was followed using 5-piperazin-1-yl-isoquinoline to give the title compound as a yellow foam which was recrystallized from Et$_2$O to give a yellow solid. MS: APCI: M+1 :432.2 (Exact Mass: 431.23).

Example A38'

Synthesis of 7-{4-[4-(3-Fluoro-quinolin-5-yl)-piperazin-1-yl]-butoxy}-3,4-dihydro-1H-[1,8]naphthyridin-2-one A first intermediate compound, 3-Fluoro-quinolin-5-ylamine and 3-Fluoro-quinolin-8-ylamine, was produced as follows: 3-Fluoro-quinoline (2.808 g, 19.10 mmol) was cooled to 0° C. and sulfuric acid (15 mL) was added. To the mixture was added fuming nitric acid (1.21 mL, 1.81 g, 29.0 mmol) dropwise. The mixture was warmed to room temperature and stirred for 1 hour. The mixture was poured into 200 mL ice, quenched with NaOH until basic and extracted with ethyl acetate (2×30 mL). The organic layers were combined and washed with brine (30 mL), dried over anhydrous sodium sulfate, filtered and concentrated in vacuo to give a mixture of 3-fluoro-5-nitro-quinoline and 3-fluoro-8-nitro-quinoline (3.50 g, 95%) as a yellow solid.

The mixture of nitroquinolines was dissolved in ethyl acetate (40 mL) and 5% palladium on charcoal (800 mg) was added. The mixture was placed in a Parr apparatus and shaken under 40 psi hydrogen atmosphere for 1.5 h. The mixture was filtered through celite, evaporated in vacuo and the residue purified by column chromatography (gradient elution 3:1 to 1:1, hexanes/ethyl acetate) to yield 3-fluoro-quinolin-5-ylamine (1.79 g, 61%) as a brown solid [$^1$H NMR (400 MHz, dmso-d$_6$) δ 8.80 (d, 1H), 8.40 (d, 1H), 7.40 (t, 1H), 7.20 (d, 1H), 6.78 (d, 1H), 6.00 (s, 2H)] and 3-fluoro-quinolin-8-ylamine (726 mg, 25%) [$^1$H NMR (400 MHz, CDCl$_3$) δ 8.60 (s, 1H), 7.64 (d, 1H), 7.38 (t, 1H), 7.10 (d, 1H), 6.84 (d, 1H), 4.99 (s, 2H)].

A second intermediate compound, 3-Fluoro-5-piperazin-1-yl-quinoline, was produced as follows: 3-Fluoro-quinolin-5-ylamine (400 mg, 2.47 mmol), bis(2-chloroethyl)amine hydrochloride (485 mg, 2.72 mmol), sodium iodide (185 mg, 1.24 mmol) and diisopropylethylamine (0.22 mL, 160 mg, 1.24 mmol) were all dissolved in a mixture of chlorobenzene (6 mL) and 1-hexanol (1 mL). The mixture was heated at 140° C. overnight. The mixture was cooled and concentrated in vacuo. The residue was loaded onto silica gel and purified by column chromatography (1:10:89, ammonium hydroxide/methanol/dichloromethane) to yield the second intermediate compound (301 mg, 53%) as a brown solid. $^1$H NMR (400 MHz, dmso-d$_6$) δ 9.00 (s, 1H), 8.20 (d, 1H), 7.80 (d, 1H), 7.65 (t, 1H), 7.24 (d, 1H), 3.30 (s, 1H), 3.20 (t, 4H), 3.05–3.00 (m, 4H).

A reductive amination procedure similar to Example A1' was followed using 3-fluoro-5-piperazin-1-yl-quinoline to give the title compound (273 mg, 57%). $^1$H NMR (400 MHz, CDCl$_3$) δ 8.80 (s, 1H), 8.15 (d, 1H), 7.80 (d, 1H), 7.62–7.50 (m, 2H), 7.40 (d, 1H), 7.20 (d, 1H), 6.40 (d, 1H), 4.24 (t, 2H), 3.20–3.00 (m, 4H), 2.80 (t, 2H), 2.78–2.60 (m, 4H), 2.60 (t, 2H), 2.56 (t, 2H), 1.80–1.64 (m, 4H); MS ES+ 450.32 (M+H)$^+$ (Exact mass: 449.22).

Example A39'

Synthesis of 7-{4-[4-(3-Fluoro-quinolin-8-yl)-piperazin-1-yl]-butoxy}-3,4-dihydro-1H-[1,8]naphthyridin-2-one An intermediate compound, 3-Fluoro-8-piperazin-1-yl-quinoline, was produced as follows: 3-Fluoro-quinolin-8-ylamine (1.15 g, 7.10 mmol, see previous example), bis(2-chloroethyl)amine hydrochloride (1.39 g, 7.81 mmol), sodium iodide (532 mg, 3.55 mmol) and diisopropylethylamine (0.62 mL, 459 mg, 3.55 mmol) were all dissolved in a mixture of chlorobenzene (15 mL) and 1-hexanol (2.5 mL). The mixture was heated at 140° C. for 48 hours. The mixture was cooled and concentrated in vacuo. The residue was loaded onto silica gel and purified by column chromatography (1:10:89, NH$_4$OH/methanol/dichloromethane) to yield the first intermediate compound (1.37 g, 83%) as a brown solid. $^1$H NMR (400 MHz, dmso-d$_6$) δ 8.84 (s, 1H), 8.20 (d, 1H), 7.60–7.52 (m, 2H), 7.15–7.10 (m, 1H), 3.60–3.20 (m, 5H), 3.18–3.04 (m, 4H).

A reductive amination procedure similar to Example A1' was followed using 3-fluoro-8-piperazin-1-yl-quinoline to give the title compound (426 mg, 66%). $^1$H NMR (400 MHz, dmso-d$_6$) δ 10.25 (s, 1H), 8.84 (s, 1H), 8.20 (d, 1H), 7.54–7.40 (m, 3H), 7.14–7.00 (m, 1H), 6.40 (d, 1H), 4.20 (t, 2H), 2.78 (t, 2H), 2.64–2.60 (m, 4H), 2.60–2.39 (m, 8H), 1.80–1.70 (m, 2H), 1.70–1.58 (m, 2H), MS ES+ 450.22 (M+H)$^+$ (Exact mass: 449.22).

Example A40'

Synthesis of 7-{4-[4-(2-Methyl-quinolin-8-yl)-piperazin-1-yl]-butoxy}-3,4-dihydro-1H-[1,8]naphthyridin-2-one A reductive amination procedure similar to Example A1' was followed using 2-methyl-8-piperazin-1-yl-quinoline. Purification by liquid chromatography (0–10% MeOH/CH$_2$Cl$_2$) gave the title compound as a foam (530 mg, 1.19 mmol, 60% mmol). MS: APCI: M+1: 446.2 (Exact Mass: 445.25).

Example A41'

Synthesis of 7-{4-[4-(2-Methoxy-quinolin-8-yl)-piperazin-1-yl]-butoxy}-3,4-dihydro-1H-[1,8]naphthyridin-2-one A first intermediate compound 8-Chloro-2-methoxy-quinoline, was produced as follows: To a suspension of 2,8-dichloro-quinoline (1.98 g, 10.00 mmol) in methanol (20 mL) was added NaOMe (0.81 g, 15.00 mmol) and the reaction mixture was heated under reflux overnight. The solvent was evaporated and the residue was dissolved in ethyl acetate (50 mL) and washed with water (2×50 mL). The organic layer was dried (Na$_2$SO$_4$) and evaporated, and the crude product was purified by chromatography (10% EtOAc/Hexane) to give the first intermediate compound as a colorless oil (1.93 g, 99%). $^1$H NMR (400 MHz, CDCl$_3$) δ: 8.00 (d, 2H), 7.70 (d, 1H), 7.60 (d, 1H), 7.28 (t, 1H), 6.98 (d, 1H), 4.10(s, 3H).

A second intermediate compound, 4-(2-Methoxy-quinolin-8-yl)-piperazine-1-carboxylic acid tert-butyl ester, was produced as follows: To an oven-dried flask, under nitrogen, was added Pd(OAc)$_2$ (0.04 g, 0.20 mmol) and 2-(dicyclohexylphosphino)biphenyl (0.072 g, 0.20 mmol). The flask was evacuated, filled with nitrogen, and then the following materials were added in this order: degassed toluene (10 mL), 8-chloro-2-methoxy-quinoline (1.00 g, 5.14 mmol), 1-Boc-piperazine (1.15 g, 6.18 mmol), and NaOtBu (0.69 g, 7.21 mmol). The mixture was stirred at 80° C. for 1.5 h. After cooling to room temperature, the mixture was diluted with ethyl acetate and filtered through a bed of celite. The filtrate was concentrated in vacuo. The crude material was purified by chromatography on silica gel (10% EtOAc/Hexane) to give the second intermediate compound as a yellow oil (1.00 g, 56%). $^1$H NMR (400 MHz, CDCl$_3$) δ: 7.98 (d, 2H), 7.40 (d, 1H), 7.30 (t, 1H), 7.10 (d, 1H), 6.90 (d, 1H), 4.05 (s, 3H), 3.75 (t, 4H), 3.38 (t, 4H), 1.50 (s, 9H).

A third intermediate compound, 2-Methoxy-8-piperazin-1-yl-quinoline, was produced as follows: To a solution of 4-(2-methoxy-quinolin-8-yl)-piperazine-1-carboxylic acid tert-butyl ester (1.00 g, 2.90 mmol) in dichloromethane (20 mL) was added trifluoroacetic acid (4 mL) at 0° C. The reaction mixture was stirred at this temperature for 3 h, and then allowed to warm to room temperature. The mixture was basified by addition of saturated NaHCO$_3$ and extracted with dichloromethane (3×20 mL). The combined organic layer was dried (Na$_2$SO$_4$) and evaporated to give the third intermediate compound (0.70 g, 99%). $^1$H NMR (400 MHz, CDCl$_3$) δ: 7.98 (d, 2H), 7.40 (d, 1H), 7.30 (t, 1H), 7.10 (d, 1H), 6.90 (d, 1H), 4.05 (s, 3H), 3.50 (m, 4H), 3.30 (m, 4H).

A reductive amination procedure similar to Example A1' was followed using 2-methoxy-8-piperazin-1-yl-quinoline to give the title compound. $^1$H NMR (400 MHz, CDCl$_3$) δ: 7.98 (d, 2H), 7.58 (br s, 1H), 7.38 (d, 1H), 7.30 (t, 1H), 7.12 (d, 1H), 6.90 (d, 1H), 6.38 (d, 1H), 4.22 (t, 2H), 4.05 (s, 3H), 2.82 (m, 6H), 2.62 (t, 2H), 2.50 (dd, 2H), 1.82 (m, 2H), 1.78 (m, 2H).

Example A42'

Synthesis of 7-{4-[4-(2-Ethoxy-quinolin-8-yl)-piperazin-1-yl]-butoxy}-3,4-dihydro-1H-[1,8]naphthyridin-2-one An intermediate compound, 2-Ethoxy-8-piperazin-1-yl-quinoline, was produced as follows: The title compound was prepared according to the procedure detailed for 2-methoxy-8-piperazin-1-yl-quinoline above in Example A41'. $^1$H NMR (400 MHz, CDCl$_3$) δ 9.30 (br s, 2H), 8.05 (d, 1H), 7.55 (d, 1H), 7.40 (t, 1H), 7.30 (d, 1H), 6.96 (d, 1H), 4.50 (q, 2H), 3.80 (m, 4H), 3.60(m, 4H), 1.50 (t, 3H).

A reductive amination procedure similar to Example A1' was followed using 2-ethoxy-8-piperazin-1-yl-quinoline to give the title compound (0.27 g, 80%). $^1$H NMR (400 MHz, CDCl$_3$) δ 7.98 (d, 1H), 7.60 (br s, 1H), 7.38 (m, 2H), 7.30 (t, 1H), 7.10 (d, 1H), 6.86 (d, 1H), 6.38 (d, 1H), 4.58 (t, 2H), 4.28 (t, 2H), 3.50 (br s, 4H), 2.90 (t, 2H), 2.82 (m, 4H), 2.62 (t, 2H), 2.58 (t, 2H), 1.90 (m, 2H), 1.80 (m, 2H), 1.50 (t, 3H); MS (ES): m/z: 476.25 (M+H)$^+$ (Exact mass: 475.26).

Example A43'

Synthesis of 7-{4-[4-(2-Methoxy-quinolin-5-yl)-piperazin-1-yl]-butoxy}-3,4-dihydro-1H-[1,8]naphthyridin-2-one A first intermediate compound 5-Bromo-2-chloro-quinoline, was produced as follows: To a solution of 5-bromo-quinoline (8.13 g, 39.27 mmol) in chloroform (70 mL) was added peroxyacetic acid and the mixture was refluxed for 3 hours. After cooling down, the mixture was poured into ice-water and basified by the addition of 4N NaOH aqueous solution to a final pH of 10. The N-oxide was extracted with ethyl acetate and dried (Na$_2$SO4). The solvent was evaporated to give the crude N-oxide as a white solid (6.61 g). To the N-oxide (5.20 g, 23.31 mmol) at −10° C. was carefully added POCl$_3$ (40 mL, highly exothermic). The mixture was then stirred at room temperature for 10 min and heated at 100° C. for 3 hours. The excess of POCl$_3$ was removed under vacuum. The residue was dissolved in dichloromethane, poured into ice-water, and the pH was adjusted to 8. The aqueous layer was extracted with dichloromethane. The combined organic layers were dried and evaporated. The crude product was purified by chromatography (5% EtOAc/Hexane) to give the first intermediate compound as a white solid (1.70 g, 30%). $^1$H NMR (400 MHz, CDCl$_3$) δ: 8.50 (d, 1H), 8.05 (d, 1H), 7.85 (d, 1H), 7.60 (dd, 1H), 7.50 (d, 1H).

A second intermediate compound, 5-Bromo-2-methoxy-quinoline, was produced as follows: To a suspension of 5-bromo-2-chloro-quinoline (0.99 g, 4.10 mmol) in methanol (20 mL) was added NaOMe (0.27 g, 4.73 mmol) and the reaction mixture was heated under reflux overnight. The solvent was evaporated and the residue was dissolved in ethyl acetate (50 mL). The organics were washed with water (2×50 mL), dried (Na$_2$SO$_4$) and evaporated. The crude product was purified by chromatography (5% EtOAc/Hexane) to give the second intermediate compound as white crystals (0.79 g, 82%). $^1$H NMR (400 MHz, CDCl$_3$) δ: 8.40 (d, 1H), 7.85 (d, 1H), 7.65 (d, 1H), 7.45 (dd, 1H), 7.00 (d, 1H), 4.10 (s, 3H).

A third intermediate compound, 2-Methoxy-5-piperazin-1-yl-quinoline, was produced as follows: To an oven-dried flask, under nitrogen, was added Pd(OAc)$_2$ (0.03 g, 0.13 mmol) and 2-(dicyclohexylphosphino)biphenyl (0.045 g, 0.13 mmol). The flask was evacuated and refilled with nitrogen. The following materials were added in the following order: degassed toluene (10 mL), 5-bromo-2-methoxy-quinoline (0.76 g, 3.23 mmol), 1-Boc-piperazine (0.72 g, 3.87 mmol), and NaOtBu (0.43 g, 4.52 mmol). The mixture was stirred at 80° C. for 1.5 h. After cooling to room temperature, the mixture was diluted with ethyl acetate and filtered through celite. The filtrate was concentrated in vaccuo and purified by chromatography on silica gel (10% EtOAc/Hexane) to give 4-(2-methoxy-quinolin-5-yl)-piperazine-1-carboxylic acid tert-butyl ester as a yellowish solid (0.73 g, 66%). $^1$H NMR (400 MHz, CDCl$_3$) δ: 8.35 (d, 1H), 7.60 (m, 2H), 7.00 (d, 1H), 6.90 (d, 1H), 4.05 (s, 3H), 3.75 (m, 4H), 3.00 (m, 4H), 1.50 (s, 9H).

To a solution of 4-(2-methoxy-quinolin-5-yl)-piperazine-1-carboxylic acid tert-butyl ester (0.73 g, 2.14 mmol) in dichloromethane (4.0 mL) was added trifluoroacetic acid (16 mL) at 0° C. The reaction mixture was stirred for 3 h, and was allowed to warm to room temperature during this time. The mixture was evaporated and the residue was treated with diethyl ether. The precipitate was filtered and washed with ether to give the title compound (0.75 g, 95%). $^1$H NMR (400 MHz, CDCl$_3$) δ: 9.90 (br.s, 2H), 8.25 (d, 1H), 7.65 (d, 1H), 7.58 (t, 1H), 7.10 (d, 1H), 6.90 (d, 1H), 4.05 (s, 3H), 3.50 (m, 4H), 3.35 (m, 4H).

A reductive amination procedure similar to Example A1' was followed using 2-methoxy-5-piperazin-1-yl-quinoline to give the title compound (0.38 g, 99%). $^1$H NMR (400 MHz, CDCl$_3$) δ: 8.35 (d, 1H), 7.60 (br.s, 1H), 7.55 (dd, 1H), 7.40 (d, 1H), 7.00 (d, 1H), 6.85 (d, 1H), 6.38 (d, 1H), 4.25 (t, 2H), 4.05 (s, 3H), 3.10 (br.s, 4H), 2.90 (t, 2H), 2.80 (br.s, 4H), 2.70 (t, 2H), 2.55 (t, 2H), 1.82 (m, 2H), 1.78 (m, 2H).

Example A44'

Synthesis of 7-[4-(4-Quinoxalin-5-yl-piperazin-1-yl)-butoxy]-3,4-dihydro-1H-[1,8]naphthyridin-2-one A first intermediate compound Trifluoro-methanesulfonic acid quinoxalin-5-yl ester, was produced as follows: To a solution of quinoxalin-5-ol (3.97 g, 27.2 mmol, prepared according to J. Org. Chem. 1951, 16, 438–442) in CH$_2$Cl$_2$ (110 mL) cooled to 0° C. was added Et$_3$N (7.6 mL, 54.3 mmol) followed by trifluoromethanesulfonic anhydride (6.0 mL, 35.4 mmol). The rxn smoked briefly and was stirred at 0° C. for 1 h. The reaction was quenched with sat. NaHCO$_3$ at 0° C. and warmed to RT. The layers were separated and the aqueous layer was extracted with CH2Cl2. The combined organic layer was washed with water and brine, dried over Na$_2$SO$_4$ and concentrated to give an organic brown solid. The crude material was absorbed onto SiO$_2$ and purified by LC (20% EtOAc/Hexanes) to give the first intermediate compound as a light orange solid (6.51 g, 23.4 mmol, 86%). MS: APCI: M+1: 279.0 (Exact Mass: 278.00).

A second intermediate compound, 4-Quinoxalin-5-yl-piperazine-1-carboxylic acid tert-butyl ester, was produced as follows: A solution of trifluoro-methanesulfonic acid quinoxalin-5-yl ester (4.23 g, 15.2 mmol) in dry DME (30 mL) was degassed for 10 min by blowing nitrogen into the solution. This solution was then added via cannula to a flask containing Boc-piperazine (3.54 g, 19.00 mmol), K$_3$PO$_4$ (4.52 g, 21.3 mmol), Pd$_2$(dba)$_3$ (348 mg, 0.380 mmol, 2.5 mol %) and 2-(di-t-butylphosphino)biphenyl (227 mg, 0.760 mmol, 5 mol %) under nitrogen. The reaction mixture was heated at 80° C. overnight (20 h). MS showed a large product peak. The reaction was allowed to cool to room temperature and Et$_2$O was added. The mixture was filtered through Celite washing with Et$_2$O. The filtrate was washed with 0.5 M citric acid (2×, to remove excess Boc-piperazine) and once with brine, dried over Na$_2$SO$_4$ and concentrated to give a dark red oil. Purification by LC (40% EtOAc/Hexanes) gave the product as a red oil which foamed on the pump (2.68 g, 8.52 mmol, 56%). MS: APCI: M+1: 315.2 (Exact Mass: 314.17).

A third intermediate compound, 5-Piperazin-1-yl-quinoxaline, was produced as follows: To a solution of 4-quinoxalin-5-yl-piperazine-1-carboxylic acid tert-butyl ester (2.65 g, 8.43 mmol) in CH$_2$Cl$_2$ (15 mL) cooled to 0° C. was added TFA (15 mL). The reaction was warmed to room temperature and stirred for 90 min. The mixture was concentrated and the remaining TFA was neutralized by adding 10% MeOH/CH2Cl2 with 1% NH$_4$OH. SiO$_2$ was added and the mixture was concentrated. Purification by LC (10% MeOH/CH$_2$Cl$_2$ with 1% NH$_4$OH) gave the third intermediate compound as an orange solid (1.65 g, 7.70 mmol, 91%). MS: APCI: M+1: 215.2 (Exact Mass: 214.12).

A reductive amination procedure similar to Example A1' was followed using 5-piperazin-1-yl-quinoxaline to give the title compound. MS: APCI: M+1: 433.3 (Exact Mass: 432.23).

Example A45'

Synthesis of 7-{4-[4-(2-Dimethylamino-quinolin-8-yl)-piperazin-1-yl]-butoxy}-3,4-dihydro-1H-[1,8] naphthyridin-2-one A first intermediate compound (8-Chloro-quinolin-2-yl)-dimethyl-amine, was produced as follows: To a suspension of 2,8-dichloro-quinoline (5.00 g, 25.2 mmol) in a water/dioxane solution (69 mL, 10:1) was added an aqueous solution of Na$_2$CO$_3$ (2N, 38 mL, 76 mmol) and dimethylamine hydrochloride (4.12 g, 50.5 mmol). The reaction mixture was heated at 160° C. for 1.5 h in a microwave. The reaction was extracted with CH$_2$Cl$_2$ (2×), dried (Na$_2$SO$_4$) and evaporated, and the crude product was purified by chromatography (2–20% EtOAc/Hexane) to give the first intermediate compound as a faint yellow solid (4.22 g, 81%). MS: APCI: M+1: 207.0 (Exact mass: 206.06).

A second intermediate compound, 4-(2-Dimethylamino-quinolin-8-yl)-piperazine-1-carboxylic acid tert-butyl ester, was produced as follows: To an oven-dried flask, under nitrogen, was added Pd$_2$ (dba)$_3$ (0.111 g, 0.121 mmol) and (2'-dicyclohexylphosphanyl-biphenyl-2-yl)-dimethyl-amine (0.190 g, 0.484 mmol). The flask was evacuated, filled with nitrogen, and then the following materials were added in this order: degassed toluene (14 mL), (8-chloro-quinolin-2-yl)-dimethyl-amine (1.00 g, 5.14 mmol), 1-Boc-piperazine (1.80 g, 9.68 mmol), and Cs$_2$CO$_3$ (2.21 g, 6.77 mmol). The mixture was stirred at 105° C. for 19 h. Another 5 mol % of the catalyst was added and heating was continued for an additional 18 h. After cooling to room temperature, the mixture was diluted and filtered through a bed of celite. The filtrate was concentrated in vacuo. The crude material was purified by chromatography on silica gel (3–40% EtOAc/Hexane) to give the second intermediate compound as yellow foam (1.26 g, 73%). MS: APCI: M+1: 357.2 (Exact mass: 356.22).

A third intermediate compound, Dimethyl-(8-piperazin-1-yl-quinolin-2-yl)-amine, was produced as follows: To a solution of 4-(2-dimethylamino-quinolin-8-yl)-piperazine-1-carboxylic acid tert-butyl ester (1.244 g, 3.63 mmol) in dichloromethane (35 mL) was added trifluoroacetic acid (10 mL) at 0° C. The reaction mixture was stirred at this temperature for 1.5 h, and then allowed to warm to room temperature. The volatiles were removed in vacuo and the crude oil was taken up in $CH_2Cl_2$, and washed with 2N KOH, dried ($Na_2SO_4$) and evaporated to give the third intermediate compound (0.895 g, >99%). MS: APCI: M+1: 257.1 (Exact mass: 256.17).

A reductive amination procedure similar to Example A1' was followed using dimethyl-(8-piperazin-1-yl-quinolin-2-yl)-amine to give the title compound (0.314 g; 79%). MS: APCI: M+1: 475.2 (Exact mass: 474.27).

Example A46'

Synthesis of 7-{4-[4-(2-Methylamino-quinolin-8-yl)-piperazin-1-yl]-butoxy}-3,4-dihydro-1H-[1,8]naphthyridin-2-one A first intermediate compound (8-Chloro-quinolin-2-yl)-methyl-amine, was produced as follows: To a suspension of 2,8-dichloro-quinoline (5.00 g, 25.2 mmol) in a water/dioxane solution (69 mL, 10:1) was added an aqueous solution of $Na_2CO_3$ (2N, 25.2 mL, 50.5 mmol) and aqueous methylamine (40% w/w, 5.4 g, 63 mmol). The reaction mixture was heated at 160° C. for 1.5 h in a microwave. The reaction was extracted with $CH_2Cl_2$ (2×), dried ($Na_2SO_4$) and evaporated, and the crude product was purified by chromatography (2–20% EtOAc/Hexane) to give the first intermediate compound as a light yellow solid (3.69 g, 76%). MS: APCI: M+1: 193.0 (Exact mass: 192.05).

A second intermediate compound, 4-(2-methylamino-quinolin-8-yl)-piperazine-1-carboxylic acid tert-butyl ester, was produced as follows: To an oven-dried flask, under nitrogen, was added $Pd_2(dba)_3$ (0.238 g, 0.260 mmol) and (2'-dicyclohexylphosphanyl-biphenyl-2-yl)-dimethyl-amine (0.409 g, 1.04 mmol). The flask was evacuated, filled with nitrogen, and then the following materials were added in this order: degassed toluene (30 mL), (8-chloro-quinolin-2-yl)-methyl-amine (2.00 g, 10.4 mmol), 1-Boc-piperazine (3.87 g, 20.8 mmol), and $Cs_2CO_3$ (4.74 g, 14.5 mmol). The mixture was stirred at 105° C. for 19 h. After cooling to room temperature, the mixture was diluted and filtered through a bed of celite. The filtrate was concentrated in vacuo. The crude material was purified by chromatography on silica gel (3–50% EtOAc/Hexane) to give the second intermediate compound as light orange oil (0.751 g, 21%). MS: APCI: M+1: 343.3 (Exact mass: 342.21).

A third intermediate compound, Dimethyl-(8-piperazin-1-yl-quinolin-2-yl)-amine, was produced as follows: To a solution of 4-(2-methylamino-quinolin-8-yl)-piperazine-1-carboxylic acid tert-butyl ester (0.751 g, 2.19 mmol) in dichloromethane (29 mL) was added trifluoroacetic acid (10 mL) at 0° C. The reaction mixture was stirred at this temperature for 1 h, and then allowed to warm to room temperature. The volatiles were removed in vacuo and the crude oil was taken up in $CH_2Cl_2$, and washed with 2N KOH, dried ($Na_2SO_4$) and evaporated to give the third intermediate compound (0.510 g, 96%). MS: APCI: M+1: 243.1 (Exact mass: 242.15).

A reductive amination procedure similar to Example A1' was followed using methyl-(8-piperazin-1-yl-quinolin-2-yl)-amine to give the title compound (0.081 g; 28%). MS: APCI: M+1: 461.3 (Exact mass: 460.26).

Example A47'

Synthesis of 7-{4-[4-(2-Oxo-1,2-dihydro-quinolin-8-yl)-piperazin-1-yl]-butoxy}-3,4-dihydro-1H-[1,8]naphthyridin-2-one In a manner similar to that of other examples above, 8-piperazin-1-yl-1H-quinolin-2-one hydrochloride (Chem. Pharm. Bull. 1984, 32, 2100–2110) was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 448.2 (Exact Mass: 447.23).

Example A48'

Synthesis of 7-{4-[4-(2-Oxo-1,2,3,4-tetrahydro-quinolin-8-yl)-piperazin-1-yl]-butoxy}-3,4-dihydro-1H-[1,8]naphthyridin-2-one In a manner similar to that of other examples above, 8-piperazin-1-yl-3,4-dihydro-1H-quinolin-2-one hydrochloride (Chem. Pharm. Bull. 1984, 32, 2100–2110) was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 450.2 (Exact Mass: 449.24).

Example A49'

Synthesis of 7-{4-[4-(1-Methyl-2-oxo-1,2,3,4-tetrahydro-quinolin-8-yl)-piperazin-1-yl]-butoxy}-3,4-dihydro-1H-[1,8]naphthyridin-2-one A first intermediate compound, 4-(2-Oxo-1,2,3,4-tetrahydro-quinolin-8-yl)-piperazine-1-carboxylic acid tert-butyl ester, was produced as follows: To dichloromethane (75 mL) was added 8-piperazin-1-yl-3,4-dihydro-1H-quinolin-2-one hydrochloride (10.8 mmol), diisopropylethylamine (1.95 mL, 11.2 mmol) and di-t-butylcarbonate (9.20 g, 9.33 mmol) followed by stirring for 16 hours at 25° C. The mixture was washed consecutively with 1N citric acid, saturated sodium bicarbonate and brine. The organic phase was dried over sodium sulfate, filtered and evaporated to give the first intermediate compound (2.78 g), mp 117–178° C.

A second intermediate compound, 1-Methyl-8-piperazin-1-yl-3,4-dihydro-1H-quinolin-2-one hydrochloride, was produced as follows: To a solution of 4-(2-oxo-1,2,3,4-tetrahydro-quinolin-8-yl)-piperazine-1-carboxylic acid tert-butyl ester (2.5 g, 7.54 mmol) in THF (45 mL) cooled to −50° C. was added a solution of potassium t-butoxide, 1M in THF (8.3 mL, 8.30 mmol). After stirring for 15 minutes, methyl iodide (0.47 mL, 7.54 mmol) was added followed by stirring for 16 hours at 25° C. The mixture was evaporated and the residue was taken up into dichloromethane. The solution was washed consecutively with 1N citric acid, saturated sodium bicarbonate and brine. The organic phase was dried over sodium sulfate, filtered and evaporated to give a white foam, which was purified by chromatography on silica gel eluting with a gradient of dichloromethane and ethyl acetate. Evaporation of the appropriate fractions gave 4-(1-methyl-2-oxo-1,2,3,4-tetrahydro-quinolin-8-yl)-piperazine-1-carboxylic acid tert-butyl ester (2.1 g).

To a mixture of dichloromethane (45 mL) and diethyl ether (5 mL) was added 4-(1-methyl-2-oxo-1,2,3,4-tetrahydro-quinolin-8-yl)-piperazine-1-carboxylic acid tert-butyl ester (2.1 g, 6.08 mmol), followed by purging with anhydrous HCl gas intermittently over several hours until the starting material was consumed. The mixture was evaporated to a solid, triturated with diethyl ether and dried in vacuo to give the second intermediate compound as a pale yellow solid (1.75 g).

In a manner similar to that of other examples above, 1-methyl-8-piperazin-1-yl-3,4-dihydro-1H-quinolin-2-one hydrochloride was coupled by reductive amination to 4-(7-oxo-5,6,7,8-tetrahydro-[1,8]naphthyridin-2-yloxy)-butyraldehyde followed by typical workup and purification to give the title compound. MS: APCI: M+1: 464.6 (Exact Mass: 463.26).

Example B1'

Synthesis of 7-[4-(4-Chroman-8-yl-piperazin-1-yl)-butoxy]-1H-[1,8]naphthyridin-2-one A first intermediate compound, 2-Benzyloxy-7-[4-(tetrahydro-pyran-2-yloxy)-butoxy]-[1,8]naphthyridine, was produced as follows: To a solution of 4-(tetrahydro-pyran-2-yloxy)-1-butanol (3.27 g, 18.8 mmol, 1.2 equiv) in THF (20 mL) cooled to 0° C. was added KO$^t$Bu (1M in THF, 18 mL, 18 mmol, 1.15 equiv). The solution was stirred at 0° C. for 20 min and then added via cannula to a suspension of 2-benzyloxy-7-chloro-[1,8]naphthyridine (4.24 g, 15.66 mmol) in THF (50 mL) cooled to 0° C. The reaction turned orange and became homogenous. After 30 min at 0° C., saturated NH$_4$Cl and H$_2$O were added to quench the reaction. The mixture was extracted with EtOAc. The organic layer was washed with saturated NaHCO$_3$, H$_2$O and brine, dried over Na$_2$SO$_4$ and concentrated. The crude was absorbed onto SiO$_2$ and purified by liquid chromatography (20–30% EtOAc/Hexanes) to give the first intermediate compound as a pale yellow oil (3.71 g, 9.08 mmol, 58%). MS: APCI: M+1: 409.2 (Exact Mass: 408.20).

A second intermediate compound, 7-(4-Hydroxy-butoxy)-1H-[1,8]naphthyridin-2-one, was produced as follows: 2-Benzyloxy-7-[4-(tetrahydro-pyran-2-yloxy)-butoxy]-[1,8]naphthyridine (620 mg, 1.52 mmol) was hydrogenated using 5% Pd/C in MeOH for 40 min. The reaction was filtered and concentrated. The residue was dissolved in EtOH (5 mL) and PPTS (25 mg, 0.10 mmol) was added. The mixture was heated at 60° C. overnight. The reaction was concentrated and purified by liquid chromatography (6% MeOH/CH$_2$Cl$_2$) to give the second intermediate compound as a white solid (282 mg, 1.20 mmol, 79%). MS: APCI: M+1: 235.1 (Exact Mass: 234.10).

This intermediate was also prepared using the following procedure: To a suspension of 60% NaH (83.6 g, 2.09 mol) in NMP (1 L) was added dry 1,4-butanediol (300 mL, 3.39 mol, concentrated from toluene) dropwise to control foaming. The reaction temperature increased to 50° C. and the mixture was stirred at 60° C. for 15 min. 7-Chloro-1H-[1,8]naphthyridin-2-one (146 g, 0.813 mol) was added with stirring and the reaction was heated at 68° C. for 20 h. CH$_3$CN (5 L) was added and the mixture was filtered and the filter cake was washed with CH$_3$CN (500 mL) and THF (500 mL). The filter cake was reslurried with THF (3 L) and 3N HCl in MeOH (290 mL, 0.870 mol) was added. The mixture was heated at 60° C. for 1 h and then filtered through celite washing with THF (1 L). The filtrate was concentrated to a volume of 500 mL and THF (1.5 L), Darco (10 g) and magnesol (100 mL) was added. The mixture was stirred at 40° C. for 30 min and then filtered washing with THF (500 mL). The filtrate was concentrated to 500 mL, CH$_3$CN was added and the mixture was concentrated to 1 L. The resulting solid was filtered, washed with CH$_3$CN (200 mL) and Et$_2$O (300 mL) and dried at 50° C. to yield the second intermediate compound (101 g, 53%). The filtrate upon standing gave additional crystals, which were collected by filtration, washed and dried as before to give additional second intermediate compound (17 g, total yield of 62%).

A third intermediate compound, 4-(7-Oxo-7,8-dihydro-[1,8]naphthyridin-2-yloxy)-butyraldehyde, was produced as follows: Using Swern oxidation: To a solution of oxalyl chloride (0.12 mL, 1.32 mmol, 1.1 equiv) in CH2Cl2 (2.5 mL) cooled to −78° C. was added DMSO (0.18 mL, 2.6 mmol). The reaction was stirred for 5 min and then 7-(4-hydroxy-butoxy)-1H-[1,8]naphthyridin-2-one (282 mg, 1.20 mmol) was added as a solution in CH2Cl2 (4.5 mL) and DMSO (1.2 mL) via cannula over 5 min. The DMSO was necessary to dissolve the alcohol. The reaction was stirred for 15 min and Et$_3$N (0.83 mL, 6.0 mmol, 5 equiv) was added. The reaction turned cloudy. The reaction was allowed to stir at −78° C. for 10 min and then warmed to RT. After 30 min at RT, H2O was added and the mixture was extracted with CH2Cl2. The organic layer was washed with brine, dried over MgSO4 and concentrated to give the third intermediate compound as a light brown oil (340 mg), which was used in the next reaction. MS: APCI: M+1: 233.1 (Exact Mass: 232.08).

Using IBX oxidation: To a solution of 7-(4-hydroxy-butoxy)-1H-[1,8]naphthyridin-2-one (223 mg, 0.952 mmol) in DMSO (3 mL) was added a solution of IBX (400 mg, 1.43 mmol) in DMSO (4.8 mL, 0.3 M). The reaction was stirred at room temperature for 6 h, cooled to 0° C. and quenched with 5% NaHCO3. The mixture was extracted with CH2Cl2 (4×). The organic layer was washed with 5% NaHCO3, dried over MgSO4 and concentrated to give the third intermediate compound as a pale yellow solid (175 mg, 0.754 mmol, 79%). MS: APCI: M+1: 233.1 (Exact Mass: 232.08).

A mixture of 4-(7-oxo-7,8-dihydro-[1,8]naphthyridin-2-yloxy)-butyraldehyde (300 mg, 1.29 mmol) and 1-chroman-8-yl-piperazine bishydrochloride (395 mg, 1.36 mmol) were suspended in DCE (8 mL)/DMF (1 mL) and Et$_3$N (0.54 mL, 3.88 mmol) was added. After about 10 min, NaBH(OAc)3 (356 mg, 1.68 mmol) was added and the reaction was stirred at room temperature for 2 h. The reaction was quenched with saturated NaHCO3 and extracted with EtOAc. The organic layer was washed with saturated NaHCO3 and brine, dried over Na2SO4 and concentrated. Purification by liquid chromatography (5% MeOH/CH2Cl2 with 0.5% NH4OH) gave the title compound as a white foam (364 mg, 0.838 mmol, 65%). The foam was dissolved in THF/Et$_2$O and 1 N HCl in Et$_2$O (0.84 mL) was added. The resulting precipitate was collected by filtration, washed with Et$_2$O and dried to give a white solid (368 mg). MS: APCI: M+1: 435.2 (Exact mass: 434.23).

Example B2'

Synthesis of 7-{4-[4-(2,2-Dimethyl-2H-chromen-8-yl)-piperazin-1-yl]-butoxy}-1H-[1,8]naphthyridin-2-one The reductive amination procedure from Example B1' was followed using 1-(2,2-dimethyl-2H-chromen-8-yl)-piperazine to give the title compound. MS: APCI: M+1: 461.2 (Exact mass: 460.25).

Example B3'

Synthesis of 7-{4-[4-(2,2-Dimethyl-chroman-8-yl)-piperazin-1-yl]-butoxy}-1H-[1,8]naphthyridin-2-one The reductive amination procedure from Example B1' was followed using 1-(2,2-dimethyl-chroman-8-yl)-piperazine to give the title compound. MS: APCI: M+1: 463.2 (Exact mass: 462.26).

Example B4'

Synthesis of 7-{4-[4-(2-Methyl-2H-chromen-8-yl)-piperazin-1-yl]-butoxy}-1H-[1,8]naphthyridin-2-one The reductive amination procedure from Example B1' was followed using 1-(2-methyl-2H-chromen-8-yl)-piperazine to give the title compound. MS: APCI: M+1: 447.3 (Exact mass: 446.23).

Example B5'

Synthesis of 7-{4-[4-(2-Methyl-chroman-8-yl)-piperazin-1-yl]-butoxy}-1H-[1,8]naphthyridin-2-one The reductive amination procedure from Example B1' was followed using 1-(2-methyl-chroman-8-yl)-piperazine to give the title compound. MS: APCI: M+1: 449.3 (Exact mass: 448.25).

Example B6'

Synthesis of 7-{4-[4-(Spiro[chromene-2,1'-cyclopentan]-8-yl)-piperazin-1-yl]-butoxy}-1H-[1,8]naphthyridin-2-one The reductive amination procedure from Example B1' was followed using 1-spiro[chromene-2,1'-cyclopentan]-8-ylpiperazine to give the title compound. MS: APCI: M+1: 487.2 (Exact mass: 486.26).

Example B7'

Synthesis of 7-{4-[4-(3,4-Dihydrospiro[chromene-2,1'-cyclopentan]-8-yl)-piperazin-1-yl]-butoxy}-1H-[1,8]naphthyridin-2-one The reductive amination procedure from Example B1' was followed using 1-(3,4-dihydrospiro[chromene-2,1'-cyclopentan]-8-yl)piperazine to give the title compound. MS: APCI: M+1: 489.3 (Exact mass: 488.28).

Example B8'

Synthesis of 7-{4-[4-(2,3-Dihydro-benzofuran-7-yl)-piperazin-1-yl]-butoxy}-1H-[1,8]naphthyridin-2-one The reductive amination procedure from Example B1' was followed using 1-(2,3-dihydro-benzofuran-7-yl)-piperazine to give the title compound. MS: APCI: M+1: 421.2 (Exact mass: 420.22).

Example B9'

Synthesis of 7-{4-[4-(2,2-Dimethyl-2,3-dihydro-benzofuran-7-yl)-piperazin-1-yl]-butoxy}-1H-[1,8]naphthyridin-2-one The reductive amination procedure from Example B1' was followed using 1-(2,2-dimethyl-2,3-dihydro-benzofuran-7-yl)-piperazine to give the title compound. MS: APCI: M+1: 449.2 (Exact mass: 448.25).

Example B10'

Synthesis of 7-[4-(4-Chroman-5-yl-piperazin-1-yl)-butoxy]-1H-[1,8]naphthyridin-2-one The reductive amination procedure from Example B1' was followed using 1-chroman-5-yl-piperazine to give the title compound. MS: APCI: M+1: 435.3 (Exact mass: 434.23).

Example B11'

Synthesis of 7-{4-[4-(2,3-Dihydro-benzofuran-4-yl)-piperazin-1-yl]-butoxy}-1H-[1,8]naphthyridin-2-one The reductive amination procedure from Example B1' was followed using 1-(2,3-dihydro-benzofuran-4-yl)-piperazine to give the title compound. MS: APCI: M+1: 421.2 (Exact mass: 420.22).

Example B12'

Synthesis of 7-{4-[4-(2,3-Dihydro-benzo[1,4]dioxin-5-yl)-piperazin-1-yl]-butoxy}-1H-[1,8]naphthyridin-2-one The reductive amination procedure from Example B1' was followed using 1-(2,3-dihydro-benzo[1,4]dioxin-5-yl)-piperazine to give the title compound. MS: APCI: M+1: 437.2 (Exact mass: 436.21).

Example B13'

Synthesis of 7-{4-[4-(2,2-Difluoro-benzo[1,3]dioxol-4-yl)-piperazin-1-yl]-butoxy}-1H-[1,8]naphthyridin-2-one The reductive amination procedure from Example B1' was followed using 1-(2,2-difluoro-benzo[1,3]dioxol-4-yl)-piperazine to give the title compound. MS: APCI: M+1: 459.2 (Exact mass: 458.18).

Example B14'

Synthesis of 7-{4-[4-(1,3-Dihydro-isobenzofuran-4-yl)-piperazin-1-yl]-butoxy}-1H-[1,8]naphthyridin-2-one To a suspension of 4-(7-oxo-7,8-dihydro-[1,8]naphthyridin-2-yloxy)-butyraldehyde (0.257 g, 1.107 mmol, 1.1 eq) and 1-(1,3-dihydro-isobenzofuran-4-yl)-piperazine (0.204 g, 0.998 mmol, 1 eq) in dichloroethane (5 mL) was added NaBH(OAc)$_3$ (0.433 g, 2.043 mmol, 1.84 eq). The slurry was allowed to stir overnight at room temperature (18 h). The mixture was diluted with EtOAc and quenched with saturated NaHCO$_3$. The organic phase was then washed with brine, dried over Na$_2$SO$_4$, filtered and evaporated in vacuo. Purification by silica gel chromatography (2% MeOH/CH$_2$Cl$_2$) followed by formation of the HCl salt using 1N HCl in ether provided the title compound (0.064 g, 12%). CHN Found: C, 64.37; H, 6.54; N, 12.13. This calculates out for C$_{24}$H$_{28}$N$_4$O$_3$×0.74HCl.

Example B15'

Synthesis of 7-{4-[4-(4-Oxo-chroman-8-yl)-piperazin-1-yl]-butoxy}-1H-[1,8]naphthyridin-2-one The reductive amination procedure from Example B1' was followed using 8-piperazin-1-yl-chroman-4-one to give the title compound (0.22 g, 48%). $^1$H NMR (400 MHz, CDCl$_3$): δ 9.00 (br s, 1H), 7.75 (d, 1H), 7.60 (m, 2H), 7.10 (d, 1H), 7.00 (t, 1H), 6.60 (d, 1H), 6.50 (d, 1H), 4.60 (t, 2H), 4.40 (t, 2H), 3.10 (br s, 4H), 2.80–2.40 (m, 8H), 1.90–1.70 (m, 4H).

Example B16'

Synthesis of 7-{4-[4-(3,3-Dimethyl-4-oxo-chroman-8-yl)-piperazin-1-yl]-butoxy}-1H-[1,8]naphthyridin-2-one The reductive amination procedure from Example B1' was followed using 3,3-dimethyl-8-piperazin-1-yl-chroman-4-one to give the title compound (0.30 g, 55%). $^1$H NMR (400 MHz, CDCl$_3$): δ 9.90 (br s, 1H), 7.71 (d, 1H), 7.63 (d, 1H), 7.60–7.58 (m, 1H), 7.10 (d, 1H), 6.98–6.94 (m, 1H), 6.60 (d, 1H), 6.54 (d, 1H), 4.20 (t, 2H), 4.22 (s, 2H), 3.12 (br s, 4H), 2.72 (br s, 4H), 2.52 (t, 2H), 1.87–1.71 (m, 4H), 1.21 (s, 6H).

Example B17'

Synthesis of 7-{4-[4-(3,3-Dimethyl-chroman-8-yl)-piperazin-1-yl]-butoxy}-1H-[1,8]naphthyridin-2-one The reductive amination procedure from Example B1' was followed using 1-(3,3-dimethyl-chroman-8-yl)-piperazine to give the title compound (0.30 g, 54%). $^1$H NMR (400 MHz, CDCl$_3$) δ 9.39 (br s, 1H), 7.71 (d, 1H), 7.63 (d, 1H), 6.80–6.78 (m, 2H), 6.71–6.69 (m, 1H), 6.58 (d, 1H), 6.52 (d, 1H), 4.38 (t, 2H), 3.82 (s, 2H), 3.09 (br s, 4H), 2.69 (br s, 4H), 2.55 (s, 2H), 2.48 (t, 2H), 1.86–1.66 (m, 6H), 1.02 (s, 6H).

Example B18'

Synthesis of 7-[4-(4-Isochroman-5-yl-piperazin-1-yl)-butoxy]-1H-[1,8]naphthyridin-2-one The reductive amination procedure from Example B1' was followed using 1-isochroman-5-yl-piperazine to give the title compound. $^1$H NMR (400 MHz, CDCl$_3$) δ 9.05 (br s, 1H), 7.72 (d, J=8.3 Hz, 1H), 7.63 (d, J=9.7 Hz, 1H), 7.16 (t, J=7.8 Hz, 1H), 6.92 (d, J=7.8 Hz, 1H), 6.72 (d, J=7.3 Hz, 1H), 6.60 (dd, J=1.0 Hz, J=8.3 Hz, 1H), 6.52 (d, J=9.8 Hz, 1H), 4.80 (s, 2H), 4.39 (t, J=6.3 Hz, 2H), 3.93 (t, J=5.8 Hz, 2H), 2.96 (br s, 4H), 2.81 (t, J=5.4 Hz, 2H), 2.63 (br s, 2H), 2.49 (s, 2H), 1.87–1.82 (m, 2H), 1.72–1.61 (m, 2H). MS (ES) m/z: 435.23 (M+1)$^+$ (Exact mass: 434.23).

Example B19'

Synthesis of 7-[4-(4-Isochroman-8-yl-piperazin-1-yl)-butoxy]-1H-[1,8]naphthyridin-2-one The reductive amination procedure from Example B1' was followed using 1-isochroman-8-yl-piperazine to give the title compound. $^1$H NMR (400 MHz, CDCl$_3$) δ 9.14 (br s, 1H), 7.72 (d, J=8.3 Hz, 1H), 7.63 (d, J=9.2 Hz, 1H), 7.16 (t, J=7.8 Hz, 1H), 6.94 (d, J=7.8 Hz, 1H), 6.88 (d, J=7.3 Hz, 1H), 6.60 (d, J=8.8 Hz, 1H), 6.52 (d, J=9.2 Hz, 1H), 4.78 (s, 2H), 4.39 (t, J=6.3 Hz, 2H), 3.96 (t, J=5.9 Hz, 2H), 2.91–2.86 (m, 4H), 2.61 (br s, 2H), 2.50 (t, J=7.8 Hz, 2H), 1.88–1.81 (m, 2H), 1.75–1.68 (m, 2H). MS (ES) m/z: 435.23 (M+1)$^+$ (Exact mass: 434.23).

Example B20'

Synthesis of 7-{4-[4-(3,4-Dihydro-2H-benzo[b][1,4]dioxepin-6-yl)-piperazin-1-yl]-butoxy}-1H-[1,8]naphthyridin-2-one In a manner similar to that of other examples above, 1-(3,4-dihydro-2H-benzo[b][1,4]dioxepin-6-yl)-piperazine hydrochloride (J. Med. Chem. 1988, 31, 1934–1940) was coupled by reductive amination to 4-(7-oxo-7,8-dihydro-[1,8]naphthyridin-2-yloxy)-butyraldehyde followed by typical workup and purification to give the title compound. MS: APCI: M+1: 451.2 (Exact Mass: 450.23).

Example B21'

Synthesis of 7-[4-(4-Quinolin-8-yl-piperazin-1-yl)-butoxy]-1H-[1,8]naphthyridin-2-one The reductive amination procedure from Example B1' was followed using 8-piperazin-1-yl-quinoline to give the title compound. MS: APCI: M+1: 430.3 (Exact mass: 429.22).

Example B22'

Synthesis of 7-[4-(4-Quinolin-5-yl-piperazin-1-yl)-butoxy]-1H-[1,8]naphthyridin-2-one The reductive amination procedure from Example B1' was followed using 5-piperazin-1-yl-quinoline to give the title compound. MS: APCI: M+1: 430.2 (Exact mass: 429.22).

Example B23'

Synthesis of 7-[4-(4-Quinoxalin-5-yl-piperazin-1-yl)-butoxy]-1H-[1,8]naphthyridin-2-one The reductive amination procedure from Example B1' was followed using 5-piperazin-1-yl-quinoxaline to give the title compound. MS: APCI: M+1: 431.2 (Exact mass: 430.21).

Example B24'

Synthesis of 7-{4-[4-(1H-Indol-4-yl)-piperazin-1-yl]-butoxy}-1H-[1,8]naphthyridin-2-one The reductive amination procedure from Example B1' was followed using 4-piperazin-1-yl-1H-indole to give the title compound. MS: APCI: M+1: 418.2 (Exact mass: 417.22).

Example B25'

Synthesis of 7-[4-(4-Benzo[b]thiophen-4-yl-piperazin-1-yl)-butoxy]-1H-[1,8]naphthyridin-2-one The reductive amination procedure from Example B1' was followed using 1-benzo[b]thiophen-4-yl-piperazine to give the title compound. MS: APCI: M+1: 435.2 (Exact mass: 434.18).

Example B26'

Synthesis of 7-[4-(4-Benzofuran-7-yl-piperazin-1-yl)-butoxy]-1H-[1,8]naphthyridin-2-one The reductive amination procedure from Example B1' was followed using 1-benzofuran-7-yl-piperazine to give the title compound. MS: APCI: M+1: 419.2 (Exact mass: 418.20).

Example B27'

Synthesis of 7-{4-[4-(1-Acetyl-1,2,3,4-tetrahydro-quinolin-5-yl)-piperazin-1-yl]-butoxy}-1H-[1,8]naphthyridin-2-one A first intermediate compound 4-(1,2,3,4-Tetrahydro-quinolin-5-yl)-piperazine-1-carboxylic acid tert-butyl ester, was produced as follows: To a stirred solution of compound 4-quinolin-5-yl-piperazine-1-carboxylic acid tert-butyl ester (3.0 g, 9.58 mmol) in methanol (60 mL) cooled to −5° C., was added nickel chloride hexahydrate (2.28 g, 9.58 mmol) and sodium borohydride (1.45 g, 38.3 mmol). The resulting mixture was stirred at room temperature overnight and quenched with saturated ammonium chloride solution. Ethyl acetate (100 mL) was added and the organic layer was separated. The aqueous layer was re-extracted with ethyl acetate (2×100 mL). The combined organic extracts were washed with brine, dried ($Na_2SO_4$) and the solvent was removed in vacuo. The residue was purified by $SiO_2$ chromatography using hexanes-ethyl acetate (2:1) as eluent to give the first intermediate compound (1.82 g, 53%) as a solid. $^1$H NMR (400 MHz, $CDCl_3$): δ 6.95 (m, 1H), 6.38 (d, 1H), 6.25 (d, 1H), 3.58 (br s, 4H), 3.30 (t, 2H), 2.84 (br s, 4H), 2.72 (t, 2H), 1.88 (m, 2H), 1.45 (s, 9H).

A second intermediate compound, 4-(1-Acetyl-1,2,3,4-tetrahydro-quinolin-5-yl)-piperazine-1-carboxylic acid tert-butyl ester, was produced as follows: To a stirred solution of 4-(1,2,3,4-tetrahydro-quinolin-5-yl)-piperazine-1-carboxylic acid tert-butyl ester (1.38 g, 4.35 mmol) in dichloromethane (30 mL) at 0° C., was added triethylamine (0.79 g, 7.83 mmol) and acetic anhydride (0.67 g, 6.53 mmol). The resulting mixture was stirred at room temperature overnight and diluted with additional dichloromethane (50 mL). Water was added and the organic layer was separated. The aqueous layer was re-extracted with dichloromethane. The combined organic extracts were washed brine, dried ($Na_2SO_4$) and the solvent was removed in vacuo. The residue was purified by silica gel chromatography using hexanes-ethyl acetate (1:2) as eluent to give the second intermediate compound (1.50 g, 97%) as a foam. $^1$H NMR (400 MHz, $CDCl_3$): δ 7.20 (m, 1H), 6.83 (br, 1H), 6.80 (d, 1H), 3.80 (t, 2H), 3.50 (br s, 4H), 2.85 (br s, 4H), 2.62 (t, 2H), 2.25 (s, 3H), 1.90 (t, 2H), 1.50 (s, 9H).

A third intermediate compound, 1-(5-Piperazin-1-yl-3,4-dihydro-2H-quinolin-1-yl)-ethanone, was produced as follows: To a stirred solution of 4-(1-acetyl-1,2,3,4-tetrahydro-quinolin-5-yl)-piperazine-1-carboxylic acid tert-butyl ester (0.90 g, 2.51 mmol) in dichloromethane (15 mL) cooled to 0° C., was added trifluoroacetic acid (2.86 g, 25.08 mmol). The resulting mixture was stirred at room temperature overnight and the solvent was removed in vacuo. The solid formed upon addition of diethyl ether was filtered to give the third intermediate compound (0.82 g, 88%). $^1$H NMR (400 MHz, DMSO-$d_6$): δ 8.84 (br s, 1H), 7.20 (br s, 2H), 6.82 (d, 2H), 3.64 (t, 2H), 3.24 (br s, 4H), 3.08 (br s, 4H), 2.64 (t, 2H), 2.20 (s, 3H), 1.80 (t, 2H). MS ES: m/z 260.15 (M+H)$^+$ (Exact mass: 259.17).

The reductive amination procedure from Example B1' was followed using 1-(5-piperazin-1-yl-3,4-dihydro-2H-quinolin-1-yl)-ethanone to give the title compound. $^1$H NMR (400 MHz, $CDCl_3$): δ 8.92 (s, 1H), 7.75 (d, 1H), 7.65 (d, 1H), 7.18 (m, 1H), 6.90 (m, 2H), 6.60 (d, 1H), 6.50 (d, 1H), 4.40 (t, 2H), 3.75 (t, 2H), 2.95 (br s, 4H), 2.65 (br s, 4H), 2.50 (t, 2H), 2.20 (s, 3H), 1.90 (m, 4H), 1.70 (m, 2H). MS ES: m/z 476.2 (M+H)$^+$ (Exact mass: 475.26).

Example B28'

Synthesis of 7-{4-[4-(1-Methyl-1,2,3,4-tetrahydro-quinolin-5-yl)-piperazin-1-yl]-butoxy}-1H-[1,8]naphthyridin-2-one The reductive amination procedure from Example B1' was followed using 1-methyl-5-piperazin-1-yl-1,2,3,4-tetrahydro-quinoline to give the title compound. $^1$H NMR (400 MHz, $CDCl_3$): δ 9.75 (br s, 1H), 7.70 (d, 1H), 7.65 (d, 1H) 7.05 (t, 1H), 6.62 (d, 1H), 6.58 (d, 1H), 6.42 (2H), 4.40 (t, 2H), 3.22 (t, 2H), 2.95 (br s, 4H), 2.85 (s, 3H), 2.80–2.45 (m, 8H), 1.95–1.65 (6H). MS ES: m/z 448.12 (M+H)$^+$ (Exact mass: 447.26).

Example B29'

Synthesis of 7-{4-[4-(1-Ethyl-1,2,3,4-tetrahydro-quinolin-5-yl)-piperazin-1-yl]-butoxy}-1H-[1,8]naphthyridin-2-one The reductive amination procedure from Example B1' was followed using 1-ethyl-5-piperazin-1-yl-1,2,3,4-tetrahydro-quinoline to give the title compound. $^1$H NMR (400 MHz, $CDCl_3$): δ 12.80 (br s, 1H), 7.70 (d, 1H), 7.65 (d, 1H), 7.25 (m, 2H), 7.05 (br s, 1H) 6.62 (d, 1H), 6.59 (d, 1H), 4.40 (m, 2H), 3.65 (m, 4H), 3.45 (m, 4H), 3.25–3.00 (m, 8H), 2.80 (m, 2H), 2.25–1.85 (m, 4H), 1.30 (t, 3H). MS ES: m/z 462.12 (M+H)$^+$ (Exact mass: 461.28).

Example B30'

Synthesis of 7-{4-[4-(2-Methoxy-quinolin-8-yl)-piperazin-1-yl]-butoxy}-1H-[1,8]naphthyridin-2-one The reductive amination procedure from Example B1' was followed using 2-methoxy-8-piperazin-1-yl-quinoline to give the title compound (0.73 g, 92%). $^1$H NMR (400 MHz, $CDCl_3$) δ 9.00 (br. s, 1H), 7.98 (d, 1H), 7.75 (d, 1H), 7.62 (d, 1H), 7.38 (d, 1H), 7.30 (t, 1H), 7.10 (d, 1H), 6.90 (d, 1H), 6.60 (d, 1H), 6.50 (d, 1H), 4.40 (t, 2H), 4.05 (s, 3H), 3.50 (br. s, 4H), 2.82 (m, 6H), 2.68 (t, 2H), 2.50 (dd, 2H), 1.82 (m, 2H), 1.78 (m, 2H).

Example B31'

Synthesis of 7-{4-[4-(2-Ethoxy-quinolin-8-yl)-piperazin-1-yl]-butoxy}-1H-[1,8]naphthyridin-2-one The reductive amination procedure from Example B1' was followed using 2-ethoxy-8-piperazin-1-yl-quinoline to give the title compound. $^1$H NMR (400 MHz, CDCl$_3$) δ 9.06 (br s, 1H), 7.98 (d, 1H), 7.75 (d, 1H), 7.62 (d, 1H), 7.38 (d, 1H), 7.30 (t, 1H), 7.10 (d, 1H), 6.90 (d, 1H), 6.65 (d, 1H), 6.55 (d, 1H), 4.58 (t, 2H), 4.40 (t, 2H), 3.50 (brs, 4H), 2.82 (m, 4H), 2.58 (t, 2H), 1.90 (m, 2H), 1.80 (m, 2H), 1.60 (t, 3H); MS (ES): m/z: 474.26 (M+H)$^+$ (Exact mass: 473.24).

Example B32'

Synthesis of 7-{4-[4-(2-Dimethylamino-quinolin-8-yl)-piperazin-1-yl]-butoxy}-1H-[1,8]naphthyridin-2-one The reductive amination procedure from Example B1' was followed using dimethyl-(8-piperazin-1-yl-quinolin-2-yl)-amine to give the title compound (0.144 g; 51%). MS: APCI: M+1: 473.2 (Exact mass: 472.26).

Example B33'

Synthesis of 7-{4-[4-(2-Methylamino-quinolin-8-yl)-piperazin-1-yl]-butoxy}-1H-[1,8]naphthyridin-2-one The reductive amination procedure from Example B1' was followed using methyl-(8-piperazin-1-yl-quinolin-2-yl)-amine to give the title compound (0.282 g; 70%). MS: APCI: M+1: 459.3 (Exact mass: 458.24).

Example B34'

Synthesis of 7-{4-[4-(3-Fluoro-quinolin-5-yl)-piperazin-1-yl]-butoxy}-1H-[1,8]naphthyridin-2-one The reductive amination procedure from Example B1' was followed using 3-fluoro-5-piperazin-1-yl-quinoline to give the title compound (433 mg, 66%). $^1$H NMR (400 MHz, dmso-d$_6$) δ 12.00 (s, 1H), 8.90 (s, 1H), 8.05 (d, 1H), 8.00 (d, 1H), 7.80 (d, 1H), 7.76 (d, 1H), 7.64 (t, 1H), 7.24 (d, 1H), 6.62 (d, 1H), 6.38 (s, 1H), 4.40 (t, 2H), 3.05–2.90 (m, 4H), 2.80–2.60 (m, 4H), 2.44 (t, 2H), 1.82–1.70 (m, 2H), 1.70–1.60 (m, 2H), MS ES+ 448.23 (M+1)$^+$ (Exact mass: 447.21).

Example B35'

Synthesis of 7-{4-[4-(3-Fluoro-quinolin-8-yl)-piperazin-1-yl]-butoxy}-1H-[1,8]naphthyridin-2-one The reductive amination procedure from Example B1' was followed using 3-fluoro-8-piperazin-1-yl-quinoline to give the title compound (420 mg, 66%). MS ES+ 448.16 (M+1)$^+$ (Exact mass: 447.21).

Example B36'

Synthesis of 7-{4-[4-(2-Oxo-1,2-dihydro-quinolin-8-yl)-piperazin-1-yl]-butoxy}-1H-[1,8]naphthyridin-2-one In a manner similar to that of other examples above, 8-piperazin-1-yl-1H-quinolin-2-one hydrochloride (*Chem. Pharm. Bull.* 1984, 32, 2100–2110) was coupled by reductive amination to 4-(7-oxo-7,8-dihydro-[1,8]naphthyridin-2-yloxy)-butyraldehyde followed by typical workup and purification to give the title compound. MS: APCI: M+1: 446.2 (Exact Mass: 445.21).

Example B37'

Synthesis of 7-{4-[4-(2-Oxo-1,2,3,4-tetrahydro-quinolin-8-yl)-piperazin-1-yl]-butoxy}-1H-[1,8]naphthyridin-2-one In a manner similar to that of other examples above, 8-piperazin-1-yl-3,4-dihydro-1H-quinolin-2-one hydrochloride (*Chem. Pharm. Bull.* 1984, 32, 2100–2110) was coupled by reductive amination to 4-(7-oxo-7,8-dihydro-[1,8]naphthyridin-2-yloxy)-butyraldehyde followed by typical workup and purification to give the title compound. MS: APCI: M+1: 448.3 (Exact Mass: 447.23).

Example B38'

Synthesis of 7-{4-[4-(1-Methyl-2-oxo-1,2,3,4-tetrahydro-quinolin-8-yl)-piperazin-1-yl]-butoxy}-1H-[1,8]naphthyridin-2-one In a manner similar to that of other examples above, 1-methyl-8-piperazin-1-yl-3,4-dihydro-1H-quinolin-2-one hydrochloride was coupled by reductive amination to 4-(7-oxo-7,8-dihydro-[1,8]naphthyridin-2-yloxy)-butyraldehyde followed by typical workup and purification to give the title compound. MS: APCI: M+1: 462.2 (Exact Mass: 461.24).

Example B39'

Synthesis of 7-[4-(4-Benzo[1,2,5]oxadiazol-4-yl-piperazin-1-yl)-butoxy]-1H-[1,8]naphthyridin-2-one The reductive amination procedure from Example B1' was followed using 4-piperazin-1-yl-benzo[1,2,5]oxadiazole hydrochloride (Vogel, Martin; Karst, Uwe. (2001) DE 19936731) to give the title compound (0.161 g; 45%). MS: APCI: M+1: 421.2 (Exact mass: 420.19).

Example B40'

Synthesis of 7-[4-(4-Benzo[1,2,5]thiadiazol-4-yl-piperazin-1-yl)-butoxy]-1H-[1,8]naphthyridin-2-one The reductive amination procedure from Example B1' was followed using 4-piperazin-1-yl-benzo[1,2,5]thiadiazole (Lowe, John A., III.; Nagel, Arthur A. (1989), U.S. Pat. No. 4,831,031) to give the title compound (0.336 g; 60%). MS: APCI: M+1: 439.2 (Exact mass: 438.17).

Example B41'

Synthesis of 7-{4-[4-(2-Trifluoromethyl-3H-benzoimidazol-4-yl)-piperazin-1-yl]-butoxy}-1H-[1,8]naphthyridin-2-one To a suspension of 4-(7-oxo-7,8-dihydro-[1,8]naphthyridin-2-yloxy)-butyraldehyde (0.211 g, 0.908 mmol, 1.29 eq) and 4-piperazin-1-yl-2-trifluoromethyl-1H-benzoimidazole (0.190 g, 0.703 mmol, 1 eq) in dichloroethane (5 mL) was added NaBH(OAc)$_3$ (0.558 g, 2.631 mmol, 3.74 eq). The slurry was allowed to stir overnight at room temperature (18 h). The mixture was diluted with EtOAc and quenched with saturated NaHCO$_3$. The organic phase was then washed with brine, dried over Na$_2$SO$_4$, filtered and evaporated in vacuo. Purification by silica gel chromatography (2% MeOH/CH$_2$Cl$_2$) followed by formation of the HCl salt using 1N HCl in ether provided the title compound (0.230 g, 62%). MS: APCI: M+1: 487.1 (Exact Mass: 486.20).

Example C1'

Synthesis of 4,4-Dimethyl-7-[4-(4-quinolin-8-yl-piperazin-1-yl)-butoxy]-3,4-dihydro-1H-[1,8]naphthyridin-2-one A first intermediate compound 3-Methyl-but-3-enoic acid (6-amino-pyridin-2-yl)-amide, was produced as follows: 2,5-Diaminopyridine (70 g, 0.641 mol) was dissolved in 2100 mL THF in a 5 L 4-neck flask equipped with mechanical stirring, N$_2$ line and a 500 mL addition funnel. Et$_3$N (447 mL, 5 eq.) was added to the reaction flask. 3,3-Dimethylacryloyl chloride (76 g, 0.641 mol) was diluted with 700 mL THF and this solution was added dropwise to the reaction flask. The moderate exotherm observed was controlled with an ice/water bath to maintain a temperature <15° C. After the addition was complete, the reaction was allowed to warm to room temperature and stirred under N$_2$ for 1.5 h. The reaction mixture was concentrated and CH$_2$Cl$_2$ was added. The CH$_2$Cl$_2$ solution was washed with H$_2$O and the aqueous layer was back extracted with CH$_2$Cl$_2$. The organic layers were combined and dried over Na$_2$SO$_4$, filtered and concentrated to an oil. The crude product was purified by column chromatography using a gradient mobile phase of 10%–30% EtOAc in hexanes. All fractions containing the desired product were pooled and concentrated to an oil. NMR analysis of the product indicated the product was a 1:1 mixture of 2 isomers, the alpha beta unsaturated and the beta gamma unsaturated isomer resulting in first intermediate compound (90.0 g, 0.47 mol, 73%). MS: APCI: M+1: 192.0 (Exact Mass: 191.11).

A second intermediate compound, 7-Amino-4,4-dimethyl-3,4-dihydro-1H-[1,8]naphthyridin-2-one, was produced as follows: 3-Methyl-but-3-enoic acid (6-amino-pyridin-2-yl)-amide (49.2 g, 0.26 mol) was dissolved in 500 mL CH$_2$Cl$_2$ in a 1000 mL 3-neck flask equipped with mechanical stirring, a 125 mL addition funnel and a thermal couple. While stirring, MeSO$_3$H (50 mL, 0.78 mol) was added to the flask dropwise. The exotherm upon addition was controlled to maintain a temperature <20° C. by an ice/water bath. The mixture was allowed to stir for 15 minutes. AlCl$_3$ (274 g, 2.08 mol) was suspended in 1500 mL CH$_2$Cl$_2$ in a 5 L 4-neck flask equipped with mechanical stirring, 1000 mL addition funnel, N$_2$ line and a thermal couple. To this suspension, the amide solution was added dropwise. The exotherm from the addition was again controlled to maintain a temperature <20° C. with an ice/water bath. The reaction was allowed to warm to room temperature and stir overnight. The reaction had consumed all the beta gamma unsaturated isomer and was deemed complete. The reaction mixture was slowly added to ice as an inverse quench. The quenched mixture was brought to pH 8–10 with 2 N KOH. The salts precipitated out of solution and saturated the aqueous phase. The suspension was transferred to a separatory funnel and extracted twice with 100:8:1 CH$_2$Cl$_2$:EtOH:NH$_4$OH. The organic layers were combined, dried over Na$_2$SO$_4$, filtered and concentrated to a crude solid. The solid was triturated with EtOAc and filtered. The resulting solids were pure second intermediate compound (22.4 g, 0.117 mol, 46%). MS: APCI: M+1: 192.2 (Exact Mass: 191.11).

A third intermediate compound, 7-Fluoro-4,4-dimethyl-3,4-dihydro-1H-[1,8]naphthyridin-2-one, was produced as follows: HF-pyridine (100 mL) was cooled to −42° C. in a 1000 mL HDPE bottle using an CH$_3$CN dry ice bath. While stirring vigorously, 7-amino-4,4-dimethyl-3,4-dihydro-1H-[1,8]naphthyridin-2-one (24.6 g, 0.129 mol) was added portionwise to control the exotherm. After the addition, NaNO$_2$ (8.9 g, 0.1291 mol) was added portionwise. Significant exotherms were observed for both additions. The reaction mixture was then allowed to warm to 0° C. and stir for 2 h. The reaction mixture was quenched into a 4 L HDPE bottle full of ice. The aqueous slurry was then neutralized using 2 N KOH. The resulting aqueous solution was extracted 3 times with CH$_2$Cl$_2$. The organic layers were dried over Na$_2$SO$_4$, filtered and concentrated to dryness. Excess pyridine was azeotroped with heptane. The product was dried under vacuum (2 mm Hg) for 3 h. The third intermediate compound was isolated as a white powder (23.06 g, 0.119 mol, 92%). MS: APCI: M+1: 195.1 (Exact Mass: 194.09).

A fourth intermediate compound, 7-(4-Hydroxy-butoxy)-4,4-dimethyl-3,4-dihydro-1H-[1,8]naphthyridin-2-one, was produced as follows: The 7-fluoro-4,4-dimethyl-3,4-dihydro-1H-[1,8]naphthyridin-2-one (5.09 g, 26.2 mmol) and butane-1,4-diol (11.81 g, 131.0 mmol) were combined in a dried 2-necked flask under N$_2$. NMP (50 mL) was added and the solution was heated in an oil bath to 70° C. overnight. The reaction was cooled to room temperature and poured into ice water. The solid that formed was collected and triturated in acetonitrile to give the fourth intermediate compound as a tan powder (1.72 g). The mother liquor was extracted with CH$_2$Cl$_2$, dried over Na$_2$SO$_4$, filtered and purified by MPLC (gradient of 100% CH$_2$Cl$_2$ to 100% ethyl acetate). The compound was isolated as a mixture with diol byproducts. The fourth intermediate compound was formed as clear crystals (1.09 g) after recrystallization in acetonitrile and another 340 mg was obtained from a second recrystallization. The products were combined to give a total of 3.15 g of the fourth intermediate compound (11.9 mmol, 45.5%). MS: APCI: M+1: 265.1 (Exact Mass: 264.15).

A fifth intermediate compound, 4-(5,5-Dimethyl-7-oxo-5,6,7,8-tetrahydro-[1,8]naphthyridin-2-yloxy)-butyraldehyde, was produced as follows: 7-(4-Hydroxy-butoxy)-4,4-dimethyl-3,4-dihydro-1H-[1,8]naphthyridin-2-one (1.72 g, 6.51 mmol) was dissolved in ethyl acetate (50 mL, 0.14 M solution) and IBX (13 g, 46.4 mmol) was added. The suspension was immersed in an oil bath set at 80° C. and stirred vigorously with a condenser. After 1.5 h, the reaction mixture was cooled to room temperature and filtered. The filtrate was concentrated to give the fifth intermediate compound as a tan solid (1.62 g, 6.18 mmol, 95%). MS: APCI: M+1: 263.1 (Exact Mass: 262.13).

The naphthyridinones of Examples C1'–C6' were synthesized in a combinatorial library format by reductive amination of the appropriate piperazine starting materials with 4-(5,5-dimethyl-7-oxo-5,6,7,8-tetrahydro-[1,8]naphthyridin-2-yloxy)-butyraldehyde using the following general procedure.

The aldehyde (0.3 mmol) and the piperazine (60.306 mmol) were combined in methylene chloride and stirred in a vial over sieves for 10 min. Sodium triacetoxyborohydride (0.42 mmol) was added and the reaction was stirred overnight. The reaction was quenched by slowly adding water and then the mixture was filtered. The residue was partitioned between $CH_2Cl_2$ and water and the organic layer was concentrated. Purification by liquid chromatography (MPLC, gradient of 100% $CH_2Cl_2$ to 100% of a 10% MeOH in $CH_2Cl_2$ solution) gave the title compound. The final products were made into hydrochloride salts by treatment with a solution of saturated HCl in MeOH.

The title compound was isolated as a foam (207 mg, 0.451 mmol, 75.1%). MS: APCI: M+1: 460.2 (Exact Mass: 459.26).

Example C2'

Synthesis of 7-{4-[4-(2,3-Dihydro-benzo[1,4]dioxin-5-yl)-piperazin-1-yl]-butoxy}-4,4-dimethyl-3,4-dihydro-1H-[1,8]naphthyridin-2-one The title compound was isolated as a white solid (91 mg, 0.195 mmol, 39.2%). MS: APCI: M+1: 467.2 (Exact Mass: 466.26).

Example C3'

Synthesis of 4,4-Dimethyl-7-{4-[4-(2-oxo-1,2,3,4-tetrahydro-quinolin-8-yl)-piperazin-1-yl]-butoxy}-3,4-dihydro-1H-[1,8]naphthyridin-2-one The title compound was isolated as the hydrochloride salt (101 mg, 0.196 mmol, 25.7%). MS: APCI: M+1: 478.3 (Exact Mass: 477.27).

Example C4'

Synthesis of 4,4-Dimethyl-7-{4-[4-(2-oxo-1,2-dihydro-quinolin-8-yl)-piperazin-1-yl]-butoxy}-3,4-dihydro-1H-[1,8]naphthyridin-2-one The title compound was isolated as the hydrochloride salt (140 mg, 0.273 mmol, 35.8%). MS: APCI: M+1: 476.2 (Exact Mass: 475.26).

Example C5'

Synthesis of 7-[4-(4-Benzofuran-7-yl-piperazin-1-yl)-butoxy]-4,4-dimethyl-3,4-dihydro-1H-[1,8]naphthyridin-2-one The title compound was isolated as the hydrochloride salt (105 mg, 0.216 mmol, 28.4%). MS: APCI: M+1: 449.3 (Exact Mass: 448.25).

Example C6'

Synthesis of 7-[4-(4-Chroman-8-yl-piperazin-1-yl)-butoxy]-4,4-dimethyl-3,4-dihydro-1H-[1,8]naphthyridin-2-one The title compound was isolated as a white solid (221 mg, 0.476 mmol, 56.7%). MS: APCI: M+1: 465.2 (Exact Mass: 464.28).

Example D1'

Synthesis of 6-Fluoro-7-[4-(4-quinolin-8-yl-piperazin-1-yl)-butoxy]-3,4-dihydro-1H-[1,8]naphthyridin-2-one A first intermediate compound 6-(4-Benzyloxy-butoxy)-2-chloro-5-fluoro-nicotinonitrile, was produced as follows: To a solution of 4-benzyloxy-1-butanol (19.44 g, 108 mmol) in THF (200 mL) cooled to −40° C. was added 1 M KO$^t$Bu in THF (108 mL, 108 mmol). The mixture was stirred for 5 min at −10° C. and then added to a solution of 2,6-dichloro-5-fluoro-nicotinonitrile (20.0 g, 105 mmol) in THF (300 mL) cooled to −70° C. over 25 min. The mixture turned brownish yellow with some cloudiness. The reaction was allowed to warm to room temperature over 2 h. The THF was evaporated and the residue was diluted with $Et_2O$. The mixture was washed with water, brine, 1N citric acid, water and brine, dried over $Na_2SO_4$ and concentrated to an oil. The oil was dissolved in $Et_2O$/hexanes and cooled in the refrigerator overnight. A crystalline solid formed which was collected by filtration, washed with hexanes and dried to give the first intermediate compound as a white solid (17.0 g). The filtrate was concentrated and purified by silica gel chromatography (Biotage 40L, 0–6% EtOAc/Hexanes) to give additional first intermediate compound as a white solid (total of 26.9 g, 80.4 mmol, 77%). MS: APCI: M+1: 335.1 (Exact Mass: 334.09).

A second intermediate compound, 2-Azido-6-(4-benzyloxy-butoxy)-5-fluoro-nicotinonitrile, was produced as follows: To a solution of 6-(4-benzyloxy-butoxy)-2-chloro-5-fluoro-nicotinonitrile (20.0 g, 60.0 mmol) in DMF (40 mL) was added sodium azide (4.27 g, 65.7 mmol) and the mixture was heated at 70° C. overnight. The mixture was poured into $Et_2O$ and washed with water and brine. The $Et_2O$ solution was passed through a silica gel Biotage 12M column, dried over $MgSO_4$ and charcoal, and concentrated to give an oil (19.67 g). Recrystallization from $Et_2O$/MeOH gave the second intermediate compound as a solid (17.24 g, 50.5 mmol, 84%). MS: APCI: M+1: (Exact Mass: 341.13).

A third intermediate compound, 2-Amino-6-(4-benzyloxy-butoxy)-5-fluoro-nicotinonitrile, was produced as follows: To a solution of 2-azido-6-(4-benzyloxy-butoxy)-5-fluoro-nicotinonitrile (17.2 g, 50.4 mmol) in MeOH (450 mL) was added hexamethyldisilthiane (19.0 g, 106.5 mmol). The reaction gives off a gas and a precipitate forms after 15 min. The reaction was stirred overnight at room temperature and then filtered to remove the precipitated sulfur. The mixture was concentrated and then redissolved in $Et_2O$. The mixture was filtered again to remove additional precipitated sulfur. The filtrate was concentrated and recrystallized from MeOH/hexanes. The solid was collected by filtration, washed with hexane/MeOH and dried to give the third intermediate compound (13.74 g, 43.57 mmol, 86%). MS: APCI: M+1: 316.4 (Exact Mass: 315.14).

A fourth intermediate compound, 2-Amino-6-(4-benzyloxy-butoxy)-5-fluoro-pyridine-3-carbaldehyde, was produced as follows: To a solution of 2-amino-6-(4-benzyloxy-butoxy)-5-fluoro-nicotinonitrile (7.25 g, 23.0 mmol) in THF (40 mL) cooled to 0° C. is added DIBALH (1M in THF, 69 mL, 69 mmol). The reaction was complete after 5 min. Chilled 2N HCl was added very slowly (strong exotherm) to quench the reaction. The mixture forms a red gelatinous material. Et$_2$O was added and the layers were separated. The organic layer was washed with brine and saturated NaHCO$_3$ and then filtered through Celite. There may still have been some aluminum complexed product so the organic solution was washed again with 2N HCl, brine, saturated NaHCO$_3$ and brine, dried over MgSO$_4$ and concentrated to give the crude fourth intermediate compound as an orange oil (5.23 g, 16.4 mmol, 71%). MS: APCI: M+1: 319.2 (Exact Mass: 318.14).

A fifth intermediate compound, 3-[2-Amino-6-(4-benzy-loxy-butoxy)-5-fluoro-pyridin-3-yl]-acrylic acid ethyl ester, was produced as follows: To a solution of 2-amino-6-(4-benzyloxy-butoxy)-5-fluoro-pyridine-3-carbaldehyde (5.23 g, 16.4 mmol, crude from previous reaction) in THF (50 mL) was added (carbethoxymethylene)triphenylphosphorane (5.72 g. 16.43 mmol) and the solution was heated at 67° C. overnight. The reaction was concentrated and the residue was purified by liquid chromatography (Biotage 65M, 0–10% EtOAc/CH$_2$Cl$_2$) to give the fifth intermediate compound as a yellow solid (73%). MS: APCI: M+1: 389.4 (Exact Mass: 388.18).

A sixth intermediate compound, 7-(4-Benzyloxy-butoxy)-6-fluoro-3,4-dihydro-1H-[1,8]naphthyridin-2-one, was produced as follows: 3-[2-Amino-6-(4-benzyloxy-butoxy)-5-fluoro-pyridin-3-yl]-acrylic acid ethyl ester (7.18 g, 18.5 mmol) was hydrogenated under an atmosphere of H$_2$ (4300 psi) using Ra—Ni (2 g) in MeOH (100 mL). The reaction was filtered and concentrated. MS indicated the double bond had been reduced and some of the material cyclized. The material was suspended in $^i$PROH and p-toluenesulfonic acid hydrate (0.41 g) was added. The mixture was heated at 80° C. for 30 min. Saturated NaHCO$_3$ was added and the mixture was concentrated. The residue was partitioned between Et$_2$O and water. The organic layer was washed with saturated NaHCO$_3$ and brine, dried over MgSO$_4$ and concentrated to give a yellow oil which solidified. Recrystallization from Et$_2$O/hexane afforded the sixth intermediate compound as a pale yellow solid. MS: APCI: M+1: 345.1 (Exact Mass: 344.15).

A seventh intermediate compound, 6-Fluoro-7-(4-hydroxy-butoxy)-3,4-dihydro-1H-[1,8]naphthyridin-2-one, was produced as follows: 7-(4-Benzyloxy-butoxy)-6-fluoro-3,4-dihydro-1H-[1,8]naphthyridin-2-one (4.79 g, 13.9 mmol) was hydrogenated under an atmosphere of H$_2$ using 20% Pd/C (1.0 g) in EtOH (100 mL). The reaction was filtered and concentrated to give a slurry. Et$_2$O was added and the solids were filtered. The filtrate was concentrated and the process was repeated to give the seventh intermediate compound as a solid (3.2 g, 13.0 mmol, 91%). MS: APCI: M+1: 255.1 (Exact Mass: 254.11).

A eighth intermediate compound, 4-(3-Fluoro-7-oxo-5,6,7,8-tetrahydro-[1,8]naphthyridin-2-yloxy)-butyraldehyde, was produced as follows: To a solution of oxalyl chloride (1.78 g, 14.0 mmol) in CH$_2$Cl$_2$ (25 mL) cooled to −70° C. was added a solution of DMSO (2.15 g, 27.6 mmol) in CH$_2$Cl$_2$ (1.5 mL) over 4 min. The mixture was stirred for 5 min and a solution of 6-fluoro-7-(4-hydroxy-butoxy)-3,4-dihydro-1H-[1,8]naphthyridin-2-one (3.1 g, 12.0 mmol) in DMSO (4.5 mL) and CH$_2$Cl$_2$ (44 mL) cooled to −50° C. was added over 5 min. The mixture was stirred for 10 min at −70° C. and it solidified. The reaction was warmed to −30° C. and triethylamine (8.9 mL, 63.8 mmol) was added resulting in a stirable suspension. The reaction was warmed to room temperature over 30 min. The mixture was added to water and the layers were separated. The organic layer was washed with water and dilute brine, dried over MgSO$_4$ and concentrated to give an oil. The residue was partitioned between Et$_2$O and aqueous citric acid (pH 4.5). The organic layer was washed with dilute aqueous NaHCO$_3$ and brine, dried over MgSO$_4$ and concentrated to give the eighth intermediate compound as a yellow oil (1.89 g) which was used directly in the next reaction. MS: APCI: M+1: 253.2 (Exact Mass: 252.09).

The title compound was prepared by reductive amination of 4-(3-fluoro-7-oxo-5,6,7,8-tetrahydro-[1,8]naphthyridin-2-yloxy)-butyraldehyde with 8-piperazin-1-yl-quinoline using a procedure similar to Example A1'. MS: APCI: M+1: 450.2 (Exact Mass: 449.22).

Example D2'

Synthesis of 6-Fluoro-7-[4-(4-isoquinolin-5-yl-piperazin-1-yl)-butoxy]-3,4-dihydro-1H-[1,8]naphthyridin-2-one The title compound was prepared by reductive amination of 4-(3-fluoro-7-oxo-5,6,7,8-tetrahydro-[1,8]naphthyridin-2-yloxy)-butyraldehyde with 5-piperazin-1-yl-isoquinoline using a procedure similar to Example A1'. MS: APCI: M+1: 450.2 (Exact Mass: 449.22).

Example E1'

Synthesis of 7-[4-(4-Chroman-8-yl-piperazin-1-yl)-butoxy]-1H-pyrido[2,3-d]pyrimidin-2-one A first intermediate compound 2-Amino-6-[4-(tetrahydro-pyran-2-yloxy)-butoxy]-pyridine-3-carbaldehyde, was produced as follows: A mixture of N-{3-formyl-6-[4-(tetrahydro-pyran-2-yloxy)-butoxy]-pyridin-2-yl}-2,2-dimethyl-propionamide (9.8 g, 25.9 mmol), 2 N KOH (35 mL) and EtOH (40 mL) was heated at 80° C. for 2 h. Ethanol was removed under reduced pressure and the residue was extracted with EtOAc (3×100 mL). The combined organic phases were washed with H$_2$O (40 mL) and brine (40 mL), dried over Na$_2$SO$_4$, and concentrated to give the first intermediate compound as an oil which was used in the next step without further purification. $^1$H NMR (400 MHz, CDCl$_3$): δ 9.70 (s, 1H), 7.62 (d, 1H), 6.17 (d, 1H), 4.60 (m, 1H), 4.40 (m, 2H), 3.90 (m, 2H), 3.50 (m, 2H), 2.00–1.50 (m, 10H).

A second intermediate compound, 7-[4-(Tetrahydro-pyran-2-yloxy)-butoxy]-1H-pyrido[2,3-d]pyrimidin-2-one, was produced as follows: To a solution of 2-amino-6-[4-(tetrahydro-pyran-2-yloxy)-butoxy]-pyridine-3-carbaldehyde obtained in the last step in CH$_2$Cl$_2$ (50 mL) was added trichloroacetyl isocyanate (5.85 g, 31.08 mmol) dropwise. After the addition was over, the mixture was stirred at room temperature for 1 h. To this mixture, MeOH (50 mL) and 1 N NaOH (40 mL) were added successively. The mixture thus obtained was kept stirring at room temperature for another 1 h. The solvent was then removed under reduced pressure and the residue was extracted with CH$_2$Cl$_2$ (3×100 mL). The combined organic phases were washed with brine, dried and concentrated. The residue was crystallized from ether to give the second intermediate compound (6.6 g, 79% in two steps) as a pale yellow solid. $^1$H NMR (400 MHz, DMSO-d$_6$): δ 9.00 (s, 1H), 8.00 (d, 1H), 6.60 (d, 1H), 4.60 (m, 1H), 4.40 (m, 2H), 3.70 (m, 2H), 3.40 (m, 2H), 1.90–1.30 (m, 10H).

A third intermediate compound, 7-(4-Hydroxy-butoxy)-1H-pyrido[2,3-d]pyrimidin-2-one, was produced as follows: A mixture of 7-[4-(tetrahydro-pyran-2-yloxy)-butoxy]-1H-pyrido[2,3-d]pyrimidin-2-one (4.9 g, 15 mmol), MeOH (30 mL), THF (15 mL) and 3 N HCl (7.5 mL) was stirred at room temperature for 1 h. The mixture was concentrated under reduced pressure. The residue was dissolved in $H_2O$ (30 mL) and neutralized carefully with saturated $NaHCO_3$. The mixture was extracted with THF (5×100 mL). The combined organic phases were washed with brine, dried and concentrated to give the third intermediate compound (3.3 g, 90%) which was used in the next step without further purification. $^1H$ NMR (400 MHz, DMSO-$d_6$): δ 9.03 (s, 1H), 8.17 (d, 1H), 6.67 (d, 1H), 4.50 (m, 1H), 4.40 (m, 2H), 3.50 (m, 3H), 1.80 (m, 2H), 1.55 (m, 2H).

A fourth intermediate compound, 4-(2-Oxo-1,2-dihydro-pyrido[2,3-d]pyrimidin-7-yloxy)-butyraldehyde, was produced as follows: A mixture of 7-(4-hydroxy-butoxy)-1H-pyrido[2,3-d]pyrimidin-2-one (0.512 g, 2.18 mmol) and IBX (1.9 g, 6.6 mmol) in $CH_3CN$ (40 mL) was heated at 87° C. for 7 h. It was cooled to RT, diluted with EtOAc (80 mL) and filtered. The pad was washed thoroughly with EtOAc. The combined filtrate was concentrated to give the fourth intermediate compound as a solid which was contaminated with some byproduct from the reaction. This solid was used in the next step without further purification. $^1H$ NMR (400 MHz, DMSO-$d_6$): δ 12.18 (s, 1H), 9.77 (s, 1H), 8.20 (d, 1H), 6.70 (d, 1H), 4.40 (m, 2H), 2.70 (m, 2H), 2.00 (m, 2H).

To a mixture of 4-(2-oxo-1,2-dihydro-pyrido[2,3-d]pyrimidin-7-yloxy)-butyraldehyde obtained in the last step, 1-chroman-8-yl-piperazine hydrochloride (0.634 g, 2.18 mmol), $Et_3N$ (0.73 mL, 5.23 mmol) in 1-methyl-2-pyrrolidinone (20 mL) was added $NaBH(OAc)_3$ (0.514 g, 2.62 mmol) in portions over 20 min. The mixture was stirred overnight. After quenching with $H_2O$ (50 mL), the reaction mixture was extracted with $CH_2Cl_2$ (3×100 mL). The combined organic phases were washed with brine (100 mL), dried and concentrated. The residue was purified by chromatography on silica gel to give a gum (520 mg). To a solution of this gum (200 mg) in THF (2 mL) was added 1 N HCl (0.43 mL) in $Et_2O$. The mixture was stirred at room temperature for 30 min and filtered. The solid was washed with $Et_2O$ and dried under vacuum to give the title compound (190 mg) as a yellow solid. $^1H$ NMR (400 MHz, DMSO-$d_6$): δ 12.30 (s, 1H), 9.20 (s, 1H), 8.20 (d, 1H), 7.80 (m, 4H), 4.45 (m, 2H), 4.20 (m, 2H), 3.60 (m, 4H), 3.20 (m, 2H), 3.00 (m, 2H), 2.00–1.70 (m, 6H).

Example E2'

Synthesis of 7-[4-(4-Chroman-8-yl-piperazin-1-yl)-butoxy]-3,4-dihydro-1H-pyrido[2,3-d]pyrimidin-2-one To a solution of 7-[4-(4-chroman-8-yl-piperazin-1-yl)-butoxy]-1H-pyrido[2,3-d]pyrimidin-2-one (320 mg) in THF (6 mL) and MeOH (2 mL) was added $NaBH_4$ (54 mg) in portions. After the addition was over, the mixture was kept stirring overnight. The reaction was quenched with $H_2O$. The mixture was extracted with $CH_2Cl_2$ (3×50 mL). The combined organic phases were dried over $Na_2SO_4$ and concentrated. The residue was purified by chromatography on silica gel to give a semi-solid which was converted to its HCl salt by treating with 1 equivalent of 1 N HCl in a mixed solvent of THF and $Et_2O$ to give the title compound (147 mg) as a white solid. $^1H$ NMR (400 MHz, DMSO-$d_6$): δ 9.20 (s, 1H), 7.40 (d, 1H), 6.98 (s, 1H), 7.70 (m, 3H), 6.25 (d, 1H), 4.30–4.06 (m, 6H), 3.60–3.30 (m, 4H), 3.15 (m, 4H), 3.00–2.70 (, 4H), 2.00–1.60 (m, 6H).

Example E3'

Synthesis of 7-{4-[4-(2,3-Dihydro-benzofuran-7-yl)-piperazin-1-yl]-butoxy}-3,4-dihydro-1H-pyrido[2,3-d]pyrimidin-2-one To a mixture of 4-(2-oxo-1,2-dihydro-pyrido[2,3-d]pyrimidin-7-yloxy)-butyraldehyde, 1-(2,3-dihydro-benzofuran-7-yl)-piperazine hydrochloride (0.76 g, 2.58 mmol), $Et_3N$ (2.15 mL, 15.5 mmol) in 1-methyl-2-pyrrolidinone (20 mL) was added $NaBH(OAc)_3$ (0.76 g, 3.61 mmol) in portions over 20 min. After the addition was over, the mixture was left stirring overnight. After quenching with $H_2O$ (50 mL), the reaction mixture was extracted with $CH_2Cl_2$ (3×100 mL). The combined organic layer was washed with brine (100 mL), dried and concentrated. The residue was purified by chromatography on silica gel to give a gum (290 mg). To a solution of this gum in THF (6 mL) and MeOH (2 mL) was added $NaBH_4$ (63 mg) in portions. After the addition was over, the mixture was kept stirring overnight. The reaction was quenched with $H_2O$. The mixture was extracted with $CH_2Cl_2$ (3×50 mL). The combined organic phases were dried over $Na_2SO_4$ and concentrated. The residue was purified by chromatography on silica gel to give a semi-solid which was converted to the HCl salt by treating with 1 equivalent of 1 M HCl in a mixed solvent of THF and $Et_2O$ to give the title compound (147 mg) as a white solid. $^1H$ NMR (400 MHz, DMSO-$d_6$): δ 9.20 (s, 1H), 7.40 (d, 1H), 7.00 (s, 1H), 6.95 (d, 1H), 6.80 (m, 1H), 6.70 (d, 1H), 6.30 (d, 1H), 4.50 (t, 2H), 4.20 (m, 4H), 3.80–3.40 (m, 4H), 3.20–2.90 (m, 8H), 1.90–1.60 (m, 4H).

Example E4'

Synthesis of 7-{4-[4-(3,4-Dihydro-2H-benzo[b][1,4]dioxepin-6-yl)-piperazin-1-yl]-butoxy}-3,4-dihydro-1H-pyrido[2,3-d]pyrimidin-2-one The procedure from Example E3' was followed using 1-(3,4-dihydro-2H-benzo[b][1,4]dioxepin-6-yl)-piperazine to give the title compound. $^1H$ NMR (400 MHz, DMSO-$d_6$): δ 9.25 (s, 1H), 7.40 (d, 1H), 6.90 (s, 1H), 6.80 (m, 1H), 6.60 (m, 2H), 6.25 (d, 1H), 4.30–4.00 (m, 8H), 3.60–3.40 (4H), 3.20–3.00 (m, 6H), 2.10 (m, 2H), 1.90–1.60 (m, 4H).

Example F1'

Synthesis of 6-{4-[4-(2-Methyl-quinolin-8-yl)-piperazin-1-yl]-butoxy}-4H-pyrido[3,2-b][1,4]oxazin-3-one A first intermediate compound 6-Amino-4H-pyrido[3,2-b][1,4]oxazin-3-one, was produced as follows: A mixture of 6-nitro-4H-pyrido[3,2-b][1,4]oxazin-3-one (34.23 g, 0.1755 mol), 20% Pd—C (3.0 g, 50% $H_2O$) and DMF (1 L) was hydrogenated at 20 psi $H_2$ pressure. After 2 h, uptake of $H_2$ ceased with 141 psi of $H_2$ being absorbed. The reaction mixture was filtered through a pad of Celite®, washing with DMF (500 mL). The filtrate was diluted with cold $H_2O$ (2 L) to give a solid. The solid was collected, washed with $H_2O$, slurried in EtOH (150 mL), collected, washed with heptane and dried to give the first intermediate compound (23.60 g, 81%) as a gray-tan solid.

A second intermediate compound, 6-Fluoro-4H-pyrido[3,2-b][1,4]oxazin-3-one, was produced as follows: A 1 gallon Nalgene jar (with openings in the top for a $N_2$ inlet and addition of solids) was cooled in an ice/salt bath and hydrogen fluoride-pyridine (500 g) was added. With magnetic stirring and under a stream of $N_2$, 6-amino-4H-pyrido [3,2-b][1,4]oxazin-3-one (88.48 g, 0.5362 mol, 1.0 equiv) was added slowly portion-wise. When addition was complete, the red-brown mixture was stirred for 0.25 h to ensure complete solution. Sodium nitrite (44.40 g, 0.6435 mol, 1.2 equiv) was added cautiously portion-wise over 0.5 hr. Each addition was exothermic and accompanied by the evolution of HF and $N_2$. When addition was complete the reaction mixture was stirred in the ice/salt bath for 1 h. The reaction was quenched by the slow, careful addition of ice-cold $H_2O$ (2 L). The resulting solid was collected, washed with $H_2O$, resuspended in $H_2O$ (3×1 L), collected, washed with $H_2O$ and dried on the filter for 1 h. The solid was washed with heptane and dried under a $N_2$ stream for 2 h. Final drying in a vacuum oven for 24 h at ~40° C. gave the second intermediate compound (69.03 g, 76%) as an orange-brown solid. Mp 179.9–181.2°.

A third intermediate compound, 6-(4-Benzyloxy-butoxy)-4H-pyrido[3,2-b][1,4]oxazin-3-one, was produced as follows: A solution of 4-benzyloxy-butan-1-ol I (34.31 g, 33.37 mL, 190.3 mmol) and potassium t-butoxide (1M solution; 181 mL) in THF (60 mL) was prepared and stirred at room temperature for 20 min. A suspension of 6-fluoro-4H-pyrido [3,2-b][1,4]oxazin-3-one (8 g, 48 mmol) in THF (100 mL) was prepared, and the alcohol/base solution was added to this solution via canula. The reaction was heated at reflux for 25 hours. The reaction was quenched with saturated $NH_4Cl$ and water. The solution was brought to a pH of 8 and extracted with ethyl acetate. The organic layer was washed with brine and concentrated to give a solid. Purification by $SiO_2$ chromatography (0–70% EtOAc/hexanes) gave the third intermediate compound as a white solid (6.6 g, 42%). MS: APCI: M+1: 329.2 (Exact Mass: 328.14).

A fourth intermediate compound, 6-(4-Hydroxy-butoxy)-4H-pyrido[3,2-b][1,4]oxazin-3-one, was produced as follows: To a solution of 6-(4-benzyloxy-butoxy)-4H-pyrido [3,2-b][1,4]oxazin-3-one (6.4 g, 19 mmol) in MeOH/THF (100 mL) was added 20% Pd/C (1.5 g) and the mixture was hydrogenated for 12 h. The reaction was filtered, concentrated and purified by liquid chromatography (0–10% MeOH/$CH_2Cl_2$) to give the fourth intermediate compound as a white solid (4.3 g, 18 mmol, 93%). MS: APCI: M+1: 239.1 (Exact Mass: 238.10).

A fifth intermediate compound, 4-(3-Oxo-3,4-dihydro-2H-pyrido[3,2-b][1,4]oxazin-6-yloxy)-butyraldehyde, was produced as follows: To a suspension of 6-(4-hydroxy-butoxy)-4H-pyrido[3,2-b][1,4]oxazin-3-one (4.3 g, 18.02 mmol) in dichloroethane (30 mL) was added IBX (15 g, 54 mmol). This mixture was heated at 80° C. for 5 hours. The reaction was cooled and stirred, and then filtered. The filter cake was washed with $CH_2Cl_2$ until the product was removed. The filtrate was concentrated to give a red oil, which was purified by $SiO_2$ chromatography (0–7% MeOH/ $CH_2Cl_2$) to give the fifth intermediate compound as a red oil (3.90 g, 16.5 mmol, 92%). MS: APCI: M+1: 237.1 (Exact Mass: 236.08).

A reductive amination procedure similar to Example A1' was followed using 2-methyl-8-piperazin-1-yl-quinoline to give the title compound (0.19 g, 51%). MS: APCI: M+1: 448.3 (Exact Mass: 447.23).

Example F2'

Synthesis of 6-[4-(4-Quinolin-8-yl-piperazin-1-yl)-butoxy]-4H-pyrido[3.2-b][1,4]oxazin-3-one A reductive amination procedure similar to Example A1' was followed using 8-piperazin-1-yl-quinoline to give the title compound (0.18 g, 64%). MS: APCI: M+1: 434.3 (Exact Mass: 433.21).

Example F3'

Synthesis of 6-{4-[4-(2-Oxo-1,23,4-tetrahydro-quinolin-8-yl)-piperazin-1-yl]-butoxy}-4H-pyrido[3, 2-b][1,4]oxazin-3-one A reductive amination procedure similar to Example A1' was followed using 8-piperazin-1-yl-3,4-dihydro-1H-quinolin-2-one to give the title compound (0.20 g, 66%). MS: APCI: M+1: 452.3 (Exact Mass: 451.22).

Example F4'

Synthesis of 6-[4-(4-Chroman-8-yl-piperazin-1-yl)-butoxy]-4H-pyrido[3,2-b][1,4]oxazin-3-one A reductive amination procedure similar to Example A1' was followed using 1-chroman-8-yl-piperazine to give the title compound (0.29 g, 79%). MS: APCI: M+1: 439.3 (Exact Mass: 438.23).

Example F5'

Synthesis of 6-{4-[4-(2,3-Dihydro-benzo[1,4]di-oxin-5-yl)-piperazin-1-yl]-butoxy}-4H-pyrido[3,2-b] [1,4]oxazin-3-one A reductive amination procedure similar to Example A1' was followed using 1-(2,3-dihydro-benzo[1,4]dioxin-5-yl)-piperazine to give the title compound (0.22 g, 67%). MS: APCI: M+1: 441.1 (Exact Mass: 440.21).

Example G1'

Synthesis of 2-{4-[4-(2,3-Dihydro-benzo[1,4]di-oxin-5-yl)-piperazin-1-yl]-butoxy}-8H-pyrido[2,3-d] pyrimidin-7-one A first intermediate compound 2-Methanesulfinyl-8H-pyrido[2,3-d]pyrimidin-7-one, was produced as follows: To a suspension of 2-methylsulfanyl-8H-pyrido[2,3-d]pyrimidin-7-one (5.0 g, 25.9 mmol) in $CH_2Cl_2$ (100 mL), $CHCl_3$ (50 mL) and MeOH (10 mL, the starting material still did not dissolve) was added the oxaziridine (8.11 g, 31.05 mmol, 1.2 equiv) as a solid. The reaction became homogenous after 3 h and was stirred overnight at RT. The reaction was concentrated and $CH_2Cl_2$/MeOH was added to dissolve the residue. Much of the solid did not dissolve so the mixture was filtered to give an off-white solid which was the first intermediate compound (2.31 g, 11.04 mmol, 43%). MS: APCI: M+1: 210.1 (Exact Mass: 209.03).

A second intermediate compound, 2-[4-(Tetrahydro-pyran-2-yloxy)-butoxy]-8H-pyrido[2,3-d]pyrimidin-7-one, was produced as follows: To a solution of 4-(tetrahydro-pyran-2-yloxy)-1-butanol (4.45 g, 25.3 mmol, 2.5 equiv) in THF (20 mL) cooled to 0° C. was added 1M KO$^t$Bu in THF (25 mL, 25 mmol). The solution was stirred at 0° C. for 20 min and then added to a suspension of 2-methanesulfinyl-8H-pyrido[2,3-d]pyrimidin-7-one (2.12 g, 10.13 mmol) in DMF (30 mL) at RT. The reaction became homogenous and was stirred at room temperature for 1 h. Saturated NH4Cl and H2O were added to quench the reaction. The mixture was extracted with EtOAc. The organic layer was washed with H2O and brine, dried over Na2SO4 and concentrated. Purification by liquid chromatography (70% EtOAc/Hexanes to 100% EtOAc) gave the second intermediate compound as a white solid (1.95 g, 6.11 mmol, 60%). MS: APCI: M+1: 320.2 (Exact Mass: 319.15).

A third intermediate compound, 2-(4-Hydroxy-butoxy)-8H-pyrido[2,3-d]pyrimidin-7-one, was produced as follows: To a suspension of 2-[4-(tetrahydro-pyran-2-yloxy)-butoxy]-8H-pyrido[2,3-d]pyrimidin-7-one (1.95 g, 6.11 mmol) in EtOH (30 mL) and CH2Cl2 (2 mL, added to help dissolve the starting material) was added PPTS (151 mg, 0.6 mmol). The solution was stirred overnight at room temperature and then heated at 60° C. for 5 h. The reaction was concentrated to give a white solid. Purification by liquid chromatography (6% MeOH/CH2Cl2) gave the third intermediate compound as a white solid (1.22 g, 5.19 mmol, 85%). MS: APCI: M+1: 236.1 (Exact Mass: 235.10).

A fourth intermediate compound, 4-(7-Oxo-7,8-dihydro-pyrido[2,3-d]pyrimidin-2-yloxy)-butyraldehyde, was produced as follows: To a solution of 2-(4-hydroxy-butoxy)-8H-pyrido[2,3-d]pyrimidin-7-one (251 mg, 1.07 mmol) in DMSO (3 mL) was added a solution of IBX (597 mg, 2.13 mmol) in DMSO (7 mL, 0.3 M). The reaction was stirred at room temperature for 90 min, cooled to 0° C. and quenched with 5% NaHCO3. The mixture was extracted with CH2Cl2 (4×). The organic layer was washed with 5% NaHCO3 and brine, dried over Na2SO4 and concentrated to give the fourth intermediate compound as a white solid (171 mg, 0.733 mmol, 69%). MS: APCI: M+1: 234.1 (Exact Mass: 233.08).

The pyrimidines of Examples G1'–G9' were synthesized in a combinatorial library format by reductive amination of the appropriate piperazine starting materials with 4-(7-oxo-7,8-dihydro-pyrido[2,3-d]pyrimidin-2-yloxy)-butyraldehyde using the procedure outlined in Example C1'.

The title compound was isolated as white solid (292 mg, 0.637 mmol, 74.3%). MS: APCI: M+1: 438.1 (Exact Mass: 437.21).

Example G2'

Synthesis of 2-[4-(4-Chroman-8-yl-piperazin-1-yl)-butoxy]-8H-pyrido[2,3-d]pyrimidin-7-one The title compound was isolated as a white solid (258 mg, 0.564 mmol, 65.8%). MS: APCI: M+1: 436.1 (Exact Mass: 435.23).

Example G3'

Synthesis of 2-[4-(4-Quinolin-8-yl-piperazin-1-yl)-butoxy]-8H-pyrido[2,3-d]pyrimidin-7-one The title compound was isolated as a yellow solid (225 mg, 0.522 mmol, 61%). MS: APCI: M+1: 431.1 (Exact Mass: 430.21).

Example G4'

Synthesis of 2-{4-[4-(2,3-Dihydro-benzofuran-7-yl)-piperazin-1-yl]-butoxy}-8H-pyrido[2,3-d]pyrimidin-7-one The title compound was isolated as a white solid (118 mg, 0.280 mmol, 32.7%). MS: APCI: M+1: 422.1 (Exact Mass: 421.21).

Example G5'

Synthesis of 2-{4-[4-(3,4-Dihydro-2H-benzo[b][1,4]dioxepin-6-yl)-piperazin-1-yl]-butoxy}-8H-pyrido[2,3-d]pyrimidin-7-one The title compound was isolated as a white solid (117 mg, 0.259 mmol, 30.2%). MS: APCI: M+1: 452.3 (Exact Mass: 451.22).

Example G6'

Synthesis of 2-{4-[4-(2,2-Dimethyl-chroman-8-yl)-piperazin-1-yl]-butoxy}-8H-pyrido[2,3-d]pyrimidin-7-one The title compound was isolated as a white solid (202 mg, 0.435 mmol, 50.8%). MS: APCI: M+1: 464.3 (Exact Mass: 463.26).

Example G7'

Synthesis of 2-{4-[4-(2,2-Difluoro-benzo[1,3]dioxol-4-yl)-piperazin-1-yl]-butoxy}-8H-pyrido[2,3-d]pyrimidin-7-one The title compound was isolated as a white foam (249 mg, 0.541 mmol, 63.2%). MS: APCI: M+1: 460.2 (Exact Mass: 459.17).

Example G8'

Synthesis of 2-{4-[4-(2,2-Dimethyl-2,3-dihydro-benzofuran-7-yl)-piperazin-1-yl]-butoxy}-8H-pyrido[2,3-d]pyrimidin-7-one The title compound was isolated as an off white foam (188 mg, 0.418 mmol, 48.8%). MS: APCI: M+1: 450.1 (Exact Mass: 449.24).

Example G9'

Synthesis of 2-{4-[4-(2-Methyl-quinolin-8-yl)-piperazin-1-yl]-butoxy}-8H-pyrido[2,3-d]pyrimidin-7-one The title compound was isolated as tan crystals (93 mg, 0.209 mmol, 24.4%). MS: APCI: M+1: 445.1 (Exact Mass: 444.23).

Example G10'

Synthesis of 2-{4-[4-(2,3-Dihydro-benzo[1,4]dioxin-5-yl)-piperazin-1-yl]-butoxy}-4-methyl-8H-pyrido[2,3-d]pyrimidin-7-one A first intermediate compound 2-Methanesulfonyl-4-methyl-8H-pyrido[2,3-d]pyrimidin-7-one, was produced as follows: A solution of 4-methyl-2-methylsulfanyl-8H-pyrido[2,3-d]pyrimidin-7-one (24 g, 0.1158 mol, U.S. Pat. No. 6,498,163) in a mixture of $CH_2Cl_2$ (1.9 L) and methanol (300 mL) is treated with m-chloroperbenzoic acid (103 g, 60%, 0.345 mol) in portions at room temperature. The mixture is stirred for 24 h, cooled to ~5° C. and quenched with saturated sodium bicarbonate solution. The solids are filtered, washed thoroughly with water followed by ether and dried in vacuum to give the first intermediate compound as a solid (10 g, 0.042 mol, 36%). MS: APCI: M+1: 240.0 (Exact Mass: 239.04).

A second intermediate compound, 4-Methyl-2-[4-(tetrahydro-pyran-2-yloxy)-butoxy]-8H-pyrido[2,3-d]pyrimidin-7-one, was produced as follows: To a ice bath cooled solution of 4-(tetrahydro-pyran-2-yloxy)-butan-1-ol (27.3 g, 0.1567 mol) in dry THF (125 mL) is added drop wise a solution of KOtBu (1M, 155 mL, 0.155 mol) in THF within 15 min. The mixture is then stirred at 0° C. for 2 h. To this mixture is added a suspension of 2-methanesulfonyl-4-methyl-8H-pyrido[2,3-d]pyrimidin-7-one (15 g, 0.0627 mol) in DMF (225 mL) at room temperature within 15 min. The orange red colored reaction mixture is stirred at room temperature for 1.5 h, cooled and quenched with saturated $NH_4Cl$ solution (150 mL) and water (2 L). The mixture is extracted with ethyl acetate (2×0.75 L) and the organic layer is washed with brine (300 mL), dried over anhydrous sodium sulfate, filtered through a small bed of silica gel eluting with 5% methanol in ethyl acetate (750 mL) and concentrated. The residue is then triturated with hexane, filtered and dried to give the second intermediate compound as a white solid (16.5 g, 0.0495 mol 78%). MS: APCI: M+1: 334.0 (Exact Mass: 333.17).

A third intermediate compound, 2-(4-Hydroxy-butoxy)-4-methyl-8H-pyrido[2,3-d]pyrimidin-7-one, was produced as follows: A mixture of 4-methyl-2-[4-(tetrahydro-pyran-2-yloxy)-butoxy]-8H-pyrido[2,3-d]pyrimidin-7-one (16.5 g, 0.049 mol) and PPTS (1.24 g, 0.0049 mol) in ethanol (250 mL) and $CH_2Cl_2$ (20 mL) is stirred at room temperature for 16 h, followed by heating at reflux (~90° C.) for 3 h. The cloudy reaction mixture is evaporated under vacuum and the residue is triturated in hexane-ethyl acetate (150 mL, 1:1) and dried to give the third intermediate compound as a yellow powder (12.5 g, 0.049 mol, 100%). MS: APCI: M+1: 250.0 (Exact Mass: 249.11).

A fourth intermediate compound, 4-(4-Methyl-7-oxo-7,8-dihydro-pyrido[2,3-d]pyrimidin-2-yloxy)-butyraldehyde, was produced as follows: A stirred solution of IBX (26 g, 0.092 mol) in DMSO (220 ml) is treated with 2-(4-hydroxy-butoxy)-4-methyl-8H-pyrido[2,3-d]pyrimidin-7-one (11 g, 0.0467 mol) portion wise while stirring at room temperature during 30 min and the reaction is stirred at room temperature for an additional 2 h. The mixture is cooled and treated with saturated $NaHCO_3$ (150 mL) and extracted with chloroform (4×0.5 L). The combined organic layer is washed with brine/ice (2×), dried over $Na_2SO_4$, filtered and concentrated. The residue is stirred with ether, filtered, washed with ether and dried to give 6 g of the crude, which shows it to be a mixture. The ether filtrate residue also shows some product, but mostly starting material. The residue from the filtrate and the crude (11 g) are subjected to re-oxidation as above using fresh IBX (15.5 g, 0.055 mol) in DMSO (150 mL), but stirred at 30° C. for 3 h. Workup as above yielded the fourth intermediate compound as an off-white powder (8.3 g, 0.057 mol, 66.8%). MS: APCI: M+1: 248.0 (Exact Mass: 247.10).

The pyrimidines of Examples G10'–G15' were synthesized in combinatorial library format by reductive amination of the appropriate piperazine starting materials with 4-(4-methyl-7-oxo-7,8-dihydro-pyrido[2,3-d]pyrimidin-2-yloxy)-butyraldehyde following the general procedure outlined in Example C1'.

The title compound was isolated as a solid (81 mg, 0.179 mmol, 59.8%). MS: APCI: M+1: 452.3 (Exact Mass: 451.22).

Example G11'

Synthesis of 2-{4-[4-(2,3-Dihydro-benzofuran-7-yl)-piperazin-1-yl]-butoxy}-4-methyl-8H-pyrido[2,3-d]pyrimidin-7-one The title compound was isolated as a solid (56 mg, 0.128 mmol, 42.86%). MS: APCI: M+1: 436.3 (Exact Mass: 435.23).

Example G12'

Synthesis of 2-[4-(4-Benzofuran-7-yl-piperazin-1-yl)-butoxy]-4-methyl-8H-pyrido[2,3-d]pyrimidin-7-one The title compound was isolated as a white solid (56 mg, 0.129 mmol, 43.06%). MS: APCI: M+1: 434.1 (Exact Mass: 433.21).

Example G13'

Synthesis of 2-[4-(4-Chroman-8-yl-piperazin-1-yl)-butoxy]-4-methyl-8H-pyrido[2,3-d]pyrimidin-7-one The title compound was isolated as a white powder (53 mg, 0.117 mmol, 39.3%). MS: APCI: M+1: 450.2 (Exact Mass: 449.24).

Example G14'

Synthesis of 4-Methyl-2-{4-[4-(2-oxo-1,2,3,4-tetrahydro-quinolin-8-yl)-piperazin-1-yl]-butoxy}-8H-pyrido[2,3-d]pyrimidin-7-one The title compound was isolated as a solid (58 mg, 0.125 mmol, 41.8%). MS: APCI: M+1: 463.2 (Exact Mass: 462.24).

Example G15'

Synthesis of 4-Methyl-2-[4-(4-quinolin-8-yl-piperazin-1-yl)-butoxy]-8H-pyrido[2,3-d]pyrimidin-7-one The title compound was isolated as a brown solid (44 mg, 0.099 mmol, 32.9%). MS: APCI: M+1: 445.3 (Exact Mass: 444.23).

Example H1'

Synthesis of 7-[4-(4-Chroman-8-yl-piperazin-1-yl)-butoxy]-3,4-dihydro-1H-[1,6]naphthyridin-2-one A first intermediate compound 3-(4,6-Diamino-pyridin-3-yl)-acrylic acid ethyl ester, was produced as follows: A mixture of (carbethoxymethylene)triphenylphosphorane (436 g, 1.25 mol) and 4,6-diaminopyridine-3-carbaldehyde (131.8 g, 0.96 mol) in 1,4-dioxane (2.0 L) was refluxed for 2.0 h. The mixture was cooled and filtered through silica gel (800 g) eluting with 0–10% MeOH/EtOAc. The filtrate was concentrated and the residue (~580 g) was used in the next step without further purification.

A second intermediate compound, 7-Amino-1H-[1,6]naphthyridin-2-one, was produced as follows: The residue obtained from the above procedure was refluxed in conc. HCl (1.5 L) for 1.5 h. The mixture was cooled and diluted with water (2.5 L). At 35–40° C., the mixture was washed with EtOAc (3×). The aqueous layer was made basic with 50% NaOH to pH>10 while cooling with a cold water bath. The resulting solid was collected via filtration, rinsed with water, methanol, and oven dried to afford the second intermediate compound (106 g, 68% for two steps) as off-white crystals.

A third intermediate compound, 7-Fluoro-1H-[1,6]naphthyridin-2-one, was produced as follows: To a stirred mixture of HF-pyridine (660 g) and 7-amino-1H-[1,6]naphthyridin-2-one (58 g, 0.36 mol) in a plastic bottle was added NaNO$_2$ (39.7 g, 0.57 mol) in small portions over 30–40 min while cooled with a cold (~10° C.) water bath in order to keep the internal temperature at around RT. After the addition, the mixture was further stirred at room temperature for 20 min before it was poured into water (2.6 L) and stirred for 3.0 h. The resulting solid was collected via filtration, rinsed with water (2×), EtOAc-heptane (1:1, 2×), and oven dried to afford the third intermediate compound (48.6 g, 82%) as pale solid.

A fourth intermediate compound, 7-(4-Benzyloxy-butoxy)-1H-[1,6]naphthyridin-2-one, was produced as follows: A solution of 4-benzyloxy-butan-1-ol (35.98 g, 199.6 mmol) and potassium t-butoxide (21 g, 188 mmol) in THF (60 mL) was prepared and stirred at room temperature for 20 min. A suspension of 7-fluoro-1H-[1,6]naphthyridin-2-one (8.1 g, 49 mmol) in THF (100 mL) was prepared, and the alcohol solution was added to this solution via canula. The reaction was stirred at 80° C. overnight. MS showed mostly product. So reaction quenched with saturated NH$_4$Cl and water. The solution was brought to a pH of 8 and extracted with ethyl acetate. The organic layer was washed with brine and concentrated to give a silky solid. EtOAc was added and the mixture was filtered to give a beige solid. The NMR indicated that it was the product and it was recrystallized from acetonitrile to give clean product. (9.70 g). The filtrate was concentrated and filtered to give more precipitate (0.788 g). The filtrate was concentrated and purified by chromatography (0–70% EtOAc/hexanes) to give additional product as a beige solid (2.716 g). (Total Product: 13.21 g, 82%). MS: APCI: M+1: 325.2 (Exact Mass: 324.15).

A fifth intermediate compound, 7-(4-Hydroxy-butoxy)-3,4-dihydro-1H-[1,6]naphthyridin-2-one, was produced as follows: To a solution of 7-(4-benzyloxy-butoxy)-1H-[1,6]naphthyridin-2-one (7.92 g, 24.4 mmol) in MeOH/THF (100 mL) was added 20% Pd/C (1.5 g) and the mixture was hydrogenated for 59 h. The reaction was filtered, concentrated and purified by liquid chromatography (0–10% MeOH/CH2Cl2) to give the fifth intermediate compound as a white solid (4.11 g, 17.4 mmol, 71%). MS: APCI: M+1: 237.1 (Exact Mass: 236.12).

A sixth intermediate compound, 4-(2-Oxo-1,2,3,4-tetrahydro-[1,6]naphthyridin-7-yloxy)-butyraldehyde, was produced as follows: To a suspension of 7-(4-hydroxybutoxy)-3,4-dihydro-1H-[1,6]naphthyridin-2-one (2.0 g, 8.5 mmol) in dichloroethane (20 mL) was added IBX (7 g, 25 mmol). This was heated at 80° C. for 5 hours. The reaction was cooled and then filtered. The filter cake was washed with CH$_2$CH$_2$ until the product was removed. The filtrate was concentrated to give a yellow solid (1.88 g, used crude in next reaction). MS: APCI: M+1: 235.1 (Exact Mass: 234.10).

A reductive amination procedure similar to Example A1' was followed using 1-chroman-8-yl-piperazine (0.24 g; 69%). MS: APCI: M+1: 437.2 (Exact Mass: 436.25).

Example H2'

Synthesis of 7-{4-[4-(2,3-Dihydro-benzofuran-7-yl)-piperazin-1-yl]-butoxy}-3,4-dihydro-1H-[1,8]naphthyridin-2-one A reductive amination procedure similar to Example A1' was followed using 1-(2,3-dihydro-benzofuran-7-yl)-piperazine to give the title compound (0.32 g, 50%). MS: APCI: M+1: 423.2 (Exact Mass: 422.23).

Example H3'

Synthesis of 7-{4-[4-(2,2,3,3-Tetrafluoro-2,3-dihydro-benzo[1,4]dioxin-5-yl)-piperazin-1-yl]-butoxy}-3,4-dihydro-1H-[1,6]naphthyridin-2-one A reductive amination procedure similar to Example A1' was followed using 1-(2,2,3,3-tetrafluoro-2,3-dihydro-benzo[1,4]dioxin-5-yl)-piperazine to give the title compound (0.21 g, 27%). MS: APCI: M+1: 511.1 (Exact Mass: 510.19).

Example H4'

Synthesis of 7-{4-[4-(2,2-Difluoro-benzo[1,3]dioxol-4-yl)-piperazin-1-yl]-butoxy}-3,4-dihydro-1H-[1,6]naphthyridin-2-one A reductive amination procedure similar to Example A1' was followed using 1-(2,2-difluoro-benzo[1,3]dioxol-4-yl)-piperazine to give the title compound (0.40 g, 56%). MS: APCI: M+1: 461.2 (Exact Mass: 460.19).

Example H5'

Synthesis of 7-{4-[4-(2,3-Dihydro-benzo[1,4]dioxin-5-yl)-piperazin-1-yl]-butoxy}-3,4-dihydro-1H-[1,6]naphthyridin-2-one A reductive amination procedure similar to Example A1' was followed using 1-(2,3-dihydro-benzo[1,4]dioxin-5-yl)-piperazine to give the title compound (0.22 g, 50%). MS: APCI: M+1: 439.3 (Exact Mass: 438.23).

Example H6'

Synthesis of 7-{4-[4-(2,3-Dihydro-benzofuran-7-yl)-piperazin-1-yl]-butoxy}-1H-[1,6]naphthyridin-2-one A first intermediate compound 7-(4-Hydroxy-butoxy)-1H-[1,6]naphthyridin-2-one, was produced as follows: Butane-1,4-diol (8.24 g, 8.12 mL, 91.3 mmol) was added to solid KO$^t$Bu (6 g, 55 mmol). The very viscous mixture was stirred for 15 min before adding 7-fluoro-1H-[1,6]naphthyridin-2-one (3 g, 18 mmol). NMP (60 mL) was then added and the reaction was heated at 70° C. overnight. The reaction was cooled and poured into ice water. No precipitate formed, so the mixture was extracted with EtOAc. The organic layer was washed with brine, dried over $Na_2SO_4$ and concentrated. Purification by $SiO_2$ chromatography (0–50% EtOAc/Hex) gave the first intermediate compound (2.36 g, 55%). MS: APCI: M+1: 235.0 (Exact Mass: 234.10).

A second intermediate compound, 4-(2-Oxo-1,2-dihydro-[1,6]naphthyridin-7-yloxy)-butyraldehyde, was produced as follows: To a suspension of 7-(4-hydroxy-butoxy)-1H-[1,6]naphthyridin-2-one (2.33 g, 9.95 mmol) in dichloroethane (30 mL) was added IBX (8 g, 30 mmol). The mixture was heated at 80° C. for 5 hours. The reaction was cooled and stirred, and then filtered. The filter cake was washed with $CH_2Cl_2$ until the product was removed. The filtrate was concentrated to give the second intermediate compound as a yellow solid (2.45 g). MS: APCI: M+1: 233.1 (Exact Mass: 232.08).

A reductive amination procedure similar to Example A1' was followed using 1-(2,3-dihydro-benzofuran-7-yl)-piperazine to give the title compound (0.225 g, 59%). MS: APCI: M+1: 421.2 (Exact Mass: 420.22).

Example H7'

Synthesis of 7-{4-[4-(2,3-Dihydro-benzo[1,4]dioxin-5-yl)-piperazin-1-yl]-butoxy}-1H-[1,6]naphthyridin-2-one A reductive amination procedure similar to Example A1' was followed using 1-(2,3-dihydro-benzo[1,4]dioxin-5-yl)-piperazine to give the title compound (0.22 g, 60%). MS: APCI: M+1: 437.2 (Exact Mass: 436.21).

Example H8'

Synthesis of 7-[4-(4-Chroman-8-yl-piperazin-1-yl)-butoxy]-1H-[1,6]naphthyridin-2-one A reductive amination procedure similar to Example A1' was followed using 1-chroman-8-yl-piperazine to give the title compound (0.23 g, 62%). MS: APCI: M+1: 435.2 (Exact Mass: 434.23).

Example H9'

Synthesis of 7-{4-[4-(2,2-Difluoro-benzo[1,3]dioxol-4-yl)-piperazin-1-yl]-butoxy}-1H-[1,6]naphthyridin-2-one A reductive amination procedure similar to Example A1' was followed using 1-(2,2-difluoro-benzo[1,3]dioxol-4-yl)-piperazine to give the title compound (0.26 g, 66%). MS: APCI: M+1: 459.2 (Exact Mass: 458.18).

The invention claimed is:

1. The compound 7-[4-(4-naphthalen-1-yl-piperazin-1-yl)-butoxy]-3,4-dihydro-1H-[1,8]naphthyridin-2-one, or a pharmaceutically acceptable salt thereof.

2. The pharmaceutically acceptable salt of the compound 7-[4-(4-naphthalen-1-yl-piperazin-1-yl)-butoxy]-3,4-dihydro-1H-[1,8]naphthyridin-2-one according to claim 1, which is a phosphoric acid addition salt.

3. A pharmaceutical composition comprising the compound 7-[4-(4-napthalen-1-yl-piperazin-1-yl)-butoxy]-3,4-dihydro-1H-[1,8]naphthyridin-2-one, or a pharmaceutically acceptable salt thereof, and a pharmaceutically acceptable carrier.

4. A pharmaceutical composition comprising a pharmaceutically acceptable salt of the compound 7-[4-(4-naphthalen-1-yl-piperazin-1-yl)-butoxy]-3,4-dihydro-1H-[1,8]naphthyridin-2-one according to claim 2, and a pharmaceutically acceptable carrier.

5. A method of treating schizophrenia or bipolar disorder in a human in need thereof, comprising administering to the human an effective amount of the compound 7-[4-(4-naphthalen-1-yl-piperazin-1-yl)-butoxy]-3,4-dihydro-1H-[1,8]naphthyridin-2-one, or a pharmaceutically acceptable salt thereof.

6. The method according to claim 5, comprising administering to the human an effective amount of a pharmaceutically acceptable salt of the compound 7-[4-(4-naphthalen-1-yl-piperazin-1-yl)-butoxy]-3,4-dihydro-1H-[1,8]naphthyridin-2-one.

7. The compound 7-{4-[4-(8-fluoro-naphthalen-1-yl)-piperazin-1-yl]-butoxy}-3,4-dihydro-1H-[1,8]naphthyridin-2-one, or a pharmaceutically acceptable salt thereof.

8. The pharmaceutically acceptable salt of the compound 7-{4-[4-(8-fluoro-naphthalen-1-yl)-piperazin-1-yl]-butoxy}-3,4-dihydro-1H-[1,8]naphthyridin-2-one according to claim 7, which is a phosphoric acid addition salt.

9. A pharmaceutical composition comprising the compound 7-{4-[4-(8-fluoro-naphthalen-1-yl)-piperazin-1-yl]-butoxy}-3,4-dihydro-1H-[1,8]naphthyridin-2-one, or a pharmaceutically acceptable salt thereof, and a pharmaceutically acceptable carrier.

10. A pharmaceutical composition comprising a pharmaceutically acceptable salt of the compound 7-{4-[4-(8-fluoro-naphthalen-1-yl)-piperazin-1-yl]-butoxy}-3,4-dihydro-1H-[1,8]naphthyridin-2-one according to claim 8, and a pharmaceutically acceptable carrier.

11. A method of treating schizophrenia or bipolar disorder in a human in need thereof, comprising administering to the human an effective amount of the compound 7-{4-[4-(8-fluoro-naphthalen-1-yl)-piperazin-1-yl]-butoxy}-3,4-dihydro-1H-[1,8]naphthyridin-2-one, or a pharmaceutically acceptable salt thereof.

12. The method according to claim 11, comprising administering to the human an effective amount of a pharmaceutically acceptable salt of the compound 7-{4-[4-(8-fluoro-naphthalen-1-yl)-piperazin-1-yl]-butoxy}-3,4-dihydro-1H-[1,8]naphthyridin-2-one.

* * * * *

UNITED STATES PATENT AND TRADEMARK OFFICE
CERTIFICATE OF CORRECTION

PATENT NO. : 7,160,888 B2  Page 1 of 1
APPLICATION NO. : 10/900210
DATED : January 9, 2007
INVENTOR(S) : Johnson et al.

It is certified that error appears in the above-identified patent and that said Letters Patent is hereby corrected as shown below:

On the Title page,

Item [*] Notice and Item 45: Subject to any disclaimer, the term of this patent is extended or adjusted under 35 USC 154(b) by (141) days Delete the phrase "by 141" and insert -- by 243 days--

Signed and Sealed this

Sixteenth Day of October, 2007

JON W. DUDAS
*Director of the United States Patent and Trademark Office*